(12) United States Patent
Schmees et al.

(10) Patent No.: US 11,040,035 B2
(45) Date of Patent: Jun. 22, 2021

(54) 3-OXO-2,6-DIPHENYL-2,3-DIHYDRO-PYRIDAZINE-4-CARBOXAMIDES

(71) Applicants: BAYER PHARMA AKTIENGESELLSCHAFT, Berlin (DE); DEUTSCHES KREBSFORSCHUNGSZENTRUM (DKFZ), Heidelberg (DE)

(72) Inventors: Norbert Schmees, Berlin (DE); Ilona Gutcher, Berlin (DE); Horst Irlbacher, Berlin (DE); Benjamin Bader, Berlin (DE); Na Zhao, Beijng (CN); Michael Platten, Heidelberg (DE); Ulrike Röhn, Berlin (DE); Ludwig Zorn, Berlin (DE); Lars Röse, Berlin (DE); Detlef Stöckigt, Potsdam (DE)

(73) Assignees: BAYER PHARMA AKTIENGESELLSCHAFT, Berlin (DE); DEUTSCHES KREBSFORSCHUNGSZENTRUM (DKFZ), Heidelberg (DE)

( * ) Notice: Subject to any disclaimer, the term of this patent is extended or adjusted under 35 U.S.C. 154(b) by 127 days.

(21) Appl. No.: 16/303,539

(22) PCT Filed: May 23, 2017

(86) PCT No.: PCT/EP2017/062355
§ 371 (c)(1),
(2) Date: Nov. 20, 2018

(87) PCT Pub. No.: WO2017/202816
PCT Pub. Date: Nov. 30, 2017

(65) Prior Publication Data
US 2020/0237757 A1 Jul. 30, 2020

(30) Foreign Application Priority Data

May 25, 2016 (WO) ............... PCT/CN2016/083308
Feb. 22, 2017 (WO) ............... PCT/CN2017/074408

(51) Int. Cl.
| | |
|---|---|
| C07D 237/14 | (2006.01) |
| C07D 237/20 | (2006.01) |
| C07D 401/10 | (2006.01) |
| C07D 405/12 | (2006.01) |
| A61K 31/501 | (2006.01) |
| A61P 35/00 | (2006.01) |
| A61K 31/50 | (2006.01) |
| A61K 45/06 | (2006.01) |
| C07D 237/24 | (2006.01) |
| C07D 403/12 | (2006.01) |

(52) U.S. Cl.
CPC ........... *A61K 31/501* (2013.01); *A61K 31/50* (2013.01); *A61K 45/06* (2013.01); *A61P 35/00* (2018.01); *C07D 237/24* (2013.01); *C07D 403/12* (2013.01); *C07D 405/12* (2013.01)

(58) Field of Classification Search
CPC .. C07D 237/14; C07D 237/20; C07D 405/12; C07D 401/10
See application file for complete search history.

(56) References Cited

U.S. PATENT DOCUMENTS 5,418,233 A 5/1995 Linz

FOREIGN PATENT DOCUMENTS

| | | |
|---|---|---|
| EP | 1130015 A1 | 9/2001 |
| EP | 1319659 A1 | 6/2003 |
| EP | 1953147 A1 | 8/2008 |
| FR | 2847235 A1 | 5/2004 |
| WO | 2004046117 A1 | 6/2004 |

OTHER PUBLICATIONS

Bauer, Journal of Validation Technology, p. 15-23 . (Year: 2008).*
Bianchi-Smiralgia et al. J Clin Invest. 2018;128(10):4682-4696. (Year: 2018).*

* cited by examiner

*Primary Examiner* — Emily A Bernhardt
(74) *Attorney, Agent, or Firm* — Morrison & Foerster LLP

(57) ABSTRACT

The present invention covers 3-oxo-2,6-diphenyl-2,3-dihydropyridazine-4-carboxamide compounds of general formula (I): in which R1, R2, R3, R4, R5 and R6 are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of cancer or conditions with 10 dysregulated immune responses or other disorders associated with aberrant AHR signaling, as a sole agent or in combination with other active ingredients.

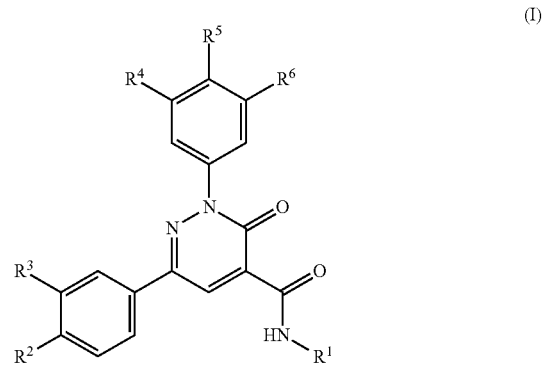

9 Claims, 1 Drawing Sheet

Results of in vivo experiment as described in the experimental section:
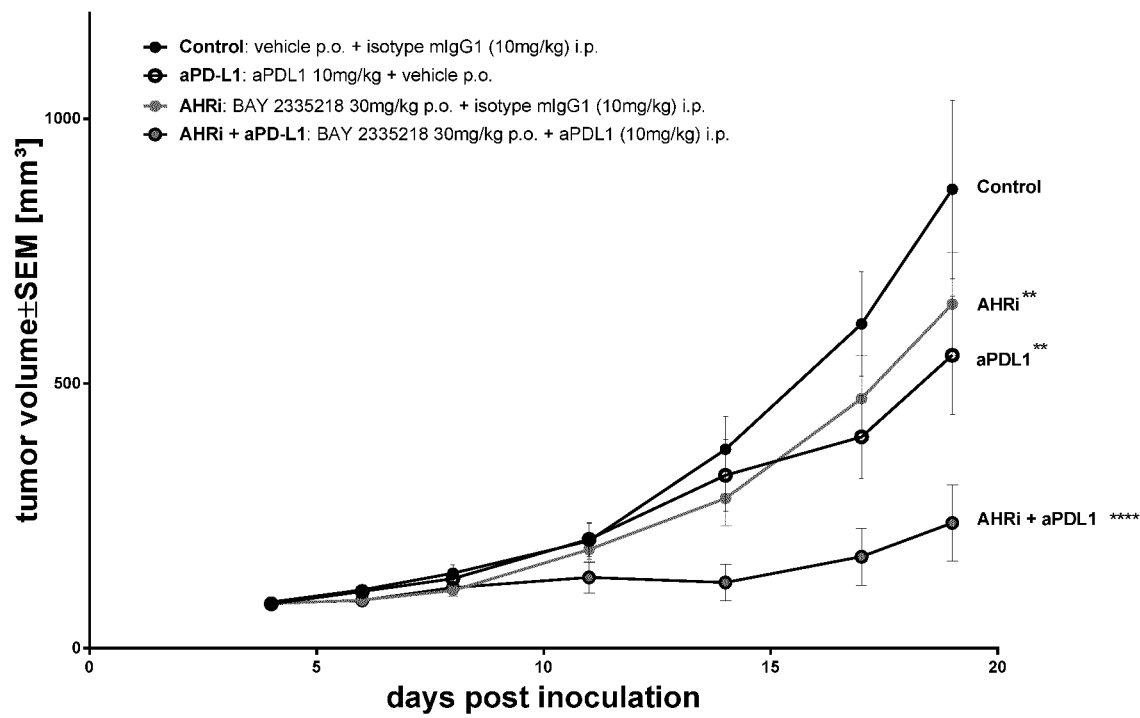

3-OXO-2,6-DIPHENYL-2,3-DIHYDRO-PYRIDAZINE-4-CARBOXAMIDES

CROSS REFERENCE TO RELATED APPLICATIONS

This application is a national phase application under 35 U.S.C. § 371 of International Application No. PCT/EP2017/062355, filed May 23, 2017, which claims priority benefit of International Application No. PCT/CN2017/074408, filed Feb. 22, 2017 and International Application No. PCT/CN2016/083308, filed May 25, 2016.

The present invention covers 3-oxo-2,6-diphenyl-2,3-dihydropyridazine-4-carboxamide compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular cancer or conditions with dysregulated immune responses, as a sole agent or in combination with other active ingredients.

BACKGROUND

The AHR (Aryl Hydrocarbon Receptor) is a ligand-activated transcription factor, belonging to the basic helix-loop-helix/Per-Arnt-Sim (bHLH/PAS) family, and is located in the cytosol. Upon ligand binding, the AHR translocates to the nucleus where it heterodimerises with ARNT (AHR Nuclear Translocator) upon which it interacts with DREs (Dioxin Response Elements) of AHR-responsive genes to regulate their transcription. The AHR is best known for binding to environmental toxins and inducing the metabolic machinery, such as cytochrome P 450 enzymes (eg. CYP1A1, CYP1A2 and CYP1B1), required for their elimination (Reyes et al., Science, 1992, 256(5060):1193-5). Activation of AHR by xenobiotics has demonstrated its role in numerous cellular processes such as embryogenesis, tumourigenesis and inflammation. AHR is expressed in many cells of the immune system, including dendritic cells (DCs), macrophages, T cells and NK cells, and plays an important role in immunoregulation (Nguyen et al., Front Immunol, 2014, 5:551). The classic exogenous AHR ligands TCDD and 3-methylcholanthrene, for example, are known to induce profound immunosuppression, promote carcinogenesis and induce tumour growth (Gramatzki et al., Oncogene, 2009, 28(28):2593-605; Bui et al., Oncogene, 2009, 28(41):3642-51; Esser et al., Trends Immunol, 2009, 30:447-454). In the context of immunosuppression, AHR activation promotes regulatory T cell generation, inhibits Th1 and Th17 differentiation, directly and indirectly, and decreases the activation and maturation of DCs (Wang et al., Clin Exp Immunol, 2014, 177(2):521-30; Mezrich et al., J Immunol, 2010, 185(6): 3190-8; Wei et al., Lab Invest, 2014, 94(5):528-35; Nguyen et al., PNAS, 2010, 107(46):19961-6). AHR activation modulates the innate immune response and constitutive AHR expression has been shown to negatively regulate the type-I interferon response to viral infection (Yamada et al., Nat Immunol, 2016). Additionally, mice with a constitutively active AHR spontaneously develop tumours (Andersson et al., PNAS, 2002, 99(15):9990-5).

In addition to xenobiotics, the AHR can also bind metabolic products of tryptophan degradation. Tryptophan metabolites, such as kynurenine and kynurenic acid, are endogenous AHR ligands that activate the AHR under physiological conditions (DiNatale et al., Toxicol Sci, 2010, 115(1):89-97; Mezrich et al., J Immunol, 2010, 185(6): 3190-8; Opitz et al., Nature, 2011, 478(7368):197-203). Other endogenous ligands are known to bind the AHR although their physiological roles are currently unknown (Nguyen & Bradfield, Chem Res Toxicol, 2008, 21(1):102-116).

The immunosuppressive properties of kynurenine and tryptophan degradation are well described and are implicated in cancer-associated immunosuppression. The enzymes indoleamine-2,3-dioxygenases 1 and 2 (IDO1/IDO2) as well as tryptophan-2,3-dioxygenase 2 (TDO2) are responsible for catalysing the first and rate-limiting step of tryptophan metabolism. IDO1/2-mediated degradation of tryptophan in tumours and tumour-draining lymph nodes reduces anti-tumour immune responses and inhibition of IDO can suppress tumour formation in animal models (Uyttenhove et al., Nat Med, 2003, 9(10):1269-74; Liu et al., Blood, 2005, 115(17): 3520-30; Muller et al., Nat Med, 11(3):312-9; Metz, Cancer Res, 2007, 67(15):7082-7).

TDO2 is also strongly expressed in cancer and can lead to the production of immunosuppressive kynurenine. In glioma, activation of the AHR by kynurenine, downstream of TDO-mediated tryptophan degradation, enhances tumour growth as a consequence of inhibiting anti-tumour immune responses as well as directly promoting tumour cell survival and motility (Opitz et al., Nature, 2011, 478(7368):197-203). AHR ligands generated by tumour cells therefore act in both an autocrine and paracrine fashion on tumour cells and lymphocytes, respectively, to promote tumour growth.

The present invention covers 3-oxo-2,6-diphenyl-2,3-dihydropyridazine-4-carboxamide compounds of general formula (I) which inhibit the AHR.

STATE OF THE ART

WO 2010/059401 relates to compounds and compositions for expanding the number of CD34+ cells for transplantation. In particular, WO 2010/059401 relates inter alia to heterocyclic compounds capable of down-regulating the activity and/or expression of AHR.

WO 2012/015914 relates to compositions and methods for modulating AHR activity. In particular, WO 2012/015914 relates inter alia to heterocyclic compounds that modulate AHR activity for use in therapeutic compositions.

WO 2007/058392 relates to novel heterocyclic compounds and a pharmaceutical use thereof. In particular, WO 2007/058392 relates inter alia to heterocyclic compounds having an hepatitis C virus cell infection inhibitory activity.

WO 2002/022587 relates to novel compounds exhibiting inhibitory activities against AMPA receptor and/or kainate receptor. In particular, WO 2002/022587 relates inter alia to pyridazinone and triazinone compounds.

U.S. Pat. No. 5,418,233 relates to heterobiaryl derivatives inhibiting cell-cell aggregation and cell-matrix interactions. In particular, U.S. Pat. No. 5,418,233 relates to heterobiaryl derivatives which are histamine receptor antagonists.

WO 2015/143164 relates to antimicrobial agents and screening methods. In particular, WO 2015/143164 relates inter alia to pyridazinone compounds as antibiotics.

WO 2009/142732 relates to substituted pyridazinone derivatives and their use as $H_3$ antagonists/inverse agonists.

However, the state of the art does not describe the 3-oxo-2,6-diphenyl-2,3-dihydropyridazine-4-carboxamide compounds of general formula (I) of the present invention as described and defined herein.

It has now been found, and this constitutes the basis of the present invention, that the compounds of the present invention have surprising and advantageous properties. In particular, the compounds of the present invention have surprisingly been found to effectively inhibit AHR for which data are given in biological experimental section and may therefore be used for the treatment or prophylaxis of cancer or other conditions where exogenous and endogenous AHR ligands induce dysregulated immune responses, uncontrolled cell growth, proliferation and/or survival of tumour cells, immunosuppression in the context of cancer, inappropriate cellular immune responses, or inappropriate cellular inflammatory responses or diseases which are accompanied with uncontrolled cell growth, proliferation and/or survival of tumour cells, immunosuppression in the context of cancer inappropriate cellular immune responses, or inappropriate cellular inflammatory responses, particularly in which the uncontrolled cell growth, proliferation and/or survival of tumour cells, immunosuppression in the context of cancer, inappropriate cellular immune responses, or inappropriate cellular inflammatory responses is mediated by AHR, such as, for example, liquid and solid tumours, and/or metastases thereof, e.g. head and neck tumours including brain tumours and brain metastases, tumours of the thorax including non-small cell and small cell lung tumours, gastrointestinal tumours including colon, colorectal and pancreatic tumours, liver tumours, endocrine tumours, mammary and other gynecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

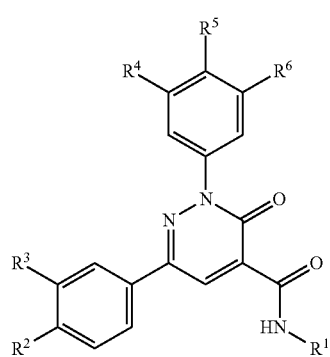

in which
$R^1$ represents $C_2$-$C_8$-hydroxyalkyl, wherein said $C_2$-$C_8$-hydroxyalkyl groups are optionally substituted once with $R^7$ and optionally one to three times with halogen, or
$C_3$-$C_6$-cycloalkyl substituted once with hydroxy or $C_1$-$C_4$-hydroxyalkyl and optionally one to three times with halogen, or
($C_3$-$C_6$-cycloalkyl substituted once with hydroxy)-$C_1$-$C_4$-alkyl, or
4- to 6-membered heterocycloalkyl substituted once with hydroxy or $C_1$-$C_3$-hydroxyalkyl and optionally one to three times with halogen, or
(4- to 6-membered heterocycloalkyl substituted once with hydroxy)-$C_1$-$C_4$-alkyl;
$R^2$ represents chloro, methyl, fluoromethyl, difluoromethyl, trifluoromethyl, methoxy, difluoromethoxy, trifluoromethoxy or —$NR^3R^9$;
$R^3$ represents hydrogen, halogen or methyl;
$R^4$ represents hydrogen, methyl, fluoromethyl, difluoromethyl, trifluoromethyl, halogen or cyano;
$R^5$ represents hydrogen;
$R^6$ represents hydrogen or halogen;
$R^7$ represents $C_1$-$C_4$-alkoxy, —$CO_2$—$R^{10}$, —CO—$NR^8R^9$, cyano, —$NR^8R^9$, $C_3$-$C_6$-cycloalkyl, 4- to 6-membered heterocycloalkyl, phenyl or monocyclic heteroaryl;
$R^8$ and $R^9$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;
$R^{10}$ represents hydrogen or $C_1$-$C_4$-alkyl;
their polymorphs, enantiomeres, diastereomeres, racemates, tautomeres, N-oxides, hydrates and solvates, as well as their physiological acceptable salts and solvates of these salts, as well as mixtures of the same.

Further, it covers their use in combination with other anti cancer medications such as immunotherapeutics, targeted anti cancer agents compounds or chemotherapy.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom. Commonly, it is possible for the number of optional substituents, when present, to be 1, 2 or 3.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen" means a fluorine, chlorine, bromine or iodine, particularly a fluorine, chlorine or bromine atom.

The term "$C_2$-$C_8$-alkyl" means a linear or branched, saturated, monovalent hydrocarbon group having 2, 3, 4, 5, 6, 7 or 8 carbon atoms, e.g. a ethyl, propyl, isopropyl, butyl, sec-butyl, isobutyl, tert-butyl, pentyl, isopentyl, 2-methyl butyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl, 1,3-dimethylbutyl, 3-ethyl-pentyl or 3-ethyl-hexyl group, or an isomer thereof. Particularly, said group has 2, 3 or 4 carbon atoms ("$C_2$-$C_4$-alkyl"), e.g. a ethyl, propyl, isopropyl, butyl, sec-butyl isobutyl, or tert-butyl group, more particularly 2 or 3 carbon atoms ("$C_2$-$C_3$-alkyl"), e.g. a ethyl, n-propyl or isopropyl group.

The term "$C_2$-$C_8$-hydroxyalkyl" means a linear or branched, saturated, monovalent hydrocarbon group in which the term "$C_2$-$C_8$-alkyl" is defined supra, and in which 1 or 2 hydrogen atoms are replaced with a hydroxy group, e.g. a 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methylpropyl, 2-hydroxy-2-methyl-propyl, 1-hydroxy-2-methylpropyl, 3-ethyl-2-hydroxypentyl or 3-ethyl-2-hydroxyhexyl group.

The term "$C_1$-$C_4$-alkoxy" means a linear or branched, saturated, monovalent group of formula ($C_1$-$C_4$-alkyl)-O—, which means methoxy, ethoxy, n-propoxy, isopropoxy, n-butoxy, sec-butoxy, isobutoxy or tert-butoxy.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is a monocyclic hydrocarbon ring, e.g. a cyclopropyl, cyclobutyl, cyclopentyl or cyclohexyl.

The term "4- to 6-membered heterocycloalkyl" means a monocyclic, saturated heterocycle with 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example.

Particularly, "4- to 6-membered heterocycloalkyl" means a 4- to 6-membered heterocycloalkyl as defined supra containing one ring oxygen atom and optionally one further ring heteroatom from the series: N, O, S. More particularly, "5- or 6-membered heterocycloalkyl" means a monocyclic, saturated heterocycle with 5 or 6 ring atoms in total, containing one ring oxygen atom.

The term "monocyclic heteroaryl" means a monovalent, aromatic ring having 5 or 6 ring atoms (a "5- or 6-membered heteroaryl" group), which contains at least one ring heteroatom and optionally one or two further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a imidazolyl group.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art. The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible crystallized and polymorphic forms of the inventive compounds, whereby the polymorphs are existing either as a single polymorph form or are existing as a mixture of several polymorphs in all concentrations.

In accordance with a second embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $R^7$ and optionally one to three times with fluoro or chloro, or $C_3$-$C_6$-cycloalkyl substituted once with hydroxy;

$R^2$ represents chloro, methyl, fluoromethyl, difluoromethyl, trifluoromethyl, methoxy or difluoromethoxy;

$R^3$ represents hydrogen or methyl;

$R^4$ represents hydrogen, fluoro or chloro;

$R^5$ represents hydrogen;

$R^6$ represents hydrogen or fluoro;

$R^7$ represents methoxy, cyclopropyl, tetrahydrofuranyl, tetrahydropyranyl or imidazolyl; their polymorphs, enantiomeres, diastereomeres, racemates, tautomeres, N-oxides, hydrates and solvates, as well as their physiological acceptable salts and solvates of these salts, as well as mixtures of the same.

In accordance with a third embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $R^7$ and optionally one to three times with fluoro;
$R^2$ represents chloro, methyl or difluoromethyl;
$R^3$ represents hydrogen or methyl;
$R^4$ represents hydrogen, fluoro or chloro;
$R^5$ represents hydrogen;
$R^6$ represents hydrogen or fluoro;
$R^7$ represents methoxy or tetrahydrofuranyl; their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $R^7$ and optionally one to three times with halogen, or $C_3$-$C_6$-cycloalkyl substituted once with hydroxy;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $R^7$ and optionally one to three times with halogen;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_3$-$C_6$-cycloalkyl substituted once with hydroxy; their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_5$-$C_6$-cycloalkyl substituted once with hydroxy;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^2$ represents chloro, methyl, fluoromethyl, difluoromethyl, trifluoromethyl, methoxy or difluoromethoxy;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^2$ represents chloro, methyl or methoxy;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^3$ represents hydrogen or methyl;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^4$ represents hydrogen or halogen;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^4$ represents hydrogen, fluoro or chloro;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents hydrogen or halogen;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents hydrogen, fluoro or chloro;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents hydrogen or fluoro;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^7$ represents $C_1$-$C_4$-alkoxy, $C_3$-$C_6$-cycloalkyl, 4- to 6-membered heterocycloalkyl or monocyclic heteroaryl;
their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^7$ represents methoxy, cyclopropyl, tetrahydrofuranyl, tetrahydropyranyl or imidazolyl;

their polymorphs, enantiomeres, diastereomeres, racemates, tautomeres, N-oxides, hydrates and solvates, as well as their physiological acceptable salts and solvates of these salts, as well as mixtures of the same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (VII). The present invention covers the compounds of general formula (I) which are disclosed in the Example Section of this text, infra.

The compounds according to the invention of general formula (I) can be prepared according to the following scheme 1. The scheme and procedures described below illustrate synthetic routes to the compounds of general formula (I) of the invention and are not intended to be limiting. It is clear to the person skilled in the art that the order of transformations as exemplified in scheme 1 can be modified in various ways. The order of transformations exemplified in this scheme is therefore not intended to be limiting. In addition, interconversion of any of the substituents $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metallation, metal-catalysed coupling reactions, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

Scheme 1 shows a route for the preparation of compounds of general formula (I) in which $R^1$, $R^2$, $R^3$, $R^4$, $R^5$ and $R^6$ have the meaning as given for general formula (I), supra. Ketomalonates represented as intermediates according to formula (III) are in some few instances commercially available or can be synthezised from alpha-halo-acetophenones (II) according to procedures known to persons skilled in the art. Related alpha-halo-acetophenones are usually commercially available. Conversion of such alpha-halo-acteophenones with malonic acid esters in the presence of a suitable base in a suitable solvent results in the formation of non-commercial ketomalonates according to formula (III). R in formula (III), (V) and (VI) represents a suitable alkyl group such as methyl, ethyl, propyl or other homologous groups. A suitable solvent can be, but should not be restricted to, acetonitril, DMF, DMA, DMSO of THF, or even mixtures of these or other solvents. A suitable base could be, but should not be restricted to, potassium carbonate, sodium hydride, caesium carbonate of potassium hexamethylendisilazane (see e.g.: J. Heterocycl. Chem., 25, (1988), p. 1689ff; Med. Chem. Lett., 12, (2002), p. 1955 ff.; J. Med. Chem., 58, (2015), p. 3471 ff.).

Formation of dihydropyrazinones according to formula (V) from intermediates (III) and suitable aryl-hydrazines (IV), which are in many cases commercially available, can be accomplished by reaction of these components in a suitable solvent at elevated temperature. $R^3$ and $R^4$ in intermediates (IV) are as defined for formula (I). A suitable sovent could be, but should not be restricted to, ethanol or acetic acid (see e.g.: J. Med. Chem. 19, (1976), p. 787 ff.; Tetrahedron, 65, (2009), p. 4212 ff., J. Med. Chem., 44, (2001), p. 2511 ff.).

Scheme 1 Route for the preparation of compounds of general formula (I) in which $R^1$, $R^2$, $R^3$, $R^4$, $R^5$ and $R^6$ have the meaning as given for the general formula (I), supra and Hal represents halogen and R represents $C_1$-$C_4$-alkyl.

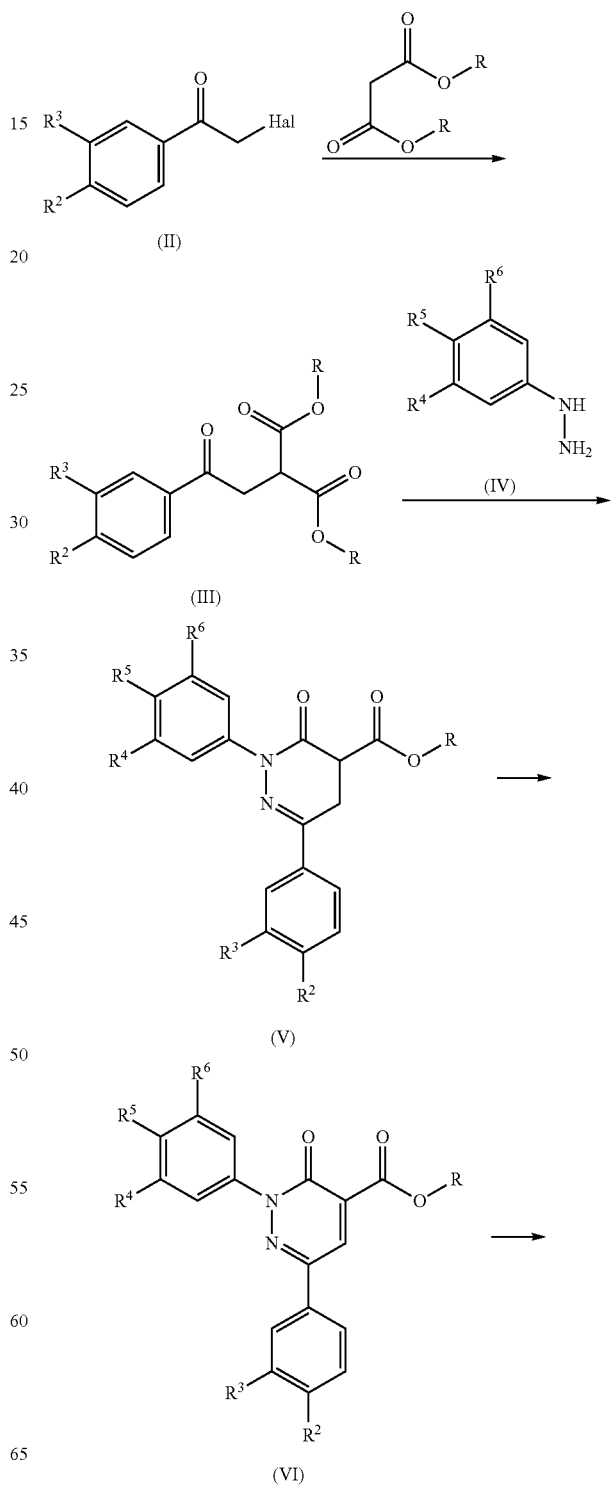

-continued

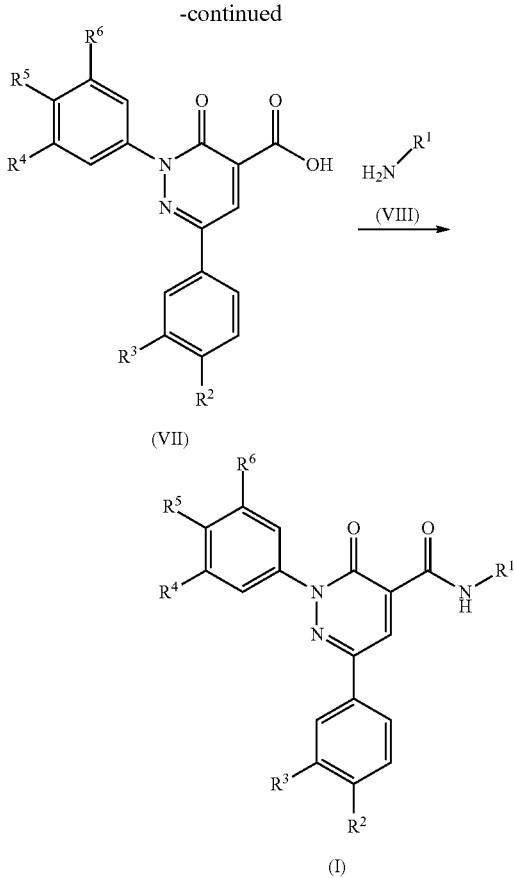

(VII)

(I)

Dihydropyrazinones according to formula (V) can be transferred to pyrazinones according to formula (VI). This can be accomplished by the use of a suitable reagents such as copper dichloride at elevated temperature (Bioorg. Med. Chem. Lett., 21, (2011), P. 6362 ff.; Synthesis, (2003), p. 436 ff.; J. Med. Chem., 46, (2003), p. 349 ff.).

The resulting pyrazinones according to formula (VI) with an ester functional group can be converted by methods known to the person skilled in the art, for example by basic hydrolysis with, for example, aqueous alkali metal hydroxides, or by acidic hydrolysis using, for example, hydrogen chloride in dioxane or trifluoroacetic acid, into the pyrazinone carboxylic acids (VII).

These can be converted by coupling with amines of the formula (VIII) in which $R^5$ and $R^6$ are as defined for the general formula (I). Coupling agents and methods for such syntheses of carboxamides from carboxylic acids and amines are known to the person skilled in the art. Examples which may be mentioned here include the use of HATU, HBTU, PyBOB or T3P with the addition of a suitable base. The conversion of the carboxylic acids to their amides is described in general terms in reference books such as "Compendium of Organic Synthetic Methods", volume I-VI (Wiley Interscience) or "The Practice of Peptide Synthesis", Bodansky (Springer Verlag).

The compounds are either commercially available or can be prepared according to procedures available from the public domain, as understandable to the person skilled in the art. Specific examples are described in the Experimental Section.

In accordance with a second aspect, the present invention covers methods of preparing compounds of general formula (I) as defined supra, said methods comprising the step of allowing an intermediate compound of general formula (VII):

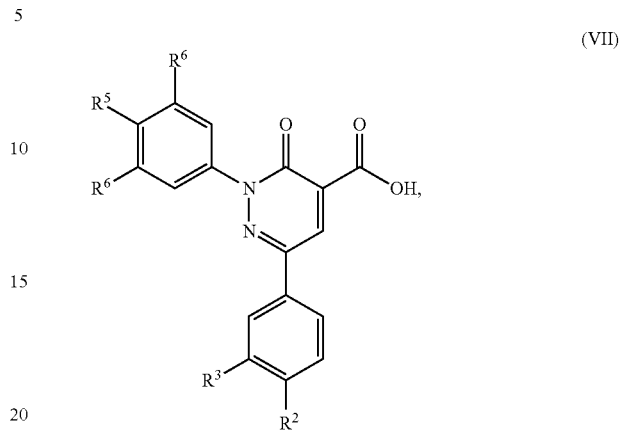

in which $R^2$ represents chloro, methyl, fluoromethyl, difluoromethyl, trifluoromethyl, methoxy or difluoromethoxy;

$R^3$ represents hydrogen or methyl;

$R^4$ represents hydrogen or halogen;

$R^5$ represents hydrogen;

$R^6$ represents hydrogen or halogen;

to react with a compound of general formula (VIII):

$$H_2N-R^1 \quad (VIII),$$

in which $R^1$ represents $C_2$-$C_6$-hydroxyalkyl, wherein said $C_2$-$C_6$-hydroxyalkyl groups are optionally substituted once with Wand optionally one to three times with halogen, in which $R^7$ is as defined supra.

thereby giving a compound of general formula (I):

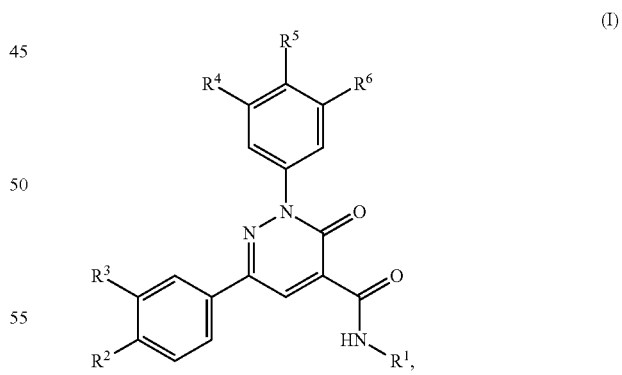

in which $R^1$, $R^2$, $R^3$, $R^4$, $R^5$ and $R^6$ are as defined supra.

The present invention covers methods of preparing compounds of the present invention of general formula (I), said methods comprising the steps as described in the Experimental Section herein.

In accordance with a third aspect, the present invention covers intermediate compounds which are useful for the preparation of the compounds of general formula (I), supra.

Particularly, the inventions covers the intermediate compounds of general formula (VII):

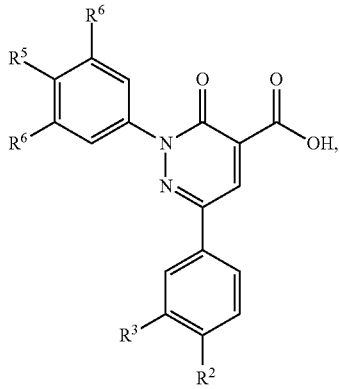

(VII)

in which
R² represents chloro, methyl, fluoromethyl, difluoromethyl, trifluoromethyl, methoxy or difluoromethoxy;
R³ represents hydrogen or methyl;
R⁴ represents hydrogen or halogen;
R⁵ represents hydrogen;
R⁶ represents hydrogen or halogen;

In accordance with a forth aspect, the present invention covers the use of said intermediate compounds for the preparation of a compound of general formula (I) as defined supra.

Particularly, the inventions covers the use of intermediate compounds of general formula (VII):

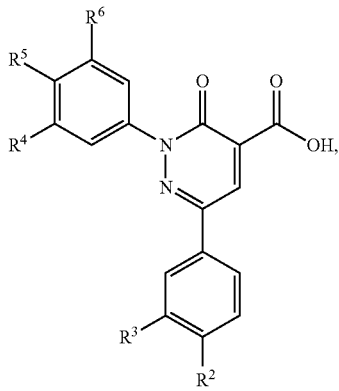

(VII)

in which
R² represents chloro, methyl, fluoromethyl, difluoromethyl, trifluoromethyl, methoxy or difluoromethoxy;
R³ represents hydrogen or methyl;
R⁴ represents hydrogen or halogen;
R⁵ represents hydrogen;
R⁶ represents hydrogen or halogen;
for the preparation of a compound of general formula (I) as defined supra.

The present invention covers the intermediate compounds which are disclosed in the Example Section of this text, infra.

The present invention covers any sub-combination within any embodiment or aspect of the present invention of intermediate compounds of general formula (VII), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit AHR and it is possible therefore that said compounds be used for the treatment or prophylaxis of diseases, preferably cancer or conditions with dysregulated immune responses or other disorders associated with aberrant AHR signaling, in humans and animals.

Disorders and conditions particularly suitable for treatment with an AHR inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers. Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms' tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

yield better efficacy in reducing the growth of a tumour or even eliminate the tumour as compared to administration of either agent alone, provide for the administration of lesser amounts of the administered chemotherapeutic agents, provide for a chemotherapeutic treatment that is well tolerated in the patient with fewer deleterious pharmacological complications than observed with single agent chemotherapies and certain other combined therapies, provide for treating a broader spectrum of different cancer types in mammals, especially humans, provide for a higher response rate among treated patients, provide for a longer survival time among treated patients compared to standard chemotherapy treatments, provide a longer time for tumour progression, and/or yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents. In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with: 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors. Compositions comprising a PD-1-L1 axis antagonist and an AHR antagonist and methods of using the same are provided herein. Data presented herein demonstrate that a combination of AHR inhibition and blockade of the PD-1-L1 axis reduces the growth of tumor cells in more than an additive manner. PD-1, along with its ligands PD-L1 and PD-L2, function as negative regulators of T cell activation. AHR suppresses immune cell function while increasing cancer cell proliferation and motility. PD-L1 is overexpressed in many cancers and overexpression of PD-1 often occurs concomitantly in tumor infiltrating T cells. Thus results in attenuation of T cell activation and evasion of immune surveillance, which contributes to impaired antitumor immune responses. (Keir M E et al. (2008) Annu. Rev. Immunol. 26:677). Simultaneously targeting both the PD-1-L1 axis and AHR enhances antitumor immune responses in more than an additive manner, leading to reduction of tumor growth that is unexpected. In some experiments, the resulting effect is greater than the expected or calculated additive effect of the individual components given separately. Thus, compositions comprising a PD-1-L1 axis antagonist and an AHR antagonist are surprisingly effective in enhancing an immune response and in the treatment of cancer.

In addition, the inventive compounds can also be used as a therapeutic in a variety of other disorders wherein AHR is involved such as, cardiovascular and lung diseases.

Accordingly, the compounds according to the invention are suitable for the treatment and/or prophylaxis in particular of cardiovascular, inflammatory and fibrotic disorders and of renal disorders, in particular of acute and chronic renal insufficiency, and also of acute and chronic renal failure.

Accordingly, the compounds according to the invention can be used in medicaments for the treatment and/or prophylaxis of cardiovascular, inflammatory and fibrotic disorders, renal disorders, in particular of acute and chronic renal insufficiency, and also of acute and chronic renal failure.

For the purpose of the present invention the term renal insufficiency comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoidnephrosis); membranous glomerulonephritis; focal segmental glomerulosclerosis (FSGS); membrane-proliferative glomerulonephritis; crescentic glomerulonephritis; mesangioproliferative glomerulonephritis (IgA nephritis, Berger's disease); post-infectious glomerulonephritis; secondary glomerulonephritides: diabetes mellitus, lupus erythematosus, amyloidosis, Goodpasture syndrome, Wegener granulomatosis, Henoch-Schönlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or aquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis. The present invention also comprises the use of the compounds according to the invention for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

The present invention also comprises the use of the compounds according to the invention for the treatment and/or prevention of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

The compounds according to the invention are further suitable for the treatment and/or prevention of polycystic kidney disease (PCKD) and of the syndrome of inappropriate ADH secretion (SIADH).

Furthermore, the compounds according to the invention are also suitable for the treatment and/or prophylaxis of metabolic syndrome, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In addition, the compounds according to the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system.

They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In addition, the compounds according to the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds according to the invention can also be used for treatment and/or prophylaxis of autoimmune diseases.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis). The compounds according to the invention are also suitable for controlling postoperative scarring, for example as a result of glaucoma operations.

The compounds according to the invention can also be used cosmetically for ageing and keratinized skin.

Moreover, the compounds according to the invention are suitable for treatment and/or prophylaxis of hepatitis, neoplasms, osteoporosis, glaucoma and gastroparesis.

The present invention further provides for the use of the compounds according to the invention for treatment and/or prophylaxis of disorders, especially the disorders mentioned above.

The present invention further provides for the use of the compounds according to the invention for the treatment and/or prophylaxis of chronic renal disorders, acute and chronic renal insufficiency, diabetic, inflammatory or hypertensive nephropaties, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention further provides a method for treatment and/or prophylaxis of disorders, in particular the disorders mentioned above, using an effective amount of at least one of the compounds according to the invention.

The present invention further provides a method for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

In another embodiment, the inventive compounds can also be used to treat or to prevent uterine fibroids (uterine leiomyoma or uterine myoma) in women.

Uterine fibroids are benign tumors of the myometrium, the smooth muscle layer of the uterus. Uterine fibroids grow slowly during a women's life, and their growth is dependent on the female sexual hormones estradiol and progesterone [Kawaguchi K et al. Immunohistochemical analysis of oestrogen receptors, progesterone receptors and Ki-67 in leiomyoma and myometrium during the menstrual cycle and pregnancy Virchows Arch A Pathol Anat Histopathol. 1991; 419(4):309-15], therefore the highest prevalence of uterine fibroids with approx. 70% and >80% in white and afroamerican women, respectively, is found from 35 years of age onwards to menopause, when they shrink due to reduced hormone levels [Baird D D et al. High cumulative incidence of uterine leiomyoma in black and white women: Ultrasound evidence Am J Obstet Gynecol. 2003 January; 188(1):100-7.]. Approx 30% and 45% of white and afro-american women, respectively, do show clinically relevant symptoms due to their fibroids, which are heavy menstrual bleeding and pain, which is related to the menstrual cycle [David M et al. Myoma-associated pain frequency and intensity: a retrospective evaluation of 1548 myoma patients. Eur J Obstet Gynecol Reprod Biol. 2016 April; 199:137-40]. Heavy menstrual bleeding in this respect is defined by a blood loss of more than 80 mL in a menstrual bleeding period [Fraser I S et al. The FIGO Recommendations on Terminologies and Definitions for Normal and Abnormal Uterine Bleeding, Semin Reprod Med 2011; 29(5): 383-390]. Submucosal position of the uterine fibroids, e.g. those located directly below the endometrium, seems to have an even more severe effect on uterine bleeding, which may result in anemia in affected women [Yang J H et al. Impact of submucous myoma on the severity of anemia. Fertil Steril. 2011 April; 95(5):1769-72]. Furthermore, uterine fibroids, due to their symptoms, do severly affect the quality of life of affected women [Downes E et al. The burden of uterine fibroids in five European countries. Eur J Obstet Gynecol Reprod Biol. 2010 September; 152(1):96-102].

So far, it is not understood how uterine fibroids do cause heavy menstrual bleeding. Disregulated genes in uterine fibroids, in comparison to normal myometrium, can give a hint to understand the underlying mechanisms. In published and internal studies, we found TDO2, Tryptophan 2,3-dioxygenase, being highly upregulated [Tsibris J C et al. Insights from gene arrays on the development and growth regulation of uterine leiomyomata. Fertil Steril. 2002 July; 78(1):114-21.]. TDO2 metabolizes the substrate L-Tryptophan to L-Kynurenine, which can be further metabolized to kynurenic acid. Both, L-Kynurenine and Kynurenic acid are physiological ligands and activators for the arylhydrocarbon receptor AHR [Opitz C A et al. An endogenous tumour-promoting ligand of the human aryl hydrocarbon receptor Nature. 2011 Oct. 5; 478(7368):197-203].

L-Kynurenine controls at least two physiological processes which are dysregulated in uterine fibroids. L-Kynurenine, synthesized by an upregulation of IDO (Indoleamine-2,3-dyoxygenase) or TDO2, and acting via the AHR receptor, suppresses the immune system and thus prevents immune cells from recognizing and clearing the tumor cells [Munn D H Blocking IDO activity to enhance anti-tumor immunity. Front Biosci (Elite Ed). 2012 Jan. 1; 4:734-45]. Furthermore, an upregulation of L-Kynurenine leads to a vasodilation of vessels, and thus can directly increase blood loss and bleeding [Wang Y et al. Kynurenine is an endothelium-derived relaxing factor produced during inflammation Nature Medicine 16, 279-285 (2010)].

In summary, the upregulation of L-Kynurenine through activation of its physiological receptor AHR seems to support uterine fibroid growth by local suppression of the immune system, and might cause heavy menstrual bleeding by vasodilation of endometrial vessels in proximity to the tumor.

Therefore, a systemic or local application of compounds from the present invention inhibiting activation of the AHR and thus blocking the effect of uterine fibroid derived L-Kynurenine presents a new and valid treatment option for uterine fibroids.

Compounds of the present invention can be utilized to inhibit, block, reduce or decrease AHR activation by exogenous and/or endogenous ligands for the reduction of tumour growth and the modulation of dysregulated immune responses e.g. to block immunosuppression and increase immune cell activation and infiltration in the context of cancer and cancer immunotherapy; This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating a variety of other disorders wherein AHR is involved such as, but not limited to, inflammation, vaccination for infection & cancer, viral infections, obesity and diet-induced obesity, adiposity, metabolic disorders, hepatic steatosis and uterine fibroids.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as liquid and solid tumours.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant AHR signaling. The pharmaceutical activity of the compounds according to the invention can be explained by their activity as AHR inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant AHR signaling, particularly liquid and solid tumours.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular cancer or conditions with dysregulated immune responses or other disorders associated with aberrant AHR signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant AHR signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant AHR signaling, particularly liquid and solid tumours.

In accordance with a further aspect, the present invention covers a method of treatment or prophylaxis of diseases, in particular cancer or conditions with dysregulated immune responses or other disorders associated with aberrant AHR signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example,) Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant AHR signalinggeneric name disorders, particularly liquid and solid tumours.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant AHR signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Experimental Section

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, qi=quintet, b=broad signal, m=multiplet. NMR signals: shift in ppm. Combinations of multiplicity could be e.g. dd=doublet from doublet.

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

Table 1: Abbreviations
ACN acetonitrile
AcOH acetic acid
BPR Back Pressure Regulator
$CDCl_3$ deuterochloroform
DAD diode array detector
DEA diethylamine
DMF N,N-dimethylformamide
DMSO-d6 deuterated dimethyl sulfoxide
DMSO dimethyl sulfoxide
Expl. example
HATU (7-aza-1H-benzotriazol-1-yl)-1,1,3,3-tetramethyluronium hexafluorophosphate
HBTU O-benzotriazole-N,N,N',N'-tetramethyluronium hexafluorophosphate
HPLC high-pressure liquid chromatography
KA kynurenic acid
LCMS liquid chromatography coupled with mass spectrometry
LPS lipopolysaccharide
mL milliliter
min. minute(s)
MTBE methyl tert-butyl ether
p pressure
PBMC peripheral blood mononuclear cells
PyBOB (benzotriazol-1-yl)oxytripyrrolidinophosphonium hexafluorophosphate
RP-HPLC reverse-phase high-pressure liquid chromatography
Rt retention time
rt room temperature
sat. saturated
T3P 2,4,6-tripropyl-1,3,5,2,4,6-trioxatriphosphorinane 2,4,6-trioxide
THF tetrahydrofuran
TFA trifluoroacetic acid
TLC thin layer chromatography
TNFa tumour necrosis factor alpha
μM micromolar
UPLC Ultra high performance chromatography The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

EXPERIMENTAL SECTION—INTERMEDIATES

Intermediate 1

Dimethyl [2-(4-methylphenyl)-2-oxoethyl]propanedioate

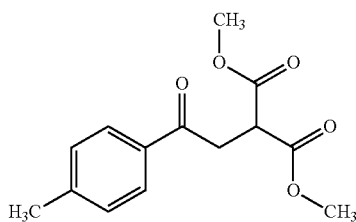

A solution of 49.6 g 2-bromo-1-(4-methylphenyl)ethanone in 300 mL of acetone was added dropwise at rt to a solution of 10 g dimethyl malonate in 120 mL of acetone. The reaction mixture was stirred at room temperature for 4 hours. Then, the solvent was removed in vacuo. The residue was purified by column chromatography (petroleum ether/ethyl acetate 10:1) to yield 10.3 g dimethyl [2-(4-methylphenyl)-2-oxoethyl]propanedioate.

$^1$H-NMR: (400 MHz, 25° C., DMSO-d6): δ=2.38 (s, 3H); 3.60 (d, 2H); 3.68 (s, 6H); 3.97 (t, 1H); 7.34 (d, 2H); 7.89 (d, 2H).

Intermediate 2

Methyl 2-(3-fluorophenyl)-6-(4-methylphenyl)-3-oxo-2,3,4,5-tetrahydropyridazine-4-carboxylate

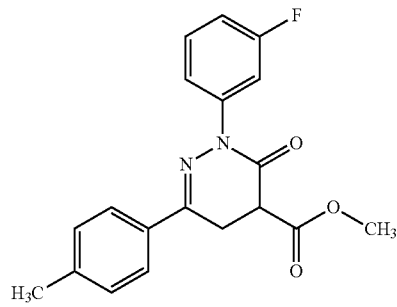

A mixture of 1.6 g intermediate 1 and 840 mg 3-(fluorophenyl)hydrazine in 50 mL of AcOH was stirred at 130° C. for 3 hours. Then. The solvent was removed in vacuo. The residue was purified by column chromatography (hexanes/ethyl acetate gradient with up to 40% ethyl acetate) to yield 1.8 g methyl 2-(3-fluorophenyl)-6-(4-methylphenyl)-3-oxo-2,3,4,5-tetrahydropyridazine-4-carboxylate.

$^1$H-NMR: (400 MHz, 25° C., DMSO-d6): δ=3.37-3.48 (m, 2H); 3.70 (s, 3H); 4.04 (dd, 1H); 7.16 (ddt, 1H); 7.28 (d, 2H); 7.39-7.52 (m, 3H); 7.72-7.78 (m, 2H).

Intermediate 3

Methyl 2-(3-fluorophenyl)-6-(4-methylphenyl)-3-oxo-2,3-dihydropyridazine-4-carboxylate

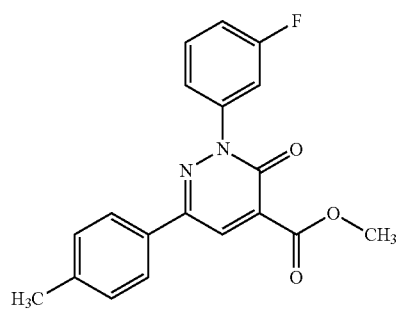

A mixture of 1.8 g intermediate 2 and 2.1 g copper(II) chloride in 75 mL of acetonitrile was stirred at 90° C. for 2 hours. After evaporation in vacuo, the residue was purified by column chromatography (hexanes/ethyl acetate gradient with up to 100% ethyl acetate) to yield 1.6 g methyl 2-(3-fluorophenyl)-6-(4-methylphenyl)-3-oxo-2,3-dihydropyridazine-4-carboxylate.

$^1$H-NMR: (400 MHz, 25° C., DMSO-d6): δ=2.36 (s, 3H); 3.88 (s, 3H); 7.29-7.38 (m, 3H); 7.52-7.63 (m, 3H); 7.84 (d, 2H); 8.46 (s, 1H).

Intermediate 4

2-(3-Fluorophenyl)-6-(4-methylphenyl)-3-oxo-2,3-dihydropyridazine-4-carboxylic acid

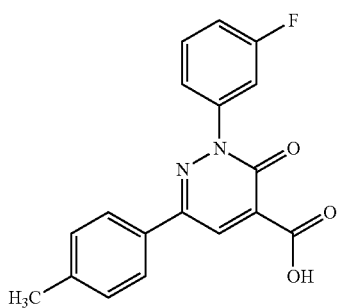 [SMILES: Cc1ccc(-c2cc(C(=O)O)c(=O)n(-c3cccc(F)c3)n2)cc1]

A mixture of 1.6 g intermediate 3 and 340 mg lithium hydroxide in 50 mL acetonitrile and 3 mL water was stirred at room temperature for 3 hours. Then the PH value was adjusted to 5-6 with hydrochloric acid (10%). The solids were collected by filtration, washed three times with 20 mL water and dried in an oven to 1.3 g 2-(3-fluorophenyl)-6-(4-methylphenyl)-3-oxo-2,3-dihydropyridazine-4-carboxylic acid.

$^1$H-NMR: (400 MHz, 25° C., DMSO-d6): δ=2.35 (s, 3H); 7.27-7.35 (m, 3H); 7.48-7.61 (m, 3H); 7.80 (d, 2H); 8.04 (s, 1H).

Intermediate 5

Dimethyl [2-(4-chlorophenyl)-2-oxoethyl]propanedioate

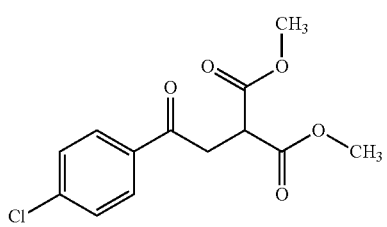 [SMILES: COC(=O)C(CC(=O)c1ccc(Cl)cc1)C(=O)OC]

A mixture of 15.0 g 2-bromo-1-(4-chlorophenyl)ethanone, 59 mL dimethyl malonate and 13.3 g potassium carbonate in 600 mL acetone was stirred at rt for 14 hours. After full conversion (TLC) the reaction mixture was poured into water, the organic phase was separated and washed with water and brine. After evaporation of the solvent in vacuo, the residue was purified by column chromatography (hexanes/ethyl acetate gradient to 50% ethyl acetate) to yield 17.0 g dimethyl [2-(4-chlorophenyl)-2-oxoethyl]propanedioate.

$^1$H-NMR (400 MHz, DMSO-d6) δ [ppm]=3.63 (d, 2H); 3.68 (s, 6H); 3.97 (t, 1H); 7.58-7.64 (m, 2H); 7.98-8.04 (m, 2H).

Intermediate 6

Methyl 6-(4-chlorophenyl)-3-oxo-2-phenyl-2,3,4,5-tetrahydropyridazine-4-carboxylate

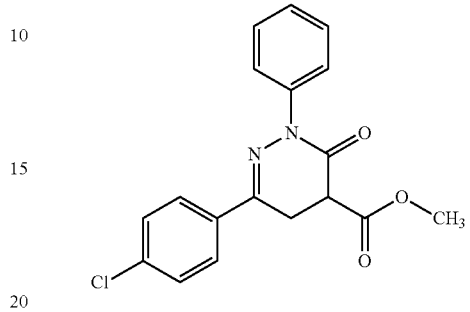

A mixture of 1.1 g intermediate 5 and 418 mg phenylhydrazine in 100 mL of AcOH was stirred at 130° C. for 3 hours. Then. The solvent was removed in vacuo. The residue was purified by column chromatography (petroleum ether/ethyl acetate 2:1) to yield 1.2 g methyl 6-(4-chlorophenyl)-3-oxo-2-phenyl-2,3,4,5-tetrahydropyridazine-4-carboxylate.

$^1$H-NMR (300 MHz, DMSO-d6) δ=3.42-3.46 (m, 2H), 3.71 (s, 3H), 4.03-4.09 (m, 1H), 7.33-7.35 (m, 1H), 7.43-7.55 (m, 6H), 7.84-7.87 (d, 2H).

Intermediate 7

Methyl 6-(4-chlorophenyl)-3-oxo-2-phenyl-2,3-dihydropyridazine-4-carboxylate

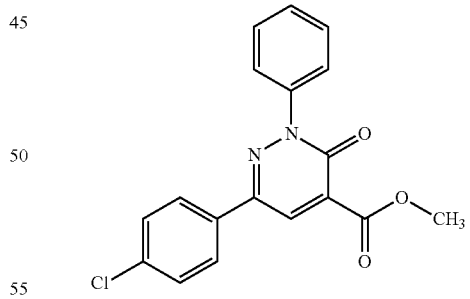

A mixture of 1.2 g Intermediate 6 and 0.94 g copper(II) chloride in 70 mL of acetonitrile was stirred at 90° C. for 2 hours. After evaporation in vacuo, the residue was purified by column chromatography (petroleum ether/ethyl acetate 2:1) to yield 1.1 g methyl 6-(4-chlorophenyl)-3-oxo-2-phenyl-2,3-dihydropyridazine-4-carboxylate.

$^1$H-NMR (400 MHz, 25° C., DMSO-d6): δ=3.86 (s, 3H), 7.51-7.56 (m, 5H), 7.62-7.65 (m, 2H), 7.94-7.96 (d, 2H), 8.48 (s, 1H).

Intermediate 8

6-(4-Chlorophenyl)-3-oxo-2-phenyl-2,3-dihydropyridazine-4-carboxylic acid

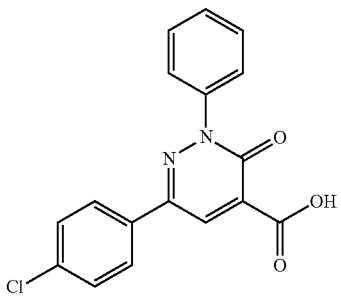 [SMILES: O=C(O)c1cc(-c2ccc(Cl)cc2)nn(-c2ccccc2)c1=O]

A mixture of 1.1 g intermediate 7 in 150 mL of Acetonitrile was treated with 0.2 g Lithium hydroxide, dissolved in 3 mL of water. The reaction mixture was stirred at room temperature for 3 hours. Then the PH value was adjusted to 5-6 with hydrochloric acid (10%). The solids were collected by filtration, washed three times with water and dried in an oven to yield 1.0 g 6-(4-Chlorophenyl)-3-oxo-2-phenyl-2,3-dihydropyridazine-4-carboxylic acid.

$^1$H-NMR (300 MHz, 25° C., Methanol-d4): δ=7.48-7.62 (m, 5H), 7.65-7.73 (m, 2H), 7.90-8.01 (d, 2H), 8.64 (s, 1H)

Intermediate 9

6-(4-Chlorophenyl)-3-oxo-2-phenyl-2,3-dihydropyridazine-4-carbonyl chloride

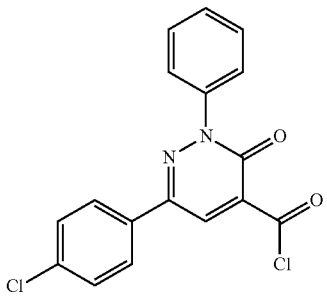 [SMILES: O=C(Cl)c1cc(-c2ccc(Cl)cc2)nn(-c2ccccc2)c1=O]

174 mg oxalylchloride were slowly added to a solution of 300 mg intermediate 8 in 10 mL of dichloromethane and 33 mg N,N-dimethylformamide. The reaction mixture was stirred at room temperature for 1 h. The mixture was evaporated to dryness to give 420 mg crude 6-(4-Chlorophenyl)-3-oxo-2-phenyl-2,3-dihydropyridazine-4-carbonyl chloride which was used into next step directly without further purification.

Intermediate 10

Dimethyl [2-(3,4-dimethyl phenyl)-2-oxoethyl]propanedidate

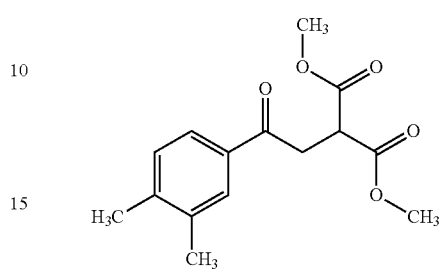

A mixture of 4.0 g 2-bromo-1-(3,4-dimethylphenyl)ethanone, 18.0 g dimethyl malonate and 3.5 g potassium carbonate in 200 mL of acetonewas stirred at room temperature for 2 hours with an inert atmosphere of nitrogen. Then the reaction was quenched by water, and the mixture was extracted with ethylacetate. The organic phase was dried over sodium sulfate, filtered and evaporated to dryness. The residue was purified by column chromatography (petroleum ether/ethyl acetate 4:1) to yield 4.4 g dimethyl [2-(3,4-dimethylphenyl)-2-oxoethyl]propanedioate.

$^1$H-NMR (300 MHz, 25° C., DMSO-d6): δ=2.28 (s, 6H), 3.51-3.56 (m, 1H), 3.56-3.58 (d, 2H), 3.60-3.66 (s, 6H), 7.23-7.30 (d, 1H), 7.68-7.71 (d, 1H), 7.76 (s, 1H).

Intermediate 11

Methyl 6-(3,4-di methyl phenyl)-2-(3-fluorophenyl)-3-oxo-2,3,4,5-tetrahydropyridazine-4-carboxylate

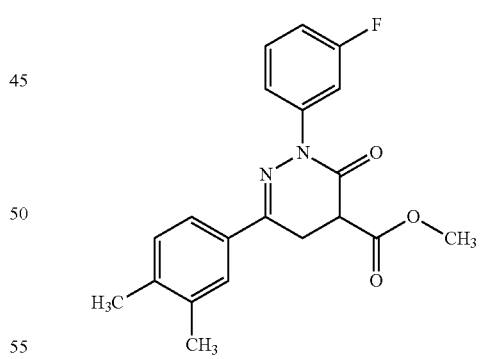

A mixture of 3.2 g intermediate 10 and 1.45 g (3-fluorophenyl)hydrazine phenylhydrazine in 100 mL of AcOH was stirred at 130° C. for 3 hours. Then. The solvent was removed in vacuo. The residue was purified by column chromatography (petroleum ether/ethyl acetate 4:1) to yield 2.7 g methyl 6-(3,4-dimethylphenyl)-2-(3-fluorophenyl)-3-oxo-2,3,4,5-tetrahydropyridazine-4-carboxylate.

$^1$H-NMR (300 MHz, DMSO-d6): δ=2.26 (s, 3H), 2.27 (s, 3H), 3.37-3.43 (d, 2H), 3.70 (s, 3H), 3.97-4.08 (t, 1H), 7.10-7.25 (m, 2H), 7.38-7.59 (m, 4H), 7.62 (s, 1H).

Intermediate 12

Methyl 6-(3,4-dimethylphenyl)-2-(3-fluorophenyl)-3-oxo-2,3-dihydropyridazine-4-carboxylate

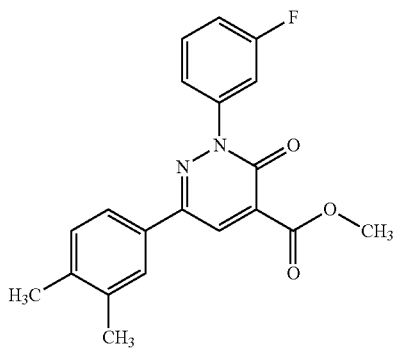

A mixture of 2.7 g Intermediate 11 and 2.05 g copper(II) chloride in 63 mL of acetonitrile was stirred at 90° C. for 2 hours. After evaporation in vacuo, the residue was purified by column chromatography (petroleum ether/ethyl acetate 3:1) to yield 2.4 g methyl 6-(3,4-dimethylphenyl)-2-(3-fluorophenyl)-3-oxo-2,3-dihydropyridazine-4-carboxylate.

$^1$H-NMR (300 MHz, DMSO-d6): δ=2.25 (s, 3H), 2.27 (s, 3H), 3.87 (s, 3H), 7.22-7.37 (m, 2H), 7.50-7.63 (m, 4H), 7.70 (s, 1H), 8.42 (s, 1H).

Intermediate 13

6-(3,4-Di methylphenyl)-2-(3-fluorophenyl)-3-oxo-2,3-dihydropyridazine-4-carboxylic acid

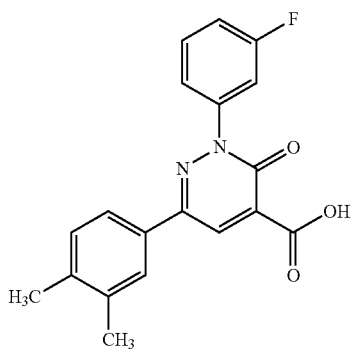 [SMILES: Cc1ccc(-c2cc(C(=O)O)c(=O)n(-c3cccc(F)c3)n2)cc1C]

A mixture of 2.4 g intermediate 12 in 41 mL of acetonitrile was treated with 0.49 g Lithium hydroxide, dissolved in 3 mL of water. The reaction mixture was stirred at room temperature for 3 hours. Then the PH value was adjusted to 5-6 with hydrochloric acid (10%). The solids were collected by filtration, washed three times with water and dried in an oven to yield 2.1 g 6-(3,4-Dimethylphenyl)-2-(3-fluorophenyl)-3-oxo-2,3-dihydropyridazine-4-carboxylic acid.

$^1$H-NMR (300 MHz, 25° C., Methanol-d4): δ=7.25-7.31 (m, 1H), 7.52-7.62 (m, 5H), 7.95-7.98 (d, 2H), 8.69 (s, 1H).

Intermediate 14

6-(3,4-Dimethylphenyl)-2-(3-fluorophenyl)-3-oxo-2,3-dihydropyridazine-4-carbonyl chloride

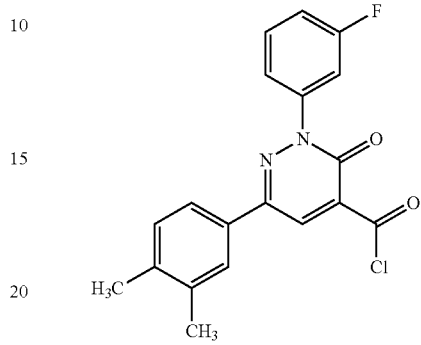

338 mg oxalylchloride were slowly added to a solution of 600 mg intermediate 13 in 30 mL of dichloromethane and 0.04 mg N,N-dimethylformamide. The reaction mixture was stirred at room temperature for 1 h. The mixture was evaporated to dryness to give 610 mg crude 6-(3,4-dimethylphenyl)-2-(3-fluorophenyl)-3-oxo-2,3-dihydropyridazine-4-carbonyl chloride which was used into next step directly without further purification.

Intermediate 15

Methyl 6-(4-chlorophenyl)-2-(3-fluorophenyl)-3-oxo-2,3,4,5-tetrahydropyridazine-4-carboxylate

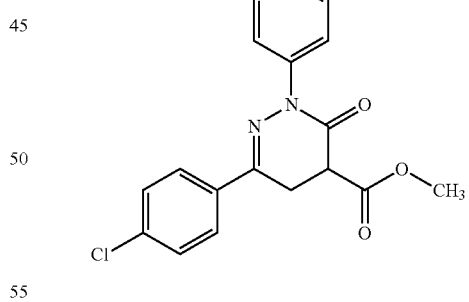

A mixture of 5.0 g intermediate 5 and 2.44 g (3-fluorophenyl)hydrazine in 100 mL of AcOH was stirred at 130° C. for 5 hours. Then. The solvent was removed in vacuo. The residue was purified by column chromatography (hexanes/ethyl acetate gradient with uo to 40% ethyl acetate) to yield 3.2 g methyl 6-(4-chlorophenyl)-2-(3-fluorophenyl)-3-oxo-2,3,4,5-tetrahydropyridazine-4-carboxylate.

$^1$H-NMR (400 MHz, 25° C., DMSO-d6): δ=3.36-3.53 (m, 2H); 3.71 (s, 3H); 4.07 (dd, 1H); 7.17 (ddt, 1H); 7.38-7.57 (m, 5H); 7.85-7.90 (m, 2H).

Intermediate 16

Methyl 6-(4-chlorophenyl)-2-(3-fluorophenyl)-3-oxo-2,3-dihydropyridazine-4-carboxylate

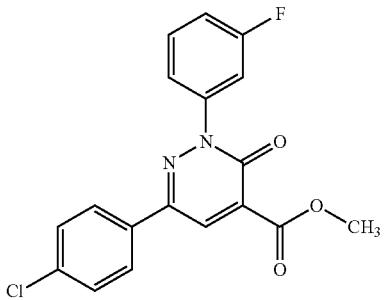 [SMILES: COC(=O)c1cc(-c2ccc(Cl)cc2)nn(-c2cccc(F)c2)c1=O]

A mixture of 3.2 g intermediate 15 and 3.58 g copper(II) chloride in 100 mL of acetonitrile was stirred at 90° C. for 3 hours. After evaporation in vacuo, the residue was purified by column chromatography (hexanes/ethyl acetate gradient with uo to 100% ethyl acetate) to yield 1.9 g methyl 6-(4-chlorophenyl)-2-(3-fluorophenyl)-3-oxo-2,3-dihydropyridazine-4-carboxylate.

$^1$H-NMR (400 MHz, 25° C., DMSO-d6): δ=3.88 (s, 3H); 7.35 (ddt, 1H); 7.52-7.64 (m, 5H); 7.95-8.01 (m, 2H); 8.51 (s, 1H).

Intermediate 17

6-(4-Chlorophenyl)-2-(3-fluorophenyl)-3-oxo-2,3-dihydropyridazine-4-carboxylic acid

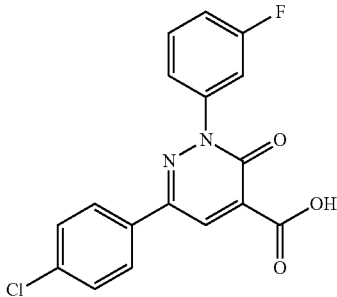

A mixture of 1.9 g intermediate 16 in 60 mL of acetonitrile was treated with 0.38 g lithium hydroxide, dissolved in 4.3 mL of water. The reaction mixture was stirred at room temperature for 5 hours. Then the PH value was adjusted to 6 with hydrochloric acid (10%). The solids were collected by filtration, washed three times with water and dried in an oven to yield 1.5 g 6-(4-Chlorophenyl)-2-(3-fluorophenyl)-3-oxo-2,3-dihydropyridazine-4-carboxylic acid.

$^1$H-NMR (300 MHz, 25° C., Methanol-d4): δ=7.32 (ddt, 1H); 7.49-7.62 (m, 5H); 7.92-7.97 (m, 2H); 8.02 (s, 1H).

Intermediate 18

Methyl 2-(3-chlorophenyl)-6-(4-chlorophenyl)-3-oxo-2,3,4,5-tetrahydropyridazine-4-carboxylate

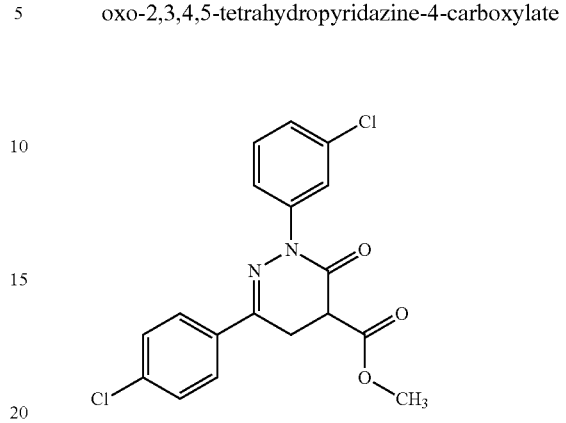

A mixture of 1.0 g intermediate 5 and 501 mg (3-chlorophenyl)hydrazine in 50 mL of AcOH was stirred at 130° C. for 3 hours. Then. The solvent was removed in vacuo. The residue was purified by column chromatography (petroleum ether/ethyl acetate gradient with uo to 25% ethyl acetate) to yield 850 mg methyl 2-(3-chlorophenyl)-6-(4-chlorophenyl)-3-oxo-2,3,4,5-tetrahydropyridazine-4-carboxylate.

$^1$H-NMR (400 MHz, 25° C., DMSO-d6): δ=3.40-3.47 (d, 2H), 3.71 (s, 3H), 4.02-4.11 (t, 1H), 7.36-7.56 (m, 5H), 7.62 (s, 1H), 7.84-7.89 (d, 2H).

Intermediate 19

Methyl 2-(3-chlorophenyl)-6-(4-chlorophenyl)-3-oxo-2,3-dihydropyridazine-4-carboxylate

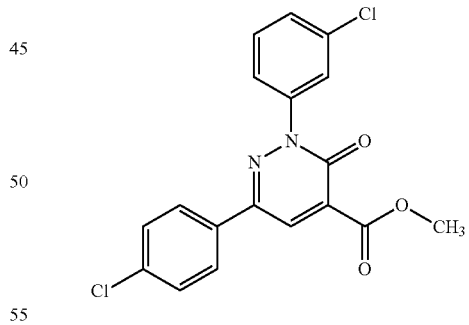

A mixture of 850 mg intermediate 18 and 606 mg copper(II) chloride in 75 mL of acetonitrile was stirred at 90° C. for 2 hours. After evaporation in vacuo, the residue was purified by column chromatography (petroleum ether/ethyl acetate gradient with uo to 25% ethyl acetate) to yield 760 mg methyl 2-(3-chlorophenyl)-6-(4-chlorophenyl)-3-oxo-2,3-dihydropyridazine-4-carboxylate.

$^1$H-NMR (400 MHz, 25° C., DMSO-d6): δ=3.88 (s, 3H), 7.51-7.70 (m, 5H), 7.72 (s, 1H), 7.79-7.82 (d, 2H), 8.50 (s, 1H).

Intermediate 20

2-(3-Chlorophenyl)-6-(4-chlorophenyl)-3-oxo-2,3-dihydropyridazine-4-carboxylic acid

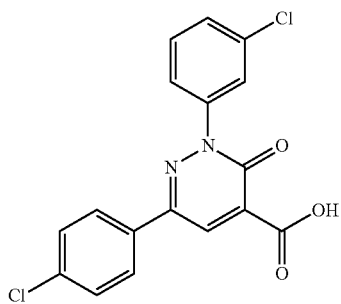 [SMILES: O=C(O)c1cc(-c2ccc(Cl)cc2)nn(-c2cccc(F)c2)c1=O]

A mixture of 760 mg intermediate 19 in 50 mL of acetonitrile was treated with 146 mg lithium hydroxide, dissolved in 3 mL of water. The reaction mixture was stirred at room temperature for 3 hours. Then the PH value was adjusted to 5-6 with hydrochloric acid (10%). The solids were collected by filtration, washed three times with water and dried in an oven to yield 650 mg 2-(3-Chlorophenyl)-6-(4-chlorophenyl)-3-oxo-2,3-dihydropyridazine-4-carboxylic acid.

$^{1}$H-NMR (300 MHz, 25° C., Methanol-d4): δ=7.49-7.62 (m, 3H); 7.63-7.74 (m, 1H); 7.77-7.83 (m, 1H); 7.97 (d, 2H); 8.19 (s, 1H).

Intermediate 21

Methyl 6-(4-methyl phenyl)-3-oxo-2-phenyl-2,3,4,5-tetrahydropyridazine-4-carboxylate

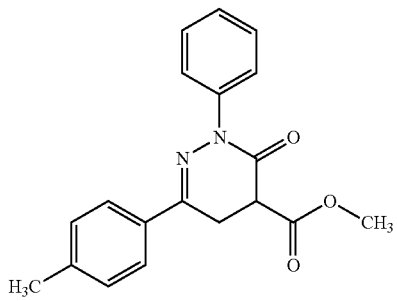

A mixture of 1.6 g intermediate 1 and 720 mg phenylhydrazine in 53 mL of AcOH was stirred at 130° C. for 3 hours. Then. The solvent was removed in vacuo. The residue was purified by column chromatography (petroleum ether/ethyl acetate gradient with up to 30% ethyl acetate) to yield 1.7 g methyl 6-(4-methylphenyl)-3-oxo-2-phenyl-2,3,4,5-tetrahydropyridazine-4-carboxylate.

$^{1}$H-NMR (300 MHz, 25° C., DMSO-d6): δ=2.34 (s, 3H), 3.36-3.43 (d, 2H), 3.70 (s, 3H), 3.98-4.05 (t, 1H), 7.25-7.36 (m, 3H), 7.40-7.55 (m, 4H), 7.70-7.75 (d, 2H).

Intermediate 22

Methyl 6-(4-methyl phenyl)-3-oxo-2-phenyl-2,3-dihydropyridazine-4-carboxylate

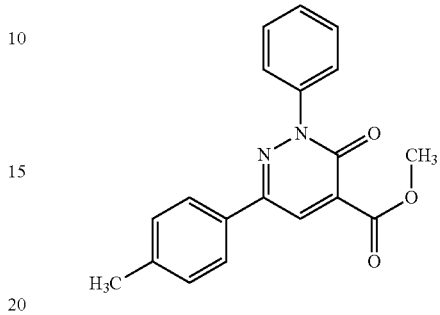

A mixture of 1.7 g intermediate 21 and 2.13 g copper(II) chloride in 75 mL of acetonitrile was stirred at 90° C. for 2 hours. After evaporation in vacuo, the residue was purified by column chromatography (petroleum ether/ethyl acetate gradient with uo to 55% ethyl acetate) to yield 1.5 g methyl 6-(4-methylphenyl)-3-oxo-2-phenyl-2,3-dihydropyridazine-4-carboxylate.

$^{1}$H-NMR (400 MHz, 25° C., DMSO-d6): δ=2.35 (s, 3H), 3.87 (s, 3H), 7.29-7.34 (m, 3H), 7.54-7.60 (m, 2H), 7.56-7.66 (d, 2H), 7.80-7.84 (d, 2H), 8.44 (s, 1H).

Intermediate 23

6-(4-Methylphenyl)-3-oxo-2-phenyl-2,3-dihydropyridazine-4-carboxylic acid

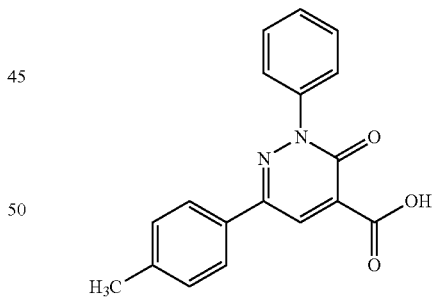

A mixture of 1.5 g intermediate 22 in 50 mL of Acetonitrile was treated with 336 mg Lithium hydroxide, dissolved in 3 mL of water. The reaction mixture was stirred at room temperature for 3 hours. Then the PH value was adjusted to 5-6 with hydrochloric acid (10%). The solids were collected by filtration, washed three times with water and dried in an oven to yield 1.2 g 6-(4-methylphenyl)-3-oxo-2-phenyl-2,3-dihydropyridazine-4-carboxylic acid.

$^{1}$H-NMR (300 MHz, DMSO-d6): δ=2.35 (s, 3H), 7.29-7.32 (m, 2H), 7.48-7.58 (m, 3H), 7.64-7.67 (m, 2H), 7.83-7.85 (d, 2H), 8.39 (s, 1H), 13.83 (s, 1H).

Intermediate 24

Methyl 6-(4-chlorophenyl)-2-(3,5-difluorophenyl)-3-oxo-2,3,4,5-tetrahydropyridazine-4-carboxylate

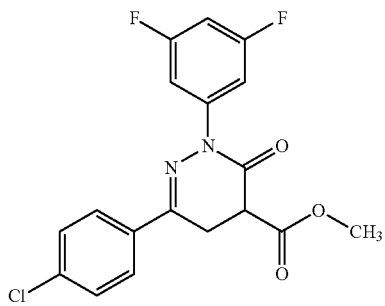 [SMILES: COC(=O)C1CC(c2ccc(Cl)cc2)=NN(c2cc(F)cc(F)c2)C1=O]

A mixture of 2.0 g intermediate 5 and 1.11 g (3,5-difluorophenyl)hydrazine in 60 mL acetic acid was stirred at 130° C. for 5 hours. Then. The solvent was removed in vacuo. The residue was purified by column chromatography (hexanes/ethyl acetate gradient with up to 40% ethyl acetate) to yield 1.4 g methyl 6-(4-chlorophenyl)-2-(3,5-difluorophenyl)-3-oxo-2,3,4,5-tetrahydropyridazine-4-carboxylate.

$^1$H-NMR: (400 MHz, 25° C., DMSO-d6): δ=3.37-3.50 (m, 2H); 3.71 (s, 3H); 4.10 (dd, 1H); 7.22 (tt, 1H); 7.35-7.40 (m, 2H); 7.53-7.57 (m, 2H); 7.89-7.92 (m, 2H).

Intermediate 25

Methyl 6-(4-chlorophenyl)-2-(3,5-difluorophenyl)-3-oxo-2,3-dihydropyridazine-4-carboxylate

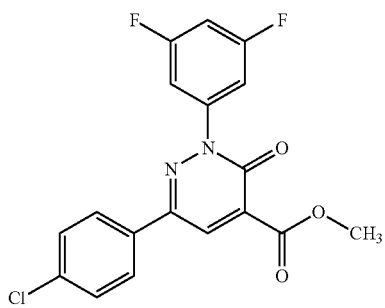 [SMILES: COC(=O)c1cc(-c2ccc(Cl)cc2)nn(-c2cc(F)cc(F)c2)c1=O]

A mixture of 1.4 g intermediate 24 and 1.49 g copper(II) chloride in 30 mL of acetonitrile was stirred at 90° C. for 3 hours. After evaporation in vacuo, the residue was purified by column chromatography (hexanes/ethyl acetate gradient with uo to 90% ethyl acetate) to yield 880 mg methyl 6-(4-chlorophenyl)-2-(3,5-difluorophenyl)-3-oxo-2,3-dihydropyridazine-4-carboxylate.

UPLC-MS: Rt=1.39 min (M$^+$+1=377/379)

Instrument: Waters Acquity UPLC-MS SQD; column: Acquity UPLC BEH C18 1.7 μm, 50×2.1 mm; eluent A: water+0.1% Vol. formic acid, eluent B: acetonitril; gradient: 0-1.6 min 1-99% B, 1.6-2.0 min 99% B; flow 0.8 mL/min; temperature: 60° C.; injection: 2 μL; DAD scan: 210-400 nm.

Intermediate 26

6-(4-Chlorophenyl)-2-(3,5-difluorophenyl)-3-oxo-2,3-dihydropyridazine-4-carboxylic acid

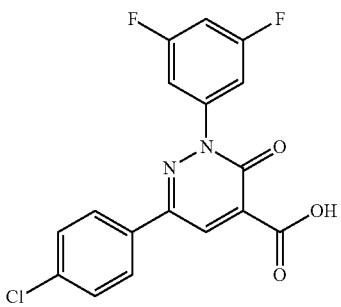 [SMILES: O=C(O)c1cc(-c2ccc(Cl)cc2)nn(-c2cc(F)cc(F)c2)c1=O]

A mixture of 880 mg intermediate 25 in 30 mL of Acetonitrile was treated with 168 mg Lithium hydroxide, dissolved in 4.3 mL of water. The reaction mixture was stirred at room temperature for 5 hours. Then the PH value was adjusted to 6 with hydrochloric acid (10%). The solids were collected by filtration, washed three times with water and dried in an oven to yield 660 mg 6-(4-Chlorophenyl)-2-(3,5-difluorophenyl)-3-oxo-2,3-dihydropyridazine-4-carboxylic acid.

$^1$H-NMR: (300 MHz, 25° C., DMSO-d6): δ=7.39 (tt, 1H); 7.49-7.57 (m, 4H); 7.94-7.98 (m, 2H); 8.01 (s, 1H).

Intermediate 27

Methyl 2-(3,5-difluorophenyl)-6-(4-methyl phenyl)-3-oxo-2,3,4,5-tetrahydropyridazine-4-carboxylate

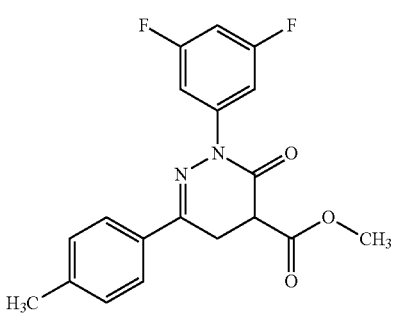

A mixture of 2.0 g intermediate 1 and 1.2 g (3,5-difluorophenyl)hydrazine in 70 mL acetic acid was stirred at 130° C. for 5 hours. Then. The solvent was removed in vacuo. The residue was purified by column chromatography (hexanes/ethyl acetate gradient with up to 40% ethyl acetate) to yield 1.5 g methyl 2-(3,5-difluorophenyl)-6-(4-methylphenyl)-3-oxo-2,3,4,5-tetrahydropyridazine-4-carboxylate.

UPLC-MS: Rt=1.39 min (M$^+$+1=359)

Instrument: Waters Acquity UPLC-MS SQD; column: Acquity UPLC BEH C18 1.7 μm, 50×2.1 mm; eluent A: water+0.1% Vol. formic acid, eluent B: acetonitril; gradient: 0-1.6 min 1-99% B, 1.6-2.0 min 99% B; flow 0.8 mL/min; temperature: 60° C.; injection: 2 μL; DAD scan: 210-400 nm.

Intermediate 28

Methyl 2-(3,5-difluorophenyl)-6-(4-methylphenyl)-3-oxo-2,3-dihydropyridazine-4-carboxylate

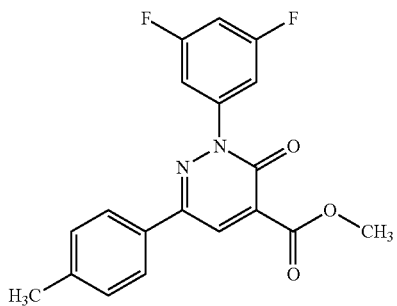

A mixture of 1.5 g intermediate 27 and 1.69 g copper(II) chloride in 40 mL of acetonitrile was stirred at 90° C. for 3 hours. After evaporation in vacuo, the residue was purified by column chromatography (hexanes/ethyl acetate gradient with uo to 100% ethyl acetate) to yield 700 mg methyl 2-(3,5-difluorophenyl)-6-(4-methylphenyl)-3-oxo-2,3-dihydropyridazine-4-carboxylate.

UPLC-MS: Rt=1.37 min (M$^+$+1=357)

Instrument: Waters Acquity UPLC-MS SQD; column: Acquity UPLC BEH C18 1.7 μm, 50×2.1 mm; eluent A: water+0.1% Vol. formic acid, eluent B: acetonitril; gradient: 0-1.6 min 1-99% B, 1.6-2.0 min 99% B; flow 0.8 mL/min; temperature: 60° C.; injection: 2 μL; DAD scan: 210-400 nm.

Intermediate 29

2-(3,5-Difluorophenyl)-6-(4-methylphenyl)-3-oxo-2,3-dihydropyridazine-4-carboxylic acid

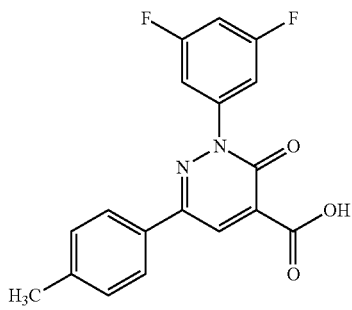 [SMILES: Cc1ccc(-c2cc(C(=O)O)c(=O)n(-c3cc(F)cc(F)c3)n2)cc1]

A mixture of 700 mg intermediate 28 in 20 mL of Acetonitrile was treated with 141 mg Lithium hydroxide, dissolved in 1.5 mL of water. The reaction mixture was stirred at room temperature for 5 hours. Then the PH value was adjusted to 5-6 with hydrochloric acid (10%). The solids were collected by filtration, washed three times with water and dried in an oven to yield 360 mg 2-(3,5-Difluorophenyl)-6-(4-methylphenyl)-3-oxo-2,3-dihydropyridazine-4-carboxylic acid.

$^1$H-NMR: (300 MHz, 25° C., Methanol-d4): δ=7.30 (d, 2H); 7.39 (tt, 1H); 7.51 (dd, 2H); 7.81 (d, 2H); 7.97 (s, 1H).

Intermediate 30

Dimethyl{2-[4-(difluoromethyl)phenyl]-2-oxoethyl}propanedioate

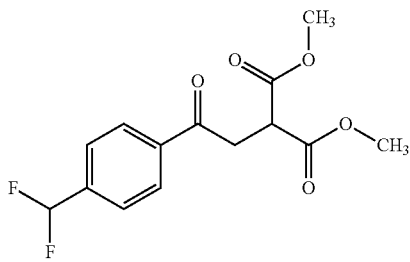 [SMILES: COC(=O)C(CC(=O)c1ccc(C(F)F)cc1)C(=O)OC]

A mixture of 2.5 g 2-bromo-1-[4-(difluoromethyl)phenyl]ethanone (CAS 1227004-73-0), 4.6 mL dimethyl malonate and 2.1 g potassium carbonate in 70 mL acetone was stirred at rt for 14 hours. After full conversion (TLC) the reaction mixture was poured into water and the acetone was evaporated under reduced pressure. The resulting solution was extracted with ethyl acetate 3 times, the combined organic phases were washed with water and brine and the solvent was evaporation in vacuo. The residue was purified by column chromatography (hexanes/ethyl acetate gradient to 40% ethyl acetate) to yield 1.45 g dimethyl{2-[4-(difluoromethyl)phenyl]-2-oxoethyl}propanedioate.

$^1$H-NMR (400 MHz, DMSO-d6) δ [ppm]=3.64-3.70 (m, 8H); 4.00 (t, 1H); 7.15 (t, 1H); 7.74 (d, 2H); 8.12 (d, 2H).

Intermediate 31

Methyl 6-[4-(difluoromethyl)phenyl]-2-(3-fluorophenyl)-3-oxo-2,3,4,5-tetrahydropyridazine-4-carboxylate

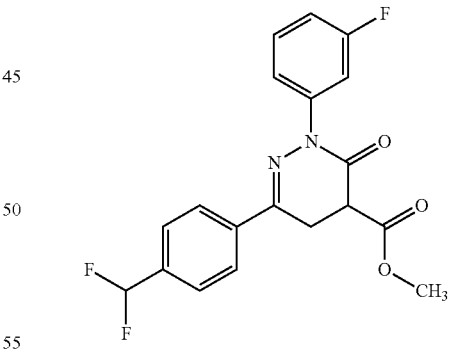

A mixture of 750 mg intermediate 30 and 542 mg (3-fluorophenyl)hydrazine in 20 mL acetic acid was stirred at 100° C. for 5 hours. Then. The solvent was removed in vacuo. The residue was purified by column chromatography (hexanes/ethyl acetate gradient with up to 50% ethyl acetate) to yield 655 mg methyl 6-[4-(difluoromethyl)phenyl]-2-(3-fluorophenyl)-3-oxo-2,3,4,5-tetrahydropyridazine-4-carboxylate.

$^1$H-NMR (400 MHz, DMSO-d6) δ [ppm]=3.41-3.54 (m, 2H); 3.71 (s, 3H); 4.10 (dd, 1H); 7.10 (t, 1H); 7.18 (ddt, 1H); 7.39-7.45 (m, 2H); 7.46-7.54 (m, 1H); 7.67 (d, 2H); 7.99 (d, 2H).

Intermediate 32

Methyl 6-[4-(difluoromethyl)phenyl]-2-(3-fluorophenyl)-3-oxo-2,3-dihydropyridazine-4-carboxylate

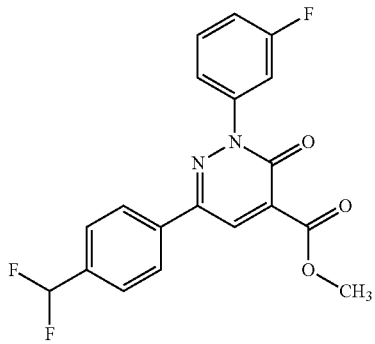 [SMILES: COC(=O)c1cc(-c2ccc(C(F)F)cc2)nn(-c2cccc(F)c2)c1=O]

A mixture of 650 mg intermediate 31 and 750 mg copper (II) chloride in 25 mL of acetonitrile was stirred at 90° C. for 3 hours. After evaporation in vacuo, the residue was diluted with water and extracted 3 times with ethyl acetate. The combined organic phases were washed with water and brine and the solvent was evaporation in vacuo to yield 566 mg methyl 6-[4-(difluoromethyl)phenyl]-2-(3-fluorophenyl)-3-oxo-2,3-dihydropyridazine-4-carboxylate.

$^1$H-NMR (400 MHz, DMSO-d6) δ [ppm]=3.89 (s, 3H); 7.12 (t, 1H); 7.36 (ddt, 1H); 7.53-7.65 (m, 3H); 7.71 (d, 2H); 8.10 (d, 2H); 8.54 (s, 1H).

Intermediate 33

6-[4-(Difluoromethyl)phenyl]-2-(3-fluorophenyl)-3-oxo-2,3-dihydropyridazine-4-carboxylic acid

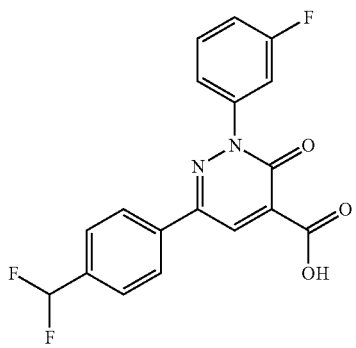 [SMILES: O=C(O)c1cc(-c2ccc(C(F)F)cc2)nn(-c2cccc(F)c2)c1=O]

A mixture of 564 mg intermediate 32 in 7.7 mL of THF was treated with 1.9 mL Sodium hydroxide solution (2N). The reaction mixture was stirred at room temperature for 14 hours. The THF was evaporated in vacuo and the remaining water solution was extracted with MTBE 2 times. Then, the PH of the water solution was adjusted to 3 with hydrochloric acid (2N). The solids were collected by filtration, washed three times with water and dried in an oven to yield 483 mg 6-[4-(difluoromethyl)phenyl]-2-(3-fluorophenyl)-3-oxo-2,3-dihydropyridazine-4-carboxylic acid.

$^1$H-NMR (400 MHz, DMSO-d6) δ [ppm]=7.11 (t, 1H); 7.34 (bt, 1H); 7.52-7.65 (m, 3H); 7.69 (d, 2H); 8.09 (d, 2H); 8.28 (bs, 1H).

Intermediate 34

Dimethyl [2-(4-methoxyphenyl)-2-oxoethyl]malonate

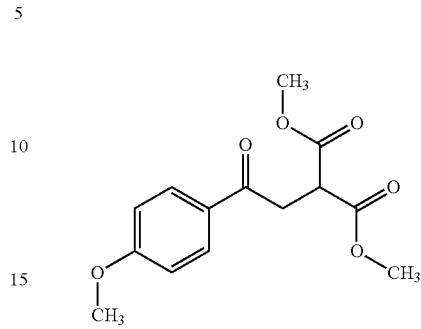

5.8 g dimethyl malonate and 4.5 g potassium carbonate were added to a solution of 5 g 2-bromo-1-(4-methoxyphenyl)ethanone in 150 mL of acetone. The reaction mixture was stirred at room temperature overnight and then quenched with water. Aceton was evaporated and the remaining aqueous phase was extracted three times with ethyl acetate. The combined organic phases were washed with brine, dried over sodium sulfate, filtrated and concentrated. The residue was purified by column chromatography (hexane/ethyl acetate gradient with up to 50% ethyl acetate) to yield 5.2 g dimethyl [2-(4-methoxyphenyl)-2-oxoethyl] malonate.

$^1$H NMR (400 MHz, DMSO-d6) δ ppm=3.57 (d, 2H), 3.67 (s, 6H), 3.81-3.88 (m, 3H), 3.96 (t, 1H), 7.05 (d, 2H), 7.93-8.01 (m, 2H).

Intermediate 35

Methyl 2-(3-fluorophenyl)-6-(4-methoxyphenyl)-3-oxo-2,3,4,5-tetrahydropyridazine-4-carboxylate

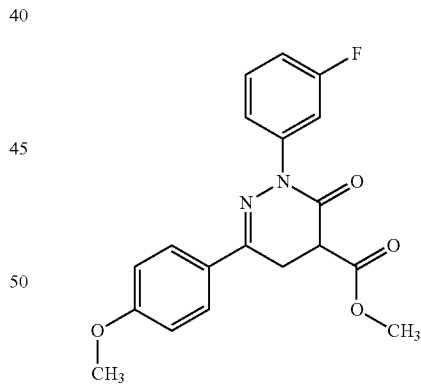

A mixture of 2 g dimethyl [2-(4-methoxyphenyl)-2-oxoethyl]malonate and 1.43 g 3-(fluorophenyl)hydrazine in 57 mL of AcOH was stirred at 100° C. for 6 hours. Then water and ethyl acetate were added and the aqueous phase was extracted three times with ethyl acetate. The combined organic phases were washed with brine, filtrated via hydrophobic filter MN 617 WA (Macherey-Nagel) and evaporated to dryness. The residue was purified by column chromatography (hexane/ethyl acetate gradient with up to 50% ethyl acetate) to yield 1.3 g methyl-2-(3-fluorophenyl)-6-(4-methoxyphenyl)-3-oxo-2,3,4,5-tetrahydropyridazine-4-carboxylate.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=1.24 min; MS (ESIpos): m/z=357 [M+H]$^+$ Intermediate 36

Methyl 2-(3-fluorophenyl)-6-(4-methoxyphenyl)-3-oxo-2,3-dihydropyridazine-4-carboxylate

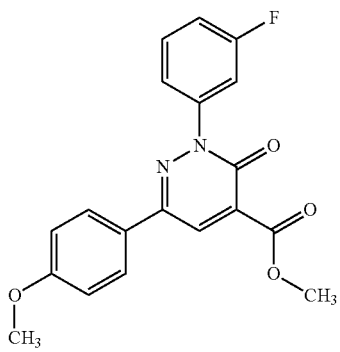 [SMILES: COC(=O)c1cc(-c2ccc(OC)cc2)nn(-c2cccc(F)c2)c1=O]

A mixture of 1.3 g methyl-2-(3-fluorophenyl)-6-(4-methoxyphenyl)-3-oxo-2,3,4,5-tetrahydropyridazine-4-carboxylate and 1.25 g copper(II) chloride in 40 mL of acetonitrile was stirred at 80° C. for 2 hours. After evaporation in vacuum, the residue was suspended in water and the precipitate was filtered to yield 1.8 g methyl 2-(3-fluorophenyl)-6-(4-methylphenyl)-3-oxo-2,3-dihydropyridazine-4-carboxylate.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=1.24 min; MS (ESIpos): m/z=355 [M+H]$^+$ Intermediate 37

2-(3-Fluorophenyl)-6-(4-methoxyphenyl)-3-oxo-2,3-dihydropyridazine-4-carboxylic acid

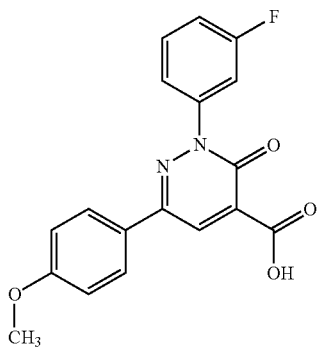 [SMILES: COc1ccc(-c2cc(C(=O)O)c(=O)n(-c3cccc(F)c3)n2)cc1]

A mixture of 1.8 g methyl 2-(3-fluorophenyl)-6-(4-methylphenyl)-3-oxo-2,3-dihydropyridazine-4-carboxylate and 6.5 mL 2N aqueous sodium hydroxide solution in 30 mL tetrahydrofurane was stirred at 50° C. for 1 hours. Then the pH value was adjusted to 3 with 1M hydrochloric acid and the reaction mixture was extracted three times with ethyl acetate. The combined organic phases were washed with brine, filtrated via hydrophobic filter MN 617 WA (Macherey-Nagel) and evaporated to dryness to yield 1.71 g 2-(3-fluorophenyl)-6-(4-methoxyphenyl)-3-oxo-2,3-dihydropyridazine-4-carboxylic acid.

LC-MS (Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=0.72 min; MS (ESIpos): m/z=341 [M+H]$^+$ Intermediate 38

Dimethyl {2-[4-(difluoromethoxy)phenyl]-2-oxoethyl}malonate

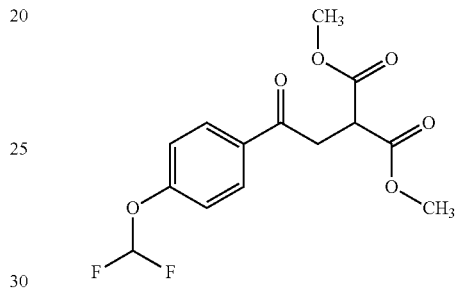

4.5 g dimethyl malonate and 3.6 g potassium carbonate were added to a solution of 4.8 g 2-bromo-1-[4-(difluoromethoxy)phenyl]ethan-1-one in 120 mL of acetone. The reaction mixture was stirred at room temperature overnight and then quenched with water. Aceton was evaporated and the remaining aqueous phase was extracted three times with ethyl acetate. The combined organic phases were washed with brine, dried over sodium sulfate, filtrated and concentrated. The residue was purified by column chromatography (hexane/ethyl acetate gradient with up to 40% ethyl acetate) to yield 4.3 g dimethyl {2-[4-(difluoromethoxy)phenyl]-2-oxoethyl}malonate.

$^1$H NMR (400 MHz, DMSO-d6) δ ppm=3.60-3.65 (m, 2H), 3.68 (s, 6H), 3.98 (t, 1H), 7.22-7.66 (m, 3H), 8.05-8.11 (m, 2H).

Intermediate 39

Methyl 6-[4-(difluoromethoxy)phenyl]-2-(3-fluorophenyl)-3-oxo-2,3,4,5-tetrahydropyridazine-4-carboxylate

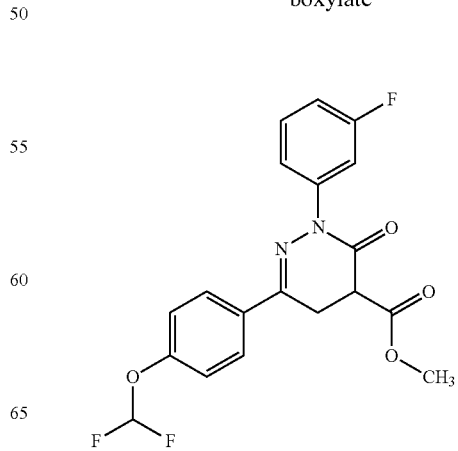

A mixture of 1.4 g dimethyl {2-[4-(difluoromethoxy)phenyl]-2-oxoethyl}malonate and 0.82 g 3-(fluorophenyl)hydrazine in 35.6 mL of AcOH was stirred at 70° C. for 3 hours, at room temperature overnight and at 90° C. for 2 hours followed by the addition of further 74 mg 3-(fluorophenyl)hydrazine and 2 hours at 100° C. The reaction mixture was evaporated to dryness. The residue was purified by column chromatography (hexane/ethyl acetate gradient with up to 50% ethyl acetate) to yield 1.25 g methyl 6-[4-(difluoromethoxy)phenyl]-2-(3-fluorophenyl)-3-oxo-2,3,4,5-tetrahydropyridazine-4-carboxylate.

$^1$H NMR (400 MHz, DMSO-d6) δ ppm=3.37-3.47 (m, 2H), 3.50-3.51 (m, 1H), 3.71 (s, 3H), 3.98-4.10 (m, 1H), 7.11-7.36 (m, 4H), 7.38-7.55 (m, 3H), 7.89-7.95 (m, 2H).

Intermediate 40

Methyl 6-[4-(difluoromethoxy)phenyl]-2-(3-fluorophenyl)-3-oxo-2,3-dihydropyridazine-4-carboxylate

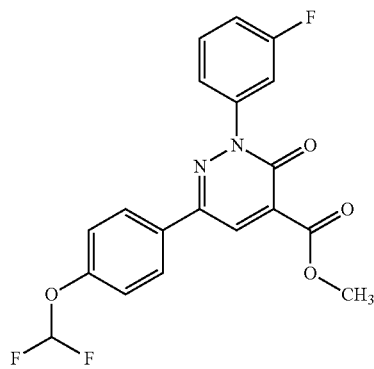 [SMILES: COC(=O)c1cc(-c2ccc(OC(F)F)cc2)nn(-c2cccc(F)c2)c1=O]

A mixture of 1.25 g methyl 6-[4-(difluoromethoxy)phenyl]-2-(3-fluorophenyl)-3-oxo-2,3,4,5-tetrahydropyridazine-4-carboxylate and 1.28 g copper(II) chloride in 43 mL of acetonitrile was stirred at 90° C. for 5 hours. After evaporation in vacuum, the residue was suspended in water and the precipitate was filtered to yield 1.12 g methyl 6-[4-(difluoromethoxy)phenyl]-2-(3-fluorophenyl)-3-oxo-2,3-dihydropyridazine-4-carboxylate.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.25 min; MS (ESIpos): m/z=391 [M+H]$^+$ Intermediate 41

6-[4-(Difluoromethoxy)phenyl]-2-(3-fluorophenyl)-3-oxo-2,3-dihydropyridazine-4-carboxylic acid

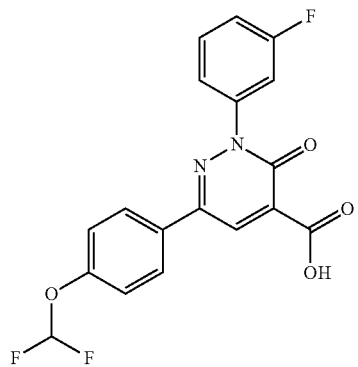 [SMILES: O=C(O)c1cc(-c2ccc(OC(F)F)cc2)nn(-c2cccc(F)c2)c1=O]

A mixture of 1.12 g methyl 6-[4-(difluoromethoxy)phenyl]-2-(3-fluorophenyl)-3-oxo-2,3-dihydropyridazine-4-carboxylate and 3.6 mL 2N aqueous sodium hydroxide solution in 15 mL tetrahydrofurane was stirred at room temperature for 14 hours. Then the pH value was adjusted to 3 with 2M hydrochloric acid and the precipitate was filtered of to yield 0.99 g 6-[4-(difluoromethoxy)phenyl]-2-(3-fluorophenyl)-3-oxo-2,3-dihydropyridazine-4-carboxylic acid.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.24 min; MS (ESIpos): m/z=377 [M+H]$^+$ Intermediate 42

Trimethyl {2-oxo-2-[4-(trifluoromethoxy)phenyl]ethyl}malonate

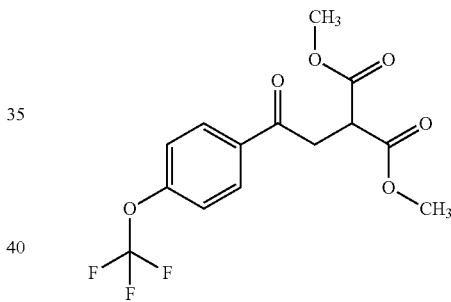

4.1 g dimethyl malonate and 3.2 g potassium carbonate were added to a solution of 4.4 g 2-bromo-1-[4-(trifluoromethoxy)phenyl]ethan-1-one in 110 mL of acetone. The reaction mixture was stirred at room temperature overnight and then quenched with water. Aceton was evaporated and the remaining aqueous phase was extracted three times with ethyl acetate. The combined organic phases were washed with brine, dried over sodium sulfate, filtrated and concentrated. The residue was purified by column chromatography (hexane/ethyl acetate gradient with up to 30% ethyl acetate) to yield 4.9 g trimethyl {2-oxo-2-[4-(trifluoromethoxy)phenyl]ethyl}malonate.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.22 min; MS (ESIpos): m/z=335 [M+H]$^+$

Intermediate 43

Methyl 2-(3-fluorophenyl)-3-oxo-6-[4-(trifluoromethoxy)phenyl]-2,3,4,5-tetrahydropyridazine-4-carboxylate

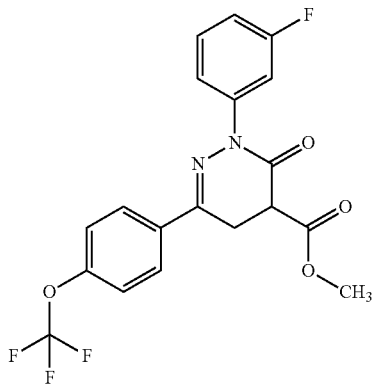 [SMILES: COC(=O)C1CC(c2ccc(OC(F)(F)F)cc2)=NN(c2cccc(F)c2)C1=O]

A mixture of 2 g trimethyl {2-[4-(difluoromethoxy)phenyl]-2-oxoethyl}malonate and 1.2 g 3-(fluorophenyl)hydrazine in 48 mL of AcOH was stirred at 100° C. for 3 hours. Then water and ethyl acetate were added and the aqueous phase was extracted three times with ethyl acetate. The combined organic phases were washed with brine, filtrated via hydrophobic filter MN 617 WA (Macherey-Nagel) and evaporated to dryness. The residue was purified by column chromatography (hexane/ethyl acetate gradient with up to 46% ethyl acetate) to yield 1.48 g methyl 2-(3-fluorophenyl)-3-oxo-6-[4-(trifluoromethoxy)phenyl]-2,3,4,5-tetrahydropyridazine-4-carboxylate.

$^1$H NMR (400 MHz, DMSO-$d_6$) δ ppm=3.38-3.53 (m, 2H), 3.71 (s, 3H), 4.06-4.12 (m, 1H), 7.14-7.21 (m, 1H), 7.38-7.53 (m, 5H), 7.96-8.02 (m, 2H).

Intermediate 44

Methyl 2-(3-fluorophenyl)-3-oxo-6-[4-(trifluoromethoxy)phenyl]-2,3-dihydropyridazine-4-carboxylate

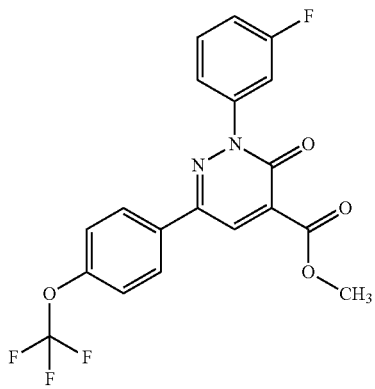 [SMILES: COC(=O)c1cc(-c2ccc(OC(F)(F)F)cc2)nn(-c2cccc(F)c2)c1=O]

A mixture of 1.48 g methyl 2-(3-fluorophenyl)-3-oxo-6-[4-(trifluoromethoxy)phenyl]-2,3,4,5-tetrahydropyridazine-4-carboxylate and 1.21 g copper(II) chloride in 38 mL of acetonitrile was stirred at 80° C. for 2 hours. After evaporation in vacuum, the residue was suspended in water and the precipitate was filtered of to yield 1.16 g methyl 6-[4-(trifluoromethoxy)phenyl]-2-(3-fluorophenyl)-3-oxo-2,3-dihydropyridazine-4-carboxylate.

LC-MS (Instrument: Waters Acquity UPLC-MS SQD 3001; column: Acquity UPLC BEH C18 1.7 50×2.1 mm; eluent A: Water+0.1% formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=1.38 min; MS (ESIpos): m/z=409.5 [M+H]$^+$

Intermediate 45

6-[4-(Trifluoromethoxy)phenyl]-2-(3-fluorophenyl)-3-oxo-2,3-dihydropyridazine-4-carboxylic acid

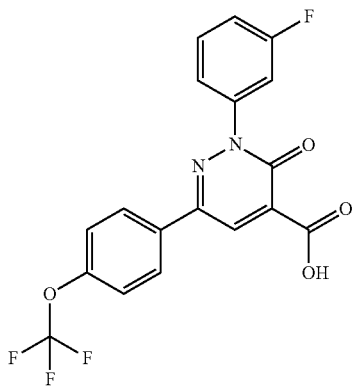 [SMILES: O=C(O)c1cc(-c2ccc(OC(F)(F)F)cc2)nn(-c2cccc(F)c2)c1=O]

A mixture of 1.16 g methyl 6-[4-(trifluoromethoxy)phenyl]-2-(3-fluorophenyl)-3-oxo-2,3-dihydropyridazine-4-carboxylate and 3.6 mL 2N aqueous sodium hydroxide solution in 15 mL tetrahydrofurane was stirred at 50° C. for 1 hours. Then the pH value was adjusted to 3 with 1M hydrochloric acid and the reaction mixture was extracted three times with ethyl acetate. The combined organic phases were washed with brine, filtrated via hydrophobic filter MN 617 WA (Macherey-Nagel) and evaporated to dryness to yield 1.06 g 6-[4-(trifluoromethoxy)phenyl]-2-(3-fluorophenyl)-3-oxo-2,3-dihydropyridazine-4-carboxylic acid.

LC-MS (Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=0.75 min; MS (ESIpos): m/z=395 [M+H]$^+$ Intermediate 46

Dimethyl {2-oxo-2-[4-(trifluoromethyl)phenyl]ethyl}malonate

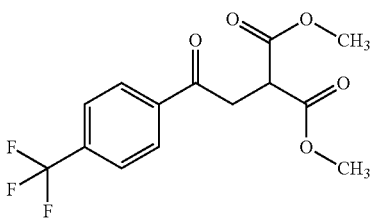 [SMILES: COC(=O)C(CC(=O)c1ccc(C(F)(F)F)cc1)C(=O)OC]

Dimethyl malonate (9.894 g, 74.89 mmol) and potassium carbonate (7.763 g, 56.17 mmol) were added to acetone (140 mL). Under cooling (0-5° C.) a solution of 2-bromo-1-[4-(trifluoromethyl)phenyl]ethanone (10 g, 37.4 mmol) in acetone (60 mL) was added dropwise. It was stirred 2 h at 0-5° C. and at rt overnight. The volatile compounds were removed on a rotavap. Water and ethyl acetate were added, the layers were separated and the aqueous phase was extracted twice with ethyl acetate. The combined organic layers were washed with concentrated aqueous sodium chloride solution, dried over magnesium sulfate and concentrated. The crude product was purified by flash chromatography (hexane/ethyl acetate) affording 8.03 g (67%) of the title product.

$^1$H-NMR (400 MHz, CHLOROFORM-$d_3$): δ [ppm]=3.65 (d, 2H), 3.79 (s, 6H), 4.10 (t, 1H), 7.73-7.77 (m, 2H), 8.07-8.11 (m, 2H).

Intermediate 47

Methyl 2-(3-fluorophenyl)-3-oxo-6-[4-(trifluoromethyl)phenyl]-2,3-dihydropyridazine-4-carboxylate

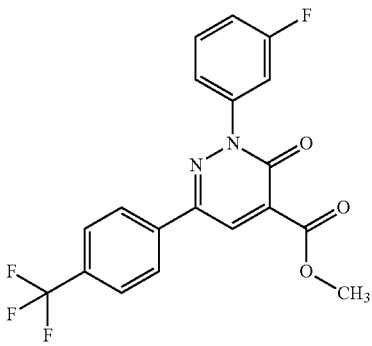 [SMILES: COC(=O)c1cc(-c2ccc(C(F)(F)F)cc2)nn(-c2cccc(F)c2)c1=O]

Step 1: Dimethyl {2-oxo-2-[4-(trifluoromethyl)phenyl]ethyl}malonate (4.00 g, 12.57 mmol) and (3-fluorophenyl)hydrazine hydrochloride (1:1) (3.065 g, 18.85 mmol) in acetic acid (50 mL) was stirred 8 h at 80° C. Two of such batches were combined and concentrated on a rotavap. Hexane was added and it was removed on a rotavap. Water and ethyl acetate were added.

The layers were separated and the aqueous phase was extracted four times with ethyl acetate. The combined organic layers were washed twice with water, dried over magnesium sulfate and concentrated to dryness affording 9.9 g (99.9%) of methyl 2-(3-fluorophenyl)-3-oxo-6-[4-(trifluoromethyl)phenyl]-2,3,4,5-tetrahydropyridazine-4-carboxylate which was used without further purification in the next step.

Step 2: Methyl 2-(3-fluorophenyl)-3-oxo-6-[4-(trifluoromethyl)phenyl]-2,3,4,5-tetrahydropyridazine-4-carboxylate (4.9 g, 7.46 mmol) was dissolved in acetonitrile (100 mL). Copper (II) chloride (3.007 g, 22.37 mmol) was added and it was stirred 9 h at 90° C. The reaction mixture was allowed to reach rt. Two of such batches and a small batch (215 mg, 0.327 mmol) were combined and silica gel (60 g) was added. The volatiles were removed under vacuum. It was purified by flash chromatography (hexane/ethyl acetate) obtaining 2.3 g (23%) of the title compound.

$^1$H-NMR (400 MHz, DMSO-$d_6$): δ [ppm]=3.89 (s, 3H), 7.33-7.39 (m, 1H), 7.54-7.58 (m, 1H), 7.58-7.64 (m, 2H), 7.88 (d, 2H), 8.17 (d, 2H), 8.57 (s, 1H).

Intermediate 48

2-(3-Fluorophenyl)-3-oxo-6-[4-(trifluoromethyl)phenyl]-2,3-dihydropyridazine-4-carboxylic acid

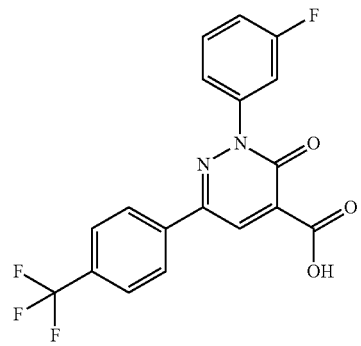 [SMILES: O=C(O)c1cc(-c2ccc(C(F)(F)F)cc2)nn(-c2cccc(F)c2)c1=O]

Methyl 2-(3-fluorophenyl)-3-oxo-6-[4-(trifluoromethyl)phenyl]-2,3-dihydropyridazine-4-carboxylate (2.3 g, 5.57 mmol) was dissolved in acetonitrile (57 mL). A solution of lithium hydroxide (400 mg, 16.71 mmol) in water (5.7 mL) was added at rt. It was stirred 24 h at rt. Water (10 mL) was added. 2N hydrochloric acid (9.56 mL) was added to adjust the pH to 4. It was stirred 1 h at rt. The precipitate was filtered off under suction, washed with water four times and dried under vacuum at 50° C. for 24 h yielding 1.89 g (85%) of the title compound which was used without further purification in the next step.

$^1$H-NMR (400 MHz, DMSO-$d_6$): δ [ppm]=7.31-7.37 (m, 1H), 7.52-7.56 (m, 1H), 7.57-7.63 (m, 2H), 7.85 (d, 2H), 8.16 (d, 2H), 8.24 (s, 1H).

Intermediate 49

Dimethyl [2-(4-chloro-3-fluorophenyl)-2-oxoethyl]malonate

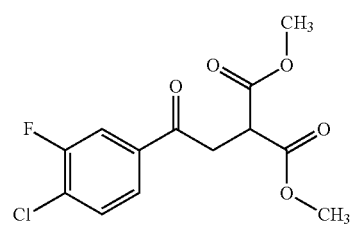 [SMILES: COC(=O)C(CC(=O)c1ccc(Cl)c(F)c1)C(=O)OC]

2-Bromo-1-(4-chloro-3-fluorophenyl)ethanone (4.67 g, 17.64 mmol) was dissolved in acetone (125 mL). Then, dimethyl malonate (4.66 g, 35.3 mmol) and potassium carbonate (3.65 g, 26.46 mmol) were added at rt. It was stirred at rt overnight. The reaction mixture was poured into water and acetone was evaporated. The aqueous phase was extracted three times with ethyl acetate. The combined organic layers were washed with water and saturated aqueous sodium chloride solution, dried over sodium sulfate and concentrated. The crude product was purified by flash chromatography (silica gel, hexane/ethyl acetate, gradient) yielding 4.43 g (83%) of the title product.

¹H NMR (400 MHz, DMSO-$d_6$) δ ppm=3.62-3.67 (m, 8H), 3.97 (t, 1H), 7.78-7.81 (m, 1H), 7.84-7.88 (m, 1H), 8.00 (dd, 1H).

Intermediate 50

Methyl 6-(4-chloro-3-fluorophenyl)-2-(3-fluorophenyl)-3-oxo-2,3,4,5-tetrahydropyridazine-4-carboxylate

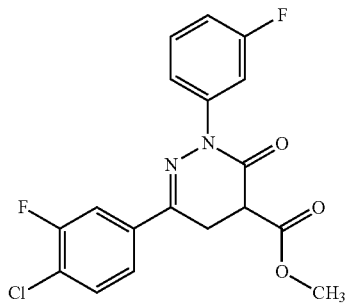

A mixture of 1.43 g intermediate dimethyl [2-(4-chloro-3-fluorophenyl)-2-oxoethyl]malonate and 871 mg (3-fluorophenyl)hydrazine in 38 mL acetic acid was stirred at 70° C. for 3 hours, overnight at rt and 1 h at 90° C. The solvent was removed in vacuo. The residue was purified by column chromatography (hexanes/ethyl acetate gradient with up to 40% ethyl acetate) to yield 986 mg of the title compound.

¹H NMR (400 MHz, DMSO-$d_6$) δ ppm=3.37-3.52 (m, 2H), 3.71 (s, 3H), 4.06-4.12 (m, 1H), 7.14-7.21 (m, 1H), 7.40-7.54 (m, 3H), 7.67-7.73 (m, 2H), 7.88 (dd, 1H).

Intermediate 51

Methyl 6-(4-chloro-3-fluorophenyl)-2-(3-fluorophenyl)-3-oxo-2,3-dihydropyridazine-4-carboxylate

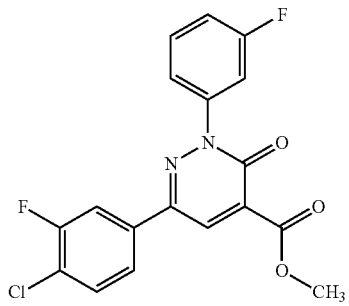

A mixture of 986 mg intermediate Methyl 6-(4-chloro-3-fluorophenyl)-2-(3-fluorophenyl)-3-oxo-2,3,4,5-tetrahydropyridazine-4-carboxylate and 1.05 g copper(II) chloride in 35 mL of acetonitrile was stirred at 90° C. for 5 hours. The reaction mixture was treated with water and the precipitate was filtered of, washed with water and dried to yield 1.03 g of the title compound.

¹H NMR (400 MHz, DMSO-$d_6$) δ ppm=3.88 (s, 3H), 7.36 (br t, 1H), 7.54-7.66 (m, 4H), 7.70-7.77 (m, 1H), 7.84 (br d, 1H), 8.03 (br d, 1H), 8.55 (s, 1H).

Intermediate 52

6-(4-Chloro-3-fluorophenyl)-2-(3-fluorophenyl)-3-oxo-2,3-dihydropyridazine-4-carboxylic acid

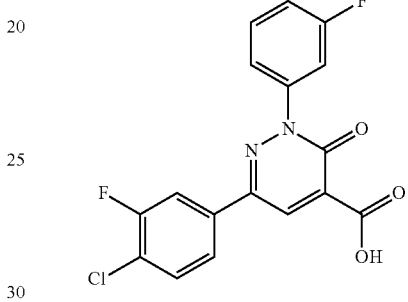

A mixture of 914 mg intermediate methyl 6-(4-chloro-3-fluorophenyl)-2-(3-fluorophenyl)-3-oxo-2,3-dihydropyridazine-4-carboxylat in 12 mL of THF was treated with 1.2 mL sodium hydroxide solution (2N). The reaction mixture was stirred at room temperature for 14 hours. After dilution of the reaction mixture with water the pH was adjusted to 3 with hydrochloric acid (2N). The solids were collected by filtration, washed three times with water and dried in an oven to yield 850 mg of the title compound.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt=1.31 min; MS (ESIpos): m/z=363.0 [M+H]⁺

Intermediate 53

Methyl 6-(4-chlorophenyl)-2-(3,5-dichlorophenyl)-3-oxo-2,3,4,5-tetrahydropyridazine-4-carboxylate

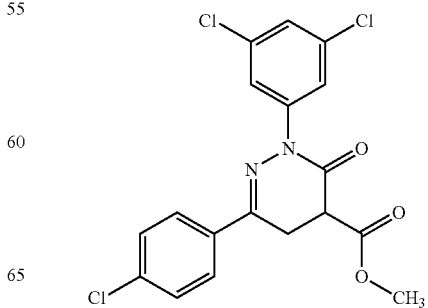

A mixture of 1.0 g intermediate 5 dimethyl [2-(4-chlorophenyl)-2-oxoethyl]propanedioate and 698 mg (3,5-dichlorophenyl)hydrazine in 30 mL acetic acid was stirred at 100° C. for 2 hours. Additional 698 mg (3,5-dichlorophenyl) hydrazine were added followed by stirring at 100° C. for 4 h. The solvent was removed in vacuo. The residue was purified by column chromatography (hexanes/ethyl acetate gradient with up to 40% ethyl acetate) to yield 815 mg of the title compound.

$^1$H NMR (400 MHz, DMSO-$d_6$) δ ppm=3.37-3.51 (m, 2H), 3.71 (s, 3H), 4.06-4.11 (m, 1H), 7.55 (d, 2H), 7.59 (d, 1H), 7.65 (d, 2H), 7.85-7.91 (m, 2H).

Intermediate 54

Methyl 6-(4-chlorophenyl)-2-(3,5-dichlorophenyl)-3-oxo-2,3-dihydropyridazine-4-carboxylate

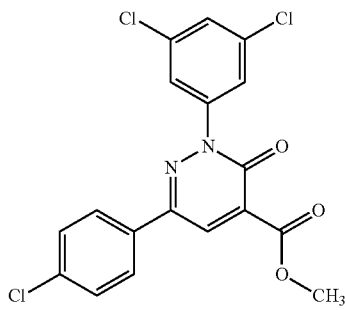 [SMILES: COC(=O)c1cc(-c2ccc(Cl)cc2)nn(-c2cc(Cl)cc(Cl)c2)c1=O]

A mixture of 810 mg intermediate 70 methyl 6-(4-chlorophenyl)-2-(3,5-dichlorophenyl)-3-oxo-2,3,4,5-tetrahydropyridazine-4-carboxylate and 795 mg copper(II) chloride in 30 mL of acetonitrile was stirred at 90° C. for 3 hours. The reaction mixture was evaporated to dryness and the residue was treated with water and the precipitate was filtered of, washed with water and dried to yield 834 mg of the title compound.

$^1$H NMR (400 MHz, DMSO-$d_6$) δ ppm=3.88 (s, 3H), 7.57-7.61 (m, 2H), 7.77-7.79 (m, 1H), 7.84 (d, 2H), 7.96-8.00 (m, 2H), 8.51 (s, 1H).

Intermediate 55

6-(4-Chlorophenyl)-2-(3,5-dichlorophenyl)-3-oxo-2,3-dihydropyridazine-4-carboxylic acid

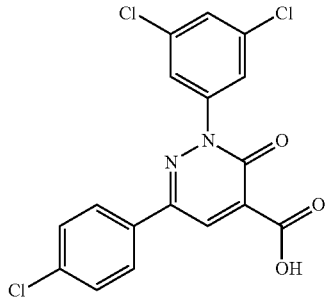 [SMILES: O=C(O)c1cc(-c2ccc(Cl)cc2)nn(-c2cc(Cl)cc(Cl)c2)c1=O]

A mixture of 834 mg intermediate methyl 6-(4-chlorophenyl)-2-(3,5-dichlorophenyl)-3-oxo-2,3-dihydropyridazine-4-carboxylate in 10 mL of THF was treated with 2.5 mL sodium hydroxide solution (2N). The reaction mixture was stirred at room temperature for 14 hours. After dilution of the reaction mixture with water the pH was adjusted to 3 with hydrochloric acid (2N). The solids were collected by filtration, washed three times with water and dried in an oven to yield 723 mg of the title compound.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.50 min; MS (ESIpos): m/z=395.0 [M−H]$^+$ Intermediate 56

Dimethyl [2-(3,4-dichlorophenyl)-2-oxoethyl]malonate

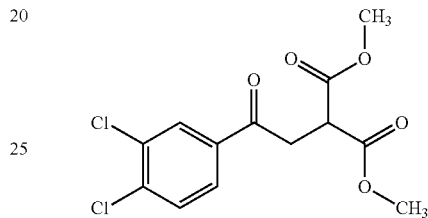

Dimethyl [2-(3,4-dichlorophenyl)-2-oxoethyl]malonate (5.0 g, 18.6 mmol) was dissolved in acetone (130 mL). Then, dimethyl malonate (4.9 g, 37.3 mmol) and potassium carbonate (3.86 g, 28.0 mmol) were added at rt. The reaction mixture was stirred at rt overnight, poured into water and acetone was evaporated. The aqueous phase was extracted three times with ethyl acetate. The combined organic layers were washed with water and saturated aqueous sodium chloride solution, dried over sodium sulfate and concentrated. The crude product was purified by flash chromatography (silica gel, hexane/ethyl acetate, gradient up to 35% ethyl acetate) yielding 3.62 g (71%) of the title product.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.24 min; MS (ESIpos): m/z=321.0 [M+H]$^+$ Intermediate 57

Methyl 6-(3,4-dichlorophenyl)-2-(3-fluorophenyl)-3-oxo-2,3,4,5-tetrahydropyridazine-4-carboxylate

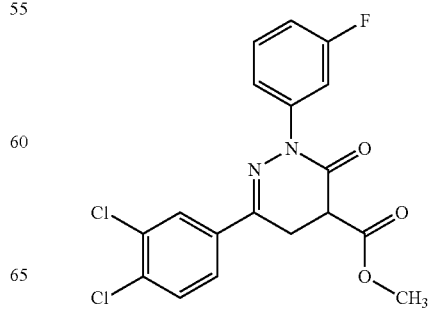

A mixture of 1.6 g intermediate dimethyl [2-(3,4-dichlorophenyl)-2-oxoethyl]malonate and 924 mg (3-fluorophenyl)hydrazine in 40 mL acetic acid was stirred at 70° C. for 3 hours, then 90° C. for 2 h and 100° C. for 1 h. The solvent was removed in vacuo. The residue was purified by column chromatography (hexanes/ethyl acetate gradient with up to 40% ethyl acetate) to yield 1.25 g of the title compound.

$^1$H NMR (400 MHz, DMSO-$d_6$) δ ppm=3.36-3.53 (m, 2H), 3.71 (s, 3H), 4.05-4.12 (m, 1H), 7.15-7.22 (m, 1H), 7.39-7.44 (m, 2H), 7.46-7.54 (m, 1H), 7.71-7.76 (m, 1H), 7.84 (dd, 1H), 8.06 (d, 1H).

Intermediate 58

Methyl 6-(3,4-dichlorophenyl)-2-(3-fluorophenyl)-3-oxo-2,3-dihydropyridazine-4-carboxylate

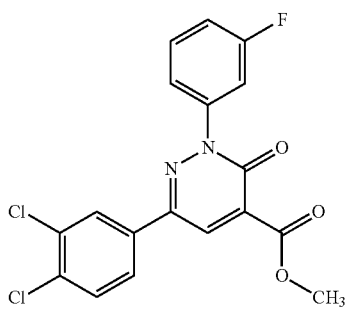

A mixture of 1.25 g intermediate methyl 6-(3,4-dichlorophenyl)-2-(3-fluorophenyl)-3-oxo-2,3,4,5-tetrahydropyridazine-4-carboxylate and 1.27 g copper(II) chloride in 43 mL of acetonitrile was stirred at 90° C. for 3 hours. The reaction mixture was evaporated to dryness and the residue was treated with water and the precipitate was filtered of, washed with water and dried to yield 1.14 g of the title compound.

$^1$H NMR (400 MHz, DMSO-$d_6$) δ ppm 3.88 (s, 3H), 7.36 (br t, 1H), 7.53-7.65 (m, 3H), 7.78 (d, 1H), 7.95 (dd, 1H), 8.23 (d, 1H), 8.57 (s, 1H).

Intermediate 59

6-(3,4-Dichlorophenyl)-2-(3-fluorophenyl)-3-oxo-2,3-dihydropyridazine-4-carboxylic acid

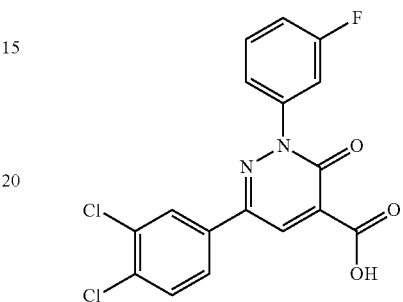

A mixture of 1.14 g intermediate methyl 6-(3,4-dichlorophenyl)-2-(3-fluorophenyl)-3-oxo-2,3-dihydropyridazine-4-carboxylate in 15 mL of THF was treated with 3.6 mL sodium hydroxide solution (2N). The reaction mixture was stirred at room temperature for 14 hours. After dilution of the reaction mixture with water the pH was adjusted to 3 with hydrochloric acid (2N). The solids were collected by filtration, washed three times with water and dried in an oven to yield 1.02 g of the title compound.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.38 min; MS (ESIpos): m/z=379.0 [M–H]$^+$ Further intermediates were prepared in a comparable manner as described by the sequence from intermediate 6 to intermediate 8.

TABLE 2

| | | further intermediates | | |
|---|---|---|---|---|
| Intermediate | structure | IUPAC name | Starting materials | analytics |
| 60 | (structure shown) | 6-(4-chlorophenyl)-2-(3-cyanophenyl)-3-oxo-2,3-dihydropyridazine-4-carboxylic acid | Intermediate 5, (3-cyanophenyl)hydrazine | $^1$H-NMR (400 MHz, DMSO-$d_6$): δ = 7.54 (d, 2H); 7.75 (t, 1H); 7.91-7.98 (m, 3H); 8.03 (bd, 1H); 8.09 (s, 1H); 8.21 (bs, 1H). |

TABLE 2-continued further intermediates

| Intermediate | structure | IUPAC name | Starting materials | analytics |
|---|---|---|---|---|
| 61 | 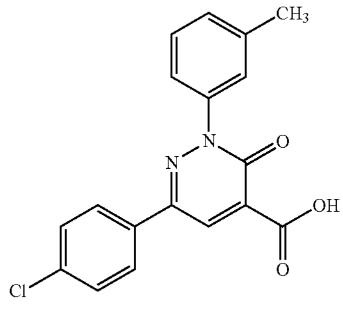 [SMILES: Cc1cccc(-n2nc(-c3ccc(Cl)cc3)cc(C(=O)O)c2=O)c1] | 6-(4-chlorophenyl)-2-(3-methylphenyl)-3-oxo-2,3-dihydropyridazine-4-carboxylic acid | Intermediate 5, (3-methylphenyl)hydrazine | $^1$H-NMR (400 MHz, DMSO-$d_6$): δ = 2.38 (s, 3H); 7.27 (bd, 1H); 7.36-7.44 (m, 3H); 7.52-7.56 (m, 2H); 7.90-7.94 (m, 2H); 8.08 (s, 1H). |
| 62 | 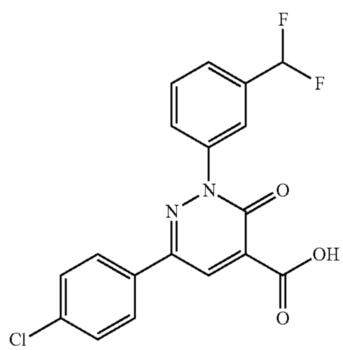 [SMILES: O=C(O)c1cc(-c2ccc(Cl)cc2)nn(-c2cccc(C(F)F)c2)c1=O] | 6-(4-chlorophenyl)-2-[3-(difluoromethyl)phenyl]-3-oxo-2,3-dihydropyridazine-4-carboxylic acid | Intermediate 5, (3-difluoromethylphenyl)hydrazine | $^1$H-NMR (400 MHz, DMSO-$d_6$): δ = 7.15 (t, 1); 7.54-7.57 (m, 2H); 7.65-7.73 (m, 2H); 7.85 (bd, 1H); 7.89 (bs, 1H); 7.95-7.99 (m, 2H); 8.19 (s, 1H) |

Intermediate 63

Dimethyl {2-[4-(dimethylamino)phenyl]-2-oxoethyl}malonate

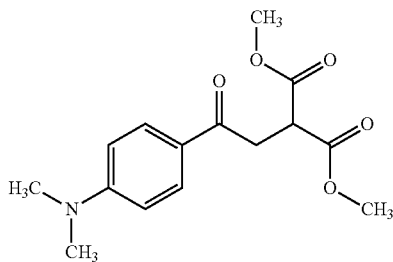

Dimethyl [2-(3,4-dichlorophenyl)-2-oxoethyl]malonate (5.0 g, 20.65 mmol) was dissolved in acetone (145 mL). Then, dimethyl malonate (5.45 g, 41.3 mmol) and potassium carbonate (4.28 g, 31 mmol) were added at rt. The reaction mixture was stirred at rt overnight, poured into water, the precipitate was filtered off, washed with water and dried by lyophilization to yield 5.52 g of the title compound.

$^1$H-NMR (400 MHz, DMSO-$d_6$): δ [ppm]=3.02 (s, 6H), 3.48 (d, 2H), 3.67 (s, 6H), 3.93 (t, 1H), 6.66-6.77 (m, 2H), 7.76-7.85 (m, 2H).

Intermediate 64

Methyl 6-[4-(dimethylamino)phenyl]-2-(3-fluorophenyl)-3-oxo-2,3,4,5-tetrahydropyridazine-4-carboxylate

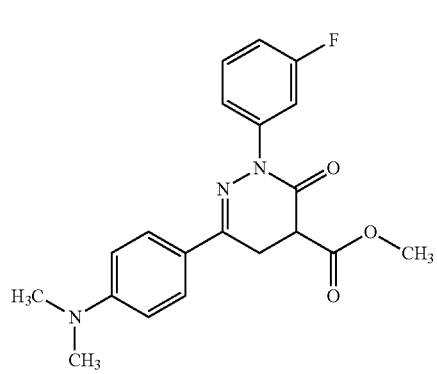

A mixture of 2.0 g intermediate dimethyl {2-[4-(dimethylamino)phenyl]-2-oxoethyl}malonate and 1372 mg (3-fluorophenyl)hydrazine in 55 mL acetic acid was stirred at 100° C. for 3 hours. The reaction mixture was cooled down to rt and treated with water. The precipitate was filtered off, washed with water and dried by lyophilization to yield 1.6 g of the title compound.

¹H NMR (400 MHz, DMSO-d₆) δ ppm=2.97 (s, 6H), 3.33-3.37 (m, 2H), 3.69 (s, 3H), 3.98 (dd, 1H), 6.75 (d, 2H), 7.10-7.17 (m, 1H), 7.40-7.49 (m, 3H), 7.70 (d, 2H).

Intermediate 65

Methyl 6-[3-chloro-4-(dimethylamino)phenyl]-2-(3-fluorophenyl)-3-oxo-2,3-dihydropyridazine-4-carboxylate

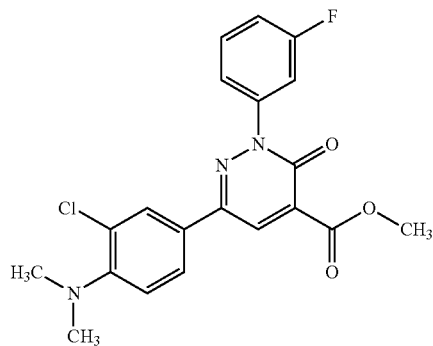

A mixture of 1.63 g intermediate methyl 6-[4-(dimethylamino)phenyl]-2-(3-fluorophenyl)-3-oxo-2,3,4,5-tetrahydropyridazine-4-carboxylate and 1.78 g copper(II) chloride in 47 mL of acetonitrile was stirred at 90° C. for 4 hours. The reaction mixture was evaporated to dryness and the residue was treated with water and the precipitate was filtered of, washed with water and dried. The crude was purified by column chromatography (hexanes/ethyl acetate gradient with up to 50% ethyl acetate) to yield 1.55 g of the title compound.
LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.38 min; MS (ESIpos): m/z=402.1 [M–H]⁺

Intermediate 66

6-[3-Chloro-4-(dimethylamino)phenyl]-2-(3-fluorophenyl)-3-oxo-2,3-dihydropyridazine-4-carboxylic acid

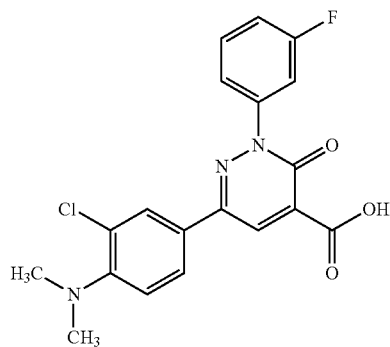 [SMILES: CN(C)c1ccc(-c2cc(C(=O)O)c(=O)n(-c3cccc(F)c3)n2)cc1Cl]

A mixture of 500 mg intermediate methyl 6-[3-chloro-4-(dimethylamino)phenyl]-2-(3-fluorophenyl)-3-oxo-2,3-dihydropyridazine-4-carboxylat in 6 mL of THF was treated with 1.55 mL sodium hydroxide solution (2N). The reaction mixture was stirred at room temperature for 14 hours. After dilution of the reaction mixture with water the pH was adjusted to 3 with hydrochloric acid (2N). The solids were collected by filtration, washed three times with water and dried in an oven to yield 397 mg of the title compound.
¹H NMR (400 MHz, DMSO-d₆) δ ppm=2.79 (s, 6H), 7.20 (d, 1H), 7.28-7.34 (m, 1H), 7.51-7.60 (m, 3H), 7.81-7.85 (m, 1H), 7.91 (d, 1H), 8.02 (s, 1H).

Intermediate 67

Dimethyl {2-[4-(morpholin-4-yl)phenyl]-2-oxoethyl}malonate

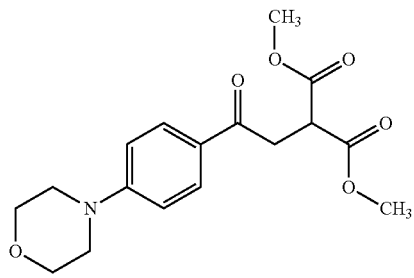 [SMILES: COC(=O)C(CC(=O)c1ccc(N2CCOCC2)cc1)C(=O)OC]

2-Bromo-1-[4-(morpholin-4-yl)phenyl]ethanone (268 mg, 0.94 mmol) was dissolved in acetone (7 mL). Then, dimethyl malonate (249 mg, 1.88 mmol) and potassium carbonate (196 mg, 1.4 mmol) were added at rt. The reaction mixture was stirred at rt overnight, poured into water, the precipitate was filtered off, washed with water and dried by lyophilization to yield 235 mg of the title compound.
¹H NMR (400 MHz, DMSO-d₆) δ ppm=3.30 (m, 4H), 3.51 (d, 2H), 3.67 (s, 6H), 3.70-3.75 (m, 4H), 3.91-3.97 (m, 1H), 6.99 (d, 2H), 7.85 (d, 2H).

Intermediate 68

Methyl 2-(3-fluorophenyl)-6-[4-(morpholin-4-yl)phenyl]-3-oxo-2,3,4,5-tetrahydropyridazine-4-carboxylate

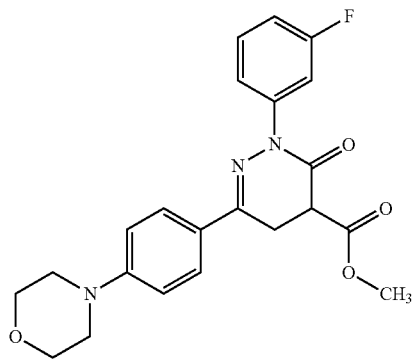 [SMILES: COC(=O)C1CC(c2ccc(N3CCOCC3)cc2)=NN(c2cccc(F)c2)C1=O]

A mixture of 235 mg intermediate dimethyl {2-[4-(morpholin-4-yl)phenyl]-2-oxoethyl}malonate and 141 mg (3-fluorophenyl)hydrazine in 5.6 mL acetic acid was stirred at 100° C. for 7 hours. The reaction mixture was cooled down to rt and treated with water and ethyl acetate. The phases were separated and the aqueous phase was extracted three times with ethyl acetate. The combined organic phases were washed with brine, dried and purified purified by column chromatography (hexanes/ethyl acetate gradient with up to 60% ethyl acetate) to yield 261 mg of the title compound $^1$H NMR (400 MHz, DMSO-$d_6$) δ ppm=3.18-3.25 (m, 4H), 3.70 (s, 3H), 3.72-3.78 (m, 4H), 3.99-4.05 (m, 1H), 6.97-7.03 (m, 2H), 7.11-7.19 (m, 1H), 7.39-7.50 (m, 3H), 7.70-7.77 (m, 2H).

Intermediate 69

Methyl 2-(3-fluorophenyl)-6-[4-(morpholin-4-yl)phenyl]-3-oxo-2,3-dihydropyridazine-4-carboxylate

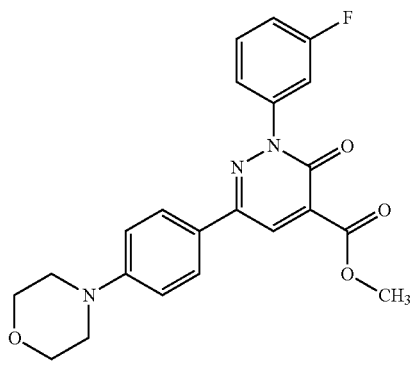 [SMILES: COC(=O)c1cc(-c2ccc(N3CCOCC3)cc2)nn(-c2cccc(F)c2)c1=O]

A mixture of 262 mg intermediate methyl 2-(3-fluorophenyl)-6-[4-(morpholin-4-yl)phenyl]-3-oxo-2,3,4,5-tetrahydropyridazine-4-carboxylate and 214 mg copper(II) chloride in 7 mL of acetonitrile was stirred at 80° C. for 2 hours. The reaction mixture was evaporated to dryness and the residue was treated with water. The aqueous phase was extracted three times with ethyl acetate. The combined organic phases were washed with brine and concentrated to yield 346 mg of the title compound.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt=1.17 min; MS (ESIpos): m/z=410.2 [M−H]$^+$ Intermediate 70

2-(3-Fluorophenyl)-6-[4-(morpholin-4-yl)phenyl]-3-oxo-2,3-dihydropyridazine-4-carboxylic acid

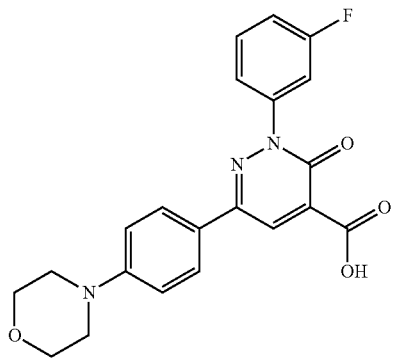 [SMILES: O=C(O)c1cc(-c2ccc(N3CCOCC3)cc2)nn(-c2cccc(F)c2)c1=O]

A mixture of 346 mg intermediate methyl 2-(3-fluorophenyl)-6-[4-(morpholin-4-yl)phenyl]-3-oxo-2,3-dihydropyridazine-4-carboxylate in 13 mL of THF was treated with 1.1 mL sodium hydroxide solution (2N). The reaction mixture was stirred at 50° C. for 1 h. After dilution of the reaction mixture with water the pH was adjusted to 3 with hydrochloric acid (2N). The solids were collected by filtration, washed three times with water and by lyophilization to yield 167 mg of the title compound.

LC-MS (Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): R$_t$=0.61 min; MS (ESIpos): m/z=396.1 [M+H]$^+$ Intermediate 71

Dimethyl {2-[4-(fluoromethyl)phenyl]-2-oxoethyl}malonate

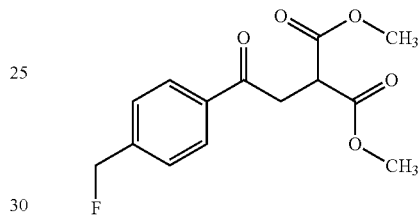

2-Bromo-1-[4-(fluoromethyl)phenyl]ethanone (5.5 g, 23.80 mmol) was dissolved in acetone (120 mL). Dimethyl malonate (6.94 g, 52.50 mmol) and potassium carbonate (5.0 g, 36.18 mmol) were added. It was stirred at rt overnight. The volume was reduced by half under vacuum on a rotavap. Then it was poured into water (550 mL) containing some brine. The layers were separated and the aqueous phase was extracted three times with ethyl acetate (200 mL). The combined organic layers were washed with water and concentrated aqueous sodium chloride solution, dried over magnesium sulfate and concentrated. A second batch prepared under analogues conditions (0.5 g starting material bromidoketone) was added and the volatiles were removed under high vacuum at 70° C. The crude product was purified by flash chromatography (hexane/ethyl acetate) affording 5.59 g (76%) of the title product.

$^1$H-NMR (400 MHz, DMSO-$d_6$): δ [ppm]=3.65 (d, 2H), 3.68 (s, 6H), 3.99 (t, 1H), 5.54 (d, 2H), 7.56 (d, 2H), 8.04 (d, 2H).

Intermediate 72

Methyl 6-[4-(fluoromethyl)phenyl]-3-oxo-2,3,4,5-tetrahydropyridazine-4-carboxylate

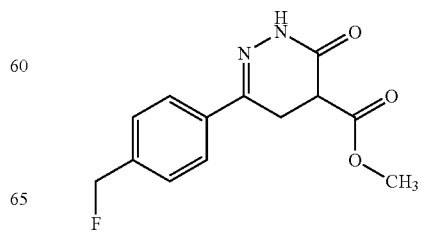

Dimethyl {2-[4-(fluoromethyl)phenyl]-2-oxoethyl}malonate (2.50 g, 8.86 mmol) was dissolved in acetic acid (31.4 mL). A solution of hydrazine in THF (14 mL, 1.0M, 14 mmol) was added at rt. Then, it was stirred at 85° C. overnight. The reaction mixture was cooled down and water (150 mL) was added. It was stirred for a while and the precipitate was filtered off under suction, washed three times with water and dried under vacuum at 50° C. yielding 834 mg (36%) of the title compound which was used without further purification in the next step. After two hour a second batch could be filtered off, washed three times with water and dried under vacuum at 50° C. giving 270 mg (12%) of the title compound which was used without further purification.

$^1$H-NMR (400 MHz, DMSO-$d_6$): δ [ppm]=3.19 (dd, 1H), 3.28 (dd, 1H), 3.67 (s, 3H), 3.75 (dd, 1H), 5.46 (d, 2H), 7.47 (dd, 2H), 7.80 (d, 2H), 11.29 (s, 1H).

Intermediate 73

Methyl 6-[4-(fluoromethyl)phenyl]-3-oxo-2,3-dihydropyridazine-4-carboxylate

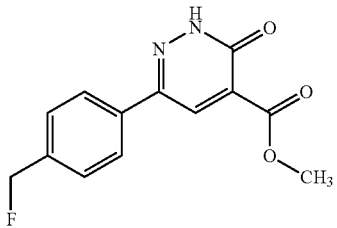 [SMILES: COC(=O)c1cc(-c2ccc(CF)cc2)n[nH]c1=O]

Methyl 6-[4-(fluoromethyl)phenyl]-3-oxo-2,3,4,5-tetrahydropyridazine-4-carboxylate (1.00 g, 3.78 mmol) was dissolved in acetonitrile (20 mL). Copper dichloride (1.60 g, 11.90 mmol) was added and it was stirred for 1 h at 90° C. The reaction mixture was cooled down and poured into water (150 mL). It was stirred for 10 min. The precipitate was filtered by suction, washed three times with water and dried at 50° C. under vacuum to yield 1.02 g of the title compound.

$^1$H-NMR (400 MHz, DMSO-$d_6$): δ [ppm]=3.85 (s, 3H), 5.48 (d, 2H), 7.53 (br d, 2H), 7.93 (br d, 2H), 8.39 (s, 1H), 13.69 (br s, 1H).

Intermediate 74

6-[4-(Fluoromethyl)phenyl]-2-(3-fluorophenyl)-3-oxo-2,3-dihydropyridazine-4-carboxylic acid

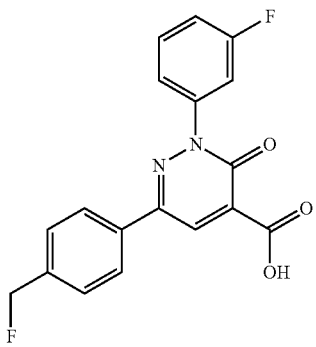 [SMILES: O=C(O)c1cc(-c2ccc(CF)cc2)nn(-c2cccc(F)c2)c1=O]

Step 1: A flask was charged with 2-(3-fluorophenyl)-4,4,5,5-tetramethyl-1,3,2-dioxaborolane (1.02 g, 4.58 mmol) and molecular sieves (800 mg, 0.4 nm, particle size: <50 μm). Acetonitrile (15 mL), methyl 6-[4-(fluoromethyl)phenyl]-3-oxo-2,3-dihydropyridazine-4-carboxylate (0.80 g, 3.05 mmol), triethylamine (851 μL, 6.10 mmol), pyridine (494 μL, 6.10 mmol), and anhydrous copper diacetate (1.20 g, 6.61 mmol) were added. It was stirred at rt overnight. 2-(3-Fluorophenyl)-4,4,5,5-tetramethyl-1,3,2-dioxaborolane (0.5 eq.) and anhydrous copper diacetate (0.25 eq.) were added and stirring at rt was continued for 24 h. Again, 2-(3-fluorophenyl)-4,4,5,5-tetramethyl-1,3,2-dioxaborolane (0.5 eq.) and anhydrous copper diacetate (0.25 eq.) were added and it was stirred at rt over the weekend. 2-(3-Fluorophenyl)-4,4,5,5-tetramethyl-1,3,2-dioxaborolane (0.5 eq.) and anhydrous copper diacetate (0.25 eq.) were added and stirring at rt was continued for 24 h. Water (80 mL) was added and the pH was adjusted to 3 with sodium hydroxide (2N, 11 mL). It was stirred awhile and the precipitate was filtered off and washed three times with water. The solid residue was stirred in methanol (15 mL) and filtered. Again, the remaining solid was stirred in methanol (15 mL) and filtered. The filtrates were combined and concentrated. The residue was dissolved in methanol and filtered over diatomaceous earth, concentrated under vacuum and dried under vaccum at 50° C. overnight to yield 1.495 g of the product containing some impurities from the boronate.

Step 2: The material from the first step was dissolved in THF (50.5 mL). Lithium hydroxide (222 mg) in water (2.7 mL) was added and stirred for 3 h at rt. Water (50 mL) was added and the pH was adjusted to pH 6 (3 mL, 2N HCl). The reaction mixture was concentrated to half of its volume. The precipitate was filtered off under suction, washed with water and dried at 50° C. yielding 340 mg of the title compound which was used without further purification in the next step.

$^1$H-NMR (400 MHz, DMSO-$d_6$): δ [ppm]=5.50 (d, 2H), 7.31-7.34 (m, 1H), 7.41-7.52 (m, 3H), 7.55 (br d, 2H), 8.01 (br d, 2H), 8.58 (br s, 1H).

Intermediate 75

Methyl 6-(4-chloro-3-fluorophenyl)-2-(3,5-difluorophenyl)-3-oxo-2,3,4,5-tetrahydropyridazine-4-carboxylate

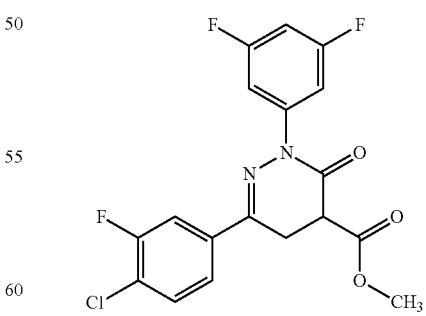

A mixture of 2.35 g dimethyl [2-(4-chloro-3-fluorophenyl)-2-oxoethyl]malonate (intermediate 49) and 1.23 g (3,5-Difluorophenyl)hydrazine in 70 mL acetic acid was stirred at 130° C. for 3 hours and overnight at rt. The solvent was removed in vacuo. The residue was purified by column chromatography (hexanes/ethyl acetate gradient with up to 30% ethyl acetate) to yield 1.5 g of the title compound.

¹H NMR (400 MHz, DMSO-d₆) δ ppm=3.15 (dd, 1H); 3.55 (dd, 1H); 3.78-3.84 (m+s, 4H); 6.75 (tt, 1H); 7.23 (t, 1H); 7.28 (dd, 2H); 7.70 (ddd, 1H); 7.87 (dd, 1H).

Intermediate 76

Methyl 6-(4-chloro-3-fluorophenyl)-2-(3,5-difluorophenyl)-3-oxo-2,3-dihydropyridazine-4-carboxylate

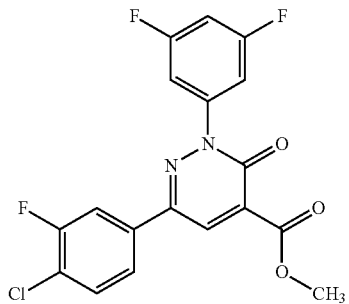 [SMILES: COC(=O)c1cc(-c2ccc(Cl)c(F)c2)nn(-c2cc(F)cc(F)c2)c1=O]

A mixture of 1.5 g methyl 6-(4-chloro-3-fluorophenyl)-2-(3,5-difluorophenyl)-3-oxo-2,3,4,5-tetrahydropyridazine-4-carboxylate (intermediate 75) and 1.52 g copper(II) chloride in 100 mL of acetonitrile was stirred at 90° C. for 3 hours. The solvent was removed in vacuo. The residue was purified by column chromatography (hexanes/ethyl acetate gradient with up to 30% ethyl acetate) to yield 740 mg of the title compound.

¹H NMR (400 MHz, DMSO-d₆) δ ppm=4.01 (s, 3H); 6.91 (tt, 1H); 7.28 (t, 1H); 7.35 (dd, 2H); 7.73 (ddd, 1H); 7.91 (dd, 1H); 8.26 (s, 1H).

Intermediate 77

6-(4-Chloro-3-fluorophenyl)-2-(3,5-difluorophenyl)-3-oxo-2,3-dihydropyridazine-4-carboxylic acid

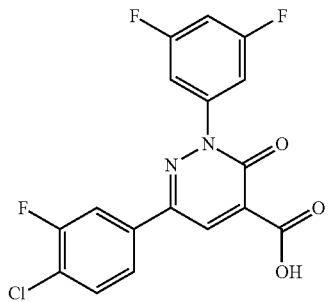 [SMILES: O=C(O)c1cc(-c2ccc(Cl)c(F)c2)nn(-c2cc(F)cc(F)c2)c1=O]

A mixture of 740 mg methyl 6-(4-chloro-3-fluorophenyl)-2-(3,5-difluorophenyl)-3-oxo-2,3-dihydropyridazine-4-carboxylate (intermediate 76) in 40 mL of acetonitrile was treated with 2 mL lithiumhydroxide solution (2N). The reaction mixture was stirred at room temperature for 3 hours. The solids were collected by filtration, washed with water and dried in an oven to yield 700 mg of the title compound.

¹H NMR (400 MHz, DMSO-d₆) δ ppm=7.39 (tt, 1H); 7.49-7.57 (m, 3H); 7.93-8.02 (m, 2H); 8.15 (dd, 1H).

EXPERIMENTAL SECTION—EXAMPLES

The following examples describe the embodiment of the instant invention, not restricting the invention to these examples only.

Example 1

2-(3-Fluorophenyl)-N-(1-hydroxy-3-methylbutan-2-yl)-6-(4-methylphenyl)-3-oxo-2,3-dihydropyridazine-4-carboxamide

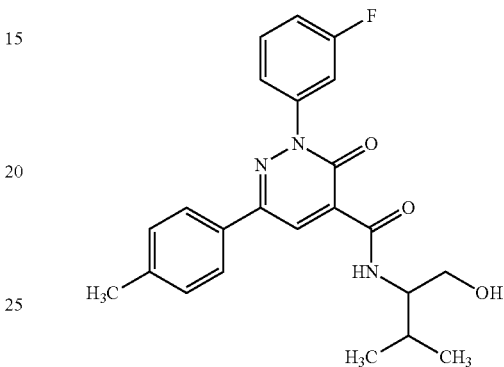

A solution of 150 mg intermediate 4, 100 mg 2-amino-3-methylbutan-1-ol, 270 mg HATU and 0.25 mL ethyldiisopropylamine in 6 mL of DMF was stirred at room temperature for 1 hour. Then the reaction was quenched by water, and the mixture was extracted with ethylacetate. The organic phase was dried over sodium sulfate and evaporated to dryness. The residue was subjected to column chromatography (ethyl acetate/petroleum ether 1:1) to yield 66.2 mg 2-(3-fluorophenyl)-N-(1-hydroxy-3-methylbutan-2-yl)-6-(4-methylphenyl)-3-oxo-2,3-dihydropyridazine-4-carboxamide.

¹H-NMR (300 MHz, DMSO-d₆): δ=0.83-0.93 (m, 6H), 1.93-2.00 (m, 1H), 2.36 (s, 3H), 3.42-3.45 (m, 1H), 3.47-3.56 (m, 1H), 3.82-3.87 (m, 1H), 4.78-4.81 (t, 1H), 7.32-7.41 (m, 3H), 7.53-7.65 (m, 3H), 7.83-7.86 (m, 2H), 8.63 (s, 1H), 9.42-9.45 (d, 1H).

Example 2

2-(3-Fluorophenyl)-N-[(2S)-1-hydroxy-3-methylbutan-2-yl]-6-(4-methylphenyl)-3-oxo-2,3-dihydropyridazine-4-carboxamide

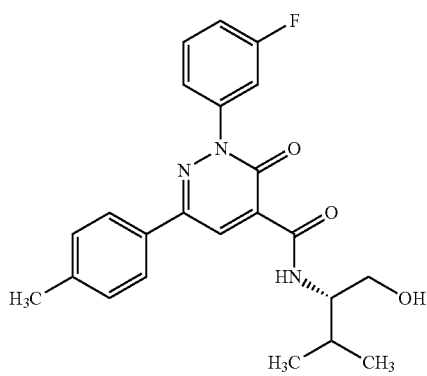 [SMILES: Cc1ccc(-c2cc(C(=O)N[C@H](CO)C(C)C)c(=O)n(-c3cccc(F)c3)n2)cc1]

Route A:

A solution of 150 mg intermediate 4, 95 mg (2S)-2-amino-3-methylbutan-1-ol, 264 mg HATU and 0.24 mL ethyldiisopropylamine in 8 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 120 mg 2-(3-fluorophenyl)-N-[(2S)-1-hydroxy-3-methylbutan-2-yl]-6-(4-methylphenyl)-3-oxo-2,3-dihydropyridazine-4-carboxamide.

Route B:

HPLC-separation of 40 mg 2-(3-fluorophenyl)-N-(1-hydroxy-3-methylbutan-2-yl)-6-(4-methylphenyl)-3-oxo-2,3-dihydropyridazine-4-carboxamide (example 1) on a chiral column (Chiralpak IB 5 μM 250×30 mm, eluent: tert-butylmethylether/methanol 50:50, flow 50 mL/min) yielded 20 mg 2-(3-fluorophenyl)-N-[(2S)-1-hydroxy-3-methylbutan-2-yl]-6-(4-methylphenyl)-3-oxo-2,3-dihydropyridazine-4-carboxamide.

¹H-NMR (300 MHz, DMSO-$d_6$): δ=0.83-0.93 (m, 6H), 1.93-2.00 (m, 1H), 2.36 (s, 3H), 3.42-3.45 (m, 1H), 3.47-3.56 (m, 1H), 3.82-3.87 (m, 1H), 4.78-4.81 (t, 1H), 7.32-7.41 (m, 3H), 7.53-7.65 (m, 3H), 7.83-7.86 (m, 2H), 8.63 (s, 1H), 9.42-9.45 (d, 1H).

Chiral HPLC: Rt=1.2 min

Instrument: Agilent HPLC 1260; column: Chiralpak IB 3 μM 100×4.6 mm; eluent: MTBE (0.1% diethylamine)/methanol 50:50, flow 1.4 mL/min; temperature: 25° C.; DAD scan: 254 nm.

Example 3

2-(3-Fluorophenyl)-N-[(2R)-1-hydroxy-3-methylbutan-2-yl]-6-(4-methylphenyl)-3-oxo-2,3-dihydropyridazine-4-carboxamide

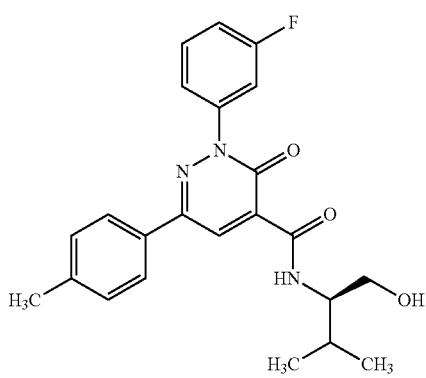 [SMILES: Cc1ccc(-c2cc(C(=O)N[C@@H](CO)C(C)C)c(=O)n(-c3cccc(F)c3)n2)cc1]

The separation of 40 mg example 1 according to example 2, route 2, additionally yielded 20 mg 2-(3-fluorophenyl)-N-[(2R)-1-hydroxy-3-methylbutan-2-yl]-6-(4-methylphenyl)-3-oxo-2,3-dihydropyridazine-4-carboxamide ¹H-NMR (300 MHz, DMSO-$d_6$): δ=0.83-0.93 (m, 6H), 1.93-2.00 (m, 1H), 2.36 (s, 3H), 3.42-3.45 (m, 1H), 3.47-3.56 (m, 1H), 3.82-3.87 (m, 1H), 4.78-4.81 (t, 1H), 7.32-7.41 (m, 3H), 7.53-7.65 (m, 3H), 7.83-7.86 (m, 2H), 8.63 (s, 1H), 9.42-9.45 (d, 1H).

Chiral HPLC: Rt=1.56 min

Instrument: Agilent HPLC 1260; column: Chiralpak IB 3 μM 100×4.6 mm; eluent: MTBE (0.1% diethylamine)/methanol 50:50, flow 1.4 mL/min; temperature: 25° C.; DAD scan: 254 nm.

Example 4

2-(3-Fluorophenyl)-6-(4-methylphenyl)-3-oxo-N-(3,3,3-trifluoro-2-hydroxypropyl)-2,3-dihydropyridazine-4-carboxamide

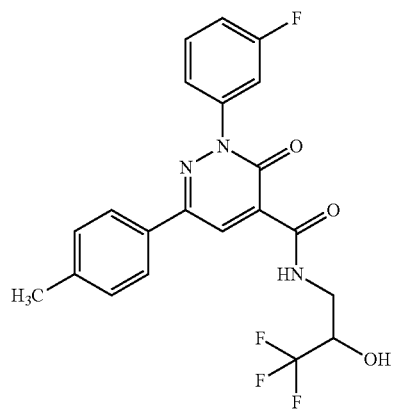

A solution of 100 mg intermediate 4, 80 mg 3-amino-1,1,1-trifluoropropan-2-ol, 176 mg HATU and 0.16 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 80 mg 2-(3-fluorophenyl)-6-(4-methylphenyl)-3-oxo-N-(3,3,3-trifluoro-2-hydroxypropyl)-2,3-dihydropyridazine-4-carboxamide.

¹H-NMR (400 MHz, DMSO-$d_6$): δ=2.37 (s, 3H); 3.42-3.52 (m, 2H); 7.71-3.79 (m, 1H); 4.17-4.27 (m, 1H); 6.66 (d, 1H); 7.34 (d, 2H); 7.38 (ddt, 1H); 7.52-7.57 (m, 1H); 7.58-7.66 (m, 2H); 7.85 (d, 2H); 8.64 (s, 1H); 9.67 (t, 1H).

Example 5

2-(3-Fluorophenyl)-6-(4-methylphenyl)-3-oxo-N-(3,3,3-trifluoro-2-hydroxypropyl)-2,3-dihydropyridazine-4-carboxamide, enantiomer 1

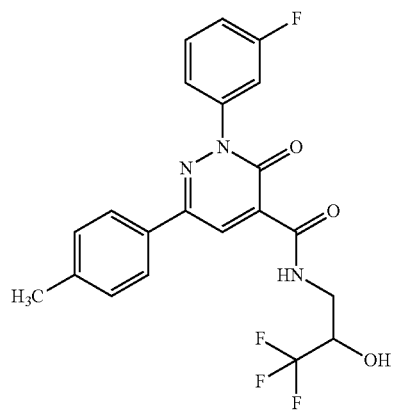 [SMILES: Cc1ccc(-c2cc(C(=O)NCC(O)C(F)(F)F)c(=O)n(-c3cccc(F)c3)n2)cc1]

HPLC-separation of 75 mg 2-(3-fluorophenyl)-6-(4-methylphenyl)-3-oxo-N-(3,3,3-trifluoro-2-hydroxypropyl)-2,3-dihydropyridazine-4-carboxamide (example 4) on a chiral column (Chiralpak IA 5 µM 250×20 mm, eluent: hexanes/ethanol gradient 20-50% ethanol, flow 20 mL/min) yielded 24 mg 2-(3-fluorophenyl)-6-(4-methylphenyl)-3-oxo-N-(3,3,3-trifluoro-2-hydroxypropyl)-2,3-dihydropyridazine-4-carboxamide, enantiomer 1.

$^1$H-NMR (400 MHz, DMSO-$d_6$): δ=2.37 (s, 3H); 3.42-3.52 (m, 2H); 7.71-3.79 (m, 1H); 4.17-4.27 (m, 1H); 6.66 (d, 1H); 7.34 (d, 2H); 7.38 (ddt, 1H); 7.52-7.57 (m, 1H); 7.58-7.66 (m, 2H); 7.85 (d, 2H); 8.64 (s, 1H); 9.67 (t, 1H).

Chiral HPLC: Rt=3.59 min

Instrument: Agilent HPLC 1260; column: Chiralpak IA 3 µM 100×4.6 mm; eluent: hexanes (0.1% diethylamine)/ethanol gradient 20-50% ethanol, flow 1.4 mL/min; temperature: 25° C.; DAD scan: 254 nm.

Example 6

2-(3-Fluorophenyl)-6-(4-methylphenyl)-3-oxo-N-(3,3,3-trifluoro-2-hydroxypropyl)-2,3-dihydropyridazine-4-carboxamide, enantiomer 2

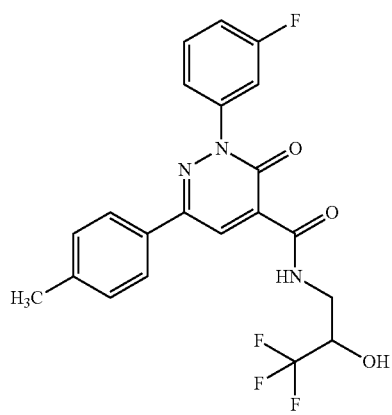 [SMILES: Cc1ccc(-c2cc(C(=O)NCC(O)C(F)(F)F)c(=O)n(-c3cccc(F)c3)n2)cc1]

The separation of 75 mg example 4 according to example 5, additionally yielded 25 mg 2-(3-fluorophenyl)-6-(4-methylphenyl)-3-oxo-N-(3,3,3-trifluoro-2-hydroxypropyl)-2,3-dihydropyridazine-4-carboxamide, enantiomer 2.

$^1$H-NMR (300 MHz, DMSO-$d_6$): δ=2.37 (s, 3H); 3.42-3.52 (m, 2H); 7.71-3.79 (m, 1H); 4.17-4.27 (m, 1H); 6.66 (d, 1H); 7.34 (d, 2H); 7.38 (ddt, 1H); 7.52-7.57 (m, 1H); 7.58-7.66 (m, 2H); 7.85 (d, 2H); 8.64 (s, 1H); 9.67 (t, 1H).

Chiral HPLC: Rt=5.36 min

Instrument: Agilent HPLC 1260; column: Chiralpak IA 3 µM 100×4.6 mm; eluent: hexanes (0.1% diethylamine)/ethanol gradient 20-50% ethanol, flow 1.4 mL/min; temperature: 25° C.; DAD scan: 254 nm.

Example 7

2-(3-Fluorophenyl)-N-(1-hydroxypropan-2-yl)-6-(4-methylphenyl)-3-oxo-2,3-dihydropyridazine-4-carboxamide

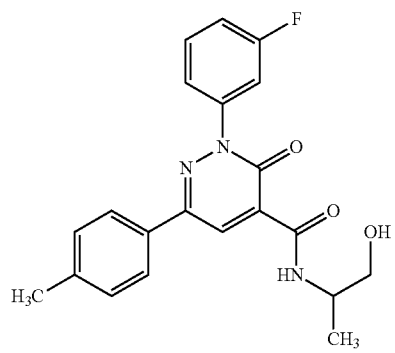 [SMILES: Cc1ccc(-c2cc(C(=O)NC(C)CO)c(=O)n(-c3cccc(F)c3)n2)cc1]

A solution of 100 mg intermediate 4, 70 mg 2-aminopropan-1-ol, 176 mg HATU and 0.23 mL ethyldiisopropylamine in 10 mL of DMF was stirred at room temperature for 14 hour. Then the reaction was quenched by water, and the mixture was extracted with ethylacetate. The organic phase was dried over sodium sulfate and evaporated to dryness. The residue was subjected to column chromatography (ethylacetate/petroleum ether 1:1) to yield 51 mg 2-(3-fluorophenyl)-N-(1-hydroxypropan-2-yl)-6-(4-methylphenyl)-3-oxo-2,3-dihydropyridazine-4-carboxamide.

$^1$H-NMR (300 MHz, DMSO-$d_6$): δ=1.13-1.15 (d, 3H), 2.35 (s, 3H), 3.42 (t, 2H), 3.98-4.04 (t, 1H), 4.90 (m, 1H), 7.48-7.56 (m, 3H), 7.51-7.53 (m, 1H), 7.56-7.62 (m, 2H), 7.93-7.94 (m, 2H), 8.60 (s, 1H), 9.43-9.45 (d, 1H).

Example 8

2-(3-Fluorophenyl)-N-[(2S)-1-hydroxypropan-2-yl]-6-(4-methylphenyl)-3-oxo-2,3-dihydropyridazine-4-carboxamide

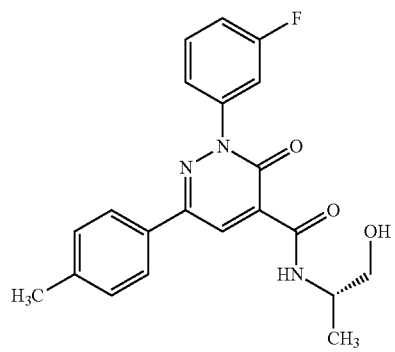 [SMILES: Cc1ccc(-c2cc(C(=O)N[C@@H](C)CO)c(=O)n(-c3cccc(F)c3)n2)cc1]

HPLC-separation of 45 mg 2-(3-fluorophenyl)-N-(1-hydroxypropan-2-yl)-6-(4-methylphenyl)-3-oxo-2,3-dihydropyridazine-4-carboxamide (example 7) on a chiral column (Chiralpak IB 5 µM 250×30 mm, eluent: hexanes/ethanol 70:30, flow 50 mL/min) yielded 10 mg 2-(3-fluorophenyl)-N-[(2S)-1-hydroxypropan-2-yl]-6-(4-methylphenyl)-3-oxo-2,3-dihydropyridazine-4-carboxamide.

¹H-NMR (400 MHz, DMSO-d$_6$): δ=1.13-1.15 (d, 3H), 2.35 (s, 3H), 3.42 (t, 2H), 3.98-4.04 (t, 1H), 4.90 (m, 1H), 7.48-7.56 (m, 3H), 7.51-7.53 (m, 1H), 7.56-7.62 (m, 2H), 7.93-7.94 (m, 2H), 8.60 (s, 1H), 9.43-9.45 (d, 1H).

Chiral HPLC: Rt=5.82 min

Instrument: Agilent HPLC 1260; column: Chiralpak IB 3 μM 100×4.6 mm; eluent: hexanes (0.1% diethylamine)/ethanol gradient 5-50% ethanol, flow 1.4 mL/min; temperature: 25° C.; DAD scan: 254 nm.

Example 9

2-(3-Fluorophenyl)-N-[(2R)-1-hydroxypropan-2-yl]-6-(4-methylphenyl)-3-oxo-2,3-dihydropyridazine-4-carboxamide

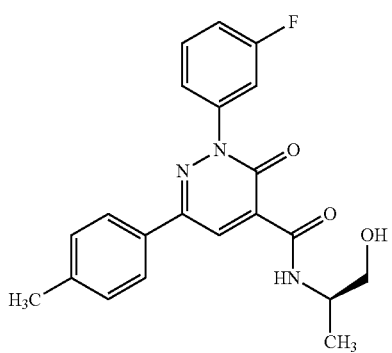 [SMILES: Cc1ccc(-c2cc(C(=O)N[C@H](C)CO)c(=O)n(-c3cccc(F)c3)n2)cc1]

The separation of 45 mg example 7, according to example 8, additionally yielded 10 mg 2-(3-fluorophenyl)-N-[(2R)-1-hydroxypropan-2-yl]-6-(4-methylphenyl)-3-oxo-2,3-dihydropyridazine-4-carboxamide.

¹H-NMR (300 MHz, DMSO-d$_6$): δ=1.13-1.15 (d, 3H), 2.35 (s, 3H), 3.42 (t, 2H), 3.98-4.04 (t, 1H), 4.90 (m, 1H), 7.48-7.56 (m, 3H), 7.51-7.53 (m, 1H), 7.56-7.62 (m, 2H), 7.93-7.94 (m, 2H), 8.60 (s, 1H), 9.43-9.45 (d, 1H).

Chiral HPLC: Rt=6.55 min

Instrument: Agilent HPLC 1260; column: Chiralpak IB 3 μM 100×4.6 mm; eluent: hexanes (0.1% diethylamine)/ethanol gradient 5-50% ethanol, flow 1.4 mL/min; temperature: 25° C.; DAD scan: 254 nm.

Example 10

2-(3-Fluorophenyl)-N-(2-hydroxy-3-methylbutyl)-6-(4-methylphenyl)-3-oxo-2,3-dihydropyridazine-4-carboxamide

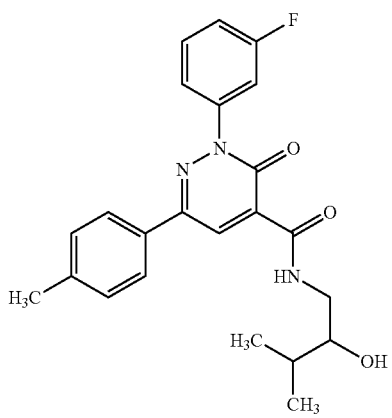 [SMILES: Cc1ccc(-c2cc(C(=O)NCC(O)C(C)C)c(=O)n(-c3cccc(F)c3)n2)cc1]

A solution of 100 mg intermediate 4, 64 mg 1-amino-3-methylbutan-2-ol, 176 mg HATU and 0.16 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 50 mg 2-(3-fluorophenyl)-N-(2-hydroxy-3-methylbutyl)-6-(4-methylphenyl)-3-oxo-2,3-dihydropyridazine-4-carboxamide.

¹H-NMR (400 MHz, DMSO-d$_6$): δ=0.88 (t, 6H); 1.61 (sp, 1H); 2.37 (s, 3H); 3.15-3.25 (m, 1H); 3.49-3.57 (m, 1H); 4.90 (d, 1H); 7.35 (d, 2H); 7.37 (ddt, 1H); 7.54 (ddd, 1H); 7.58-7.65 (m, 2H); 7.85 (d, 2H); 8.62 (s, 1H); 9.57 (t, 1H).

Example 11

2-(3-Fluorophenyl)-N-(2-hydroxy-3-methylbutyl)-6-(4-methylphenyl)-3-oxo-2,3-dihydropyridazine-4-carboxamide, enantiomer 1

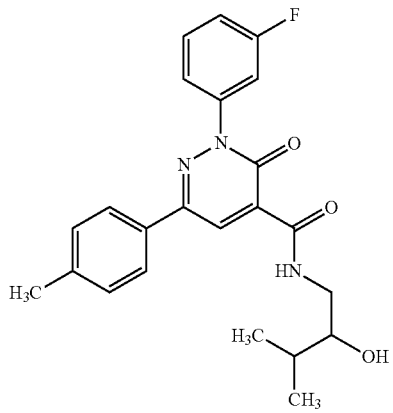 [SMILES: Cc1ccc(-c2cc(C(=O)NCC(O)C(C)C)c(=O)n(-c3cccc(F)c3)n2)cc1]

HPLC-separation of 45 mg 2-(3-fluorophenyl)-N-(2-hydroxy-3-methylbutyl)-6-(4-methylphenyl)-3-oxo-2,3-dihydropyridazine-4-carboxamide (example 10) on a chiral column (Chiralpak IB 5 μM 250×30 mm, eluent: hexanes/ethanol gradient with 20-50% ethanol, flow 40 mL/min) yielded 17 mg 2-(3-fluorophenyl)-N-(2-hydroxy-3-methylbutyl)-6-(4-methylphenyl)-3-oxo-2,3-dihydropyridazine-4-carboxamide, enantiomer 1.

¹H-NMR (400 MHz, DMSO-d$_6$): δ=0.88 (t, 6H); 1.61 (sp, 1H); 2.37 (s, 3H); 3.15-3.25 (m, 1H); 3.49-3.57 (m, 1H); 4.90 (d, 1H); 7.35 (d, 2H); 7.37 (ddt, 1H); 7.54 (ddd, 1H); 7.58-7.65 (m, 2H); 7.85 (d, 2H); 8.62 (s, 1H); 9.57 (t, 1H).

Chiral HPLC: Rt=5.40 min

Instrument: Agilent HPLC 1260; column: Chiralpak IB 3 μM 100×4.6 mm; eluent: hexanes (0.1% diethylamine)/ethanol gradient 20-50% ethanol, flow 1.4 mL/min; temperature: 25° C.; DAD scan: 254 nm.

Example 12

2-(3-Fluorophenyl)-N-(2-hydroxy-3-methylbutyl)-6-(4-methylphenyl)-3-oxo-2,3-dihydropyridazine-4-carboxamide, enantiomer 2

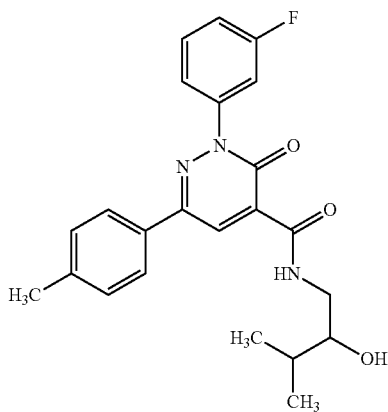 [SMILES: Cc1ccc(-c2cc(C(=O)NCC(O)C(C)C)c(=O)n(-c3cccc(F)c3)n2)cc1]

The separation of 45 mg example 10, according to example 11, additionally yielded 17 mg 2-(3-fluorophenyl)-N-(2-hydroxy-3-methylbutyl)-6-(4-methylphenyl)-3-oxo-2,3-dihydropyridazine-4-carboxamide, enantiomer 2.

$^1$H-NMR (300 MHz, DMSO-$d_6$): δ=0.88 (t, 6H); 1.61 (sp, 1H); 2.37 (s, 3H); 3.15-3.25 (m, 1H); 3.49-3.57 (m, 1H); 4.90 (d, 1H); 7.35 (d, 2H); 7.37 (ddt, 1H); 7.54 (ddd, 1H); 7.58-7.65 (m, 2H); 7.85 (d, 2H); 8.62 (s, 1H); 9.57 (t, 1H).

Chiral HPLC: Rt=6.34 min

Instrument: Agilent HPLC 1260; column: Chiralpak IB 3 µM 100×4.6 mm; eluent: hexanes (0.1% diethylamine)/ethanol gradient 20-50% ethanol, flow 1.4 mL/min; temperature: 25° C.; DAD scan: 254 nm.

Example 13

2-(3-Fluorophenyl)-N-(2-hydroxypropyl)-6-(4-methyl phenyl)-3-oxo-2,3-dihydropyridazine-4-carboxamide

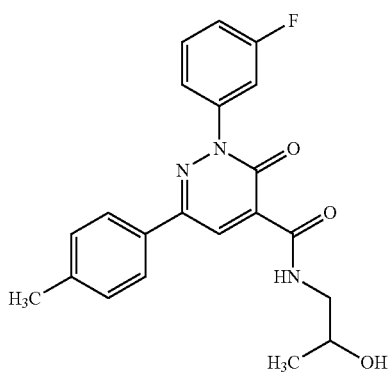 [SMILES: Cc1ccc(-c2cc(C(=O)NCC(C)O)c(=O)n(-c3cccc(F)c3)n2)cc1]

A solution of 90 mg intermediate 4, 42 mg 1-aminopropan-2-ol, 158 mg HATU and 0.15 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 50 mg 2-(3-fluorophenyl)-N-(2-hydroxypropyl)-6-(4-methylphenyl)-3-oxo-2,3-dihydropyridazine-4-carboxamide.

$^1$H-NMR (400 MHz, DMSO-$d_6$): δ=1.08 (d, 3H); 2.37 (s, 3H); 3.20 (ddd, 1H); 3.41 (ddd, 1H); 3.74-3.82 (m, 1H); 4.89 (d, 1H); 7.34 (d, 2H); 7.37 (ddt, 1H); 7.52-7.57 (m, 1H); 7.58-7.65/m, 2H); 7.85 (d, 1H); 8.62 (s, 1H); 9.55 (t, 1H).

Example 14

2-(3-Fluorophenyl)-N-(2-hydroxypropyl)-6-(4-methylphenyl)-3-oxo-2,3-dihydropyridazine-4-carboxamide, Enantiomer 1

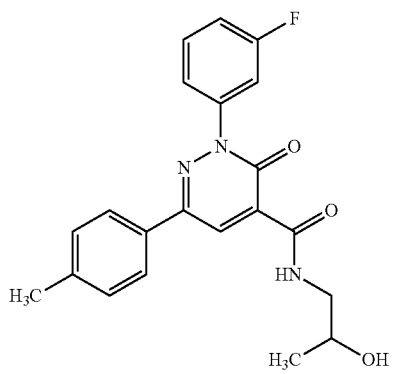 [SMILES: Cc1ccc(-c2cc(C(=O)NCC(C)O)c(=O)n(-c3cccc(F)c3)n2)cc1]

HPLC-separation of 45 mg 2-(3-fluorophenyl)-N-(2-hydroxypropyl)-6-(4-methylphenyl)-3-oxo-2,3-dihydropyridazine-4-carboxamide (example 13) on a chiral column (Chiralpak IA 5 µM 250×20 mm, eluent: hexanes/2-propanol gradient with 20-50% 2-propanol, flow 20 mL/min) yielded 12 mg 2-(3-fluorophenyl)-N-(2-hydroxypropyl)-6-(4-methylphenyl)-3-oxo-2,3-dihydropyridazine-4-carboxamide, enantiomer 1.

$^1$H-NMR (400 MHz, DMSO-$d_6$): δ=1.08 (d, 3H); 2.37 (s, 3H); 3.20 (ddd, 1H); 3.41 (ddd, 1H); 3.74-3.82 (m, 1H); 4.89 (d, 1H); 7.34 (d, 2H); 7.37 (ddt, 1H); 7.52-7.57 (m, 1H); 7.58-7.65/m, 2H); 7.85 (d, 1H); 8.62 (s, 1H); 9.55 (t, 1H).

Chiral HPLC: Rt=4.97 min

Instrument: Agilent HPLC 1260; column: Chiralpak IA 3 µM 100×4.6 mm; eluent: hexanes (0.1% diethylamine)/2-propanol gradient 20-50% 2-propanol, flow 1.4 mL/min; temperature: 25° C.; DAD scan: 254 nm.

Example 15

2-(3-Fluorophenyl)-N-(2-hydroxypropyl)-6-(4-methylphenyl)-3-oxo-2,3-dihydropyridazine-4-carboxamide, Enantiomer 2

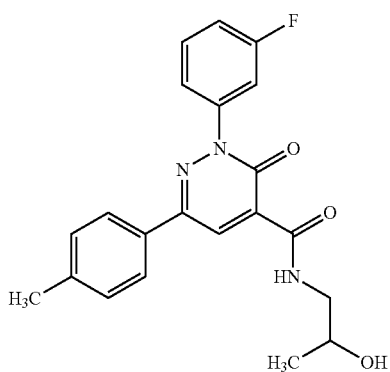 [SMILES: Cc1ccc(-c2cc(C(=O)NCC(C)O)c(=O)n(-c3cccc(F)c3)n2)cc1]

The separation of 45 mg example 13, according to example 14, additionally yielded 12 mg 2-(3-fluorophenyl)-N-(2-hydroxypropyl)-6-(4-methylphenyl)-3-oxo-2,3-dihydropyridazine-4-carboxamide, enantiomer 2.

$^1$H-NMR (300 MHz, DMSO-$d_6$): δ=1.08 (d, 3H); 2.37 (s, 3H); 3.20 (ddd, 1H); 3.41 (ddd, 1H); 3.74-3.82 (m, 1H); 4.89 (d, 1H); 7.34 (d, 2H); 7.37 (ddt, 1H); 7.52-7.57 (m, 1H); 7.58-7.65/m, 2H); 7.85 (d, 1H); 8.62 (s, 1H); 9.55 (t, 1H).

Chiral HPLC: Rt=6.31 min

Instrument: Agilent HPLC 1260; column: Chiralpak IA 3 μM 100×4.6 mm; eluent: hexanes (0.1% diethylamine)/2-propanol gradient 20-50% 2-propanol, flow 1.4 mL/min; temperature: 25° C.; DAD scan: 254 nm.

Example 16

2-(3-Fluorophenyl)-N-(2-hydroxy-3-methoxypropyl)-6-(4-methylphenyl)-3-oxo-2,3-dihydropyridazine-4-carboxamide

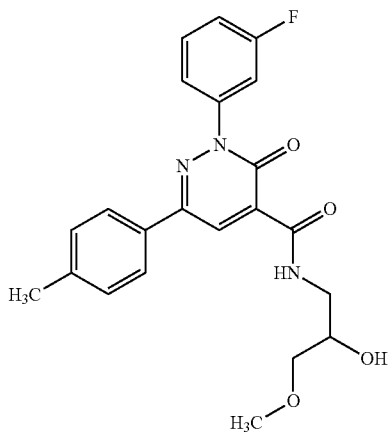 [SMILES: COCC(O)CNC(=O)c1cc(-c2ccc(C)cc2)nn(-c2cccc(F)c2)c1=O]

A solution of 110 mg intermediate 4, 71 mg 1-amino-3-methoxypropan-2-ol, 193 mg HATU and 0.18 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 32 mg 2-(3-fluorophenyl)-N-(2-hydroxy-3-methoxypropyl)-6-(4-methylphenyl)-3-oxo-2,3-dihydropyridazine-4-carboxamide.

$^1$H-NMR (400 MHz, DMSO-$d_6$): δ=2.37 (s, 3H); 3.22-3.32 (m+s, 6H); 3.53 (ddd, 1H); 3.71-3.80 (m, 1H); 5.16 (d, 1H); 7.34 (d, 2H); 7.37 (ddt, 1H); 7.52-7.57 (m, 1H); 7.58-7.65 (m, 2H); 7.85 (d, 2H); 8.62 (s, 1H); 9.56 (t, 1H).

Example 17

2-(3-Fluorophenyl)-N-(2-hydroxy-3-methoxypropyl)-6-(4-methylphenyl)-3-oxo-2,3-dihydropyridazine-4-carboxamide, Enantiomer 1

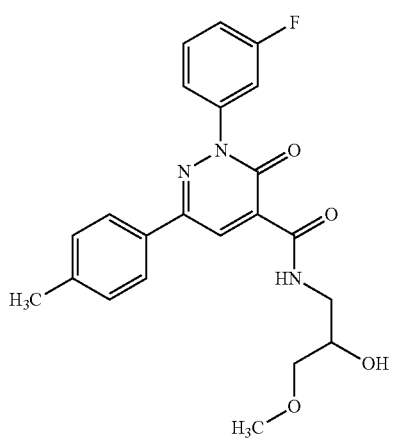 [SMILES: COCC(O)CNC(=O)c1cc(-c2ccc(C)cc2)nn(-c2cccc(F)c2)c1=O]

HPLC-separation of 30 mg 2-(3-fluorophenyl)-N-(2-hydroxy-3-methoxypropyl)-6-(4-methylphenyl)-3-oxo-2,3-dihydropyridazine-4-carboxamide (example 16) on a chiral column (Chiralpak IA 5 μM 250×30 mm, eluent: tert-Butylmethylether/acetonitril 50-50%, flow 40 mL/min) yielded 10 mg 2-(3-fluorophenyl)-N-(2-hydroxy-3-methoxypropyl)-6-(4-methylphenyl)-3-oxo-2,3-dihydropyridazine-4-carboxamide, enantiomer 1.

$^1$H-NMR (400 MHz, DMSO-$d_6$): δ=2.37 (s, 3H); 3.22-3.32 (m+s, 6H); 3.53 (ddd, 1H); 3.71-3.80 (m, 1H); 5.16 (d, 1H); 7.34 (d, 2H); 7.37 (ddt, 1H); 7.52-7.57 (m, 1H); 7.58-7.65 (m, 2H); 7.85 (d, 2H); 8.62 (s, 1H); 9.56 (t, 1H).

Chiral HPLC: Rt=2.08 min

Instrument: Agilent HPLC 1260; column: Chiralpak IA 3 μM 100×4.6 mm; eluent: tert-Butylmethylether (0.1% diethylamine)/acetonitril 50-50%, flow 1.4 mL/min; temperature: 25° C.; DAD scan: 254 nm.

Example 18

2-(3-Fluorophenyl)-N-(2-hydroxy-3-methoxypropyl)-6-(4-methylphenyl)-3-oxo-2,3-dihydropyridazine-4-carboxamide, Enantiomer 2

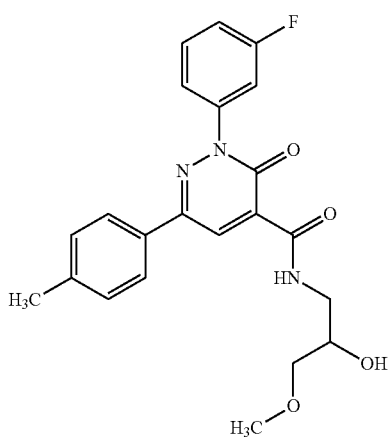 [SMILES: COCC(O)CNC(=O)c1cc(-c2ccc(C)cc2)nn(-c2cccc(F)c2)c1=O]

The separation of 30 mg example 16, according to example 17, additionally yielded 10 mg 2-(3-fluorophenyl)-N-(2-hydroxy-3-methoxypropyl)-6-(4-methylphenyl)-3-oxo-2,3-dihydropyridazine-4-carboxamide, enantiomer 2.

$^1$H-NMR (300 MHz, DMSO-$d_6$): δ=2.37 (s, 3H); 3.22-3.32 (m+s, 6H); 3.53 (ddd, 1H); 3.71-3.80 (m, 1H); 5.16 (d, 1H); 7.34 (d, 2H); 7.37 (ddt, 1H); 7.52-7.57 (m, 1H); 7.58-7.65 (m, 2H); 7.85 (d, 2H); 8.62 (s, 1H); 9.56 (t, 1H).

Chiral HPLC: Rt=3.63 min

Instrument: Agilent HPLC 1260; column: Chiralpak IA 3 µM 100×4.6 mm; eluent: tert-Butylmethylether (0.1% diethylamine)/acetonitril 50-50%, flow 1.4 mL/min; temperature: 25° C.; DAD scan: 254 nm.

Example 19

2-(3-Fluorophenyl)-N-(2-hydroxyethyl)-6-(4-methylphenyl)-3-oxo-2,3-dihydropyridazine-4-carboxamide

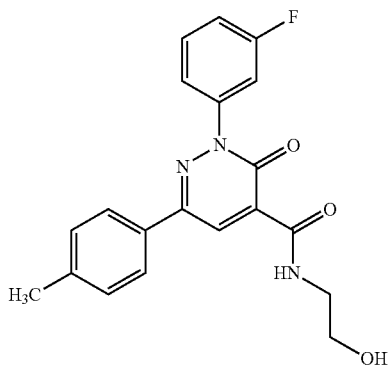 [SMILES: Cc1ccc(-c2cc(C(=O)NCCO)c(=O)n(-c3cccc(F)c3)n2)cc1]

A solution of 150 mg intermediate 5, 54 mg 2-aminoethanol and 0.06 mL triethylamine in 20 mL dichloromethane was stirring under ice-water bath for 10 min. Then the reaction was quenched by addition of water and the mixture was extracted with dichloromethane. The organic phase was dried over sodium sulfate and evaporated to dryness. The residue was subjected to flash chromatography (ethylacetate/petroleum ether 1:3) to yield 39 mg 2-(3-fluorophenyl)-N-(2-hydroxyethyl)-6-(4-methylphenyl)-3-oxo-2,3-dihydropyridazine-4-carboxamide.

$^1$H-NMR (300 MHz, DMSO-$d_6$): δ=3.31 (s, 3H), 3.39-3.43 (t, 2H), 3.50-3.54 (m, 2H), 4.83-4.86 (t, 1H), 7.28-7.38 (m, 3H), 7.52-7.62 (m, 3H), 7.82-8.19 (m, 2H), 8.60 (s, 1H), 9.50-9.53 (t, 1H).

Example 20

6-(4-Chlorophenyl)-2-(3-fluorophenyl)-N-[(2S)-1-hydroxy-3-methylbutan-2-yl]-3-oxo-2,3-dihydropyridazine-4-carboxamide

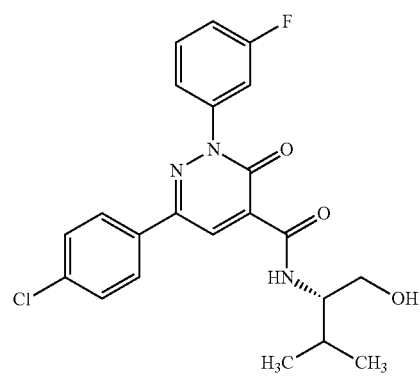 [SMILES: CC(C)[C@@H](CO)NC(=O)c1cc(-c2ccc(Cl)cc2)nn(-c2cccc(F)c2)c1=O]

A solution of 80 mg intermediate 17, 48 mg (2S)-2-amino-3-methylbutan-1-ol, 132 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 12 mg 6-(4-chlorophenyl)-2-(3-fluorophenyl)-N-[(2S)-1-hydroxy-3-methylbutan-2-yl]-3-oxo-2,3-dihydropyridazine-4-carboxamide.

$^1$H-NMR (400 MHz, DMSO-$d_6$): δ=0.87-0.94 (m, 6H); 1.90-2.03 (m, 1H); 3.40-3.48 (m, 1H); 3.51-3.58 (m, 1H); 3.81-3.89 (m, 1H); 4.80 (t, 1H); 7.39 (ddt, 1H); 7.53-7.65 (m, 5H); 8.00 (d, 2H); 8.66 (s, 1H); 9.40 (d, 1H).

Example 21

6-(4-Chlorophenyl)-2-(3-fluorophenyl)-N-[(2S)-1-hydroxybutan-2-yl]-3-oxo-2,3-dihydropyridazine-4-carboxamide

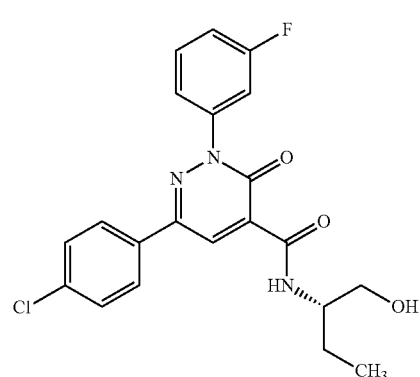

A solution of 100 mg intermediate 17, 52 mg (2S)-2-aminobutan-1-ol, 165 mg HATU and 0.15 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 8 mg 6-(4-chlorophenyl)-2-(3-fluorophenyl)-N-[(2S)-1-hydroxybutan-2-yl]-3-oxo-2,3-dihydropyridazine-4-carboxamide.

$^1$H-NMR (400 MHz, DMSO-$d_6$): δ=0.85-0.91 (m, 3H); 1.43-1.54 (m, 1H); 1.60-1.70 (m, 1H); 3.39-3.46 (m, 1H); 3.48-3.55 (m, 1H); 3.85-3.93 (m, 1H); 4.86 (t, 1H); 7.39 (ddt, 1H); 7.53-7.65 (m, 5H); 8.00 (d, 2H); 8.65 (s, 1H); 9.37 (d, 1H).

Example 22

6-(4-Chlorophenyl)-2-(3-fluorophenyl)-N-(1-hydroxypropan-2-yl)-3-oxo-2,3-dihydropyridazine-4-carboxamide

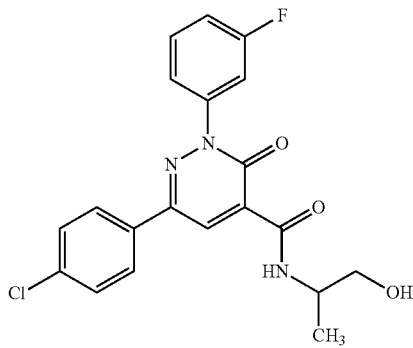 [SMILES: CC(CO)NC(=O)c1cc(-c2ccc(Cl)cc2)nn(-c2cccc(F)c2)c1=O]

166 mg oxalylchloride were slowly added to a solution of 300 mg intermediate 17 in 20 mL of dichloromethane and 32 mg N,N-dimethylformamide. The reaction mixture was stirred at room temperature for 1 h. The mixture was evaporated to dryness to give 450 mg crude 6-(4-chlorophenyl)-2-(3-fluorophenyl)-3-oxo-2,3-dihydropyridazine-4-carbonyl chloride. A solution of 200 mg of this material, 83 mg 2-aminopropan-1-ol and 0.08 mL triethylamine in 20 mL dichloromethane was stirring under ice-water bath for 10 min. Then the reaction was quenched by addition of water and the mixture was extracted with dichloromethane. The organic phase was dried over sodium sulfate and evaporated to dryness. The residue was subjected to flash chromatography (petroleum ether/ethylacetate 4:1) to yield 75 mg 6-(4-chlorophenyl)-2-(3-fluorophenyl)-N-(1-hydroxypropan-2-yl)-3-oxo-2,3-dihydropyridazine-4-carboxamide.

$^1$H-NMR (400 MHz, DMSO-$d_6$): δ=1.16 (d, 3H); 3.40-3.49 (m, 2H); 3.99-4.07 (m, 1H); 4.94 (t, 1H); 7.38 (ddt, 1H); 7.52-7.65 (m, 5H); 7.99 (d, 2H); 8.65 (s, 1H); 9.44 (d, 1H).

Example 23

6-(4-Chlorophenyl)-2-(3-fluorophenyl)-N-[(2S)-1-hydroxypropan-2-yl]-3-oxo-2,3-dihydropyridazine-4-carboxamide

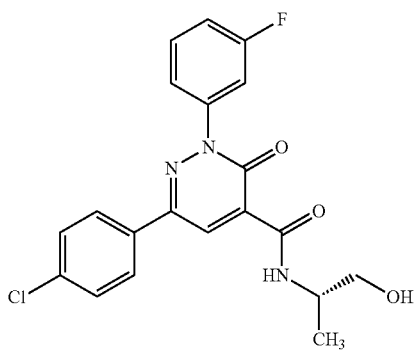 [SMILES: C[C@@H](CO)NC(=O)c1cc(-c2ccc(Cl)cc2)nn(-c2cccc(F)c2)c1=O]

Route A:

HPLC-separation of 60 mg 6-(4-Chlorophenyl)-2-(3-fluorophenyl)-N-(1-hydroxypropan-2-yl)-3-oxo-2,3-dihydropyridazine-4-carboxamide (example 22) on a chiral column (Chiralpak IC 5 µM 250×30 mm, eluent: ethanol/methanol 50-50%, flow 50 mL/min) yielded 22 mg 6-(4-Chlorophenyl)-2-(3-fluorophenyl)-N-[(2S)-1-hydroxypropan-2-yl]-3-oxo-2,3-dihydropyridazine-4-carboxamide.

Route B:

A solution of 580 mg intermediate 17, 253 mg (2S)-2-aminopropan-1-ol, 960 mg HATU and 0.88 mL ethyldiisopropylamine in 30 mL of DMF was stirred at room temperature for 90 min. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 3% methanol) to yield 560 mg 6-(4-chlorophenyl)-2-(3-fluorophenyl)-N-[(2S)-1-hydroxypropan-2-yl]-3-oxo-2,3-dihydropyridazine-4-carboxamide.

$^1$H-NMR (400 MHz, DMSO-$d_6$): δ=1.16 (d, 3H); 3.40-3.49 (m, 2H); 3.99-4.07 (m, 1H); 4.94 (t, 1H); 7.38 (ddt, 1H); 7.52-7.65 (m, 5H); 7.99 (d, 2H); 8.65 (s, 1H); 9.44 (d, 1H).

Chiral HPLC: Rt=2.74 min

Instrument: Agilent HPLC 1260; column: Chiralpak IC 3 µM 100×4.6 mm; eluent: ethanol (0.1% diethylamine)/methanol 50:50, flow 1.4 mL/min; temperature: 25° C.; DAD scan: 254 nm.

Example 24

6-(4-Chlorophenyl)-2-(3-fluorophenyl)-N-[(2R)-1-hydroxypropan-2-yl]-3-oxo-2,3-dihydropyridazine-4-carboxamide

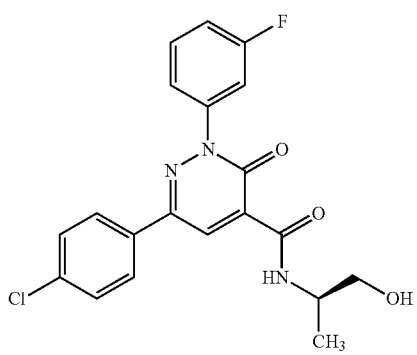 [SMILES: C[C@H](CO)NC(=O)c1cc(-c2ccc(Cl)cc2)nn(-c2cccc(F)c2)c1=O]

The separation of 60 mg example 22, according to example 23, additionally yielded 22 mg 6-(4-chlorophenyl)-2-(3-fluorophenyl)-N-[(2R)-1-hydroxypropan-2-yl]-3-oxo-2,3-dihydropyridazine-4-carboxamide.

$^1$H-NMR (300 MHz, DMSO-d$_6$): δ=1.16 (d, 3H); 3.40-3.49 (m, 2H); 3.99-4.07 (m, 1H); 4.94 (t, 1H); 7.38 (ddt, 1H); 7.52-7.65 (m, 5H); 7.99 (d, 2H); 8.65 (s, 1H); 9.44 (d, 1H).

Chiral HPLC: Rt=2.22 min

Instrument: Agilent HPLC 1260; column: Chiralpak IC 3 µM 100×4.6 mm; eluent: ethanol (0.1% diethylamine)/methanol 50:50, flow 1.4 mL/min; temperature: 25° C.; DAD scan: 254 nm.

Example 25

6-(4-Chlorophenyl)-2-(3-fluorophenyl)-3-oxo-N-(3,3,3-trifluoro-2-hydroxypropyl)-2,3-dihydropyridazine-4-carboxamide

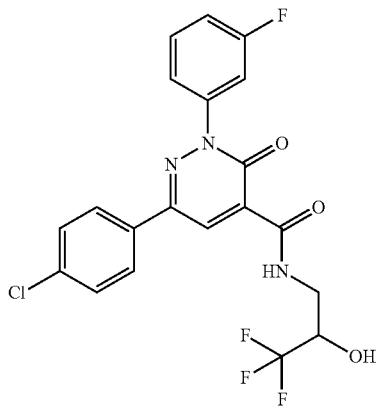 [SMILES: O=C(NCC(O)C(F)(F)F)c1cc(-c2ccc(Cl)cc2)nn(-c2cccc(F)c2)c1=O]

A solution of 150 mg intermediate 17, 112 mg 3-amino-1,1,1-trifluoropropan-2-ol, 248 mg HATU and 0.23 mL ethyldiisopropylamine in 7.5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 130 mg 6-(4-chlorophenyl)-2-(3-fluorophenyl)-3-oxo-N-(3,3,3-trifluoro-2-hydroxypropyl)-2,3-dihydropyridazine-4-carboxamide.

$^1$H-NMR (400 MHz, DMSO-d$_6$): δ=3.47 (ddd, 1H); 3.75 (ddd, 1H); 4.17-4.27 (m, 1H); 6.66 (d, 1H); 7.39 (ddt, 1H); 7.53-7.66 (m, 5H); 8.00 (d, 2H); 8.67 (s, 1H); 9.64 (t, 1H).

Example 26

6-(4-Chlorophenyl)-2-(3-fluorophenyl)-3-oxo-N-(3,3,3-trifluoro-2-hydroxypropyl)-2,3-dihydropyridazine-4-carboxamide, Enantiomer 1

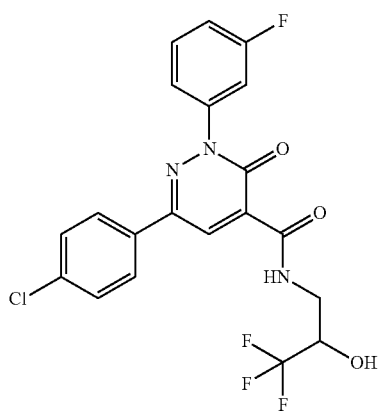 [SMILES: O=C(NCC(O)C(F)(F)F)c1cc(-c2ccc(Cl)cc2)nn(-c2cccc(F)c2)c1=O]

HPLC-separation of 130 mg 6-(4-Chlorophenyl)-2-(3-fluorophenyl)-3-oxo-N-(3,3,3-trifluoro-2-hydroxypropyl)-2,3-dihydropyridazine-4-carboxamide (example 25) on a chiral column (Chiralpak IA 5 µM 250×20 mm, eluent: hexanes/ethanol gradient 20-50% ethanol, flow 20 mL/min) yielded 65 mg 6-(4-chlorophenyl)-2-(3-fluorophenyl)-3-oxo-N-(3,3,3-trifluoro-2-hydroxypropyl)-2,3-dihydropyridazine-4-carboxamide, Enantiomer 1.

$^1$H-NMR (400 MHz, DMSO-d$_6$): δ=3.47 (ddd, 1H); 3.75 (ddd, 1H); 4.17-4.27 (m, 1H); 6.66 (d, 1H); 7.39 (ddt, 1H); 7.53-7.66 (m, 5H); 8.00 (d, 2H); 8.67 (s, 1H); 9.64 (t, 1H).

Chiral HPLC: Rt=6.4 min

Instrument: Agilent HPLC 1260; column: Chiralpak IA 3 µM 100×4.6 mm; eluent: hexanes (0.1% diethylamine)/ethanol gradient 5-50% ethanol, flow 1.4 mL/min; temperature: 25° C.; DAD scan: 254 nm.

Example 27

6-(4-Chlorophenyl)-2-(3-fluorophenyl)-3-oxo-N-(3,3,3-trifluoro-2-hydroxypropyl)-2,3-dihydropyridazine-4-carboxamide. Enantiomer 2

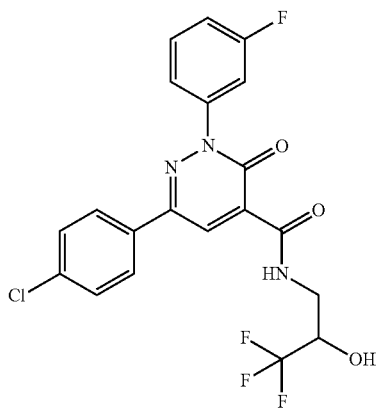 [SMILES: O=C(NCC(O)C(F)(F)F)c1cc(-c2ccc(Cl)cc2)nn(-c2cccc(F)c2)c1=O]

The separation of 130 mg example 25, according to example 26, additionally yielded 65 mg 6-(4-chlorophenyl)-2-(3-fluorophenyl)-3-oxo-N-(3,3,3-trifluoro-2-hydroxypropyl)-2,3-dihydropyridazine-4-carboxamide, Enantiomer 2.

$^1$H-NMR (300 MHz, DMSO-d$_6$): δ=3.47 (ddd, 1H); 3.75 (ddd, 1H); 4.17-4.27 (m, 1H); 6.66 (d, 1H); 7.39 (ddt, 1H); 7.53-7.66 (m, 5H); 8.00 (d, 2H); 8.67 (s, 1H); 9.64 (t, 1H).

Chiral HPLC: Rt=8.3 min

Instrument: Agilent HPLC 1260; column: Chiralpak IA 3 µM 100×4.6 mm; eluent: hexanes (0.1% diethylamine)/ethanol gradient 5-50% ethanol, flow 1.4 mL/min; temperature: 25° C.; DAD scan: 254 nm.

Example 28

6-(4-Chlorophenyl)-2-(3-fluorophenyl)-N-(2-hydroxy-3-methylbutyl)-3-oxo-2,3-dihydropyridazine-4-carboxamide

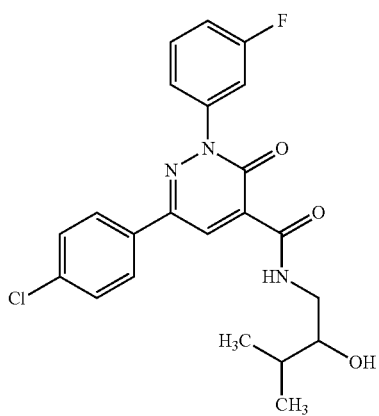

A solution of 100 mg intermediate 17, 60 mg 1-amino-3-methylbutan-2-ol, 165 mg HATU and 0.15 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 50 mg 6-(4-Chlorophenyl)-2-(3-fluorophenyl)-N-(2-hydroxy-3-methylbutyl)-3-oxo-2,3-dihydropyridazine-4-carboxamide.

$^1$H-NMR (400 MHz, DMSO-d$_6$): δ=0.85-0-91 (m, 6H); 1.56-1.67 (m, 1H); 3.16-3.26 (m, 1H); 3.53 (ddd, 1H); 4.90 (d, 1H); 7.38 (ddt, 1H); 7.53-7.66 (m, 5H); 7.99 (d, 2H); 8.65 (s, 1H); 9.54 (t, 1H).

Example 29

6-(4-Chlorophenyl)-2-(3-fluorophenyl)-N-(2-hydroxy-3-methylbutyl]-3-oxo-2,3-dihydropyridazine-4-carboxamide, Enantiomer 1

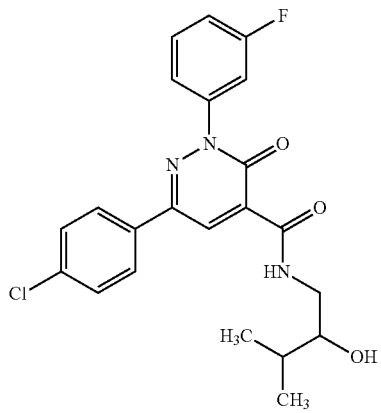

HPLC-separation of 50 mg 6-(4-Chlorophenyl)-2-(3-fluorophenyl)-N-(2-hydroxy-3-methylbutyl)-3-oxo-2,3-dihydropyridazine-4-carboxamide (example 28) on a chiral column (Chiralpak IB 5 µM 250×30 mm, eluent: hexanes/ethanol gradient 20-50% ethanol, flow 40 mL/min) yielded 15 mg 6-(4-Chlorophenyl)-2-(3-fluorophenyl)-N-(2-hydroxy-3-methylbutyl)-3-oxo-2,3-dihydropyridazine-4-carboxamide, Enantiomer 1.

$^1$H-NMR (400 MHz, DMSO-d$_6$): δ=0.85-0-91 (m, 6H); 1.56-1.67 (m, 1H); 3.16-3.26 (m, 1H); 3.53 (ddd, 1H); 4.90 (d, 1H); 7.38 (ddt, 1H); 7.53-7.66 (m, 5H); 7.99 (d, 2H); 8.65 (s, 1H); 9.54 (t, 1H).

Chiral HPLC: Rt=5.67 min

Instrument: Agilent HPLC 1260; column: Chiralpak IB 3 µM 100×4.6 mm; eluent: hexanes (0.1% diethylamine)/ethanol gradient 20-50% ethanol, flow 1.4 mL/min; temperature: 25° C.; DAD scan: 254 nm.

Example 30

6-(4-Chlorophenyl)-2-(3-fluorophenyl)-N-(2-hydroxy-3-methylbutyl]-3-oxo-2,3-dihydropyridazine-4-carboxamide, Enantiomer 2

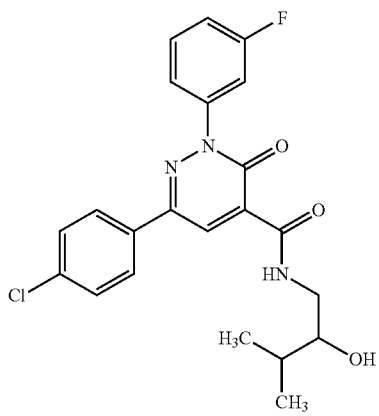

The separation of 50 mg example 28, according to example 29, additionally yielded 15 mg 6-(4-Chlorophenyl)-2-(3-fluorophenyl)-N-(2-hydroxy-3-methylbutyl)-3-oxo-2,3-dihydropyridazine-4-carboxamide, Enantiomer 2.

$^1$H-NMR (300 MHz, DMSO-d$_6$): δ=0.85-0-91 (m, 6H); 1.56-1.67 (m, 1H); 3.16-3.26 (m, 1H); 3.53 (ddd, 1H); 4.90 (d, 1H); 7.38 (ddt, 1H); 7.53-7.66 (m, 5H); 7.99 (d, 2H); 8.65 (s, 1H); 9.54 (t, 1H).

Chiral HPLC: Rt=6.78 min

Instrument: Agilent HPLC 1260; column: Chiralpak IB 3 µM 100×4.6 mm; eluent: hexanes (0.1% diethylamine)/ethanol gradient 20-50% ethanol, flow 1.4 mL/min; temperature: 25° C.; DAD scan: 254 nm.

Example 31

6-(4-Chlorophenyl)-2-(3-fluorophenyl)-N-(2-hydroxy-3-methoxypropyl)-3-oxo-2,3-dihydropyridazine-4-carboxamide

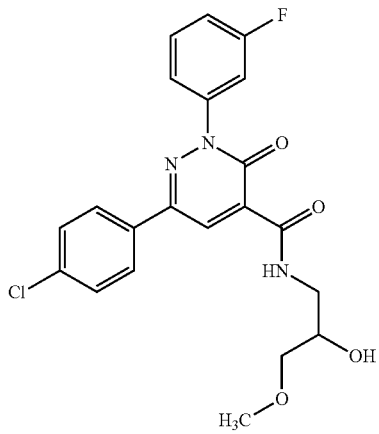 [SMILES: COCC(O)CNC(=O)c1cc(-c2ccc(Cl)cc2)nn(-c2cccc(F)c2)c1=O]

A solution of 110 mg intermediate 17, 67 mg 1-amino-3-methoxypropan-2-ol, 182 mg HATU and 0.17 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 2% methanol) to yield 28 mg 6-(4-Chlorophenyl)-2-(3-fluorophenyl)-N-(2-hydroxy-3-methoxypropyl)-3-oxo-2,3-dihydropyridazine-4-carboxamide.

$^1$H-NMR (400 MHz, DMSO-d$_6$): δ=3.22-3.34 (m+s, 6H); 3.53 (ddd, 1H); 3.71-3.79 (m, 1H); 5.17 (d, 1H); 7.38 (ddt, 1H); 6.53-7.66 (m, 5H); 8.00 (d, 2H); 8.65 (s, 1H); 9.53 (t, 1H).

Example 32

6-(4-Chlorophenyl)-2-(3-fluorophenyl)-N-(2-hydroxy-3-methoxypropyl)-3-oxo-2,3-dihydropyridazine-4-carboxamide, Enantiomer 1

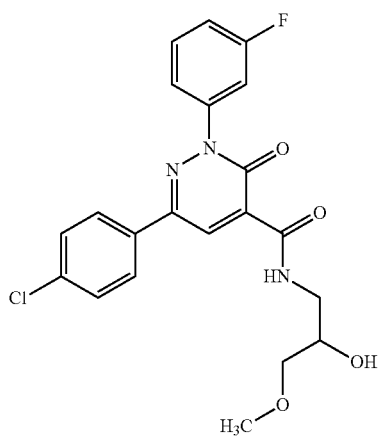 [SMILES: COCC(O)CNC(=O)c1cc(-c2ccc(Cl)cc2)nn(-c2cccc(F)c2)c1=O]

HPLC-separation of 26 mg 6-(4-Chlorophenyl)-2-(3-fluorophenyl)-N-(2-hydroxy-3-methoxypropyl)-3-oxo-2,3-dihydropyridazine-4-carboxamide (example 31) on a chiral column (Chiralpak IB 5 µM 250×30 mm, eluent: hexanes (A)/ethanol (B) gradient 85-45% A+15-55% B, flow 40 mL/min) yielded 10 mg 6-(4-Chlorophenyl)-2-(3-fluorophenyl)-N-(2-hydroxy-3-methoxypropyl)-3-oxo-2,3-dihydropyridazine-4-carboxamide, Enantiomer 1.

$^1$H-NMR (400 MHz, DMSO-d$_6$): δ=3.22-3.34 (m+s, 6H); 3.53 (ddd, 1H); 3.71-3.79 (m, 1H); 5.17 (d, 1H); 7.38 (ddt, 1H); 6.53-7.66 (m, 5H); 8.00 (d, 2H); 8.65 (s, 1H); 9.53 (t, 1H).

Chiral HPLC: Rt=7.23 min

Instrument: Agilent HPLC 1260; column: Chiralpak IB 3 µM 100×4.6 mm; eluent: hexanes (0.1% diethylamine) (A)/ethanol (B) gradient 95-50% A+5-50% B, flow 1.4 mL/min; temperature: 25° C.; DAD scan: 254 nm.

Example 33

6-(4-Chlorophenyl)-2-(3-fluorophenyl)-N-(2-hydroxy-3-methoxypropyl)-3-oxo-2,3-dihydropyridazine-4-carboxamide, Enantiomer 2

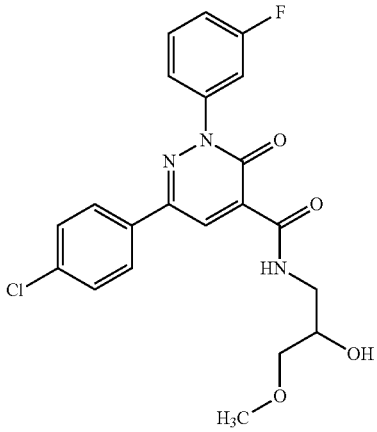 [SMILES: COCC(O)CNC(=O)c1cc(-c2ccc(Cl)cc2)nn(-c2cccc(F)c2)c1=O]

The separation of 26 mg example 31, according to example 32, additionally yielded 12 mg 6-(4-Chlorophenyl)-2-(3-fluorophenyl)-N-(2-hydroxy-3-methoxypropyl)-3-oxo-2,3-dihydropyridazine-4-carboxamide, Enantiomer 2.

$^1$H-NMR (400 MHz, DMSO-d$_6$): δ=3.22-3.34 (m+s, 6H); 3.53 (ddd, 1H); 3.71-3.79 (m, 1H); 5.17 (d, 1H); 7.38 (ddt, 1H); 6.53-7.66 (m, 5H); 8.00 (d, 2H); 8.65 (s, 1H); 9.53 (t, 1H).

Chiral HPLC: Rt=8.02 min

Instrument: Agilent HPLC 1260; column: Chiralpak IB 3 µM 100×4.6 mm; eluent: hexanes (0.1% diethylamine) (A)/ethanol (B) gradient 95-50% A+5-50% B, flow 1.4 mL/min;

temperature: 25° C.; DAD scan: 254 nm.

Example 34

6-(4-Chlorophenyl)-2-(3-fluorophenyl)-N-(2-hydroxypropyl)-3-oxo-2,3-dihydropyridazine-4-carboxamide

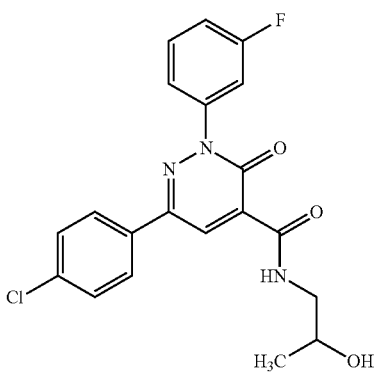 [SMILES: CC(O)CNC(=O)c1cc(-c2ccc(Cl)cc2)nn(-c2cccc(F)c2)c1=O]

A solution of 200 mg intermediate 17, 87 mg 1-aminopropan-2-ol, 331 mg HATU and 0.3 mL ethyldiisopropylamine in 10 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 2% methanol) to yield 220 mg 6-(4-Chlorophenyl)-2-(3-fluorophenyl)-N-(2-hydroxypropyl)-3-oxo-2,3-dihydropyridazine-4-carboxamide.

$^1$H-NMR (400 MHz, CDCl$_3$): δ=1.26 (d, 3H); 2.46-2.55 (m, 1H); 3.41 (ddd, 1H); 3.63 (ddd, 1H); 4.00-4.10 (m, 1H); 7.20 (ddt, 1H); 7.39-7.44 (m, 1H); 7.45-7.55 (m, 4H); 7.85 (d, 2H); 8.79 (s, 1H); 9.85 (t, 1H).

Example 35

6-(4-Chlorophenyl)-2-(3-fluorophenyl)-N-[(2R)-2-hydroxypropyl]-3-oxo-2,3-dihydropyridazine-4-carboxamide

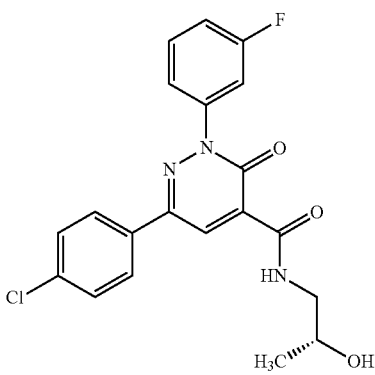 [SMILES: C[C@@H](O)CNC(=O)c1cc(-c2ccc(Cl)cc2)nn(-c2cccc(F)c2)c1=O]

HPLC-separation of 220 mg 6-(4-Chlorophenyl)-2-(3-fluorophenyl)-N-(2-hydroxy-3-methoxypropyl)-3-oxo-2,3-dihydropyridazine-4-carboxamide (example 34) on a chiral column (Chiralpak IA 5 µM 250×30 mm, eluent: hexanes/2-propanol 50:50+0.1% diethylamine, flow 40 mL/min) yielded 69 mg 6-(4-Chlorophenyl)-2-(3-fluorophenyl)-N-[(2R)-2-hydroxypropyl]-3-oxo-2,3-dihydropyridazine-4-carboxamide.

$^1$H-NMR (400 MHz, CDCl$_3$): δ=1.26 (d, 3H); 2.46-2.55 (m, 1H); 3.41 (ddd, 1H); 3.63 (ddd, 1H); 4.00-4.10 (m, 1H); 7.20 (ddt, 1H); 7.39-7.44 (m, 1H); 7.45-7.55 (m, 4H); 7.85 (d, 2H); 8.79 (s, 1H); 9.85 (t, 1H).

Chiral HPLC: Rt=2.98 min

Instrument: Agilent HPLC 1260; column: Chiralpak IB 3 µM 100×4.6 mm; eluent: hexanes (0.1% diethylamine)/2-propanol 50:50, flow 1.4 mL/min; temperature: 25° C.; DAD scan: 254 nm.

Example 36

6-(4-Chlorophenyl)-2-(3-fluorophenyl)-N-[(2S)-2-hydroxypropyl]-3-oxo-2,3-dihydropyridazine-4-carboxamide

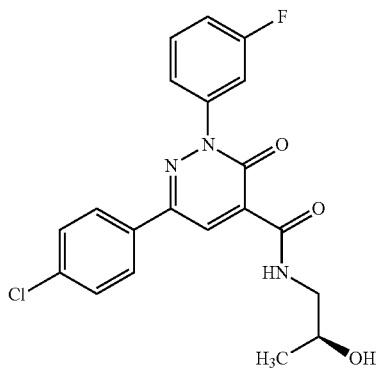 [SMILES: C[C@H](O)CNC(=O)c1cc(-c2ccc(Cl)cc2)nn(-c2cccc(F)c2)c1=O]

Route A:

A solution of 100 mg intermediate 17, 44 mg (S)-(+)-1-aminopropan-2-ol, 165 mg HATU and 0.15 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 65 mg 6-(4-chlorophenyl)-2-(3-fluorophenyl)-N-[(2S)-2-hydroxypropyl]-3-oxo-2,3-dihydropyridazine-4-carboxamide.

Route B:

The separation of 220 mg example 34, according to example 35, additionally yielded 58 mg 6-(4-chlorophenyl)-2-(3-fluorophenyl)-N-[(2S)-2-hydroxypropyl]-3-oxo-2,3-dihydropyridazine-4-carboxamide.

$^1$H-NMR (400 MHz, CDCl$_3$): δ=1.26 (d, 3H); 2.46-2.55 (m, 1H); 3.41 (ddd, 1H); 3.63 (ddd, 1H); 4.00-4.10 (m, 1H); 7.20 (ddt, 1H); 7.39-7.44 (m, 1H); 7.45-7.55 (m, 4H); 7.85 (d, 2H); 8.79 (s, 1H); 9.85 (t, 1H).

Chiral HPLC: Rt=4.58 min

Instrument: Agilent HPLC 1260; column: Chiralpak IB 3 μM 100×4.6 mm; eluent: hexanes (0.1% diethylamine)/2-propanol 50:50, flow 1.4 mL/min; temperature: 25° C.; DAD scan: 254 nm.

Optical Rotation:
[α]$_D^{20}$=11.8°+/−0.07° (c=9.7 mg/mL, methanol).

Example 37

6-(4-Chlorophenyl)-2-(3-fluorophenyl)-N-[(2S)-1-hydroxy-4-methylpentan-2-yl]-3-oxo-2,3-dihydropyridazine-4-carboxamide

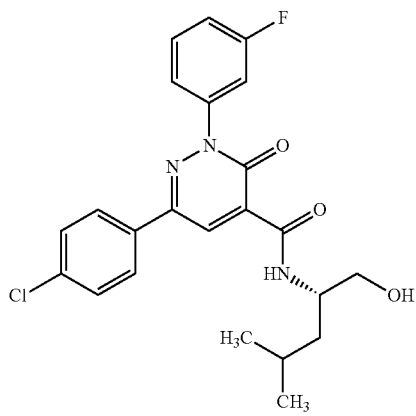 [SMILES: CC(C)C[C@@H](CO)NC(=O)c1cc(-c2ccc(Cl)cc2)nn(-c2cccc(F)c2)c1=O]

A solution of 80 mg intermediate 17, 54 mg (S)-(+)-2-amino-4-methylpentan-1-ol, 132 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 Vol % formic acid)-gradient)) to yield 11 mg 6-(4-Chlorophenyl)-2-(3-fluorophenyl)-N-[(2S)-1-hydroxy-4-methylpentan-2-yl]-3-oxo-2,3-dihydropyridazine-4-carboxamide.

$^1$H-NMR (400 MHz, DMSO-d$_6$): δ=0.89 (d, 6H); 1.38-1.45 (m, 2H); 1.56-1.66 (m, 1H); 3.38-3.51 (m, 2H); 4.03-4.13 (m, 1H); 4.86 (t, 1H); 7.38 (ddt, 1H); 7.52-7.65 (m, 5H); 8.00 (d, 2H); 8.66 (s, 1H); 9.32 (d, 1H).

Example 38

6-(4-Chlorophenyl)-2-(3-fluorophenyl)-N-[2-hydroxy-1-(tetrahydrofuran-3-yl)ethyl]-3-oxo-2,3-dihydropyridazine-4-carboxamide

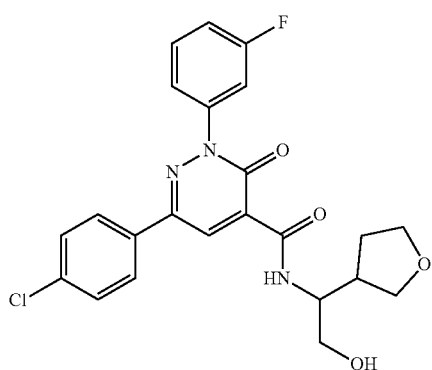 [SMILES: O=C(NC(CO)C1CCOC1)c1cc(-c2ccc(Cl)cc2)nn(-c2cccc(F)c2)c1=O]

A solution of 300 mg intermediate 17, 228 mg 2-amino-2-(tetrahydrofuran-3-yl)ethanol, 496 mg HATU and 0.45 mL ethyldiisopropylamine in 15 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 3% methanol) to yield 360 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide.

UPLC-MS: Rt=1.25 min (M$^+$+1=458)

Instrument: Waters Acquity UPLC-MS SQD; column: Acquity UPLC BEH C18 1.7 50×2.1 mm; eluent A: water+ 0.1% Vol. formic acid, eluent B: acetonitril; gradient: 0-1.6 min 1-99% B, 1.6-2.0 min 99% B; flow 0.8 mL/min; temperatur: 60° C.; injektion: 2 μL; DAD scan: 210-400 nm.

Example 39

6-(4-Chlorophenyl)-2-(3-fluorophenyl)-[(2-hydroxy-1-(tetrahydrofuran-3-yl)ethyl]-3-oxo-2,3-dihydropyridazine-4-carboxamide, Stereoisomer 1

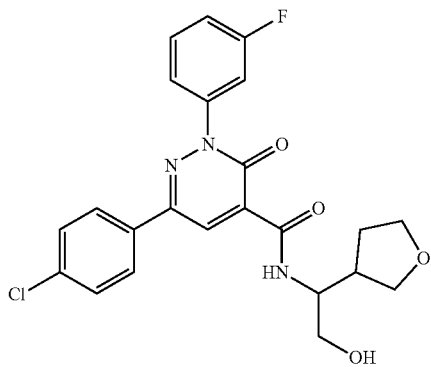

HPLC-separation of 360 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide (example 38) on a chiral column (Chiralpak IB 5 μM 250×30 mm, eluent: ethanol/MTBE gradient with 10-20% ethanol, flow 50 mL/min) yielded 137 of a mixture of isomers, that was again subjected to chiral HPLC (Chiralpak ID 5 μM 250×30 mm, eluent: ethanol/MTBE 10:90, flow 50 mL/min) to yield 74 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide, stereoisomer 1.

$^1$H-NMR (400 MHz, CDCl$_3$): δ=1.69-1.78 (m, 1H); 2.07-2.15 (m, 1H); 2.58-2.68 (m, 1H); 3.64 (dd, 1H); 3.71-3.81 (m, 2H); 3.86-3.96 (m, 3H); 4.13-4.21 (m, 1H); 7.20 (ddt, 1H); 7.41 (td, 1H); 7.44-7.55 (m, 4H); 7.84 (d, 2H); 8.78 (s, 1H); 9.85 (d, 1H).

Chiral HPLC: Rt=2.72 min

Instrument: Agilent HPLC 1260; column: Chiralpak ID 3 μM 100×4.6 mm; eluent: MTBE/ethanol 90:10, flow 1.4 mL/min; temperature: 25° C.; DAD scan: 254 nm.

Example 40

6-(4-Chlorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 2

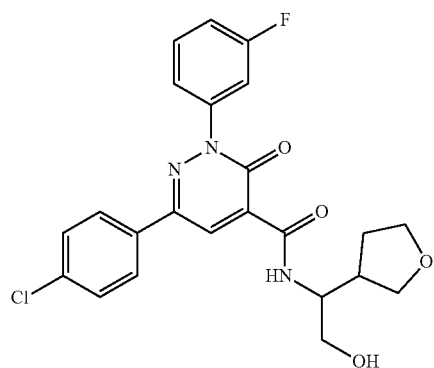 [SMILES: O=C(NC(CO)C1CCOC1)c1cc(-c2ccc(Cl)cc2)nn(-c2cccc(F)c2)c1=O]

HPLC-separation of 360 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide (example 38) on a chiral column (Chiralpak IB 5 μM 250×30 mm, eluent: ethanol/MTBE gradient with 10-20% ethanol, flow 50 mL/min) yielded 137 of a mixture of isomers, that was again subjected to chiral HPLC (Chiralpak ID 5 μM 250×30 mm, eluent: ethanol/MTBE 10:90, flow 50 mL/min) to yield 52 mg 6-(chlorophenyl)-2-(3-fluorophenyl)-[(2-hydroxy-1-(tetrahydrofuran-3-yl)ethyl]-3-oxo-2,3-dihydropyridazine-4-carboxamide, stereoisomer 2.

$^1$H-NMR (400 MHz, CDCl$_3$): δ=1.75-1.84 (m, 1H); 2.06-2.15 (m, 1H); 2.60-2.69 (m, 1H); 3.63 (dd, 1H); 3.67-3.81 (m, 3H); 3.86-3.96 (m, 2H); 4.11-4.20 (m, 1H); 7.20 (ddt, 1H); 7.41 (td, 1H); 7.45-7.56 (m, 4H); 7.84 (d, 2H); 8.79 (s, 1H); 9.93 (d, 1H).

Chiral HPLC: Rt=3.28 min

Instrument: Agilent HPLC 1260; column: Chiralpak ID 3 μM 100×4.6 mm; eluent: MTBE/ethanol 90:10, flow 1.4 mL/min; temperature: 25° C.; DAD scan: 254 nm.

Example 41

6-(4-Chlorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 3

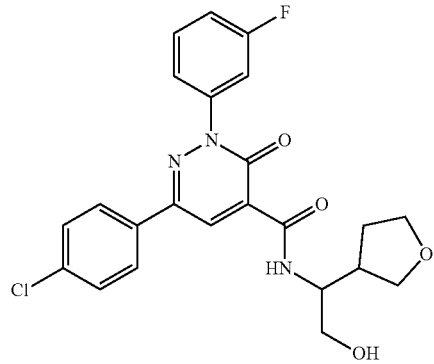 [SMILES: O=C(NC(CO)C1CCOC1)c1cc(-c2ccc(Cl)cc2)nn(-c2cccc(F)c2)c1=O]

HPLC-separation of 360 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide (example 38) on a chiral column (Chiralpak IB 5 μM 250×30 mm, eluent: ethanol/MTBE gradient with 10-20% ethanol, flow 50 mL/min) yielded 55 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide, stereoisomer 3.

$^1$H-NMR (400 MHz, CDCl$_3$): δ=1.75-1.84 (m, 1H); 2.06-2.15 (m, 1H); 2.60-2.69 (m, 1H); 3.63 (dd, 1H); 3.67-3.81 (m, 3H); 3.86-3.96 (m, 2H); 4.11-4.20 (m, 1H); 7.20 (ddt, 1H); 7.41 (td, 1H); 7.45-7.56 (m, 4H); 7.84 (d, 2H); 8.79 (s, 1H); 9.93 (d, 1H).

Chiral HPLC: Rt=2.72 min

Instrument: Agilent HPLC 1260; column: Chiralpak IB 3 μM 100×4.6 mm; eluent: MTBE/ethanol gradient 10-20% ethanol, flow 1.4 mL/min; temperature: 25° C.; DAD scan: 254 nm.

Example 42

6-(4-Chlorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 4

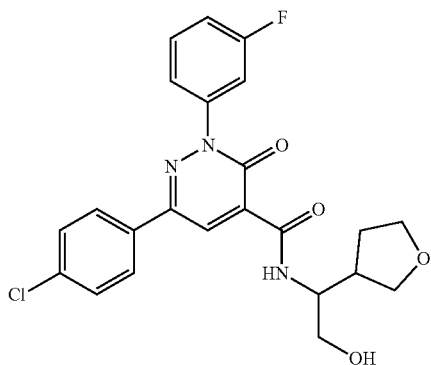

HPLC-separation of 360 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide (example 38) on a chiral column (Chiralpak IB 5 μM 250×30 mm, eluent: ethanol/MTBE gradient with 10-20% ethanol, flow 50 mL/min) yielded 72 mg 6-(chlorophenyl)-2-(3-fluorophenyl)-N-[2-hydroxy-1-(tetrahydrofuran-3-yl)ethyl]-3-oxo-2,3-dihydropyridazine-4-carboxamide, stereoisomer 4.

$^1$H-NMR (400 MHz, CDCl$_3$): δ=1.69-1.78 (m, 1H); 2.07-2.15 (m, 1H); 2.58-2.68 (m, 1H); 3.64 (dd, 1H); 3.71-3.81 (m, 2H); 3.86-3.96 (m, 3H); 4.13-4.21 (m, 1H); 7.20 (ddt, 1H); 7.41 (td, 1H); 7.44-7.55 (m, 4H); 7.84 (d, 2H); 8.78 (s, 1H); 9.85 (d, 1H).

Chiral HPLC: Rt=4.27 min

Instrument: Agilent HPLC 1260; column: Chiralpak IB 3 μM 100×4.6 mm; eluent: MTBE/ethanol gradient 10-20% ethanol, flow 1.4 mL/min; temperature: 25° C.; DAD scan: 254 nm.

Example 43

6-(4-Chlorophenyl)-2-(3,5-difluorophenyl)-N-[(2S)-1-hydroxy-3-methylbutan-2-yl]-3-oxo-2,3-dihydropyridazine-4-carboxamide

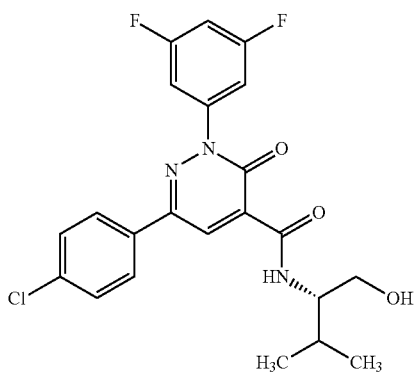 [SMILES: CC(C)[C@@H](CO)NC(=O)c1cc(-c2ccc(Cl)cc2)nn(-c2cc(F)cc(F)c2)c1=O]

A solution of 80 mg intermediate 29, 46 mg (2S)-2-amino-3-methylbutan-1-ol, 126 mg HATU and 0.12 mL ethyldiisopropylamine in 3.8 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 55 mg 6-(4-chlorophenyl)-2-(3,5-difluorophenyl)-N-[(2S)-1-hydroxy-3-methylbutan-2-yl]-3-oxo-2,3-dihydropyridazine-4-carboxamide.

$^1$H-NMR (500 MHz, DMSO-d6): δ=0.89 (d, 3H); 0.92 (d, 3H); 1.92-2.02 (m, 1H); 3.41-3.47 (m, 1H); 3.52-3.58 (m, 1H); 3.81-3.88 (m, 1H); 4.81 (t, 1H); 7.48 (tt, 1H); 7.54-7.61 (m, 4H); 8.01 (d, 2H); 8.66 (s, 1H); 9.33 (d, 1H).

Example 44

6-(4-Chlorophenyl)-2-(3,5-difluorophenyl)-3-oxo-N-(3,3,3-trifluoro-2-hydroxypropyl)-2,3-dihydropyridazine-4-carboxamide

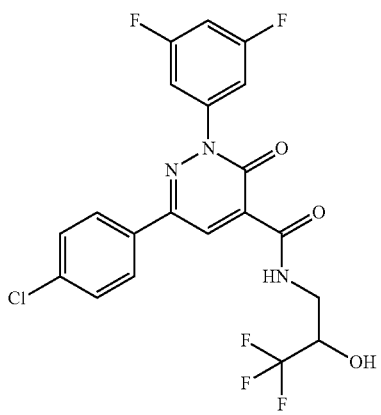 [SMILES: O=C(NCC(O)C(F)(F)F)c1cc(-c2ccc(Cl)cc2)nn(-c2cc(F)cc(F)c2)c1=O]

A solution of 100 mg intermediate 29, 71 mg 3-amino-1,1,1-trifluoropropan-2-ol, 157 mg HATU and 0.14 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 µm 100×30 mm, mobile phase: acetonitrile/water (0.1 Vol % formic acid)-gradient)) to yield 80 mg 6-(4-chlorophenyl)-2-(3,5-difluorophenyl)-3-oxo-N-(3,3,3-trifluoro-2-hydroxypropyl)-2,3-dihydropyridazine-4-carboxamide.

$^1$H-NMR (500 MHz, DMSO-d6): δ=3.47 (ddd, 1H); 3.74 (ddd, 1H); 4.17-4.28 (m, 1H); 6.67 (d, 1H); 7.48 (tt, 1H); 7.53-7.62 (m, 4H); 8.02 (d, 2H); 8.67 (s, 1H); 9.57 (t, 1H).

Example 45

6-(4-Chlorophenyl)-2-(3,5-difluorophenyl)-3-oxo-N-(3,3,3-trifluoro-2-hydroxypropyl)-2,3-dihydropyridazine-4-carboxamide, Enantiomer 1

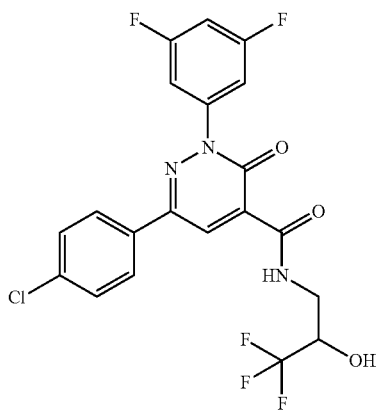 [SMILES: O=C(NCC(O)C(F)(F)F)c1cc(-c2ccc(Cl)cc2)nn(-c2cc(F)cc(F)c2)c1=O]

HPLC-separation of 80 mg 6-(4-chlorophenyl)-2-(3,5-difluorophenyl)-3-oxo-N-(3,3,3-trifluoro-2-hydroxypropyl)-2,3-dihydropyridazine-4-carboxamide (example 44) on a chiral column (Chiralpak IB 5 µM 250×30 mm, eluent: CO$_2$/ethanol 90:10, flow 100 mL/min, T=40° C., p=150 bar) yielded 22 mg 6-(4-chlorophenyl)-2-(3,5-difluorophenyl)-3-oxo-N-(3,3,3-trifluoro-2-hydroxypropyl)-2,3-dihydropyridazine-4-carboxamide, enantiomer 1.

$^1$H-NMR (400 MHz, DMSO-d6): δ=3.47 (ddd, 1H); 3.74 (ddd, 1H); 4.17-4.28 (m, 1H); 6.67 (d, 1H); 7.48 (tt, 1H); 7.53-7.62 (m, 4H); 8.02 (d, 2H); 8.67 (s, 1H); 9.57 (t, 1H).

Chiral HPLC: Rt=2.01 min

Instrument: Agilent HPLC 1260; Aurora SFC module; column: Chiralpak IB 5 µM 100×4.6 mm; eluent: CO$_2$/ethanol gradient 90:10, flow 4 mL/min; temperature: 37.5° C.; p=100 bar, DAD scan: 254 nm.

Example 46

6-(4-Chlorophenyl)-2-(3,5-difluorophenyl)-3-oxo-N-(3,3,3-trifluoro-2-hydroxypropyl)-2,3-dihydropyridazine-4-carboxamide, Enantiomer 2

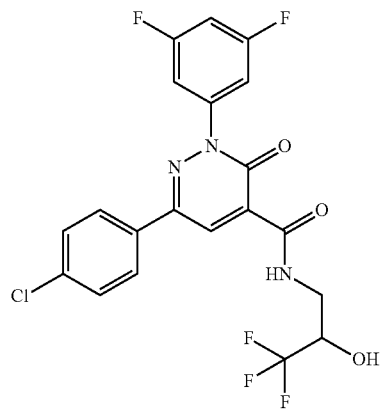 [SMILES: O=C(NCC(O)C(F)(F)F)c1cc(-c2ccc(Cl)cc2)nn(-c2cc(F)cc(F)c2)c1=O]

The separation of 80 mg example 44, according to example 45, additionally yielded 37 mg 6-(4-chlorophenyl)-2-(3,5-difluorophenyl)-3-oxo-N-(3,3,3-trifluoro-2-hydroxypropyl)-2,3-dihydropyridazine-4-carboxamide, enantiomer 2.

$^1$H-NMR (400 MHz, DMSO-d6): δ=3.47 (ddd, 1H); 3.74 (ddd, 1H); 4.17-4.28 (m, 1H); 6.67 (d, 1H); 7.48 (tt, 1H); 7.53-7.62 (m, 4H); 8.02 (d, 2H); 8.67 (s, 1H); 9.57 (t, 1H).

Chiral HPLC: Rt=3.28 min

Instrument: Agilent HPLC 1260; Aurora SFC module; column: Chiralpak IB 5 µM 100×4.6 mm; eluent: CO$_2$/ethanol gradient 90:10, flow 4 mL/min; temperature: 37.5° C.; p=100 bar, DAD scan: 254 nm.

Example 47

6-(4-Chlorophenyl)-2-(3,5-difluorophenyl)-N-[(2S)-1-hydroxypropan-2-yl]-3-oxo-2,3-dihydropyridazine-4-carboxamide

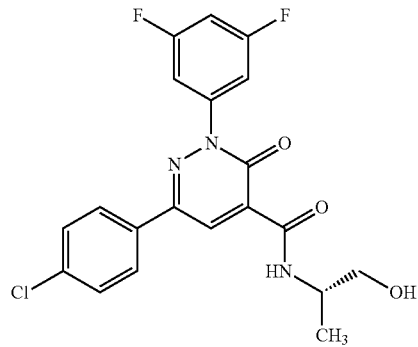 [SMILES: C[C@@H](CO)NC(=O)c1cc(-c2ccc(Cl)cc2)nn(-c2cc(F)cc(F)c2)c1=O]

A solution of 80 mg intermediate 29, 33 mg (2S)-2-aminopropan-1-ol, 126 mg HATU and 0.12 mL ethyldiisopropylamine in 3.8 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 µm 100×30 mm, mobile phase: acetonitrile/water (0.1 Vol % formic acid)-gradient)) to yield 35 mg 6-(4-chlorophenyl)-2-(3,5-difluorophenyl)-N-[(2S)-1-hydroxypropan-2-yl]-3-oxo-2,3-dihydropyridazine-4-carboxamide.

$^1$H-NMR (500 MHz, DMSO-d6): δ=1.16 (d, 3H); 3.41-3.48 (m, 2H); 4.00-4.07 (m, 1H); 4.94 (t, 1H); 7.48 (tt, 1H); 7.53-7.61 (m, 4H); 8.01 (d, 2H); 8.65 (s, 1H); 9.37 (d, 1H).

Example 48

6-(4-Chlorophenyl)-2-(3,5-difluorophenyl)-N-(2-hydroxy-3-methylbutyl)-3-oxo-2,3-dihydro-pyridazine-4-carboxamide

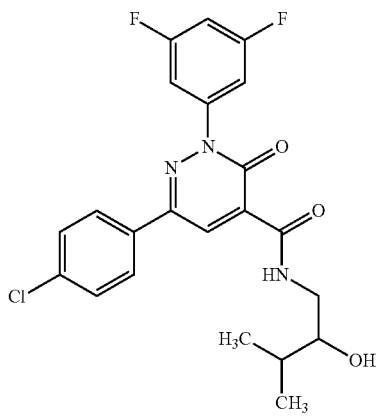 [SMILES: CC(C)C(O)CNC(=O)c1cc(-c2ccc(Cl)cc2)nn(-c2cc(F)cc(F)c2)c1=O]

A solution of 100 mg intermediate 29, 77 mg 1-amino-3-methylbutan-2-ol hydrochloride (1:1), 157 mg HATU and 0.19 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 µm 100×30 mm, mobile phase: acetonitrile/water (0.1 Vol % formic acid)-gradient)) to yield 40 mg 6-(4-chlorophenyl)-2-(3,5-difluorophenyl)-N-(2-hydroxy-3-methylbutyl)-3-oxo-2,3-dihydropyridazine-4-carboxamide.

$^1$H-NMR (500 MHz, DMSO-d6): δ=0.85-0.91 (m, 6H); 1.56-1.67 (m, 1H); 3.19-3.26 (m, 1H); 3.28-3.36 (m, 1H, signal below water signal); 3.53 (ddd, 1H); 4.90 (d, 1H); 7.48 (tt, 1H); 7.53-7.61 (m, 4H); 8.01 (d, 2H); 8.65 (s, 1H); 9.47 (t, 1H).

Example 49

6-(4-Chlorophenyl)-2-(3,5-difluorophenyl)-N-(2-hydroxy-3-methylbutyl)-3-oxo-2,3-dihydro-pyridazine-4-carboxamide, Enantiomer 1

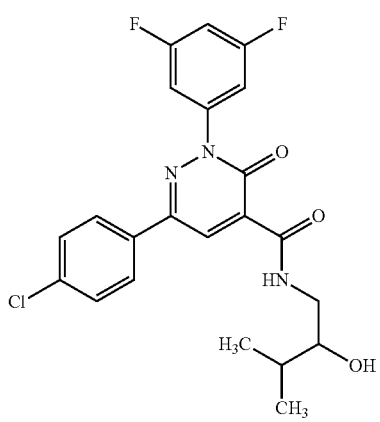 [SMILES: CC(C)C(O)CNC(=O)c1cc(-c2ccc(Cl)cc2)nn(-c2cc(F)cc(F)c2)c1=O]

HPLC-separation of 40 mg 6-(4-chlorophenyl)-2-(3,5-difluorophenyl)-N-(2-hydroxy-3-methylbutyl)-3-oxo-2,3-dihydropyridazine-4-carboxamide (example 48) on a chiral column (Chiralpak IA 5 µM 250×30 mm, eluent: hexanes/2-propanol (0.1% diethylamine) gradient 20-50% 2-propanol, flow 40 mL/min, temperature: 25° C.) yielded 15 mg 6-(4-chlorophenyl)-2-(3,5-difluorophenyl)-N-(2-hydroxy-3-methylbutyl)-3-oxo-2,3-dihydropyridazine-4-carboxamide, enantiomer 1.

$^1$H-NMR (400 MHz, DMSO-d6): δ=0.85-0.91 (m, 6H); 1.56-1.67 (m, 1H); 3.19-3.26 (m, 1H); 3.28-3.36 (m, 1H, signal below water signal); 3.53 (ddd, 1H); 4.90 (d, 1H); 7.48 (tt, 1H); 7.53-7.61 (m, 4H); 8.01 (d, 2H); 8.65 (s, 1H); 9.47 (t, 1H).

Chiral HPLC: Rt=4.17 min

Instrument: Agilent HPLC 1260; Aurora SFC module; column: Chiralpak IA 3 µM 100×4.6 mm; eluent: hexanes/2-propanol (0.1% diethylamine) gradient 20-50% 2-propanol, flow 1.4 mL/min; temperature: 25° C.; DAD scan: 254 nm.

Example 50

6-(4-Chlorophenyl)-2-(3,5-difluorophenyl)-N-(2-hydroxy-3-methylbutyl)-3-oxo-2,3-dihydro-pyridazine-4-carboxamide, Enantiomer 2

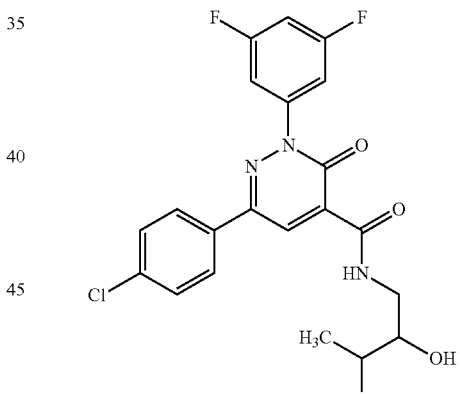

The separation of 40 mg example 48, according to example 49, additionally yielded 15 mg 6-(4-chlorophenyl)-2-(3,5-difluorophenyl)-N-(2-hydroxy-3-methylbutyl)-3-oxo-2,3-dihydropyridazine-4-carboxamide, enantiomer 2.

$^1$H-NMR (400 MHz, DMSO-d6): δ=0.85-0.91 (m, 6H); 1.56-1.67 (m, 1H); 3.19-3.26 (m, 1H); 3.28-3.36 (m, 1H, signal below water signal); 3.53 (ddd, 1H); 4.90 (d, 1H); 7.48 (tt, 1H); 7.53-7.61 (m, 4H); 8.01 (d, 2H); 8.65 (s, 1H); 9.47 (t, 1H).

Chiral HPLC: Rt=6.13 min

Instrument: Agilent HPLC 1260; Aurora SFC module; column: Chiralpak IA 3 µM 100×4.6 mm; eluent: hexanes/2-propanol (0.1% diethylamine) gradient 20-50% 2-propanol, flow 1.4 mL/min; temperature: 25° C.; DAD scan: 254 nm.

Example 51

2-(3,5-Difluorophenyl)-N-[(2S)-1-hydroxy-3-methylbutan-2-yl]-6-(4-methylphenyl)-3-oxo-2,3-dihydropyridazine-4-carboxamide

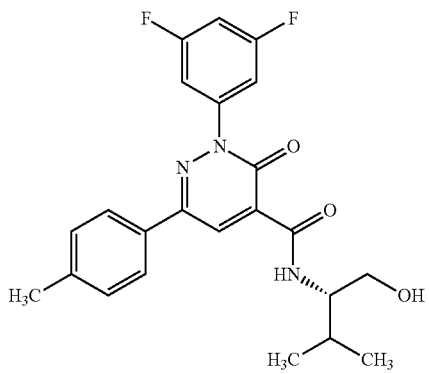 [SMILES: Cc1ccc(-c2cc(C(=O)N[C@H](CO)C(C)C)c(=O)n(-c3cc(F)cc(F)c3)n2)cc1]

A solution of 80 mg intermediate 32, 48 mg (2S)-2-amino-3-methylbutan-1-ol, 133 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100× 30 mm, mobile phase: acetonitrile/water (0.1 Vol % formic acid)-gradient)) to yield 50 mg 2-(3,5-difluorophenyl)-N-[(2S)-1-hydroxy-3-methylbutan-2-yl]-6-(4-methylphenyl)-3-oxo-2,3-dihydropyridazine-4-carboxamide.

$^1$H-NMR (500 MHz, DMSO-d6): δ=0.89 (d, 3H); 0.92 (d, 3H); 1.93-2.01 (m, 1H); 2.37 (s, 3H); 3.41-3.47 (m, 1H); 3.51-3.58 (m, 1H); 3.81-3.88 (m, 1H); 4.81 (t, 1H); 7.34 (d, 2H); 7.47 (tt, 1H); 7.52-7.58 (m, 2H); 7.86 (d, 2H); 8.63 (s, 1H); 9.37 (d, 1H).

Example 52

2-(3,5-Difluorophenyl)-6-(4-methylphenyl)-3-oxo-N-(3,3,3-trifluoro-2-hydroxypropyl)-2,3-dihydropyridazine-4-carboxamide

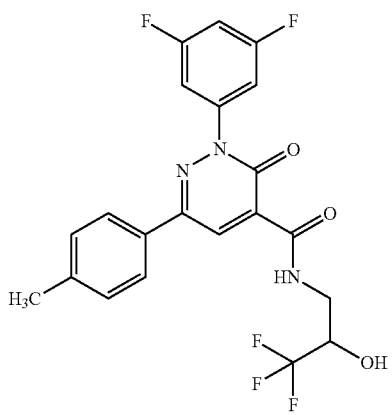 [SMILES: Cc1ccc(-c2cc(C(=O)NCC(O)C(F)(F)F)c(=O)n(-c3cc(F)cc(F)c3)n2)cc1]

A solution of 100 mg intermediate 32, 75 mg 3-amino-1,1,1-trifluoropropan-2-ol, 167 mg HATU and 0.15 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100× 30 mm, mobile phase: acetonitrile/water (0.1 Vol % formic acid)-gradient)) to yield 90 mg 2-(3,5-difluorophenyl)-6-(4-methylphenyl)-3-oxo-N-(3,3,3-trifluoro-2-hydroxypropyl)-2,3-dihydropyridazine-4-carboxamide.

$^1$H-NMR (400 MHz, DMSO-d6): δ=2.37 (s, 3H); 3.47 (ddd, 1H); 3.74 (ddd, 1H); 4.17-4.28 (m, 1H); 6.66 (d, 1H); 7.34 (d, 2H); 7.47 (tt, 1H); 7.53-7.58 (m, 2H); 7.87 (d, 2H); 8.64 (s, 1H); 9.60 (t, 1H).

Example 53

2-(3,5-Difluorophenyl)-6-(4-methylphenyl)-3-oxo-N-(3,3,3-trifluoro-2-hydroxypropyl)-2,3-dihydropyridazine-4-carboxamide, Enantiomer 1

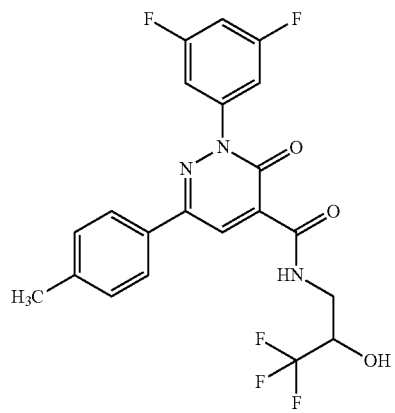 [SMILES: Cc1ccc(-c2cc(C(=O)NCC(O)C(F)(F)F)c(=O)n(-c3cc(F)cc(F)c3)n2)cc1]

HPLC-separation of 90 mg 2-(3,5-difluorophenyl)-6-(4-methylphenyl)-3-oxo-N-(3,3,3-trifluoro-2-hydroxypropyl)-2,3-dihydropyridazine-4-carboxamide (example 52) on a chiral column (Chiralpak IA 5 μM 250×30 mm, eluent: hexanes/2-propanol (0.1% diethylamine) gradient 20-50% 2-propanol, flow 40 mL/min, temperature: 25° C.) yielded 38 mg 2-(3,5-difluorophenyl)-6-(4-methylphenyl)-3-oxo-N-(3,3,3-trifluoro-2-hydroxypropyl)-2,3-dihydropyridazine-4-carboxamide, enantiomer 1.

$^1$H-NMR (400 MHz, DMSO-d6): δ=2.37 (s, 3H); 3.47 (ddd, 1H); 3.74 (ddd, 1H); 4.17-4.28 (m, 1H); 6.66 (d, 1H); 7.34 (d, 2H); 7.47 (tt, 1H); 7.53-7.58 (m, 2H); 7.87 (d, 2H); 8.64 (s, 1H); 9.60 (t, 1H).

Chiral HPLC: Rt=2.92 min

Instrument: Agilent HPLC 1260; Aurora SFC module; column: Chiralpak IA 3 μM 100×4.6 mm; eluent: hexanes/2-propanol (0.1% diethylamine) gradient 20-50% 2-propanol, flow 1.4 mL/min; temperature: 25° C.; DAD scan: 254 nm.

Example 54

2-(3,5-Difluorophenyl)-6-(4-methylphenyl)-3-oxo-N-(3,3,3-trifluoro-2-hydroxypropyl)-2,3-dihydropyridazine-4-carboxamide, Enantiomer 2

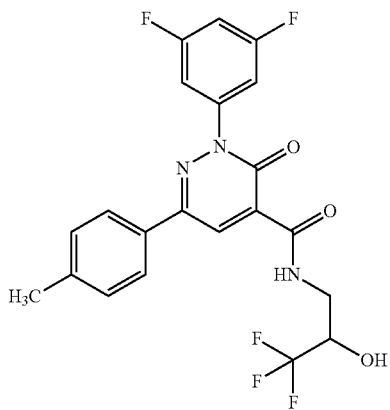 [SMILES: Cc1ccc(-c2cc(C(=O)NCC(O)C(F)(F)F)c(=O)n(-c3cc(F)cc(F)c3)n2)cc1]

The separation of 90 mg example 52, according to example 53, additionally yielded 40 mg 2-(3,5-difluorophenyl)-6-(4-methylphenyl)-3-oxo-N-(3,3,3-trifluoro-2-hydroxypropyl)-2,3-dihydropyridazine-4-carboxamide, enantiomer 2.

$^1$H-NMR (400 MHz, DMSO-d6): δ=2.37 (s, 3H); 3.47 (ddd, 1H); 3.74 (ddd, 1H); 4.17-4.28 (m, 1H); 6.66 (d, 1H); 7.34 (d, 2H); 7.47 (tt, 1H); 7.53-7.58 (m, 2H); 7.87 (d, 2H); 8.64 (s, 1H); 9.60 (t, 1H).

Chiral HPLC: Rt=6.36 min

Instrument: Agilent HPLC 1260; Aurora SFC module; column: Chiralpak IA 3 μM 100×4.6 mm; eluent: hexanes/2-propanol (0.1% diethylamine) gradient 20-50% 2-propanol, flow 1.4 mL/min; temperature: 25° C.; DAD scan: 254 nm.

Example 55

2-(3,5-Difluorophenyl)-N-[(2S)-1-hydroxypropan-2-yl]-6-(4-methylphenyl)-3-oxo-2,3-dihydropyridazine-4-carboxamide

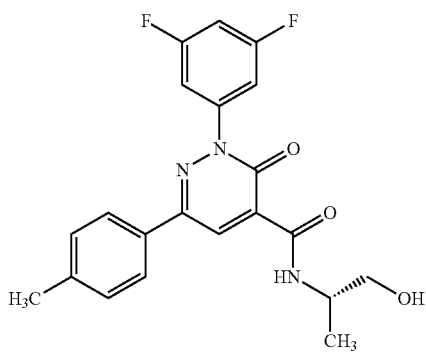 [SMILES: Cc1ccc(-c2cc(C(=O)N[C@@H](C)CO)c(=O)n(-c3cc(F)cc(F)c3)n2)cc1]

A solution of 80 mg intermediate 32, 35 mg (2S)-2-aminopropan-1-ol, 133 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge $C_{18}$ 5 μm 100×30 mm, mobile phase: acetonitrile/water (0.1 Vol % formic acid)-gradient)) to yield 45 mg 2-(3,5-difluorophenyl)-N-[(2S)-1-hydroxypropan-2-yl]-6-(4-methylphenyl)-3-oxo-2,3-dihydropyridazine-4-carboxamide.

$^1$H-NMR (400 MHz, DMSO-d6): δ=1.16 (d, 3H); 2.37 (s, 3H); 3.41-3.48 (m, 2H); 4.00-4.08 (m, 1H); 4.94 (t, 1H); 7.34 (d, 2H); 7.47 (tt, 1H); 7.52-7.58 (m, 2H); 7.86 (d, 2H); 8.62 (s, 1H); 9.40 (d, 1H).

Example 56

2-(3,5-Difluorophenyl)-N-(2-hydroxy-3-methyl butyl)-6-(4-methyl phenyl)-3-oxo-2,3-dihydropyridazine-4-carboxamide

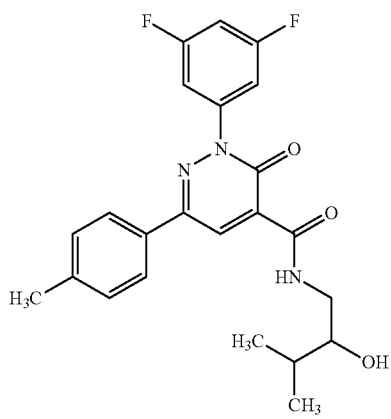 [SMILES: Cc1ccc(-c2cc(C(=O)NCC(O)C(C)C)c(=O)n(-c3cc(F)cc(F)c3)n2)cc1]

A solution of 100 mg intermediate 32, 82 mg 1-amino-3-methylbutan-2-ol hydrochloride, 167 mg HATU and 0.2 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 70 mg 2-(3,5-difluorophenyl)-N-(2-hydroxy-3-methylbutyl)-6-(4-methylphenyl)-3-oxo-2,3-dihydropyridazine-4-carboxamide.

$^1$H-NMR (500 MHz, DMSO-d6): δ=0.87 (d, 3H); 0.89 (d, 3H); 1.57-1.66 (m, 1H); 2.37 (s, 3H); 3.21 (ddd, 1H); 3.30-3.34 (m, 1H, signal below water signal); 3.53 (ddd, 1H); 4.90 (d, 1H); 7.34 (d, 2H); 7.47 (tt, 1H); 7.52-7.57 (m, 2H); 7.86 (d, 2H); 8.62 (s, 1H); 9.50 (t, 1H).

Example 57

2-(3,5-Difluorophenyl)-N-(2-hydroxy-3-methyl-butyl)-6-(4-methylphenyl)-3-oxo-2,3-dihydropyridazine-4-carboxamide, Enantiomer 1

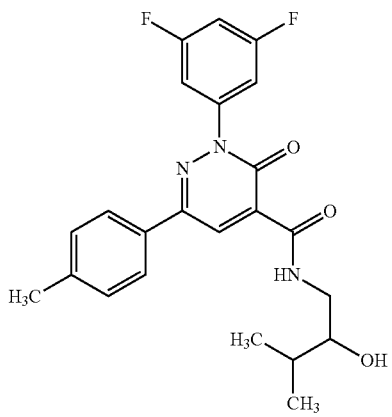 [SMILES: Cc1ccc(-c2cc(C(=O)NCC(O)C(C)C)c(=O)n(-c3cc(F)cc(F)c3)n2)cc1]

HPLC-separation of 70 mg 2-(3,5-difluorophenyl)-N-(2-hydroxy-3-methylbutyl)-6-(4-methylphenyl)-3-oxo-2,3-dihydropyridazine-4-carboxamide (example 56) on a chiral column (Chiralpak IA 5 μM 250×30 mm, eluent: hexanes/2-propanol (0.1% diethylamine) gradient 20-50% 2-propanol, flow 40 mL/min, temperature: 25° C.) yielded 35 mg 2-(3,5-difluorophenyl)-N-(2-hydroxy-3-methylbutyl)-6-(4-methylphenyl)-3-oxo-2,3-dihydropyridazine-4-carboxamide, enantiomer 1.

$^1$H-NMR (400 MHz, DMSO-d6): δ=0.87 (d, 3H); 0.89 (d, 3H); 1.57-1.66 (m, 1H); 2.37 (s, 3H); 3.21 (ddd, 1H); 3.30-3.34 (m, 1H, signal below water signal); 3.53 (ddd, 1H); 4.90 (d, 1H); 7.34 (d, 2H); 7.47 (tt, 1H); 7.52-7.57 (m, 2H); 7.86 (d, 2H); 8.62 (s, 1H); 9.50 (t, 1H).

Chiral HPLC: Rt=3.44 min

Instrument: Agilent HPLC 1260; Aurora SFC module; column: Chiralpak IA 3 μM 100×4.6 mm; eluent: hexanes/2-propanol (0.1% diethylamine) gradient 20-50% 2-propanol, flow 1.4 mL/min; temperature: 25° C.; DAD scan: 254 nm.

Example 58

2-(3,5-Difluorophenyl)-N-(2-hydroxy-3-methyl butyl)-6-(4-methyl phenyl)-3-oxo-2,3-dihydropyridazine-4-carboxamide, Enantiomer 2

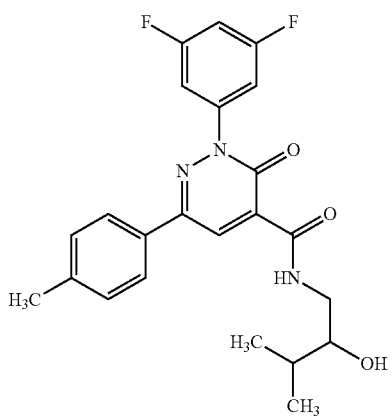 [SMILES: Cc1ccc(-c2cc(C(=O)NCC(O)C(C)C)c(=O)n(-c3cc(F)cc(F)c3)n2)cc1]

The separation of 70 mg example 56, according to example 57, additionally yielded 35 mg 2-(3,5-difluorophenyl)-N-(2-hydroxy-3-methylbutyl)-6-(4-methylphenyl)-3-oxo-2,3-dihydropyridazine-4-carboxamide, enantiomer 2.

$^1$H-NMR (400 MHz, DMSO-d6): δ=0.87 (d, 3H); 0.89 (d, 3H); 1.57-1.66 (m, 1H); 2.37 (s, 3H); 3.21 (ddd, 1H); 3.30-3.34 (m, 1H, signal below water signal); 3.53 (ddd, 1H); 4.90 (d, 1H); 7.34 (d, 2H); 7.47 (tt, 1H); 7.52-7.57 (m, 2H); 7.86 (d, 2H); 8.62 (s, 1H); 9.50 (t, 1H).

Chiral HPLC: Rt=5.14 min

Instrument: Agilent HPLC 1260; Aurora SFC module; column: Chiralpak IA 3 μM 100×4.6 mm; eluent: hexanes/2-propanol (0.1% diethylamine) gradient 20-50% 2-propanol, flow 1.4 mL/min; temperature: 25° C.; DAD scan: 254 nm.

Example 59

2-(3-Chlorophenyl)-6-(4-chlorophenyl)-N-[(2S)-1-hydroxy-3-methylbutan-2-yl]-3-oxo-2,3-dihydropyridazine-4-carboxamide

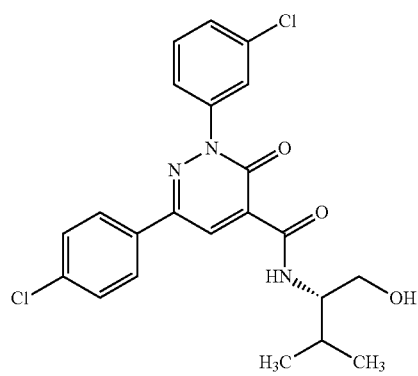 [SMILES: CC(C)[C@@H](CO)NC(=O)c1cc(-c2ccc(Cl)cc2)nn(-c2cccc(Cl)c2)c1=O]

A solution of 80 mg intermediate 20, 46 mg (2S)-2-amino-3-methylbutan-1-ol, 126 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 55 mg 2-(3-chlorophenyl)-6-(4-chlorophenyl)-N-[(2S)-1-hydroxy-3-methylbutan-2-yl]-3-oxo-2,3-dihydropyridazine-4-carboxamide.

$^1$H-NMR (400 MHz, DMSO-d6): δ=0.88 (d, 3H); 0.92 (d, 3H); 1.91.2.02 (m, 1H); 3.41-3.47 (m, 1H); 3.52-3.57 (m, 1H); 3.81-3.88 (m, 1H); 4.82 (t, 1H); 7.55-7.62 (m, 4H); 7.65-7.70 (m, 1H); 7.81-7.84 (m, 1H); 7.98 (d, 2H); 8.65 (s, 1H); 9.40 (d, 1H).

Example 60

2-(3-Chlorophenyl)-6-(4-chlorophenyl)-N-[(2S)-1-hydroxybutan-2-yl]-3-oxo-2,3-dihydropyridazine-4-carboxamide

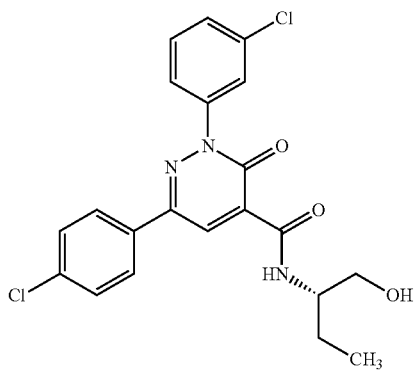 [SMILES: CC[C@@H](CO)NC(=O)c1cc(-c2ccc(Cl)cc2)nn(-c2cccc(Cl)c2)c1=O]

A solution of 80 mg intermediate 20, 40 mg (2S)-2-aminobutan-1-ol, 126 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 50 mg 2-(3-chlorophenyl)-6-(4-chlorophenyl)-N-[(2S)-1-hydroxybutan-2-yl]-3-oxo-2,3-dihydropyridazine-4-carboxamide.

$^1$H-NMR (400 MHz, DMSO-d6): δ=0.89 (t, 3H); 1.43-1.54 (m, 1H); 1.60-1.70 (m, 1H); 3.39-3.46 (m, 1H); 3.48-3.55 (m, 1H); 3.85-3.93 (m, 1H); 4.87 (t, 1H); 7.55-7.62 (m, 4H); 7.65-7.69 (m, 1H); 7.81-7.84 (m, 1H); 7.99 (d, 2H); 8.65 (s, 1H); 9.37 (d, 1H).

Example 61

2-(3-Chlorophenyl)-6-(4-chlorophenyl)-N-[(2S)-1-hydroxy-4-methylpentan-2-yl]-3-oxo-2,3-dihydropyridazine-4-carboxamide

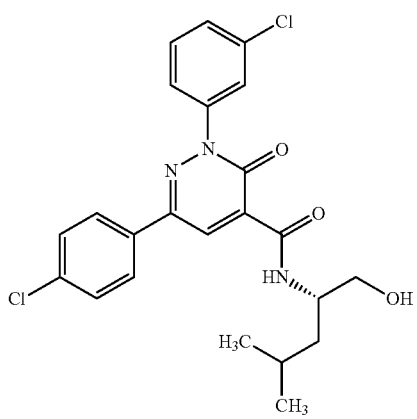 [SMILES: CC(C)C[C@@H](CO)NC(=O)c1cc(-c2ccc(Cl)cc2)nn(-c2cccc(Cl)c2)c1=O]

A solution of 80 mg intermediate 20, 52 mg (2S)-2-amino-4-methylpentan-1-ol, 126 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 60 mg 2-(3-chlorophenyl)-6-(4-chlorophenyl)-N-[(2S)-1-hydroxy-4-methylpentan-2-yl]-3-oxo-2,3-dihydropyridazine-4-carboxamide.

$^1$H-NMR (400 MHz, DMSO-d6): δ=0.89 (d, 6H); 1.36-1.47 (m, 2H); 1.55-1.68 (m, 1H); 3.37-3.51 (m, 2H); 4.03-4.12 (m, 1H); 4.87 (t, 1H); 7.55-7.62 (m, 4H); 7.64-7.69 (m, 1H); 7.81-7.84 (m, 1H); 7.99 (d, 2H); 8.65 (s, 1H); 9.31 (d, 1H).

Example 62

2-(3-Chlorophenyl)-6-(4-chlorophenyl)-3-oxo-N-(3,3,3-trifluoro-2-hydroxypropyl)-2,3-dihydropyridazine-4-carboxamide

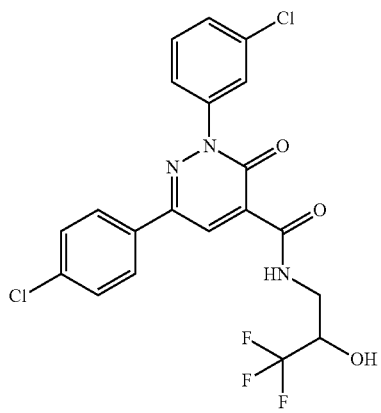 [SMILES: O=C(NCC(O)C(F)(F)F)c1cc(-c2ccc(Cl)cc2)nn(-c2cccc(Cl)c2)c1=O]

A solution of 100 mg intermediate 20, 72 mg 3-amino-1,1,1-trifluoropropan-2-ol, 158 mg HATU and 0.14 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 60 mg 2-(3-chlorophenyl)-6-(4-chlorophenyl)-3-oxo-N-(3,3,3-trifluoro-2-hydroxypropyl)-2,3-dihydropyridazine-4-carboxamide.

$^1$H-NMR (400 MHz, DMSO-d6): δ=3.47 (ddd, 1H); 3.74 (ddd, 1H); 4.17-4.27 (m, 1H); 6.66 (d, 1H); 7.55-7.62 (m, 4H); 7.64-7.70 (m, 1H); 7.81-7.84 (m, 1H); 7.99 (d, 2H); 8.66 (s, 1H); 9.63 (t, 1H).

Example 63

2-(3-Chlorophenyl)-6-(4-chlorophenyl)-3-oxo-N-(3,3,3-trifluoro-2-hydroxypropyl)-2,3-dihydropyridazine-4-carboxamide, Enantiomer 1

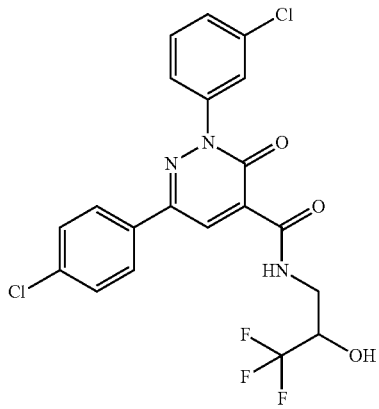

HPLC-separation of 60 mg 2-(3-chlorophenyl)-6-(4-chlorophenyl)-3-oxo-N-(3,3,3-trifluoro-2-hydroxypropyl)-2,3-dihydropyridazine-4-carboxamide (example 62) on a chiral column (Chiralpak IB 5 µM 250×30 mm, eluent: hexanes/ethanol gradient 5-50% ethanol, flow 40 mL/min, temperature: 25° C.) yielded 20 mg 2-(3-chlorophenyl)-6-(4-chlorophenyl)-3-oxo-N-(3,3,3-trifluoro-2-hydroxypropyl)-2,3-dihydropyridazine-4-carboxamide, enantiomer 1.

$^1$H-NMR (400 MHz, DMSO-d6): δ=3.47 (ddd, 1H); 3.74 (ddd, 1H); 4.17-4.27 (m, 1H); 6.66 (d, 1H); 7.55-7.62 (m, 4H); 7.64-7.70 (m, 1H); 7.81-7.84 (m, 1H); 7.99 (d, 2H); 8.66 (s, 1H); 9.63 (t, 1H).

Chiral HPLC: Rt=5.37 min

Instrument: Agilent HPLC 1260; Aurora SFC module; column: Chiralpak IB 3 µM 100×4.6 mm; eluent: hexanes (0.1% diethylamine)/ethanol gradient 5-50% ethanol, flow 1.4 mL/min; temperature: 25° C.; DAD scan: 254 nm.

Example 64

2-(3-Chlorophenyl)-6-(4-chlorophenyl)-3-oxo-N-(3,3,3-trifluoro-2-hydroxypropyl)-2,3-dihydropyridazine-4-carboxamide, Enantiomer 2

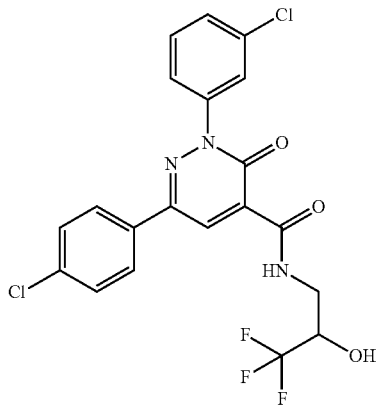

The separation of 60 mg example 62, according to example 63, additionally yielded 15 mg 2-(3-chlorophenyl)-6-(4-chlorophenyl)-3-oxo-N-(3,3,3-trifluoro-2-hydroxypropyl)-2,3-dihydropyridazine-4-carboxamide, enantiomer 2.

$^1$H-NMR (400 MHz, DMSO-d6): δ=3.47 (ddd, 1H); 3.74 (ddd, 1H); 4.17-4.27 (m, 1H); 6.66 (d, 1H); 7.55-7.62 (m, 4H); 7.64-7.70 (m, 1H); 7.81-7.84 (m, 1H); 7.99 (d, 2H); 8.66 (s, 1H); 9.63 (t, 1H).

Chiral HPLC: Rt=6.20 min

Instrument: Agilent HPLC 1260; Aurora SFC module; column: Chiralpak IB 3 µM 100×4.6 mm; eluent: hexanes (0.1% diethylamine)/ethanol gradient 5-50% ethanol, flow 1.4 mL/min; temperature: 25° C.; DAD scan: 254 nm.

Example 65

2-(3-Chlorophenyl)-6-(4-chlorophenyl)-N-(1-hydroxypropan-2-yl)-3-oxo-2,3-dihydropyridazine-4-carboxamide

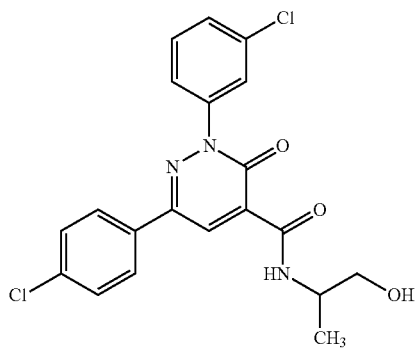 [SMILES: CC(CO)NC(=O)c1cc(-c2ccc(Cl)cc2)nn(-c2cccc(Cl)c2)c1=O]

79 mg oxalylchloride were slowly added to a solution of 150 mg intermediate 20 in 10 mL of dichloromethane and 15 mg N,N-dimethylformamide. The reaction mixture was stirred at room temperature for 1 h. The mixtrue was evaporated to dryness to give 200 mg crude 2-(3-chlorophenyl)-6-(4-chlorophenyl)-3-oxo-2,3-dihydropyridazine-4-carbonyl chloride. A solution of these 200 mg material, 79 mg 2-aminopropan-1-ol and 0.073 mL triethylamine in 20 mL dichloromethane was stirring under ice-water bath for 10 min. Then the reaction was quenched by addition of water and the mixture was extracted with dichloromethane. The organic phase was dried over sodium sulfate and evaporated to dryness. The residue was subjected to flash chromatography (petroleum ether/ethylacetate gradient with up to 25% ethyl acetate) to yield 57 mg 2-(3-chlorophenyl)-6-(4-chlorophenyl)-N-(1-hydroxypropan-2-yl)-3-oxo-2,3-dihydropyridazine-4-carboxamide.

$^1$H-NMR (400 MHz, DMSO-d$_6$): δ=1.15 (d, 3H); 3.39-3.46 (m, 2H, signal below water signal); 3.98-4.07 (m, 1H); 4.94 (t, 1H); 7.55-7.61 (m, 4H); 7.63-7.68 (m, 1H); 7.80-7.83 (m, 1H); 7.97 (d, 2H); 8.63 (s, 1H); 9.42 (d, 1H).

Example 66

2-(3-Chlorophenyl)-6-(4-chlorophenyl)-N-[(2S)-1-hydroxypropan-2-yl]-3-oxo-2,3-dihydropyridazine-4-carboxamide

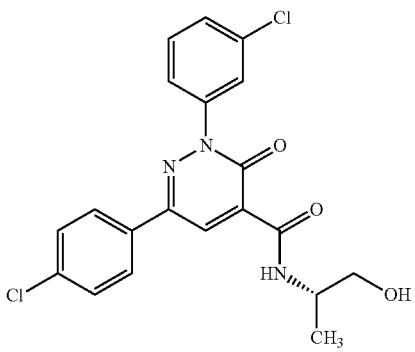

A solution of 80 mg intermediate 20, 33 mg (2S)-2-aminopropan-1-ol, 126 mg HATU and 0.12 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 55 mg 2-(3-chlorophenyl)-6-(4-chlorophenyl)-N-[(2S)-1-hydroxypropan-2-yl]-3-oxo-2,3-dihydropyridazine-4-carboxamide.

$^1$H-NMR (400 MHz, DMSO-d$_6$): δ=1.15 (d, 3H); 3.39-3.46 (m, 2H, signal below water signal); 3.98-4.07 (m, 1H); 4.94 (t, 1H); 7.55-7.61 (m, 4H); 7.63-7.68 (m, 1H); 7.80-7.83 (m, 1H); 7.97 (d, 2H); 8.63 (s, 1H); 9.42 (d, 1H).

Example 67

2-(3-Chlorophenyl)-6-(4-chlorophenyl)-N-(2-hydroxy-3-methylbutyl)-3-oxo-2,3-dihydropyridazine-4-carboxamide

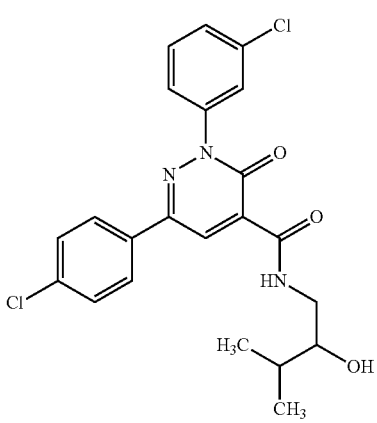

A solution of 100 mg intermediate 20, 57 mg 1-amino-3-methylbutan-2-ol, 158 mg HATU and 0.14 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC (column: X-Bridge C18 5 μm 100×30 mm, mobile phase: acetonitrile/water (0.1 Vol % formic acid)-gradient)) to yield 45 mg 2-(3-chlorophenyl)-6-(4-chlorophenyl)-N-(2-hydroxy-3-methylbutyl)-3-oxo-2,3-dihydropyridazine-4-carboxamide.

$^1$H-NMR (400 MHz, DMSO-d$_6$, selected signals): δ=9.85-0.91 (m, 6H); 1.56-1.67 (m, 1H); 3.21 (ddd, 1H); 3.53 (ddd, 1H); 4.90 (d, 1H); 7.56-7.62 (m, 4H); 7.65-7.70 (m, 1H); 7.81-7.84 (m, 1H); 7.99 (d, 2H); 8.65 (s, 1H); 9.53 (t, 1H).

Example 68

2-(3-Chlorophenyl)-6-(4-chlorophenyl)-N-(2-hydroxy-3-methylbutyl)-3-oxo-2,3-dihydropyridazine-4-carboxamide, Enantiomer 1

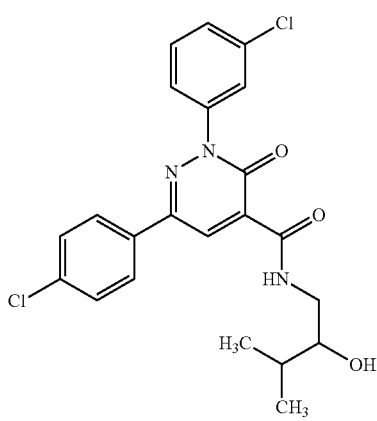 [SMILES: CC(C)C(O)CNC(=O)c1cc(-c2ccc(Cl)cc2)nn(-c2cccc(Cl)c2)c1=O]

HPLC-separation of 45 mg 2-(3-chlorophenyl)-6-(4-chlorophenyl)-N-(2-hydroxy-3-methylbutyl)-3-oxo-2,3-dihydropyridazine-4-carboxamide (example 67) on a chiral column (Chiralpak IA 5 μM 250×30 mm, eluent: MTBE/ethanol 90:10 (0.1% diethylamine), flow 50 mL/min, temperature: 25° C.) yielded 17 mg 2-(3-chlorophenyl)-6-(4-chlorophenyl)-N-(2-hydroxy-3-methylbutyl)-3-oxo-2,3-dihydropyridazine-4-carboxamide, enantiomer 1.

$^1$H-NMR (400 MHz, DMSO-d$_6$, selected signals): δ=9.85-0.91 (m, 6H); 1.56-1.67 (m, 1H); 3.21 (ddd, 1H); 3.53 (ddd, 1H); 4.90 (d, 1H); 7.56-7.62 (m, 4H); 7.65-7.70 (m, 1H); 7.81-7.84 (m, 1H); 7.99 (d, 2H); 8.65 (s, 1H); 9.53 (t, 1H).

Chiral HPLC: Rt=2.58 min

Instrument: Agilent HPLC 1260; Aurora SFC module; column: Chiralpak IA 3 μM 100×4.6 mm; eluent: MTBE/ethanol 90:10 (0.1% diethylamine), flow 1.4 mL/min; temperature: 25° C.; DAD scan: 254 nm.

Example 69

2-(3-Chlorophenyl)-6-(4-chlorophenyl)-N-(2-hydroxy-3-methylbutyl)-3-oxo-2,3-dihydropyridazine-4-carboxamide, Enantiomer 2

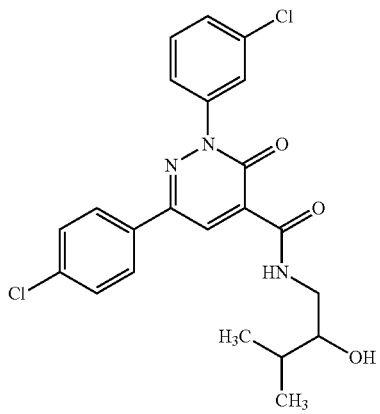 [SMILES: CC(C)C(O)CNC(=O)c1cc(-c2ccc(Cl)cc2)nn(-c2cccc(Cl)c2)c1=O]

The separation of 45 mg example 67, according to example 68, additionally yielded 15 mg 2-(3-chlorophenyl)-6-(4-chlorophenyl)-N-(2-hydroxy-3-methylbutyl)-3-oxo-2,3-dihydropyridazine-4-carboxamide, enantiomer 2.

$^1$H-NMR (400 MHz, DMSO-d$_6$, selected signals): δ=9.85-0.91 (m, 6H); 1.56-1.67 (m, 1H); 3.21 (ddd, 1H); 3.53 (ddd, 1H); 4.90 (d, 1H); 7.56-7.62 (m, 4H); 7.65-7.70 (m, 1H); 7.81-7.84 (m, 1H); 7.99 (d, 2H); 8.65 (s, 1H); 9.53 (t, 1H).

Chiral HPLC: Rt=3.19 min

Instrument: Agilent HPLC 1260; Aurora SFC module; column: Chiralpak IA 3 μM 100×4.6 mm; eluent: MTBE/ethanol 90:10 (0.1% diethylamine), flow 1.4 mL/min; temperature: 25° C.; DAD scan: 254 nm.

The following examples were prepared from the starting materials stated in the table using the procedure described in example 4. Enantiomers were separated from their racemate by chiral HPLC using the column and solvent conditions stated.

TABLE 3

Examples 70-93

| Expl. | structure | IUPAC name | Starting materials | analytics |
|---|---|---|---|---|
| 70 | 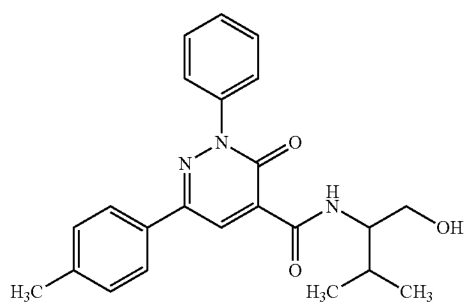 [SMILES: Cc1ccc(-c2cc(C(=O)NC(CO)C(C)C)c(=O)n(-c3ccccc3)n2)cc1] | N-(1-hydroxy-3-methylbutan-2-yl)-6-(4-methylphenyl)-3-oxo-2-phenyl-2,3-dihydropyridazine-4-carboxamide | Intermediate 23, 2-amino-3-methylbutan-1-ol | $^1$H-NMR (400 MHz, DMSO-d$_6$): δ = 0.86-0.91 (m, 6H), 1.90-1.98 (m, 1H), 2.35 (s, 3H), 3.42-3.43 (m, 1H), 3.50-3.51 (m, 1H), 3.81-3.88 (m, 1H), 4.75-4.78 (t, 1H), 7.30-7.32 (m, 2H), 7.49-7.57 (m, 3H), 7.63-7.65 (m, 2H), 7.81-7.83 (m, 2H), 8.61 (s, 1H), 9.47-9.50 (d, 1H) |
| 71 | 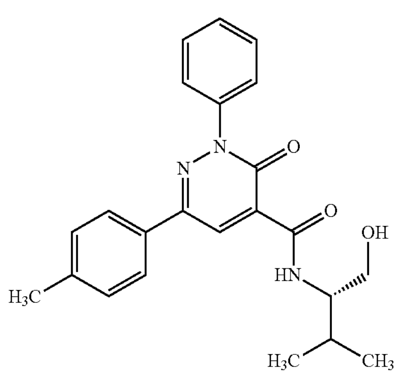 [SMILES: Cc1ccc(-c2cc(C(=O)N[C@H](CO)C(C)C)c(=O)n(-c3ccccc3)n2)cc1] | N-[(2S)-1-hydroxy-3-methylbutan-2-yl]-6-(4-methylphenyl)-3-oxo-2-phenyl-2,3-dihydropyridazine-4-carboxamide | Intermediate 23, (2S)-2-amino-3-methylbutan-1-ol | $^1$H-NMR (400 MHz, DMSO-d$_6$): δ = 0.86-0.91 (m, 6H), 1.90-1.98 (m, 1H), 2.35 (s, 3H), 3.42-3.43 (m, 1H), 3.50-3.51 (m, 1H), 3.81-3.88 (m, 1H), 4.75-4.78 (t, 1H), 7.30-7.32 (m, 2H), 7.49-7.57 (m, 3H), 7.63-7.65 (m, 2H), 7.81-7.83 (m, 2H), 8.61 (s, 1H), 9.47-9.50 (d, 1H) |

TABLE 3-continued

Examples 70-93

| Expl. | structure | IUPAC name | Starting materials | analytics |
|---|---|---|---|---|
| 72 | 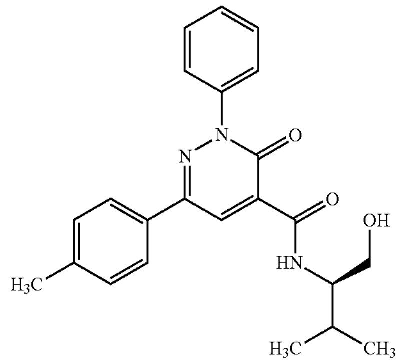 [SMILES: Cc1ccc(-c2cc(C(=O)N[C@@H](CO)C(C)C)c(=O)n(-c3ccccc3)n2)cc1] | N-[(2R)-1-hydroxy-3-methylbutan-2-yl]-6-(4-methylphenyl)-3-oxo-2-phenyl-2,3-dihydropyridazine-4-carboxamide | Intermediate 23, (2R)-2-amino-3-methylbutan-1-ol | $^1$H-NMR (400 MHz, DMSO-d$_6$): δ = 0.86-0.91 (m, 6H), 1.90-1.98 (m, 1H), 2.35 (s, 3H), 3.42-3.43 (m, 1H), 3.50-3.51 (m, 1H), 3.81-3.88 (m, 1H), 4.75-4.78 (t, 1H), 7.30-7.32 (m, 2H), 7.49-7.57 (m, 3H), 7.63-7.65 (m, 2H), 7.81-7.83 (m, 2H), 8.61 (s, 1H), 9.47-9.50 (d, 1H) |
| 73 | 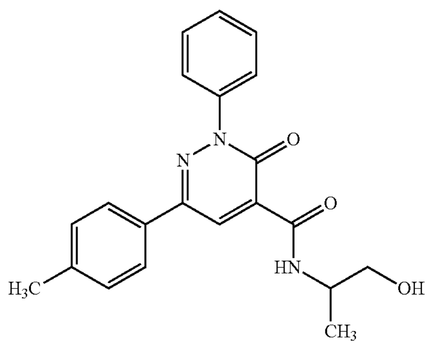 [SMILES: Cc1ccc(-c2cc(C(=O)NC(C)CO)c(=O)n(-c3ccccc3)n2)cc1] | N-(1-hydroxypropan-2-yl)-6-(4-methylphenyl)-3-oxo-2-phenyl-2,3-dihydropyridazine-4-carboxamide | Intermediate 23, 2-aminopropan-1-ol | $^1$H-NMR (400 MHz, DMSO-d$_6$): δ= 1.13-1.15 (d, 3H), 3.24 (s, 3H), 3.41-3.43 (m, 2H), 3.97-4.03 (m, 1H), 4.90-4.92 (t, 1H), 7.30-7.32 (m, 2H), 7.48-7.56 (m, 3H), 7.62-7.64 (m, 2H), 7.80-7.82 (m, 2H), 8.60 (s, 1H), 9.50-9.52 (d, 1H) |
| 74 | 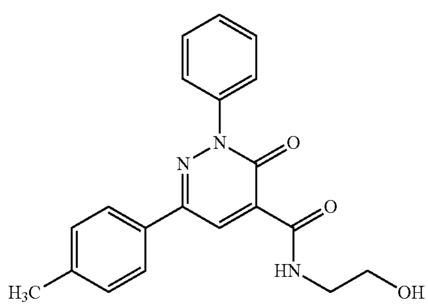 [SMILES: Cc1ccc(-c2cc(C(=O)NCCO)c(=O)n(-c3ccccc3)n2)cc1] | N-(2-hydroxyethyl)-6-(4-methylphenyl)-3-oxo-2-phenyl-2,3-dihydropyridazine-4-carboxamide | Intermediate 23, 2-aminoethanol | $^1$H-NMR (400 MHz, DMSO-d$_6$): δ = |
| 75 | 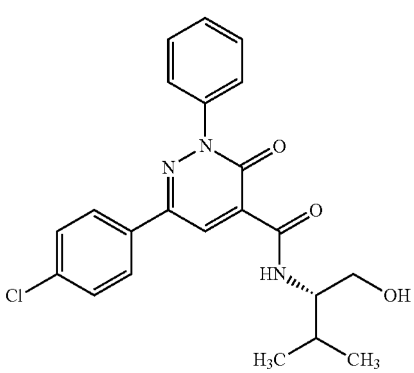 [SMILES: CC(C)[C@@H](CO)NC(=O)c1cc(-c2ccc(Cl)cc2)nn(-c2ccccc2)c1=O] | 6-(4-chlorophenyl)-N-[(2S)-1-hydroxy-3-methylbutan-2-yl]-3-oxo-2-phenyl-2,3-dihydropyridazine-4-carboxamide | Intermediate 9, (2S)-2-amino-3-methylbutan-1-ol | $^1$H-NMR (400 MHz, DMSO-d$_6$): δ = 0.88 (d, 3H); 0.92 (d, 3H); 1.91-2.02 (m, 1H); 3.40-3.47 (m, 1H); 3.50-3.57 (m, 1H); 3.81-3.89(m, 1H); 4.80 (t, 1H); 7.48-7.60 (m, 5H); 7.65-7.69 (m, 2H); 7.98 (d, 2H); 8.66 (s, 1H); 9.48 (d, 1H). |

TABLE 3-continued

Examples 70-93

| Expl. | structure | IUPAC name | Starting materials | analytics |
|---|---|---|---|---|
| 76 | 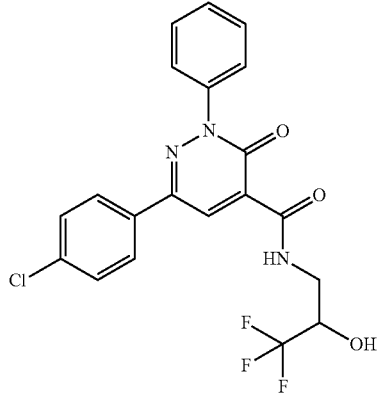 [SMILES: O=C(NCC(O)C(F)(F)F)c1cc(-c2ccc(Cl)cc2)nn(-c2ccccc2)c1=O] | 6-(4-chlorophenyl)-3-oxo-2-phenyl-N-(3,3,3-trifluoro-2-hydroxypropyl)-2,3-dihydropyridazine-4-carboxamide | Intermediate 8, 3-amino-1,1,1-trifluoropropan-2-ol | $^1$H-NMR (400 MHz, DMSO-$d_6$): δ = 3.46 (ddd, 1H); 3.75 (ddd, 1H); 4.17-4.27 (m, 1H); 6.65 (d, 1H); 7.48-7.60 (m, 5H); 7.64-7.69 (m, 2H); 7.99 (d, 2H); 8.67 (s, 1H); 9.71 (t, 1H). |
| 77 | 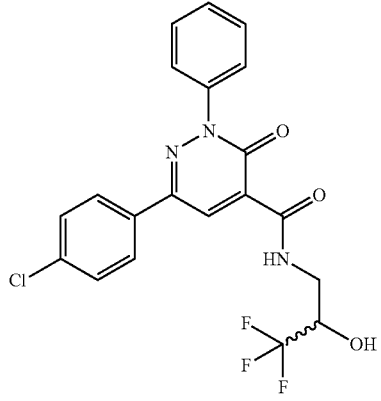 [SMILES: O=C(NCC(O)C(F)(F)F)c1cc(-c2ccc(Cl)cc2)nn(-c2ccccc2)c1=O] | 6-(4-chlorophenyl)-3-oxo-2-phenyl-N-(3,3,3-trifluoro-2-hydroxypropyl)-2,3-dihydropyridazine-4-carboxamide, enantiomer 1 | Example 76, chiral HPLC on Chiralpak IA, hexanes/ethanol gradient 20-50% ethanol | $^1$H-NMR (400 MHz, DMSO-$d_6$): δ = 3.46 (ddd, 1H); 3.75 (ddd, 1H); 4.17-4.27 (m, 1H); 6.65 (d, 1H); 7.48-7.60 (m, 5H); 7.64-7.69 (m, 2H); 7.99 (d, 2H); 8.67 (s, 1H); 9.71 (t, 1H). Chiral HPLC: Rt = 4.09 min; (Chiralpak IA 3 μM, hexanes (0.1% diethylamine)/ethanol gradient 20-50% ethanol, flow 1.4 mL/min) |
| 78 | 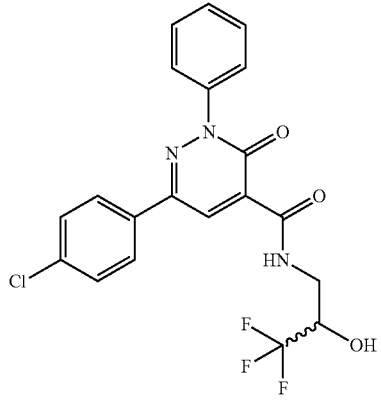 [SMILES: O=C(NCC(O)C(F)(F)F)c1cc(-c2ccc(Cl)cc2)nn(-c2ccccc2)c1=O] | 6-(4-chlorophenyl)-3-oxo-2-phenyl-N-(3,3,3-trifluoro-2-hydroxypropyl)-2,3-dihydropyridazine-4-carboxamide, enantiomer 2 | Example 76, chiral HPLC on Chiralpak IA, hexanes/ethanol gradient 20-50% ethanol | $^1$H-NMR (400 MHz, DMSO-$d_6$): δ = 3.46 (ddd, 1H); 3.75 (ddd, 1H); 4.17-4.27 (m, 1H); 6.65 (d, 1H); 7.48-7.60 (m, 5H); 7.64-7.69 (m, 2H); 7.99 (d, 2H); 8.67 (s, 1H); 9.71 (t, 1H). Chiral HPLC: Rt = 5.52 min; (Chiralpak IA 3 μM, hexanes (0.1% diethylamine)/ethanol gradient 20-50% ethanol, flow 1.4 mL/min) |
| 79 | 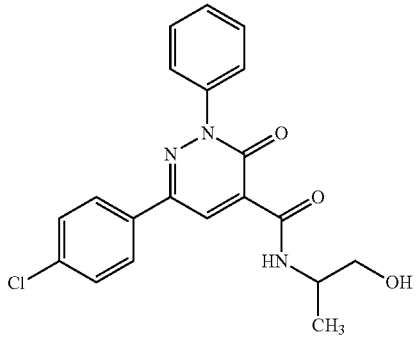 [SMILES: CC(CO)NC(=O)c1cc(-c2ccc(Cl)cc2)nn(-c2ccccc2)c1=O] | 6-(4-chlorophenyl)-N-(1-hydroxypropan-2-yl)-3-oxo-2-phenyl-2,3-dihydropyridazine-4-carboxamide | Intermediate 9, 2-aminopropan-1-ol | $^1$H-NMR (400 MHz, DMSO-$d_6$): δ = 1.16 (d, 3H); 3.40-3.48 (m, 2H); 3.99-4.08 (m, 1H); 4.93 (t, 1H); 7.48-7.61 (m, 5H); 7.64-7.68 (m, 2H); 7.98 (d, 2H); 8.65 (s, 1H); 9.50 (d, 1H). |

TABLE 3-continued

Examples 70-93

| Expl. | structure | IUPAC name | Starting materials | analytics |
|---|---|---|---|---|
| 80 | 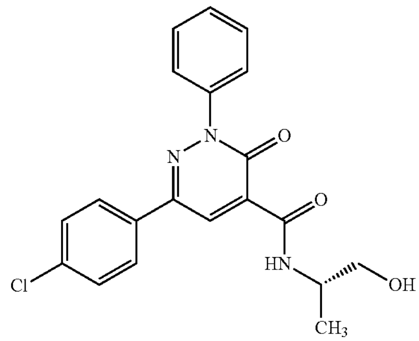 [SMILES: C[C@@H](CO)NC(=O)c1cc(-c2ccc(Cl)cc2)nn(-c2ccccc2)c1=O] | 6-(4-chlorophenyl)-N-[(2S)-1-hydroxypropan-2-yl]-3-oxo-2-phenyl-2,3-dihydropyridazine-4-carboxamide | Example 79, chiral HPLC on Chiralpak IB. $CO_2$/ethanol 83:17 | $^1$H-NMR (400 MHz, DMSO-$d_6$): δ = 1.16 (d, 3H); 3.40-3.48 (m, 2H); 3.99-4.08 (m, 1H); 4.93 (t, 1H); 7.48-7.61 (m, 5H); 7.64-7.68 (m, 2H); 7.98 (d, 2H); 8.65 (s, 1H); 9.50 (d, 1H). Chiral HPLC: Rt = 2.65 min; (Chiralpak IB 5 μM, $CO_2$/ethanol 83:17, flow 1.4 mL/min) |
| 81 | 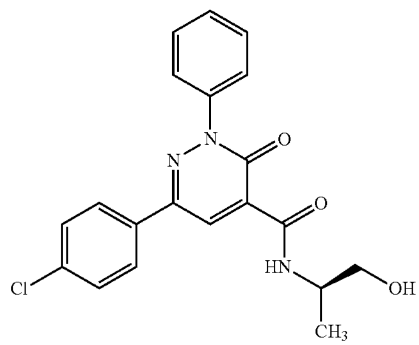 [SMILES: C[C@H](CO)NC(=O)c1cc(-c2ccc(Cl)cc2)nn(-c2ccccc2)c1=O] | 6-(4-chlorophenyl)-N-[(2R)-1-hydroxypropan-2-yl]-3-oxo-2-phenyl-2,3-dihydropyridazine-4-carboxamide | Example 79, chiral HPLC on Chiralpak IB. $CO_2$/ethanol 83:17 | $^1$H-NMR (400 MHz, DMSO-$d_6$): δ = 1.16 (d, 3H); 3.40-3.48 (m, 2H); 3.99-4.08 (m, 1H); 4.93 (t, 1H); 7.48-7.61 (m, 5H); 7.64-7.68 (m, 2H); 7.98 (d, 2H); 8.65 (s, 1H); 9.50 (d, 1H). Chiral HPLC: Rt = 3.67 min; (Chiralpak IB 5 μM, $CO_2$/ethanol 83:17, flow 1.4 mL/min) |
| 82 | 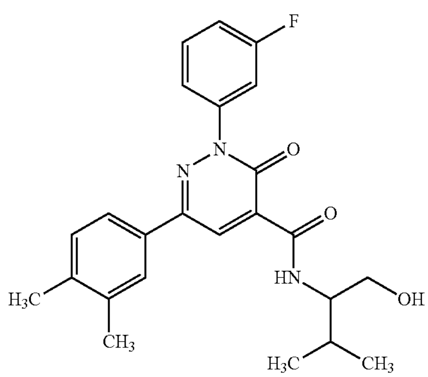 [SMILES: Cc1ccc(-c2cc(C(=O)N[C@H](CO)C(C)C)c(=O)n(-c3cccc(F)c3)n2)cc1C] | 6-(3,4-dimethylphenyl)-2-(3-fluorophenyl)-N-(1-hydroxy-3-methylbutan-2-yl)-3-oxo-2,3-dihydropyridazine-4-carboxamide | Intermediate 14, 2-amino-3-methylbutan-1-ol | $^1$H-NMR (400 MHz, DMSO-$d_6$): δ = 0.88 (d, 3H); 0.92 (d, 3H); 1.92-2.02 (m, 1H); 2,28 (s, 3H); 2.30 (s, 3H); 3.40-3.48 (m, 1H); 3.51-3.58 (m, 1H); 3.81-3.89 (m, 1H); 4.80 (t, 1H); 7.29 (d, 1H); 7.38 (ddt, 1H); 7.52-7.69 (m, 4H); 7.71-7.75 (m, 1H); 8.63 (s, 1H); 9.44 (d, 1H). |
| 83 | 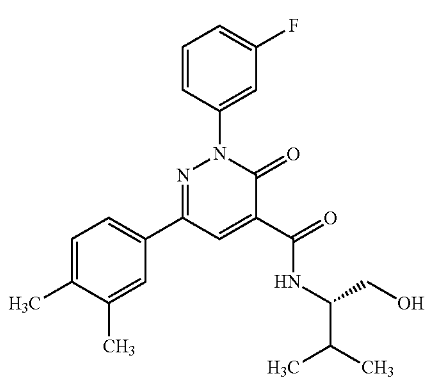 | 6-(3,4-dimethylphenyl)-2-(3-fluorophenyl)-N-[(2S)-1-hydroxy-3-methylbutan-2-yl]-3oxo-2,3-dihydropyridazine-4-carboxamide | Example 82, chiral HPLC on Chiralpak IB, $CO_2$/ethanol 83:17 | $^1$H-NMR (400 MHz, DMSO-$d_6$): δ = 0.88 (d, 3H); 0.92 (d, 3H); 1.92-2.02 (m, 1H); 2,28 (s, 3H); 2.30 (s, 3H); 3.40-3.48 (m, 1H); 3.51-3.58 (m, 1H); 3.81-3.89 (m, 1H); 4.80 (t, 1H); 7.29 (d, 1H); 7.38 (ddt, 1H); 7.52-7.69 (m, 4H); 7.71-7.75 (m, 1H); 8.63 (s, 1H); 9.44 (d, 1H). Chiral HPLC: Rt= 1.58 min; (Chiralpak IB 5 μM. $CO_2$/ethanol 83:17, flow 1.4 mL/min) |

TABLE 3-continued

Examples 70-93

| Expl. | structure | IUPAC name | Starting materials | analytics |
|---|---|---|---|---|
| 84 | 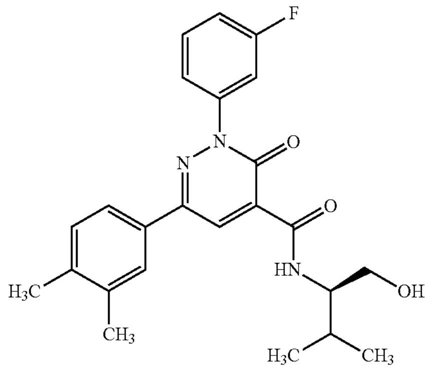 [SMILES: Cc1ccc(-c2cc(C(=O)N[C@@H](CO)C(C)C)c(=O)n(-c3cccc(F)c3)n2)cc1C] | 6-(3,4-dimethylphenyl)-2-(3-fluorophenyl)-N-[(2R)-1-hydroxy-3-methylbutan-2-yl]-3oxo-2,3-dihydropyridazine-4-carboxamide | Example 82, chiral HPLC on Chiralpak IB, $CO_2$/ethanol 83:17 | $^1$H-NMR (400 MHz, DMSO-$d_6$): δ = 0.88 (d, 3H); 0.92 (d, 3H); 1.92-2.02 (m, 1H); 2,28 (s, 3H); 2.30 (s, 3H); 3.40-3.48 (m, 1H); 3.51-3.58 (m, 1H); 3.81-3.89(171, 1H); 4.80 (t, 1H); 7.29 (d, 1H); 7.38 (ddt, 1H); 7.52-7.69 (m, 4H); 7.71-7.75 (m, 1H); 8.63 (s, 1H); 9.44 (d, 1H). Chiral HPLC: Rt = 2.80 min; (Chiralpak IB 5 μM, $CO_2$/ethanol 83:17, flow 1.4 mL/min) |
| 85 | 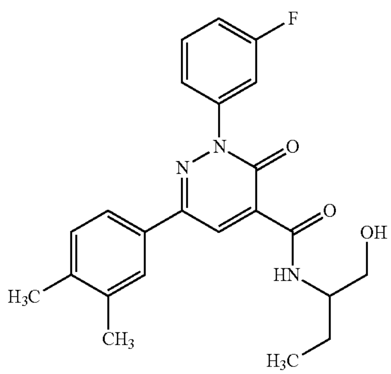 [SMILES: CCC(CO)NC(=O)c1cc(-c2ccc(C)c(C)c2)nn(-c2cccc(F)c2)c1=O] | 6-(3,4-dimethylphenyl)-2-(3-fluorophenyl)-N-(1-hydroxybutan-2-yl)-3-oxo-2,3-dihydropyridazine-4-carboxamide | Intermediate 14, 2-aminobutan-1-ol | $^1$H-NMR (400 MHz, DMSO-$d_6$): δ = 0.89 (t, 3H); 1.43-1.54 (m, 1H); 1.60-1.70 (m, 1H); 2.28 (s, 3H); 2.30 (s, 3H); 3.39-3.46 (m, 1H); 3.48-3.55 (m, 1H); 3.85-3.93 (m, 1H); 4.86 (t, 1H): 7.28 (d, 1H); 7.38 (ddt, 1H); 7.51-7.68 (m, 4H); 7.71-7.74 (m, 1H); 8.62 (s, 1H); 9.41 (d, 1H). |
| 86 | 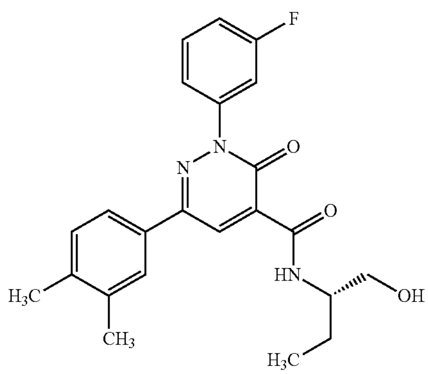 [SMILES: CC[C@@H](CO)NC(=O)c1cc(-c2ccc(C)c(C)c2)nn(-c2cccc(F)c2)c1=O] | 6-(3,4-dimethylphenyl)-2-(3-fluorophenyl)-N-[(2S)-1-hydroxybutan-2-yl]-3-oxo-2,3-dihydropyridazine-4-carboxamide | Example 85, chiral HPLC on Chiralpak IC, methanol/ethanol 50:50 | $^1$H-NMR (400 MHz, DMSO-$d_6$): δ = 0.89 (t, 3H); 1.43-1.54 (m, 1H); 1.60-1.70 (m, 1H); 2.28 (s, 3H); 2.30 (s, 3H); 3.39-3.46 (m, 1H); 3.48-3.55 (m, 1H); 3.85-3.93 (m, 1H); 4.86 (t, 1H); 7.28 (d, 1H); 7.38 (ddt, 1H); 7.51-7.68 (m, 4H); 7.71-7.74 (m, 1H); 8.62 (s, 1H); 9.41 (d, 1H). Chiral HPLC: Rt = 2.25 min; (Chiralpak IC 3 μM, methanol/ethanol 50:50, flow 1.4 mL/min) |
| 87 | 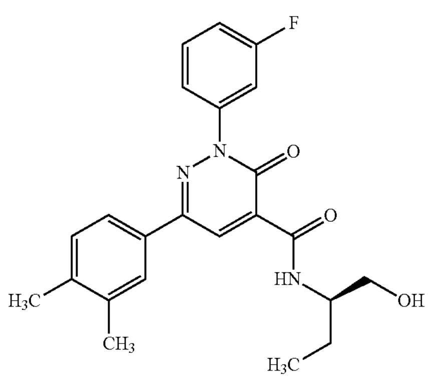 [SMILES: CC[C@H](CO)NC(=O)c1cc(-c2ccc(C)c(C)c2)nn(-c2cccc(F)c2)c1=O] | 6-(3,4-dimethylphenyl)-2-(3-fluorophenyl)-N-[(2R)-1-hydroxybutan-2-yl]-3-oxo-2,3-dihydropyridazine-4-carboxamide | Example 85, chiral HPLC on Chiralpak IC, methanol/ethanol 50:50 | $^1$H-NMR (400 MHz, DMSO-$d_6$): δ = 0.89 (t, 3H); 1.43-1.54 (m, 1H); 1.60-1.70 (m, 1H); 2.28 (s, 3H); 2.30 (s, 3H); 3.39-3.46 (m, 1H); 3.48-3.55 (m, 1H); 3.85-3.93 (m, 1H); 4.86 (t, 1H); 7.28 (d, 1H); 7.38 (ddt, 1H); 7.51-7.68 (m, 4H); 7.71-7.74 (m, 1H); 8.62 (s, 1H); 9.41 (d, 1H). Chiral HPLC: Rt = 2.97 min; (Chiralpak IC 3 μM, methanol/ethanol 50:50, flow 1.4 mL/min) |

TABLE 3-continued

Examples 70-93

| Expl. | structure | IUPAC name | Starting materials | analytics |
|---|---|---|---|---|
| 88 | 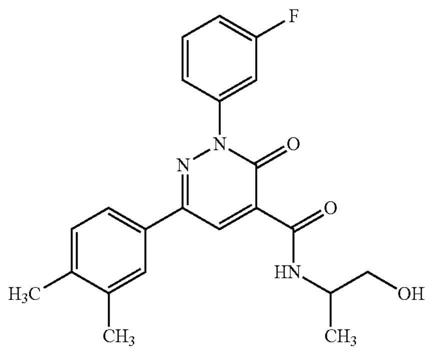 [SMILES: Cc1ccc(-c2cc(C(=O)NC(C)CO)c(=O)n(-c3cccc(F)c3)n2)cc1C] | 6-(3,4-dimethylphenyl)-2-(3-fluorophenyl)-N-(1-hydroxypropan-2-yl)-3-oxo-2,3-dihydropyridazine-4-carboxamide | Intermediate 14, 2-aminopropan-1-ol | $^1$H-NMR (400 MHz, DMSO-$d_6$): δ = 1.16 (d, 3H); 2.28 (s, 3H); 2.30 (s, 3H): 3.40-3.48 (m, 2H); 3.99-4.07 (m, 1H); 4.93 (t, 1H); 7.28 (d, 1H); 7.38 (ddt, 1H); 7.51-7.69 (m, 4H); 7.71-7.74 (m, 1H); 8.62 (s, 1H); 9.47 (d, 1H). |
| 89 | 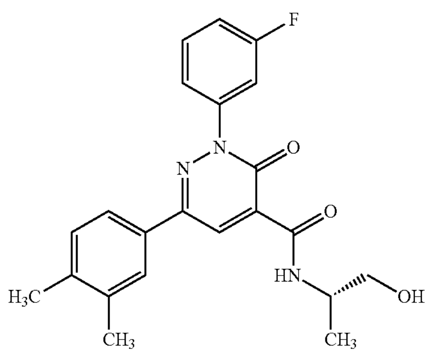 [SMILES: Cc1ccc(-c2cc(C(=O)N[C@@H](C)CO)c(=O)n(-c3cccc(F)c3)n2)cc1C] | 6-(3,4-dimethylphenyl)-2-(3-fluorophenyl)-N-[(2S)-1-hydroxypropan-2-yl]-3-oxo-2,3-dihydropyridazine-4-carboxamide | Example 88, chiral HPLC on Chiralpak IC, $CO_2$/2-propanol 75:25 | $^1$H-NMR (400 MHz, DMSO-$d_6$): δ = 1.16 (d, 3H); 2.28 (s, 3H); 2.30 (s, 3H); 3.40-3.48 (m, 2H); 3.99-4.07 (m, 1H); 4.93 (t, 1H); 7.28 (d, 1H); 7.38 (ddt, 1H); 7.51-7.69 (m, 4H); 7.71-7.74 (m, 1H); 8.62 (s, 1H); 9.47 (d, 1H). Chiral HPLC: Rt = 2.50 min; (Chiralpak IC 5 μM, $CO_2$/2-propanol 75:25, flow 4 mL/min) |
| 90 | 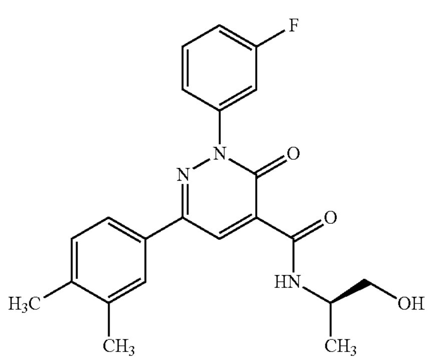 [SMILES: Cc1ccc(-c2cc(C(=O)N[C@H](C)CO)c(=O)n(-c3cccc(F)c3)n2)cc1C] | 6-(3,4-dimethylphenyl)-2-(3-fluorophenyl)-N-[(2R)-1-hydroxypropan-2-yl]-3-oxo-2,3-dihydropyridazine-4-carboxamide | Example 88, chiral HPLC on Chiralpak IC, $CO_2$/2-propanol 75:25 | $^1$H-NMR (400 MHz, DMSO-$d_6$): δ= 1.16 (d, 3H); 2.28 (s, 3H); 2.30 (s, 3H); 3.40-3.48 (m, 2H); 3.99-4.07 (m, 1H); 4.93 (t, 1H); 7.28 (d, 1H); 7.38 (ddt, 1H); 7.51-7.69 (m, 4H); 7.71-7.74 (m, 1H); 8.62 (s, 1H); 9.47 (d, 1H). Chiral HPLC: Rt = 4.16 min; (Chiralpak IC 5 μM, $CO_2$/2-propanol 75:25, flow 4 mL/min) |

Example 91

6-[4-(Difluoromethyl)phenyl]-2-(3-fluorophenyl)-N-[(2S)-1-hydroxy-3-methylbutan-2-yl]-3-oxo-2,3-dihydropyridazine-4-carboxamide

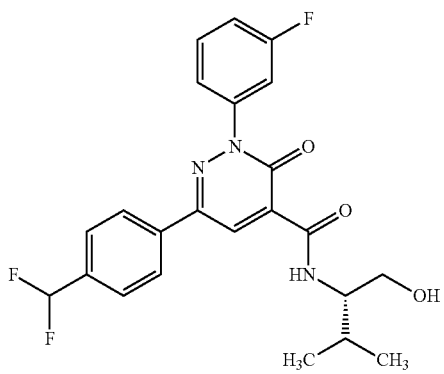 [SMILES: CC(C)[C@@H](CO)NC(=O)c1cc(-c2ccc(C(F)F)cc2)nn(-c2cccc(F)c2)c1=O]

A solution of 75 mg intermediate 33, 43 mg (2S)-2-amino-3-methylbutan-1-ol, 158 mg HATU, 1.2 mg 4-dimethylaminopyridine and 0.11 mL ethyldiisopropylamine in 1.5 mL of DMF was stirred at room temperature for 14 hours. Then the reaction was filtered and the solution was subjected to RP-HPLC ((column: X-Bridge C18 5 μm 100×30 mm, mobile phase: acetonitrile/water (0.1 Vol % formic acid)-gradient)) to yield 54 mg 6-[4-(difluoromethyl)phenyl]-2-(3-fluorophenyl)-N-[(2S)-1-hydroxy-3-methylbutan-2-yl]-3-oxo-2,3-dihydropyridazine-4-carboxamide.

$^1$H-NMR (400 MHz, DMSO-$d_6$): δ=0.89 (d, 3H); 0.92 (d, 3H); 1.91-2.03 (m, 1H); 3.41-3.48 (m, 1H); 3.51-3.59 (m, 1H); 3.81-3.90 (m, 1H); 4.81 (t, 1H); 7.12 (t, 1H); 7.39 (ddt, 1H); 7.54-7.67 (m, 3H); 7.72 (d, 2H); 8.11 (d, 2H); 8.71 (s, 1H); 9.41 (d, 1H).

Example 92

6-[4-(Difluoromethyl)phenyl]-2-(3-fluorophenyl)-N-[(2S)-1-hydroxybutan-2-yl]-3-oxo-2,3-dihydropyridazine-4-carboxamide

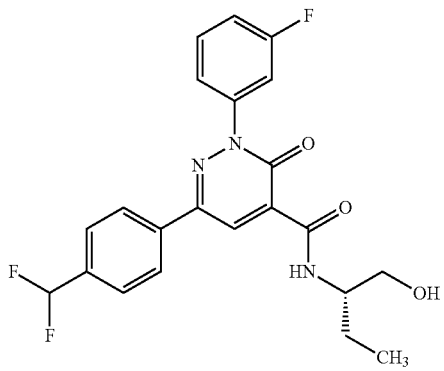 [SMILES: CC[C@@H](CO)NC(=O)c1cc(-c2ccc(C(F)F)cc2)nn(-c2cccc(F)c2)c1=O]

A solution of 75 mg intermediate 33, 38 mg (2S)-2-aminobutan-1-ol, 158 mg HATU, 1.2 mg 4-dimethylaminopyridine and 0.11 mL ethyldiisopropylamine in 1.5 mL of DMF was stirred at room temperature for 14 hours. Then the reaction was filtered and the solution was subjected to RP-HPLC ((column: X-Bridge C18 5 μm 100×30 mm, mobile phase: acetonitrile/water (0.1 Vol % formic acid)-gradient)) to yield 68 mg 6-[4-(difluoromethyl)phenyl]-2-(3-fluorophenyl)-N-[(2S)-1-hydroxybutan-2-yl]-3-oxo-2,3-dihydropyridazine-4-carboxamide.

$^1$H-NMR (400 MHz, DMSO-$d_6$): δ=0.89 (t, 3H); 1.43-1.55 (m, 1H); 1.60-1.70 (m, 1H); 3.40-3.46 (m, 1H); 3.49-3.55 (m, 1H); 3.86-3.94 (m, 1H); 7.12 (t, 1H); 7.39 (ddt, 1H); 7.54-7.67 (m, 3H); 7.72 (d, 2H); 8.11 (d, 2H); 8.69 (s, 1H); 9.38 (d, 1H).

Example 93

6-[4-(Difluoromethyl)phenyl]-2-(3-fluorophenyl)-N-[(2S)-1-hydroxypropan-2-yl]-3-oxo-2,3-dihydropyridazine-4-carboxamide

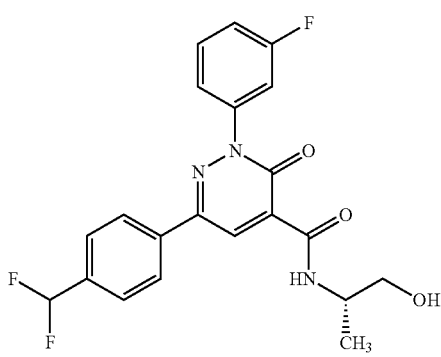 [SMILES: C[C@@H](CO)NC(=O)c1cc(-c2ccc(C(F)F)cc2)nn(-c2cccc(F)c2)c1=O]

A solution of 15 mg intermediate 33, 7 mg (2S)-2-aminopropan-1-ol, 32 mg HATU, 0.2 mg 4-dimethylaminopyridine and 0.02 mL ethyldiisopropylamine in 0.3 mL of DMF was stirred at room temperature for 4 hours. Then the reaction was filtered and the solution was subjected to RP-HPLC ((column: X-Bridge C18 5 μm 100×30 mm, mobile phase: acetonitrile/water (0.1 Vol % formic acid)-gradient)) to yield 5.3 mg 6-[4-(difluoromethyl)phenyl]-2-(3-fluorophenyl)-N-[(2S)-1-hydroxypropan-2-yl]-3-oxo-2,3-dihydropyridazine-4-carboxamide.

$^1$H-NMR (400 MHz, DMSO-$d_6$): δ=1.16 (d, 3H); 3.41-3.49 (m, 2H); 4.00-4.08 (m, 1H); 4.94 (t, 1H); 7.13 (t, 1H); 7.39 (ddt, 1H); 7.53-7.66 (m, 3H); 7.72 (d, 2H); 8.11 (d, 2H); 8.70 (s, 1H); 9.44 (d, 1H).

Example 94

6-[4-(Difluoromethyl)phenyl]-2-(3-fluorophenyl)-3-oxo-N-(3,3,3-trifluoro-2-hydroxypropyl)-2,3-dihydropyridazine-4-carboxamide

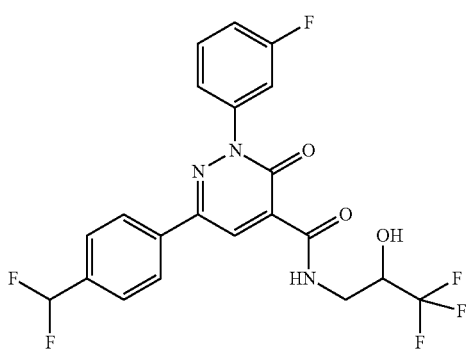 [SMILES: O=C(NCC(O)C(F)(F)F)c1cc(-c2ccc(C(F)F)cc2)nn(-c2cccc(F)c2)c1=O]

A solution of 150 mg intermediate 33, 107 mg 3-amino-1,1,1-trifluoropropan-2-ol, 317 mg HATU, 2.5 mg 4-dimethylaminopyridine and 0.22 mL ethyldiisopropylamine in 3.1 mL of DMF was stirred at room temperature for 14 hours. Then the reaction was filtered and the solution was subjected to RP-HPLC ((column: X-Bridge C18 5 μm 100×30 mm, mobile phase: acetonitrile/water (0.2 Vol % ammonia 32%)-gradient)) to yield 114 mg 6-[4-(difluoromethyl)phenyl]-2-(3-fluorophenyl)-3-oxo-N-(3,3,3-trifluoro-2-hydroxypropyl)-2,3-dihydropyridazine-4-carboxamide.

$^1$H-NMR (400 MHz, DMSO-d$_6$): δ=3.43-3.52 (m, 1H); 3.72-3.80 (m, 1H); 4.19-4.27 (m, 1H); 6.67 (s, 1H); 7.13 (t, 1H); 7.40 (ddt, 1H); 7.54-7.67 (m, 3H); 7.72 (d, 2H); 8.12 (d, 2H); 8.71 (s, 1H); 9.64 (t, 1H).

Example 95

6-[4-(Difluoromethyl)phenyl]-2-(3-fluorophenyl)-3-oxo-N-(3,3,3-trifluoro-2-hydroxypropyl)-2,3-dihydropyridazine-4-carboxamide, Enantiomer 1

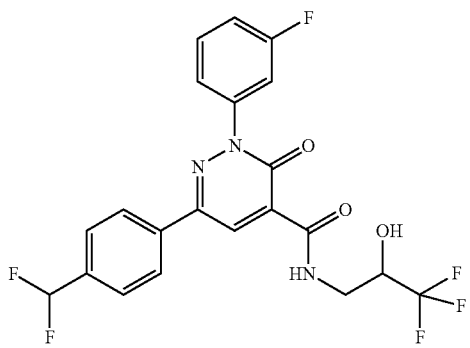 [SMILES: O=C(NCC(O)C(F)(F)F)c1cc(-c2ccc(C(F)F)cc2)nn(-c2cccc(F)c2)c1=O]

HPLC-separation of 110 mg 6-[4-(difluoromethyl)phenyl]-2-(3-fluorophenyl)-3-oxo-N-(3,3,3-trifluoro-2-hydroxypropyl)-2,3-dihydropyridazine-4-carboxamide (example 94) on a chiral column (Chiralpak IA 5 μM 250×30 mm, eluent: hexanes/2-propanol (0.1% diethylamine) gradient 20-50% 2-propanol, flow 40 mL/min, temperature: 25° C.) yielded 30 mg 6-[4-(difluoromethyl)phenyl]-2-(3-fluorophenyl)-3-oxo-N-(3,3,3-trifluoro-2-hydroxypropyl)-2,3-dihydropyridazine-4-carboxamide, enantiomer 1.

$^1$H-NMR (400 MHz, DMSO-d6): δ=3.43-3.52 (m, 1H); 3.72-3.80 (m, 1H); 4.19-4.27 (m, 1H); 6.67 (s, 1H); 7.13 (t, 1H); 7.40 (ddt, 1H); 7.54-7.67 (m, 3H); 7.72 (d, 2H); 8.12 (d, 2H); 8.71 (s, 1H); 9.64 (t, 1H).

Chiral HPLC: Rt=5.02 min

Instrument: Agilent HPLC 1260; Aurora SFC module; column: Chiralpak IA 3 μM 100×4.6 mm; eluent: hexanes/ethanol (0.1% diethylamine) gradient 20-50% ethanol, flow 4 mL/min; temperature: 37.5° C.; p=100 bar, DAD scan: 254 nm.

Example 96

6-[4-(Difluoromethyl)phenyl]-2-(3-fluorophenyl)-3-oxo-N-(3,3,3-trifluoro-2-hydroxypropyl)-2,3-dihydropyridazine-4-carboxamide, Enantiomer 2

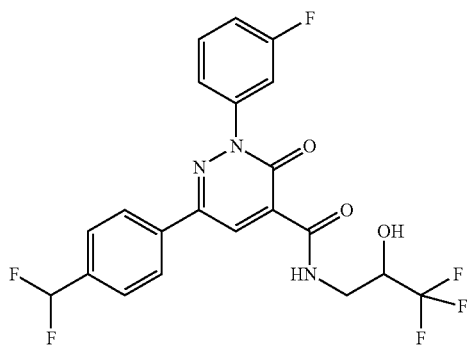 [SMILES: O=C(NCC(O)C(F)(F)F)c1cc(-c2ccc(C(F)F)cc2)nn(-c2cccc(F)c2)c1=O]

The separation of 110 mg example 94, according to example 95, additionally yielded 30 mg 6-[4-(difluoromethyl)phenyl]-2-(3-fluorophenyl)-3-oxo-N-(3,3,3-trifluoro-2-hydroxypropyl)-2,3-dihydropyridazine-4-carboxamide, enantiomer 2.

$^1$H-NMR (400 MHz, DMSO-d6): δ=3.43-3.52 (m, 1H); 3.72-3.80 (m, 1H); 4.19-4.27 (m, 1H); 6.67 (s, 1H); 7.13 (t, 1H); 7.40 (ddt, 1H); 7.54-7.67 (m, 3H); 7.72 (d, 2H); 8.12 (d, 2H); 8.71 (s, 1H); 9.64 (t, 1H).

Chiral HPLC: Rt=7.33 min

Instrument: Agilent HPLC 1260; Aurora SFC module; column: Chiralpak IA 3 μM 100×4.6 mm; eluent: hexanes/ethanol (0.1% diethylamine) gradient 20-50% ethanol, flow 4 mL/min; temperature: 37.5° C.; p=100 bar, DAD scan: 254 nm.

Example 97

6-(4-Chlorophenyl)-2-(3-fluorophenyl)-3-oxo-N-(1,1,1-trifluoro-3-hydroxypropan-2-yl)-2,3-dihydropyridazine-4-carboxamide

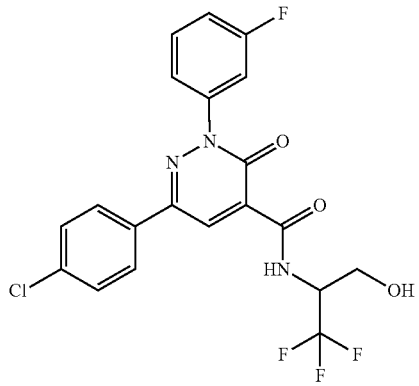 [SMILES: O=C(NC(CO)C(F)(F)F)c1cc(-c2ccc(Cl)cc2)nn(-c2cccc(F)c2)c1=O]

A solution of 150 mg intermediate 17, 144 mg 2-amino-3,3,3-trifluoropropan-1-ol hydrochloride (1:1), 248 mg HATU and 0.23 mL ethyldiisopropylamine in 7.5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 µm 100×30 mm, mobile phase: acetonitrile/water (0.1 Vol % formic acid)-gradient)) to yield 120 mg 6-(4-chlorophenyl)-2-(3-fluorophenyl)-3-oxo-N-(1,1,1-trifluoro-3-hydroxypropan-2-yl)-2,3-dihydropyridazine-4-carboxamide.

$^1$H-NMR (400 MHz, CDCl$_3$): δ=1.98 (t, 1H); 3.94-4.09 (m, 2H); 4.87-4.96 (m, 1H); 7.20 (ddt, 1H); 7.42 (td, 1H); 7.46-7.56 (m, 4H); 7.82-7.87 (m, 2H); 8.61 (s, 1H); 10.22 (bd, 1H).

Example 98

(−)-6-(4-Chlorophenyl)-2-(3-fluorophenyl)-3-oxo-N-(1,1,1-trifluoro-3-hydroxypropan-2-yl)-2,3-dihydropyridazine-4-carboxamide, Enantiomer 1

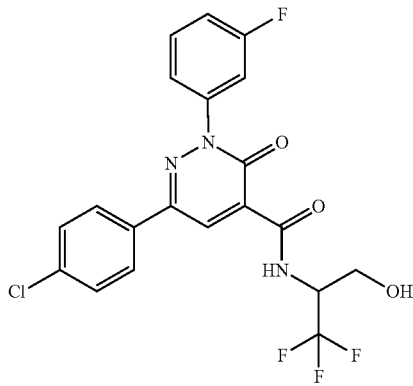 [SMILES: O=C(NC(CO)C(F)(F)F)c1cc(-c2ccc(Cl)cc2)nn(-c2cccc(F)c2)c1=O]

HPLC-separation of 118 mg 6-(4-chlorophenyl)-2-(3-fluorophenyl)-3-oxo-N-(1,1,1-trifluoro-3-hydroxypropan-2-yl)-2,3-dihydropyridazine-4-carboxamide (example 97) on a chiral column (Chiralpak IB 5 µM 250×30 mm, eluent: CO2/2-propanol 86:14, flow 100 mL/min, temperature: 40° C., pressure: 150 bar) yielded 45 mg (−)-6-(4-chlorophenyl)-2-(3-fluorophenyl)-3-oxo-N-(1,1,1-trifluoro-3-hydroxypropan-2-yl)-2,3-dihydropyridazine-4-carboxamide, enantiomer 1.

$^1$H-NMR (400 MHz, CDCl$_3$): δ=1.98 (t, 1H); 3.94-4.09 (m, 2H); 4.87-4.96 (m, 1H); 7.20 (ddt, 1H); 7.42 (td, 1H); 7.46-7.56 (m, 4H); 7.82-7.87 (m, 2H); 8.61 (s, 1H); 10.22 (bd, 1H).

Chiral HPLC: Rt=2.32 min

Instrument: Agilent HPLC 1260; Aurora SFC module; column: Chiralpak IB 3 µM 100×4.6 mm; eluent: CO2/2-propanol 86:14, flow 4 mL/min; temperature: 37.5° C.; p=100 bar, DAD scan: 254 nm.

Optical Rotation:

$[α]_D^{20}$=−9.1°+/−0.25° (c=4.9 mg/mL, methanol).

Example 99

(+)-6-(4-Chlorophenyl)-2-(3-fluorophenyl)-3-oxo-N-(1,1,1-trifluoro-3-hydroxypropan-2-yl)-2,3-dihydropyridazine-4-carboxamide, Enantiomer 2

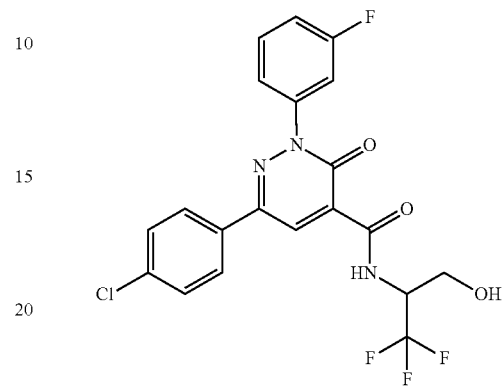

The separation of 118 mg example 97, according to example 98, additionally yielded 35 mg (+)-6-(4-chlorophenyl)-2-(3-fluorophenyl)-3-oxo-N-(1,1,1-trifluoro-3-hydroxypropan-2-yl)-2,3-dihydropyridazine-4-carboxamide, enantiomer 2.

$^1$H-NMR (400 MHz, CDCl$_3$): δ=1.98 (t, 1H); 3.94-4.09 (m, 2H); 4.87-4.96 (m, 1H); 7.20 (ddt, 1H); 7.42 (td, 1H); 7.46-7.56 (m, 4H); 7.82-7.87 (m, 2H); 8.61 (s, 1H); 10.22 (bd, 1H).

Chiral HPLC: Rt=3.25 min

Instrument: Agilent HPLC 1260; Aurora SFC module; column: Chiralpak IB 3 µM 100×4.6 mm; eluent: CO2/2-propanol 86:14, flow 4 mL/min; temperature: 37.5° C.; p=100 bar, DAD scan: 254 nm.

Optical Rotation:

$[α]_D^{20}$=6.7°+/−1.88° (c=2.7 mg/mL, methanol).

Example 100

2-(3-Fluorophenyl)-6-(4-methoxyphenyl)-3-oxo-N-(1,1,1-trifluoro-3-hydroxypropan-2-yl)-2,3-dihydropyridazine-4-carboxamide

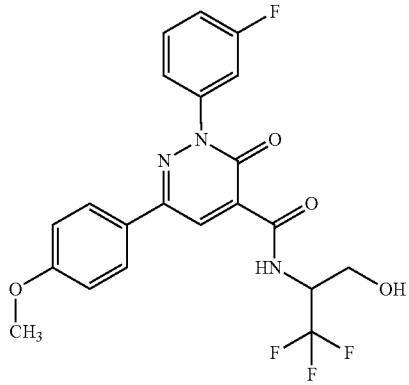 [SMILES: COc1ccc(-c2cc(C(=O)NC(CO)C(F)(F)F)c(=O)n(-c3cccc(F)c3)n2)cc1]

A solution of 100 mg intermediate 2-(3-fluorophenyl)-6-(4-methoxyphenyl)-3-oxo-2,3-dihydropyridazine-4-carboxylic acid, 99 mg 2-amino-3,3,3-trifluoropropan-1-ol hydrochloride (1:1), 223.5 mg HATU, 0.15 mL ethyldiisopropylamine and 2 mg 4-dimethylaminopyridine in 2.2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 46 mg 2-(3-fluorophenyl)-6-(4-methoxyphenyl)-3-oxo-N-(1,1,1-trifluoro-3-hydroxypropan-2-yl)-2,3-dihydropyridazine-4-carboxamide.

$^1$H NMR (400 MHz, DMSO-d$_6$) δ ppm=3.64-3.74 (m, 1H), 3.76-3.82 (m, 1H), 3.82 (s, 3H), 4.80-4.90 (m, 1H), 5.42 (t, 1H), 7.05-7.11 (m, 2H), 7.34-7.42 (m, 1H), 7.53-7.58 (m, 1H), 7.58-7.66 (m, 2H), 7.89-7.97 (m, 2H), 8.68 (s, 1H), 10.06 (d, 1H).

Example 101

2-(3-fluorophenyl)-6-(4-methoxyphenyl)-3-oxo-N-(1,1,1-trifluoro-3-hydroxypropan-2-yl)-2,3-dihydropyridazine-4-carboxamide, Enantiomer 1

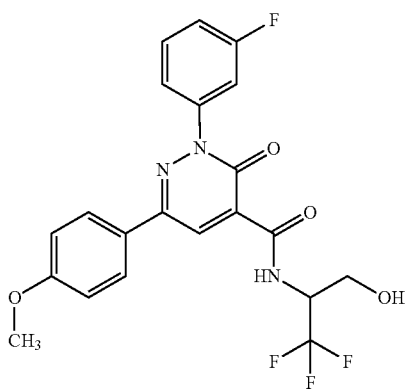 [SMILES: COc1ccc(-c2cc(C(=O)NC(CO)C(F)(F)F)c(=O)n(-c3cccc(F)c3)n2)cc1]

HPLC-separation of 28 mg 2-(3-fluorophenyl)-6-(4-methoxyphenyl)-3-oxo-N-(1,1,1-trifluoro-3-hydroxypropan-2-yl)-2,3-dihydropyridazine-4-carboxamide (example 100) on a chiral column (instrument: Sepiatec: Prep SFC100; Säule: Chiralpak IA 5 μm 250×30 mm; eluent A: CO2, eluent B: 2-propanol; isocratic: 17% B; flow 100.0 mL/min; temperature: 40° C.; BPR: 150 bar; MWD @ 254 nm) yielded 5 mg 2-(3-fluorophenyl)-6-(4-methoxyphenyl)-3-oxo-N-(1,1,1-trifluoro-3-hydroxypropan-2-yl)-2,3-dihydropyridazine-4-carboxamide, enantiomer 1.

Chiral HPLC: Rt=2.64 min (Instrument: Agilent HPLC 1260; Aurora SFC module; Chiralpak IA 3 μM 100×4.6 mm; eluent: CO2/2-propanol 83:17, flow 4 mL/min; temperature: 37.5° C.; p=100 bar, DAD scan: 254 nm.)

Example 102

2-(3-Fluorophenyl)-6-(4-methoxyphenyl)-3-oxo-N-(1,1,1-trifluoro-3-hydroxypropan-2-yl)-2,3-dihydropyridazine-4-carboxamide, Enantiomer 2

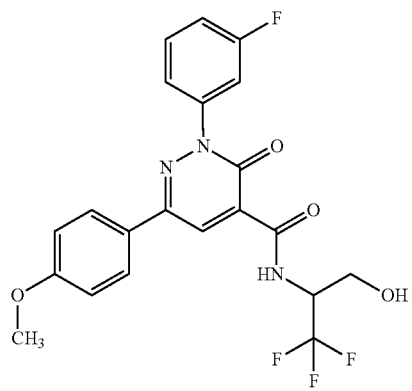 [SMILES: COc1ccc(-c2cc(C(=O)NC(CO)C(F)(F)F)c(=O)n(-c3cccc(F)c3)n2)cc1]

The separation of 28 mg 2-(3-fluorophenyl)-6-(4-methoxyphenyl)-3-oxo-N-(1,1,1-trifluoro-3-hydroxypropan-2-yl)-2,3-dihydropyridazine-4-carboxamide (example 100), according to example 101, additionally yielded 5.9 mg 2-(3-fluorophenyl)-6-(4-methoxyphenyl)-3-oxo-N-(1,1,1-trifluoro-3-hydroxypropan-2-yl)-2,3-dihydropyridazine-4-carboxamide, enantiomer 2.

Chiral HPLC: Rt=4.4 min (Instrument: Agilent HPLC 1260; Aurora SFC module; column: Chiralpak IA 3 μM 100×4.6 mm; eluent: CO2/2-propanol 83:17, flow 4 mL/min; temperature: 37.5° C.; p=100 bar, DAD scan: 254 nm).

Example 103

6-(4-Chlorophenyl)-2-(3-fluorophenyl)-N-(cis-2-hydroxycyclohexyl)-3-oxo-2,3-dihydropyridazine-4-carboxamide

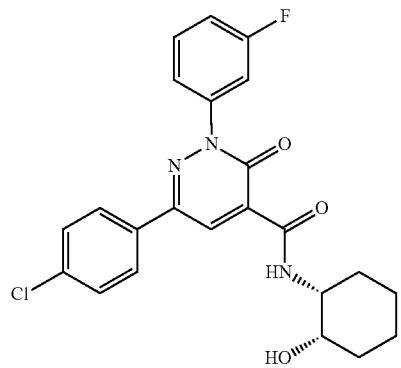 [SMILES: O=C(N[C@@H]1CCCC[C@@H]1O)c1cc(-c2ccc(Cl)cc2)nn(-c2cccc(F)c2)c1=O]

A solution of 75 mg intermediate 17, 66 mg cis-2-aminocyclohexanol hydrochloride (1:1), 165 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min;

temperature: 25° C.; DAD scan: 210-400 nm) to yield 49 mg 6-(4-chlorophenyl)-2-(3-fluorophenyl)-N-(cis-2-hydroxycyclohexyl)-3-oxo-2,3-dihydropyridazine-4-carboxamide.

¹H NMR (400 MHz, DMSO-d₆) δ ppm=1.33 (m, 2H), 1.46-1.71 (m, 6H), 3.77 (m, 1H), 3.87-3.96 (m, 1H), 4.87 (d, 1H), 7.39 (tdd, 1H), 7.51-7.66 (m, 5H), 7.95-8.03 (m, 2H), 8.66 (s, 1H), 9.64 (d, 1H).

Example 104

6-(4-Chlorophenyl)-2-(3-fluorophenyl)-N-(cis-2-hydroxycyclohexyl)-3-oxo-2,3-dihydropyridazine-4-carboxamide, Enantiomer 1

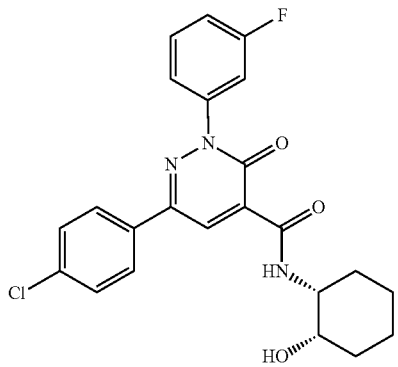 [SMILES: O=C(N[C@@H]1CCCC[C@@H]1O)c1cc(-c2ccc(Cl)cc2)nn(-c2cccc(F)c2)c1=O]

HPLC-separation of 43 mg 6-(4-chlorophenyl)-2-(3-fluorophenyl)-N-(cis-2-hydroxycyclohexyl)-3-oxo-2,3-dihydropyridazine-4-carboxamide (example 103) on a chiral column (instrument: Sepiatec: Prep SFC100; column: Chiralpak IB 5 µm 250×30 mm; eluent A: CO2, eluent B: ethanol; isocratic: 24% B; flow 100.0 mL/min temperature: 40° C.; BPR: 150 bar; MWD @ 254 nm) yielded 16 mg 6-(4-chlorophenyl)-2-(3-fluorophenyl)-N-(cis-2-hydroxycyclohexyl)-3-oxo-2,3-dihydropyridazine-4-carboxamide, enantiomer 1.

Chiral HPLC: Rt=2.58 min (Instrument: Agilent: 1260, Aurora SFC-Modul; column: Chiralpak IB 5 µm 100×4.6 mm; eluent A: CO2, eluent B: ethanol; isocratic: 24% B; flow 4.0 mL/min; temperature: 37.5° C.; BPR: 100 bar; MWD @ 254 nm)

Example 105

6-(4-Chlorophenyl)-2-(3-fluorophenyl)-N-(cis-2-hydroxycyclohexyl)-3-oxo-2,3-dihydropyridazine-4-carboxamide, Enantiomer 2

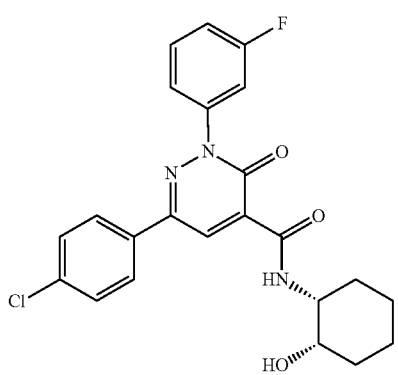 [SMILES: O=C(N[C@@H]1CCCC[C@@H]1O)c1cc(-c2ccc(Cl)cc2)nn(-c2cccc(F)c2)c1=O]

HPLC-separation of 43 mg 6-(4-chlorophenyl)-2-(3-fluorophenyl)-N-(cis-2-hydroxycyclohexyl)-3-oxo-2,3-dihydropyridazine-4-carboxamide (example 103) on a chiral column (Instrument: Sepiatec: Prep SFC100; column: Chiralpak IB 5 µm 250×30 mm; eluent A: CO2, eluent B: ethanol; isocratic: 24% B; flow 100.0 mL/min temperature: 40° C.; BPR: 150 bar; MWD @ 254 nm) yielded 15 mg 6-(4-chlorophenyl)-2-(3-fluorophenyl)-N-[(cis-2-hydroxycyclohexyl]-3-oxo-2,3-dihydropyridazine-4-carboxamide, enantiomer 2.

Chiral HPLC: Rt=4.67 min (Instrument: Agilent: 1260, Aurora SFC-Modul; column: Chiralpak IB 5 µm 100×4.6 mm; eluent A: CO2, eluent B: ethanol; isocratic: 24% B; flow 4.0 mL/min; temperature: 37.5° C.; BPR: 100 bar; MWD @ 254 nm.)

Example 106

2-(3-Fluorophenyl)-N-(cis-2-hydroxycyclohexyl)-6-(4-methoxyphenyl)-3-oxo-2,3-dihydropyridazine-4-carboxamide

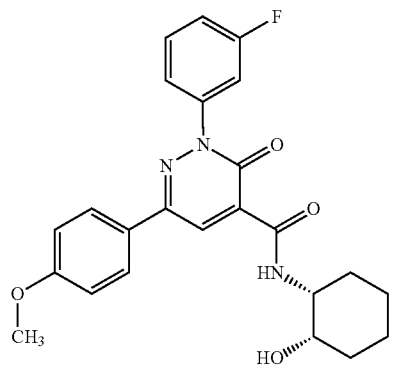 [SMILES: COc1ccc(-c2cc(C(=O)N[C@@H]3CCCC[C@@H]3O)c(=O)n(-c3cccc(F)c3)n2)cc1]

A solution of 100 mg intermediate 2-(3-fluorophenyl)-6-(4-methoxyphenyl)-3-oxo-2,3-dihydropyridazine-4-carboxylic acid, 82 mg cis-2-amino-cyclohexanol hydrochloride (1:1), 201 mg HATU, 0.14 mL ethyldiisopropylamine and 1.6 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 41 mg 2-(3-fluorophenyl)-N-(cis-2-hydroxycyclohexyl)-6-(4-methoxyphenyl)-3-oxo-2,3-dihydropyridazine-4-carboxamide.

¹H NMR (400 MHz, DMSO-d₆) δ ppm=1.32 (m, 2H), 1.48-1.70 (m, 6H), 3.77 (m, 1H), 3.82 (s, 3H), 3.91 (m, 1H), 4.86 (d, 1H), 7.04-7.11 (m, 2H), 7.34-7.42 (m, 1H), 7.50-7.56 (m, 1H), 7.56-7.66 (m, 2H), 7.87-7.93 (m, 2H), 8.62 (s, 1H), 9.69 (d, 1H).

Example 107

2-(3-Fluorophenyl)-N-(cis-2-hydroxycyclohexyl)-6-(4-methoxyphenyl)-3-oxo-2,3-dihydropyridazine-4-carboxamide, Enantiomer 1

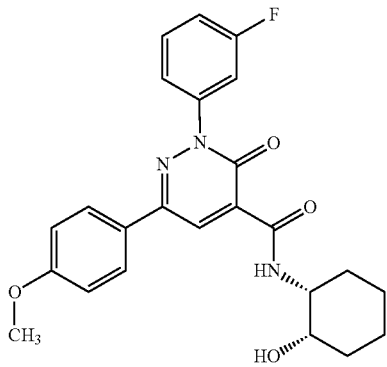 [SMILES: COc1ccc(-c2cc(C(=O)N[C@@H]3CCCC[C@@H]3O)c(=O)n(-c3cccc(F)c3)n2)cc1]

HPLC-separation of 24 mg 2-(3-fluorophenyl)-N-(cis-2-hydroxycyclohexyl)-6-(4-methoxyphenyl)-3-oxo-2,3-dihydropyridazine-4-carboxamide (example 106) on a chiral column (instrument: Sepiatec: Prep SFC100; column: Chiralpak IB 5 µm 250×30 mm; eluent A: CO2, eluent B: methanol; isocratic: 25% B; flow 100.0 mL/min temperature: 40° C.; BPR: 150 bar; MWD 254 nm) yielded 8 mg 2-(3-fluorophenyl)-N-(cis-2-hydroxycyclohexyl)-6-(4-methoxyphenyl)-3-oxo-2,3-dihydropyridazine-4-carboxamide, enantiomer 1.

Chiral HPLC: Rt=2.46 min (Instrument: Agilent HPLC 1260; Aurora SFC module; column: Chiralpak IB 5 µM 100×4.6 mm; eluent A: CO2, eluent B: methanol; isocratic 25% B, flow 4 mL/min; temperature: 37.5° C.; p=100 bar, DAD scan: 254 nm.)

Example 108

2-(3-Fluorophenyl)-N-(cis-2-hydroxycyclohexyl)-6-(4-methoxyphenyl)-3-oxo-2,3-dihydropyridazine-4-carboxamide, Enantiomer 2

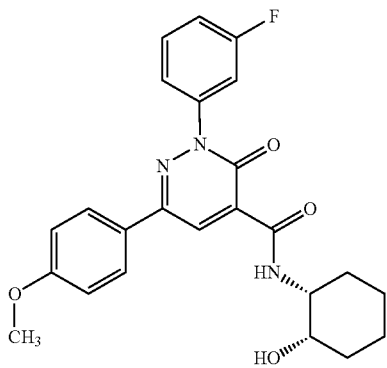 [SMILES: COc1ccc(-c2cc(C(=O)N[C@@H]3CCCC[C@@H]3O)c(=O)n(-c3cccc(F)c3)n2)cc1]

HPLC-separation of 24 mg 2-(3-fluorophenyl)-N-(cis-2-hydroxycyclohexyl)-6-(4-methoxyphenyl)-3-oxo-2,3-dihydropyridazine-4-carboxamide (example 106) on a chiral column (instrument: Sepiatec: Prep SFC100; column: Chiralpak IB 5 µm 250×30 mm; eluent A: CO2, eluent B: methanol; isocratic: 25% B; flow 100.0 mL/min temperature: 40° C.; BPR: 150 bar; MWD 254 nm) yielded 8 mg 2-(3-fluorophenyl)-N-(cis-2-hydroxycyclohexyl)-6-(4-methoxyphenyl)-3-oxo-2,3-dihydropyridazine-4-carboxamide, enantiomer 2.

Chiral HPLC: Rt=3.84 min (Instrument: Agilent HPLC 1260; Aurora SFC module; column: Chiralpak IB 5 µM 100×4.6 mm; eluent A: CO2, eluent B: methanol; isocratic 25% B, flow 4 mL/min; temperature: 37.5° C.; p=100 bar, DAD scan: 254 nm.)

Example 109

6-(4-Chlorophenyl)-2-(3-fluorophenyl)-N-(cis-2-hydroxycyclopentyl)-3-oxo-2,3-dihydropyridazine-4-carboxamide

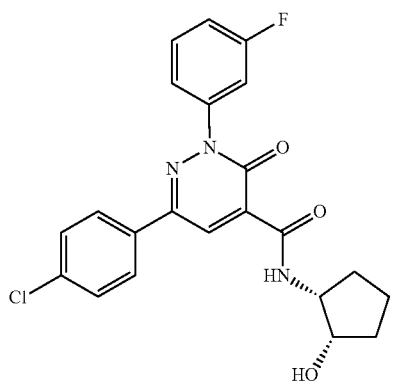 [SMILES: O=C(N[C@@H]1CCC[C@@H]1O)c1cc(-c2ccc(Cl)cc2)nn(-c2cccc(F)c2)c1=O]

A solution of 75 mg intermediate 17, 60 mg cis-2-aminocyclopentanol hydrochloride (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Labomatic HD5000, Labocord-5000; Gilson GX-241, Labcol Vario 4000, column: XBrigde C18 5µ 150×30 mm; eluent B: water+0.2 Vol-% aqueous ammonia (32%); eluent D: methanol; gradient: 3-7 min 69-89% D; flow 50.0 mL/min; UV 254 nm) to yield 32.5 mg 6-(4-chlorophenyl)-2-(3-fluorophenyl)-N-(cis-2-hydroxycyclopentyl)-3-oxo-2,3-dihydropyridazine-4-carboxamide.

$^1$H NMR (400 MHz, DMSO-$d_6$) δ ppm=1.45-1.64 (m, 3H), 1.69-1.88 (m, 2H), 1.90-2.05 (m, 1H), 3.97-4.13 (m, 2H), 5.03 (d, 1H), 7.38 (tdd, 1H), 7.50-7.71 (m, 5H), 7.95-8.09 (m, 2H), 8.66 (s, 1H), 9.70 (d, 1H).

Example 110

6-[4-(Difluoromethoxy)phenyl]-2-(3-fluorophenyl)-N-[(2S)-1-hydroxy-3-methylbutan-2-yl]-3-oxo-2,3-dihydropyridazine-4-carboxamide

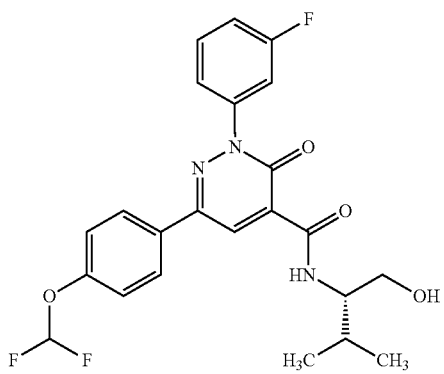 [SMILES: CC(C)[C@@H](CO)NC(=O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 37 mg (S)-(+)-2-amino-3-methyl-1-butanol, 136 mg HATU, 0.09 mL ethyldiisopropylamine and 1 mg 4-dimethylaminopyridine in 1.5 mL of DMF was stirred at room temperature for 48 hours. Then the reaction mixture was filtered and subjected to RP-HPLC (Instrument: Waters Autopurification MS SingleQuad; Colum: Waters XBrigde C18 5μ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 62 mg 6-[4-(difluoromethoxy)phenyl]-2-(3-fluorophenyl)-N-[(2S)-1-hydroxy-3-methylbutan-2-yl]-3-oxo-2,3-dihydropyridazine-4-carboxamide.

$^1$H NMR (400 MHz, DMSO-$d_6$) δ ppm=0.89 (d, 3H), 0.92 (d, 3H), 1.90-2.05 (m, 1H), 3.39-3.47 (m, 1H), 3.50-3.60 (m, 1H), 3.79-3.91 (m, 1H), 4.81 (t, 1H), 7.12-7.67 (m, 7H), 7.99-8.05 (m, 2H), 8.66 (s, 1H), 9.43 (d, 1H).

Example 111

6-(4-Chlorophenyl)-2-(3-fluorophenyl)-N-[(1S,2R)-2-hydroxycyclopentyl]-3-oxo-2,3-dihydropyridazine-4-carboxamide

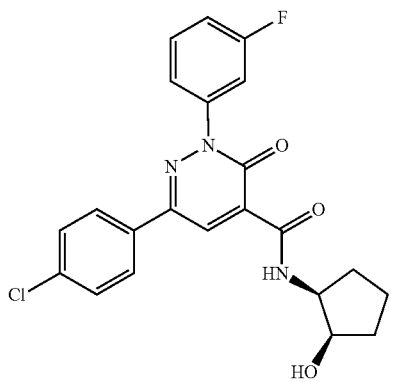 [SMILES: O=C(N[C@H]1CCC[C@H]1O)c1cc(-c2ccc(Cl)cc2)nn(-c2cccc(F)c2)c1=O]

A solution of 75 mg intermediate 17, 60 mg cis-(1R,2S)-2-aminocyclopentanol hydrochlorid (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 36.7 mg 6-(4-chlorophenyl)-2-(3-fluorophenyl)-N-[(1S,2R)-2-hydroxycyclopentyl]-3-oxo-2,3-dihydropyridazine-4-carboxamide.

$^1$H NMR (400 MHz, DMSO-$d_6$) δ ppm=1.46-1.63 (m, 3H), 1.68-1.89 (m, 2H), 1.93-2.05 (m, 1H), 3.92-4.13 (m, 2H), 5.03 (d, 1H), 7.33-7.44 (m, 1H), 7.52-7.67 (m, 5H), 7.94-8.03 (m, 2H), 8.66 (s, 1H), 9.70 (d, 1H).

Example 112

6-(4-Chlorophenyl)-2-(3-fluorophenyl)-N-[(1S,2S)-2-methylcyclohexyl]-3-oxo-2,3-dihydropyridazine-4-carboxamide

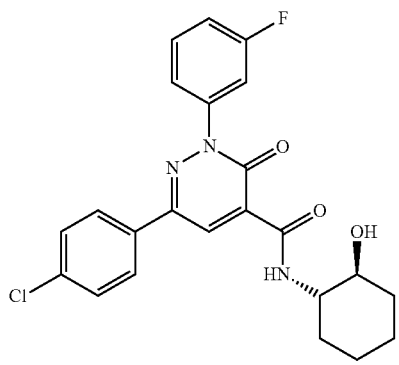

A solution of 75 mg intermediate 17, 66 mg (1S,2S)-(+)-2-amino-cyclohexanol hydrochlorid (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 46.9 mg 6-(4-chlorophenyl)-2-(3-fluorophenyl)-N-[(1S,2S)-2-methylcyclohexyl]-3-oxo-2,3-dihydropyridazine-4-carboxamide.

$^1$H NMR (400 MHz, DMSO-$d_6$) δ ppm=1.15-1.36 (m, 4H), 1.48-1.71 (m, 2H), 1.85 (m, 1H), 1.97-2.10 (m, 1H), 3.55-3.72 (m, 1H), 4.83 (d, 1H), 7.31-7.42 (m, 1H), 7.50-7.74 (m, 5H), 7.99 (d, 2H), 8.64 (s, 1H), 9.42 (d, 1H).

Example 113

2-(3-Fluorophenyl)-N-[(2S)-1-hydroxy-3-methylbutan-2-yl]-6-(4-methoxyphenyl)-3-oxo-2,3-dihydropyridazine-4-carboxamide

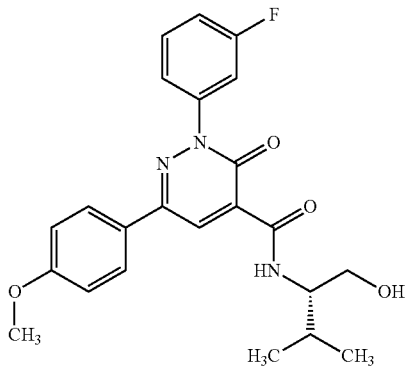 [SMILES: COc1ccc(-c2cc(C(=O)N[C@H](CO)C(C)C)c(=O)n(-c3cccc(F)c3)n2)cc1]

A solution of 75 mg intermediate 2-(3-fluorophenyl)-6-(4-methoxyphenyl)-3-oxo-2,3-dihydropyridazine-4-carboxylic acid, 41 mg (S)-(+)-2-amino-3-methyl-1-butanol, 150 mg HATU, 0.1 mL ethyldiisopropylamine and 1.2 mg 4-dimethylaminopyridine in 1.5 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 70%/B 30%→A 30%/B 70%; flow: 150 mL/min; UV-detection: 254 nm) to yield 28 mg 2-(3-fluorophenyl)-N-[(2S)-1-hydroxy-3-methylbutan-2-yl]-6-(4-methoxyphenyl)-3-oxo-2,3-dihydropyridazine-4-carboxamide.

$^1$H NMR (400 MHz, DMSO-$d_6$) δ ppm=0.89 (d, 3H), 0.92 (d, 3H), 1.97 (dq, 1H), 3.44 (dt, 1H), 3.51-3.58 (m, 1H), 3.82 (s, 3H), 3.83-3.89 (m, 1H), 4.80 (t, 1H), 7.04-7.11 (m, 2H), 7.33-7.43 (m, 1H), 7.51-7.57 (m, 1H), 7.57-7.65 (m, 2H), 7.87-7.95 (m, 2H), 8.62 (s, 1H), 9.46 (d, 1H).

Example 114

6-(4-Chlorophenyl)-2-(3-fluorophenyl)-N-[(2S,3S)-3-hydroxybutan-2-yl]-3-oxo-2,3-dihydropyridazine-4-carboxamide

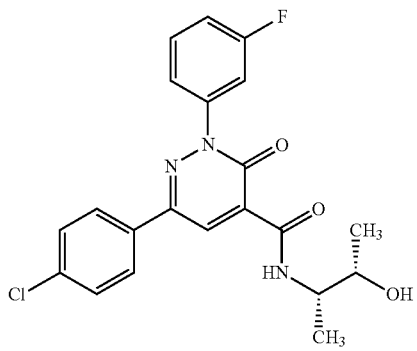 [SMILES: C[C@H](O)[C@H](C)NC(=O)c1cc(-c2ccc(Cl)cc2)nn(-c2cccc(F)c2)c1=O]

A solution of 70 mg intermediate 17, 51 mg (2S,3S)-3-aminobutan-2-ol hydrochloride (1:1), 154.5 mg HATU, 0.14 mL ethyldiisopropylamine and 1.3 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 49 mg 6-(4-chlorophenyl)-2-(3-fluorophenyl)-N-[(2S,3S)-3-hydroxybutan-2-yl]-3-oxo-2,3-dihydropyridazine-4-carboxamide.

$^1$H NMR (400 MHz, DMSO-$d_6$) δ ppm=1.04 (d, 3H), 1.15 (d, 3H), 3.70 (dt, 1H), 3.90-3.99 (m, 1H), 4.96 (br d, 1H), 7.34-7.42 (m, 1H), 7.52-7.65 (m, 5H), 7.96-8.00 (m, 2H), 8.65 (s, 1H), 9.46 (d, 1H).

$[α]_D^{20}$=18.1°+/−0.25° (c=10.2 mg/mL, DMSO).

Example 115

6-(4-Chlorophenyl)-2-(3-fluorophenyl)-N-[(1S,2S)-2-hydroxycyclopentyl]-3-oxo-2,3-dihydropyridazine-4-carboxamide

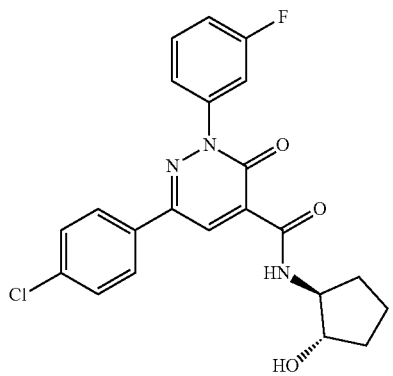 [SMILES: O=C(N[C@H]1CCC[C@@H]1O)c1cc(-c2ccc(Cl)cc2)nn(-c2cccc(F)c2)c1=O]

A solution of 75 mg intermediate 17, 60 mg trans-(1S,2S)-2-aminocyclopentanol hydrochloride (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 49 mg 6-(4-chlorophenyl)-2-(3-fluorophenyl)-N-[(1S,2S)-2-hydroxycyclopentyl]-3-oxo-2,3-dihydropyridazine-4-carboxamide.

$^1$H NMR (400 MHz, DMSO-$d_6$) δ ppm=1.37-1.55 (m, 2H), 1.57-1.76 (m, 2H), 1.77-1.89 (m, 1H), 2.03-2.15 (m, 1H), 3.89-3.97 (m, 1H), 3.97-4.07 (m, 1H), 4.94 (d, 1H), 7.33-7.42 (m, 1H), 7.51-7.67 (m, 5H), 7.95-8.04 (m, 2H), 8.63 (s, 1H), 9.34 (d, 1H).

Example 116 rel-2-(3-Fluorophenyl)-N-[(2S,3S)-3-hydroxybutan-2-yl]-6-(4-methoxyphenyl)-3-oxo-2,3-dihydropyridazine-4-carboxamide

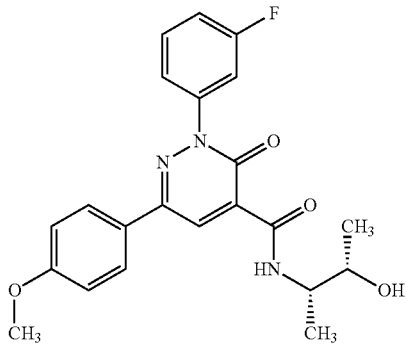 [SMILES: COc1ccc(-c2cc(C(=O)N[C@@H](C)[C@H](C)O)c(=O)n(-c3cccc(F)c3)n2)cc1]

A solution of 75 mg intermediate 2-(3-fluorophenyl)-6-(4-methoxyphenyl)-3-oxo-2,3-dihydropyridazine-4-carboxylic acid, 36 mg rel-(2S,3S)-3-aminobutan-2-ol hydrochloride (1:1), 150 mg HATU, 0.1 mL ethyldiisopropylamine and 1.2 mg 4-dimethylaminopyridine in 1.5 mL of DMF was stirred at room temperature for 14 hours. Then the reaction mixture was filtered and subjected to RP-HPLC (Instrument: Waters Autopurificationsystem; column: Waters XBrigde C18 5μ 100×30 mm; eluent A: Wasser+0.2 Vol-% aqueous ammonia (32%), eluent B: Methanol; gradient: 0.00-0.50 min 29% B (25→70 mL/min), 0.51-5.50 min 59-79% B (70 mL/min), DAD scan: 210-400 nm) to yield 20 mg rel-2-(3-fluorophenyl)-N-[(2S,3S)-3-hydroxybutan-2-yl]-6-(4-methoxyphenyl)-3-oxo-2,3-dihydropyridazine-4-carboxamide.

$^1$H NMR (400 MHz, DMSO-$d_6$) δ ppm=1.04 (d, 3H), 1.15 (d, 3H), 3.70 (dt, 1H), 3.82 (s, 3H), 3.88-4.00 (m, 1H), 4.94 (d, 1H), 7.01-7.10 (m, 2H), 7.33-7.41 (m, 1H), 7.51-7.58 (m, 1H), 7.58-7.66 (m, 2H), 7.85-7.93 (m, 2H), 8.61 (s, 1H), 9.47-9.54 (m, 1H).

Example 117

6-(4-Chlorophenyl)-2-(3-fluorophenyl)-N-(trans-2-hydroxycyclohexyl)-3-oxo-2,3-dihydropyridazine-4-carboxamide

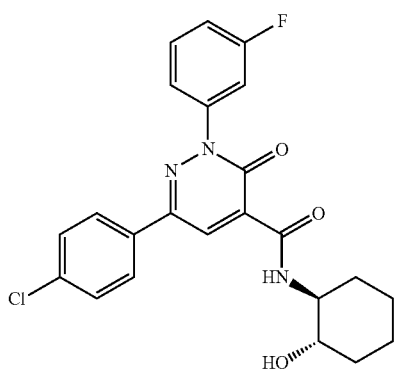 [SMILES: O=C(N[C@H]1CCCC[C@@H]1O)c1cc(-c2ccc(Cl)cc2)nn(-c2cccc(F)c2)c1=O]

A solution of 75 mg intermediate 17, 50 mg trans-2-aminocyclohexanol, 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 53 mg 6-(4-chlorophenyl)-2-(3-fluorophenyl)-N-(trans-2-hydroxycyclohexyl)-3-oxo-2,3-dihydropyridazine-4-carboxamide.

$^1$H NMR (400 MHz, DMSO-$d_6$) δ ppm=1.14-1.36 (m, 4H), 1.52-1.68 (m, 2H), 1.85 (br d, 1H), 2.02 (br d, 1H), 3.34-3.41 (m, 1H), 3.58-3.70 (m, 1H), 4.83 (d, 1H), 7.34-7.44 (m, 1H), 7.49-7.65 (m, 5H), 8.00 (d, 2H), 8.64 (s, 1H), 9.42 (d, 1H).

Example 118

6-(4-Chlorophenyl)-2-(3-fluorophenyl)-N-(trans-2-hydroxycyclohexyl)-3-oxo-2,3-dihydropyridazine-4-carboxamide, Enantiomer 1

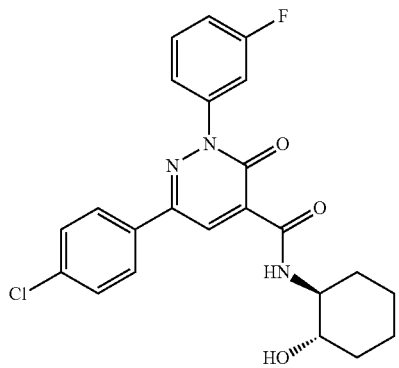 [SMILES: O=C(N[C@H]1CCCC[C@@H]1O)c1cc(-c2ccc(Cl)cc2)nn(-c2cccc(F)c2)c1=O]

HPLC-separation of 46 mg 6-(4-chlorophenyl)-2-(3-fluorophenyl)-N-(trans-2-hydroxycyclohexyl)-3-oxo-2,3-dihydropyridazine-4-carboxamide (example 117) on a chiral column (instrument: Sepiatec: Prep SFC100; column: Chiralpak IC 5 μm 250×30 mm; eluent A: CO2, eluent B: methanol; isocratic: 31% B; flow 100.0 mL/min temperature: 40° C.; BPR: 150 bar; MWD 254 nm) yielded 15 mg 6-(4-chlorophenyl)-2-(3-fluorophenyl)-N-(trans-2-hydroxycyclohexyl)-3-oxo-2,3-dihydropyridazine-4-carboxamide, enantiomer 1.

Chiral HPLC: Rt=3.9 min (Instrument: Agilent HPLC 1260; Aurora SFC module; column: Chiralpak IC 5 μM 100×4.6 mm; eluent A: CO2, eluent B: methanol; isocratic 31% B, flow 4 mL/min; temperature: 37.5° C.; p=100 bar, DAD scan: 254 nm.)

Example 119

6-(4-Chlorophenyl)-2-(3-fluorophenyl)-N-(trans-2-hydroxycyclohexyl)-3-oxo-2,3-dihydropyridazine-4-carboxamide, Enantiomer 2

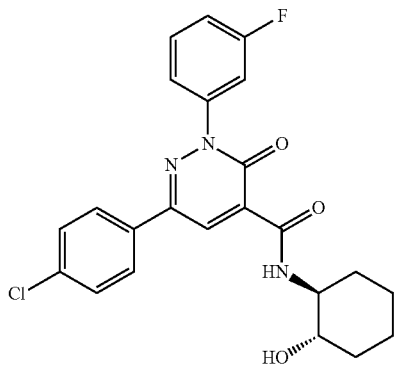 [SMILES: O=C(N[C@H]1CCCC[C@@H]1O)c1cc(-c2ccc(Cl)cc2)nn(-c2cccc(F)c2)c1=O]

HPLC-separation of 46 mg 6-(4-chlorophenyl)-2-(3-fluorophenyl)-N-(trans-2-hydroxycyclohexyl)-3-oxo-2,3-dihydropyridazine-4-carboxamide (example 117) on a chiral column (instrument: Sepiatec: Prep SFC100; column: Chiralpak IC 5 μm 250×30 mm; eluent A: CO2, eluent B: methanol; isocratic: 31% B; flow 100.0 mL/min temperature: 40° C.; BPR: 150 bar; MWD 254 nm) yielded 14 mg 6-(4-chlorophenyl)-2-(3-fluorophenyl)-N-(trans-2-hydroxycyclohexyl)-3-oxo-2,3-dihydropyridazine-4-carboxamide, enantiomer 2.

Chiral HPLC: Rt=2.61 min (Instrument: Agilent HPLC 1260; Aurora SFC module; column: Chiralpak IC 5 μM 100×4.6 mm; eluent A: CO2, eluent B: methanol; isocratic 31% B, flow 4 mL/min; temperature: 37.5° C.; p=100 bar, DAD scan: 254 nm.)

Example 120

6-[4-(Difluoromethoxy)phenyl]-2-(3-fluorophenyl)-3-oxo-N-(3,3,3-trifluoro-2-hydroxypropyl)-2,3-dihydropyridazine-4-carboxamide

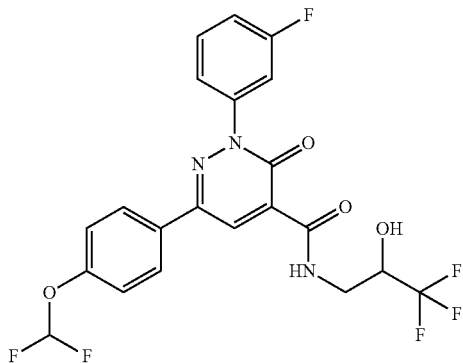 [SMILES: O=C(NCC(O)C(F)(F)F)c1cc(-c2ccc(OC(F)F)cc2)nn(-c2cccc(F)c2)c1=O]

A solution of 150 mg intermediate 6-[4-(difluoromethoxy)phenyl]-2-(3-fluorophenyl)-3-oxo-2,3-dihydropyridazine-4-carboxylic acid, 92.6 mg amino-1,1,1-trifluoro-2-propanol, 273 mg HATU, 0.19 mL ethyldiisopropylamine and 2.2 mg 4-dimethylaminopyridine in 3 mL of DMF was stirred at room temperature for 48 hours. Then the reaction mixture was filtered and subjected to RP-HPLC (Instrument: Waters Autopurification MS SingleQuad; Colum: Waters XBrigde C18 5μ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 62 mg 6-[4-(difluoromethoxy)phenyl]-2-(3-fluorophenyl)-3-oxo-N-(3,3,3-trifluoro-2-hydroxypropyl)-2,3-dihydropyridazine-4-carboxamide.

$^1$H NMR (400 MHz, DMSO-$d_6$) δ ppm=3.48 (br dd, 1H), 3.69-3.81 (m, 1H), 4.22 (br s, 1H), 6.66 (br d, 1H), 7.27-7.43 (m, 4H), 7.55 (br d, 1H), 7.58-7.66 (m, 2H), 7.99-8.08 (m, 2H), 8.67 (s, 1H), 8.62-8.74 (m, 1H), 9.66 (br s, 1H).

Example 121

6-[4-(Difluoromethoxy)phenyl]-2-(3-fluorophenyl)-3-oxo-N-(3,3,3-trifluoro-2-hydroxypropyl)-2,3-dihydropyridazine-4-carboxamide, Enantiomer 1

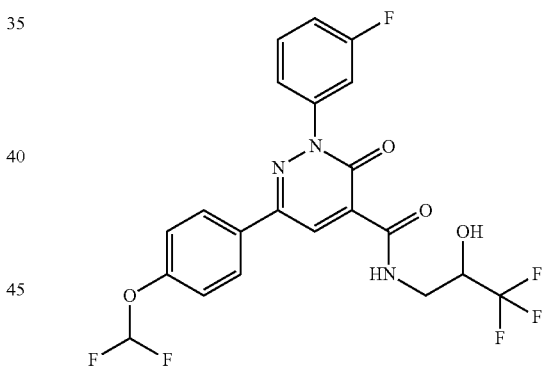

HPLC-separation of 94 mg 6-[4-(difluoromethoxy)phenyl]-2-(3-fluorophenyl)-3-oxo-N-(3,3,3-trifluoro-2-hydroxypropyl)-2,3-dihydropyridazine-4-carboxamide (example 120) on a chiral column (instrument: Sepiatec: Prep SFC100; column: Chiralpak IB 5 μm 250×30 mm; eluent A: CO2, eluent B: ethanol; isocratic: 9% B; flow 100.0 mL/min temperature: 40° C.; BPR: 150 bar; MWD 254 nm) yielded 33 mg 6-[4-(difluoromethoxy)phenyl]-2-(3-fluorophenyl)-3-oxo-N-(3,3,3-trifluoro-2-hydroxypropyl)-2,3-dihydropyridazine-4-carboxamide, enantiomer 1.

Chiral HPLC: Rt=2.58 min (Instrument: Agilent HPLC 1260; Aurora SFC module; column: Chiralpak IB 5 μM 100×4.6 mm; eluent A: CO2, eluent B: ethanol; isocratic 9% B, flow 4 mL/min; temperature: 37.5° C.; p=100 bar, DAD scan: 254 nm.)

$[α]_D^{20}$=−9.2°+/−0.22° (c=5.9 mg/mL, DMSO).

Example 122

6-[4-(Difluoromethoxy)phenyl]-2-(3-fluorophenyl)-3-oxo-N-(3,3,3-trifluoro-2-hydroxypropyl)-2,3-dihydropyridazine-4-carboxamide, Enantiomer 2

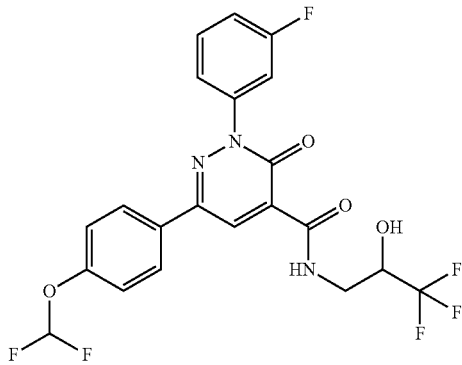 [SMILES: O=C(NCC(O)C(F)(F)F)c1cc(-c2ccc(OC(F)F)cc2)nn(-c2cccc(F)c2)c1=O]

HPLC-separation of 94 mg 6-[4-(difluoromethoxy)phenyl]-2-(3-fluorophenyl)-3-oxo-N-(3,3,3-trifluoro-2-hydroxypropyl)-2,3-dihydropyridazine-4-carboxamide (example 120) on a chiral column (instrument: Sepiatec: Prep SFC100; column: Chiralpak IB 5 μm 250×30 mm; eluent A: CO2, eluent B: ethanol; isocratic: 9% B; flow 100.0 mL/min temperature: 40° C.; BPR: 150 bar; MWD 254 nm) yielded 33 mg 6-[4-(difluoromethoxy)phenyl]-2-(3-fluorophenyl)-3-oxo-N-(3,3,3-trifluoro-2-hydroxypropyl)-2,3-dihydropyridazine-4-carboxamide, enantiomer 2.

Chiral HPLC: Rt=4.85 min (Instrument: Agilent HPLC 1260; Aurora SFC module; column: Chiralpak IB 5 μM 100×4.6 mm; eluent A: CO2, eluent B: ethanol; isocratic 9% B, flow 4 mL/min; temperature: 37.5° C.; p=100 bar, DAD scan: 254 nm.)

$[\alpha]_D^{20}$=11.2°+/−0.16° (c=5.7 mg/mL, DMSO).

Example 123

6-(4-Chlorophenyl)-2-(3-fluorophenyl)-N-(trans-2-hydroxycyclopentyl)-3-oxo-2,3-dihydropyridazine-4-carboxamide

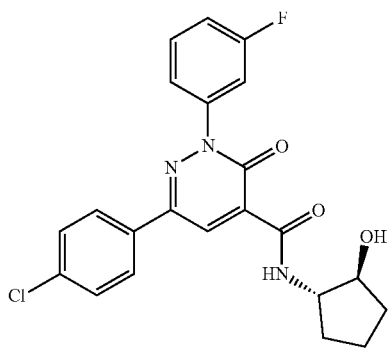

A solution of 75 mg intermediate 17, 50 mg trans-2-aminocyclopentanol, 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 70%/B 30%→A 30%/B 70%; flow: 150 mL/min; UV-detection: 254 nm) to yield 33 mg 6-(4-chlorophenyl)-2-(3-fluorophenyl)-N-(trans-2-hydroxycyclopentyl)-3-oxo-2,3-dihydropyridazine-4-carboxamide.

$^1$H NMR (400 MHz, DMSO-$d_6$) δ ppm=1.38-1.56 (m, 2H), 1.57-1.76 (m, 2H), 1.76-1.89 (m, 1H), 2.04-2.14 (m, 1H), 3.93 (dt, 1H), 3.98-4.07 (m, 1H), 4.94 (d, 1H), 7.38 (td, 1H), 7.52-7.65 (m, 5H), 8.00 (d, 2H), 8.63 (s, 1H), 9.32-9.39 (m, 1H).

Example 124

6-(4-Chlorophenyl)-2-(3-fluorophenyl)-N-(trans-2-hydroxycyclopentyl)-3-oxo-2,3-dihydropyridazine-4-carboxamide, Enantiomer 1

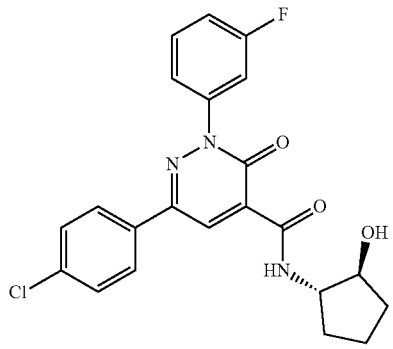 [SMILES: O=C(N[C@H]1CCC[C@@H]1O)c1cc(-c2ccc(Cl)cc2)nn(-c2cccc(F)c2)c1=O]

HPLC-separation of 18 mg 6-(4-chlorophenyl)-2-(3-fluorophenyl)-N-(trans-2-hydroxycyclopentyl)-3-oxo-2,3-dihydropyridazine-4-carboxamide (example 123) on a chiral column (instrument: Sepiatec: Prep SFC100; column: Chiralpak IC 5 μm 250×30 mm; eluent A: CO2, eluent B: methanol; isocratic: 30% B; flow 100.0 mL/min temperature: 40° C.; BPR: 150 bar; MWD 254 nm) yielded 5 mg 6-(4-chlorophenyl)-2-(3-fluorophenyl)-N-(trans-2-hydroxycyclopentyl)-3-oxo-2,3-dihydropyridazine-4-carboxamide, enantiomer 1.

Chiral HPLC: Rt=2.62 min (Instrument: Agilent HPLC 1260; Aurora SFC module; column: Chiralpak IC 5 μM 100×4.6 mm; eluent A: CO2, eluent B: methanol; isocratic 30% B, flow 4 mL/min; temperature: 37.5° C.; p=100 bar, DAD scan: 254 nm.)

Example 125

6-(4-Chlorophenyl)-2-(3-fluorophenyl)-N-(trans-2-hydroxycyclopentyl)-3-oxo-2,3-dihydropyridazine-4-carboxamide, Enantiomer 2

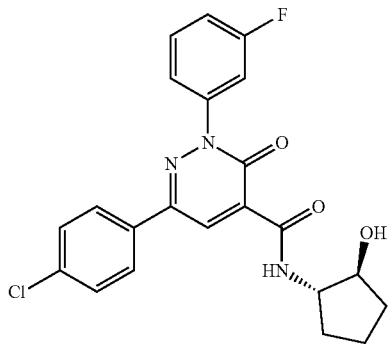 [SMILES: O=C(N[C@H]1CCC[C@@H]1O)c1cc(-c2ccc(Cl)cc2)nn(-c2cccc(F)c2)c1=O]

HPLC-separation of 18 mg 6-(4-chlorophenyl)-2-(3-fluorophenyl)-N-(trans-2-hydroxycyclopentyl)-3-oxo-2,3-dihydropyridazine-4-carboxamide (example 123) on a chiral column (instrument: Sepiatec: Prep SFC100; column: Chiralpak IC 5 μm 250×30 mm; eluent A: CO2, eluent B: methanol; isocratic: 30% B; flow 100.0 mL/min temperature: 40° C.; BPR: 150 bar; MWD 254 nm) yielded 14 mg 6-(4-chlorophenyl)-2-(3-fluorophenyl)-N-(trans-2-hydroxycyclopentyl)-3-oxo-2,3-dihydropyridazine-4-carboxamide, enantiomer 2.

Chiral HPLC: Rt=3.42 min (Instrument: Agilent HPLC 1260; Aurora SFC module; column: Chiralpak IC 5 μM 100×4.6 mm; eluent A: CO2, eluent B: methanol; isocratic 30% B, flow 4 mL/min; temperature: 37.5° C.; p=100 bar, DAD scan: 254 nm.)

Example 126

2-(3-Fluorophenyl)-6-(4-methoxyphenyl)-3-oxo-N-(3,3,3-trifluoro-2-hydroxypropyl)-2,3-dihydropyridazine-4-carboxamide

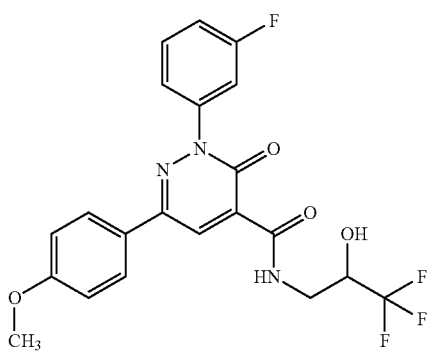 [SMILES: COc1ccc(-c2cc(C(=O)NCC(O)C(F)(F)F)c(=O)n(-c3cccc(F)c3)n2)cc1]

A solution of 150 mg intermediate 2-(3-fluorophenyl)-6-(4-methoxyphenyl)-3-oxo-2,3-dihydropyridazine-4-carboxylic acid, 104.5 mg 3-amino-1,1,1-trifluoro-2-propanol, 301.6 mg HATU, 0.21 mL ethyldiisopropylamine and 2.4 mg 4-dimethylaminopyridine in 3 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 70%/B 30%→A 30%/B 70%; flow: 150 mL/min; UV-detection: 254 nm) to yield 74 mg 2-(3-fluorophenyl)-6-(4-methoxyphenyl)-3-oxo-N-(3,3,3-trifluoro-2-hydroxypropyl)-2,3-dihydropyridazine-4-carboxamide.

$^1$H NMR (400 MHz, DMSO-$d_6$) δ ppm=3.46 (ddd, 1H), 3.71-3.80 (m, 1H), 3.82 (s, 3H), 4.17-4.29 (m, 1H), 6.66 (d, 1H), 7.05-7.11 (m, 2H), 7.33-7.42 (m, 1H), 7.52-7.57 (m, 1H), 7.57-7.66 (m, 2H), 7.86-7.95 (m, 2H), 8.63 (s, 1H), 9.69 (t, 1H).

Example 127

2-(3-Fluorophenyl)-6-(4-methoxyphenyl)-3-oxo-N-(3,3,3-trifluoro-2-hydroxypropyl)-2,3-dihydropyridazine-4-carboxamide, Enantiomer 1

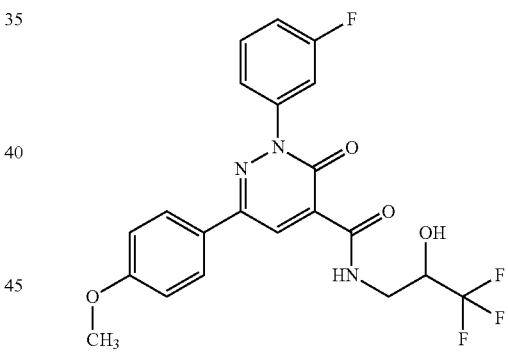

HPLC-separation of 58 mg 2-(3-fluorophenyl)-6-(4-methoxyphenyl)-3-oxo-N-(3,3,3-trifluoro-2-hydroxypropyl)-2,3-dihydropyridazine-4-carboxamide (example 126) on a chiral column (instrument: Sepiatec: Prep SFC100; column: Chiralpak IB 5 μm 250×30 mm; eluent A: CO2, eluent B: ethanol+0.4 Vol-% diethylamine (99%); isocratic: 12% B; flow 100.0 mL/min temperature: 40° C.; BPR: 150 bar; MWD 254 nm) yielded 14 mg 2-(3-fluorophenyl)-6-(4-methoxyphenyl)-3-oxo-N-(3,3,3-trifluoro-2-hydroxypropyl)-2,3-dihydropyridazine-4-carboxamide, enantiomer 1.

Chiral HPLC: Rt=2.08 min (Instrument: Agilent HPLC 1260; Aurora SFC module; column: Chiralpak IB 5 μM 100×4.6 mm; eluent A: CO2, eluent B: ethanol+0.4 Vol-% diethylamine (99%); isocratic: 12% B, flow 4 mL/min; temperature: 37.5° C.; p=100 bar, DAD scan: 254 nm.)

Example 128

2-(3-Fluorophenyl)-6-(4-methoxyphenyl)-3-oxo-N-(3,3,3-trifluoro-2-hydroxypropyl)-2,3-dihydropyridazine-4-carboxamide, Enantiomer 2

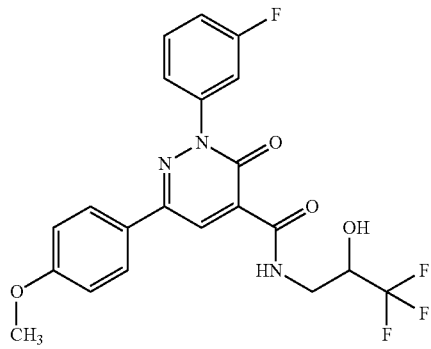 [SMILES: COc1ccc(-c2cc(C(=O)NCC(O)C(F)(F)F)c(=O)n(-c3cccc(F)c3)n2)cc1]

HPLC-separation of 58 mg 2-(3-fluorophenyl)-6-(4-methoxyphenyl)-3-oxo-N-(3,3,3-trifluoro-2-hydroxypropyl)-2,3-dihydropyridazine-4-carboxamide (example 126) on a chiral column (instrument: Sepiatec: Prep SFC100; column: Chiralpak IB 5 μm 250×30 mm; eluent A: CO2, eluent B: ethanol+0.4 Vol-% diethylamine (99%); isocratic: 12% B; flow 100.0 mL/min temperature: 40° C.; BPR: 150 bar; MWD 254 nm) yielded 20 mg 2-(3-fluorophenyl)-6-(4-methoxyphenyl)-3-oxo-N-(3,3,3-trifluoro-2-hydroxypropyl)-2,3-dihydropyridazine-4-carboxamide, enantiomer 2.

Chiral HPLC: Rt=3.84 min (Instrument: Agilent HPLC 1260; Aurora SFC module; column: Chiralpak IB 5 μM 100×4.6 mm; eluent A: CO2, eluent B: ethanol+0.4 Vol-% diethylamine (99%); isocratic: 12% B, flow 4 mL/min; temperature: 37.5° C.; p=100 bar, DAD scan: 254 nm.)

Example 129

6-(4-Chlorophenyl)-2-(3-fluorophenyl)-N-[(1-hydroxycyclohexyl)methyl]-3-oxo-2,3-dihydropyridazine-4-carboxamide

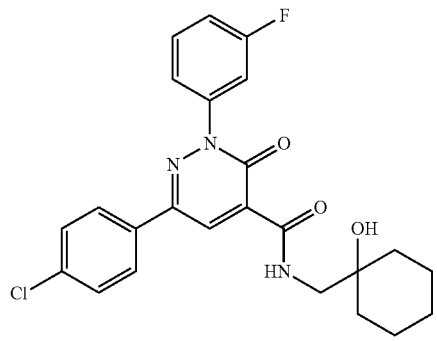 [SMILES: O=C(NCC1(O)CCCCC1)c1cc(-c2ccc(Cl)cc2)nn(-c2cccc(F)c2)c1=O]

A solution of 75 mg intermediate 17, 72 mg 1-aminomethyl-1-cyclohexanol hydrochloride (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 48 mg 6-(4-chlorophenyl)-2-(3-fluorophenyl)-N-[(1-hydroxycyclohexyl)methyl]-3-oxo-2,3-dihydropyridazine-4-carboxamide.

$^1$H NMR (400 MHz, DMSO-$d_6$) δ ppm=1.19-1.65 (m, 10H), 3.34 (s, 2H), 4.47 (s, 1H), 7.33-7.43 (m, 1H), 7.51-7.67 (m, 5H), 7.95-8.03 (m, 2H), 8.66 (s, 1H), 9.54 (t, 1H).

Example 130

6-[4-(Difluoromethoxy)phenyl]-2-(3-fluorophenyl)-N-(cis-2-hydroxycyclohexyl)-3-oxo-2,3-dihydropyridazine-4-carboxamide

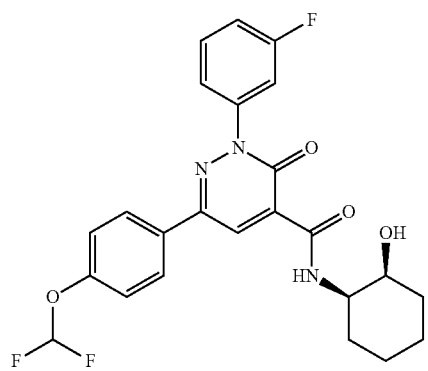 [SMILES: O=C(N[C@@H]1CCCC[C@@H]1O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 55.5 mg cis-amino-cyclohexanol, 136.4 mg HATU, 0.13 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Colum: Waters XBrigde C18 5μ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 62 mg 6-[4-(difluoromethoxy)phenyl]-2-(3-fluorophenyl)-N-(cis-2-hydroxycyclohexyl)-3-oxo-2,3-dihydropyridazine-4-carboxamide.

$^1$H NMR (400 MHz, DMSO-$d_6$) δ ppm=1.19-1.38 (m, 2H), 1.45-1.69 (m, 6H), 3.77 (m, 1H), 3.91 (m, 1H), 4.87 (d, 1H), 7.13-7.36 (m, 3H), 7.36-7.43 (m, 1H), 7.51-7.58 (m, 1H), 7.57-7.67 (m, 2H), 7.98-8.05 (m, 2H), 8.65 (s, 1H), 9.66 (d, 1H).

Example 131

6-(4-Chlorophenyl)-2-(3-fluorophenyl)-N-(3-hydroxybutan-2-yl]-3-oxo-2,3-dihydropyridazine-4-carboxamide

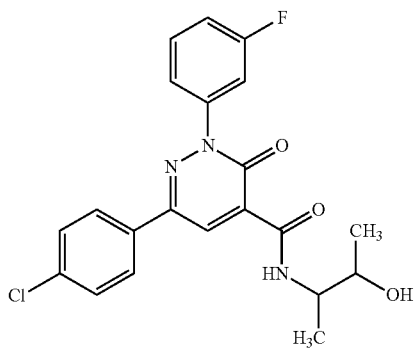 [SMILES: CC(O)C(C)NC(=O)c1cc(-c2ccc(Cl)cc2)nn(-c2cccc(F)c2)c1=O]

A solution of 70 mg intermediate 17, 36.2 mg 3-aminobutan-2-ol, 154.5 mg HATU, 0.1 mL ethyldiisopropylamine and 1.2 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 45 mg 6-(4-chlorophenyl)-2-(3-fluorophenyl)-N-(3-hydroxybutan-2-yl]-3-oxo-2,3-dihydropyridazine-4-carboxamide.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.31 min; MS (ESIpos): m/z=416.1 [M−H]+

Example 132

6-(4-Chlorophenyl)-N-[(2S,3S)-1,3-dihydroxybutan-2-yl]-2-(3-fluorophenyl)-3-oxo-2,3-dihydropyridazine-4-carboxamide

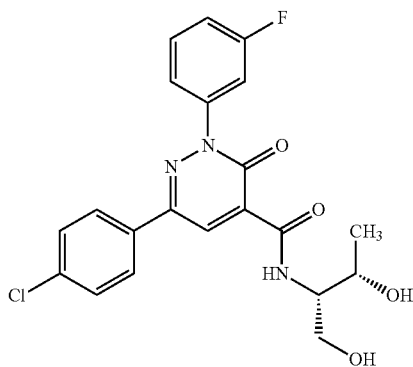 [SMILES: C[C@H](O)[C@H](CO)NC(=O)c1cc(-c2ccc(Cl)cc2)nn(-c2cccc(F)c2)c1=O]

A solution of 75 mg intermediate 17, 45.8 mg (2S,3S)-2-amino-butane-1,3-diol hydrochloride (1:1), 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 47 mg 6-(4-chlorophenyl)-N-[(2S,3S)-1,3-dihydroxybutan-2-yl]-2-(3-fluorophenyl)-3-oxo-2,3-dihydropyridazine-4-carboxamide.

$^1$H NMR (400 MHz, DMSO-d$_6$) δ ppm=1.05 (d, 3H), 3.42-3.53 (m, 2H), 3.78-3.89 (m, 1H), 4.03 (ddd, 1H), 4.81 (t, 1H), 4.89 (d, 1H), 7.35-7.43 (m, 1H), 7.53-7.67 (m, 5H), 7.94-8.04 (m, 2H), 8.67 (s, 1H), 9.49 (d, 1H).

Example 133

6-(4-Chlorophenyl)-2-(3-fluorophenyl)-N-[(1R,2S)-2-hydroxycyclopentyl]-3-oxo-2,3-dihydropyridazine-4-carboxamide

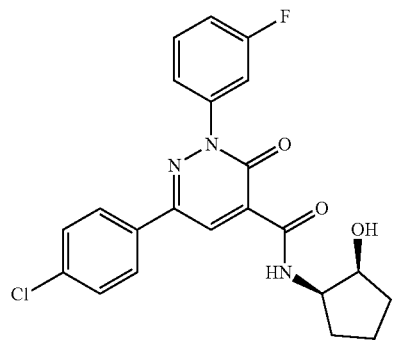 [SMILES: O=C(N[C@@H]1CCC[C@@H]1O)c1cc(-c2ccc(Cl)cc2)nn(-c2cccc(F)c2)c1=O]

A solution of 75 mg intermediate 17, 59.9 mg (1S,2R)-2-amino-cyclopentanol hydrochloride (1:1), 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitril; gradient: A 60%/B 40%→A 20%/B 80%; flow: 150 mL/min; UV-detection: 254 nm) to yield 34 mg 6-(4-chlorophenyl)-2-(3-fluorophenyl)-N-[(1R,2S)-2-hydroxycyclopentyl]-3-oxo-2,3-dihydropyridazine-4-carboxamide.

$^1$H NMR (400 MHz, DMSO-d$_6$) δ ppm=1.45-1.66 (m, 3H), 1.66-1.90 (m, 2H), 1.92-2.03 (m, 1H), 3.97-4.11 (m, 2H), 5.03 (d, 1H), 7.35-7.41 (m, 1H), 7.51-7.68 (m, 5H), 7.97-8.03 (m, 2H), 8.66 (s, 1H), 9.67-9.74 (m, 1H).

Example 134

6-(4-Chlorophenyl)-2-(3-fluorophenyl)-N-(trans-4-hydroxytetrahydrofuran-3-yl)-3-oxo-2,3-dihydropyridazine-4-carboxamide

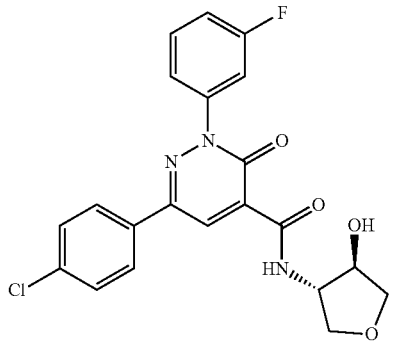 [SMILES: O=C(N[C@H]1COC[C@@H]1O)c1cc(-c2ccc(Cl)cc2)nn(-c2cccc(F)c2)c1=O]

A solution of 100 mg intermediate 17, 59.8 mg trans-4-aminooxolanol, 220.6 mg HATU, 0.15 mL ethyldiisopropylamine and 1.7 mg 4-dimethylaminopyridine in 1.5 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 70%/B 30%→A 30%/B 70%; flow: 150 mL/min; UV-detection: 254 nm) to yield 45.8 mg 6-(4-chlorophenyl)-2-(3-fluorophenyl)-N-(trans-4-hydroxytetrahydrofuran-3-yl)-3-oxo-2,3-dihydropyridazine-4-carboxamide.

$^{1}$H NMR (400 MHz, DMSO-d$_{6}$) δ ppm=3.54 (dd, 1H), 3.64 (dd, 1H), 3.89 (dd, 1H), 3.97 (dd, 1H), 4.17 (br s, 1H), 4.24 (ddd, 1H), 5.50 (d, 1H), 7.34-7.42 (m, 1H), 7.51-7.66 (m, 5H), 7.97-8.04 (m, 2H), 8.63 (s, 1H), 9.46 (d, 1H).

Example 135

6-(4-Chlorophenyl)-2-(3-fluorophenyl)-N-(trans-4-hydroxytetrahydrofuran-3-yl)-3-oxo-2,3-dihydropyridazine-4-carboxamide, Enantiomer 1

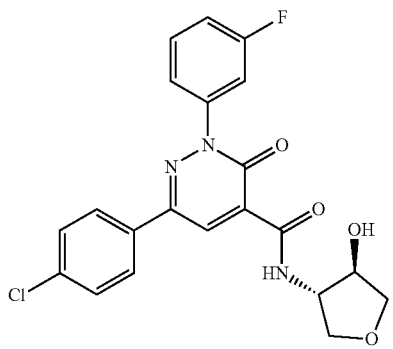 [SMILES: O=C(N[C@H]1COC[C@@H]1O)c1cc(-c2ccc(Cl)cc2)nn(-c2cccc(F)c2)c1=O]

HPLC-separation of 40 mg 6-(4-chlorophenyl)-2-(3-fluorophenyl)-N-(trans-4-hydroxytetrahydrofuran-3-yl)-3-oxo-2,3-dihydropyridazine-4-carboxamide (example 134) on a chiral column (instrument: Sepiatec: Prep SFC100; column: Chiralpak IC 5 μm 250×30 mm; eluent A: CO2, eluent B: 2-propanol; isocratic: 29% B; flow 100.0 mL/min temperature: 40° C.; BPR: 150 bar; MWD 254 nm) yielded 14 mg 6-(4-chlorophenyl)-2-(3-fluorophenyl)-N-(trans-4-hydroxytetrahydrofuran-3-yl)-3-oxo-2,3-dihydropyridazine-4-carboxamide, enantiomer 1.

Chiral HPLC: Rt=2.8 min (Instrument: Agilent HPLC 1260; Aurora SFC module; column: Chiralpak IC 5 μM 100×4.6 mm; eluent A: CO2, eluent B: 2-propanol; isocratic: 29% B, flow 4 mL/min; temperature: 37.5° C.; p=100 bar, DAD scan: 254 nm.)

$[α]_{D}^{20}$=35.0°+/−0.20° (c=8 mg/mL, DMSO).

Example 136

6-(4-Chlorophenyl)-2-(3-fluorophenyl)-N-(trans-4-hydroxytetrahydrofuran-3-yl)-3-oxo-2,3-dihydropyridazine-4-carboxamide, Enantiomer 2

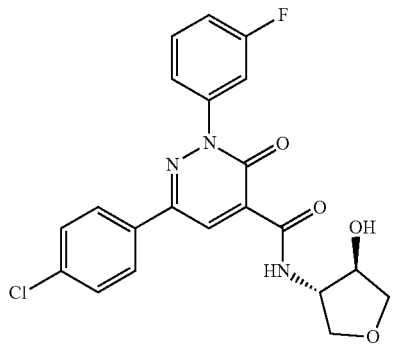 [SMILES: O=C(N[C@H]1COC[C@@H]1O)c1cc(-c2ccc(Cl)cc2)nn(-c2cccc(F)c2)c1=O]

HPLC-separation of 40 mg 6-(4-chlorophenyl)-2-(3-fluorophenyl)-N-(trans-4-hydroxytetrahydrofuran-3-yl)-3-oxo-2,3-dihydropyridazine-4-carboxamide (example 134) on a chiral column (instrument: Sepiatec: Prep SFC100; column: Chiralpak IC 5 μm 250×30 mm; eluent A: CO2, eluent B: 2-propanol; isocratic: 29% B; flow 100.0 mL/min temperature: 40° C.; BPR: 150 bar; MWD 254 nm) yielded 14 mg 6-(4-chlorophenyl)-2-(3-fluorophenyl)-N-(trans-4-hydroxytetrahydrofuran-3-yl)-3-oxo-2,3-dihydropyridazine-4-carboxamide, enantiomer 2.

Chiral HPLC: Rt=4.08 min (Instrument: Agilent HPLC 1260; Aurora SFC module; column: Chiralpak IB 5 μM 100×4.6 mm; eluent A: CO2, eluent B: 2-propanol; isocratic: 29% B, flow 4 mL/min; temperature: 37.5° C.; p=100 bar, DAD scan: 254 nm.)

Example 137

6-[4-(Difluoromethoxy)phenyl]-2-(3-fluorophenyl)-
N-[(2S)-1-hydroxybutan-2-yl]-3-oxo-2,3-dihydro-
pyridazine-4-carboxamide

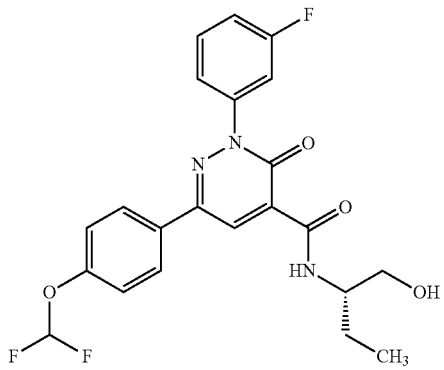 [SMILES: CC[C@@H](CO)NC(=O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 32.6 mg (S)-(+)-2-amino-butanol, 136.4 mg HATU, 0.13 mL ethyldiisopropylamine and 1 mg 4-dimethylaminopyridine in 1.5 mL of DMF was stirred at room temperature for 48 hours. Then the reaction mixture was filtered and subjected to RP-HPLC (Instrument: Waters Autopurification MS SingleQuad; Colum: Waters XBrigde C18 5µ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 46 mg 6-[4-(difluoromethoxy)phenyl]-2-(3-fluorophenyl)-N-[(2S)-1-hydroxybutan-2-yl]-3-oxo-2,3-dihydropyridazine-4-carboxamide.

$^1$H NMR (400 MHz, DMSO-d$_6$) δ ppm=0.89 (t, 3H), 1.43-1.56 (m, 1H), 1.59-1.72 (m, 1H), 3.39-3.47 (m, 1H), 3.48-3.56 (m, 1H), 3.84-3.96 (m, 1H), 4.87 (t, 1H), 7.15-7.68 (m, 8H), 7.99-8.06 (m, 2H), 8.65 (s, 1H), 9.40 (d, 1H).

Example 138

2-(3-Fluorophenyl)-N-(3-hydroxybutan-2-yl)-6-(4-methoxyphenyl)-3-oxo-2,3-dihydropyridazine-4-carboxamide

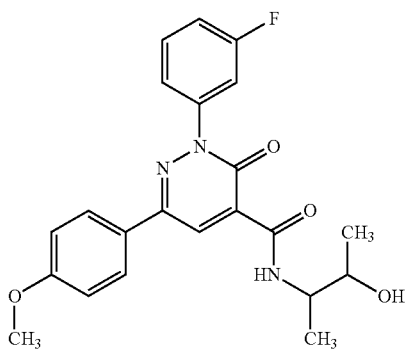 [SMILES: COc1ccc(-c2cc(C(=O)NC(C)C(C)O)c(=O)n(-c3cccc(F)c3)n2)cc1]

A solution of 75 mg intermediate 2-(3-fluorophenyl)-6-(4-methoxyphenyl)-3-oxo-2,3-dihydropyridazine-4-carboxylic acid, 36.1 mg 3-amino-butan-2-ol, 150.8 mg HATU, 0.1 mL ethyldiisopropylamine and 1.2 mg 4-dimethylaminopyridine in 1.5 mL of DMF was stirred at room temperature for 14 hours. Then the reaction mixture was filtered and subjected to RP-HPLC (Instrument: Waters Autopurificationsystem; column: Waters XBrigde C18 5µ 100×30 mm; eluent A: water+0.2 Vol-% aqueous ammonia (32%), eluent B: methanol; gradient: 0.00-0.50 min 29% B (25→70 mL/min), 0.51-5.50 min 59-79% B (70 mL/min), DAD scan: 210-400 nm) to yield 13 mg 2-(3-fluorophenyl)-N-(3-hydroxybutan-2-yl)-6-(4-methoxyphenyl)-3-oxo-2,3-dihydropyridazine-4-carboxamide.

$^1$H NMR (400 MHz, DMSO-d$_6$) δ ppm=0.97-1.20 (m, 6H), 3.63-3.77 (m, 1H), 3.82 (s, 3H), 3.88-4.05 (m, 1H), 4.85 (d, 1H), 6.93-7.16 (m, 2H), 7.29-7.43 (m, 1H), 7.48-7.68 (m, 3H), 7.85-7.94 (m, 2H), 8.62 (s, 1H), 9.57 (d, 1H).

Example 139

2-(3-Fluorophenyl)-N-[(1R,2S)-2-hydroxycyclopentyl]-6-(4-methoxyphenyl)-3-oxo-2,3-dihydropyridazine-4-carboxamide

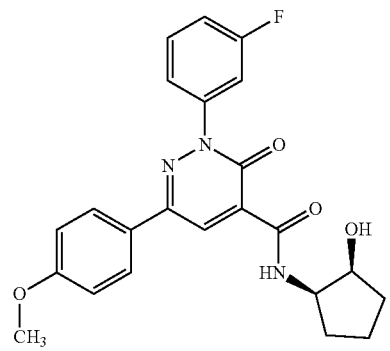 [SMILES: COc1ccc(-c2cc(C(=O)N[C@@H]3CCC[C@@H]3O)c(=O)n(-c3cccc(F)c3)n2)cc1]

A solution of 83 mg intermediate 2-(3-fluorophenyl)-6-(4-methoxyphenyl)-3-oxo-2,3-dihydropyridazine-4-carboxylic acid, 37 mg (1S,2R)-2-aminocyclopentanol hydrochloride, 167 mg HATU, 0.12 mL ethyldiisopropylamine and 1.3 mg 4-dimethylaminopyridine in 1.6 mL of DMF was stirred at room temperature for 14 hours. Then the reaction mixture was filtered and subjected to RP-HPLC (Instrument: Waters Autopurificationsystem; column: Waters XBrigde C18 5µ 100×30 mm; eluent A: water+0.2 Vol-% aqueous ammonia (32%), eluent B: methanol; gradient: 0.00-0.50 min 32% B (25→70 mL/min), 0.51-5.50 min 67-87% B (70 mL/min), DAD scan: 210-400 nm) to yield 36 mg 2-(3-fluorophenyl)-N-(3-hydroxybutan-2-yl)-6-(4-methoxyphenyl)-3-oxo-2,3-dihydropyridazine-4-carboxamide.

$^1$H NMR (400 MHz, DMSO-d$_6$) δ ppm=1.45-1.68 (m, 3H), 1.70-1.89 (m, 2H), 1.89-2.06 (m, 1H), 3.82 (s, 3H), 3.96-4.12 (m, 2H), 5.02 (d, 1H), 7.00-7.15 (m, 2H), 7.29-7.45 (m, 1H), 7.51-7.57 (m, 1H), 7.57-7.69 (m, 2H), 7.86-7.94 (m, 2H), 8.62 (s, 1H), 9.74 (d, 1H).

Example 140

6-[4-(Difluoromethoxy)phenyl]-2-(3-fluorophenyl)-N-(3-hydroxybutan-2-yl)-3-oxo-2,3-dihydropyridazine-4-carboxamide

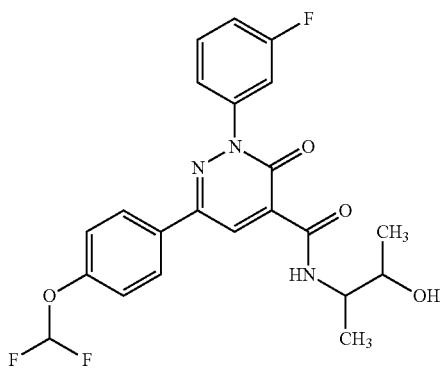

A solution of 75 mg intermediate 6-[4-(difluoromethoxy)phenyl]-2-(3-fluorophenyl)-3-oxo-2,3-dihydropyridazine-4-carboxylic acid, 32.6 mg 3-amino-butan-2-ol, 136.4 mg HATU, 0.13 mL ethyldiisopropylamine and 1 mg 4-dimethylaminopyridine in 1.5 mL of DMF was stirred at room temperature for 48 hours. Then the reaction mixture was filtered and subjected to RP-HPLC (Instrument: Waters Autopurification MS SingleQuad; Colum: Waters XBrigde C18 5µ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 61 mg 6-[4-(difluoromethoxy)phenyl]-2-(3-fluorophenyl)-N-(3-hydroxybutan-2-yl)-3-oxo-2,3-dihydropyridazine-4-carboxamide.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt=1.24 min; MS (ESIpos): m/z=448.2 [M−H]+

Example 141

6-[4-(Difluoromethoxy)phenyl]-2-(3-fluorophenyl)-N-(3-hydroxybutan-2-yl)-3-oxo-2,3-dihydropyridazine-4-carboxamide, Stereoisomer 1

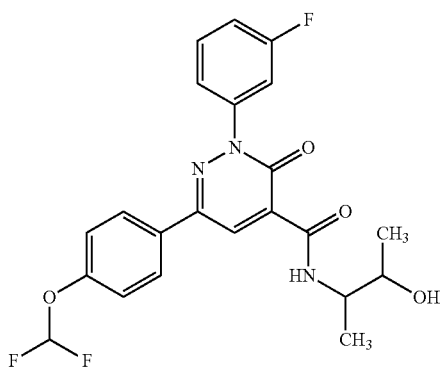

HPLC-separation of 55 mg 6-[4-(difluoromethoxy)phenyl]-2-(3-fluorophenyl)-N-(3-hydroxybutan-2-yl)-3-oxo-2,3-dihydropyridazine-4-carboxamide (example 140) on a chiral column (instrument: Sepiatec: Prep SFC100; column: Chiralpak IB 5 µm 250×30 mm; eluent A: CO2, eluent B: ethanol; isocratic: 15% B; flow 100.0 mL/min temperature: 40° C.; BPR: 150 bar; MWD 254 nm) yielded 15 mg 6-[4-(difluoromethoxy)phenyl]-2-(3-fluorophenyl)-N-(3-hydroxybutan-2-yl)-3-oxo-2,3-dihydropyridazine-4-carboxamide, stereoisomer 1.

Chiral HPLC: Rt=2.42 min (Instrument: Agilent HPLC 1260; Aurora SFC module; column: Chiralpak IB 5 µM 100×4.6 mm; eluent A: CO2, eluent B: ethanol; isocratic: 15% B, flow 4 mL/min; temperature: 37.5° C.; p=100 bar, DAD scan: 254 nm.)

$^1$H NMR (400 MHz, DMSO-$d_6$) δ ppm=1.06-1.10 (m, 6H), 3.62-3.76 (m, 1H), 3.85-4.00 (m, 1H), 4.85 (d, 1H), 7.26-7.43 (m, 4H), 7.49-7.56 (m, 1H), 7.59-7.67 (m, 2H), 7.98-8.06 (m, 2H), 8.65 (s, 1H), 9.54 (d, 1H).

Example 142

6-[4-(Difluoromethoxy)phenyl]-2-(3-fluorophenyl)-N-(3-hydroxybutan-2-yl)-3-oxo-2,3-dihydropyridazine-4-carboxamide, Stereoisomer 2 2

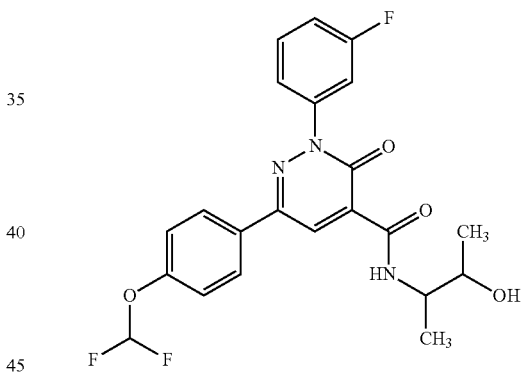

HPLC-separation of 55 mg 6-[4-(difluoromethoxy)phenyl]-2-(3-fluorophenyl)-N-(3-hydroxybutan-2-yl)-3-oxo-2,3-dihydropyridazine-4-carboxamide (example 140) on a chiral column (instrument: Sepiatec: Prep SFC100; column: Chiralpak IB 5 µm 250×30 mm; eluent A: CO2, eluent B: ethanol; isocratic: 15% B; flow 100.0 mL/min temperature: 40° C.; BPR: 150 bar; MWD 254 nm) yielded 20 mg 6-[4-(difluoromethoxy)phenyl]-2-(3-fluorophenyl)-N-(3-hydroxybutan-2-yl)-3-oxo-2,3-dihydropyridazine-4-carboxamide, stereoisomer 2.

Chiral HPLC: Rt=4.68 min (Instrument: Agilent HPLC 1260; Aurora SFC module; column: Chiralpak IB 5 µM 100×4.6 mm; eluent A: CO2, eluent B: ethanol; isocratic: 15% B, flow 4 mL/min; temperature: 37.5° C.; p=100 bar, DAD scan: 254 nm.)

$^1$H NMR (400 MHz, DMSO-$d_6$) δ ppm=1.06-1.10 (m, 6H), 3.64-3.74 (m, 1H), 3.88-3.97 (m, 1H), 4.85 (d, 1H), 7.28-7.41 (m, 4H), 7.53-7.57 (m, 1H), 7.60-7.65 (m, 2H), 8.00-8.05 (m, 2H), 8.65 (s, 1H), 9.54 (d, 1H).

Example 143 rel-6-[4-(Difluoromethoxy)phenyl]-2-(3-fluorophenyl)-N-[(2S,3S)-3-hydroxybutan-2-yl]-3-oxo-2,3-dihydropyridazine-4-carboxamide

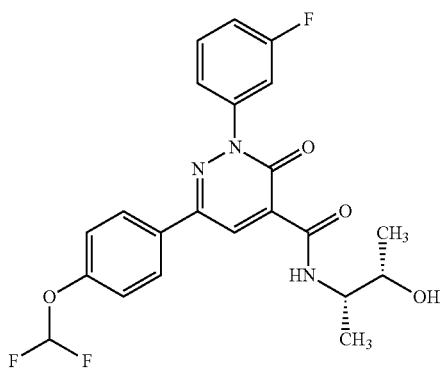 [SMILES: C[C@H](O)[C@H](C)NC(=O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 45.1 mg rel-(2S,3S)-3-aminobutan-2-ol hydrochloride (1:1), 136.4 mg HATU, 0.13 mL ethyldiisopropylamine and 1 mg 4-dimethylaminopyridine in 1.5 mL of DMF was stirred at room temperature for 3 hours. Then the reaction mixture was filtered and subjected to RP-HPLC (Instrument: Waters Autopurification MS SingleQuad; Colum: Waters XBrigde C18 5µ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 60 mg rel-6-[4-(difluoromethoxy)phenyl]-2-(3-fluorophenyl)-N-[(2S,3S)-3-hydroxybutan-2-yl]-3-oxo-2,3-dihydropyridazine-4-carboxamide.

$^1$H NMR (400 MHz, DMSO-$d_6$) δ ppm=1.04 (d, 3H), 1.15 (d, 3H), 3.65-3.75 (m, 1H), 3.88-3.99 (m, 1H), 4.95 (d, 1H), 7.14-7.66 (m, 8H), 8.00-8.04 (m, 2H), 8.65 (s, 1H), 9.47 (d, 1H).

Example 144

6-[4-(Difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide

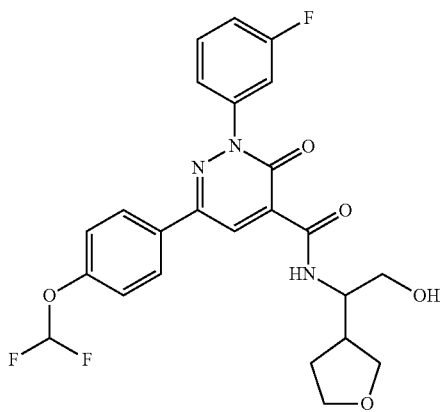 [SMILES: O=C(NC(CO)C1CCOC1)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 49.5 mg 2-amino-2-(tetrahydro-furan-3-yl)-ethanol, 136.4 mg HATU, 0.13 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Colum: Waters XBrigde C18 5µ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 34 mg 6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide.

LC-MS (Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=0.75 min; MS (ESIpos): m/z=490.4 [M+H]$^+$

Example 145

6-[4-(Difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide, Stereoisomer 1

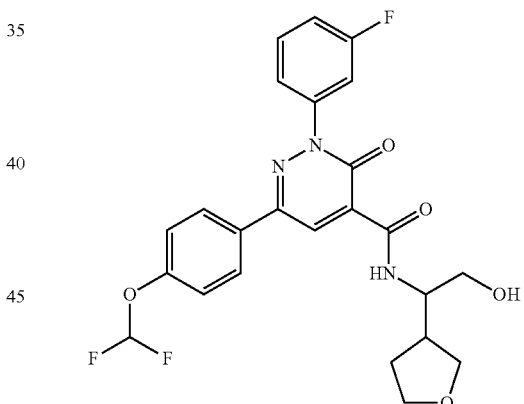

HPLC-separation of 28 mg 6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide (example 144) on a chiral column (instrument: Sepiatec: Prep SFC100; column: Chiralpak IC 5 µm 250×30 mm; eluent A: CO2, eluent B: 2-propanol; isocratic: 35% B; flow 100.0 mL/min temperature: 40° C.; BPR: 150 bar; MWD 254 nm) yielded 5 mg 6-[4-(difluoromethoxy)phenyl]-2-(3-fluorophenyl)-N-{(2-hydroxy-1-tetrahydrofuran-3-yl) ethyl}-3-oxo-2,3-dihydropyridazine-4-carboxamide, stereoisomer 1.

Chiral HPLC: Rt=1.74 min (Instrument: Agilent HPLC 1260; Aurora SFC module; column: Chiralpak IC 5 µM 100×4.6 mm; eluent A: CO2, eluent B: 2-propanol; isocratic: 35% B, flow 4 mL/min; temperature: 37.5° C.; p=100 bar, DAD scan: 254 nm.)

Example 146

6-[4-(Difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide, Stereoisomer 2

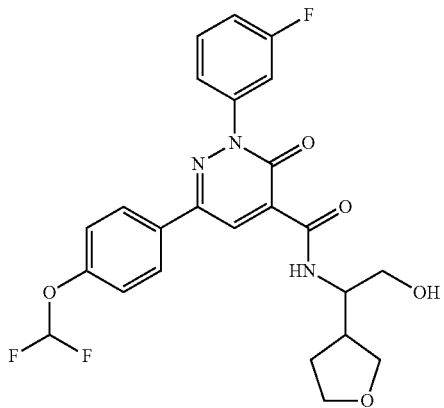 [SMILES: O=C(NC(CO)C1CCOC1)c1cc(-c2ccc(OC(F)F)cc2)nn(-c2cccc(F)c2)c1=O]

HPLC-separation of 28 mg 6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide (example 144) on a chiral column (instrument: Sepiatec: Prep SFC100; column: Chiralpak IC 5 μm 250×30 mm; eluent A: CO2, eluent B: 2-propanol; isocratic: 35% B; flow 100.0 mL/min temperature: 40° C.; BPR: 150 bar; MWD 254 nm) yielded 5 mg 6-[4-(difluoromethoxy)phenyl]-2-(3-fluorophenyl)-N-{(2-hydroxy-1-tetrahydrofuran-3-yl) ethyl}-3-oxo-2,3-dihydropyridazine-4-carboxamide, stereoisomer 2.

Chiral HPLC: Rt=2.61 min (Instrument: Agilent HPLC 1260; Aurora SFC module; column: Chiralpak IC 5 μM 100×4.6 mm; eluent A: CO2, eluent B: 2-propanol; isocratic: 35% B, flow 4 mL/min; temperature: 37.5° C.; p=100 bar, DAD scan: 254 nm.)

Example 147

6-[4-(Difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide, Stereoisomer 3

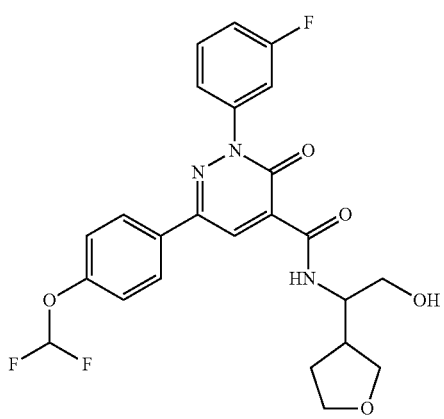 [SMILES: O=C(NC(CO)C1CCOC1)c1cc(-c2ccc(OC(F)F)cc2)nn(-c2cccc(F)c2)c1=O]

HPLC-separation of 28 mg 6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide (example 144) on a chiral column (instrument: Sepiatec: Prep SFC100; column: Chiralpak IC 5 μm 250×30 mm; eluent A: CO2, eluent B: 2-propanol; isocratic: 35% B; flow 100.0 mL/min temperature: 40° C.; BPR: 150 bar; MWD 254 nm) yielded 5 mg 6-[4-(difluoromethoxy)phenyl]-2-(3-fluorophenyl)-N-{(2-hydroxy-1-tetrahydrofuran-3-yl) ethyl}-3-oxo-2,3-dihydropyridazine-4-carboxamide, stereoisomer 3.

Chiral HPLC: Rt=3.69 min (Instrument: Agilent HPLC 1260; Aurora SFC module; column: Chiralpak IC 5 μM 100×4.6 mm; eluent A: CO2, eluent B: 2-propanol; isocratic: 35% B, flow 4 mL/min; temperature: 37.5° C.; p=100 bar, DAD scan: 254 nm.)

Example 148

6-[4-(Difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide, Stereoisomer 4

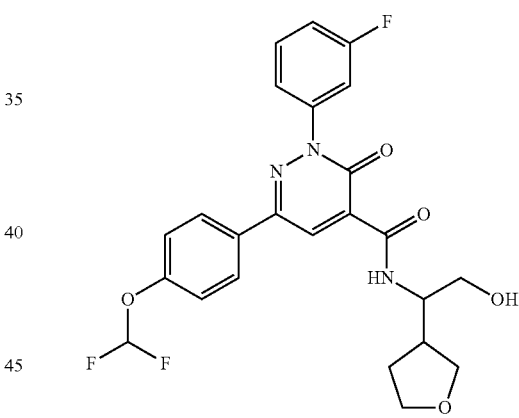

HPLC-separation of 28 mg 6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide (example 144) on a chiral column (instrument: Sepiatec: Prep SFC100; column: Chiralpak IC 5 μm 250×30 mm; eluent A: CO2, eluent B: 2-propanol; isocratic: 35% B; flow 100.0 mL/min temperature: 40° C.; BPR: 150 bar; MWD 254 nm) yielded 5 mg 6-[4-(difluoromethoxy)phenyl]-2-(3-fluorophenyl)-N-{(2-hydroxy-1-tetrahydrofuran-3-yl) ethyl}-3-oxo-2,3-dihydropyridazine-4-carboxamide, stereoisomer 4.

Chiral HPLC: Rt=5.85 min (Instrument: Agilent HPLC 1260; Aurora SFC module; column: Chiralpak IC 5 μM 100×4.6 mm; eluent A: CO2, eluent B: 2-propanol; isocratic: 35% B, flow 4 mL/min; temperature: 37.5° C.; p=100 bar, DAD scan: 254 nm.)

Example 149

6-(4-Chlorophenyl)-2-(3-fluorophenyl)-[(2-hydroxy-1-(tetrahydro-2H-pyran-4-yl)ethyl]-3-oxo-2,3-dihydropyridazine-4-carboxamide

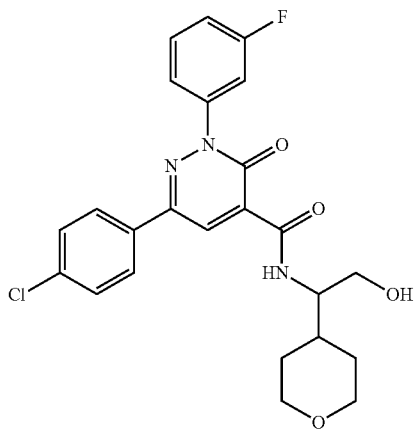 [SMILES: O=C(NC(CO)C1CCOCC1)c1cc(-c2ccc(Cl)cc2)nn(-c2cccc(F)c2)c1=O]

A solution of 75 mg intermediate 17, 63 mg 2-amino-2-(tetrahydro-2H-pyran-4-yl)ethanol, 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 30 mg 6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide.

$^1$H NMR (400 MHz, DMSO-$d_6$) δ ppm=1.17-1.39 (m, 2H), 1.58 (br d, 2H), 1.88 (dtd, 1H), 3.18-3.30 (m, 2H), 3.46 (dt, 1H), 3.59 (dt, 1H), 3.80-3.91 (m, 3H), 4.87 (t, 1H), 7.35-7.43 (m, 1H), 7.53-7.66 (m, 5H), 7.95-8.04 (m, 2H), 8.66 (s, 1H), 9.45 (d, 1H).

Example 150

6-(4-Chlorophenyl)-2-(3-fluorophenyl)-N-[2-hydroxy-1-(tetrahydro-2H-pyran-4-yl)ethyl]-3-oxo-2,3-dihydropyridazine-4-carboxamide, Enantiomer 1

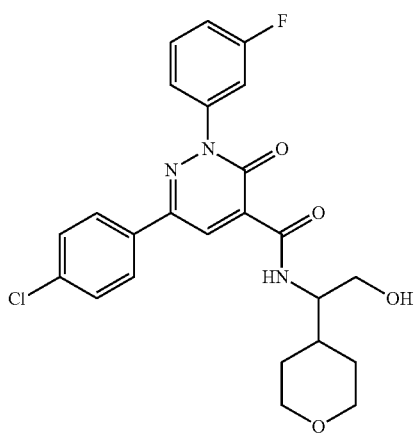 [SMILES: O=C(NC(CO)C1CCOCC1)c1cc(-c2ccc(Cl)cc2)nn(-c2cccc(F)c2)c1=O]

HPLC-separation of 14 mg 6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide (example 149) on a chiral column (instrument: Sepiatec: Prep SFC100; column: Chiralpak IC 5 μm 250×30 mm; eluent A: CO2, eluent B: ethanol; isocratic: 26% B; flow 100.0 mL/min temperature: 40° C.; BPR: 150 bar; MWD 254 nm) yielded 5 mg 6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide, enantiomer 1.

Chiral HPLC: Rt=2.54 min (Instrument: Agilent HPLC 1260; Aurora SFC module; column: Chiralpak IC 5 μM 100×4.6 mm; eluent A: CO2, eluent B: ethanol; isocratic: 26% B, flow 4 mL/min; temperature: 37.5° C.; p=100 bar, DAD scan: 254 nm.)

Example 151

6-(4-Chlorophenyl)-2-(3-fluorophenyl)-N-[2-hydroxy-1-(tetrahydro-2H-pyran-4-yl)ethyl]-3-oxo-2,3-dihydropyridazine-4-carboxamide, Enantiomer 2

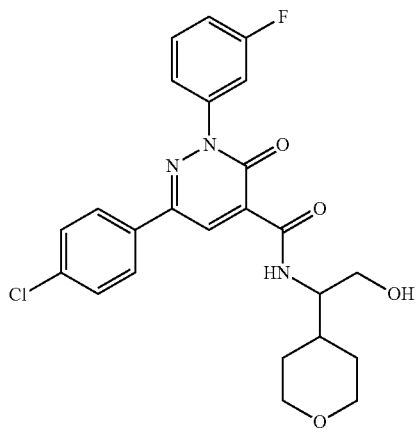 [SMILES: O=C(NC(CO)C1CCOCC1)c1cc(-c2ccc(Cl)cc2)nn(-c2cccc(F)c2)c1=O]

HPLC-separation of 14 mg 6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide (example 149) on a chiral column (instrument: Sepiatec: Prep SFC100; column: Chiralpak IC 5 μm 250×30 mm; eluent A: CO2, eluent B: ethanol; isocratic: 26% B; flow 100.0 mL/min temperature: 40° C.; BPR: 150 bar; MWD 254 nm) yielded 5 mg 6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide, enantiomer 2.

Chiral HPLC: Rt=5.53 min (Instrument: Agilent HPLC 1260; Aurora SFC module; column: Chiralpak IC 5 μM 100×4.6 mm; eluent A: CO2, eluent B: ethanol; isocratic: 26% B, flow 4 mL/min; temperature: 37.5° C.; p=100 bar, DAD scan: 254 nm.)

Example 152

2-(3-Fluorophenyl)-N-trans-2-hydroxycyclohexyl-6-(4-methoxyphenyl)-3-oxo-2,3-dihydropyridazine-4-carboxamide

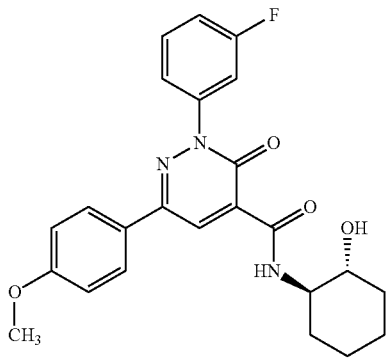 [SMILES: COc1ccc(-c2cc(C(=O)N[C@@H]3CCCC[C@H]3O)c(=O)n(-c3cccc(F)c3)n2)cc1]

A solution of 100 mg intermediate 2-(3-fluorophenyl)-6-(4-methoxyphenyl)-3-oxo-2,3-dihydropyridazine-4-carboxylic acid, 82 mg trans-aminocyclohexanol hydrochloride (1:1), 201 mg HATU, 0.14 mL ethyldiisopropylamine and 1.6 mg 4-dimethylaminopyridine in 2 mL of DMF was stirred at room temperature for 14 hours. Then the reaction mixture was filtered and subjected to RP-HPLC twice (Instrument: Waters Autopurification MS SingleQuad; Column: Waters XBrigde C18 5μ 100×30 mm; eluent A: water+ 0.1 vol % formic acid (99%), eluent B: acetonitrile; gradient: 0-5.5 min 5-100% B; flow 70 mL/min; temperature: 25° C.; DAD scan: 210-400 nm and Instrument: Waters Autopurificationsystem; column: Waters XBrigde C18 5μ 100×30 mm; eluent A: water+0.1 Vol-% formic acid (99%), eluent B: acetonitrile; gradient: 0.00-0.50 min 21% B (25→70 mL/min), 0.51-5.50 min 42-60% B (70 mL/min), DAD scan: 210-400 nm) to yield 32 mg 2-(3-fluorophenyl)-N-trans-2-hydroxycyclohexyl-6-(4-methoxyphenyl)-3-oxo-2,3-dihydropyridazine-4-carboxamide.

$^1$H NMR (400 MHz, DMSO-d6) δ ppm=1.12-1.36 (m, 4H), 1.51-1.69 (m, 2H), 1.84 (br d, 1H), 2.02 (br d, 1H), 3.57-3.71 (m, 1H), 3.82 (s, 3H), 4.83 (d, 1H), 6.97-7.12 (m, 2H), 7.32-7.42 (m, 1H), 7.50-7.56 (m, 1H), 7.56-7.65 (m, 2H), 7.87-7.96 (m, 2H), 8.61 (s, 1H), 9.47 (d, 1H).

Example 153

Methyl N-{[6-(4-chlorophenyl)-2-(3-fluorophenyl)-3-oxo-2,3-dihydropyridazin-4-yl]carbonyl}-L-serinate

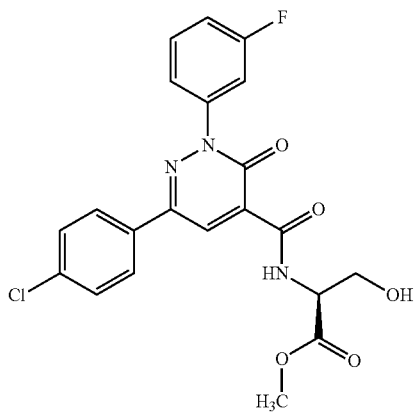 [SMILES: COC(=O)[C@H](CO)NC(=O)c1cc(-c2ccc(Cl)cc2)nn(-c2cccc(F)c2)c1=O]

A solution of 150 mg intermediate 17, 135 mg L-serine methylester hydrochloride (1:1), 331 mg HATU, 0.23 mL ethyldiisopropylamine and 2.6 mg 4-dimethylaminopyridine in 2 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 30 mg methyl N-{[6-(4-chlorophenyl)-2-(3-fluorophenyl)-3-oxo-2,3-dihydropyridazin-4-yl]carbonyl}-L-serinate.

$^1$H NMR (400 MHz, DMSO-d$_6$) δ ppm=3.68 (s, 3H), 3.73 (ddd, 1H), 3.88 (ddd, 1H), 4.61-4.68 (m, 1H), 5.32 (t, 1H), 7.40 (s, 1H), 7.53-7.66 (m, 5H), 7.96-8.04 (m, 2H), 8.68 (s, 1H), 9.99 (d, 1H).

Example 154

2-(3-Fluorophenyl)-N-(trans-2-hydroxycyclopentyl)-6-(4-methoxyphenyl)-3-oxo-2,3-dihydropyridazine-4-carboxamide

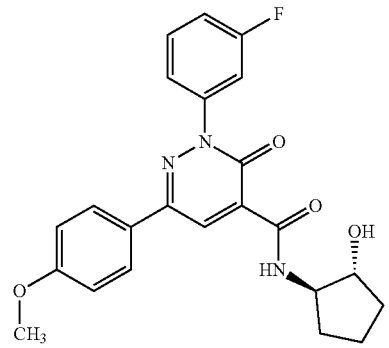 [SMILES: COc1ccc(-c2cc(C(=O)N[C@@H]3CCC[C@H]3O)c(=O)n(-c3cccc(F)c3)n2)cc1]

A solution of 100 mg intermediate 2-(3-fluorophenyl)-6-(4-methoxyphenyl)-3-oxo-2,3-dihydropyridazine-4-carboxylic acid, 74.3 mg trans-aminocyclopentanol hydrochloride (1:1), 201 mg HATU, 0.14 mL ethyldiisopropylamine and 1.6 mg 4-dimethylaminopyridine in 2 mL of DMF was stirred at room temperature for 14 hours. Then the reaction mixture was filtered and subjected to RP-HPLC twice (Instrument: Waters Autopurification MS SingleQuad; Column: Waters XBrigde C18 5μ 100×30 mm; eluent A: water+ 0.1 vol % formic acid (99%), eluent B: acetonitrile; gradient: 0-5.5 min 5-100% B; flow 70 mL/min; temperature: 25° C.; DAD scan: 210-400 nm and Instrument: Waters Autopurificationsystem; column: Waters XBrigde C18 5μ 100×30 mm; eluent A: water+0.2 Vol-% aqueous ammonia (32%), eluent B: methanol; gradient: 0.00-0.50 min 32% B (25→70 mL/min), 0.51-5.50 min 67-87% B (70 mL/min), DAD scan: 210-400 nm) to yield 20 mg 2-(3-fluorophenyl)-N-(trans-2-hydroxycyclopentyl)-6-(4-methoxyphenyl)-3-oxo-2,3-dihydropyridazine-4-carboxamide.

$^1$H NMR (400 MHz, DMSO-d$_6$) δ ppm=1.37-1.56 (m, 2H), 1.57-1.76 (m, 2H), 1.76-1.88 (m, 1H), 2.02-2.14 (m, 1H), 3.82 (s, 3H), 3.93 (quin, 1H), 3.97-4.06 (m, 1H), 4.94 (d, 1H), 7.07 (d, 2H), 7.37 (td, 1H), 7.49-7.56 (m, 1H), 7.56-7.66 (m, 2H), 7.91 (d, 2H), 8.60 (s, 1H), 9.40 (d, 1H).

Example 155

6-[4-(Difluoromethoxy)phenyl]-2-(3-fluorophenyl)-N-[(2S)-1-hydroxypropan-2-yl]-3-oxo-2,3-dihydro-pyridazine-4-carboxamide

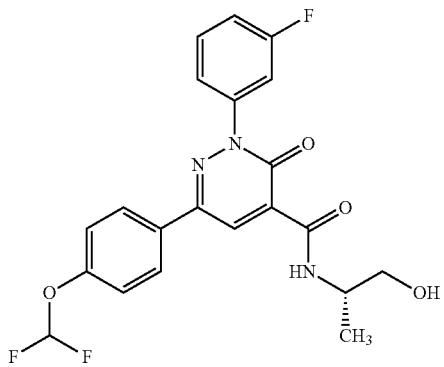 [SMILES: C[C@@H](CO)NC(=O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 27.5 mg (S)-(+)-2-amino-1-propanol, 136.4 mg HATU, 0.13 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Colum: Waters XBrigde C18 5µ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 51 mg 6-[4-(difluoromethoxy)phenyl]-2-(3-fluorophenyl)-N-[(2S)-1-hydroxypropan-2-yl]-3-oxo-2,3-dihydropyridazine-4-carboxamide.

$^1$H NMR (400 MHz, DMSO-$d_6$) δ ppm=1.16 (d, 3H), 3.39-3.50 (m, 2H), 3.97-4.10 (m, 1H), 4.94 (t, 1H), 7.10-7.67 (m, 7H), 7.98-8.07 (m, 2H), 8.65 (s, 1H), 9.45 (d, 1H).

Example 156

6-(4-Chlorophenyl)-N-[(2S)-2,3-dihydroxypropyl]-2-(3-fluorophenyl)-3-oxo-2,3-dihydropyridazine-4-carboxamide

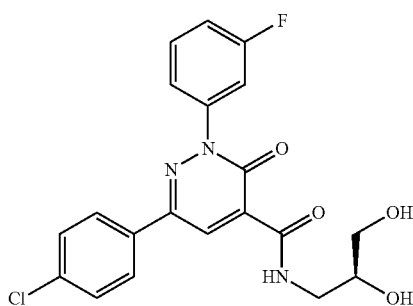

A solution of 75 mg intermediate 17, 39.6 mg (−)-3-amino-1,2-propandiol, 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 42 mg 6-(4-chlorophenyl)-N-[(2S)-2,3-dihydroxypropyl]-2-(3-fluorophenyl)-3-oxo-2,3-dihydropyridazine-4-carboxamide.

$^1$H NMR (400 MHz, DMSO-$d_6$) δ ppm=3.12-3.31 (m, 2H), 3.39 (dt, 1H), 3.52-3.66 (m, 2H), 4.69 (t, 1H), 5.00 (d, 1H), 7.31-7.44 (m, 1H), 7.50-7.69 (m, 5H), 7.95-8.04 (m, 2H), 8.66 (s, 1H), 9.54 (t, 1H).

Example 157

6-(4-Chlorophenyl)-N-[(1S)-1-cyclopentyl-2-hydroxyethyl]-2-(3-fluorophenyl)-3-oxo-2,3-dihydro-pyridazine-4-carboxamide

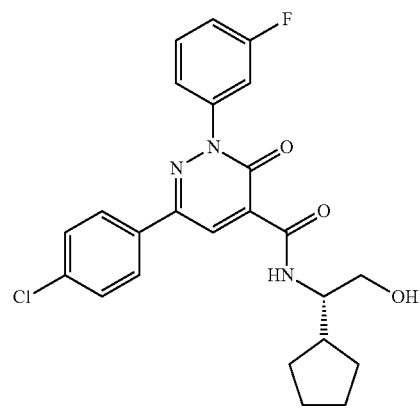 [SMILES: O=C(N[C@H](CO)C1CCCC1)c1cc(-c2ccc(Cl)cc2)nn(-c2cccc(F)c2)c1=O]

A solution of 75 mg intermediate 17, 72.1 mg (2S)-2-amino-2-cyclopentanol, 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 35%/B 65%→A 0%/B 100%; flow: 150 mL/min; UV-detection: 254 nm) to yield 25 mg 6-(4-chlorophenyl)-N-[(1S)-1-cyclopentyl-2-hydroxyethyl]-2-(3-fluorophenyl)-3-oxo-2,3-dihydropyridazine-4-carboxamide.

$^1$H NMR (400 MHz, DMSO-$d_6$) δ ppm=1.16-1.33 (m, 2H), 1.40-1.62 (m, 4H), 1.62-1.79 (m, 2H), 2.07-2.20 (m, 1H), 3.44-3.56 (m, 2H), 3.92 (tt, 1H), 4.81 (t, 1H), 7.34-7.43 (m, 1H), 7.52-7.67 (m, 5H), 7.95-8.03 (m, 2H), 8.66 (s, 1H), 9.46 (d, 1H).

Example 158

2-(3-Fluorophenyl)-N-{(2-hydroxy-1-[tetrahydrofuran-3-yl]ethyl}-6-(4-methoxyphenyl)-3-oxo-2,3-dihydropyridazine-4-carboxamide

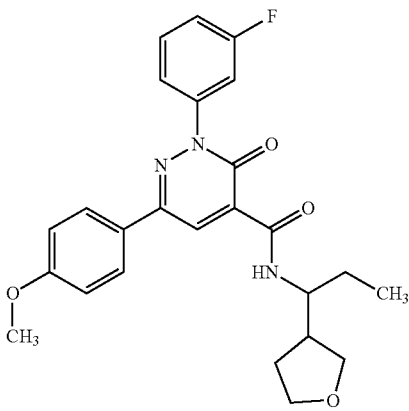 [SMILES: CCC(NC(=O)c1cc(-c2ccc(OC)cc2)nn(-c2cccc(F)c2)c1=O)C1CCOC1]

A solution of 100 mg intermediate 2-(3-fluorophenyl)-6-(4-methoxyphenyl)-3-oxo-2,3-dihydropyridazine-4-carboxylic acid, 70.8 mg 2-amino-2-(tetrahydrofuran-3-yl)ethanol, 201 mg HATU, 0.14 mL ethyldiisopropylamine and 1.6 mg 4-dimethylaminopyridine in 2 mL of DMF was stirred at room temperature for 14 hours. Then the reaction mixture was filtered and subjected to RP-HPLC (Instrument: Waters Autopurificationsystem; column: Waters XBrigde C18 5μ 100×30 mm; eluent A: water+0.1 Vol-% formic acid (99%), eluent B: acetonitrile; gradient: 0.00-0.50 min 32% B (25→70 mL/min), 0.51-7.50 min 32-46% B (70 mL/min), DAD scan: 210-400 nm) to yield 20 mg 2-(3-fluorophenyl)-N-{(2-hydroxy-1-[tetrahydrofuran-3-yl]ethyl}-6-(4-methoxyphenyl)-3-oxo-2,3-dihydropyridazine-4-carboxamide.

$^1$H NMR (400 MHz, DMSO-$d_6$) δ ppm=1.65 (m, 1H), 1.91 (dtd, 1H), 3.41 (t, 1H), 3.45-3.52 (m, 2H), 3.60 (q, 1H), 3.72 (td, 1H), 3.76-3.81 (m, 1H), 3.82 (s, 3H), 4.01 (tt, 1H), 4.93 (t, 1H), 7.01-7.12 (m, 2H), 7.33-7.42 (m, 1H), 7.50-7.66 (m, 3H), 7.86-7.95 (m, 2H), 8.62 (s, 1H), 9.59 (d, 1H).

Example 159

6-(4-Chlorophenyl)-N-[(2R)-2,3-dihydroxypropyl]-2-(3-fluorophenyl)-3-oxo-2,3-dihydropyridazine-4-carboxamide

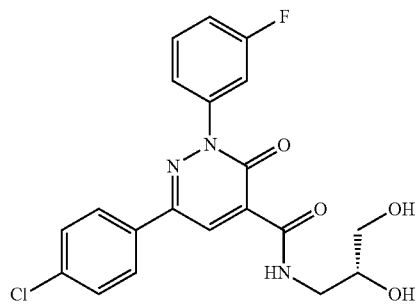 [SMILES: O=C(NC[C@@H](O)CO)c1cc(-c2ccc(Cl)cc2)nn(-c2cccc(F)c2)c1=O]

A solution of 75 mg intermediate 17, 39.6 mg (R)-3-amino-1,2-propandiol, 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 37 mg 6-(4-chlorophenyl)-N-[(2R)-2,3-dihydroxypropyl]-2-(3-fluorophenyl)-3-oxo-2,3-dihydropyridazine-4-carboxamide.

$^1$H NMR (400 MHz, DMSO-$d_6$) δ ppm=3.19-3.27 (m, 1H), 3.27-3.32 (m, 1H), 3.36-3.44 (m, 1H), 3.54-3.65 (m, 2H), 4.69 (br s, 1H), 5.00 (br d, 1H), 7.35-7.42 (m, 1H), 7.52-7.66 (m, 5H), 7.96-8.04 (m, 2H), 8.65 (s, 1H), 9.54 (t, 1H).

Example 160

6-[4-(Difluoromethoxy)phenyl]-2-(3-fluorophenyl)-N-(2-hydroxy-3-methoxypropyl)-3-oxo-2,3-dihydropyridazine-4-carboxamide

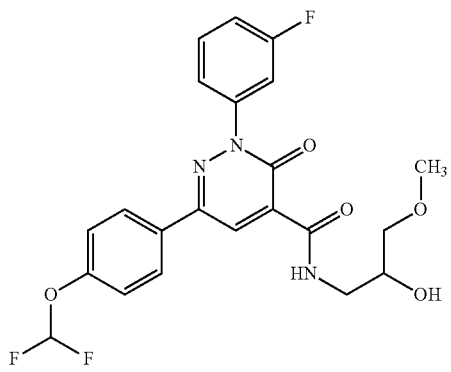 [SMILES: COCC(O)CNC(=O)c1cc(-c2ccc(OC(F)F)cc2)nn(-c2cccc(F)c2)c1=O]

A solution of 75 mg intermediate 6-[4-(difluoromethoxy)phenyl]-2-(3-fluorophenyl)-3-oxo-2,3-dihydropyridazine-4-carboxylic acid, 59.5 mg 1-amino-3-methoxy-2-propanol, 204.6 mg HATU, 0.13 mL ethyldiisopropylamine and 1 mg 4-dimethylaminopyridine in 1.5 mL of DMF was stirred at room temperature for 14 hours and 2 h at 60° C. Then the reaction mixture was filtered and subjected to RP-HPLC (Instrument: Waters Autopurification MS SingleQuad; Colum: Waters XBrigde C18 5μ 100×30 mm; eluent A: water+0.2 vol % aqueous ammonia (32%), eluent B: acetonitrile; gradient: 0-5.5 min 5-100% B; flow 70 mL/min; temperature: 25° C.; DAD scan: 210-400 nm) to yield 28.6 mg 6-[4-(difluoromethoxy)phenyl]-2-(3-fluorophenyl)-N-(2-hydroxy-3-methoxypropyl)-3-oxo-2,3-dihydropyridazine-4-carboxamide.

$^1$H NMR (400 MHz, DMSO-$d_6$) δ ppm=3.26 (s, 3H), 3.27-3.32 (m, 2H), 3.50-3.60 (m, 1H), 3.71-3.82 (m, 1H), 5.17 (d, 1H), 7.15-7.67 (m, 7H), 7.99-8.06 (m, 2H), 8.65 (s, 1H), 9.55 (t, 1H).

Example 161

6-(4-Chlorophenyl)-2-(3-fluorophenyl)-N-[(2R)-1-hydroxy-3-(1H-imidazol-5-yl)propan-2-yl]-3-oxo-2,3-dihydropyridazine-4-carboxamide

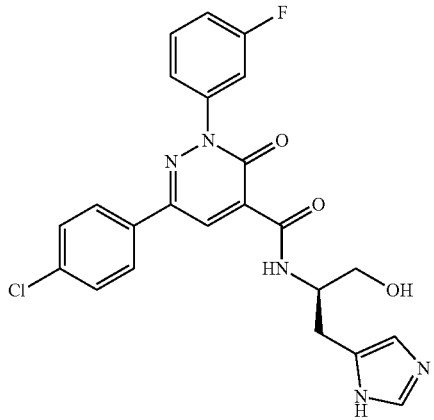 [SMILES: O=C(N[C@@H](CO)Cc1cnc[nH]1)c1cc(-c2ccc(Cl)cc2)nn(-c2cccc(F)c2)c1=O]

A solution of 75 mg intermediate 17, 93.2 mg L-histidinol dihydrochloride, 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+ 0.1 vol % formic acid (99%), eluent B: acetonitrile; gradient: 0-5.5 min 5-100% B; flow 70 mL/min; temperature: 25° C.; DAD scan: 210-400 nm) to yield 32 mg 6-(4-chlorophenyl)-2-(3-fluorophenyl)-N-[(2R)-1-hydroxy-3-(1H-imidazol-5-yl)propan-2-yl]-3-oxo-2,3-dihydropyridazine-4-carboxamide.

$^1$H NMR (400 MHz, DMSO-$d_6$) δ ppm=2.85-2.93 (m, 1H), 2.94-3.03 (m, 1H), 3.47-3.56 (m, 2H), 4.32 (br d, 1H), 7.32 (s, 1H), 7.36-7.44 (m, 1H), 7.53-7.68 (m, 5H), 7.94-8.02 (m, 2H), 8.59 (s, 1H), 8.69 (br s, 1H), 9.49 (d, 1H).

Example 162

N-[(2S)-1-Amino-3-hydroxy-1-oxopropan-2-yl]-6-(4-chlorophenyl)-2-(3-fluorophenyl)-3-oxo-2,3-dihydropyridazine-4-carboxamide

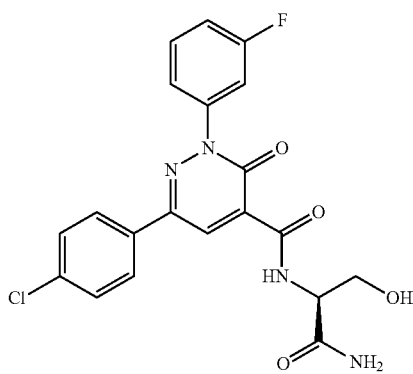 [SMILES: NC(=O)[C@H](CO)NC(=O)c1cc(-c2ccc(Cl)cc2)nn(-c2cccc(F)c2)c1=O]

A solution of 75 mg intermediate 17, 61.2 mg L-serine amide hydrochloride, 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+ 0.1 vol % formic acid (99%), eluent B: acetonitrile; gradient: 0-5.5 min 5-100% B; flow 70 mL/min; temperature: 25° C.; DAD scan: 210-400 nm) to yield 39.5 mg N-[(2S)-1-amino-3-hydroxy-1-oxopropan-2-yl]-6-(4-chlorophenyl)-2-(3-fluorophenyl)-3-oxo-2,3-dihydropyridazine-4-carboxamide.

$^1$H NMR (400 MHz, DMSO-$d_6$) δ ppm=3.65 (dt, 1H), 3.72-3.83 (m, 1H), 4.40-4.49 (m, 1H), 5.09 (t, 1H), 7.23 (s, 1H), 7.40 (br d, 1H), 7.51 (s, 1H), 7.53-7.66 (m, 5H), 7.95-8.05 (m, 2H), 8.66 (s, 1H), 9.86 (d, 1H).

Example 163

N-(4-Amino-1-hydroxy-4-oxobutan-2-yl)-6-(4-chlorophenyl)-2-(3-fluorophenyl)-3-oxo-2,3-dihydropyridazine-4-carboxamide

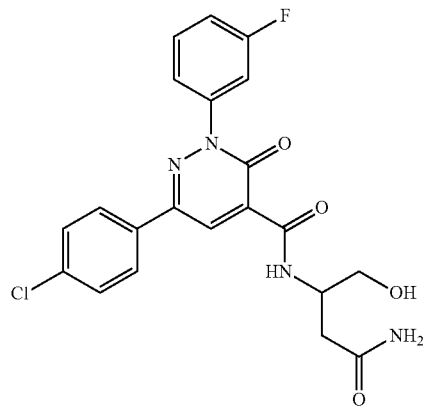 [SMILES: NC(=O)CC(CO)NC(=O)c1cc(-c2ccc(Cl)cc2)nn(-c2cccc(F)c2)c1=O]

A solution of 150 mg intermediate 17, 134.5 mg 3-Amino-4-hydroxybutanamid hydrochloride (1:1), 330.9 mg HATU, 0.23 mL ethyldiisopropylamine and 2.6 mg 4-dimethylaminopyridine in 4 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 16 mg N-(4-amino-1-hydroxy-4-oxobutan-2-yl)-6-(4-chlorophenyl)-2-(3-fluorophenyl)-3-oxo-2,3-dihydropyridazine-4-carboxamide.

$^1$H NMR (400 MHz, DMSO-$d_6$) δ ppm=2.34-2.47 (m, 2H), 3.43-3.57 (m, 2H), 4.25-4.37 (m, 1H), 4.97 (t, 1H), 6.85 (br s, 1H), 7.31-7.42 (m, 1H), 7.31-7.42 (m, 1H), 7.51-7.66 (m, 5H), 7.97-8.02 (m, 2H), 8.65 (s, 1H), 9.56 (d, 1H).

Example 164

6-(4-Chlorophenyl)-2-(3-fluorophenyl)-N-[(1R,2R)-2-hydroxycyclohexyl]-3-oxo-2,3-dihydropyridazine-4-carboxamide

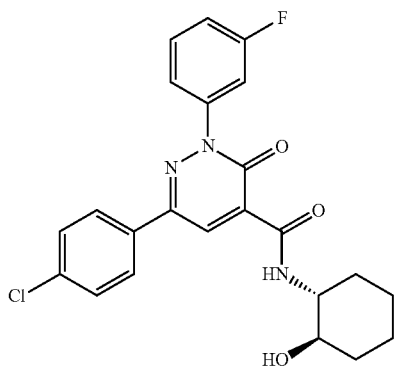 [SMILES: O=C(N[C@@H]1CCCC[C@H]1O)c1cc(-c2ccc(Cl)cc2)nn(-c2cccc(F)c2)c1=O]

A solution of 75 mg intermediate 17, 50.1 mg (1R,2R)-2-aminocyclohexan-1-ol, 165.5 mg HATU, 0.11 mL ethyldiisopropylamine and 1.3 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 56 mg 6-(4-chlorophenyl)-2-(3-fluorophenyl)-N-[(1R,2R)-2-hydroxycyclohexyl]-3-oxo-2,3-dihydropyridazine-4-carboxamide.

$^1$H NMR (400 MHz, DMSO-$d_6$) δ ppm=1.15-1.35 (m, 4H), 1.53-1.68 (m, 2H), 1.85 (br d, 1H), 2.02 (br d, 1H), 3.34-3.40 (m, 1H), 3.59-3.70 (m, 1H), 4.83 (d, 1H), 7.34-7.44 (m, 1H), 7.53-7.65 (m, 5H), 7.95-8.03 (m, 2H), 8.64 (s, 1H), 9.42 (d, 1H).

Example 165

N-{[6-(4-Chlorophenyl)-2-(3-fluorophenyl)-3-oxo-2,3-dihydropyridazin-4-yl]carbonyl}-L-serine

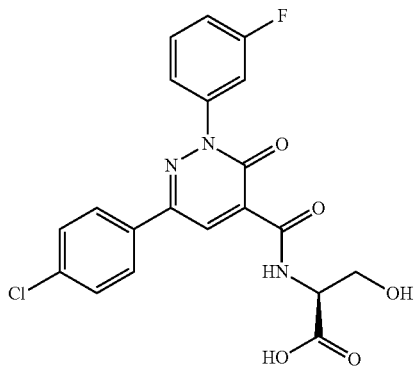 [SMILES: O=C(N[C@@H](CO)C(=O)O)c1cc(-c2ccc(Cl)cc2)nn(-c2cccc(F)c2)c1=O]

A solution of 24.5 mg methyl N-{[6-(4-chlorophenyl)-2-(3-fluorophenyl)-3-oxo-2,3-dihydropyridazin-4-yl]carbonyl}-L-serinate and 4.6 mg lithium hydroxid in 1.5 mL tetrahydrofurane was stirred at room temperature for 14 hours. 4.4 mg sodium hydroxid was added at 0° C. and the reaction mixture was stirred for 1 hour, diluted with water, adjusted to pH 3 with 1M hydrogen chloride solution and extracted with ethyl acetate. The combined organic phase was dried over sodium sulfate, filtrated and the solvent evaporated. The crude product was purified by RP-HPLC ( ) to yield 5 mg N-{[6-(4-chlorophenyl)-2-(3-fluorophenyl)-3-oxo-2,3-dihydropyridazin-4-yl]carbonyl}-L-serine.

$^1$H NMR (400 MHz, DMSO-$d_6$) δ ppm=3.71 (dd, 1H), 3.87 (dd, 1H), 4.45-4.54 (m, 1H), 7.35-7.44 (m, 1H), 7.54-7.69 (m, 5H), 7.97-8.05 (m, 2H), 8.68 (s, 1H), 9.94 (d, 1H).

Example 166

6-(4-Chlorophenyl)-2-(3-fluorophenyl)-N-[(3S,4S)-4-hydroxytetrahydrofuran-3-yl]-3-oxo-2,3-dihydropyridazine-4-carboxamide

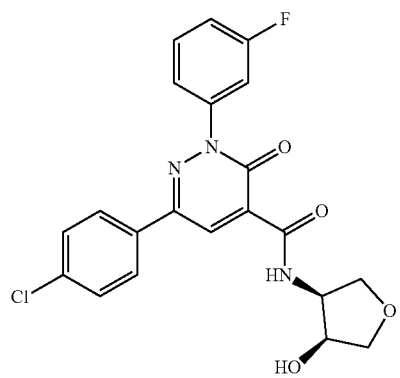 [SMILES: O=C(N[C@H]1COC[C@H]1O)c1cc(-c2ccc(Cl)cc2)nn(-c2cccc(F)c2)c1=O]

A solution of 75 mg intermediate 17, 60.7 mg (3S,4S)-4-aminotetrahydrofuran-3-ol hydrochloride (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 48 mg 6-(4-chlorophenyl)-2-(3-fluorophenyl)-N-[(3S,4S)-4-hydroxytetrahydrofuran-3-yl]-3-oxo-2,3-dihydropyridazine-4-carboxamide.

$^1$H NMR (400 MHz, DMSO-$d_6$) δ ppm=3.45 (dd, 1H), 3.61 (dd, 1H), 3.93 (dd, 1H), 4.00 (dd, 1H), 4.23-4.30 (m, 1H), 4.31-4.40 (m, 1H), 5.68 (d, 1H), 7.39 (m, 1H), 7.52-7.66 (m, 5H), 7.96-8.03 (m, 2H), 8.67 (s, 1H), 9.84 (d, 1H).

Example 167

6-(4-Chlorophenyl)-2-(3-fluorophenyl)-N-[(3S,4R)-4-hydroxytetrahydrofuran-3-yl]-3-oxo-2,3-dihydropyridazine-4-carboxamide

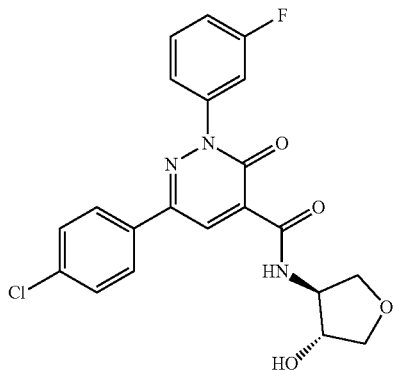 [SMILES: O=C(N[C@H]1COC[C@@H]1O)c1cc(-c2ccc(Cl)cc2)nn(-c2cccc(F)c2)c1=O]

A solution of 75 mg intermediate 17, 60.7 mg (3S,4R)-4-aminotetrahydrofuran-3-ol hydrochloride (1:1), 165.5 mg HATU, 0.11 mL ethyldiisopropylamine and 1.3 mg 4-dimethylaminopyridine in 2 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 38.5 mg 6-(4-chlorophenyl)-2-(3-fluorophenyl)-N-[(3S,4R)-4-hydroxytetrahydrofuran-3-yl]-3-oxo-2,3-dihydropyridazine-4-carboxamide.

$^1$H NMR (400 MHz, DMSO-d$_6$) δ ppm=3.54 (dd, 1H), 3.64 (dd, 1H), 3.89 (dd, 1H), 3.98 (dd, 1H), 4.17 (tt, 1H), 4.25 (ddt, 1H), 5.49 (d, 1H), 7.34-7.43 (m, 1H), 7.52-7.66 (m, 5H), 7.97-8.02 (m, 2H), 8.63 (s, 1H), 9.45 (d, 1H).

Example 168

2-(3-Fluorophenyl)-N-[(2S)-1-hydroxy-3-methylbutan-2-yl]-3-oxo-6-[4-(trifluoromethoxy)phenyl]-2,3-dihydropyridazine-4-carboxamide

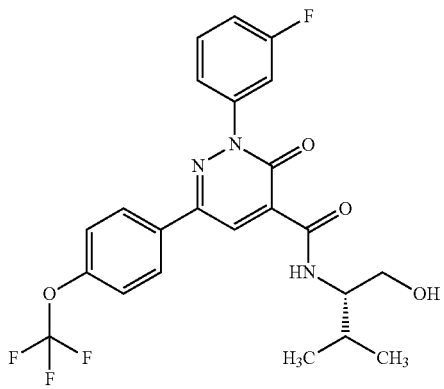 [SMILES: CC(C)[C@@H](CO)NC(=O)c1cc(-c2ccc(OC(F)(F)F)cc2)nn(-c2cccc(F)c2)c1=O]

A solution of 75 mg intermediate 6-[4-(trifluoromethoxy)phenyl]-2-(3-fluorophenyl)-3-oxo-2,3-dihydropyridazine-4-carboxylic acid, 35.3 mg (S)-(+)-2-amino-3-methyl-1-butanol, 130.2 mg HATU, 0.09 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 38 mg 2-(3-fluorophenyl)-N-[(2S)-1-hydroxy-3-methylbutan-2-yl]-3-oxo-6-[4-(trifluoromethoxy)phenyl]-2,3-dihydropyridazine-4-carboxamide.

$^1$H NMR (400 MHz, DMSO-d$_6$) δ ppm=0.89 (d, 3H), 0.92 (d, 3H), 1.89-2.04 (m, 1H), 3.44 (dt, 1H), 3.51-3.60 (m, 1H), 3.80-3.91 (m, 1H), 4.81 (t, 1H), 7.35-7.43 (m, 1H), 7.51 (d, 2H), 7.54-7.67 (m, 3H), 8.08-8.15 (m, 2H), 8.68 (s, 1H), 9.41 (d, 1H).

Example 169

2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide

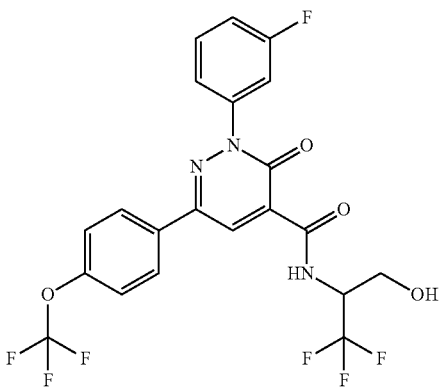 [SMILES: O=C(NC(CO)C(F)(F)F)c1cc(-c2ccc(OC(F)(F)F)cc2)nn(-c2cccc(F)c2)c1=O]

A solution of 90 mg intermediate 6-[4-(trifluoromethoxy)phenyl]-2-(3-fluorophenyl)-3-oxo-2,3-dihydropyridazine-4-carboxylic acid, 77.1 mg 2-amino-3,3,3-trifluoropropan-1-ol hydrochlorid (1:1), 173.6 mg HATU, 0.12 mL ethyldiisopropylamine and 1.4 mg 4-dimethylaminopyridine in 1.7 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 46.5 mg 2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide.

$^1$H NMR (400 MHz, DMSO-d$_6$) δ ppm=3.65-3.75 (m, 1H), 3.82 (dt, 1H), 4.76-4.93 (m, 1H), 5.43 (t, 1H), 7.35-7.45 (m, 1H), 7.51 (d, 2H), 7.55-7.60 (m, 1H), 7.60-7.67 (m, 2H), 8.07-8.16 (m, 2H), 8.74 (s, 1H), 10.01 (d, 1H).

Example 170

2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide, Enantiomer 1

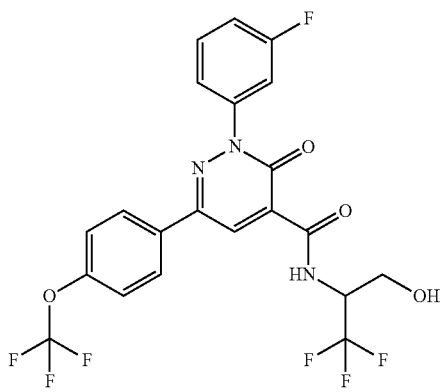 [SMILES: O=C(NC(CO)C(F)(F)F)c1cc(-c2ccc(OC(F)(F)F)cc2)nn(-c2cccc(F)c2)c1=O]

HPLC-separation of 30 mg 2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide (example 169) on a chiral column (instrument: Sepiatec: Prep SFC100; column: Chiralpak IB 5 μm 250×30 mm; eluent A: CO2, eluent B: 2-propanol; isocratic: 8% B; flow 100.0 mL/min temperature: 40° C.; BPR: 150 bar; MWD 254 nm) yielded 15 mg 2-(3-fluorophenyl)-3-oxo-N-(1,1,1-trifluoro-3-hydroxypropan-2-yl)-6-[4-(trifluoromethoxy)phenyl]-2,3-dihydropyridazine-4-carboxamide, enantiomer 1.

Chiral HPLC: Rt=2.72 min (Instrument: Agilent HPLC 1260; Aurora SFC module; column: Chiralpak IB 5 μM 100×4.6 mm; eluent A: CO2, eluent B: 2-propanol; isocratic: 8% B, flow 4 mL/min; temperature: 37.5° C.; p=100 bar, DAD scan: 254 nm.).

Example 171

2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide, Enantiomer 2

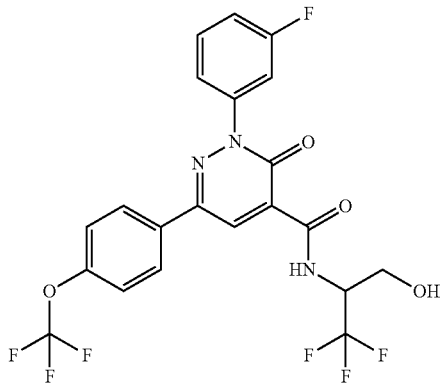 [SMILES: O=C(NC(CO)C(F)(F)F)c1cc(-c2ccc(OC(F)(F)F)cc2)nn(-c2cccc(F)c2)c1=O]

HPLC-separation of 30 mg 2-(3-Fluorophenyl)-3-oxo-N-(1,1,1-trifluoro-3-hydroxypropan-2-yl)-6-[4-(trifluoromethoxy)phenyl]-2,3-dihydropyridazine-4-carboxamide (example 169) on a chiral column (instrument: Sepiatec: Prep SFC100; column: Chiralpak IB 5 μm 250×30 mm; eluent A: CO2, eluent B: 2-propanol; isocratic: 8% B; flow 100.0 mL/min temperature: 40° C.; BPR: 150 bar; MWD 254 nm) yielded 10 mg 2-(3-fluorophenyl)-3-oxo-N-(1,1,1-trifluoro-3-hydroxypropan-2-yl)-6-[4-(trifluoromethoxy)phenyl]-2,3-dihydropyridazine-4-carboxamide, enantiomer 2.

Chiral HPLC: Rt=4.17 min (Instrument: Agilent HPLC 1260; Aurora SFC module; column: Chiralpak IB 5 μM 100×4.6 mm; eluent A: CO2, eluent B: 2-propanol; isocratic: 8% B, flow 4 mL/min; temperature: 37.5° C.; p=100 bar, DAD scan: 254 nm.).

Example 172

2-(3-Fluorophenyl)-N-[(2S)-1-hydroxybutan-2-yl]-3-oxo-6-[4-(trifluoromethoxy)phenyl]-2,3-dihydropyridazine-4-carboxamide

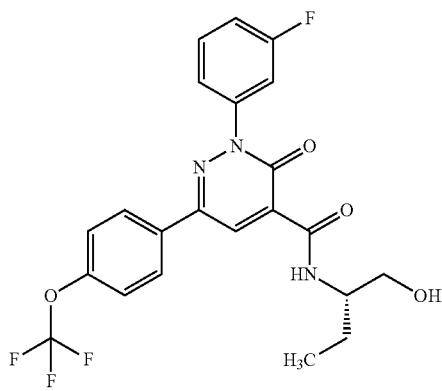 [SMILES: CC[C@@H](CO)NC(=O)c1cc(-c2ccc(OC(F)(F)F)cc2)nn(-c2cccc(F)c2)c1=O]

A solution of 75 mg intermediate 6-[4-(trifluoromethoxy)phenyl]-2-(3-fluorophenyl)-3-oxo-2,3-dihydropyridazine-4-carboxylic acid, 31.2 mg (S)-(+)-2-amino-1-butanol, 130.2 mg HATU, 0.09 mL ethyldiisopropylamine and 1 mg 4-dimethylaminopyridine in 1.5 mL of DMF was stirred at room temperature for 14 hours. Then the reaction mixture was filtered and subjected to RP-HPLC twice (Instrument: Waters Autopurification MS SingleQuad; Column: Waters XBrigde C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm and Instrument: Waters Autopurification-system; column: Waters XBrigde C18 5μ 100×30 mm; eluent A: water+0.2 Vol-% aqueous ammonia (32%), eluent B: methanol; gradient: 0.00-0.50 min 34% B (25→70 mL/min), 0.51-5.50 min 68-88% B (70 mL/min), DAD scan: 210-400 nm) to yield 21 mg 2-(3-fluorophenyl)-N-[(2S)-1-hydroxybutan-2-yl]-3-oxo-6-[4-(trifluoromethoxy)phenyl]-2,3-dihydropyridazine-4-carboxamide.

$^1$H NMR (400 MHz, DMSO-$d_6$) δ ppm=0.89 (t, 3H), 1.41-1.57 (m, 1H), 1.59-1.73 (m, 1H), 3.38-3.47 (m, 1H), 3.47-3.56 (m, 1H), 3.83-3.96 (m, 1H), 4.87 (t, 1H), 7.35-7.44 (m, 1H), 7.51 (d, 2H), 7.53-7.58 (m, 1H), 7.59-7.68 (m, 2H), 8.05-8.13 (m, 2H), 8.67 (s, 1H), 9.38 (d, 1H).

Example 173

2-(3-Fluorophenyl)-N-[(2S)-1-hydroxypropan-2-yl]-3-oxo-6-[4-(trifluoromethoxy)phenyl]-2,3-dihydropyridazine-4-carboxamide

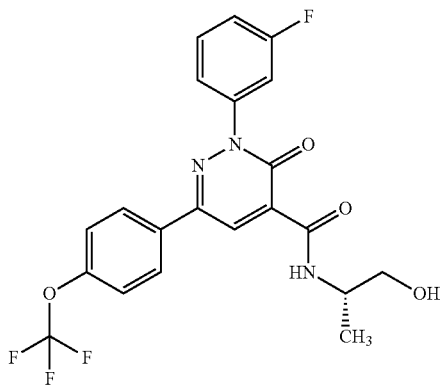 [SMILES: C[C@@H](CO)NC(=O)c1cc(-c2ccc(OC(F)(F)F)cc2)nn(-c2cccc(F)c2)c1=O]

A solution of 75 mg intermediate 6-[4-(trifluoromethoxy)phenyl]-2-(3-fluorophenyl)-3-oxo-2,3-dihydropyridazine-4-carboxylic acid, 26.2 mg (S)-(+)-2-amino-1-propanol (L-Alaninol), 130.2 mg HATU, 0.09 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 46 mg 2-(3-fluorophenyl)-N-[(2S)-1-hydroxypropan-2-yl]-3-oxo-6-[4-(trifluoromethoxy)phenyl]-2,3-dihydropyridazine-4-carboxamide.

$^1$H NMR (400 MHz, DMSO-d$_6$) δ ppm=1.16 (d, 3H), 3.40-3.49 (m, 2H), 3.99-4.10 (m, 1H), 4.94 (t, 1H), 7.26-7.44 (m, 1H), 7.51 (d, 2H), 7.53-7.58 (m, 1H), 7.58-7.66 (m, 2H), 8.04-8.15 (m, 2H), 8.67 (s, 1H), 9.44 (d, 1H).

Example 174

2-(3-Fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide

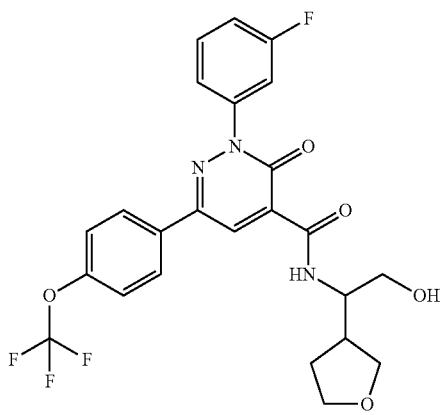

A solution of 100 mg intermediate 6-[4-(trifluoromethoxy)phenyl]-2-(3-fluorophenyl)-3-oxo-2,3-dihydropyridazine-4-carboxylic acid, 67.9 mg 2-amino-2-(tetrahydrofuran-3-yl)ethanol, 192.9 mg HATU, 0.13 mL ethyldiisopropylamine and 1.5 mg 4-dimethylaminopyridine in 2 mL of DMF was stirred at room temperature for 3 hours. Then the reaction mixture was filtered and subjected to RP-HPLC (Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 76 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt=1.30 min; MS (ESIpos): m/z=508.3 [M–H]$^+$

Example 175

2-(3-Fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, Stereoisomer 1

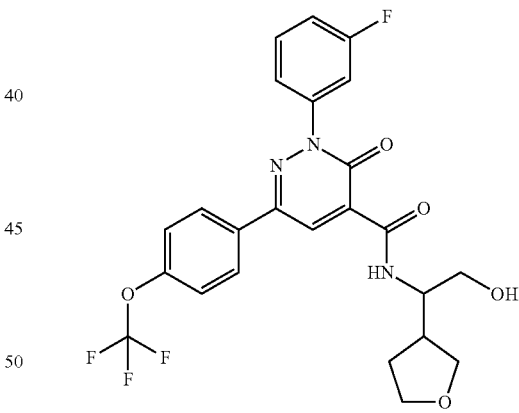

HPLC-separation of 59 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide (example 174) on a chiral column (Instrument: Labomatic HD5000, Labocord-5000; Gilson GX-241, Labcol Vario 4000, column: Chiralpak IC 5µ 250×30 mm; eluent A: hexane+0.1 Vol-% diethylamine (99%); eluent B: ethanol; gradient: 20-50% B in 15 min; flow 40.0 mL/min; UV 254 nm) yielded 6 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, stereoisomer 1.

Chiral HPLC: Rt=4.87 min (Instrument: Agilent HPLC 1260; Aurora SFC module; column: Chiralpak IC 3 μM 100×4.6 mm; eluent A: hexane+0.1 Vol-% diethylamine (99%), eluent B: ethanol; gradient: 20-50% B in 7 min; flow 1.4 mL/min; temperature: 25° C.; DAD 254 nm.)

$^1$H NMR (400 MHz, DMSO-$d_6$) δ ppm=1.63 (dq, 1H), 1.98 (dtd, 1H), 3.43-3.64 (m, 4H), 3.68-3.78 (m, 2H), 3.97-4.08 (m, 1H), 4.94 (t, 1H), 7.33-7.42 (m, 1H), 7.48-7.54 (m, 2H), 7.54-7.58 (m, 1H), 7.58-7.68 (m, 2H), 8.07-8.13 (m, 2H), 8.67 (s, 1H), 9.53 (d, 1H).

Example 176

2-(3-Fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, Stereoisomer 2

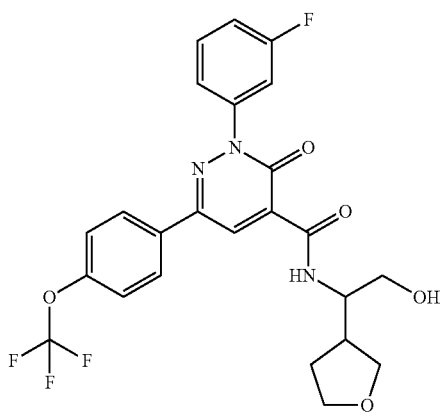 [SMILES: O=C(NC(CO)C1CCOC1)c1cc(-c2ccc(OC(F)(F)F)cc2)nn(-c2cccc(F)c2)c1=O]

HPLC-separation of 59 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide (example 174) on a chiral column (Instrument: Labomatic HD5000, Labocord-5000; Gilson GX-241, Labcol Vario 4000, column: Chiralpak IC 5μ 250×30 mm; eluent A: hexane+0.1 Vol-% diethylamine (99%); eluent B: ethanol; gradient: 20-50% B in 15 min; flow 40.0 mL/min; UV 254 nm) yielded 6.5 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, stereoisomer 2.

Chiral HPLC: Rt=5.2 min (Instrument: Agilent HPLC 1260; Aurora SFC module; column: Chiralpak IC 3 μM 100×4.6 mm; eluent A: hexane+0.1 Vol-% diethylamine (99%), eluent B: ethanol; gradient: 20-50% B in 7 min; flow 1.4 mL/min; temperature: 25° C.; DAD 254 nm.)

$^1$H NMR (400 MHz, DMSO-$d_6$) δ ppm=1.65 (dq, 1H), 1.85-1.99 (m, 1H), 3.39-3.44 (m, 1H), 3.45-3.51 (m, 2H), 3.60 (q, 1H), 3.67-3.76 (m, 1H), 3.80 (t, 1H), 4.02 (tt, 1H), 4.94 (t, 1H), 7.35-7.44 (m, 1H), 7.51 (d, 2H), 7.54-7.58 (m, 1H), 7.60-7.68 (m, 2H), 8.05-8.15 (m, 2H), 8.68 (s, 1H), 9.55 (d, 1H).

Example 177

2-(3-Fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, Stereoisomer 3

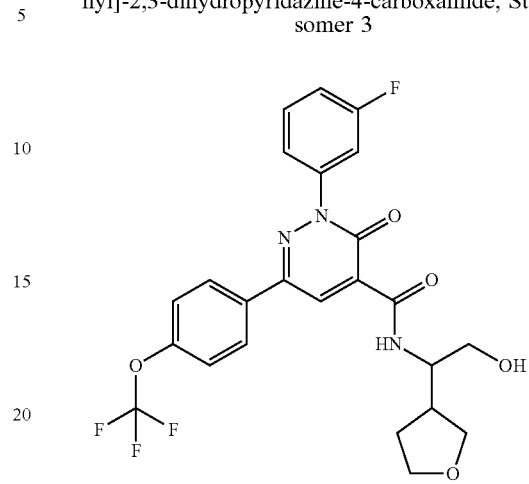

HPLC-separation of 59 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide (example 174) on a chiral column (Instrument: Labomatic HD5000, Labocord-5000; Gilson GX-241, Labcol Vario 4000, column: Chiralpak IC 5μ 250×30 mm; eluent A: hexane+0.1 Vol-% diethylamine (99%); eluent B: ethanol; gradient: 20-50% B in 15 min; flow 40.0 mL/min; UV 254 nm) yielded 6.4 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, stereoisomer 3.

Chiral HPLC: Rt=5.97 min (Instrument: Agilent HPLC 1260; Aurora SFC module; column: Chiralpak IC 3 μM 100×4.6 mm; eluent A: hexane+0.1 Vol-% diethylamine (99%), eluent B: ethanol; gradient: 20-50% B in 7 min; flow 1.4 mL/min; temperature: 25° C.; DAD 254 nm.)

$^1$H NMR (400 MHz, DMSO-$d_6$) δ ppm=1.63 (dq, 1H), 1.98 (dtd, 1H), 3.43-3.64 (m, 4H), 3.68-3.79 (m, 2H), 4.03 (tt, 1H), 4.94 (t, 1H), 7.34-7.44 (m, 1H), 7.48-7.54 (m, 2H), 7.54-7.59 (m, 1H), 7.59-7.67 (m, 2H), 8.06-8.15 (m, 2H), 8.67 (s, 1H), 9.53 (d, 1H).

Example 178

2-(3-Fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, Stereoisomer 4

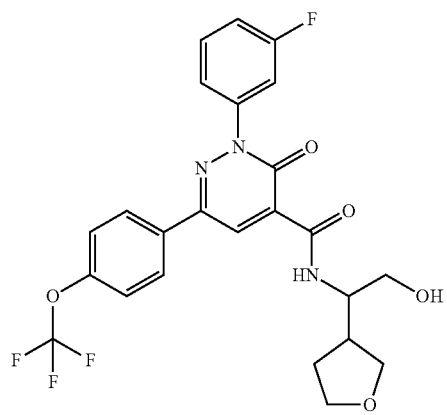 [SMILES: O=C(NC(CO)C1CCOC1)c1cc(-c2ccc(OC(F)(F)F)cc2)nn(-c2cccc(F)c2)c1=O]

HPLC-separation of 59 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide (example 174) on a chiral column (Instrument: Labomatic HD5000, Labocord-5000; Gilson GX-241, Labcol Vario 4000, column: Chiralpak IC 5μ 250×30 mm; eluent A: hexane+0.1 Vol-% diethylamine (99%); eluent B: ethanol; gradient: 20-50% B in 15 min; flow 40.0 mL/min; UV 254 nm) yielded 4.8 mg 2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide, stereoisomer 4.

Chiral HPLC: Rt=7.05 min (Instrument: Agilent HPLC 1260; Aurora SFC module; column: Chiralpak IC 3 μM 100×4.6 mm; eluent A: hexane+0.1 Vol-% diethylamine (99%), eluent B: ethanol; gradient: 20-50% B in 7 min; flow 1.4 mL/min; temperature: 25° C.; DAD 254 nm.)

$^1$H NMR (400 MHz, DMSO-d$_6$) δ ppm=1.65 (dq, 1H), 1.91 (dtd, 1H), 3.37-3.52 (m, 3H), 3.60 (q, 1H), 3.72 (td, 1H), 3.80 (t, 1H), 4.02 (tt, 1H), 4.94 (t, 1H), 7.35-7.43 (m, 1H), 7.49-7.54 (m, 2H), 7.54-7.58 (m, 1H), 7.59-7.67 (m, 2H), 8.07-8.13 (m, 2H), 8.68 (s, 1H), 9.55 (d, 1H).

Example 179

2-(3-Fluorophenyl)-N-(3-hydroxybutan-2-yl)-3-oxo-6-[4-(trifluoromethoxy)phenyl]-2,3-dihydropyridazine-4-carboxamide

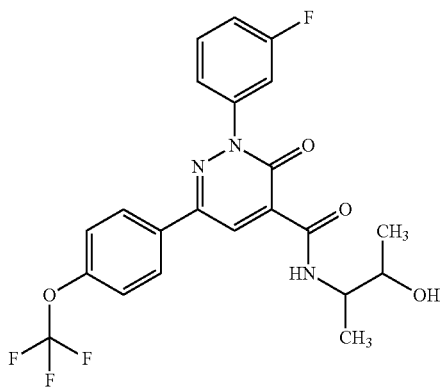 [SMILES: CC(O)C(C)NC(=O)c1cc(-c2ccc(OC(F)(F)F)cc2)nn(-c2cccc(F)c2)c1=O]

A solution of 75 mg intermediate 6-[4-(trifluoromethoxy)phenyl]-2-(3-fluorophenyl)-3-oxo-2,3-dihydropyridazine-4-carboxylic acid, 31.1 mg 3-aminobutan-2-ol, 130.2 mg HATU, 0.09 mL ethyldiisopropylamine and 1 mg 4-dimethylaminopyridine in 1.5 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 32.6 mg 2-(3-fluorophenyl)-N-(3-hydroxybutan-2-yl)-3-oxo-6-[4-(trifluoromethoxy)phenyl]-2,3-dihydropyridazine-4-carboxamide.

LC-MS (instrument: Waters Acquity UPLC-MS SQD 3001; column: Acquity UPLC BEH C18 1.7 50×2.1 mm; eluent A: Water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt=1.38 min; MS (ESIpos): m/z=466.7 [M−H]$^+$ Example 180

2-(3-Fluorophenyl)-N-(3-hydroxybutan-2-yl)-3-oxo-6-[4-(trifluoromethoxy)phenyl]-2,3-dihydropyridazine-4-carboxamide, Stereoisomer 1

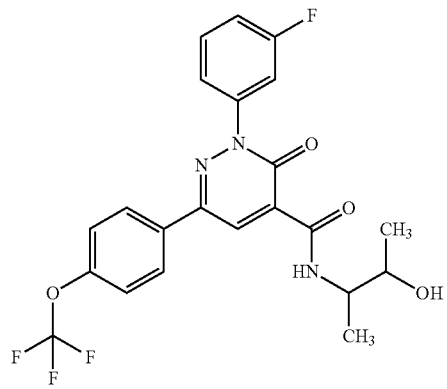 [SMILES: CC(O)C(C)NC(=O)c1cc(-c2ccc(OC(F)(F)F)cc2)nn(-c2cccc(F)c2)c1=O]

HPLC-separation of 24 mg 2-(3-Fluorophenyl)-N-(3-hydroxybutan-2-yl)-3-oxo-6-[4-(trifluoromethoxy)phenyl]-2,3-dihydropyridazine-4-carboxamide (example 179) on a chiral column (Instrument: Labomatic HD5000, Labocord-5000; Gilson GX-241, Labcol Vario 4000, column: Chiralpak IB 5μ 250×30 mm; eluent A: methyl tert. butyl ether+0.1 Vol-% diethylamine (99%); eluent B: ethanol; isocratic 90% A+10% B; flow 50.0 mL/min; UV 254 nm) yielded 2 mg 2-(3-fluorophenyl)-N-(3-hydroxybutan-2-yl)-3-oxo-6-[4-(trifluoromethoxy)phenyl]-2,3-dihydropyridazine-4-carboxamide, stereoisomer 1.

Chiral HPLC: Rt=1.45 min (Instrument: Agilent HPLC 1260; Aurora SFC module; column: Chiralpak IB 3 μM 100×4.6 mm; eluent A: methyl tert. butyl ether+0.1 Vol-% diethylamine (99%), eluent B: ethanol; isocratic 90% A+10% B; flow 1.4 mL/min; temperature: 25° C.; DAD 254 nm.)

$^1$H NMR (400 MHz, DMSO-d$_6$) δ ppm=1.09 (2xd, 6H), 3.65-3.75 (m, 1H), 3.92 (ddd, 1H), 4.86 (d, 1H), 7.36-7.42 (m, 1H), 7.51 (d, 2H), 7.56 (s, 1H), 7.59-7.67 (m, 2H), 8.08-8.13 (m, 2H), 8.67 (s, 1H), 9.52 (d, 1H).

Example 181

2-(3-Fluorophenyl)-N-(3-hydroxybutan-2-yl)-3-oxo-6-[4-(trifluoromethoxy)phenyl]-2,3-dihydropyridazine-4-carboxamide, Stereoisomer 2

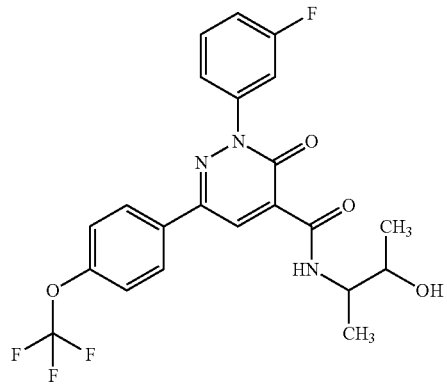 [SMILES: CC(O)C(C)NC(=O)c1cc(-c2ccc(OC(F)(F)F)cc2)nn(-c2cccc(F)c2)c1=O]

HPLC-separation of 24 mg 2-(3-Fluorophenyl)-N-(3-hydroxybutan-2-yl)-3-oxo-6-[4-(trifluoromethoxy)phenyl]-2,3-dihydropyridazine-4-carboxamide (example 179) on a chiral column (Instrument: Labomatic HD5000, Labocord-5000; Gilson GX-241, Labcol Vario 4000, column: Chiralpak IB 5μ 250×30 mm; eluent A: methyl tert. butyl ether+0.1 Vol-% diethylamine (99%); eluent B: ethanol; isocratic 90% A+10% B; flow 50.0 mL/min; UV 254 nm) yielded 2 mg 2-(3-Fluorophenyl)-N-(3-hydroxybutan-2-yl)-3-oxo-6-[4-(trifluoromethoxy)phenyl]-2,3-dihydropyridazine-4-carboxamide, stereoisomer 2.

Chiral HPLC: Rt=2.01 min (Instrument: Agilent HPLC 1260; Aurora SFC module; column: Chiralpak IB 3 μM 100×4.6 mm; eluent A: methyl tert. butyl ether+0.1 Vol-% diethylamine (99%), eluent B: ethanol; isocratic 90% A+10% B; flow 1.4 mL/min; temperature: 25° C.; DAD 254 nm).

$^1$H NMR (400 MHz, DMSO-$d_6$) δ ppm=1.09 (dd, 6H), 3.65-3.73 (m, 1H), 3.92 (ddd, 1H), 4.86 (d, 1H), 7.35-7.42 (m, 1H), 7.51 (dd, 2H), 7.53-7.57 (m, 1H), 7.58-7.62 (m, 1H), 7.62-7.66 (m, 1H), 8.07-8.12 (m, 2H), 8.67 (s, 1H), 9.52 (d, 1H).

Example 182

2-(3-Fluorophenyl)-3-oxo-N-(3,3,3-trifluoro-2-hydroxypropyl)-6-[4-(trifluoromethoxy)phenyl]-2,3-dihydropyridazine-4-carboxamide

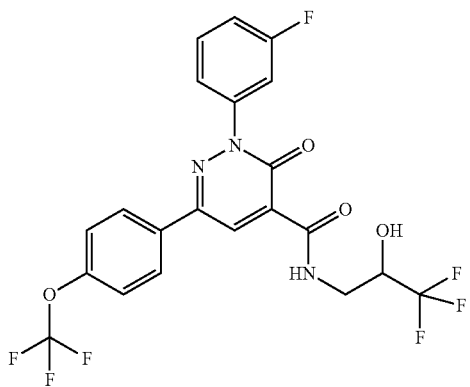 [SMILES: O=C(NCC(O)C(F)(F)F)c1cc(-c2ccc(OC(F)(F)F)cc2)nn(-c2cccc(F)c2)c1=O]

A solution of 150 mg intermediate 6-[4-(trifluoromethoxy)phenyl]-2-(3-fluorophenyl)-3-oxo-2,3-dihydropyridazine-4-carboxylic acid, 90.2 mg 3-amino-1,1,1-trifluoro-2-propanol, 260.4 mg HATU, 0.18 mL ethyldiisopropylamine and 2 mg 4-dimethylaminopyridine in 2.5 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 101 mg 2-(3-fluorophenyl)-3-oxo-N-(3,3,3-trifluoro-2-hydroxypropyl)-6-[4-(trifluoromethoxy)phenyl]-2,3-dihydropyridazine-4-carboxamide.

$^1$H NMR (400 MHz, DMSO-$d_6$) δ ppm=3.47 (ddd, 1H), 3.70-3.81 (m, 1H), 4.18-4.28 (m, 1H), 6.66 (d, 1H), 7.36-7.44 (m, 1H), 7.51 (d, 2H), 7.54-7.59 (m, 1H), 7.59-7.67 (m, 2H), 8.10 (d, 2H), 8.69 (s, 1H), 9.64 (t, 1H).

Example 183

2-(3-Fluorophenyl)-3-oxo-N-(3,3,3-trifluoro-2-hydroxypropyl)-6-[4-(trifluoromethoxy)phenyl]-2,3-dihydropyridazine-4-carboxamide, Enantiomer 1

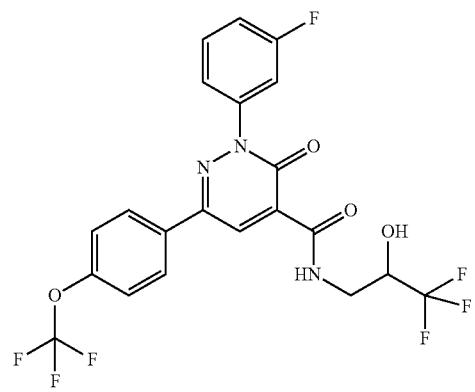 [SMILES: O=C(NCC(O)C(F)(F)F)c1cc(-c2ccc(OC(F)(F)F)cc2)nn(-c2cccc(F)c2)c1=O]

HPLC-separation of 24 mg 2-(3-Fluorophenyl)-3-oxo-N-(3,3,3-trifluoro-2-hydroxypropyl)-6-[4-(trifluoromethoxy)phenyl]-2,3-dihydropyridazine-4-carboxamide (example 182) on a chiral column (Instrument: Sepiatec: Prep SFC100; column: Chiralpak IB 5 μm 250×30 mm; eluent A: CO2, Eluent B: ethanol+0.4 Vol-% diethylamine (99%); isocratic: 7% B; flow 100.0 mL/min temperature: 40° C.; BPR: 150 bar; MWD 254 nm) yielded 14 mg 2-(3-Fluorophenyl)-3-oxo-N-(3,3,3-trifluoro-2-hydroxypropyl)-6-[4-(trifluoromethoxy)phenyl]-2,3-dihydropyridazine-4-carboxamide, enantiomer 1.

Chiral H PLC: Rt=2.04 min (Instrument: Agilent HPLC 1260; Aurora SFC module; column: Chiralpak IB 3 μM 100×4.6 mm; eluent A: CO2, eluent B: ethanol+0.2 Vol-% diethylamine (99%); isocratic 7% B; flow 4 mL/min; temperature: 25° C.; DAD 254 nm.).

Example 184

2-(3-Fluorophenyl)-3-oxo-N-(3,3,3-trifluoro-2-hydroxypropyl)-6-[4-(trifluoromethoxy)phenyl]-2,3-dihydropyridazine-4-carboxamide, Enantiomer 2

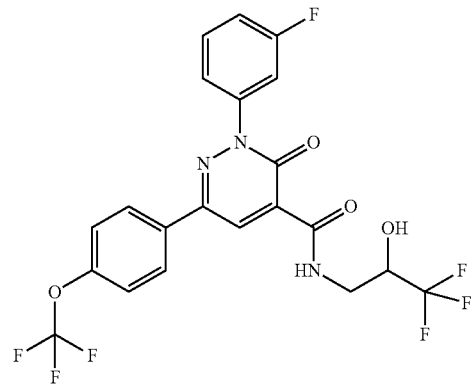 [SMILES: O=C(NCC(O)C(F)(F)F)c1cc(-c2ccc(OC(F)(F)F)cc2)nn(-c2cccc(F)c2)c1=O]

HPLC-separation of 24 mg 2-(3-Fluorophenyl)-3-oxo-N-(3,3,3-trifluoro-2-hydroxypropyl)-6-[4-(trifluoromethoxy)

phenyl]-2,3-dihydropyridazine-4-carboxamide (example 182) on a chiral column (Instrument: Sepiatec: Prep SFC100; column: Chiralpak IB 5 µm 250×30 mm; eluent A: CO2, Eluent B: ethanol+0.4 Vol-% diethylamine (99%); isocratic: 7% B; flow 100.0 mL/min temperature: 40° C.; BPR: 150 bar; MWD 254 nm) yielded 8 mg 2-(3-fluorophenyl)-3-oxo-N-(3,3,3-trifluoro-2-hydroxypropyl)-6-[4-(trifluoromethoxy)phenyl]-2,3-dihydropyridazine-4-carboxamide, enantiomer 2.

Chiral HPLC: Rt=3.17 min (Instrument: Agilent HPLC 1260; Aurora SFC module; column: Chiralpak IB 3 µM 100×4.6 mm; eluent A: CO2, eluent B: ethanol+0.2 Vol-% diethylamine (99%); isocratic 7% B; flow 4 mL/min; temperature: 25° C.; DAD 254 nm.).

Example 185

2-(3-Fluorophenyl)-N-[(2S,3S)-3-hydroxybutan-2-yl]-3-oxo-6-[4-(trifluoromethoxy)phenyl]-2,3-dihydropyridazine-4-carboxamide

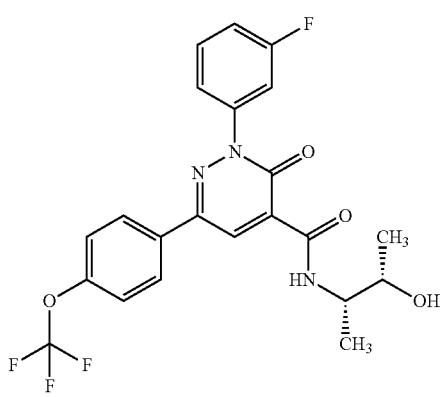 [SMILES: C[C@H](O)[C@H](C)NC(=O)c1cc(-c2ccc(OC(F)(F)F)cc2)nn(-c2cccc(F)c2)c1=O]

A solution of 75 mg intermediate 6-[4-(trifluoromethoxy)phenyl]-2-(3-fluorophenyl)-3-oxo-2,3-dihydropyridazine-4-carboxylic acid, 31.1 mg (2S,3S)-3-aminobutan-2-ol hydrochloride (1:1), 130.2 mg HATU, 0.09 mL ethyldiisopropylamine and 1 mg 4-dimethylaminopyridine in 1.5 mL of DMF was stirred at room temperature for 3 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 60%/B 40%→A 20%/B 80%; flow: 150 mL/min; UV-detection: 254 nm) to yield 47 mg 2-(3-fluorophenyl)-N-[(2S,3S)-3-hydroxybutan-2-yl]-3-oxo-6-[4-(trifluoromethoxy)phenyl]-2,3-dihydropyridazine-4-carboxamide.

$^1$H NMR (400 MHz, DMSO-$d_6$) δ ppm=1.04 (d, 3H), 1.15 (d, 3H), 3.66-3.75 (m, 1H), 3.89-3.98 (m, 1H), 4.95 (d, 1H), 7.35-7.42 (m, 1H), 7.51 (d, 2H), 7.54-7.58 (m, 1H), 7.58-7.66 (m, 2H), 8.07-8.13 (m, 2H), 8.67 (s, 1H), 9.46 (d, 1H).

Example 186

6-(4-Chlorophenyl)-2-(3-fluorophenyl)-N-(1-hydroxy-2-methylpropan-2-yl)-3-oxo-2,3-dihydropyridazine-4-carboxamide

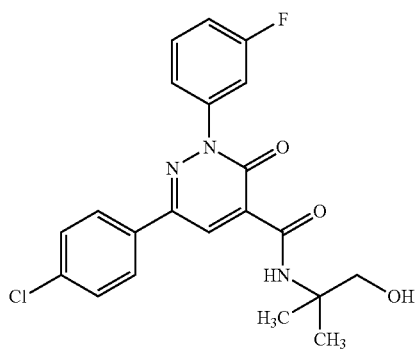 [SMILES: CC(C)(CO)NC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). 2-Amino-2-methylpropan-1-ol (103 mg, 1.16 mmol), N-ethyl-N-isopropylpropan-2-amine (0.455 mL, 2.61 mmol), and propane phosphonic acid anhydride (T3P, 508 µL, 50% in DMF, 870 µmol) were successively added. It was stirred at rt overnight.

Water and dichloromethane were added. Some insoluble particles were filtered off. The layers were separated, and the aqueous layer was extracted twice with dichloromethane. The combined organic phases were concentrated, dissolved in DMSO and purified by RP-HPLC (column: X-Bridge C18 5 µm 100×30 mm, mobile phase: (water+0.2 vol % aqueous ammonia (32%))/acetonitrile, gradient) to yield 107 mg (44%) of the title compound.

$^1$H-NMR (400 MHz, DMSO-$d_6$): δ [ppm]=1.33 (s, 6H), 3.41-3.48 (m, 2H), 5.02-5.08 (m, 1H), 7.34-7.42 (m, 1H), 7.51-7.65 (m, 5H), 7.96-8.02 (m, 2H), 8.65 (s, 1H), 9.52 (s, 1H).

Example 187

6-(4-Chlorophenyl)-2-(3-fluorophenyl)-N-[1-(hydroxymethyl)cyclopropyl]-3-oxo-2,3-dihydropyridazine-4-carboxamide

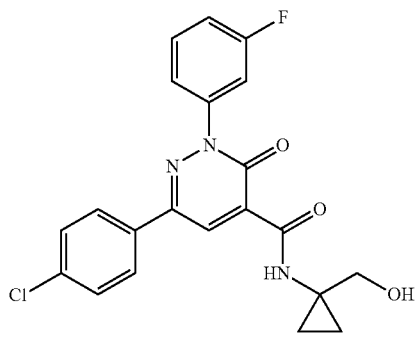 [SMILES: O=C(NC1(CO)CC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). (1-Aminocyclopropyl)methanol (101 mg, 1.16 mmol), N-ethyl-N-isopropylpropan-2-amine (0.455 mL, 2.61 mmol), and propane phosphonic acid anhydride (T3P, 508 µL, 50% in DMF, 870 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 114 mg (48%) of the title compound.

$^1$H-NMR (400 MHz, DMSO-d$_6$): δ [ppm]=0.72-0.78 (m, 2H), 0.78-0.84 (m, 2H), 3.52 (d, 2H), 4.81 (t, 1H), 7.35-7.42 (m, 1H), 7.51-7.65 (m, 5H), 7.96-8.02 (m, 2H), 8.63 (s, 1H), 9.56 (s, 1H).

Example 188

6-(4-Chlorophenyl)-2-(3-fluorophenyl)-N-(2-hydroxy-2-methylpropyl)-3-oxo-2,3-dihydropyridazine-4-carboxamide

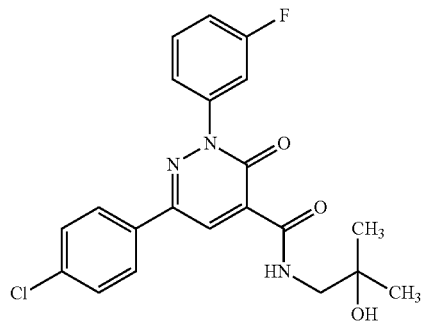 [SMILES: CC(C)(O)CNC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (90 mg, 0.26 mmol) was dissolved in anhydrous DMF (1.5 mL). 1-Amino-2-methylpropan-2-ol (46.5 mg, 0.52 mmol), N-ethyl-N-isopropylpropan-2-amine (0.205 mL, 1.18 mmol), and propane phosphonic acid anhydride (T3P, 229 µL, 50% in DMF, 392 µmol) were successively added. It was stirred at rt overnight.

The crude reaction mixture was concentrated and dissolved in DMSO. The insoluble material was filtered off and discarded. The filtrate was purified by RP-HPLC (column: X-Bridge C18 5 µm 100×30 mm, mobile phase: (water+0.2 vol % aqueous ammonia (32%))/acetonitrile, gradient) to yield 55 mg (51%) of the title compound.

$^1$H-NMR (400 MHz, DMSO-d$_6$): δ [ppm]=1.13 (s, 6H), 3.31 (d, 2H), 4.67 (s, 1H), 7.35-7.42 (m, 1H), 7.54-7.66 (m, 5H), 7.97-8.03 (m, 2H), 8.66 (s, 1H), 9.55 (t, 1H).

Example 189

6-(4-Chlorophenyl)-2-(3-fluorophenyl)-N-(3-hydroxypropyl)-3-oxo-2,3-dihydropyridazine-4-carboxamide

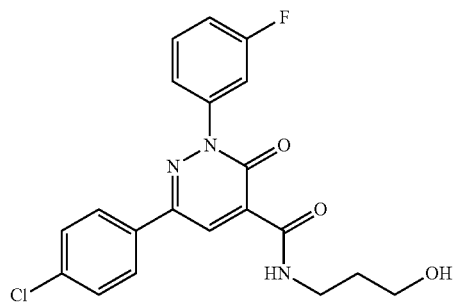 [SMILES: O=C(NCCCO)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (1.5 mL). 3-Aminopropan-1-ol (43.6 mg, 0.58 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight. 3-Aminopropan-1-ol (43.6 mg, 0.58 mmol) were added and it was stirred at rt for 2 h.

The crude reaction mixture was concentrated and dissolved in DMSO. It was purified by RP-HPLC (column: X-Bridge C18 5 µm 100×30 mm, mobile phase: (water+0.2 vol % aqueous ammonia (32%))/methanol, gradient) to yield 62.5 mg (54%) of the title compound.

$^1$H-NMR (400 MHz, DMSO-d$_6$): δ [ppm]=1.68 (quin, 2H), 3.42 (q, 2H), 3.48 (q, 2H), 4.57 (t, 1H), 7.35-7.41 (m, 1H), 7.53-7.66 (m, 5H), 7.96-8.02 (m, 2H), 8.63 (s, 1H), 9.40 (t, 1H).

Example 190

6-(4-Chlorophenyl)-N-[(2RS)-2-cyclopropyl-2-hydroxyethyl]-2-(3-fluorophenyl)-3-oxo-2,3-dihydropyridazine-4-carboxamide

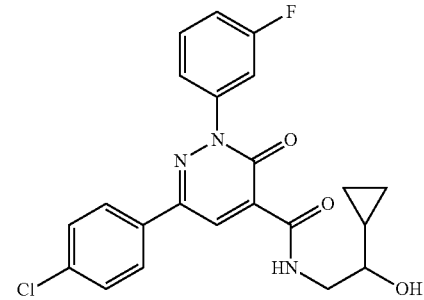 [SMILES: O=C(NCC(O)C1CC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). 2-amino-(1RS)-1-cyclopropylethanol (70 mg, 0.70 mmol), N-ethyl-N-isopropylpropan-2-amine (0.455 mL, 2.61 mmol), and propane phosphonic acid anhydride (T3P, 508 µL, 50% in DMF, 870 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 115 mg (46%) of the title compound.

$^1$H-NMR (400 MHz, DMSO-d$_6$): δ [ppm]=0.17-0.33 (m, 2H), 0.34-0.44 (m, 2H), 0.80-0.89 (m, 1H), 3.00-3.08 (m, 1H), 3.27-3.36 (m, 1H and water signal), 3.53-3.61 (m, 1H), 4.98 (d, 1H), 7.35-7.42 (m, 1H), 7.53-7.66 (m, 5H), 7.97-8.03 (m, 2H), 8.66 (s, 1H), 9.57 (t, 1H).

Example 191

(−)-6-(4-Chlorophenyl)-N-(2-cyclopropyl-2-hydroxyethyl)-2-(3-fluorophenyl)-3-oxo-2,3-dihydropyridazine-4-carboxamide

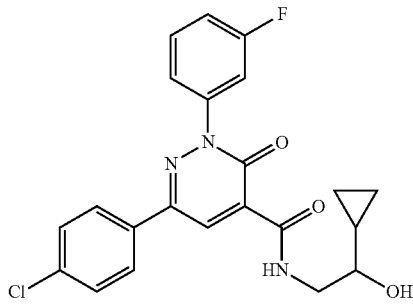 [SMILES: O=C(NCC(O)C1CC1)c1cc(-c2ccc(Cl)cc2)nn(-c2cccc(F)c2)c1=O]

6-(4-Chlorophenyl)-N-[(2RS)-2-cyclopropyl-2-hydroxyethyl]-2-(3-fluorophenyl)-3-oxo-2,3-dihydropyridazine-4-carboxamide was separated by chiral HPLC (column: Chiralpak IA 5μ 250×30 mm, mobile phase: gradient of (acetonitril+0.1 vol % diethylamine (99%))/isopropanol, 40 mL/min, UV: 280 nm) to yield the title product which was further purified by RP-HPLC (column: X-Bridge C18 5 μm 100×30 mm, mobile phase: (water+0.1 vol % formic acid (99%))/acetonitrile, gradient) to yield 33 mg (13%) of the title compound.

$^1$H-NMR (400 MHz, DMSO-d$_6$): δ [ppm]=0.16-0.33 (m, 2H), 0.34-0.44 (m, 2H), 0.79-0.90 (m, 1H), 3.00-3.08 (m, 1H), 3.27-3.36 (m, 1H and water signal), 3.53-3.61 (m, 1H), 4.98 (d, 1H), 7.35-7.41 (m, 1H), 7.54-7.65 (m, 5H), 7.97-8.03 (m, 2H), 8.66 (s, 1H), 9.57 (t, 1H).

Chiral HPLC: Rt=5.41 min

Instrument: Agilent HPLC 1260: Chiralpak IA 3μ 100×4.6 mm; eluent: (A: hexanes+0.1 vol % diethylamine (99%))/B: isopropanol, gradient: 20-50% B in 7 min, flow: 1.4 mL/min, temperature: 25° C., UV: 280 nm.

$[α]_D^{20}$=−10.1° (c=1.00, methanol).

Example 192

(+)-6-(4-Chlorophenyl)-N-(2-cyclopropyl-2-hydroxyethyl)-2-(3-fluorophenyl)-3-oxo-2,3-dihydropyridazine-4-carboxamide

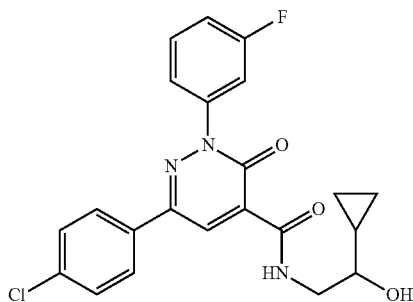 [SMILES: O=C(NCC(O)C1CC1)c1cc(-c2ccc(Cl)cc2)nn(-c2cccc(F)c2)c1=O]

6-(4-Chlorophenyl)-N-[(2RS)-2-cyclopropyl-2-hydroxyethyl]-2-(3-fluorophenyl)-3-oxo-2,3-dihydropyridazine-4-carboxamide was separated by chiral HPLC (column: Chiralpak IA 5μ 250×30 mm, mobile phase: gradient of (acetonitril+0.1 vol % diethylamine (99%))/isopropanol, 40 mL/min, UV: 280 nm) to yield the title product which was further purified by RP-HPLC (column: X-Bridge C18 5 μm 100×30 mm, mobile phase: (water+0.1 vol % formic acid (99%))/acetonitrile, gradient) to yield 27 mg (11%) of the title compound.

$^1$H-NMR (400 MHz, DMSO-d$_6$): δ [ppm]=0.17-0.33 (m, 2H), 0.34-0.44 (m, 2H), 0.80-0.90 (m, 1H), 3.00-3.07 (m, 1H), 3.27-3.35 (m, 1H and water signal), 3.53-3.61 (m, 1H), 4.98 (d, 1H), 7.35-7.42 (m, 1H), 7.53-7.66 (m, 5H), 7.96-8.02 (m, 2H), 8.66 (s, 1H), 9.57 (t, 1H).

Chiral HPLC: Rt=7.81 min

Instrument: Agilent HPLC 1260: Chiralpak IA 3μ 100×4.6 mm; eluent: (A: hexanes+0.1 vol % diethylamine (99%))/B: isopropanol, gradient: 20-50% B in 7 min, flow: 1.4 mL/min, temperature: 25° C., UV: 280 nm.

$[α]_D^{20}$=+12.4° (c=1.00, methanol).

Example 193

6-(4-Chlorophenyl)-N-[(1RS)-1-cyclopropyl-2-hydroxyethyl]-2-(3-fluorophenyl)-3-oxo-2,3-dihydropyridazine-4-carboxamide

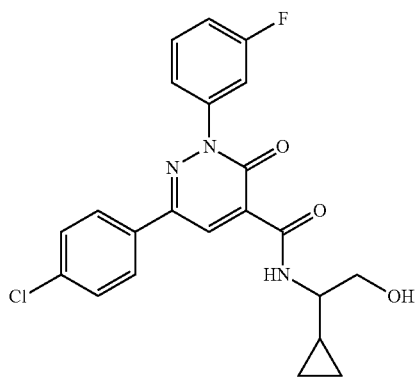 [SMILES: O=C(NC(CO)C1CC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). 2-Amino-(2RS)-2-cyclopropylethanol hydrochloride (1:1) (96 mg, 0.70 mmol), N-ethyl-N-isopropylpropan-2-amine (0.576 mL, 3.31 mmol), and propane phosphonic acid anhydride (T3P, 508 μL, 50% in DMF, 870 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to give 120 mg (48%) of the title compound.

$^1$H-NMR (400 MHz, DMSO-d$_6$): δ [ppm]=0.25-0.50 (m, 4H), 1.02-1.13 (m, 1H), 3.40-3.48 (m, 1H), 3.52-3.62 (m, 2H), 4.92 (t, 1H), 7.36-7.42 (m, 1H), 7.53-7.67 (m, 5H), 7.97-8.03 (m, 2H), 8.66 (s, 1H), 9.56 (d, 1H).

Example 194

(−)-6-(4-Chlorophenyl)-N-(1-cyclopropyl-2-hydroxyethyl)-2-(3-fluorophenyl)-3-oxo-2,3-dihydropyridazine-4-carboxamide

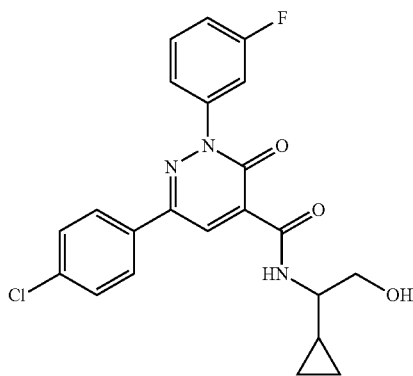 [SMILES: O=C(NC(CO)C1CC1)c1cc(-c2ccc(Cl)cc2)nn(-c2cccc(F)c2)c1=O]

6-(4-Chlorophenyl)-N-[(1RS)-1-cyclopropyl-2-hydroxyethyl]-2-(3-fluorophenyl)-3-oxo-2,3-dihydropyridazine-4-carboxamide was separated by chiral HPLC (column: Chiralpak IB 5µ 250×30 mm, mobile phase: isocratic (1:1) of (acetonitril+0.1 vol % diethylamine (99%))/isopropanol, 40 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to obtain 44.6 mg (18%) of the title compound.

$^1$H-NMR (400 MHz, DMSO-$d_6$): δ [ppm]=0.25-0.50 (m, 4H), 1.02-1.12 (m, 1H), 3.39-3.48 (m, 1H), 3.51-3.62 (m, 2H), 4.92 (t, 1H), 7.36-7.42 (m, 1H), 7.53-7.66 (m, 5H), 7.97-8.03 (m, 2H), 8.66 (s, 1H), 9.56 (d, 1H).

Chiral HPLC: Rt=1.64 min

Instrument: Agilent HPLC 1260: Chiralpak IB 3µ 100×4.6 mm; eluent: (A: acetonitril+0.1 vol % diethylamine (99%))/B: methanol, A:B=1:1, flow: 1.4 mL/min, temperature: 25° C., UV: 254 nm.

$[α]_D^{20}$=−30.5° (c=1.00, methanol).

Example 195

(+)-6-(4-Chlorophenyl)-N-(1-cyclopropyl-2-hydroxyethyl)-2-(3-fluorophenyl)-3-oxo-2,3-dihydropyridazine-4-carboxamide

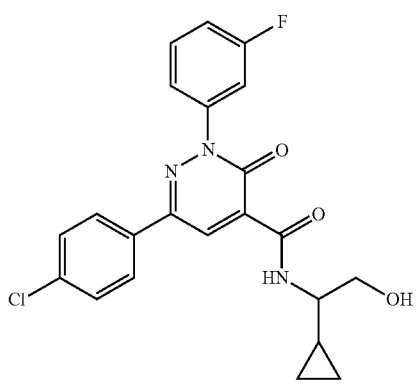 [SMILES: O=C(NC(CO)C1CC1)c1cc(-c2ccc(Cl)cc2)nn(-c2cccc(F)c2)c1=O]

6-(4-Chlorophenyl)-N-[(1RS)-1-cyclopropyl-2-hydroxyethyl]-2-(3-fluorophenyl)-3-oxo-2,3-dihydropyridazine-4-carboxamide was separated by chiral HPLC (column: Chiralpak IB 5β 250×30 mm, mobile phase: isocratic (1:1) of (acetonitril+0.1 vol % diethylamine (99%))/isopropanol, 40 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to obtain 36.1 mg (15%) of the title compound.

$^1$H-NMR (400 MHz, DMSO-$d_6$): δ [ppm]=0.25-0.50 (m, 4H), 1.02-1.13 (m, 1H), 3.40-3.48 (m, 1H), 3.51-3.62 (m, 2H), 4.92 (t, 1H), 7.35-7.42 (m, 1H), 7.53-7.66 (m, 5H), 7.97-8.03 (m, 2H), 8.66 (s, 1H), 9.56 (d, 1H).

Chiral HPLC: Rt=2.98 min

Instrument: Agilent HPLC 1260: Chiralpak IB 3⊖ 100×4.6 mm; eluent: (A: acetonitril+0.1 vol % diethylamine (99%))/B: methanol, A:B=1:1, flow: 1.4 mL/min, temperature: 25° C., UV: 254 nm.

$[α]_D^{20}$=+28.0° (c=1.00, methanol).

Example 196

6-(4-Chlorophenyl)-2-(3-fluorophenyl)-N-[(1-hydroxycyclopropyl)methyl]-3-oxo-2,3-dihydropyridazine-4-carboxamide

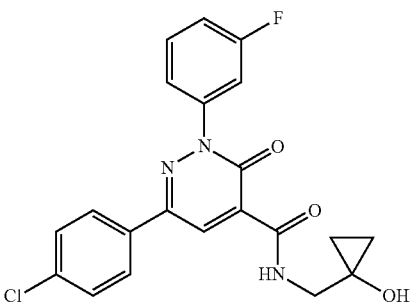 [SMILES: O=C(NCC1(O)CC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). 1-(Aminomethyl)cyclopropanol (76 mg, 0.87 mmol), N-ethyl-N-isopropylpropan-2-amine (0.455 mL, 2.61 mmol), and propane phosphonic acid anhydride (T3P, 508 µL, 50% in DMF, 870 µmol) were successively added. After 2 h 1-(Aminomethyl)cyclopropanol (35 mg, 0.41 mmol) were added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to afford 108 mg (45%) of the title compound.

$^1$H-NMR (400 MHz, DMSO-$d_6$): δ [ppm]=0.51-0.57 (m, 2H), 0.58-0.64 (m, 2H), 3.46 (d, 2H), 5.51 (s, 1H), 7.35-7.42 (m, 1H), 7.53-7.67 (m, 5H), 7.97-8.04 (m, 2H), 8.66 (s, 1H), 9.62 (t, 1H).

Example 197

6-(4-Chlorophenyl)-2-(3-fluorophenyl)-3-oxo-N-[(2RS, 3RS)-1,1,1-trifluoro-3-hydroxybutan-2-yl]-2,3-dihydropyridazine-4-carboxamide and 6-(4-Chlorophenyl)-2-(3-fluorophenyl)-3-oxo-N-[(2RS, 3SR)-1,1,1-trifluoro-3-hydroxybutan-2-yl]-2,3-dihydropyridazine-4-carboxamide

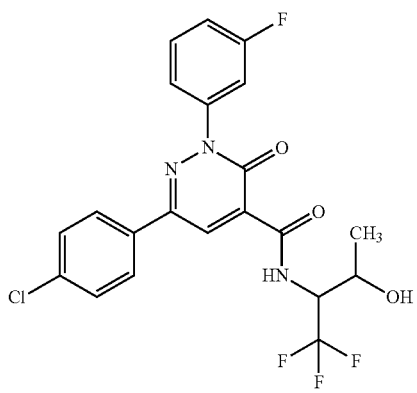 [SMILES: CC(O)C(NC(=O)c1cc(-c2ccc(Cl)cc2)nn(-c2cccc(F)c2)c1=O)C(F)(F)F]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). (2RS,3RS)-3-amino-4,4,4-trifluorobutan-2-ol hydrochloride (1:1) (125 mg, 0.70 mmol), N-ethyl-N-isopropylpropan-2-amine (0.576 mL, 3.31 mmol), and propane phosphonic acid anhydride (T3P, 508 µL, 50% in DMF, 870 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 125 mg (46%) of the title compound.

$^1$H-NMR (400 MHz, DMSO-d$_6$): δ [ppm]=1.21 (d, 3H), 4.00-4.09 (m, 1H), 4.71-4.83 (m, 1H), 5.35 (d, 1H), 7.36-7.43 (m, 1H), 7.54-7.67 (m, 5H), 7.99-8.04 (m, 2H), 8.71 (s, 1H), 9.94 (d, 1H).

Example 198

Isomer no. 1 of 6-(4-chlorophenyl)-2-(3-fluorophenyl)-3-oxo-N-(1,1,1-trifluoro-3-hydroxybutan-2-yl)-2,3-dihydropyridazine-4-carboxamide

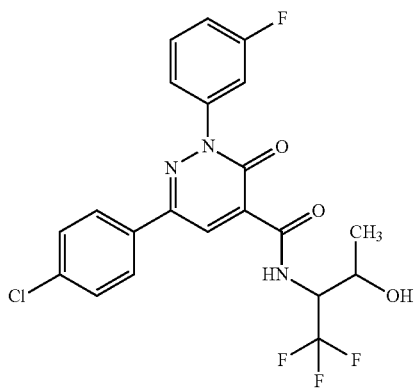 [SMILES: CC(O)C(NC(=O)c1cc(-c2ccc(Cl)cc2)nn(-c2cccc(F)c2)c1=O)C(F)(F)F]

6-(4-Chlorophenyl)-2-(3-fluorophenyl)-3-oxo-N-[(2RS, 3RS)-1,1,1-trifluoro-3-hydroxybutan-2-yl]-2,3-dihydropyridazine-4-carboxamide or 6-(4-chlorophenyl)-2-(3-fluorophenyl)-3-oxo-N-[(2 RS, 3SR)-1,1,1-trifluoro-3-hydroxybutan-2-yl]-2,3-dihydropyridazine-4-carboxamide were separated by chiral HPLC (column: Chiralpak IC 5µ 250×30 mm, mobile phase: A: hexane/B: ethanol, gradient: 20-50% B in 20 min, 40 mL/min, UV: 254 nm) to yield the title compound which was dissolved in dichloromethane. The solvent was removed on a rotavap affording and 52 mg (19%) of the title compound.

$^1$H-NMR (400 MHz, DMSO-d$_6$): δ [ppm]=1.21 (d, 3H), 3.99-4.09 (m, 1H), 4.71-4.83 (m, 1H), 5.35 (d, 1H), 7.36-7.44 (m, 1H), 7.54-7.67 (m, 5H), 7.98-8.05 (m, 2H), 8.71 (s, 1H), 9.94 (d, 1H).

Chiral HPLC: Rt=2.54 min

Instrument: Agilent HPLC 1260: Chiralpak IC 3µ 100× 4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=+27.7° (c=1.00, methanol).

Example 199

Isomer no. 2 of 6-(4-chlorophenyl)-2-(3-fluorophenyl)-3-oxo-N-(1,1,1-trifluoro-3-hydroxybutan-2-yl)-2,3-dihydropyridazine-4-carboxamide

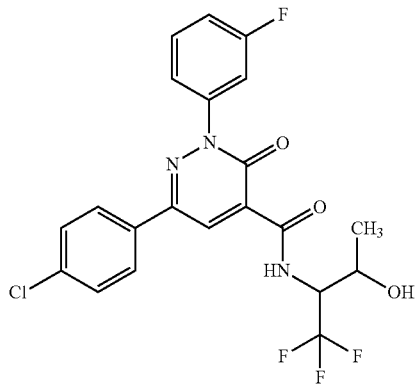 [SMILES: CC(O)C(NC(=O)c1cc(-c2ccc(Cl)cc2)nn(-c2cccc(F)c2)c1=O)C(F)(F)F]

6-(4-Chlorophenyl)-2-(3-fluorophenyl)-3-oxo-N-[(2RS, 3RS)-1,1,1-trifluoro-3-hydroxybutan-2-yl]-2,3-dihydropyridazine-4-carboxamide or 6-(4-chlorophenyl)-2-(3-fluorophenyl)-3-oxo-N-[(2RS, 3SR)-1,1,1-trifluoro-3-hydroxybutan-2-yl]-2,3-dihydropyridazine-4-carboxamide were separated by chiral HPLC (column: Chiralpak IC 5µ 250×30 mm, mobile phase: A: hexane/B: ethanol, gradient: 20-50% B in 20 min, 40 mL/min, UV: 254 nm) to yield the title compound. The product was dried under vacuum at 50° C. overnight affording 52 mg (19%) of the title compound.

$^1$H-NMR (400 MHz, DMSO-d$_6$): δ [ppm]=1.21 (d, 3H), 3.99-4.09 (m, 1H), 4.71-4.83 (m, 1H), 5.35 (d, 1H), 7.36-7.43 (m, 1H), 7.55-7.67 (m, 5H), 7.99-8.05 (m, 2H), 8.71 (s, 1H), 9.94 (d, 1H).

Chiral HPLC: Rt=3.83 min

Instrument: Agilent HPLC 1260: Chiralpak IC 3β 100× 4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=−31.7° (c=1.00, methanol).

Example 200

6-(4-Chlorophenyl)-2-(3-fluorophenyl)-N-[(2RS)-3-hydroxy-2-methylpropyl]-3-oxo-2,3-dihydropyridazine-4-carboxamide

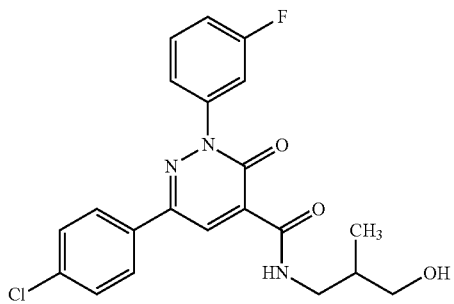 [SMILES: CC(CO)CNC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (70 mg, 0.20 mmol) was dissolved in anhydrous DMF (1.5 mL). (2RS)-3-Amino-2-methylpropan-1-ol (36.2 mg, 0.41 mmol), N-ethyl-N-isopropylpropan-2-amine (0.159 mL, 0.91 mmol), and propane phosphonic acid anhydride (T3P, 178 µL, 50% in DMF, 305 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 40 mg (47%) of the title compound.

$^1$H-NMR (400 MHz, DMSO-$d_6$): δ [ppm]=0.87 (d, 3H), 1.74-1.86 (m, 1H), 3.22-3.42 (m, 4H and water signal), 4.62 (t, 1H), 7.35-7.42 (m, 1H), 7.53-7.66 (m, 5H), 7.97-8.02 (m, 2H), 8.63 (s, 1H), 9.44 (t, 1H).

Example 201

(+)-6-(4-Chlorophenyl)-2-(3-fluorophenyl)-N-(3-hydroxy-2-methylpropyl)-3-oxo-2,3-dihydropyridazine-4-carboxamide

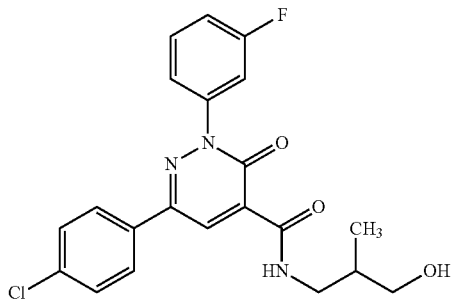 [SMILES: CC(CO)CNC(=O)c1cc(-c2ccc(Cl)cc2)nn(-c2cccc(F)c2)c1=O]

6-(4-Chlorophenyl)-2-(3-fluorophenyl)-N-[(2RS)-3-hydroxy-2-methylpropyl]-3-oxo-2,3-dihydropyridazine-4-carboxamide was separated by chiral HPLC (column: Chiralpak IA 5µ 250×30 mm, mobile phase: isocratic (1:1) of (methanol+0.1 vol % diethylamine (99%))/ethanol, 30 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to yield 6 mg (7%) of the title compound.

$^1$H-NMR (400 MHz, DMSO-$d_6$): δ [ppm]=0.87 (d, 3H), 1.74-1.86 (m, 1H), 3.22-3.41 (m, 4H and water signal), 4.62 (t, 1H), 7.35-7.42 (m, 1H), 7.53-7.66 (m, 5H), 7.96-8.02 (m, 2H), 8.63 (s, 1H), 9.44 (t, 1H).

Chiral HPLC: Rt=4.17 min

Instrument: Agilent HPLC 1260: Chiralpak IA 3µ 100×4.6 mm; eluent: A: (methanol+0.1 vol % diethylamine (99%))/B: ethanol, isocratic: 50% A-50% B, flow: 1.4 mL/min, temperature: 25° C., UV: 254 nm.

$[α]_D^{20}$=+7.0° (c=1.00, methanol).

Example 202

(−)-6-(4-Chlorophenyl)-2-(3-fluorophenyl)-N-(3-hydroxy-2-methylpropyl)-3-oxo-2,3-dihydropyridazine-4-carboxamide

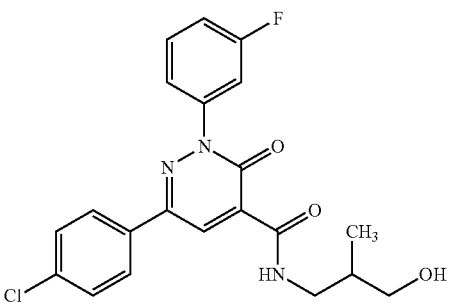 [SMILES: CC(CO)CNC(=O)c1cc(-c2ccc(Cl)cc2)nn(-c2cccc(F)c2)c1=O]

6-(4-Chlorophenyl)-2-(3-fluorophenyl)-N-[(2 RS)-3-hydroxy-2-methylpropyl]-3-oxo-2,3-dihydropyridazine-4-carboxamide was separated by chiral HPLC (column: Chiralpak IA 5µ 250×30 mm, mobile phase: isocratic (1:1) of (methanol+0.1 vol % diethylamine (99%))/ethanol, 30 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to yield 6 mg (7%) of the title compound.

$^1$H-NMR (400 MHz, DMSO-$d_6$): δ [ppm]=0.87 (d, 3H), 1.74-1.87 (m, 1H), 3.22-3.42 (m, 4H and water signal), 4.62 (t, 1H), 7.34-7.42 (m, 1H), 7.53-7.66 (m, 5H), 7.97-8.03 (m, 2H), 8.63 (s, 1H), 9.44 (t, 1H).

Chiral HPLC: Rt=5.20 min

Instrument: Agilent HPLC 1260: Chiralpak IA 3β 100×4.6 mm; eluent: A: (methanol+0.1 vol % diethylamine (99%))/B: ethanol, isocratic: 50% A-50% B, flow: 1.4 mL/min, temperature: 25° C., UV: 254 nm.

$[α]_D^{20}$=−0.7° (c=1.00, methanol).

Example 203

6-(4-Chlorophenyl)-2-(3-fluorophenyl)-N-[(3RS)-3-hydroxybutyl]-3-oxo-2,3-dihydropyridazine-4-carboxamide

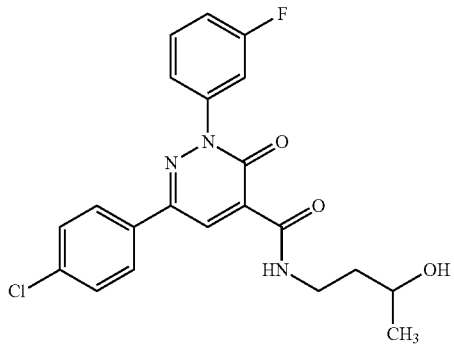 [SMILES: CC(O)CCNC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (70 mg, 0.20 mmol) was dissolved in anhydrous DMF (1.5 mL). (2RS)-4-Aminobutan-2-ol (36.2 mg, 0.41 mmol), N-ethyl-N-isopropylpropan-2-amine (0.159 mL, 0.91 mmol), and propane phosphonic acid anhydride (T3P, 178 µL, 50% in DMF, 305 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 41 mg (47%) of the title compound.

$^1$H-NMR (400 MHz, DMSO-$d_6$): δ [ppm]=1.08 (d, 3H), 1.47-1.66 (m, 2H), 3.35-3.49 (m, 2H), 3.63-3.74 (m, 1H), 4.61 (br d, 1H), 7.34-7.42 (m, 1H), 7.53-7.65 (m, 5H), 7.96-8.03 (m, 2H), 8.63 (s, 1H), 9.43 (t, 1H).

Example 204

(−)-6-(4-Chlorophenyl)-2-(3-fluorophenyl)-N-[(3R)-3-hydroxybutyl]-3-oxo-2,3-dihydropyridazine-4-carboxamide

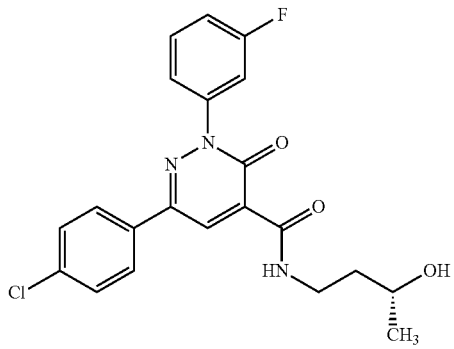 [SMILES: C[C@@H](O)CCNC(=O)c1cc(-c2ccc(Cl)cc2)nn(-c2cccc(F)c2)c1=O]

6-(4-Chlorophenyl)-2-(3-fluorophenyl)-N-[(3RS)-3-hydroxybutyl]-3-oxo-2,3-dihydropyridazine-4-carboxamide was separated by chiral HPLC (column: Chiralpak ID 5µ 250×30 mm, mobile phase: A: (hexane+0.1 vol % diethylamine (99%))/B: ethanol, gradient: 20-50% B in 15 min, 40 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to yield 10 mg (12%) of the title compound.

$^1$H-NMR (400 MHz, DMSO-$d_6$): δ [ppm]=1.08 (d, 3H), 1.48-1.66 (m, 2H), 3.35-3.49 (m, 2H), 3.64-3.74 (m, 1H), 4.61 (d, 1H), 7.35-7.42 (m, 1H), 7.53-7.65 (m, 5H), 7.96-8.02 (m, 2H), 8.63 (s, 1H), 9.43 (t, 1H).

Chiral HPLC: Rt=5.29 min

Instrument: Agilent HPLC 1260: Chiralpak ID 3µ 100×4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=−12.4° (c=1.00, methanol).

Example 205

(+)-6-(4-Chlorophenyl)-2-(3-fluorophenyl)-N-[(3S)-3-hydroxybutyl]-3-oxo-2,3-dihydropyridazine-4-carboxamide

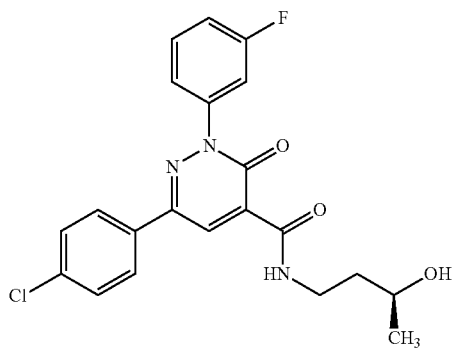 [SMILES: C[C@H](O)CCNC(=O)c1cc(-c2ccc(Cl)cc2)nn(-c2cccc(F)c2)c1=O]

Route A:

6-(4-Chlorophenyl)-2-(3-fluorophenyl)-N-[(3RS)-3-hydroxybutyl]-3-oxo-2,3-dihydropyridazine-4-carboxamide was separated by chiral HPLC (column: Chiralpak ID 5µ 250×30 mm, mobile phase: A: (hexane+0.1 vol % diethylamine (99%))/B: ethanol, gradient: 20-50% B in 15 min, 40 mL/min, UV: 254 nm) to yield the title product which was further purified by RP-HPLC (column: X-Bridge C18 5 µm 100×30 mm, mobile phase: (water+0.1 vol % formic acid (99%))/acetonitrile, gradient) to yield 8.5 mg (10%) of the title compound.

$^1$H-NMR (400 MHz, DMSO-$d_6$): δ [ppm]=1.08 (d, 3H), 1.48-1.66 (m, 2H), 3.35-3.49 (m, 2H), 3.64-3.75 (m, 1H), 4.61 (d, 1H), 7.35-7.41 (m, 1H), 7.53-7.65 (m, 5H), 7.96-8.03 (m, 2H), 8.63 (s, 1H), 9.43 (t, 1H).

Chiral HPLC: Rt=6.02 min

Instrument: Agilent HPLC 1260: Chiralpak ID 3β 100×4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=+16.4° (c=1.00, methanol).

Route B:

6-(4-Chlorophenyl)-2-(3-fluorophenyl)-3-oxo-2,3-dihydropyridazine-4-carboxylic acid (60 mg, 0.17 mmol) was dissolved in anhydrous DMF (1.5 mL). (2S)-4-Aminobutan-2-ol (35 mg, 0.28 mmol), N-ethyl-N-isopropylpropan-2-amine (0.182 mL, 1.04 mmol), and propane phosphonic acid anhydride (T3P, 152 µL, 50% in DMF, 261 µmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 35 mg (48%) of the title compound.

¹H-NMR (400 MHz, DMSO-d₆): δ [ppm]=1.08 (d, 3H), 1.48-1.67 (m, 2H), 3.35-3.49 (m, 2H), 3.64-3.75 (m, 1H), 4.61 (d, 1H), 7.33-7.42 (m, 1H), 7.52-7.66 (m, 5H), 7.96-8.03 (m, 2H), 8.63 (s, 1H), 9.43 (t, 1H).

$[\alpha]_D^{20}$=+13.1° (c=1.00, methanol).

Example 206

6-(4-Chlorophenyl)-2-(3-fluorophenyl)-N-[(2RS)-4-hydroxybutan-2-yl]-3-oxo-2,3-dihydropyridazine-4-carboxamide

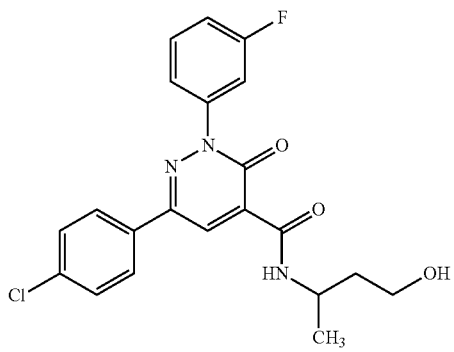 [SMILES: CC(CCO)NC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (70 mg, 0.20 mmol) was dissolved in anhydrous DMF (1.5 mL). (3RS)-3-Aminobutan-1-ol (36.2 mg, 0.41 mmol), N-ethyl-N-isopropylpropan-2-amine (0.159 mL, 0.91 mmol), and propane phosphonic acid anhydride (T3P, 178 μL, 50% in DMF, 305 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 47 mg (56%) of the title compound.

¹H-NMR (400 MHz, DMSO-d₆): δ [ppm]=1.19 (d, 3H), 1.59-1.74 (m, 2H), 3.48 (t, 2H), 4.08-4.20 (m, 1H), 4.50 (br s, 1H), 7.34-7.42 (m, 1H), 7.52-7.66 (m, 5H), 7.96-8.03 (m, 2H), 8.63 (s, 1H), 9.31 (d, 1H).

Example 207

(+)-6-(4-Chlorophenyl)-2-(3-fluorophenyl)-N-(4-hydroxybutan-2-yl)-3-oxo-2,3-dihydropyridazine-4-carboxamide

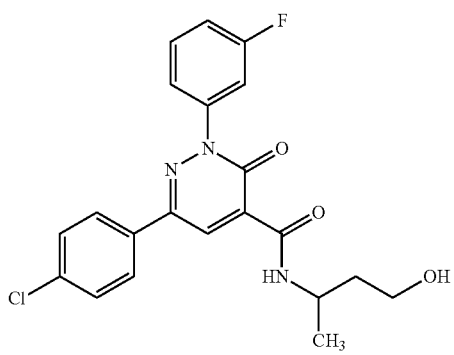 [SMILES: CC(CCO)NC(=O)c1cc(-c2ccc(Cl)cc2)nn(-c2cccc(F)c2)c1=O]

6-(4-Chlorophenyl)-2-(3-fluorophenyl)-N-[(2RS)-4-hydroxybutan-2-yl]-3-oxo-2,3-dihydropyridazine-4-carboxamide was separated by chiral HPLC (column: Chiralpak IA 5μ 250×30 mm, mobile phase: A: (hexane+0.1 vol % diethylamine (99%))/B: isopropanol, gradient: 20-50% B in 7 min, 40 mL/min, UV: 254 nm) to yield the title product which was further purified by RP-HPLC (column: X-Bridge C18 5 μm 100×30 mm, mobile phase: (water+0.1 vol % formic acid (99%))/acetonitrile, gradient) to yield 11.8 mg (14%) of the title compound.

¹H-NMR (400 MHz, DMSO-d₆): δ [ppm]=1.19 (d, 3H), 1.59-1.73 (m, 2H), 3.48 (q, 2H), 4.08-4.20 (m, 1H), 4.50 (t, 1H), 7.35-7.41 (m, 1H), 7.52-7.65 (m, 5H), 7.96-8.03 (m, 2H), 8.63 (s, 1H), 9.31 (d, 1H).

Chiral HPLC: Rt=3.58 min

Instrument: Agilent HPLC 1260: Chiralpak IA 3μ 100×4.6 mm; eluent: A: (hexane+0.1 vol % diethylamine (99%))/B: isopropanol, gradient: 20-50% B in 7 min, flow: 1.4 mL/min, temperature: 25° C., UV: 254 nm.

$[\alpha]_D^{20}$=+34.2° (c=1.00, methanol).

Example 208

(−)-6-(4-Chlorophenyl)-2-(3-fluorophenyl)-N-(4-hydroxybutan-2-yl)-3-oxo-2,3-dihydropyridazine-4-carboxamide

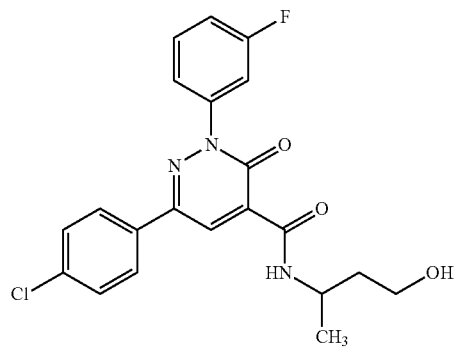 [SMILES: CC(CCO)NC(=O)c1cc(-c2ccc(Cl)cc2)nn(-c2cccc(F)c2)c1=O]

6-(4-Chlorophenyl)-2-(3-fluorophenyl)-N-[(2RS)-4-hydroxybutan-2-yl]-3-oxo-2,3-dihydropyridazine-4-carboxamide was separated by chiral HPLC (column: Chiralpak IA 5μ 250×30 mm, mobile phase: A: (hexane+0.1 vol % diethylamine (99%))/B: isopropanol, gradient: 20-50% B in 7 min, 40 mL/min, UV: 254 nm) to yield the title product which was further purified by RP-HPLC (column: X-Bridge C18 5 μm 100×30 mm, mobile phase: (water+0.1 vol % formic acid (99%))/acetonitrile, gradient) to yield 11.8 mg (14%) of the title compound.

¹H-NMR (400 MHz, DMSO-d₆): δ [ppm]=1.19 (d, 3H), 1.59-1.73 (m, 2H), 3.48 (q 2H), 4.08-4.20 (m, 1H), 4.50 (t, 1H), 7.35-7.41 (m, 1H), 7.53-7.65 (m, 5H), 7.97-8.02 (m, 2H), 8.63 (s, 1H), 9.31 (d, 1H).

Chiral HPLC: Rt=5.32 min

Instrument: Agilent HPLC 1260: Chiralpak IA 3μ 100×4.6 mm; eluent: A: (hexane+0.1 vol % diethylamine (99%))/B: isopropanol, gradient: 20-50% B in 7 min, flow: 1.4 mL/min, temperature: 25° C., UV: 254 nm.

$[\alpha]_D^{20}$=−34.0° (c=1.00, methanol).

Example 209

6-(4-Chlorophenyl)-N-[(1RS)-1-cyclobutyl-2-hydroxyethyl]-2-(3-fluorophenyl)-3-oxo-2,3-dihydropyridazine-4-carboxamide

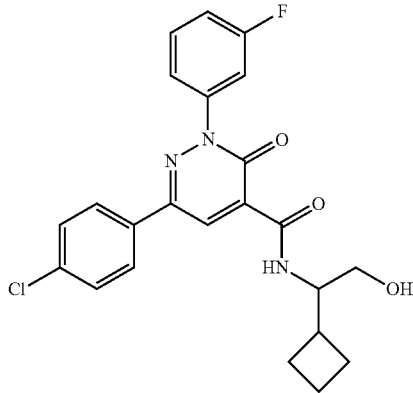 [SMILES: O=C(NC(CO)C1CCC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (120 mg, 0.35 mmol) was dissolved in anhydrous DMF (2.6 mL). (2RS)-2-Amino-2-cyclobutylethanol hydrochloride (1:1) (79 mg, 0.52 mmol), N-ethyl-N-isopropylpropan-2-amine (0.364 mL, 2.09 mmol), and propane phosphonic acid anhydride (T3P, 305 μL, 50% in DMF, 522 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 75 mg (49%) of the title compound.

$^1$H-NMR (400 MHz, DMSO-d$_6$): δ [ppm]=1.68-2.00 (m, 6H), 2.53-2.64 (m, 1H), 3.35-3.45 (m, 2H), 3.97-4.06 (m, 1H), 4.78 (t, 1H), 7.35-7.42 (m, 1H), 7.53-7.66 (m, 5H), 7.97-8.03 (m, 2H), 8.67 (s, 1H), 9.41 (d, 1H).

Example 210

(+)-6-(4-Chlorophenyl)-N-(1-cyclobutyl-2-hydroxyethyl)-2-(3-fluorophenyl)-3-oxo-2,3-dihydropyridazine-4-carboxamide

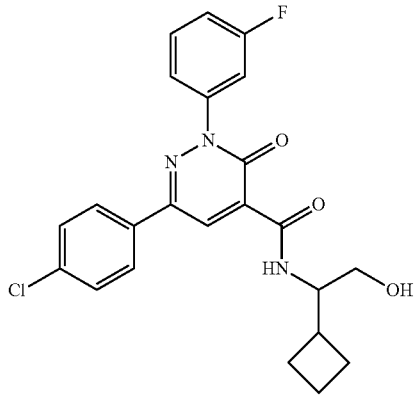 [SMILES: O=C(NC(CO)C1CCC1)c1cc(-c2ccc(Cl)cc2)nn(-c2cccc(F)c2)c1=O]

6-(4-Chlorophenyl)-N-[(1RS)-1-cyclobutyl-2-hydroxyethyl]-2-(3-fluorophenyl)-3-oxo-2,3-dihydropyridazine-4-carboxamide was separated by chiral HPLC (column: Chiralpak IC 5μ 250×30 mm, mobile phase: A: carbon dioxide/B: ethanol, isocratic: 20% B, 100 mL/min, temperature: 40° C., BPR: 150 bar, UV: 254 nm) to yield 28 mg (18%) of the title compound.

$^1$H-NMR (400 MHz, DMSO-d$_6$): δ [ppm]=1.69-2.00 (m, 6H), 2.53-2.64 (m, 1H), 3.35-3.45 (m, 2H), 3.97-4.06 (m, 1H), 4.78 (t, 1H), 7.36-7.42 (m, 1H), 7.53-7.66 (m, 5H), 7.97-8.02 (m, 2H), 8.67 (s, 1H), 9.41 (d, 1H).

Chiral HPLC: Rt=2.62 min

Instrument: Agilent HPLC 1260: Chiralpak IC 5β 100×4.6 mm; eluent: A: carbon dioxide/B: ethanol, isocratic: 20% B, flow: 4 mL/min, temperature: 37.5° C., BPR: 100 bar, MWD: 254 nm.

$[α]_D^{20}$=+37.7° (c=1.00, methanol).

Example 211

(−)-6-(4-Chlorophenyl)-N-(1-cyclobutyl-2-hydroxyethyl)-2-(3-fluorophenyl)-3-oxo-2,3-dihydropyridazine-4-carboxamide

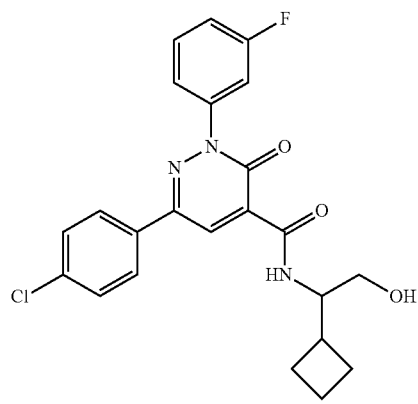 [SMILES: O=C(NC(CO)C1CCC1)c1cc(-c2ccc(Cl)cc2)nn(-c2cccc(F)c2)c1=O]

6-(4-Chlorophenyl)-N-[(1RS)-1-cyclobutyl-2-hydroxyethyl]-2-(3-fluorophenyl)-3-oxo-2,3-dihydropyridazine-4-carboxamide was separated by chiral HPLC (column: Chiralpak IC 5β 250×30 mm, mobile phase: A: carbon dioxide/B: ethanol, isocratic: 20% B, 100 mL/min, temperature: 40° C., BPR: 150 bar, UV: 254 nm) to yield 25 mg (16%) of the title compound.

$^1$H-NMR (400 MHz, DMSO-d$_6$): δ [ppm]=1.73-1.98 (m, 6H), 2.53-2.64 (m, 1H), 3.35-3.46 (m, 2H), 3.98-4.06 (m, 1H), 4.78 (t, 1H), 7.35-7.42 (m, 1H), 7.52-7.66 (m, 5H), 7.97-8.03 (m, 2H), 8.67 (s, 1H), 9.41 (d, 1H).

Chiral HPLC: Rt=4.15 min

Instrument: Agilent HPLC 1260: Chiralpak IC 5μ 100×4.6 mm; eluent: A: carbon dioxide/B: ethanol, isocratic: 20% B, flow: 4 mL/min, temperature: 37.5° C., BPR: 100 bar, MWD: 254 nm.

$[α]_D^{20}$=−32.4° (c=1.00, methanol).

Example 212

6-(4-Chlorophenyl)-2-(3-fluorophenyl)-N-[(1-hydroxycyclobutyl)methyl]-3-oxo-2,3-dihydropyridazine-4-carboxamide

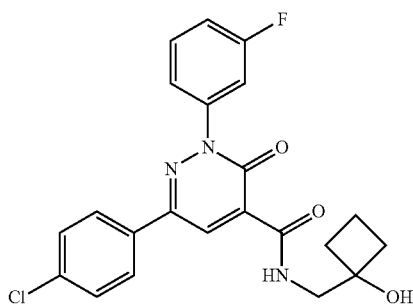

6-(4-Chlorophenyl)-2-(3-fluorophenyl)-3-oxo-2,3-dihydropyridazine-4-carboxylic acid (50 mg, 0.15 mmol) was dissolved in anhydrous DMF (1.5 mL). 1-(Aminomethyl)cyclobutanol (29 mg, 0.29 mmol), N-ethyl-N-isopropylpropan-2-amine (0.114 mL, 0.65 mmol), and propane phosphonic acid anhydride (T3P, 127 µL, 50% in DMF, 218 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 32 mg (52%) of the title compound.

$^1$H-NMR (400 MHz, DMSO-$d_6$): δ [ppm]=1.42-1.55 (m, 1H), 1.58-1.69 (m, 1H), 1.90-2.00 (m, 4H), 3.48 (d, 2H), 5.40 (s, 1H), 7.35-7.42 (m, 1H), 7.52-7.65 (m, 5H), 7.97-8.02 (m, 2H), 8.67 (s, 1H), 9.53 (t, 1H).

Example 213

6-(4-Chlorophenyl)-2-(3-fluorophenyl)-N-[1-(hydroxymethyl)cyclobutyl]-3-oxo-2,3-dihydropyridazine-4-carboxamide

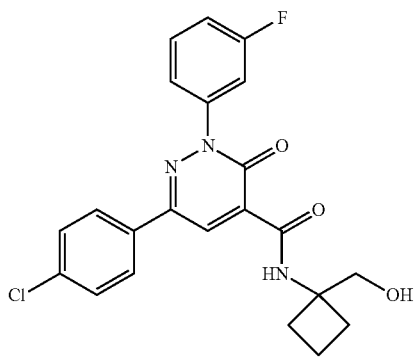 [SMILES: O=C(NC1(CO)CCC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (120 mg, 0.35 mmol) was dissolved in anhydrous DMF (2.57 mL). (1-Aminocyclobutyl)methanol hydrochloride (1:1) (72 mg, 0.52 mmol), N-ethyl-N-isopropylpropan-2-amine (0.364 mL, 2.09 mmol), and propane phosphonic acid anhydride (T3P, 305 µL, 50% in DMF, 522 µmol) were successively added. It was stirred at rt overnight.

The volume of the crude reaction mixture was reduced slightly and afterwards diluted with DMSO to purify the reaction mixture by RP-HPLC (column: X-Bridge C18 5 µm 100×30 mm, mobile phase: (water+0.2 vol % aqueous ammonia (32%))/acetonitrile, gradient) yielding 81 mg (54%) of the title compound.

$^1$H-NMR (400 MHz, DMSO-$d_6$): δ [ppm]=1.68-1.92 (m, 2H), 2.04-2.13 (m, 2H), 2.31-2.43 (m, 2H), 3.62 (d, 2H), 4.99 (t, 1H), 7.35-7.42 (m, 1H), 7.52-7.65 (m, 5H), 7.96-8.02 (m, 2H), 8.65 (s, 1H), 9.53 (s, 1H).

Example 214

6-(4-Chlorophenyl)-2-(3-fluorophenyl)-N-[1-(hydroxymethyl)cyclopentyl]-3-oxo-2,3-dihydropyridazine-4-carboxamide

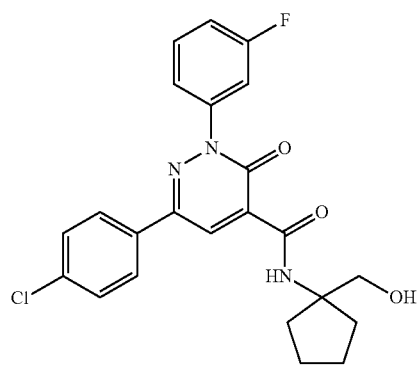 [SMILES: O=C(NC1(CO)CCCC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (120 mg, 0.35 mmol) was dissolved in anhydrous DMF (2.57 mL). (1-Aminocyclopentyl)methanol (60.1 mg, 0.52 mmol), N-ethyl-N-isopropylpropan-2-amine (0.273 mL, 1.57 mmol), and propane phosphonic acid anhydride (T3P, 305 µL, 50% in DMF, 522 µmol) were successively added. It was stirred at rt overnight. (1-Aminocyclopentyl)methanol (40 mg, 0.35 mmol), N-ethyl-N-isopropylpropan-2-amine (0.182 mL, 1.04 mmol), and propane phosphonic acid anhydride (T3P, 203 µL, 50% in DMF, 348 µmol) were successively added. It was stirred at rt overnight.

The volume of the crude reaction mixture was reduced slightly and afterwards diluted with DMSO to purify the reaction mixture by RP-HPLC (column: X-Bridge C18 5 µm 100×30 mm, mobile phase: (water+0.2 vol % aqueous ammonia (32%))/acetonitrile, gradient) yielding 63 mg (41%) of the title compound.

$^1$H-NMR (400 MHz, DMSO-$d_6$): δ [ppm]=1.51-1.64 (m, 2H), 1.67-1.79 (m, 4H), 1.87-1.99 (m, 2H), 3.53 (d, 2H), 4.99 (t, 1H), 7.35-7.42 (m, 1H), 7.51-7.66 (m, 5H), 7.96-8.02 (m, 2H), 8.65 (s, 1H), 9.50 (s, 1H).

Example 215

6-(4-Chlorophenyl)-2-(3-fluorophenyl)-N-[1-(hydroxymethyl)cyclohexyl]-3-oxo-2,3-dihydropyridazine-4-carboxamide

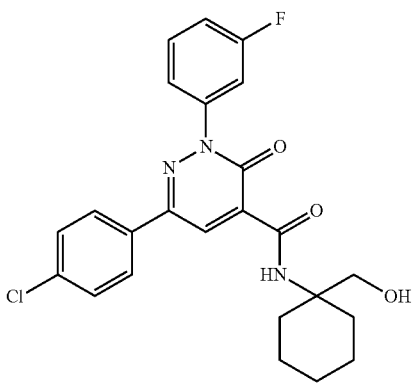 [SMILES: O=C(NC1(CO)CCCCC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (120 mg, 0.35 mmol) was dissolved in anhydrous DMF (2.57 mL). (1-Aminocyclohexyl)methanol (67.5 mg, 0.52 mmol), N-ethyl-N-isopropylpropan-2-amine (0.273 mL, 1.57 mmol), and propane phosphonic acid anhydride (T3P, 305 µL, 50% in DMF, 522 µmol) were successively added. It was stirred at rt overnight.

The volume of the crude reaction mixture was reduced slightly and afterwards diluted with DMSO to purify the reaction mixture by RP-HPLC (column: X-Bridge C18 5 µm 100×30 mm, mobile phase: (water+0.2 vol % aqueous ammonia (32%))/acetonitrile, gradient) yielding 55 mg (35%) of the title compound.

$^1$H-NMR (400 MHz, DMSO-d$_6$): δ [ppm]=1.16-1.28 (m, 1H), 1.33-1.59 (m, 8H), 2.05-2.16 (m, 2H), 3.60 (d, 2H), 4.74 (t, 1H), 7.35-7.43 (m, 1H), 7.53-7.66 (m, 5H), 7.96-8.02 (m, 2H), 8.65 (s, 1H), 9.28 (s, 1H).

Example 216

6-(4-Chlorophenyl)-2-(3-fluorophenyl)-3-oxo-N-[(2RS,3RS)-4,4,4-trifluoro-3-hydroxybutan-2-yl]-2,3-dihydropyridazine-4-carboxamide and 6-(4-Chlorophenyl)-2-(3-fluorophenyl)-3-oxo-N-[(2RS,3SR)-4,4,4-trifluoro-3-hydroxybutan-2-yl]-2,3-dihydropyridazine-4-carboxamide

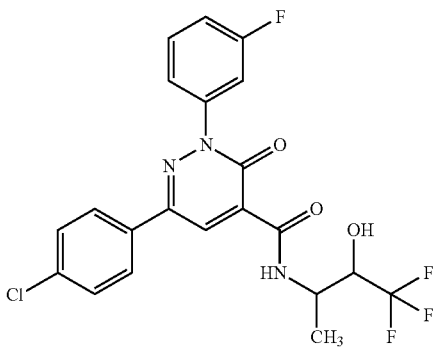 [SMILES: CC(NC(=O)c1cc(-c2ccc(Cl)cc2)nn(-c2cccc(F)c2)c1=O)C(O)C(F)(F)F]

6-(4-Chlorophenyl)-2-(3-fluorophenyl)-3-oxo-2,3-dihydropyridazine-4-carboxylic acid (200 mg, 0.58 mmol) was dissolved in anhydrous DMF (3 mL). (2RS,3RS)-3-Amino-1,1,1-trifluorobutan-2-ol hydrochloride (1:1) (156 mg, 0.87 mmol), N-ethyl-N-isopropylpropan-2-amine (0.606 mL, 3.48 mmol), and propane phosphonic acid anhydride (T3P, 508 µL, 50% in DMF, 870 µmol) were successively added. It was stirred at rt overnight.

The volume of the crude reaction mixture was reduced slightly and afterwards diluted with DMSO to purify the reaction mixture by RP-HPLC (column: X-Bridge C18 5 µm 100×30 mm, mobile phase: (water+0.2 vol % aqueous ammonia (32%))/acetonitrile, gradient) affording 75 mg (28%) of the title compound as 3:1 diastereomeric mixture according to the $^1$H-NMR.

$^1$H-NMR (400 MHz, DMSO-d$_6$): δ [ppm]=1.22 (d, 3H minor), 1.25 (d, 3H, major), 4.09-4.23 (m, 1H, major and minor), 4.30-4.48 (m, 1H, major and minor), 6.71 (br d, 1H, minor), 6.91 (br d, 1H, major), 7.36-7.43 (m, 1H, major and minor), 7.53-7.66 (m, 5H, major and minor), 7.96-8.02 (m, 2H, major and minor), 8.67 (s, 1H, major and minor), 9.61 (d, 1H, minor), 9.74 (d, 1H, major).

Example 217

Isomeric mixture no. 1 of 6-(4-chlorophenyl)-2-(3-fluorophenyl)-3-oxo-N-(4,4,4-trifluoro-3-hydroxybutan-2-yl)-2,3-dihydropyridazine-4-carboxamide

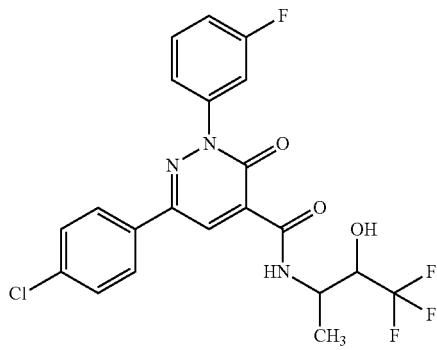 [SMILES: CC(NC(=O)c1cc(-c2ccc(Cl)cc2)nn(-c2cccc(F)c2)c1=O)C(O)C(F)(F)F]

6-(4-Chlorophenyl)-2-(3-fluorophenyl)-3-oxo-N-[(2RS,3RS)-4,4,4-trifluoro-3-hydroxybutan-2-yl]-2,3-dihydropyridazine-4-carboxamide and 6-(4-Chlorophenyl)-2-(3-fluorophenyl)-3-oxo-N-[(2RS,3SR)-4,4,4-trifluoro-3-hydroxybutan-2-yl]-2,3-dihydropyridazine-4-carboxamide were separated by chiral HPLC (column: Chiralpak IB 5µ 250×30 mm, mobile phase: A: hexane/B: isopropanol, gradient: 20-50% B in 20 min, 40 mL/min, UV: 254 nm) to yield 35 mg (13%) of the title compound. The $^1$H-NMR showed two diastereomeric sets of signals in the ratio of 5:6.

$^1$H-NMR (400 MHz, DMSO-d$_6$): δ [ppm]=1.22 (d, 3H, major), 1.25 (d, 3H, minor), 4.09-4.23 (m, 1H, major and minor), 4.30-4.48 (m, 1H, major and minor), 6.72 (br d, 1H, major), 6.92 (br s, 1H, minor), 7.36-7.42 (m, 1H, major and minor), 7.52-7.66 (m, 5H, major and minor), 7.96-8.03 (m, 2H, major and minor), 8.67 (s, 1H, major and minor), 9.61 (d, 1H, major), 9.74 (d, 1H, minor).

Chiral HPLC: Rt=2.73 min

Instrument: Agilent HPLC 1260: Chiralpak IB 3β 100× 4.6 mm; eluent: A: hexane/B: isopropanol, gradient: 20-50% B in 7 min, flow: 1.4 mL/min, temperature: 25° C., UV: 254 nm.

$[\alpha]_D^{20}$=+4.2° (c=1.00, methanol).

Example 218

Stereoisomer no. 1 of 6-(4-chlorophenyl)-2-(3-fluorophenyl)-3-oxo-N-(4,4,4-trifluoro-3-hydroxybutan-2-yl)-2,3-dihydropyridazine-4-carboxamide

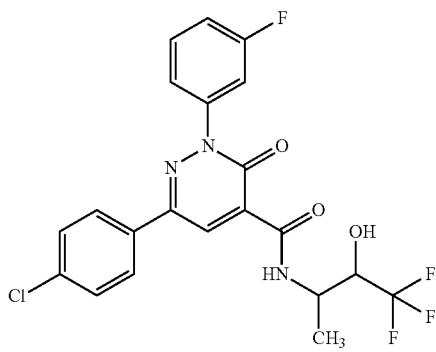 [SMILES: CC(NC(=O)c1cc(-c2ccc(Cl)cc2)nn(-c2cccc(F)c2)c1=O)C(O)C(F)(F)F]

6-(4-Chlorophenyl)-2-(3-fluorophenyl)-3-oxo-N-[(2RS,3RS)-4,4,4-trifluoro-3-hydroxybutan-2-yl]-2,3-dihydropyridazine-4-carboxamide and 6-(4-chlorophenyl)-2-(3-fluorophenyl)-3-oxo-N-[(2RS,3SR)-4,4,4-trifluoro-3-hydroxybutan-2-yl]-2,3-dihydropyridazine-4-carboxamide were separated by chiral HPLC (column: Chiralpak IB 5β 250×30 mm, mobile phase: A: hexane/B: isopropanol, gradient: 20-50% B in 20 min, 40 mL/min, UV: 254 nm) to yield 19 mg (7%) of the title compound.

$^1$H-NMR (400 MHz, DMSO-d$_6$): δ [ppm]=1.22 (d, 3H), 4.12-4.23 (m, 1H), 4.30-4.40 (m, 1H), 6.69-6.74 (m, 1H), 7.36-7.43 (m, 1H), 7.53-7.66 (m, 5H), 7-97-8.03 (m, 2H), 8.67 (s, 1H), 9.61 (d, 1H).

Chiral HPLC: Rt=3.92 min

Instrument: Agilent HPLC 1260: Chiralpak IB 3µ 100× 4.6 mm; eluent: A: hexane/B: isopropanol, gradient: 20-50% B in 7 min, flow: 1.4 mL/min, temperature: 25° C., UV: 254 nm.

$[\alpha]_D^{20}$=−6.0° (c=1.00, methanol).

Example 219

(+)-6-(4-Chlorophenyl)-2-(3-fluorophenyl)-N-[(2R)-1-hydroxy-3-phenylpropan-2-yl]-3-oxo-2,3-dihydropyridazine-4-carboxamide

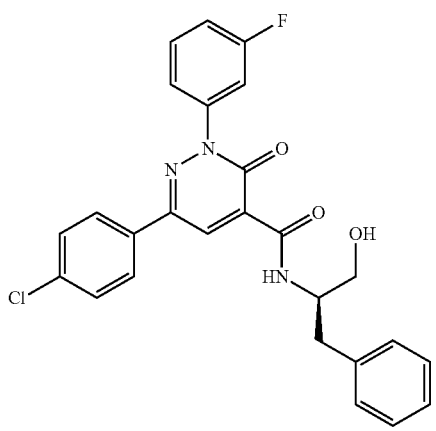 [SMILES: O=C(N[C@@H](CO)Cc1ccccc1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2.1 mL). (2R)-2-Amino-3-phenylpropan-1-ol (65.8 mg, 0.44 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 81 mg (58%) of the title compound.

$^1$H-NMR (400 MHz, DMSO-d$_6$): δ [ppm]=2.82 (dd, 1H), 2.93 (dd, 1H), 3.39-3.50 (m, 2H), 4.15-4.24 (m, 1H), 5.03 (t, 1H), 7.16-7.22 (m, 1H), 7.23-7.31 (m, 4H), 7.36-7.42 (m, 1H), 7.53-7.66 (m, 5H), 7.95-8.01 (m, 2H), 8.62 (s, 1H), 9.53 (d, 1H).

$[\alpha]_D^{°}$=+102.0° (c=1.00, methanol).

Example 220

(−)-6-(4-Chlorophenyl)-2-(3-fluorophenyl)-N-[(2S)-1-hydroxy-3-phenylpropan-2-yl]-3-oxo-2,3-dihydropyridazine-4-carboxamide

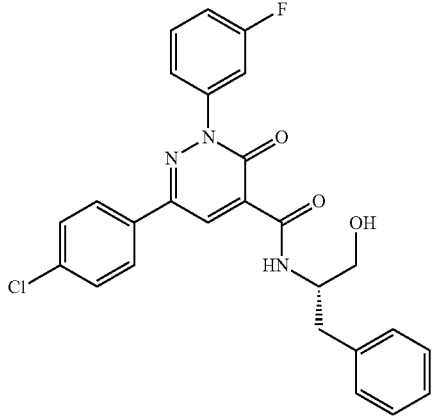 [SMILES: O=C(N[C@H](CO)Cc1ccccc1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2.1 mL). (2S)-2-Amino-3-phenylpropan-1-ol (65.8 mg, 0.44 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 80 mg (58%) of the title compound.

$^1$H-NMR (400 MHz, DMSO-d$_6$): δ [ppm]=2.82 (dd, 1H), 2.93 (dd, 1H), 3.39-3.51 (m, 2H), 4.14-4.24 (m, 1H), 5.03 (t, 1H), 7.16-7.22 (m, 1H), 7.23-7.31 (m, 4H), 7.36-7.43 (m, 1H), 7.58 (d, 5H), 7.95-8.01 (m, 2H), 8.62 (s, 1H), 9.53 (d, 1H).

$[\alpha]_D^{20}$=−101.6° (c=1.00, methanol).

Example 221

6-(4-Chlorophenyl)-N-[(2RS)-3,3-difluoro-2-hydroxypropyl]-2-(3-fluorophenyl)-3-oxo-2,3-dihydropyridazine-4-carboxamide

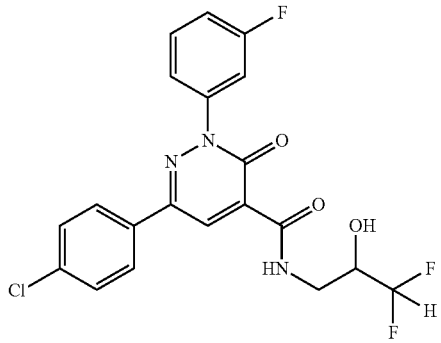

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (2R)-3-Amino-1,1-difluoropropan-2-ol hydrochloride (1:1) (64 mg, 0.44 mmol), N-ethyl-N-isopropylpropan-2-amine (0.303 mL, 1.74 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 70 mg (55%) of the title compound $^1$H-NMR (400 MHz, DMSO-$d_6$): δ [ppm]=3.35-3.43 (m, 1H), 3.61-3.69 (m, 1H), 3.63 (s, 1H), 3.78-3.90 (m, 1H), 5.93 (dt, 1H), 5.99 (d, 1H), 7.35-7.42 (m, 1H), 7.53-7.66 (m, 5H), 7.97-8.03 (m, 2H), 8.66 (s, 1H), 9.57 (t, 1H).

Example 222

(−)-6-(4-Chlorophenyl)-N-(3,3-difluoro-2-hydroxypropyl)-2-(3-fluorophenyl)-3-oxo-2,3-dihydropyridazine-4-carboxamide

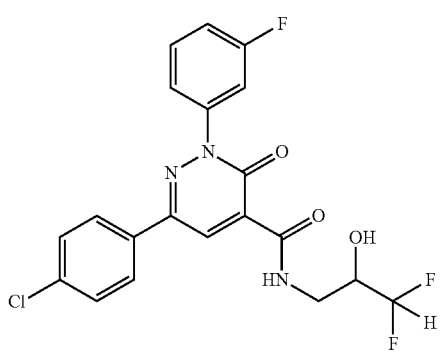 [SMILES: O=C(NCC(O)C(F)F)c1cc(-c2ccc(Cl)cc2)nn(-c2cccc(F)c2)c1=O]

6-(4-Chlorophenyl)-N-[(2RS)-3,3-difluoro-2-hydroxypropyl]-2-(3-fluorophenyl)-3-oxo-2,3-dihydropyridazine-4-carboxamide was separated by chiral HPLC (column: Chiralpak AD 5µ 250×30 mm, mobile phase: A: (hexane+0.1 vol % trifluoroacetic acid (99%))/B: (50 vol % ethanol+50 vol % methanol), gradient: 40-50% B in 20 min and 50% B 20-25 min, 40 mL/min, UV: 280 nm) to yield the title product which was further purified by RP-HPLC (column: X-Bridge C18 5 µm 100×30 mm, mobile phase: (water+0.1 vol % formic acid (99%))/acetonitrile, gradient) to yield 17.7 mg (14%) of the title product.

$^1$H-NMR (400 MHz, DMSO-$d_6$): δ [ppm]=3.35-3.43 (m, 1H), 3.61-3.69 (m, 1H), 3.78-3.91 (m, 1H), 5.93 (dt, 1H), 5.99 (d, 1H), 7.36-7.42 (m, 1H), 7.53-7.66 (m, 5H), 7.98-8.03 (m, 2H), 8.66 (s, 1H), 9.57 (t, 1H).

Chiral HPLC: Rt=7.17 min

Instrument: Agilent HPLC 1260: Chiralpak AD 3µ 100×4.6 mm; eluent: A: (hexane+0.1 vol % trifluoroacetic acid (99%))/B: (50 vol % ethanol+50 vol % methanol), gradient: 40-50% B in 7 min, flow: 1.4 mL/min, temperature: 25° C., UV: 280 nm.

$[α]_D^{20}$=−10.8° (c=1.00, methanol).

Example 223

(+)-6-(4-Chlorophenyl)-N-(3,3-difluoro-2-hydroxypropyl)-2-(3-fluorophenyl)-3-oxo-2,3-dihydropyridazine-4-carboxamide

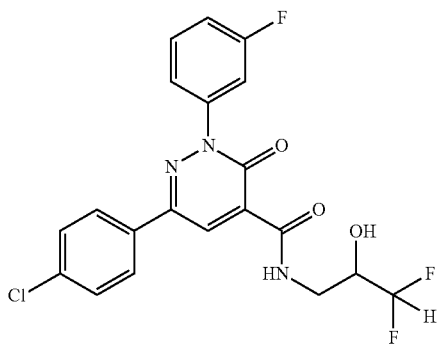 [SMILES: O=C(NCC(O)C(F)F)c1cc(-c2ccc(Cl)cc2)nn(-c2cccc(F)c2)c1=O]

6-(4-Chlorophenyl)-N-[(2RS)-3,3-difluoro-2-hydroxypropyl]-2-(3-fluorophenyl)-3-oxo-2,3-dihydropyridazine-4-carboxamide was separated by chiral HPLC (column: Chiralpak AD 5µ 250×30 mm, mobile phase: A: (hexane+0.1 vol % trifluoroacetic acid (99%))/B: (50 vol % ethanol+50 vol % methanol), gradient: 40-50% B in 20 min and 50% B 20-25 min, 40 mL/min, UV: 280 nm) to yield the title product which was further purified by RP-HPLC (column: X-Bridge C18 5 µm 100×30 mm, mobile phase: (water+0.1 vol % formic acid (99%))/acetonitrile, gradient) to yield 17.7 mg (14%) of the title product.

$^1$H-NMR (400 MHz, DMSO-$d_6$): δ [ppm]=3.39 (ddd, 1H), 3.61-3.70 (m, 1H), 3.78-3.91 (m, 1H), 5.94 (dt, 1H), 5.99 (d, 1H), 7.35-7.43 (m, 1H), 7.53-7.66 (m, 5H), 7.97-8.04 (m, 2H), 8.66 (s, 1H), 9.57 (t, 1H).

Chiral HPLC: Rt=7.17 min

Instrument: Agilent HPLC 1260: Chiralpak AD 3µ 100×4.6 mm; eluent: A: (hexane+0.1 vol % trifluoroacetic acid (99%))/B: (50 vol % ethanol+50 vol % methanol), gradient: 40-50% B in 7 min, flow: 1.4 mL/min, temperature: 25° C., UV: 280 nm.

$[α]_D^{20}$=+11.4° (c=1.00, methanol).

Example 224

6-(4-Chlorophenyl)-N-[(2RS)-1,4-dihydroxybutan-2-yl]-2-(3-fluorophenyl)-3-oxo-2,3-dihydropyridazine-4-carboxamide

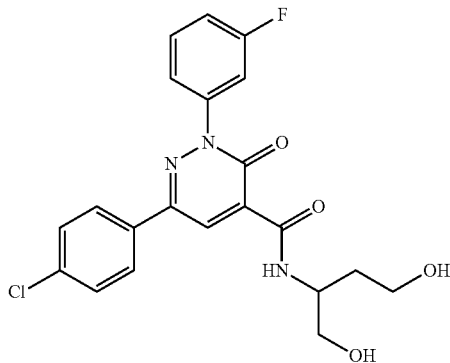 [SMILES: O=C(NC(CO)CCO)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (2RS)-2-Aminobutane-1,4-diol (55 mg, 0.52 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 67 mg (53%) of the title compound.

$^1$H-NMR (400 MHz, DMSO-$d_6$): δ [ppm]=1.59-1.69 (m, 1H), 1.74-1.83 (m, 1H), 3.41-3.56 (m, 4H), 4.05-4.14 (m, 1H), 4.50 (t, 1H), 4.89 (t, 1H), 7.35-7.41 (m, 1H), 7.53-7.65 (m, 6H), 7.97-8.02 (m, 2H), 8.65 (s, 1H), 9.43 (d, 1H).

Example 225

(+)-6-(4-Chlorophenyl)-N-(1,4-dihydroxybutan-2-yl)-2-(3-fluorophenyl)-3-oxo-2,3-dihydropyridazine-4-carboxamide

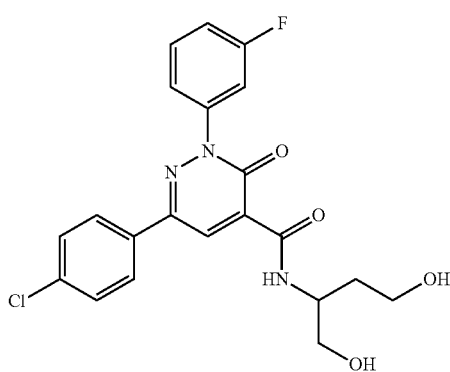 [SMILES: O=C(NC(CO)CCO)c1cc(-c2ccc(Cl)cc2)nn(-c2cccc(F)c2)c1=O]

6-(4-Chlorophenyl)-N-[(2RS)-1,4-dihydroxybutan-2-yl]-2-(3-fluorophenyl)-3-oxo-2,3-dihydropyridazine-4-carboxamide was separated by chiral HPLC (column: Chiralpak IC 5µ 250×30 mm, mobile phase: A: hexane/B: ethanol, gradient: 20-50% B in 15 min, 40 mL/min, UV: 254 nm) to yield the title compound which was further purified by RP-HPLC (column: X-Bridge C18 5 µm 100×30 mm, mobile phase: (water+0.1 vol % formic acid (99%))/acetonitrile, gradient) affording 19 mg (7%) of the title compound.

$^1$H-NMR (400 MHz, DMSO-$d_6$): δ [ppm]=1.59-1.69 (m, 1H), 1.73-1.83 (m, 1H), 3.41-3.56 (m, 4H), 4.04-4.14 (m, 1H), 4.50 (t, 1H), 4.89 (t, 1H), 7.36-7.41 (m, 1H), 7.52-7.65 (m, 5H), 7.96-8.02 (m, 2H), 7.96-8.02 (m, 2H), 8.65 (s, 1H), 9.43 (d, 1H).

Chiral HPLC: Rt=5.57 min

Instrument: Agilent HPLC 1260: Chiralpak IC 3µ 100×4.6 mm; eluent: A: hexane/B: ethanol, gradient: 20-50% B in 7 min, flow: 1.4 mL/min, temperature: 25° C., UV: 254 nm.

$[α]_D^{20}$=+26.7° (c=1.00, methanol).

Example 226

(−)-6-(4-Chlorophenyl)-N-(1,4-dihydroxybutan-2-yl)-2-(3-fluorophenyl)-3-oxo-2,3-dihydropyridazine-4-carboxamide

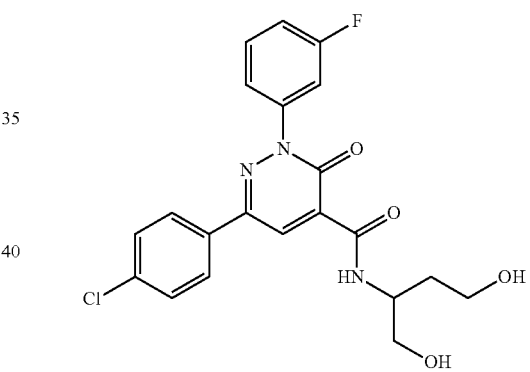

6-(4-Chlorophenyl)-N-[(2RS)-1,4-dihydroxybutan-2-yl]-2-(3-fluorophenyl)-3-oxo-2,3-dihydropyridazine-4-carboxamide was separated by chiral HPLC (column: Chiralpak IC 5µ 250×30 mm, mobile phase: A: hexane/B: ethanol, gradient: 20-50% B in 15 min, 40 mL/min, UV: 254 nm) to yield the title compound which was further purified by RP-HPLC (column: X-Bridge C18 5 µm 100×30 mm, mobile phase: (water+0.1 vol % formic acid (99%))/acetonitrile, gradient) affording 19 mg (7%) of the title compound.

$^1$H-NMR (400 MHz, DMSO-$d_6$): δ [ppm]=1.59-1.69 (m, 1H), 1.73-1.83 (m, 1H), 3.41-3.56 (m, 4H), 4.04-4.13 (m, 1H), 4.50 (t, 1H), 4.89 (t, 1H), 7.35-7.42 (m, 1H), 7.53-7.65 (m, 5H), 7.97-8.02 (m, 2H), 8.65 (s, 1H), 9.43 (d, 1H).

Chiral HPLC: Rt=7.29 min

Instrument: Agilent HPLC 1260: Chiralpak IC 3µ 100×4.6 mm; eluent: A: hexane/B: ethanol, gradient: 20-50% B in 7 min, flow: 1.4 mL/min, temperature: 25° C., UV: 254 nm.

$[α]_D^{20}$=−22.1° (c=1.00, methanol).

Example 227

6-(4-Chlorophenyl)-2-(3-fluorophenyl)-N-[(2RS)-1-hydroxy-4-methoxybutan-2-yl]-3-oxo-2,3-dihydropyridazine-4-carboxamide

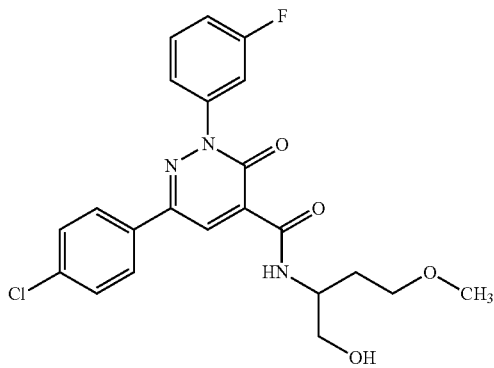 [SMILES: COCCC(CO)NC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (2RS)-2-Amino-4-methoxybutan-1-ol (62 mg, 0.52 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 14.1 mg (11%) of the title compound.

$^1$H-NMR (400 MHz, DMSO-d$_6$): δ [ppm]=1.66-1.76 (m, 1H), 1.81-1.91 (m, 1H), 3.21 (s, 3H), 3.38 (t, 2H), 3.41-3.47 (m, 1H), 3.48-3.54 (m, 1H), 4.04-4.13 (m, 1H), 4.90 (t, 1H), 7.35-7.42 (m, 1H), 7.53-7.65 (m, 5H), 7.97-8.02 (m, 2H), 8.65 (s, 1H), 9.42 (d, 1H).

Example 228

6-(4-Chlorophenyl)-N-(1,3-dihydroxypropan-2-yl)-2-(3-fluorophenyl)-3-oxo-2,3-dihydropyridazine-4-carboxamide

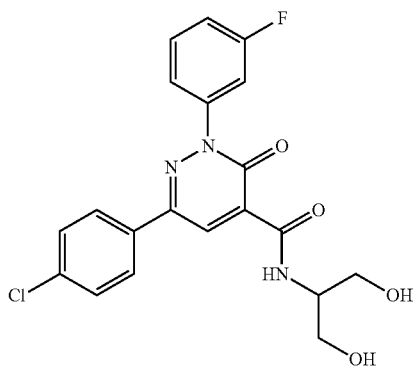 [SMILES: O=C(NC(CO)CO)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). 2-Aminopropane-1,3-diol (40 mg, 0.44 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 45 mg (37%) of the title compound.

$^1$H-NMR (400 MHz, DMSO-d$_6$): δ [ppm]=3.44-3.52 (m, 2H), 3.54-3.61 (m, 2H), 3.91-4.00 (m, 1H), 4.87 (t, 2H), 7.35-7.42 (m, 1H), 7.52-7.65 (m, 5H), 7.97-8.02 (m, 2H), 8.67 (s, 1H), 9.54 (d, 1H).

Example 229

6-(4-Chlorophenyl)-2-(3-fluorophenyl)-N-[(2S)-1-hydroxy-3-methoxypropan-2-yl]-3-oxo-2,3-dihydropyridazine-4-carboxamide

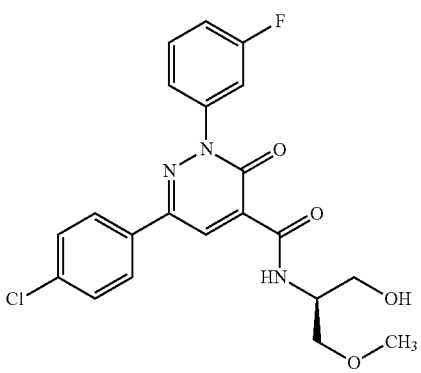 [SMILES: COC[C@H](CO)NC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (2S)-2-Amino-3-methoxypropan-1-ol (46 mg, 0.44 mmol), N-ethyl-N-isopropylpropan-2-amine (0.227 mL, 1.31 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 78 mg (62%) of the title compound.

$^1$H-NMR (400 MHz, DMSO-d$_6$): δ [ppm]=3.28 (s, 3H), 3.41-3.58 (m, 4H), 4.08-4.16 (m, 1H), 4.97 (t, 1H), 7.36-7.42 (m, 1H), 7.97-8.02 (m, 2H), 8.67 (s, 1H), 9.54 (d, 1H).

Example 230

3,6-Anhydro-2-({[6-(4-chlorophenyl)-2-(3-fluorophenyl)-3-oxo-2,3-dihydropyridazin-4-yl]carbonyl}amino)-2,4,5-trideoxy-DL-erythro-hexitol and 1,4-anhydro-5-({[6-(4-chlorophenyl)-2-(3-fluorophenyl)-3-oxo-2,3-dihydropyridazin-4-yl]carbonyl}amino)-2,3,5-trideoxy-DL-threo-hexitol

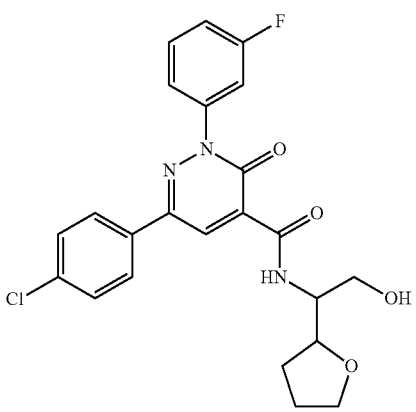 [SMILES: O=C(NC(CO)C1CCCO1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). 5-Amino-1,4-anhydro-2,3,5-trideoxyhexitol hydrochloride (1:1) (73 mg, 0.44 mmol), N-ethyl-N-isopropylpropan-2-amine (0.303 mL, 1.74 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) yielding 77 mg (58%) of the title compound as a diastereomeric mixture of 58:42 according to $^1$H-NMR analysis.

$^1$H-NMR (400 MHz, DMSO-d$_6$): δ [ppm]=1.56 (ddd, 1H, major), 1.67-1.97 (m, 3H, major, 4H, minor), 3.45-3.53 (m, 2H, major, 1H, minor), 3.60-3.68 (m, 1H, major, 2H, minor), 3.72-3.81 (m, 1H, major, 1H, minor), 3.92-4.14 (m, 2H, major, 2H, minor), 4.88 (t, 1H, minor), 4.91 (t, 1H, major), 7.35-7.42 (m, 1H, major, 1H minor), 7.52-7.66 (m, 5H, major, 5H, minor), 8.67 (s, 1H, major, 1H, minor), 9.45 (d, 1H, major), 9.57 (d, 1H, minor).

Example 231

6-(4-Chlorophenyl)-2-(3-fluorophenyl)-N-[(2R,3R)-3-hydroxybutan-2-yl]-3-oxo-2,3-dihydropyridazine-4-carboxamide

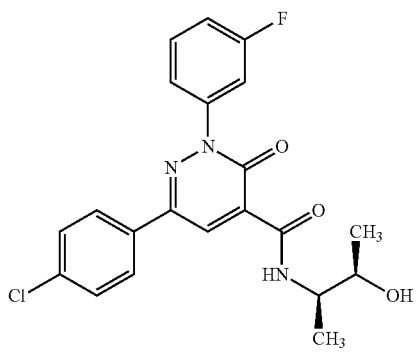 [SMILES: C[C@@H](O)[C@@H](C)NC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (60 mg, 0.17 mmol) was dissolved in anhydrous DMF (1.5 mL). (2R,3R)-3-Aminobutan-2-ol (31 mg, 0.35 mmol), N-ethyl-N-isopropylpropan-2-amine (0.136 mL, 0.78 mmol), and propane phosphonic acid anhydride (T3P, 152 µL, 50% in DMF, 261 µmol) were successively added. It was stirred at rt for 1 h.

The reaction mixture was purified by RP-HPLC (column: X-Bridge C18 5 µm 100×30 mm, mobile phase: (water+0.2 vol % aqueous ammonia (32%))/acetonitrile, gradient) affording 50 mg (69%) of the title compound.

$^1$H-NMR (400 MHz, DMSO-d$_6$): δ [ppm]=1.04 (d, 3H), 1.15 (d, 3H), 3.66-3.75 (m, 1H), 3.88-3.98 (m, 1H), 4.95 (d, 1H), 7.35-7.42 (m, 1H), 7.53-7.66 (m, 5H), 7.96-8.02 (m, 2H), 8.65 (s, 1H), 9.46 (d, 1H).

$[α]_D^{20}$=−19.4° (c=1.00, methanol).

Example 232

6-(4-Chlorophenyl)-N-[(2RS)-2-cyclopentyl-2-hydroxyethyl]-2-(3-fluorophenyl)-3-oxo-2,3-dihydropyridazine-4-carboxamide

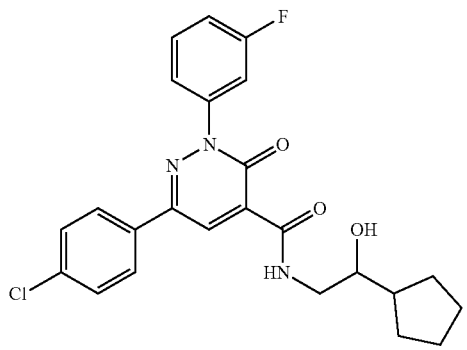 [SMILES: O=C(NCC(O)C1CCCC1)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (1RS)-2-Amino-1-cyclopentylethanol hydrochloride (1:1) (72 mg, 0.44 mmol), N-ethyl-N-isopropylpropan-2-amine (0.303 mL, 1.74 mmol), and propane phosphonic acid anhydride (T3P, 254 µL, 50% in DMF, 435 µmol) were successively added. It was stirred at rt overnight.

The reaction mixture was purified by RP-HPLC (column: X-Bridge C18 5 µm 100×30 mm, mobile phase: (water+0.2 vol % aqueous ammonia (32%))/acetonitrile, gradient) affording 60 mg (45%) of the title compound.

$^1$H-NMR (400 MHz, DMSO-d$_6$): δ [ppm]=1.16-1.27 (m, 1H), 1.32-1.74 (m, 7H), 1.78-1.90 (m, 1H), 3.16-3.24 (m, 1H), 3.30-3.42 (m, 1H and water signal), 3.53 (ddd, 1H), 4.93 (d, 1H), 7.35-7.42 (m, 1H), 7.53-7.65 (m, 5H), 7.97-8.02 (m, 2H), 8.65 (s, 1H), 9.56 (t, 1H).

Example 233

6-(4-Chlorophenyl)-N-[(2RS)-3-ethyl-2-hydroxypentyl]-2-(3-fluorophenyl)-3-oxo-2,3-dihydropyridazine-4-carboxamide

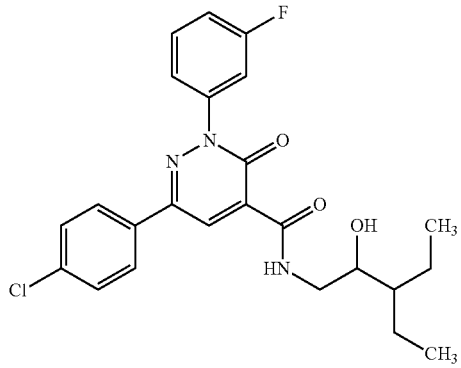 [SMILES: CCC(CC)C(O)CNC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (2 mL). (2RS)-1-Amino-3-ethylpentan-2-ol (57 mg, 0.44 mmol), N-ethyl-N-isopropylpropan-2-amine (0.227 mL, 1.31 mmol), and propane phosphonic acid anhydride (T3P, 254 μL, 50% in DMF, 435 μmol) were successively added. It was stirred at rt for 1 h.

The reaction mixture was purified by RP-HPLC (column: X-Bridge C18 5 μm 100×30 mm, mobile phase: (water+0.2 vol % aqueous ammonia (32%))/acetonitrile, gradient) affording 60 mg (45%) of the title compound.

$^1$H-NMR (400 MHz, DMSO-$d_6$): δ [ppm]=0.81-0.88 (m, 6H), 1.16-1.51 (m, 5H), 3.18 (ddd, 1H), 3.52-3.61 (m, 2H), 4.83 (d, 1H), 7.35-7.42 (m, 1H), 7.53-7.66 (m, 5H), 7.97-8.03 (m, 2H), 8.66 (s, 1H), 9.55 (t, 1H).

Example 234

6-(4-Chlorophenyl)-2-(3-fluorophenyl)-N-[(4-hydroxy-1-methylpiperidin-4-yl)methyl]-3-oxo-2,3-dihydropyridazine-4-carboxamide

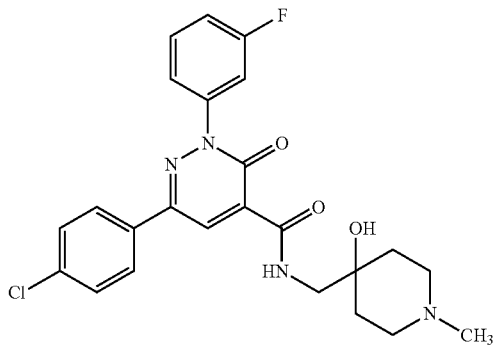 [SMILES: CN1CCC(O)(CNC(=O)c2cc(-c3ccc(Cl)cc3)nn(-c3cccc(F)c3)c2=O)CC1]

6-(4-Chlorophenyl)-2-(3-fluorophenyl)-3-oxo-2,3-dihydropyridazine-4-carboxylic acid (50 mg, 0.15 mmol) was dissolved in anhydrous DMF (1.5 mL). 4-(Aminomethyl)-1-methylpiperidin-4-ol (31 mg, 0.22 mmol), N-ethyl-N-isopropylpropan-2-amine (0.114 mL, 0.65 mmol), and propane phosphonic acid anhydride (T3P, 127 μL, 50% in DMF, 218 μmol) were successively added. It was stirred at rt for 1 h.

The reaction mixture was purified by RP-HPLC (column: X-Bridge C18 5 μm 100×30 mm, mobile phase: (water+0.2 vol % aqueous ammonia (32%))/acetonitrile, gradient) affording 32 mg (47%) of the title compound.

$^1$H-NMR (400 MHz, DMSO-$d_6$): δ [ppm]=1.44-1.54 (m, 4H), 2.13 (s, 3H), 2.20-2.29 m, 2H), 2.31-2.40 (m, 2H), 4.52 (s, 1H), 7.35-7.42 (m, 1H), 7.53-7.66 (m, 5H), 7.97-8.03 (m, 2H), 8.66 (s, 1H), 9.54 (t, 1H).

Example 235

6-(4-Chlorophenyl)-N-[(2RS)-3-(dimethylamino)-2-hydroxypropyl]-2-(3-fluorophenyl)-3-oxo-2,3-dihydropyridazine-4-carboxamide

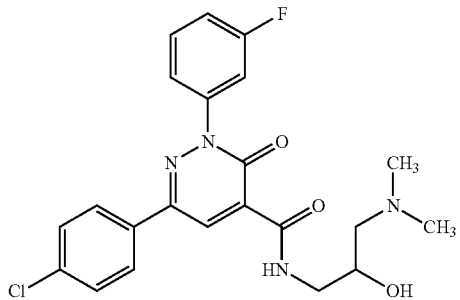 [SMILES: CN(C)CC(O)CNC(=O)c1cc(-c2ccc(Cl)cc2)nn(-c2cccc(F)c2)c1=O]

6-(4-Chlorophenyl)-2-(3-fluorophenyl)-3-oxo-2,3-dihydropyridazine-4-carboxylic acid (100 mg, 0.29 mmol) was dissolved in anhydrous DMF (1.5 mL). 1-Amino-3-(dimethylamino)propan-(2RS)-2-ol (51 mg, 0.44 mmol), N-ethyl-N-isopropylpropan-2-amine (0.227 mL, 1.31 mmol), and propane phosphonic acid anhydride (T3P, 254 μL, 50% in DMF, 435 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 65 mg (50%) of the title compound.

$^1$H-NMR (400 MHz, DMSO-$d_6$): δ [ppm]=2.16 (s, 6H), 2.19-2.28 (m, 2H), 3.15-3.24 (m, 1H), 3.56-3.64 (m, 1H), 3.68-3.76 (m, 1H), 4.90 (d, 1H), 7.35-7.42 (m, 1H), 7.53-7.66 (m, 5H), 7.97-8.03 (m, 2H), 8.66 (s, 1H), 9.56 (t, 1H).

Example 236

N-[(1RS)-1-Cyclopropyl-2-hydroxyethyl]-2-(3-fluorophenyl)-6-(4-methylphenyl)-3-oxo-2,3-dihydropyridazine-4-carboxamide

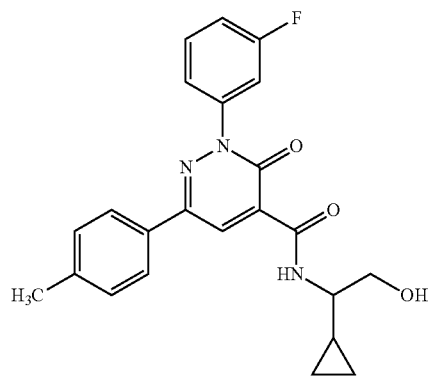 [SMILES: Cc1ccc(-c2cc(C(=O)NC(CO)C3CC3)c(=O)n(-c3cccc(F)c3)n2)cc1]

2-(3-Fluorophenyl)-6-(4-methylphenyl)-3-oxo-2,3-dihydropyridazine-4-carboxylic acid (75 mg, 0.25 mmol) was dissolved in anhydrous DMF (1.5 mL). (2RS)-2-Amino-2-cyclopropylethanol hydrochloride (1:1) (51 mg, 0.37 mmol), N-ethyl-N-isopropylpropan-2-amine (0.256 mL, 1.47 mmol), and propane phosphonic acid anhydride (T3P, 214 μL, 50% in DMF, 367 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 50 mg (52%) of the title compound.

$^1$H-NMR (400 MHz, DMSO-$d_6$): δ [ppm]=0.25-0.50 (m, 4H), 1.02-1.12 (m, 1H), 2.36 (s, 3H), 3.40-3.47 (m, 1H), 3.52-3.61 (m, 2H), 4.91 (t, 1H), 7.30-7.35 (m, 2H), 7.48-7.60 (m, 3H), 7.63-7.69 (m, 2H), 7.81-7.86 (m, 2H), 8.63 (s, 1H), 9.65 (d, 1H).

Example 237

2-(3-Fluorophenyl)-N-[(2S)-1-hydroxypropan-2-yl]-3-oxo-6-[4-(trifluoromethyl)phenyl]-2,3-dihydropyridazine-4-carboxamide

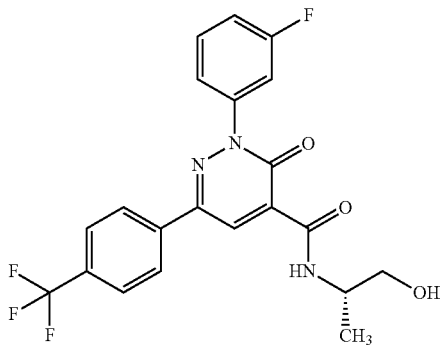 [SMILES: C[C@@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1 mL). (2S)-2-Aminopropan-1-ol (20 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.1 vol % formic acid (99%))/acetonitrile, gradient) to yield 37.2 mg (65%) of the title compound.

$^1$H-NMR (400 MHz, DMSO-$d_6$): δ [ppm]=1.17 (d, 3H), 3.40-3.50 (m, 2H), 3.99-4.09 (m, 1H), 4.94 (t, 1H), 7.37-7.43 (m, 1H), 7.54-7.58 (m, 1H), 7.59-7.66 (m, 2H), 7.88 (d, 2H), 8.20 (d, 2H), 8.72 (s, 1H), 9.42 (d, 1H).

[α]$_D^{20}$=+9.0° (c=1.00, DMSO).

Example 238

2-(3-Fluorophenyl)-N-[(2R)-1-hydroxypropan-2-yl]-3-oxo-6-[4-(trifluoromethyl)phenyl]-2,3-dihydropryridazine-4-carboxamide

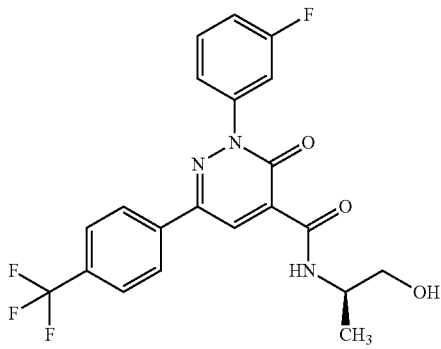 [SMILES: C[C@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1 mL). (2R)-2-Aminopropan-1-ol (20 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.1 vol % formic acid (99%))/acetonitrile, gradient) to yield 35 mg (61%) of the title compound.

$^1$H-NMR (400 MHz, DMSO-$d_6$): δ [ppm]=1.17 (d, 3H), 3.40-3.50 (m, 2H), 3.99-4.10 (m, 1H), 4.94 (t, 1H), 7.37-7.43 (m, 1H), 7.54-7.58 (m, 1H), 7.59-7.66 (m, 2H), 7.88 (d, 2H), 8.20 (d, 2H), 8.72 (s, 1H), 9.42 (d, 1H).

Example 239

2-(3-Fluorophenyl)-N-[(2S)-1-hydroxy-3-methylbutan-2-yl]-3-oxo-6-[4-(trifluoromethyl)phenyl]-2,3-dihydropyridazine-4-carboxamide

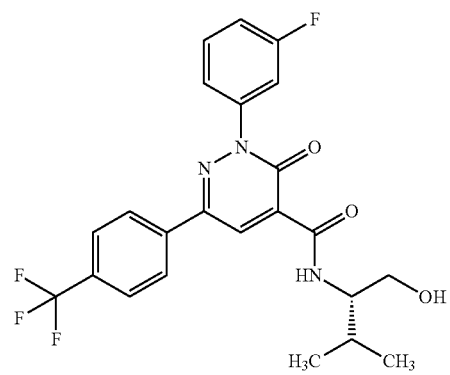 [SMILES: CC(C)[C@@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1 mL). (2S)-2-Amino-3-methylbutan-1-ol (27.3 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.1 vol % formic acid (99%))/acetonitrile, gradient) to yield 50 mg (82%) of the title compound.

$^1$H-NMR (400 MHz, DMSO-$d_6$): δ [ppm]=0.89 (d, 3H), 0.93 (d, 3H), 1.91-2.04 (m, 1H), 3.41-3.49 (m, 1H), 3.51-3.59 (m, 1H), 3.81-3.90 (m, 1H), 4.81 (br s, 1H), 7.37-7.43 (m, 1H), 7.55-7.59 (m, 1H), 7.60-7.67 (m, 2H), 7.88 (d, 2H), 8.20 (d, 2H), 8.73 (s, 1H), 9.39 (d, 1H).

Example 240

2-(3-Fluorophenyl)-N-[(2R)-1-hydroxy-3-methylbutan-2-yl]-3-oxo-6-[4-(trifluoromethyl)phenyl]-2,3-dihydropyridazine-4-carboxamide

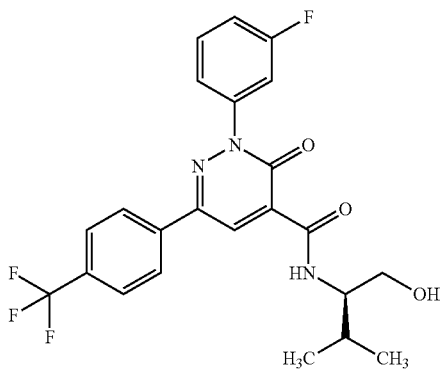 [SMILES: CC(C)[C@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1 mL). (2R)-2-Amino-3-methylbutan-1-ol (27.3 mg, 0.26 mmol), N-ethyl-N-isopropylpropan-2-amine (0.104 mL, 0.60 mmol), and propane phosphonic acid anhydride (T3P, 116 μL, 50% in DMF, 198 μmol) were successively added. It was stirred at rt overnight.

The crude reaction mixture was purified by RP-HPLC (column: X-Bridge C18 5 μm 100×30 mm, mobile phase: (water+0.1 vol % formic acid (99%))/acetonitrile, gradient) to yield 44 mg (72%) of the title compound.

$^1$H-NMR (400 MHz, DMSO-$d_6$): δ [ppm]=0.89 (d, 3H), 0.93 (d, 3H), 1.91-2.04 (m, 1H), 3.41-3.48 (m, 1H), 3.41-3.48 (m, 1H), 3.82-3.89 (m, 1H), 4.81 (br s, 1H), 7.37-7.43 (m, 1H), 7.55-7.59 (m, 1H), 7.60-7.67 (m, 2H), 7.88 (d, 2H), 8.20 (d, 2H), 8.73 (s, 1H), 9.39 (d, 1H).

Example 241

2-(3-Fluorophenyl)-N-[(2RS)-2-hydroxy-3-methylbutyl]-3-oxo-6-[4-(trifluoromethyl)phenyl]-2,3-dihydropyridazine-4-carboxamide

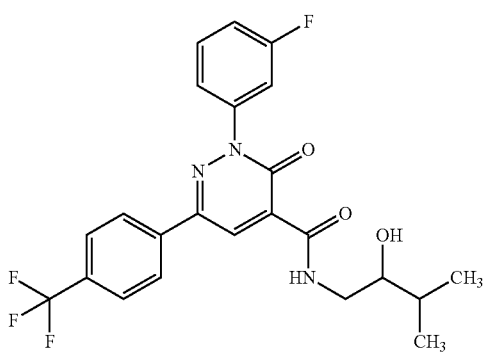 [SMILES: CC(C)C(O)CNC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2 mL). (2RS)-1-Amino-3-methylbutan-2-ol hydrochloride (1:1) (73.8 mg, 0.53 mmol), N-ethyl-N-isopropylpropan-2-amine (0.253 mL, 1.45 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 90.8 mg (74%) of the title compound.

$^1$H-NMR (400 MHz, DMSO-$d_6$): δ [ppm]=0.88 (t, 6H), 1.55-1.69 (m, 1H), 3.18-3.27 (m, 1H), 3.29-3.36 (m, 1H and water signal), 3.54 (ddd, 1H), 4.91 (d, 1H), 7.36-7.43 (m, 1H), 7.54-7.59 (m, 1H), 7.60-7.67 (m, 2H), 7.88 (d, 2H), 8.20 (d, 2H), 8.72 (s, 1H), 9.53 (t, 1H).

Example 242

2-(3-Fluorophenyl)-3-oxo-N-[(2RS)-3,3,3-trifluoro-2-hydroxypropyl]-6-[4-(trifluoromethyl)phenyl]-2,3-dihydropyridazine-4-carboxamide

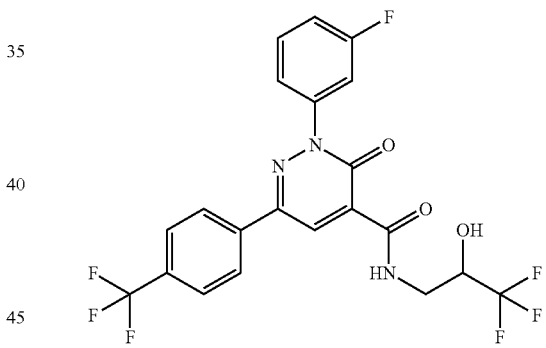

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2 mL). (2RS)-3-Amino-1,1,1-trifluoropropan-2-ol (68 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.1 vol % formic acid (99%))/acetonitril gradient) to yield 73.9 mg (57%) of the title compound.

$^1$H-NMR (400 MHz, DMSO-$d_6$): δ [ppm]=3.48 (ddd, 1H), 3.71-3.80 (m, 1H), 4.17-4.29 (m, 1H), 6.67 (d, 1H), 7.37-7.44 (m, 1H), 7.55-7.59 (m, 1H), 7.60-7.67 (m, 2H), 7.89 (d, 2H), 8.20 (d, 2H), 8.74 (s, 1H), 9.62 (t, 1H).

Example 243

(−)-2-(3-Fluorophenyl)-3-oxo-N-3,3,3-trifluoro-2-hydroxypropyl)-6-[4-(trifluoromethyl)phenyl]-2,3-dihydropyridazine-4-carboxamide

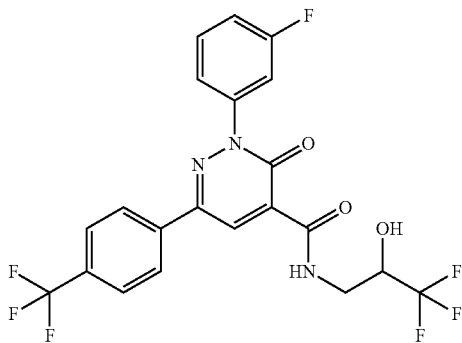

2-(3-Ffluorophenyl)-3-oxo-N-[(2RS)-3,3,3-trifluoro-2-hydroxypropyl]-6-[4-(trifluoromethyl)phenyl]-2,3-dihydropyridazine-4-carboxamide was separated by chiral HPLC (column: Chiralpak IA 5μ 250×30 mm, mobile phase: A: (hexane+0.1 vol % diethylamine (99%))/B: ethanol, gradient: 20-50% B in 15 min, 40 mL/min, UV: 254 nm) to yield the title compound which was further purified by RP-HPLC (column: X-Bridge C18 5 μm 100×30 mm, mobile phase: (water+0.1 vol % formic acid (99%))/acetonitrile, gradient) affording 22 mg (17%) of the title compound.

$^1$H-NMR (400 MHz, DMSO-d$_6$): δ [ppm]=3.48 (ddd, 1H), 3.72-3.79 (m, 1H), 4.17-4.28 (m, 1H), 6.67 (s, 1H), 7.37-7.44 (m, 1H), 7.55-7.59 (m, 1H), 7.60-7.67 (m, 2H), 7.89 (d, 2H), 8.20 (d, 2H), 8.74 (s, 1H), 9.62 (t, 1H).

Chiral HPLC: Rt=4.09 min

Instrument: Agilent HPLC 1260: Chiralpak IA 3μ 100× 4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=−4.7° (c=1.00, DMSO).

Example 244

(+)-2-(3-Fluorophenyl)-3-oxo-N-3,3,3-trifluoro-2-hydroxypropyl)-6-[4-(trifluoromethyl)phenyl]-2,3-dihydropyridazine-4-carboxamide

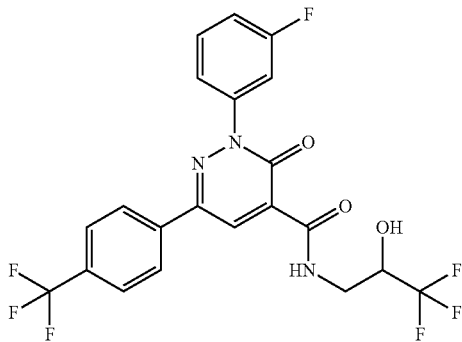

2-(3-Ffluorophenyl)-3-oxo-N-[(2RS)-3,3,3-trifluoro-2-hydroxypropyl]-6-[4-(trifluoromethyl)phenyl]-2,3-dihydropyridazine-4-carboxamide was separated by chiral HPLC (column: Chiralpak IA 5μ 250×30 mm, mobile phase: A: (hexane+0.1 vol % diethylamine (99%))/B: ethanol, gradient: 20-50% B in 15 min, 40 mL/min, UV: 254 nm) to yield the title compound which was further purified by RP-HPLC (column: X-Bridge C18 5 μm 100×30 mm, mobile phase: (water+0.1 vol % formic acid (99%))/acetonitrile, gradient) affording 17.5 mg (14%) of the title compound.

$^1$H-NMR (400 MHz, DMSO-d$_6$): δ [ppm]=3.48 (ddd, 1H), 3.72-3.79 (m, 1H), 4.17-4.29 (m, 1H), 6.67 (s, 1H), 7.37-7.44 (m, 1H), 7.55-7.59 (m, 1H), 7.60-7.68 (m, 2H), 7.89 (d, 2H), 8.20 (d, 2H), 8.74 (s, 1H), 9.62 (t, 1H).

Chiral HPLC: Rt=5.68 min

Instrument: Agilent HPLC 1260: Chiralpak IA 3μ 100× 4.6 mm; eluent: A: (hexane+0.1 vol % diethylamine (99%))/B: ethanol, gradient: 20-50% B in 7 min, flow: 1.4 mL/min, temperature: 25° C., UV: 254 nm.

$[α]_D^{20}$=+13.3° (c=1.00, DMSO).

Example 245

2-(3-Fluorophenyl)-N-[(2RS)-3-hydroxy-2-methylpropyl]-3-oxo-6-[4-(trifluoromethyl)phenyl]-2,3-dihydropyridazine-4-carboxamide

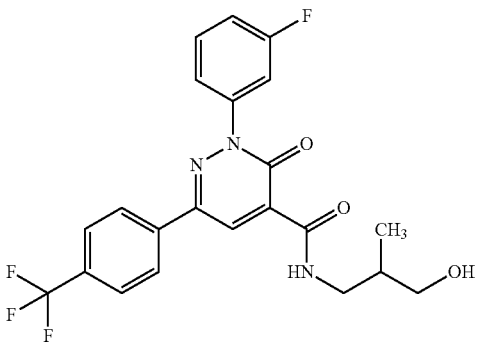 [SMILES: CC(CO)CNC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2 mL). (2RS)-3-Amino-2-methylpropan-1-ol (47.1 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 87.4 mg (74%) of the title compound.

$^1$H-NMR (400 MHz, DMSO-d$_6$): δ [ppm]=0.88 (d, 3H), 1.75-1.87 (m, 1H), 3.23-3.42 (m, 4H and water signal), 4.62 (t, 1H), 7.36-7.43 (m, 1H), 7.55-7.59 (m, 1H), 7.60-7.67 (m, 2H), 7.88 (d, 2H), 8.20 (d, 2H), 8.70 (s, 1H), 9.43 (t, 1H).

Example 246

(−)-2-(3-Fluorophenyl)-N-[(2S)-3-hydroxy-2-methylpropyl]-3-oxo-6-[4-(trifluoromethyl)phenyl]-2,3-dihydropyridazine-4-carboxamide

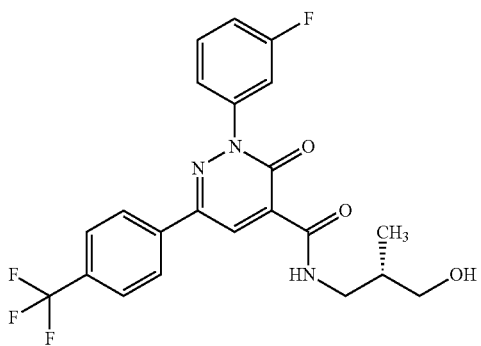 [SMILES: C[C@H](CO)CNC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2S)-3-Amino-2-methylpropan-1-ol (68 mg, 0.53 mmol), N-ethyl-N-isopropylpropan-2-amine (0.145 mL, 0.83 mmol), and propane phosphonic acid anhydride (T3P, 162 µL, 50% in DMF, 278 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 55 mg (66%) of the title compound.

$^1$H-NMR (400 MHz, DMSO-$d_6$): δ [ppm]=0.88 (d, 3H), 1.74-1.88 (m, 1H), 3.21-3.43 (m, 4H and water signal), 4.62 (t, 1H), 7.36-7.43 (m, 1H), 7.55-7.59 (m, 1H), 7.60-7.67 (m, 2H), 7.88 (d, 2H), 8.20 (d, 2H), 8.70 (s, 1H), 9.43 (t, 1H).
$[α]_D^{20}$=−3.3° (c=1.00, DMSO).

Example 247

2-(3-Fluorophenyl)-N-[(3RS)-3-hydroxybutyl]-3-oxo-6-[4-(trifluoromethyl)phenyl]-2,3-dihydropyridazine-4-carboxamide

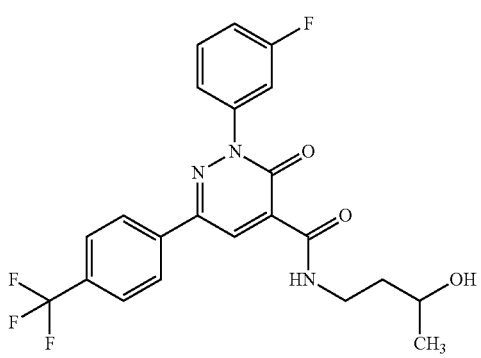 [SMILES: CC(O)CCNC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2 mL). (2RS)-4-Aminobutan-2-ol (47.1 mg, 0.53 mmol), N-ethyl-N-isopropylpropan-2-amine (0.207 mL, 1.19 mmol), and propane phosphonic acid anhydride (T3P, 231 µL, 50% in DMF, 397 µmol) were successively added. It was stirred at rt overnight.

(2RS)-4-Aminobutan-2-ol (30 mg, 0.34 mmol) was added and it was stirred at rt overnight. (2RS)-4-Aminobutan-2-ol (20 mg, 0.22 mmol), N-ethyl-N-isopropylpropan-2-amine (0.100 mL, 0.57 mmol), and propane phosphonic acid anhydride (T3P, 115 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 59 mg (50%) of the title compound.

$^1$H-NMR (400 MHz, DMSO-$d_6$): δ [ppm]=1.08 (d, 3H), 1.48-1.67 (m, 2H), 3.36-3.50 (m, 2H), 3.64-3.75 (m, 1H), 4.62 (d, 1H), 7.36-7.42 (m, 1H), 7.54-7.58 (m, 1H), 7.59-7.66 (m, 2H), 7.88 (d, 2H), 8.20 (d, 2H), 8.69 (s, 1H), 9.42 (t, 1H).

Example 248

2-(3-Fluorophenyl)-N-[(3S)-3-hydroxybutyl]-3-oxo-6-[4-(trifluoromethyl)phenyl]-2,3-dihydropyridazine-4-carboxamide

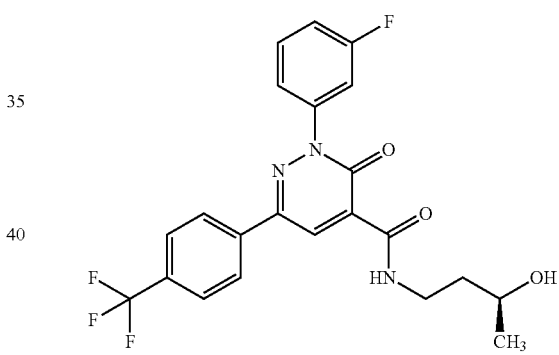

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2S)-4-Aminobutan-2-ol hydrochloride (1:1) (47.1 mg, 0.53 mmol), N-ethyl-N-isopropylpropan-2-amine (0.210 mL, 1.20 mmol), and propane phosphonic acid anhydride (T3P, 162 µL, 50% in DMF, 278 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to afford 54 mg (65%) of the title compound.

$^1$H-NMR (400 MHz, DMSO-$d_6$): δ [ppm]=1.08 (d, 3H), 1.48-1.67 (m, 2H), 3.36-3.50 (m, 2H), 3.64-3.75 (m, 1H), 4.62 (d, 1H), 7.36-7.43 (m, 1H), 7.54-7.58 (m, 1H), 7.59-7.67 (m, 2H), 7.88 (d, 2H), 8.20 (d, 2H), 8.70 (s, 1H), 9.42 (t, 1H).
$[α]_D^{20}$=+12.3° (c=1.00, DMSO).

Example 249

2-(3-Fluorophenyl)-N-(3-hydroxypropyl)-3-oxo-6-[4-(trifluoromethyl)phenyl]-2,3-dihydropyridazine-4-carboxamide

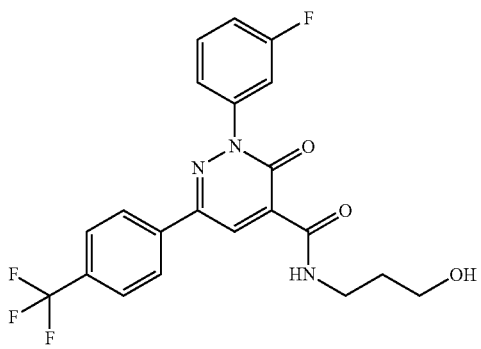 [SMILES: O=C(NCCCO)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1.0 mL). 3-Aminopropan-1-ol (19.9 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/methanol, gradient) to afford the title compound which was further purified by RP-HPLC (column: X-Bridge C18 5 µm 100×30 mm, mobile phase: (water+0.1 vol % formic acid (99%))/acetonitrile, gradient) to yield 7.6 mg (13%) of the title compound.

$^1$H-NMR (400 MHz, DMSO-$d_6$): δ [ppm]=1.68 (quin, 2H), 3.42 (q, 2H), 3.48 (q, 2H), 4.57 (t, 1H), 7.36-7.43 (m, 1H), 7.55-7.59 (m, 1H), 7.60-7.67 (m, 2H), 7.88 (d, 2H), 8.20 (d, 2H), 8.70 (s, 1H), 9.39 (t, 1H).

Example 250

N-(1,3-Dihydroxypropan-2-yl)-2-(3-fluorophenyl)-3-oxo-6-[4-(trifluoromethyl)phenyl]-2,3-dihydropyridazine-4-carboxamide

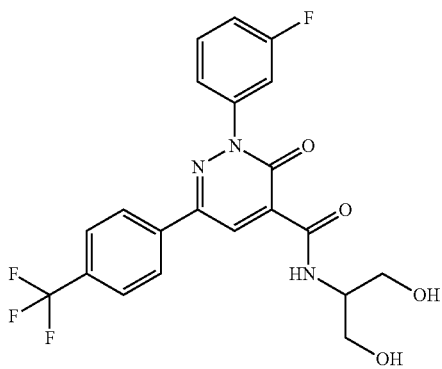 [SMILES: O=C(NC(CO)CO)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1.0 mL). 2-Aminopropane-1,3-diol (24.1 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.1 vol % formic acid (99%))/acetonitrile, gradient) to yield 48 mg (60%) of the title compound.

$^1$H-NMR (400 MHz, DMSO-$d_6$): δ [ppm]=3.44-3.52 (m, 2H), 3.55-3.62 (m, 2H), 3.92-4.01 (m, 1H), 4.88 (t, 2H), 7.37-7.43 (m, 1H), 7.54-7.58 (m, 1H), 7.59-7.66 (m, 2H), 7.88 (d, 2H), 8.20 (d, 2H), 8.74 (s, 1H), 9.53 (d, 1H).

Example 251

2-(3-Fluorophenyl)-N-[(2S)-1-hydroxy-3-phenylpropan-2-yl]-3-oxo-6-[4-(trifluoromethyl)phenyl]-2,3-dihydropyridazine-4-carboxamide

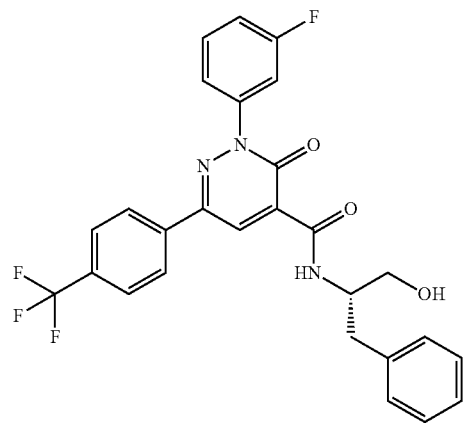 [SMILES: O=C(N[C@H](CO)Cc1ccccc1)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1.0 mL). (2S)-2-Amino-3-phenylpropan-1-ol (40.0 mg, 0.26 mmol), N-ethyl-N-isopropylpropan-2-amine (0.104 mL, 0.60 mmol), and propane phosphonic acid anhydride (T3P, 116 µL, 50% in DMF, 198 µmol) were successively added. It was stirred at rt overnight.

The crude reaction mixture was purified by RP-HPLC (column: X-Bridge C18 5 µm 100×30 mm, mobile phase: (water+0.2 vol % aqueous ammonia (32%))/acetonitrile, gradient) to yield 41.4 mg (61%) of the title compound.

$^1$H-NMR (400 MHz, DMSO-$d_6$): δ [ppm]=2.79-2.86 (m, 1H), 2.90-2.97 (m, 1H), 3.40-3.51 (m, 2H), 4.15-4.25 (m, 1H), 5.03 (t, 1H), 7.16-7.22 (m, 1H), 7.23-7.32 (m, 4H), 7.37-7.43 (m, 1H), 7.54-7.59 (m, 1H), 7.60-7.67 (m, 2H), 7.88 (d, 2H), 8.18 (d, 2H), 8.69 (s, 1H), 9.51 (d, 1H).

Example 252

2-(3-Fluorophenyl)-N-[(2R)-1-hydroxy-3-phenylpropan-2-yl]-3-oxo-6-[4-(trifluoromethyl)phenyl]-2,3-dihydropyridazine-4-carboxamide

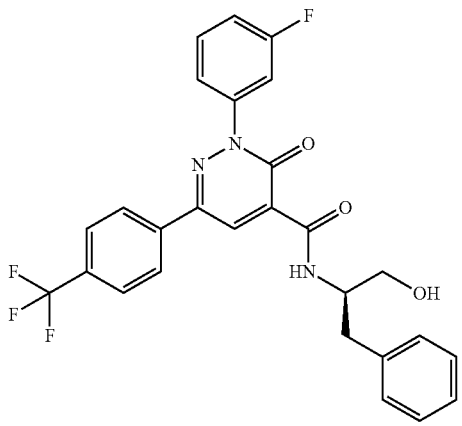 [SMILES: O=C(N[C@@H](CO)Cc1ccccc1)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (50 mg, 0.13 mmol) was dissolved in anhydrous DMF (1.0 mL). (2R)-2-Amino-3-phenylpropan-1-ol (40.0 mg, 0.26 mmol), N-ethyl-N-isopropylpropan-2-amine (0.104 mL, 0.60 mmol), and propane phosphonic acid anhydride (T3P, 116 μL, 50% in DMF, 198 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 45.7 mg (68%) of the title compound.

$^1$H-NMR (400 MHz, DMSO-$d_6$): δ [ppm]=2.78-2.86 (m, 1H), 2.90-2.97 (m, 1H), 3.40-3.51 (m, 2H), 4.15-4.25 (m, 1H), 5.03 (t, 1H), 7.15-7.22 (m, 1H), 7.24-7.32 (m, 4H), 7.37-7.44 (m, 1H), 7.54-7.58 (m, 1H), 7.60-7.67 (m, 2H), 7.88 (d, 2H), 8.18 (d, 2H), 8.69 (s, 1H), 9.51 (d, 1H).

Example 253

2-(3-Fluorophenyl)-N-[(2RS)-4-hydroxybutan-2-yl]-3-oxo-6-[4-(trifluoromethyl)phenyl]-2,3-dihydropyridazine-4-carboxamide

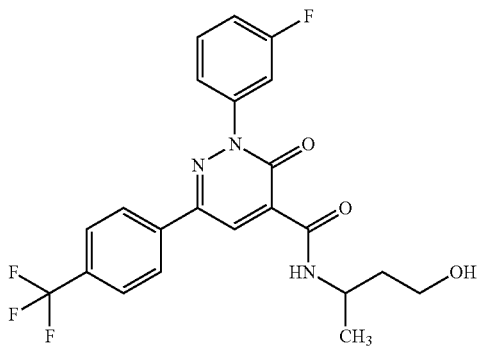 [SMILES: CC(CCO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (3RS)-3-Aminobutan-1-ol (47.1 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.1 vol % formic acid (99%))/acetonitrile, gradient) to yield 88.3 mg (74%) of the title compound.

$^1$H-NMR (400 MHz, DMSO-$d_6$): δ [ppm]=1.19 (d, 3H), 1.60-1.74 (m, 2H), 3.45-3.51 (m, 2H), 4.09-4.21 (m, 1H), 4.51 (t, 1H), 7.36-7.43 (m, 1H), 7.54-7.58 (m, 1H), 7.59-7.66 (m, 2H), 7.88 (d, 2H), 8.20 (d, 2H), 8.70 (s, 1H), 9.29 (d, 1H).

Example 254

(+)-2-(3-Fluorophenyl)-N-(4-hydroxybutan-2-yl)-3-oxo-6-[4-(trifluoromethyl)phenyl]-2,3-dihydropyridazine-4-carboxamide

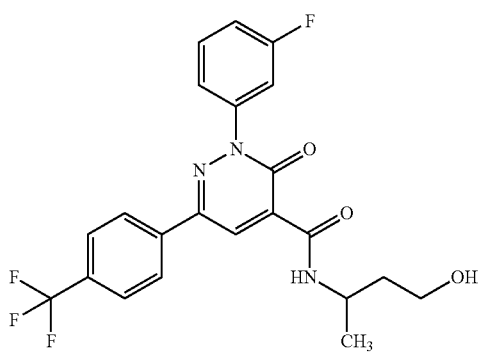 [SMILES: CC(CCO)NC(=O)c1cc(-c2ccc(C(F)(F)F)cc2)nn(-c2cccc(F)c2)c1=O]

2-(3-Fluorophenyl)-N-[(2RS)-4-hydroxybutan-2-yl]-3-oxo-6-[4-(trifluoromethyl)phenyl]-2,3-dihydropyridazine-4-carboxamide was separated by chiral HPLC (column: Chiralpak IB 5μ 250×30 mm, mobile phase: A: carbon dioxide/B: methanol, isocratic: 12% B, 100 mL/min, temperature: 40° C., BPR: 150 bar, UV: 254 nm) to yield 30 mg (25%) of the title compound.

$^1$H-NMR (400 MHz, DMSO-$d_6$): δ [ppm]=1.19 (d, 3H), 1.60-1.74 (m, 2H), 3.45-3.51 (m, 2H), 4.09-4.21 (m, 1H), 4.51 (t, 1H), 7.36-7.42 (m, 1H), 7.54-7.58 (m, 1H), 7.59-7.66 (m, 2H), 7.88 (d, 2H), 8.20 (d, 2H), 8.70 (s, 1H), 9.29 (d, 1H).

Chiral HPLC: Rt=2.22 min

Instrument: Agilent HPLC 1260: Chiralpak IB 5μ 100×4.6 mm; eluent: A: carbon dioxide/B: methanol, isocratic: 12% B, flow: 4 mL/min, temperature: 37.5° C., BPR: 100 bar, UV: 254 nm.

[α]$_D$=+32.6° (c=1.00, DMSO).

Example 255

(−)-2-(3-Fluorophenyl)-N-(4-hydroxybutan-2-yl)-3-oxo-6-[4-(trifluoromethyl)phenyl]-2,3-dihydro-pyridazine-4-carboxamide

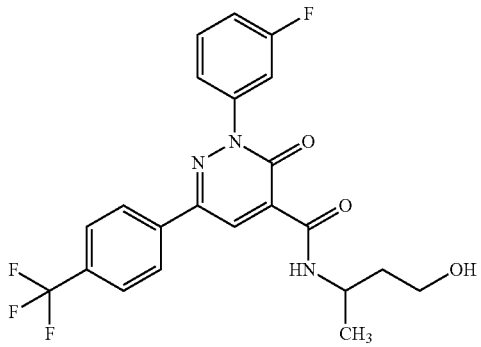 [SMILES: CC(CCO)NC(=O)c1cc(-c2ccc(C(F)(F)F)cc2)nn(-c2cccc(F)c2)c1=O]

2-(3-Fluorophenyl)-N-[(2RS)-4-hydroxybutan-2-yl]-3-oxo-6-[4-(trifluoromethyl)phenyl]-2,3-dihydropyridazine-4-carboxamide was separated by chiral HPLC (column: Chiralpak IB 5μ 250×30 mm, mobile phase: A: carbon dioxide/B: methanol, isocratic: 12% B, 100 mL/min, temperature: 40° C., BPR: 150 bar, UV: 254 nm) to yield the title compound which was further purified by RP-HPLC (column: X-Bridge C18 5 μm 100×30 mm, mobile phase: (water+0.1 vol % formic acid (99%))/acetonitrile, gradient) affording 28 mg (24%) of the title compound.

$^1$H-NMR (400 MHz, DMSO-d$_6$): δ [ppm]=1.19 (d, 3H), 1.60-1.74 (m, 2H), 3.45-3.52 (m, 2H), 4.15 (spt, 1H), 4.51 (t, 1H), 7.36-7.43 (m, 1H), 7.54-7.58 (m, 1H), 7.59-7.66 (m, 2H), 7.88 (d, 2H), 8.20 (d, 2H), 8.70 (s, 1H), 9.29 (d, 1H).

Chiral HPLC: Rt=3.33 min

Instrument: Agilent HPLC 1260: Chiralpak IB 5μ 100×4.6 mm; eluent: A: carbon dioxide/B: methanol, isocratic: 12% B, flow: 4 mL/min, temperature: 37.5° C., BPR: 100 bar, UV: 254 nm.

[α]$_D^{20}$=−16.4° (c=1.00, DMSO).

Example 256

2-(3-Fluorophenyl)-N-(2-hydroxy-2-methylpropyl)-3-oxo-6-[4-(trifluoromethyl)phenyl]-2,3-dihydro-pyridazine-4-carboxamide

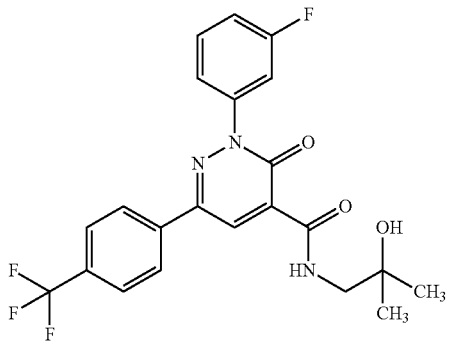 [SMILES: CC(C)(O)CNC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). 1-Amino-2-methylpropan-2-ol (33.0 mg, 0.37 mmol), N-ethyl-N-isopropylpropan-2-amine (0.145 mL, 0.83 mmol), and propane phosphonic acid anhydride (T3P, 162 μL, 50% in DMF, 278 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 54.6 mg (66%) of the title compound.

$^1$H-NMR (400 MHz, DMSO-d$_6$): δ [ppm]=1.13 (s, 6H), 3.31-3.33 (m, 2H and water signal), 4.68 (s, 1H), 7.37-7.43 (m, 1H), 7.55-7.59 (m, 1H), 7.60-7.67 (m, 2H), 7.88 (d, 2H), 8.20 (d, 2H), 8.73 (s, 1H), 9.53 (t, 1H).

Example 257

(+)-2-(3-Fluorophenyl)-N-[(2S)-1-hydroxy-3-methoxypropan-2-yl]-3-oxo-6-[4-(trifluoromethyl)phenyl]-2,3-dihydropyridazine-4-carboxamide

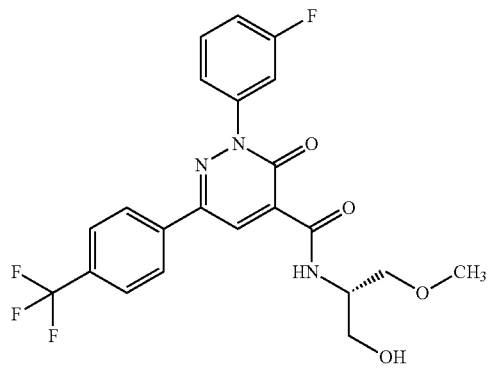 [SMILES: COC[C@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2S)-2-Amino-3-methoxypropan-1-ol (38.9 mg, 0.37 mmol), N-ethyl-N-isopropylpropan-2-amine (0.145 mL, 0.83 mmol), and propane phosphonic acid anhydride (T3P, 162 μL, 50% in DMF, 278 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 59 mg (69%) of the title compound.

$^1$H-NMR (400 MHz, DMSO-d$_6$): δ [ppm]=3.28 (s, 3H), 3.41-3.59 (m, 4H), 4.09-4.17 (m, 1H), 4.98 (t, 1H), 7.37-7.43 (m, 1H), 7.53-7.58 (m, 1H), 7.60-7.66 (m, 2H), 7.88 (d, 2H), 8.20 (d, 2H), 8.74 (s, 1H), 9.53 (d, 1H).

[α]$_D^{20}$=+5.9° (c=1.00, DMSO).

Example 258

(−)-2-(3-Fluorophenyl)-N-[(2R)-1-hydroxy-3-methoxypropan-2-yl]-3-oxo-6-[4-(trifluoromethyl)phenyl]-2,3-dihydropyridazine-4-carboxamide

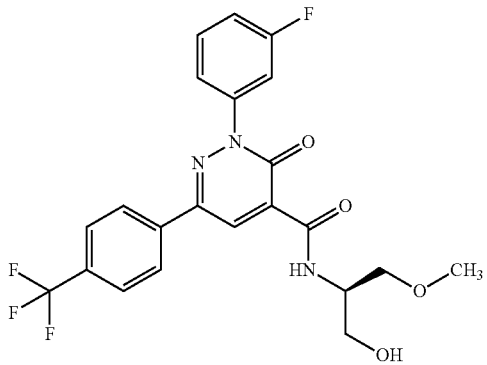 [SMILES: COC[C@@H](CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2R)-2-Amino-3-methoxypropan-1-ol (38.9 mg, 0.37 mmol), N-ethyl-N-isopropylpropan-2-amine (0.145 mL, 0.83 mmol), and propane phosphonic acid anhydride (T3P, 162 μL, 50% in DMF, 278 μmol) were successively added. It was stirred at rt overnight.

The crude reaction mixture was purified by RP-HPLC (column: X-Bridge C18 5 μm 100×30 mm, mobile phase: (water+0.2 vol % aqueous ammonia (32%))/acetonitrile, gradient) to yield 65 mg (75%) of the title compound.

$^1$H-NMR (400 MHz, DMSO-$d_6$): δ [ppm]=3.28 (s, 3H), 3.42-3.59 (m, 4H), 4.09-4.18 (m, 1H), 4.98 (t, 1H), 7.37-7.43 (m, 1H), 7.53-7.58 (m, 1H), 7.59-7.67 (m, 2H), 7.88 (d, 2H), 8.20 (d, 2H), 8.74 (s, 1H), 9.53 (d, 1H).

$[α]_D^{20}$=−3.3° (c=1.00, DMSO).

Example 259

2-(3-Fluorophenyl)-N-[(2RS)-1-hydroxy-4-methoxybutan-2-yl]-3-oxo-6-[4-(trifluoromethyl)phenyl]-2,3-dihydropyridazine-4-carboxamide

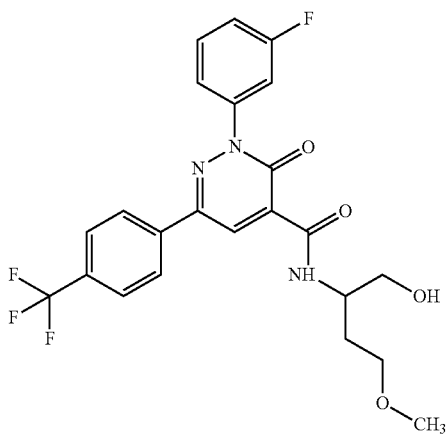 [SMILES: COCCC(CO)NC(=O)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-4-methoxybutan-1-ol (63 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.1 vol % formic acid (99%))/acetonitrile, gradient) to yield 84 mg (66%) of the title compound.

$^1$H-NMR (400 MHz, DMSO-$d_6$): δ [ppm]=1.66-1.77 (m, 1H), 1.81-1.91 (m, 1H), 3.39 (t, 2H), 3.42-3.55 (m, 2H), 4.04-4.14 (m, 1H), 4.91 (t, 1H), 7.36-7.43 (m, 1H), 7.54-7.59 (m, 1H), 7.60-7.67 (m, 2H), 7.88 (d, 2H), 8.20 (d, 2H), 8.72 (s, 1H), 9.40 (d, 1H).

Example 260

2-(3-Fluorophenyl)-3-oxo-N-[(2RS,3RS)-1,1,1-trifluoro-3-hydroxybutan-2-yl]-6-[4-(trifluoromethyl)phenyl]-2,3-dihydropyridazine-4-carboxamide or 2-(3-fluorophenyl)-3-oxo-N-[(2SR,3RS)-1,1,1-trifluoro-3-hydroxybutan-2-yl]-6-[4-(trifluoromethyl)phenyl]-2,3-dihydropyridazine-4-carboxamide

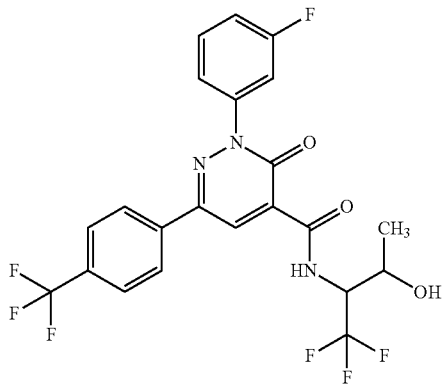 [SMILES: CC(O)C(NC(=O)c1cc(-c2ccc(C(F)(F)F)cc2)nn(-c2cccc(F)c2)c1=O)C(F)(F)F]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS,3RS)-3-Amino-4,4,4-trifluorobutan-2-ol or (2SR,3RS)-3-amino-4,4,4-trifluorobutan-2-ol (75.7 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.1 vol % formic acid (99%))/acetonitrile, gradient) to yield 119 mg (90%) of the title compound.

$^1$H-NMR (400 MHz, DMSO-d6): δ [ppm]=1.21 (d, 3H), 4.00-4.10 (m, 1H), 4.78 (td, 1H), 5.36 (d, 1H), 7.38-7.45 (m, 1H), 7.56-7.60 (m, 1H), 7.61-7.68 (m, 2H), 7.89 (d, 2H), 8.22 (d, 2H), 8.78 (s, 1H), 9.92 (d, 1H).

Example 261

N-[(2RS)-3,3-Difluoro-2-hydroxypropyl]-2-(3-fluorophenyl)-3-oxo-6-[4-(trifluoromethyl)phenyl]-2,3-dihydropyridazine-4-carboxamide

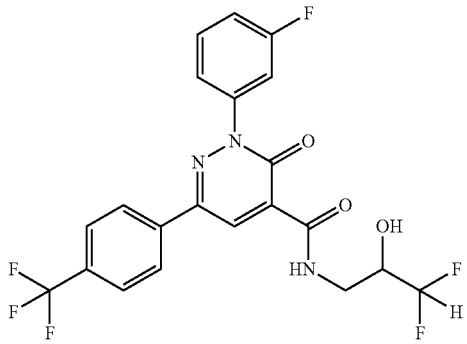 [SMILES: O=C(NCC(O)C(F)F)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-3-Amino-1,1-difluoropropan-2-ol hydrochloride (1:1) (78.0 mg, 0.53 mmol), N-ethyl-N-isopropylpropan-2-amine (0.299 mL, 1.72 mmol), and propane phosphonic acid anhydride (T3P, 231 μL, 50% in DMF, 397 μmol) were successively added. It was stirred at rt overnight.

The crude reaction mixture was purified by RP-HPLC (column: X-Bridge C18 5 μm 100×30 mm, mobile phase: (water+0.2 vol % ammonia (32%))/acetonitrile, gradient) to yield 85 mg (68%) of the title compound.

$^1$H-NMR (400 MHz, DMSO-d6): δ [ppm]=3.40 (ddd, 1H), 3.66 (dt, 1H), 3.85 (br s, 1H), 5.94 (dt, 1H), 6.00 (d, 1H), 7.37-7.43 (m, 1H), 7.55-7.59 (m, 1H), 7.60-7.67 (m, 2H), 7.89 (d, 2H), 8.20 (d, 2H), 8.73 (s, 1H), 9.56 (t, 1H).

Example 262

N-[(2RS)-1,4-Dihydroxybutan-2-yl]-2-(3-fluorophenyl)-3-oxo-6-[4-(trifluoromethyl)phenyl]-2,3-dihydropyridazine-4-carboxamide

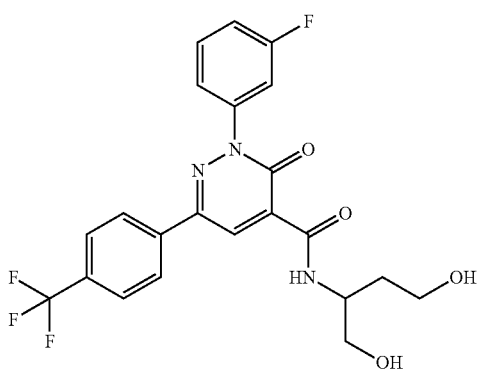 [SMILES: O=C(NC(CO)CCO)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Aminobutane-1,4-diol (55.6 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

(2RS)-2-Aminobutane-1,4-diol (20 mg, 0.36 mmol), N-ethyl-N-isopropylpropan-2-amine (0.070 mL, 0.40 mmol), and propane phosphonic acid anhydride (T3P, 080 μL, 50% in DMF, 137 μmol) were successively added. It was stirred at rt overnight.

The crude reaction mixture was purified by RP-HPLC (column: X-Bridge C18 5 μm 100×30 mm, mobile phase: (water+0.2 vol % ammonia (32%))/acetonitrile, gradient) to yield 30 mg (24%) of the title compound.

$^1$H-NMR (400 MHz, DMSO-d6): δ [ppm]=1.60-1.70 (m, 1H), 1.74-1.84 (m, 1H), 3.41-3.56 (m, 4H), 4.05-4.15 (m, 1H), 4.50 (t, 1H), 4.89 (t, 1H), 7.36-7.43 (m, 1H), 7.54-7.58 (m, 1H), 7.59-7.66 (m, 2H), 7.88 (d, 2H), 8.20 (d, 2H), 8.72 (s, 1H), 9.42 (d, 1H).

Example 263

3,6-Anhydro-2,4,5-trideoxy-2-[({2-(3-fluorophenyl)-3-oxo-6-[4-(trifluoromethyl)phenyl]-2,3-dihydropyridazin-4-yl}carbonyl)amino]-DL-erythro-hexitol and 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]-DL-threo-hexitol

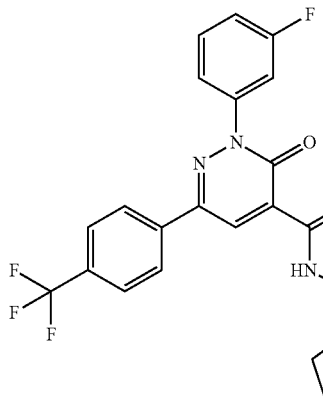

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). 5-Amino-1,4-anhydro-2,3,5-trideoxyhexitol (69.4 mg, 0.53 mmol), N-ethyl-N-isopropylpropan-2-amine (0.207 mL, 1.19 mmol), and propane phosphonic acid anhydride (T3P, 231 μL, 50% in DMF, 397 μmol) were successively added. It was stirred at rt overnight.

5-Amino-1,4-anhydro-2,3,5-trideoxyhexitol (20 mg, 0.15 mmol), N-ethyl-N-isopropylpropan-2-amine (0.105 mL, 0.60 mmol), and propane phosphonic acid anhydride (T3P, 115 μL, 50% in DMF, 198 μmol) were successively added. It was stirred at rt overnight.

The crude reaction mixture was purified by RP-HPLC (column: X-Bridge C18 5 μm 100×30 mm, mobile phase: (water+0.2 vol % ammonia (32%))/acetonitrile, gradient) to yield 30 mg (24%) of the title compound.

$^1$H-NMR (400 MHz, DMSO-d$_6$): δ [ppm]=1.60-1.70 (m, 1H), 1.74-1.84 (m, 1H), 3.41-3.56 (m, 4H), 4.05-4.15 (m, 1H), 4.50 (t, 1H), 4.89 (t, 1H), 7.36-7.43 (m, 1H), 7.54-7.58 (m, 1H), 7.59-7.66 (m, 2H), 7.88 (d, 2H), 8.20 (d, 2H), 8.72 (s, 1H), 9.42 (d, 1H).

Example 264

(−)-N-[(2S)-2,3-Dihydroxypropyl]-2-(3-fluorophenyl)-3-oxo-6-[4-(trifluoromethyl)phenyl]-2,3-dihydropyridazine-4-carboxamide

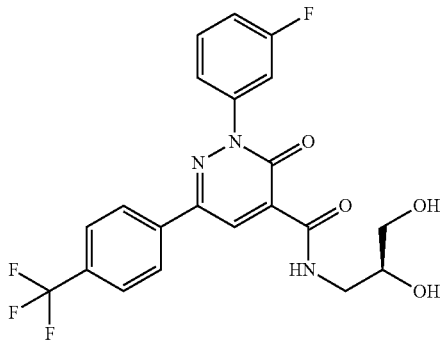 [SMILES: O=C(NC[C@H](O)CO)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2S)-3-Aminopropane-1,2-diol (33.7 mg, 0.37 mmol), N-ethyl-N-isopropylpropan-2-amine (0.145 mL, 0.83 mmol), and propane phosphonic acid anhydride (T3P, 162 µL, 50% in DMF, 278 µmol) were successively added. It was stirred at rt overnight.

The crude reaction mixture was purified by RP-HPLC (column: X-Bridge C18 5 µm 100×30 mm, mobile phase: (water+0.2 vol % ammonia (32%))/acetonitrile, gradient) to yield 51 mg (61%) of the title compound.

$^1$H-NMR (400 MHz, DMSO-$d_6$): δ [ppm]=3.19-3.43 (m, 3H and water signal), 3.55-3.65 (m, 2H), 4.69 (t, 1H), 5.01 (d, 1H), 7.36-7.43 (m, 1H), 7.54-7.59 (m, 1H), 7.59-7.67 (m, 2H), 7.88 (d, 2H), 8.20 (d, 2H), 8.72 (s, 1H), 9.52 (t, 1H). $[α]_D^{20}$=−8.1° (c=1.00, DMSO).

Example 265

(+)-N-[(2R)-2,3-Dihydroxypropyl]-2-(3-fluorophenyl)-3-oxo-6-[4-(trifluoromethyl)phenyl]-2,3-dihydropyridazine-4-carboxamide

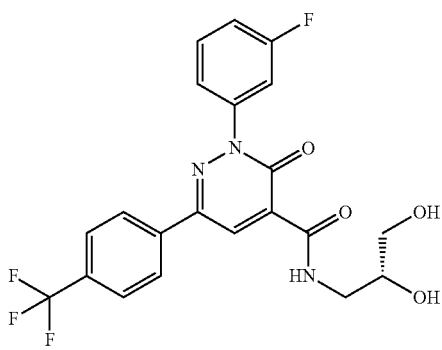 [SMILES: O=C(NC[C@@H](O)CO)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (70 mg, 0.19 mmol) was dissolved in anhydrous DMF (1.4 mL). (2R)-3-Aminopropane-1,2-diol (33.7 mg, 0.37 mmol), N-ethyl-N-isopropylpropan-2-amine (0.145 mL, 0.83 mmol), and propane phosphonic acid anhydride (T3P, 162 µL, 50% in DMF, 278 µmol) were successively added. It was stirred at rt overnight.

The crude reaction mixture was purified by RP-HPLC (column: X-Bridge C18 5 µm 100×30 mm, mobile phase: (water+0.2 vol % ammonia (32%))/acetonitrile, gradient) to yield 57 mg (68%) of the title compound.

$^1$H-NMR (400 MHz, DMSO-$d_6$): δ [ppm]=3.19-3.43 (m, 3H and water signal), 3.55-3.65 (m, 2H), 4.69 (t, 1H), 5.01 (d, 1H), 7.36-7.43 (m, 1H), 7.55-7.59 (m, 1H), 7.60-7.66 (m, 2H), 7.88 (d, 2H), 8.20 (d, 2H), 8.72 (s, 1H), 9.52 (t, 1H). $[α]_D^{20}$=+18.3° (c=1.00, DMSO).

Example 266

2-(3-Fluorophenyl)-3-oxo-N-[(2RS)-1,1,1-trifluoro-3-hydroxypropan-2-yl]-6-[4-(trifluoromethyl)phenyl]-2,3-dihydropyridazine-4-carboxamide

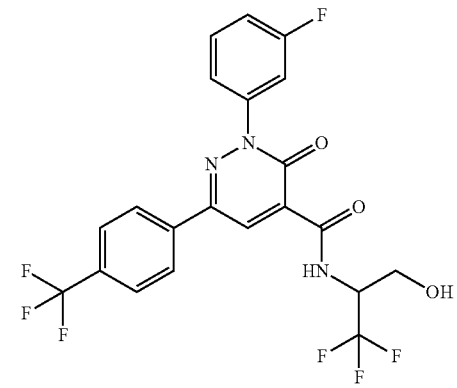 [SMILES: O=C(NC(CO)C(F)(F)F)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-3,3,3-trifluoropropan-1-ol hydrochloride (1:1) (87.5 mg, 0.53 mmol), N-ethyl-N-isopropylpropan-2-amine (0.299 mL, 1.72 mmol), and propane phosphonic acid anhydride (T3P, 231 µL, 50% in DMF, 397 µmol) were successively added. It was stirred at rt overnight.

The crude reaction mixture was purified by RP-HPLC (column: X-Bridge C18 5 µm 100×30 mm, mobile phase: (water+0.2 vol % ammonia (32%))/acetonitrile, gradient) to yield 85 mg (66%) of the title compound.

$^1$H-NMR (400 MHz, DMSO-$d_6$): δ [ppm]=3.66-3.74 (m, 1H), 3.83 (dt, 1H), 4.80-4.92 (m, 1H), 5.44 (t, 1H), 7.38-7.45 (m, 1H), 7.55-7.59 (m, 1H), 7.61-7.68 (m, 2H), 7.89 (d, 2H), 8.22 (d, 2H), 8.79 (s, 1H), 9.99 (d, 1H).

Example 267

N-[(1RS)-1-Cyclopropyl-2-hydroxyethyl]-2-(3-fluorophenyl)-3-oxo-6-[4-(trifluoromethyl)phenyl]-2,3-dihydropyridazine-4-carboxamide

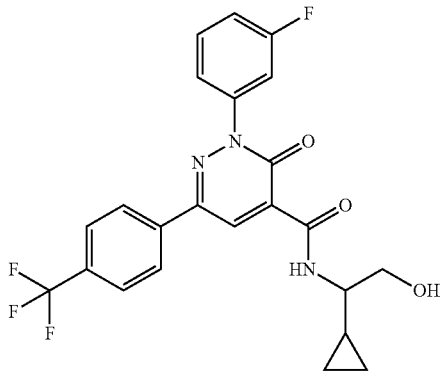 [SMILES: O=C(NC(CO)C1CC1)c1cc(-c2ccc(C(F)(F)F)cc2)nn(-c2cccc(F)c2)c1=O]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-2-cyclopropylethanol hydrochloride (1:1) (72.8 mg, 0.53 mmol), N-ethyl-N-isopropylpropan-2-amine (0.299 mL, 1.72 mmol), and propane phosphonic acid anhydride (T3P, 231 µL, 50% in DMF, 397 µmol) were successively added. It was stirred at rt overnight.

The crude reaction mixture was purified by RP-HPLC (column: X-Bridge C18 5 µm 100×30 mm, mobile phase: (water+0.2 vol % ammonia (32%))/acetonitrile, gradient) to yield 84 mg (69%) of the title compound.

$^1$H-NMR (400 MHz, DMSO-d$_6$): δ [ppm]=0.26-0.50 (m, 4H), 1.03-1.13 (m, 1H), 3.41-3.48 (m, 1H), 3.52-3.62 (m, 2H), 4.93 (t, 1H), 7.37-7.43 (m, 1H), 7.55-7.58 (m, 1H), 7.60-7.67 (m, 2H), 7.88 (d, 2H), 8.20 (d, 2H), 8.73 (s, 1H), 9.55 (d, 1H).

Example 268

Isomer no. 1 of 2-(3-fluorophenyl)-3-oxo-N-(4,4,4-trifluoro-3-hydroxybutan-2-yl)-6-[4-(trifluoromethyl)phenyl]-2,3-dihydropyridazine-4-carboxamide

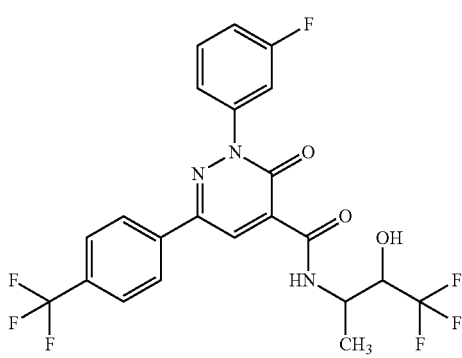

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-2-cyclopropylethanolhydrochloride (1:1) (72.8 mg, 0.53 mmol), N-ethyl-N-isopropylpropan-2-amine (0.299 mL, 1.72 mmol), and propane phosphonic acid anhydride (T3P, 231 µL, 50% in DMF, 397 µmol) were successively added. It was stirred at rt overnight.

The crude material was separated by chiral HPLC (column: Chiralpak IB 5µ 250×30 mm, mobile phase: A: carbon dioxide/B: isopropanol, isocratic: 7% B, 100 mL/min, temperature: 40° C., BPR: 150 bar, UV: 254 nm) to yield 42.3 mg (32%) of the title compound.

$^1$H-NMR (400 MHz, DMSO-d$_6$): δ [ppm]=1.22 (d, 3H), 4.13-4.24 (m, 1H), 4.31-4.41 (m, 1H), 6.72 (d, 1H), 7.37-7.44 (m, 1H), 7.54-7.59 (m, 1H), 7.60-7.67 (m, 2H), 7.89 (d, 2H), 8.20 (d, 2H), 8.74 (s, 1H), 9.59 (d, 1H).

Chiral HPLC: Rt=2.78 min

Instrument: Agilent HPLC 1260: Chiralpak IB 5µ 100×4.6 mm; eluent: A: carbon dioxide/B: isopropanol, isocratic: 7% B, flow: 4 mL/min, temperature: 37.5° C., BPR: 100 bar, UV: 254 nm.

$[\alpha]_D^{20}$=+13.1° (c=1.00, DMSO).

Example 269

Isomer no. 2 of 2-(3-fluorophenyl)-3-oxo-N-(4,4,4-trifluoro-3-hydroxybutan-2-yl)-6-[4-(trifluoromethyl)phenyl]-2,3-dihydropyridazine-4-carboxamide

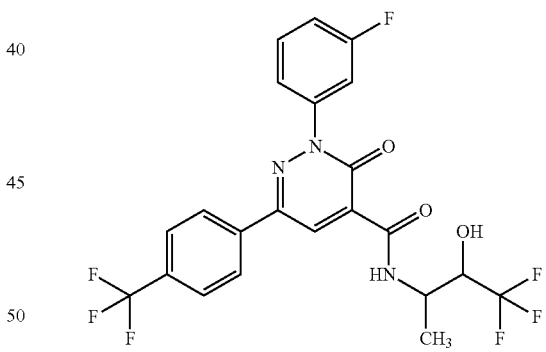

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-2-cyclopropylethanolhydrochloride (1:1) (72.8 mg, 0.53 mmol), N-ethyl-N-isopropylpropan-2-amine (0.299 mL, 1.72 mmol), and propane phosphonic acid anhydride (T3P, 231 µL, 50% in DMF, 397 µmol) were successively added. It was stirred at rt overnight.

The crude material was separated by chiral HPLC (column: Chiralpak IB 5µ 250×30 mm, mobile phase: A: carbon dioxide/B: isopropanol, isocratic: 7% B, 100 mL/min, temperature: 40° C., BPR: 150 bar, UV: 254 nm) to yield 17.1 mg (13%) of the title compound.

¹H-NMR (400 MHz, DMSO-d₆): δ [ppm]=1.25 (d, 3H), 4.09-4.20 (m, 1H), 4.39-4.48 (m, 1H), 6.92 (d, 1H), 7.37-7.44 (m, 1H), 7.54-7.58 (m, 1H), 7.59-7.67 (m, 2H), 7.88 (d, 2H), 8.19 (d, 2H), 8.74 (s, 1H), 9.73 (d, 1H).

Chiral HPLC: Rt=3.49 min

Instrument: Agilent HPLC 1260: Chiralpak IB 5μ 100× 4.6 mm; eluent: A: carbon dioxide/B: isopropanol, isocratic: 7% B, flow: 4 mL/min, temperature: 37.5° C., BPR: 100 bar, UV: 254 nm.

$[\alpha]_D^{20}$=+11.5° (c=1.00, DMSO).

Example 270

Isomer no. 3 of 2-(3-fluorophenyl)-3-oxo-N-(4,4,4-trifluoro-3-hydroxybutan-2-yl)-6-[4-(trifluoromethyl)phenyl]-2,3-dihydropyridazine-4-carboxamide

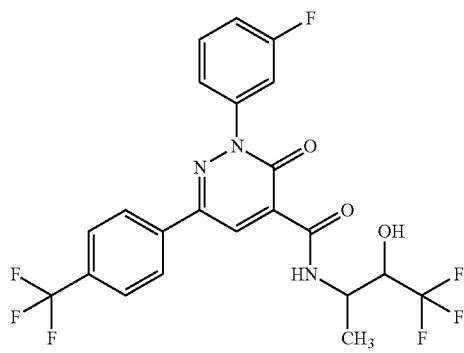 [SMILES: CC(NC(=O)c1cc(-c2ccc(C(F)(F)F)cc2)nn(-c2cccc(F)c2)c1=O)C(O)C(F)(F)F]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-2-cyclopropylethanolhydrochloride (1:1) (72.8 mg, 0.53 mmol), N-ethyl-N-isopropylpropan-2-amine (0.299 mL, 1.72 mmol), and propane phosphonic acid anhydride (T3P, 231 μL, 50% in DMF, 397 μmol) were successively added. It was stirred at rt overnight.

The crude material was separated by chiral HPLC (column: Chiralpak IB 5μ 250×30 mm, mobile phase: A: carbon dioxide/B: isopropanol, isocratic: 7% B, 100 mL/min, temperature: 40° C., BPR: 150 bar, UV: 254 nm) yielding the title product which was further purified by RP-HPLC (column: X-Bridge C18 5 μm 100×30 mm, mobile phase: (water+0.2 vol % ammonia (32%))/acetonitrile, gradient) to afford 9.6 mg (7%) of the title compound.

¹H-NMR (400 MHz, DMSO-d₆): δ [ppm]=1.25 (d, 3H), 4.09-4.19 (m, 1H), 4.39-4.48 (m, 1H), 6.92 (d, 1H), 7.41 (s, 1H), 7.54-7.58 (m, 1H), 7.59-7.66 (m, 2H), 7.88 (d, 2H), 8.19 (d, 2H), 8.74 (s, 1H), 9.73 (d, 1H).

Chiral HPLC: Rt=4.64 min

Instrument: Agilent HPLC 1260: Chiralpak IB 5μ 100× 4.6 mm; eluent: A: carbon dioxide/B: isopropanol, isocratic: 7% B, flow: 4 mL/min, temperature: 37.5° C., BPR: 100 bar, UV: 254 nm.

$[\alpha]_D^{20}$=-3.4° (c=1.00, DMSO).

Example 271

Isomer no. 4 of 2-(3-fluorophenyl)-3-oxo-N-(4,4,4-trifluoro-3-hydroxybutan-2-yl)-6-[4-(trifluoromethyl)phenyl]-2,3-dihydropyridazine-4-carboxamide

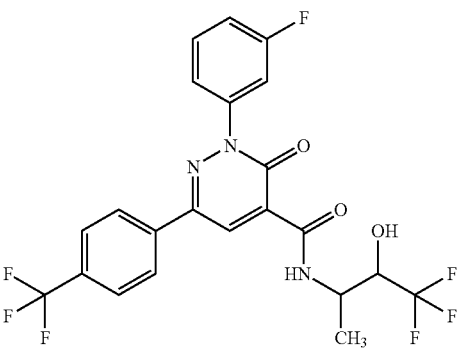 [SMILES: CC(NC(=O)c1cc(-c2ccc(C(F)(F)F)cc2)nn(-c2cccc(F)c2)c1=O)C(O)C(F)(F)F]

2-(3-Fluorophenyl)-3-oxo-6-[4-(trifluoromethyl)phenyl]-2,3-dihydropyridazine-4-carboxylic acid (100 mg, 0.26 mmol) was dissolved in anhydrous DMF (2.0 mL). (2RS)-2-Amino-2-cyclopropylethanolhydrochloride (1:1) (72.8 mg, 0.53 mmol), N-ethyl-N-isopropylpropan-2-amine (0.299 mL, 1.72 mmol), and propane phosphonic acid anhydride (T3P, 231 μL, 50% in DMF, 397 μmol) were successively added. It was stirred at rt overnight.

The crude material was separated by chiral HPLC (column: Chiralpak IB 5μ 250×30 mm, mobile phase: A: carbon dioxide/B: isopropanol, isocratic: 7% B, 100 mL/min, temperature: 40° C., BPR: 150 bar, UV: 254 nm) yielding the title product which was further purified by RP-HPLC (column: X-Bridge C18 5 μm 100×30 mm, mobile phase: (water+0.2 vol % ammonia (32%))/acetonitrile, gradient) to afford 24.3 mg (18%) of the title compound.

¹H-NMR (400 MHz, DMSO-d₆): δ [ppm]=1.22 (d, 3H), 4.13-4.24 (m, 1H), 4.31-4.41 (m, 1H), 6.72 (d, 1H), 7.41 (br d, 1H), 7.54-7.58 (m, 1H), 7.60-7.67 (m, 2H), 7.89 (d, 2H), 8.20 (d, 2H), 8.74 (s, 1H), 9.59 (d, 1H).

Chiral HPLC: Rt=6.66 min

Instrument: Agilent HPLC 1260: Chiralpak IB 5μ 100× 4.6 mm; eluent: A: carbon dioxide/B: isopropanol, isocratic: 7% B, flow: 4 mL/min, temperature: 37.5° C., BPR: 100 bar, UV: 254 nm.

$[\alpha]_D^{20}$=-9.5° (c=1.00, DMSO).

The following examples were prepared from the starting materials stated in the table using the procedure described in example 164. Enantiomers were separated from their racemate by chiral HPLC using the column and solvent conditions stated.

TABLE 4

Examples 272-312

| Example | structure | IUPAC name | Starting materials | analytics |
|---|---|---|---|---|
| 272 | 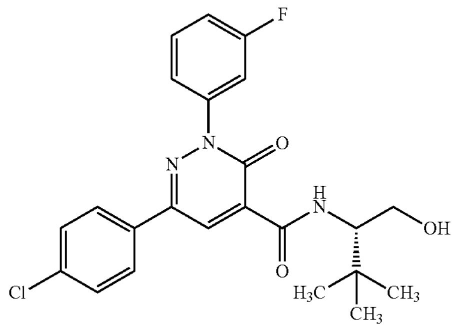 [SMILES: CC(C)(C)[C@@H](CO)NC(=O)c1cc(-c2ccc(Cl)cc2)nn(-c2cccc(F)c2)c1=O] | 6-(4-Chlorophenyl)-2-(3-fluorophenyl)-N-[(2S)-1-hydroxy-3,3-dimethylbutan-2-yl]-3-oxo-2,3-dihydropyridazine-4-carboxamide | 6-(4-Chlorophenyl)-2-(3-fluorophenyl)-3-oxo-2,3-dihydropyridazine-4-carboxylic acid; (2S)-2-amino-3,3-dimethylbutan-1-ol | $^1$H NMR (400 MHz, DMSO-d6) δ ppm 0.94 (s, 9 H), 3.44-3.52 (m, 1 H), 3.59-3.67 (m, 1 H), 3.87 (ddd, 1 H), 4.65 (t, 1 H), 7.36-7.43 (m, 1 H), 7.54-7.67 (m, 5 H), 7.97-8.03 (m, 2 H), 8.67 (s, 1 H), 9.46 (d, 1 H) |
| 273 | 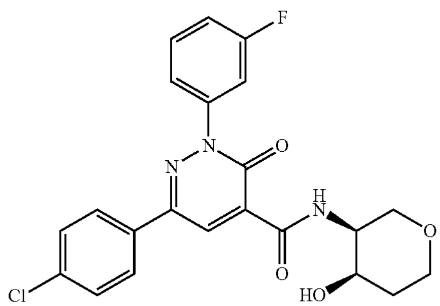 [SMILES: O=C(N[C@H]1COCC[C@H]1O)c1cc(-c2ccc(Cl)cc2)nn(-c2cccc(F)c2)c1=O] | 1,5-Anhydro-2-({[6-(4-chlorophenyl)-2-(3-fluorophenyl)-3-oxo-2,3-dihydropyridazin-4-yl]carbonyl}amino)-2,4-dideoxy-D-erythro-pentitol | 6-(4-Chlorophenyl)-2-(3-fluorophenyl)-3-oxo-2,3-dihydropyridazine-4-carboxylic acid; (3S,4R)-3-aminooxan-4-ol hydrochloride | $^1$H NMR (400 MHz, DMSO-d$_6$) δ ppm 1.57-1.66 (m, 1 H), 1.71-1.81 (m, 1 H), 3.47-3.53 (m, 1 H), 3.55 (d, 2 H), 3.65-3.73 (m, 1 H), 3.89-3.95 (m, 1 H), 4.03-4.11 (m, 1 H), 5.23 (br d, 1 H), 7.39 (tdd, 1 H), 7.52-7.66 (m, 6 H), 7.97-8.01 (m, 2 H), 8.67 (s, 1 H), 9.69 (d, 1 H) |
| 274 | 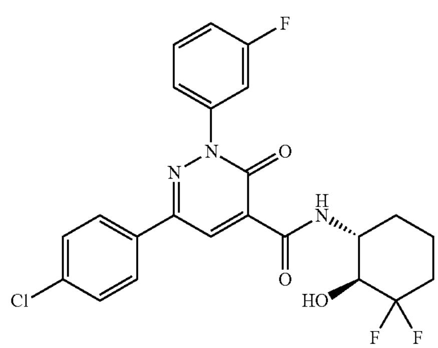 [SMILES: O=C(N[C@@H]1CCCC(F)(F)[C@H]1O)c1cc(-c2ccc(Cl)cc2)nn(-c2cccc(F)c2)c1=O] | 6-(4-Chlorophenyl)-N-[(trans)-3,3-difluoro-2-hydroxycyclohexyl]-2-(3-fluorophenyl)-3-oxo-2,3-dihydropyridazine-4-carboxamide | 6-(4-Chlorophenyl)-2-(3-fluorophenyl)-3-oxo-2,3-dihydropyridazine-4-carboxylic acid; rel-(1R,6S)-6-amino-2,2-difluorocyclohexan-1-ol hydrochloride | $^1$H NMR (400 MHz, DMSO-d$_6$) δ ppm 1.47 (br t, 2 H), 1.66 (br s, 1 H), 1.72-1.90 (m, 1 H), 1.93-2.10 (m, 2 H), 3.75 (br d, 1 H), 3.96 (br s, 1 H), 5.78 (br d, 1 H), 7.35-7.44 (m, 1 H), 7.52-7.67 (m, 5 H), 8.00 (d, 2 H), 8.66 (s, 1 H), 9.55 (br d, 1 H) |
| 275 | 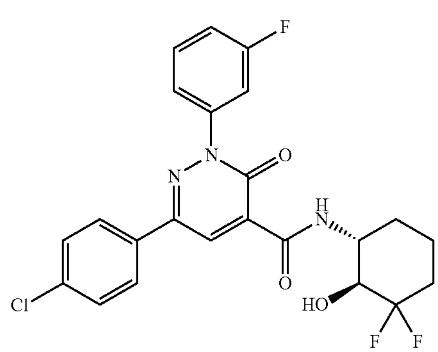 [SMILES: O=C(N[C@@H]1CCCC(F)(F)[C@H]1O)c1cc(-c2ccc(Cl)cc2)nn(-c2cccc(F)c2)c1=O] | 6-(4-Chlorophenyl)-N-[(trans)-3,3-difluoro-2-hydroxycyclohexyl]-2-(3-fluorophenyl)-3-oxo-2,3-dihydropyridazine-4-carboxamide, Enantiomer 1 | 6-(4-Chlorophenyl)-N-[(trans)-3,3-difluoro-2-hydroxycyclohexyl]-2-(3-fluorophenyl)-3-oxo-2,3-dihydropyridazine-4-carboxamide | preparation: instrument: Sepiatec: Prep SFC100; column: Chiralpak IB 5 μm 250 × 30 mm; eluent A: CO2, eluent B: methanol; isocratic: 24% B; flow 100.0 mL/min temperature: 40° C.; BPR: 150 bar; MWD @ 254 nm analytics: instrument: Agilent: 1260, Aurora SFC-Modul; column: Chiralpak IB 5 μm 100 × 4.6 mm; |

TABLE 4-continued

Examples 272-312

| Example | structure | IUPAC name | Starting materials | analytics |
|---|---|---|---|---|
| | | | | eluent A: CO2, eluent B: methanol; Isocratic: 24% B; flow 4.0 mL/min; temperature: 37.5° C.; BPR: 100 bar; MWD @ 254 nm rt = 2.01 min |
| 276 | 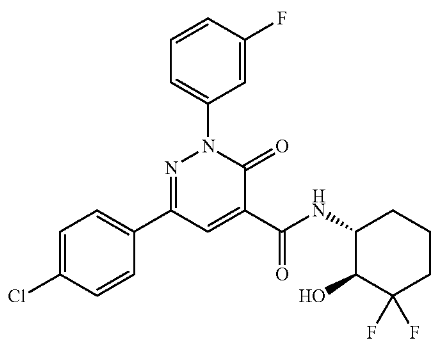 [SMILES: O=C(N[C@@H]1CCCC(F)(F)[C@H]1O)c1cc(-c2ccc(Cl)cc2)nn(-c2cccc(F)c2)c1=O] | 6-(4-Chlorophenyl)-N-[(trans)-3,3-difluoro-2-hydroxycyclohexyl]-2-(3-fluorophenyl)-3-oxo-2,3-dihydropyridazine-4-carboxamide, Enantiomer 2 | 6-(4-Chlorophenyl)-N-[(trans)-3,3-difluoro-2-hydroxycyclohexyl]-2-(3-fluorophenyl)-3-oxo-2,3-dihydropyridazine-4-carboxamide | preparation and analytics see example 275 rt = 5.56 min |
| 277 | 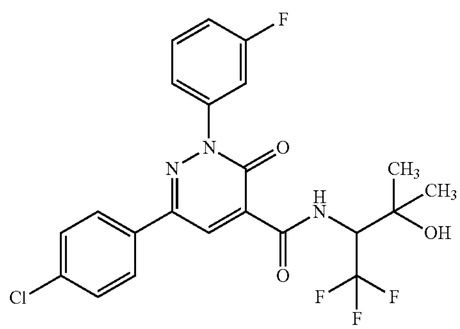 [SMILES: CC(C)(O)C(NC(=O)c1cc(-c2ccc(Cl)cc2)nn(-c2cccc(F)c2)c1=O)C(F)(F)F] | 6-(4-Chlorophenyl)-2-(3-fluorophenyl)-3-oxo-N-(1,1,1-trifluoro-3-hydroxy-3-methylbutan-2-yl)-2,3-dihydropyridazine-4-carboxamide | 6-(4-Chlorophenyl)-2-(3-fluorophenyl)-3-oxo-2,3-dihydropyridazine-4-carboxylic acid; 3-amino-4,4,4-trifluoro-2-methylbutan-2-ol hydrochloride | $^1$H NMR (400 MHz, DMSO-$d_6$) δ ppm 1.19 (s, 3 H), 1.34 (s, 3 H), 4.66 (quin, 1 H), 5.21 (s, 1 H), 7.36-7.44 (m, 1 H), 7.54-7.67 (m, 5 H), 7.99-8.05 (m, 2 H), 8.72 (s, 1 H), 10.05 (d, 1 H) |
| 278 | 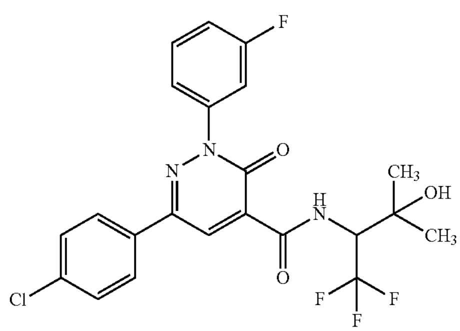 [SMILES: CC(C)(O)C(NC(=O)c1cc(-c2ccc(Cl)cc2)nn(-c2cccc(F)c2)c1=O)C(F)(F)F] | 6-(4-Chlorophenyl)-2-(3-fluorophenyl)-3-oxo-N-(1,1,1-trifluoro-3-hydroxy-3-methylbutan-2-yl)-2,3-dihydropyridazine-4-carboxamide, Enantiomer 1 | 6-(4-Chlorophenyl)-2-(3-fluorophenyl)-3-oxo-N-(1,1,1-trifluoro-3-hydroxy-3-methylbutan-2-yl)-2,3-dihydropyridazine-4-carboxamide | preparation: instrument: Labomatic HD5000, Labocord-5000; Gilson GX-241, Labcol Vario 4000, column: Amylose SA 5μ 250 × 30 mm; eluent A: ethanol + 0.1 Vol-% diethylamin (99%); eluent B: methanol + 0.1 Vol-% diethylamin (99%); isocratic: 50% A + 50% B; flow 30.0 mL/min; UV 254 nm; analytics: instrument: Agilent HPLC 1260; column: Amylose SA 3μ 100 × 4.6 mm; eluent A: methanol + 0.1 |

TABLE 4-continued

Examples 272-312

| Example | structure | IUPAC name | Starting materials | analytics |
|---|---|---|---|---|
| | | | | Vol-% diethylamin (99%); eluent B: ethanol; isocratic: 50% A + 50% B; flow 1.4 mL/min; temperature: 25° C.; DAD 254 nm rt = 1.30 min |
| 279 | 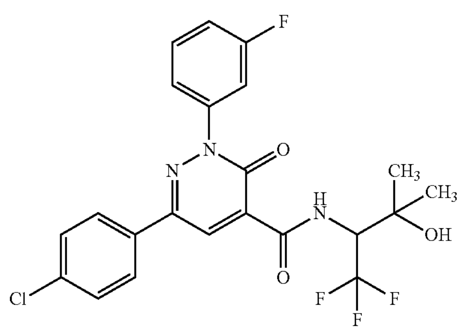 [SMILES: CC(C)(O)C(NC(=O)c1cc(-c2ccc(Cl)cc2)nn(-c2cccc(F)c2)c1=O)C(F)(F)F] | 6-(4-Chlorophenyl)-2-(3-fluorophenyl)-3-oxo-N-(1,1,1-trifluoro-3-hydroxy-3-methylbutan-2-yl)-dihydropyridazine-4-carboxamide, Enantiomer 2 | 6-(4-Chlorophenyl)-2-(3-fluorophenyl)-3-oxo-N-(1,1,1-trifluoro-3-hydroxy-3-methylbutan-2-yl)-2,3-dihydropyridazine-4-carboxamide | preparation and analytics see example 278; rt = 1.67 |
| 280 | 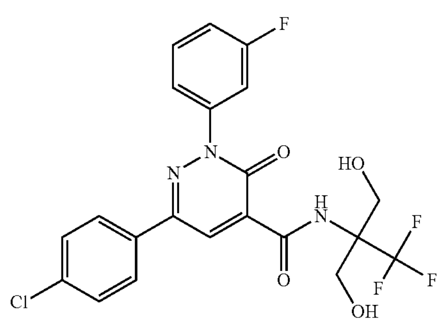 [SMILES: O=C(NC(CO)(CO)C(F)(F)F)c1cc(-c2ccc(Cl)cc2)nn(-c2cccc(F)c2)c1=O] | 6-(4-Chlorophenyl)-2-(3-fluorophenyl)-3-oxo-N-[1,1,1-trifluoro-3-hydroxy-2-(hydroxymethyl)propan-2-yl]-2,3-dihydropyridazine-4-carboxamide | 6-(4-Chlorophenyl)-2-(3-fluorophenyl)-3-oxo-2,3-dihydropyridazine-4-carboxylic acid; 2-amino-2-(trifluoromethyl)propane-1,3-diol | $^1$H NMR (400 MHz, DMSO-$d_6$) δ ppm 3.88 (dd, 2 H), 3.99-4.05 (dd, 2 H), 5.38 (dd, 2 H), 7.36-7.43 (m, 1 H), 7.53-7.65 (m, 6 H), 8.00 (d, 2 H), 8.71 (s, 1 H), 10.10 (s, 1 H) |
| 281 | 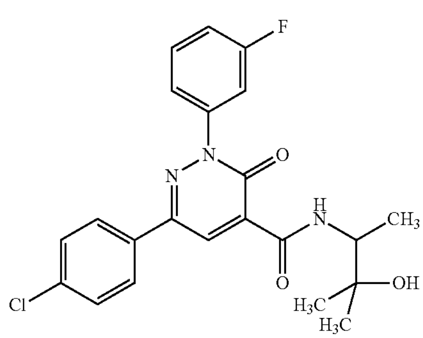 [SMILES: CC(NC(=O)c1cc(-c2ccc(Cl)cc2)nn(-c2cccc(F)c2)c1=O)C(C)(C)O] | 6-(4-Chlorophenyl)-2-(3-fluorophenyl)-N-(3-hydroxy-3-methylbutan-2-yl)-3-oxo-2,3-dihydropyridazine-4-carboxamide | 6-(4-Chlorophenyl)-2-(3-fluorophenyl)-3-oxo-2,3-dihydropyridazine-4-carboxylic acid; 3-amino-2-methylbutan-2-ol hydrochlorid | $^1$H NMR (400 MHz, DMSO-$d_6$) δ ppm 1.07-1.18 (m, 9 H), 3.86-3.96 (m, 1 H), 4.65 (s, 1 H), 7.35-7.42 (m, 1 H), 7.53-7.66 (m, 5 H), 7.97-8.02 (m, 2 H), 8.66 (s, 1 H), 9.54 (d, 1 H) |

TABLE 4-continued

Examples 272-312

| Example | structure | IUPAC name | Starting materials | analytics |
|---|---|---|---|---|
| 282 | 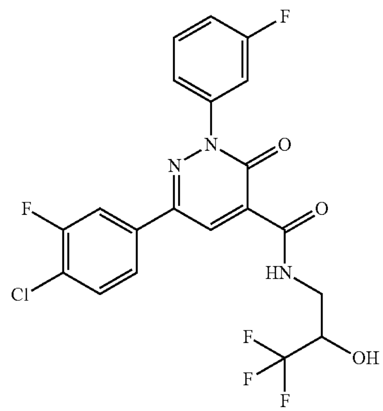 [SMILES: O=C(NCC(O)C(F)(F)F)c1cc(-c2ccc(Cl)c(F)c2)nn(-c2cccc(F)c2)c1=O] | 6-(4-chloro-3-fluorophenyl)-2-(3-fluorophenyl)-3-oxo-N-(3,3,3-trifluoro-2-hydroxypropyl)-2,3-dihydropyridazine-4-carboxamide | 6-(4-Chloro-3-fluorophenyl)-2-(3-fluorophenyl)-3-oxo-2,3-dihydropyridazine-4-carboxylic acid: 3-amino-1,1,1-trifluoro-2-propanol | $^1$H NMR (400 MHz, DMSO-$d_6$) δ ppm 3.43-3.51 (m, 1 H), 3.75 (dt, 1 H), 4.17-4.28 (m, 1 H), 6.67 (br d, 1 H), 7.35-7.44 (m, 1 H), 7.54-7.68 (m, 3 H), 7.70-7.77 (m, 1 H), 7.86 (br d, 1 H), 8.02-8.08 (m, 1 H), 8.70 (s, 1 H), 9.61 (br t, 1 H) |
| 283 | 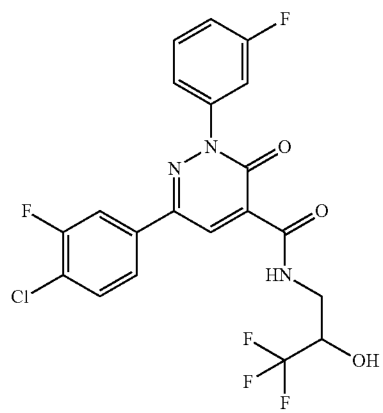 [SMILES: O=C(NCC(O)C(F)(F)F)c1cc(-c2ccc(Cl)c(F)c2)nn(-c2cccc(F)c2)c1=O] | 6-(4-chloro-3-fluorophenyl)-2-(3-fluorophenyl)-3-oxo-N-(3,3,3-trifluoro-2-hydroxypropyl)-2,3-dihydropyridazine-4-carboxamide, Enantiomer 1 | 6-(4-chloro-3-fluorophenyl)-2-(3-fluorophenyl)-3-oxo-N-(3,3,3-trifluoro-2-hydroxypropyl)-2,3-dihydropyridazine-4-carboxamide | preparation: instrument: Sepiatec: Prep SFC100; column: Chiralpak IB 5 μm 250 × 30 mm; eluent A CO2, eluent B: 2-propanol; isocratic: 12% B; flow 100.0 mL/min temperature: 40° C.; BPR: 150 bar; MWD 254 nm; analytics: instrument: Agilent: 1260, Aurora SFC-Modul; column: Chiralpak IB 5 μm 100 × 4.6 mm; eluent A: CO2, eluent B: 2-propanol; isocratic: 12% B; flow 4.0 mL/min; temperature: 37.5° C.; BPR: 100 bar; MWD 254 nm rt = 2.50 min |
| 284 | 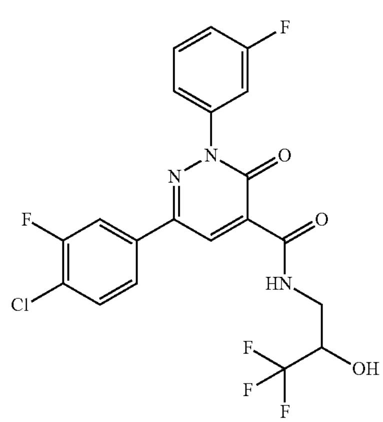 [SMILES: O=C(NCC(O)C(F)(F)F)c1cc(-c2ccc(Cl)c(F)c2)nn(-c2cccc(F)c2)c1=O] | 6-(4-chloro-3-fluorophenyl)-2-(3-fluorophenyl)-3-oxo-N-(3,3,3-trifluoro-2-hydroxypropyl)-2,3-dihydropyridazine-4-carboxamide, Enantiomer 2 | 6-(4-chloro-3-fluorophenyl)-2-(3-fluorophenyl)-3-oxo-N-(3,3,3-trifluoro-2-hydroxypropyl)-2,3-dihydropyridazine-4-carboxamide | preparation and analytics see example 283; rt = 3.69 min |

TABLE 4-continued

Examples 272-312

| Example | structure | IUPAC name | Starting materials | analytics |
|---|---|---|---|---|
| 285 | 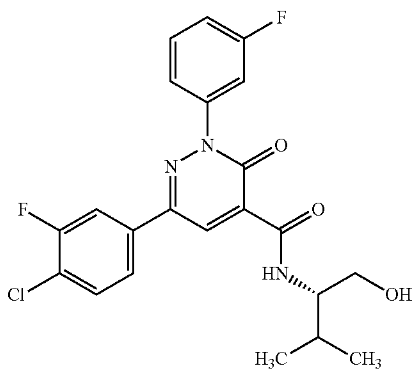 [SMILES: CC(C)[C@@H](CO)NC(=O)c1cc(-c2ccc(Cl)c(F)c2)nn(-c2cccc(F)c2)c1=O] | 6-(4-Chloro-3-fluorophenyl)-2-(3-fluorophenyl)-N-[(2S)-1-hydroxy-3-methylbutan-2-yl]-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; (S)-(+)-2-amino-3-methyl-1-butanol | $^1$H NMR (400 MHz, DMSO-$d_6$) δ ppm 0.88 (d, 3 H), 0.92 (d, 3 H), 1.96 (dq, 1 H), 3.42-3.49 (m, 1 H), 3.51-3.58 (m, 1 H), 3.85 (dd, 1 H), 4.82 (t, 1 H), 7.35-7.42 (m, 1 H), 7.54-7.67 (m, 3 H), 7.70-7.76 (m, 1 H), 7.85 (dd, 1 H), 8.04 (dd, 1 H), 8.69 (s, 1 H), 9.37 (d, 1 H) |
| 286 | 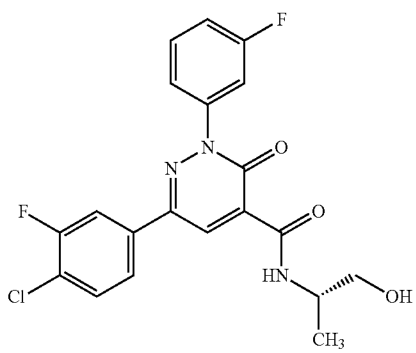 [SMILES: C[C@@H](CO)NC(=O)c1cc(-c2ccc(Cl)c(F)c2)nn(-c2cccc(F)c2)c1=O] | 6-(4-Chloro-3-fluorophenyl)-2-(3-fluorophenyl)-N-[(2S)-1-hydroxypropan-2-yl]-3-oxo-2,3-dihydropyridazine-4-carboxamide | VOIG6987-1-2 6-(4-Chloro-3-fluorophenyl)-2-(3-fluorophenyl)-3-oxo-2,3-dihydropyridazine-4-carboxylic acid; (S)-(+)-2-Amino-1-propanol (L-Alaninol) | $^1$H NMR (400 MHz, DMSO-$d_6$) δ ppm 1.16 (d, 3 H), 3.98-4.07 (m, 1 H), 4.96 (t, 1 H), 7.35-7.42 (m, 1 H), 7.54-7.66 (m, 3 H), 7.71-7.76 (m, 1 H), 7.85 (dd, 1 H), 8.04 (dd, 1 H), 8.68 (s, 1 H), 9.40 (d, 1 H) |
| 287 | 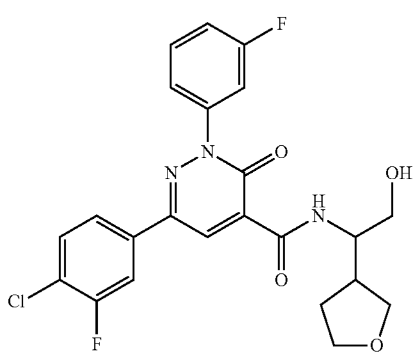 [SMILES: O=C(NC(CO)C1CCOC1)c1cc(-c2ccc(Cl)c(F)c2)nn(-c2cccc(F)c2)c1=O] | 6-(4-Chloro-3-fluorophenyl)-2-(3-fluorophenyl)-N-[2-hydroxy-1-[tetrahydrofuran-3-yl]ethyl]-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; 2-amino-2-(tetrahydrofuran-3-yl)-ethanol | LC-MS (instrument: Waters Acquity UPLC-MS SQD 3001; column: Acquity UPLC BEH C18 1.7 50 × 2.1 mm; eluent A: Water + 0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt = 1.27 min; MS (ESIpos): m/z = 476.4 [M + H]+ |

TABLE 4-continued

Examples 272-312

| Example | structure | IUPAC name | Starting materials | analytics |
|---|---|---|---|---|
| 288 | 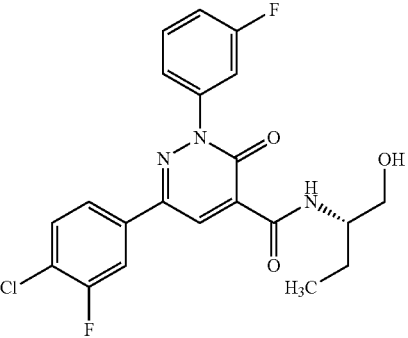 [SMILES: CC[C@@H](CO)NC(=O)c1cc(-c2ccc(Cl)c(F)c2)nn(-c2cccc(F)c2)c1=O] | 6-(4-Chloro-3-fluorophenyl)-2-(3-fluorophenyl)-N-[(2S)-1-hydroxybutan-2-yl]-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; (S)-(+)-2-amino-1-butanol | $^1$H NMR (400 MHz, DMSO-d6) δ ppm 0.89 (t, 3 H), 1.42-1.55 (m, 1 H), 1.59-1.71 (m, 1 H), 3.42 (dt, 1 H), 3.48-3.55 (m, 1 H), 3.84-3.95 (m, 1 H), 4.87 (t, 1 H), 7.35-7.43 (m, 1 H), 7.54-7.67 (m, 3 H), 7.70-7.77 (m, 1 H), 7.85 (dd, 1 H), 8.05 (dd, 1 H), 8.68 (s, 1 H), 9.33 (d, 1 H) |
| 289 | 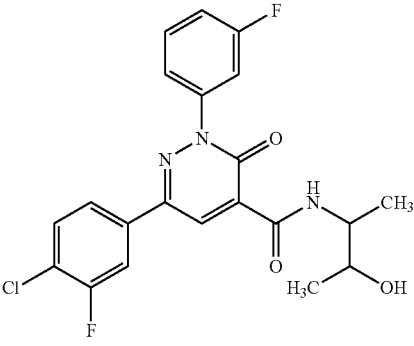 [SMILES: CC(O)C(C)NC(=O)c1cc(-c2ccc(Cl)c(F)c2)nn(-c2cccc(F)c2)c1=O] | 6-(4-Chloro-3-fluorophenyl)-2-(3-fluorophenyl)-N-(3-hydroxybutan-2-yl)-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; 3-amino-butan-2-ol | LC-MS (instrument: Waters Acquity UPLC-MS SQD 3001; column: Acquity UPLC BEH C18 1.7 50 × 2.1 mm; eluent A: Water + 0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt = 1.35 min; MS (ESIpos): m/z = 434.1 [M + H]+ |
| 290 | 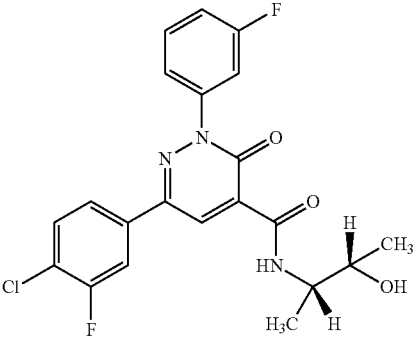 [SMILES: C[C@H](O)[C@H](C)NC(=O)c1cc(-c2ccc(Cl)c(F)c2)nn(-c2cccc(F)c2)c1=O] | rel-6-(4-Chloro-3-fluorophenyl)-2-(3-fluorophenyl)-N-[(2S,3S)-3-hydroxybutan-2-yl]-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; rel-(2S,3S)-3-aminobutan-2-ol hydrochloride | $^1$H NMR (400 MHz, DMSO-d$_6$) δ ppm 1.04 (d, 3 H), 1.15 (d, 3 H), 3.66-3.75 (m, 1 H), 3.88-3.98 (m, 1 H), 4.95 (d, 1 H), 7.36-7.42 (m, 1 H), 7.54-7.67 (m, 3 H), 7.70-7.77 (m, 1 H), 7.85 (dd, 1 H), 8.05 (dd, 1 H), 8.69 (s, 1 H), 9.42 (d, 1 H) |

TABLE 4-continued

Examples 272-312

| Example | structure | IUPAC name | Starting materials | analytics |
|---|---|---|---|---|
| 291 | 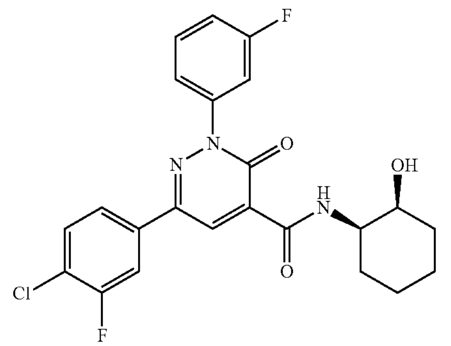 [SMILES: O=C(N[C@@H]1CCCC[C@@H]1O)c1cc(-c2ccc(Cl)c(F)c2)nn(-c2cccc(F)c2)c1=O] | 6-(4-Chloro-3-fluorophenyl)-2-(3-fluorophenyl)-N-(cis-2-hydroxycyclohexyl)-3-oxo-2,3-dihydropyridazine-4-carboxamide | 6-(4-Chloro-3-fluorophenyl)-2-(3-fluorophenyl)-3-oxo-2,3-dihydropyridazine-4-carboxylic acid; cis-2-aminocyclohexanol hydrochloride | $^1$H NMR (400 MHz, DMSO-d$_6$) δ ppm 1.33 (br d, 2 H), 1.47-1.70 (m, 6 H), 3.77 (br d, 1 H), 3.86-3.95 (m, 1 H), 4.88 (d, 1 H), 7.35-7.42 (m, 1 H), 7.53-7.66 (m, 3 H), 7.70-7.76 (m, 1 H), 7.84 (dd, 1 H), 8.03 (dd, 1 H), 8.68 (s, 1 H), 9.61 (d, 1 H) |
| 292 | 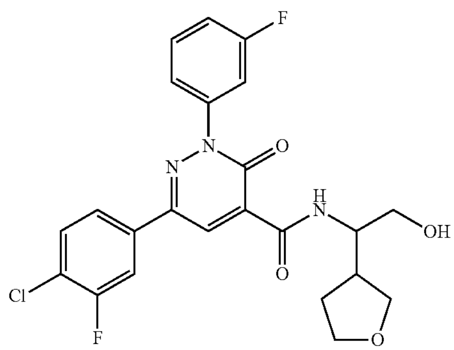 [SMILES: O=C(NC(CO)C1CCOC1)c1cc(-c2ccc(Cl)c(F)c2)nn(-c2cccc(F)c2)c1=O] | 6-(4-Chloro-3-fluorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 1 | 6-(4-Chloro-3-fluorophenyl)-2-(3-fluorophenyl)-N-{-2-hydroxy-1-[-tetrahydrofuran-3-yl]ethyl}-3-oxo-2,3-dihydropyridazine-4-carboxamide | preparation: instrument: Sepiatec: Prep SFC100; column: Chiralpak IB 5 μm 250 × 30 mm; eluent A CO2, Eluent B: ethanol; isocratic: 26% B; flow 100.0 mL/min temperature: 40° C.; BPR: 150 bar; MWD 254 nm; analytics: instrument: Agilent: 1260, Aurora SFC-Modul; column: Chiralpak IB 5 μm 100 × 4.6 mm; eluent A: CO2, eluent B: ethanol; isocratic: 26% B; flow 4.0 mL/min; temperature: 37.5° C.; BPR: 100 bar; MWD 254 nm; rt = 1.97 |
| 293 | 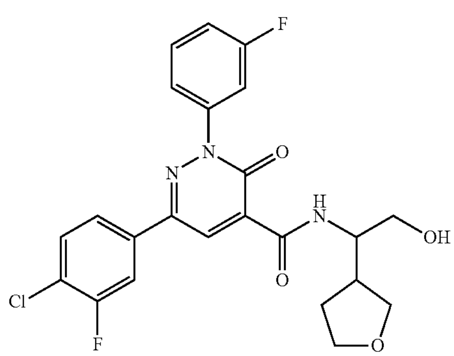 [SMILES: O=C(NC(CO)C1CCOC1)c1cc(-c2ccc(Cl)c(F)c2)nn(-c2cccc(F)c2)c1=O] | 6-(4-Chloro-3-fluorophenyl)-2-(3-fluorophenyl)-N-[2-hydroxy-1-(tetrahydrofuran-3-yl)ethyl]-3-oxo-2,3-dihydropyridazine-4-carboxamide, EStereoisomer 2 | 6-(4-Chloro-3-fluorophenyl)-2-(3-fluorophenyl)-N-{-2-hydroxy-1-[-tetrahydrofuran-3-yl]ethyl}-3-oxo-2,3-dihydropyridazine-4-carboxamide | preparation and analytics see example 292; rt = 2.23 |

TABLE 4-continued

Examples 272-312

| Example | structure | IUPAC name | Starting materials | analytics |
|---|---|---|---|---|
| 294 | 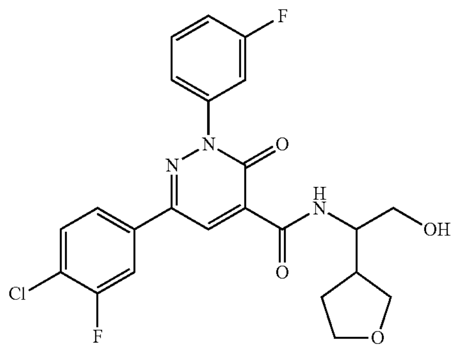 [SMILES: O=C(NC(CO)C1CCOC1)c1cc(-c2ccc(Cl)c(F)c2)nn(-c2cccc(F)c2)c1=O] | 6-(4-Chloro-3-fluorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 3 | 6-(4-Chloro-3-fluorophenyl)-2-(3-fluorophenyl)-N-{-2-hydroxy-1-[-tetrahydrofuran-3-yl]ethyl}-3-oxo-2,3-dihydropyridazine-4-carboxamide | preparation and analytics see example 292; rt = 2.61 |
| 295 | 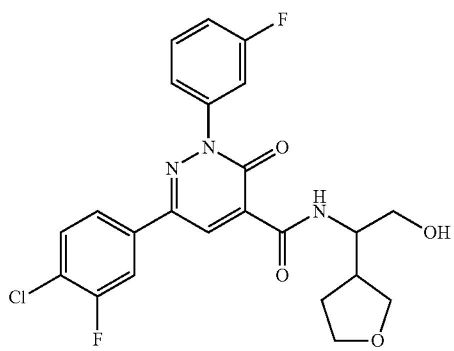 [SMILES: O=C(NC(CO)C1CCOC1)c1cc(-c2ccc(Cl)c(F)c2)nn(-c2cccc(F)c2)c1=O] | 6-(4-Chloro-3-fluorophenyl)-2-(3-fluorophenyl)-N-[2-hydroxy-1-(tetrahydrofuran-3-yl)ethyl]-3-oxo-2,3-dihydropyridazine-4-carboxamide, Stereoisomer 4 | 6-(4-Chloro-3-fluorophenyl)-2-(3-fluorophenyl)-N-{-2-hydroxy-1-[-tetrahydrofuran-3-yl]ethyl}-3-oxo-2,3-dihydropyridazine-4-carboxamide | preparation and analytics see example 292; rt = 4.47 |
| 296 | 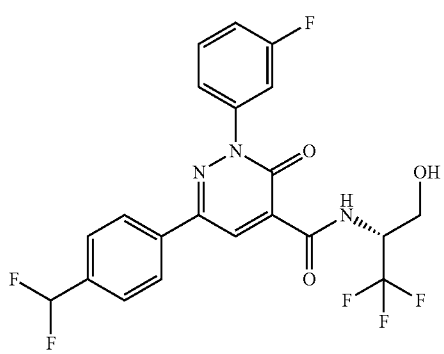 [SMILES: O=C(N[C@H](CO)C(F)(F)F)c1cc(-c2ccc(C(F)F)cc2)nn(-c2cccc(F)c2)c1=O] | 6-[4-(Difluoromethyl)phenyl]-2-(3-fluorophenyl)-3-oxo-N-[(2R)-1,1,1-trifluoro-3-hydroxypropan-2-yl]-2,3-dihydropyridazine-4-carboxamide | 6-[4-(Difluoromethyl)phenyl]-2-(3-fluorophenyl)-3-oxo-2,3-dihydropyridazine-4-carboxylic acid; (2R)-2-amino-3,3,3-trifluoropropan-1-ol hydrochloride | $^1$H NMR (400 MHz, DMSO-$d_6$) δ ppm 3.71 (br s, 1 H), 3.83 (br d, 1 H), 4.86 (dt, 1 H), 5.44 (br s, 1 H), 6.97-7.29 (m, 1 H), 7.41 (br t, 1 H), 7.54-7.67 (m, 3 H), 7.72 (br d, 2 H), 8.13 (br d, 2 H), 8.76 (s, 1 H), 10.01 (br d, 1 H) |
| 297 | 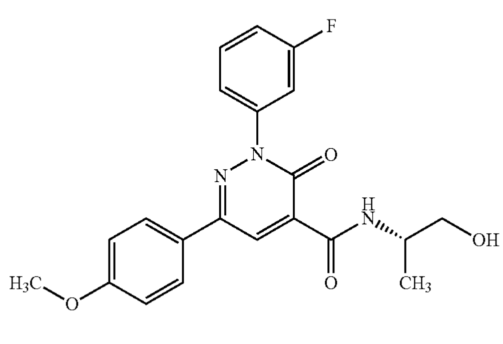 [SMILES: COc1ccc(-c2cc(C(=O)N[C@@H](C)CO)c(=O)n(-c3cccc(F)c3)n2)cc1] | 2-(3-Fluorophenyl)-N-[(2S)-1-hydroxypropan-2-yl]-6-(4-methoxyphenyl)-3-oxo-2,3-dihydropyridazine-4-carboxamide | 2-(3-Fluorophenyl)-6-(4-methoxyphenyl)-3-oxo-2,3-dihydropyridazine-4-carboxylic acid; (S)-(+)-2-amino-1-propanol (L-Alaninol) | $^1$H NMR (400 MHz, DMSO-$d_6$) δ ppm 1.16 (d, 3 H), 3.39-3.50 (m, 2 H), 3.82 (s, 3 H), 3.97-4.09 (m, 1 H), 4.93 (t, 1 H), 7.04-7.10 (m, 2 H), 7.33-7.40 (m, 1 H), 7.51-7.56 (m, 1 H), 7.57-7.64 (m, 2 H), 7.87-7.93 (m, 2 H), 8.61 (s, 1 H), 9.48 (d, 1 H) |

TABLE 4-continued

Examples 272-312

| Example | structure | IUPAC name | Starting materials | analytics |
|---|---|---|---|---|
| 298 | 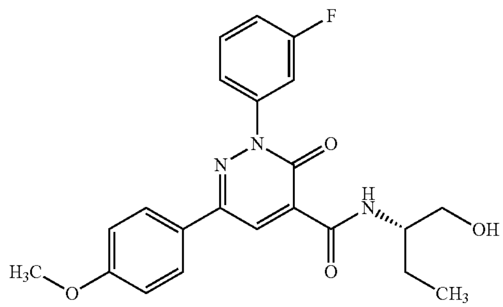 [SMILES: CC[C@@H](CO)NC(=O)c1cc(-c2ccc(OC)cc2)nn(-c2cccc(F)c2)c1=O] | 2-(3-Fluorophenyl)-N-[(2S)-1-hydroxybutan-2-yl]-6-(4-methoxyphenyl)-3-oxo-2,3-dihydropyridazine-4-carboxamide | 2-(3-Fluorophenyl)-6-(4-methoxyphenyl)-3-oxo-2,3-dihydropyridazine-4-carboxylic acid; (S)-(+)-2-amino-1-butanol | $^1$H NMR (400 MHz, DMSO-$d_6$) δ ppm 0.89 (t, 3 H), 1.42-1.55 (m, 1 H), 1.59-1.72 (m, 1 H), 3.42 (dt, 1 H), 3.48-3.55 (m, 1 H), 3.82 (s, 3 H), 3.85-3.94 (m, 1 H), 4.86 (br t, 1 H), 7.07 (d, 2 H), 7.37 (td, 1 H), 7.52-7.56 (m, 1 H), 7.57-7.65 (m, 2 H), 7.87-7.93 (m, 2 H), 8.61 (s, 1 H), 9.42 (d, 1 H) |
| 299 | 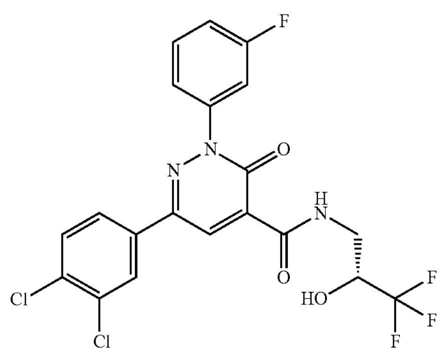 [SMILES: O=C(NC[C@@H](O)C(F)(F)F)c1cc(-c2ccc(Cl)c(Cl)c2)nn(-c2cccc(F)c2)c1=O] | 6-(3,4-Dichlorophenyl)-2-(3-fluorophenyl)-3-oxo-N-(3,3,3-trifluoro-2-hydroxypropyl)-2,3-dihydropyridazine-4-carboxamide, Enantiomer 2 | 6-(3,4-Dichlorophenyl)-2-(3-fluorophenyl)-3-oxo-N-(3,3,3-trifluoro-2-hydroxypropyl)-2,3-dihydropyridazine-4-carboxamide | preparation: instrument: Sepiatec: Prep SFC100; column: Chiralpak IB 5 µm 250 × 30 mm; eluent A: CO2, eluent B: 2-propanol; isocratic: 13% B; flow 100.0 mL/min temperature: 40° C.; BPR: 150 bar; MWD @ 254 nm; analytics: instrument: Agilent: 1260, Aurora SFC-Modul; column: Chiralpak IB 5 µm 100 × 4.6 mm; eluent A: CO2, eluent B: 2-propanol; isocratic: 13% B; flow 4.0 mL/min; temperature: 37.5° C.; BPR: 100 bar; MWD @ 254 nm rt = 4.55 |
| 300 | 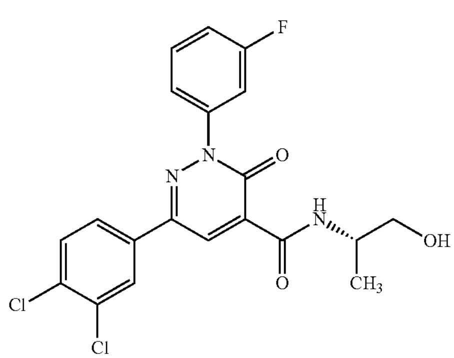 [SMILES: C[C@@H](CO)NC(=O)c1cc(-c2ccc(Cl)c(Cl)c2)nn(-c2cccc(F)c2)c1=O] | 6-(3,4-Dichlorophenyl)-2-(3-fluorophenyl)-N-[(2S)-1-hydroxypropan-2-yl]-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; (S)-(+)-2-amino-1-propanol (L-Alaninol) | $^1$H NMR (400 MHz, DMSO-$d_6$) δ ppm 1.15 (d, 3 H), 3.99-4.07 (m, 1 H), 4.97 (t, 1 H), 7.35-7.42 (m, 1 H), 7.52-7.57 (m, 1 H), 7.58-7.66 (m, 2 H), 7.77 (d, 1 H), 7.95 (dd, 1 H), 8.20 (d, 1 H), 8.67 (s, 1 H), 9.40 (d, 1 H) |

TABLE 4-continued

Examples 272-312

| Example | structure | IUPAC name | Starting materials | analytics |
|---|---|---|---|---|
| 301 | 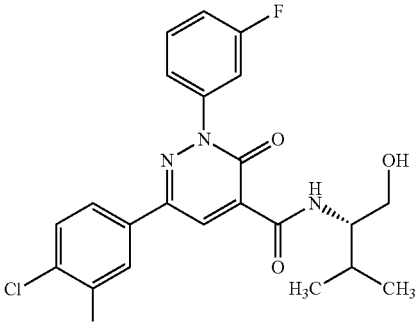 | 6-(3,4-Dichlorophenyl)-2-(3-fluorophenyl)-N-[(2S)-1-hydroxy-3-methylbutan-2-yl]-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; (S)-(+)-2-amino-3-methyl-1-butanol | $^1$H NMR (400 MHz, DMSO-$d_6$) δ ppm 0.88 (d, 3 H), 0.92 (d, 3 H), 1.96 (dq, 1 H), 3.50-3.57 (m, 1 H), 3.80-3.88 (m, 1 H), 4.84 (t, 1 H), 7.35-7.42 (m, 1 H), 7.53-7.57 (m, 1 H), 7.59-7.66 (m, 2 H), 7.77 (d, 1 H), 7.95 (dd, 1 H), 8.20 (d, 1 H), 8.68 (s, 1 H), 9.37 (d, 1 H) |
| 302 | 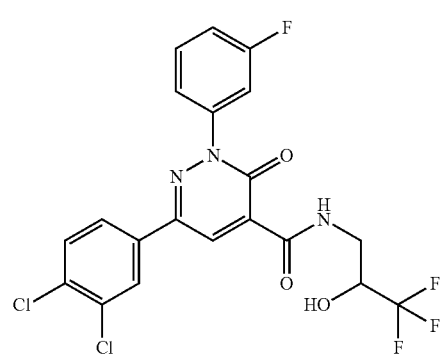 | 6-(3,4-Dichlorophenyl)-2-(3-fluorophenyl)-3-oxo-N-(3,3,3-trifluoro-2-hydroxypropyl)-2,3-dihydropyridazine-4-carboxamide | 6-(3,4-Dichlorophenyl)-2-(3-fluorophenyl)-3-oxo-2,3-dihydropyridazine-4-carboxylic acid; 3-amino-1,1,1-trifluoro-2-propanol | $^1$H NMR (400 MHz, DMSO-$d_6$) δ ppm 3.47 (ddd, 1 H), 3.70-3.79 (m, 1 H), 4.17-4.27 (m, 1 H), 6.67 (d, 1 H), 7.40 (tdd, 1 H), 7.54-7.58 (m, 1 H), 7.59-7.67 (m, 2 H), 7.78 (d, 1 H), 7.94-7.99 (m, 1 H), 8.23 (d, 1 H), 8.71 (s, 1 H), 9.57-9.63 (m, 1 H), 9.60 (t, 1 H) |
| 303 | 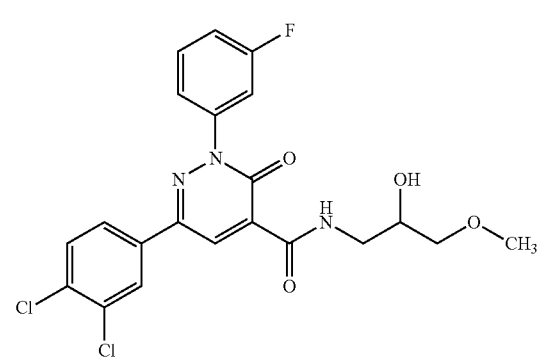 [SMILES: COCC(O)CNC(=O)c1cc(-c2ccc(Cl)c(Cl)c2)nn(-c2cccc(F)c2)c1=O] | 6-(3,4-Dichlorophenyl)-2-(3-fluorophenyl)-N-(2-hydroxy-3-methoxypropyl)-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; 1-amino-3-methoxy-2-propanol | $^1$H NMR (400 MHz, DMSO-$d_6$) δ ppm 3.26 (s, 3 H), 3.27-3.32 (m, 2 H), 3.50-3.57 (m, 2 H), 3.72-3.80 (m, 1 H), 5.20 (d, 1 H), 7.35-7.41 (m, 1 H), 7.53-7.57 (m, 1 H), 7.58-7.66 (m, 2 H), 7.78 (d, 1 H), 7.94-7.98 (m, 1 H), 8.21 (d, 1 H), 8.68 (s, 1 H), 9.50 (t, 1 H) |
| 304 | 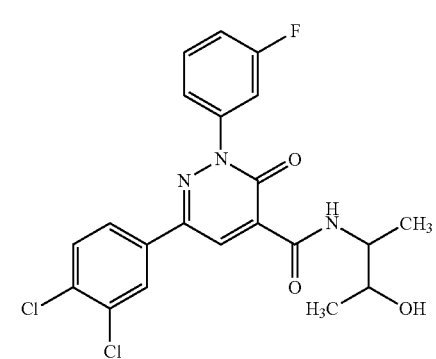 | 6-(3,4-Dichlorophenyl)-2-(3-fluorophenyl)-N-(3-hydroxybutan-2-yl)-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; 3-amino-butan-2-ol | LC-MS (instrument: Waters Acquity UPLC-MS SQD 3001; column: Acquity UPLC BEH C18 1.7 50 × 2.1 mm; eluent A: Water + 0.1 vol % formic acid, eluent B: acetonitrile; gradient: 0-1.6 min 1-99% B, 1.6-2.0 min 99% B; flow 0.8 mL/min; |

TABLE 4-continued

Examples 272-312

| Example | structure | IUPAC name | Starting materials | analytics |
|---|---|---|---|---|
| | | | | temperature: 60° C.; injection: 2 µL; DAD scan: 210-400 nm; ELSD): Rt = 1.42 min; MS (ESIpos): m/z = 452.1 [M + H]+ |
| 305 | 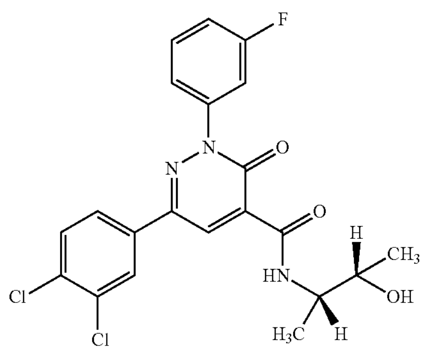 [SMILES: C[C@H](O)[C@H](C)NC(=O)c1cc(-c2ccc(Cl)c(Cl)c2)nn(-c2cccc(F)c2)c1=O] | rel-6-(3,4-Dichlorophenyl)-2-(3-fluorophenyl)-N-[(2S,3S)-3-hydroxybutan-2-yl]-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; rel-(2S,3S)-3-aminobutan-2-ol hydrochloride | $^1$H NMR (400 MHz, DMSO-d$_6$) δ ppm 1.04 (d, 3 H), 1.15 (d, 3 H), 3.65-3.75 (m, 1 H), 3.88-4.00 (m, 1 H), 4.95 (d, 1 H), 7.35-7.42 (m, 1 H), 7.53-7.58 (m, 1 H), 7.58-7.68 (m, 2 H), 7.78 (d, 1 H), 7.97 (dd, 1 H), 8.22 (d, 1 H), 8.69 (s, 1 H), 9.41 (d, 1 H) |
| 306 | 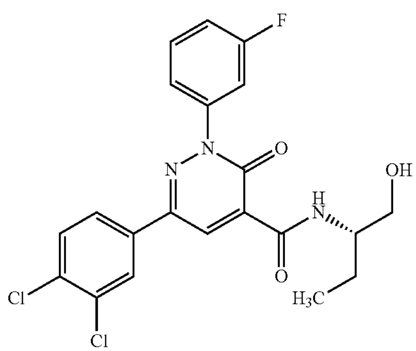 | 6-(3,4-Dichlorophenyl)-2-(3-fluorophenyl)-N-[(2S)-1-hydroxybutan-2-yl]-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; (S)-(+)-2-amino-1-butanol | $^1$H NMR (400 MHz, METHANOL-d$_4$) δ ppm 0.99 (t, 3 H), 1.54-1.65 (m, 1 H), 1.68-1.80 (m, 1 H), 3.65 (d, 2 H), 3.99-4.07 (m, 1 H), 7.23-7.30 (m, 1 H), 7.48-7.61 (m, 3 H), 7.67 (d, 1 H), 7.89 (dd, 1 H), 8.12 (d, 1 H), 8.74 (s, 1 H) |
| 307 | 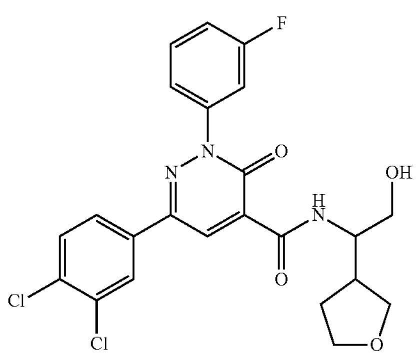 [SMILES: O=C(NC(CO)C1CCOC1)c1cc(-c2ccc(Cl)c(Cl)c2)nn(-c2cccc(F)c2)c1=O] | 6-(3,4-Dichlorophenyl)-2-(3-fluorophenyl)-N-[2-hydroxy-1-(tetrahydrofuran-3-yl)ethyl]-3-oxo-2,3-dihydropyridazine-4-carboxamide | 6-(3,4-Dichlorophenyl)-2-(3-fluorophenyl)-3-oxo-2,3-dihydropyridazine-4-carboxylic acid; 2-amino-2-(tetrahydro-furan-3-yl)-ethanol | LC-MS (instrument: Waters Acquity UPLC-MS SQD 3001; column: Acquity UPLC BEH C18 1.7 50 × 2.1 mm; eluent A: Water + 0.1 vol % formic acid, eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): Rt = 1.34 min; MS (ESIpos): m/z = 492.1 [M + H]+ |

TABLE 4-continued

Examples 272-312

| Example | structure | IUPAC name | Starting materials | analytics |
|---|---|---|---|---|
| 308 | 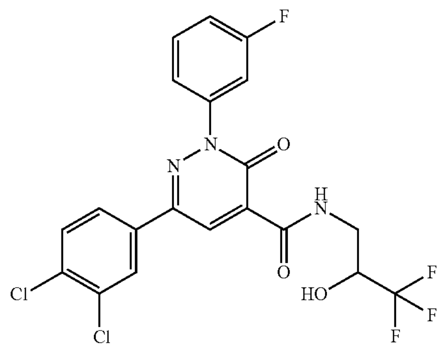 [SMILES: O=C(NCC(O)C(F)(F)F)c1cc(-c2ccc(Cl)c(Cl)c2)nn(-c2cccc(F)c2)c1=O] | 6-(3,4-Dichlorophenyl)-2-(3-fluorophenyl)-3-oxo-N-(3,3,3-trifluoro-2-hydroxypropyl)-2,3-dihydropyridazine-4-carboxamide, Enantiomer 1 | 6-(3,4-Dichlorophenyl)-2-(3-fluorophenyl)-3-oxo-N-(3,3,3-trifluoro-2-hydroxypropyl)-2,3-dihydropyridazine-4-carboxamide | preparation and analytics see example 302; rt = 3.06 |
| 309 | 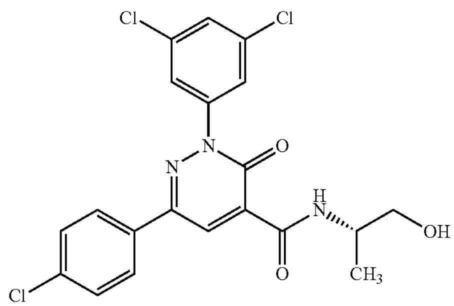 [SMILES: C[C@@H](CO)NC(=O)c1cc(-c2ccc(Cl)cc2)nn(-c2cc(Cl)cc(Cl)c2)c1=O] | 6-(4-Chlorophenyl)-2-(3,5-dichlorophenyl)-N-[(2S)-1-hydroxypropan-2-yl]-3-oxo-2,3-dihydropyridazine-4-carboxamide | 6-(4-Chlorophenyl)-2-(3,5-dichlorophenyl)-3-oxo-2,3-dihydropyridazine-4-carboxylic acid; 3-amino-butan-2-ol | $^1$H NMR (400 MHz, DMSO-$d_6$) δ ppm 1.16 (d, 3 H), 3.40-3.49 (m, 2 H), 3.98-4.09 (m, 1 H), 4.95 (t, 1 H), 7.56-7.62 (m, 2 H), 7.80-7.84 (m, 1 H), 7.84-7.86 (m, 2 H), 7.97-8.02 (m, 2 H), 8.65 (s, 1 H), 9.36 (d, 1 H) |
| 310 | 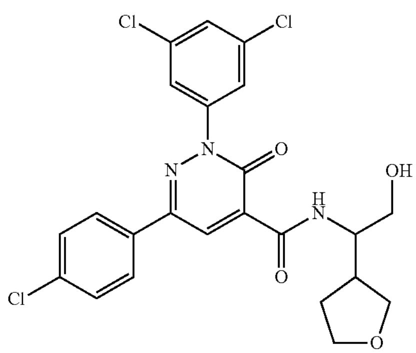 [SMILES: O=C(NC(CO)C1CCOC1)c1cc(-c2ccc(Cl)cc2)nn(-c2cc(Cl)cc(Cl)c2)c1=O] | 6-(4-Chlorophenyl)-2-(3,5-dichlorophenyl)-N-[2-hydroxy-1-(tetrahydrofuran-3-yl)ethyl]-3-oxo-2,3-dihydropyridazine-4-carboxamide | 6-(4-Chlorophenyl)-2-(3,5-dichlorophenyl)-3-oxo-2,3-dihydropyridazine-4-carboxylic acid; 2-amino-2-(tetrahydro-furan-3-yl)-ethanol | LC-MS (instrument: Waters Acquity UPLC-MS SQD 3001; column: Acquity UPLC BEH C18 1.7 50 × 2.1 mm; eluent A: Water + 0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): Rt = 1.42 min; MS (ESIpos): m/z = 510.0 [M + H]+ |
| 311 | 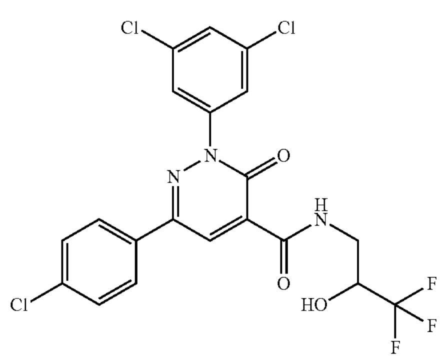 [SMILES: O=C(NCC(O)C(F)(F)F)c1cc(-c2ccc(Cl)cc2)nn(-c2cc(Cl)cc(Cl)c2)c1=O] | 6-(4-Chlorophenyl)-2-(3,5-dichlorophenyl)-3-oxo-N-(3,3,3-trifluoro-2-hydroxypropyl)-2,3-dihydropyridazine-4-carboxamide | 6-(4-Chlorophenyl)-2-(3,5-dichlorophenyl)-3-oxo-2,3-dihydropyridazine-4-carboxylic acid; 3-amino-1,1,1-trifluoro-2-propanol | $^1$H NMR (400 MHz, DMSO-$d_6$) δ ppm 3.47 (ddd, 1 H), 3.70-3.79 (m, 1 H), 4.18-4.29 (m, 1 H), 6.66 (d, 1 H), 7.56-7.62 (m, 2 H), 7.81-7.84 (m, 1 H), 7.86 (d, 2 H), 7.98-8.03 (m, 2 H), 8.66 (s, 1 H), 9.56 (t, 1 H) |

TABLE 4-continued

Examples 272-312

| Example | structure | IUPAC name | Starting materials | analytics |
|---|---|---|---|---|
| 312 | 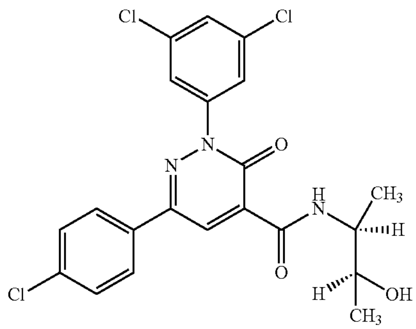 [SMILES: C[C@H](O)[C@H](C)NC(=O)c1cc(-c2ccc(Cl)cc2)nn(-c2cc(Cl)cc(Cl)c2)c1=O] | 6-(4-Chlorophenyl)-2-(3,5-dichlorophenyl)-N-[(2S,3S)-3-hydroxybutan-2-yl]-3-oxo-2,3-dihydropyridazine-4-carboxamide | 6-(4-Chlorophenyl)-2-(3,5-dichlorophenyl)-3-oxo-2,3-dihydropyridazine-4-carboxylic acid; rel-(2S,3S)-3-aminobutan-2-ol hydrochloride | $^1$H NMR (400 MHz, DMSO-$d_6$) δ ppm 1.04 (d, 3 H), 1.15 (d, 3 H), 3.67-3.76 (m, 1 H), 3.88-3.98 (m, 1 H), 4.96 (d, 1 H), 7.56-7.61 (m, 2 H), 7.80-7.84 (m, 1 H), 7.86 (d, 2 H), 7.97-8.03 (m, 2 H), 8.65 (s, 1 H), 9.38 (d, 1 H) |

The following examples were prepared from the starting materials stated in the table using the procedure described in example 267. Enantiomers were separated from their racemate by chiral HPLC using the column and solvent conditions stated.

TABLE 5

Examples 313-378

| Example | structure | IUPAC name | Starting materials | analytics |
|---|---|---|---|---|
| 313 | 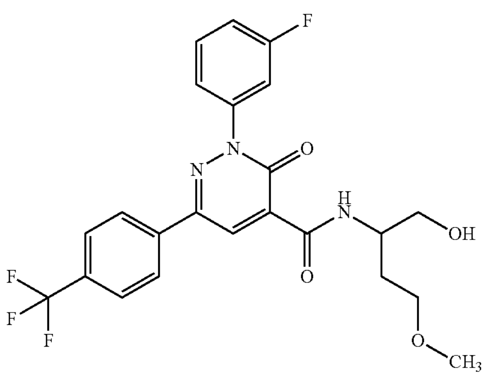 [SMILES: COCCC(CO)NC(=O)c1cc(-c2ccc(C(F)(F)F)cc2)nn(-c2cccc(F)c2)c1=O] | (−)-2-(3-fluorophenyl)-N-(1-hydroxy-4-methoxybutan-2-yl)-3-oxo-6-[4-(trifluoromethyl)phenyl]-2,3-dihydropyridazine-4-carboxamide, enantiomer 2, $[α]_D^{20}$ = −24.0° (c = 1.00, methanol) | 2-(3-fluorophenyl)-N-[(2RS)-1-hydroxy-4-methoxybutan-2-yl]-3-oxo-6-[4-(trifluoromethyl)phenyl]-2,3-dihydropyridazine-4-carboxamide, Chiralpak IC 5μ 250 × 30 mm, eluent A: $CO_2$, eluent B: ethanol, isocratic: 13% B, 100 mL/min, 40° C., BRP: 150 bar, 254 nm | $^1$H-NMR (400 MHz, DMSO-$d_6$): δ [ppm] = 1.67-1.76 (m, 1H), 1.82-1.91 (m, 1H), 3.21 (s, 3H), 3.39 (t, 2H), 3.42-3.48 (m, 1H), 3.49-3.55 (m, 1H), 4.04-4.14 (m, 1H), 4.91 (t, 1H), 7.37-7.43 (m, 1H), 7.55-7.59 (m, 1H), 7.59-7.67 (m, 2H), 7.88 (d, 2H), 8.20 (d, 2H), 8.72 (s, 1H), 9.40 (d, 1H). Rt = 4.11 min, Chiralpak IC 5 μm 100 × 4.6 mm, eluent A: $CO_2$, eluent B: ethanol, isocratic: 13% B, 4.0 mL/min, 37.5° C., BPR: 100 bar, 254 nm |
| 314 | 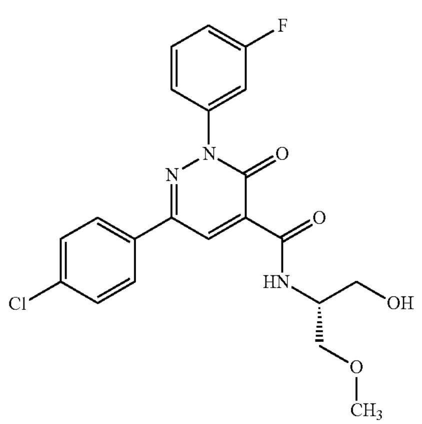 [SMILES: COC[C@@H](CO)NC(=O)c1cc(-c2ccc(Cl)cc2)nn(-c2cccc(F)c2)c1=O] | 6-(4-chlorophenyl)-2-(3-fluorophenyl)-N-[(2R)-1-hydroxy-3-methoxypropan-2-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, (2R)-2-amino-3-methoxypropan-1-ol | $^1$H-NMR (400 MHz, DMSO-$d_6$): δ [ppm] = 3.28 (s, 3H), 3.41-3.58 (m, 4H), 4.08-4.16 (ddt, 1H), 4.97 (t, 1H), 7.37-7.43 (m, 1H), 7.52-7.65 (m, 5H), 7.97-8.02 (m, 2H), 8.67 (s, 1H), 9.54 (d, 1H). |

TABLE 5-continued

Examples 313-378

| Example | structure | IUPAC name | Starting materials | analytics |
|---|---|---|---|---|
| 315 | 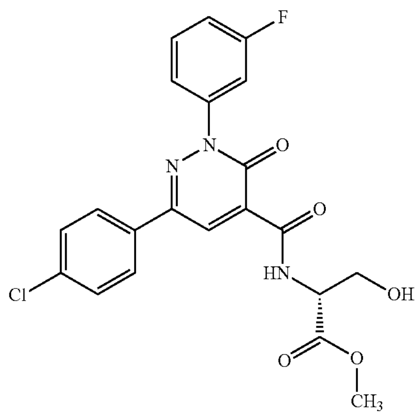 [SMILES: COC(=O)[C@@H](CO)NC(=O)c1cc(-c2ccc(Cl)cc2)nn(-c2cccc(F)c2)c1=O] | methyl N-{[6-(4-chlorophenyl)-2-(3-fluorophenyl)-3-oxo-2,3-dihydropyridazin-4-yl]carbonyl}-D-serinate, $[\alpha]_D^{20}$ = −16.2° (c = 1.00, methanol) | 6-(4-chlorophenyl)-2-(3-fluorophenyl)-3-oxo-2,3-dihydropyridazine-4-carboxylic acid, methyl D-serinate hydrochloride (1:1) | $^1$H-NMR (400 MHz, DMSO-d$_6$): δ [ppm] = 3.68 (s, 3H), 3.73 (ddd, 1H), 3.88 (ddd, 1H), 4.62-4.67 (m, 1H), 5.32 (t, 1H), 7.37-7.43 (m, 1H), 7.54-7.67 (m, 5H), 7.98-8.03 (m, 2H), 8.68 (s, 1H), 9.99 (d, 1H). |
| 316 | 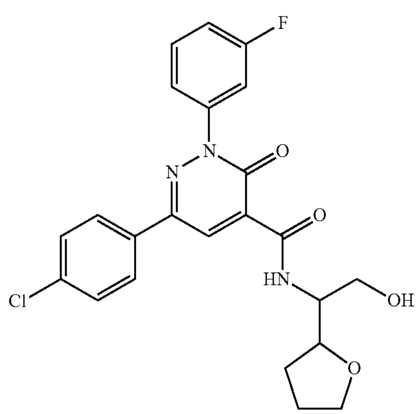 | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, isomer 1, $[\alpha]_D^{20}$ = +27.9° (c = 1.00, methanol) | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, Chiralpak IC 5µ 250 × 30 mm, eluent A: MTBE, eluent B: ethanol, isocratic: 10% B, 50 mL/min, 254 nm | $^1$H-NMR (400 MHz, DMSO-d$_6$): δ [ppm] = 1.56 (dq, 1H), 1.75-1.83 (m, 2H), 1.88-1.97 (m, 1H), 3.48 (t, 2H), 3.61-3.67 (m, 1H), 3.72-3.80 (m, 1H), 4.01-4.14 (m, 2H), 4.91 (t, 1H), 7.36-7.42 (m, 1H), 7.52-7.66 (m, 5H), 7.97-8.02 (m, 2H), 8.67 (s, 1H), 9.45 (d, 1H). Rt = 3.15 min, Chiralpak IC 3 µm 100 × 4.6 mm, eluent A: MTBE, eluent B: ethanol, isocratic: 10% B, 1.4 mL/min, 25° C., 254 nm |
| 317 | 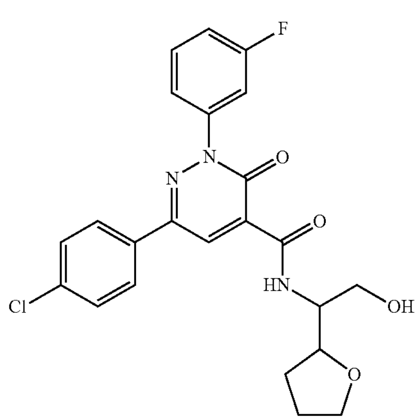 | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, isomer 2, $[\alpha]_D^{20}$ = +21.8° (c = 1.00, methanol) | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, Chiralpak IC 5µ 250 × 30 mm, eluent A: MTBE, eluent B: ethanol, isocratic: 10% B, 50 mL/min, 254 nm | $^1$H-NMR (400 MHz, DMSO-d$_6$): δ [ppm] = 1.68-1.93 (m, 4H), 3.46-3.53 (m, 1H), 3.60-3.68 (m, 2H), 3.74-3.81 (m, 1H), 3.92-4.05 (m, 2H), 4.88 (t, 1H), 7.35-7.43 (m, 1H), 7.53-7.66 (m, 5H), 7.97-8.03 (m, 2H), 8.67 (s, 1H), 9.57 (d, 1H). Rt = 3.96 min, Chiralpak IC 3 µm 100 × 4.6 mm, eluent A: MTBE, eluent B: ethanol, isocratic: 10% B, 1.4 mL/min, 25° C., 254 nm |

TABLE 5-continued

Examples 313-378

| Example | structure | IUPAC name | Starting materials | analytics |
|---|---|---|---|---|
| 318 | 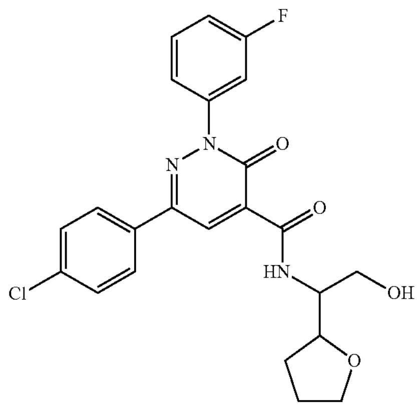 | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, isomer 3, $[\alpha]_D^{20}$ = -22.3° (c = 1.00, methanol) | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, Chiralpak IC 5μ 250 × 30 mm, eluent A: MTBE, eluent B: ethanol, isocratic: 10% B, 50 mL/min, 254 nm | $^1$H-NMR (400 MHz, DMSO-d$_6$): δ [ppm] = 1.56 (dq, 1H), 1.75-1.83 (m, 2H), 1.88-1.97 (m, 1H), 3.48 (t, 2H), 3.61-3.67 (m, 1H), 3.73-3.78 (m, 1H), 4.01-4.14 (m, 2H), 4.91 (t, 1H), 7.36-7.42 (m, 1H), 7.53-7.65 (m, 5H), 7.97-8.02 (m, 2H), 8.67 (s, 1H), 9.45 (d, 1H). Rt = 4.94 min, Chiralpak IC 3 μm 100 × 4.6 mm, eluent A: MTBE, eluent B: ethanol, isocratic: 10% B, 1.4 mL/min, 25° C., 254 nm |
| 319 | 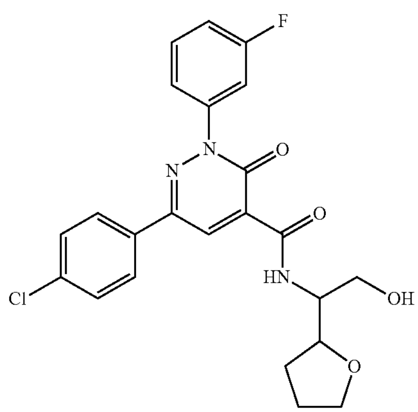 | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, isomer 4, $[\alpha]_D^{20}$ = -20.0° (c = 1.00, methanol) | 1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol, Chiralpak IC 5μ 250 × 30 mm, eluent A: MTBE, eluent B: ethanol, isocratic: 10% B, 50 mL/min, 254 nm | $^1$H-NMR (400 MHz, DMSO-d$_6$): δ [ppm] = 1.68-1.92 (m, 4H), 3.47-3.53 (m, 1H), 3.61-3.68 (m, 2H), 3.75-3.81 (m, 1H), 3.92-4.05 (m, 2H), 7.36-7.42 (m, 1H), 7.36-7.42 (m, 1H), 7.54-7.65 (m, 5H), 7.98-8.02 (m, 2H), 8.67 (s, 1H), 9.57 (d, 1H). Rt = 6.34 min, Chiralpak IC 3 μm 100 × 4.6 mm, eluent A: MTBE, eluent B: ethanol, isocratic: 10% B, 1.4 mL/min, 25° C., 254 nm |
| 320 | 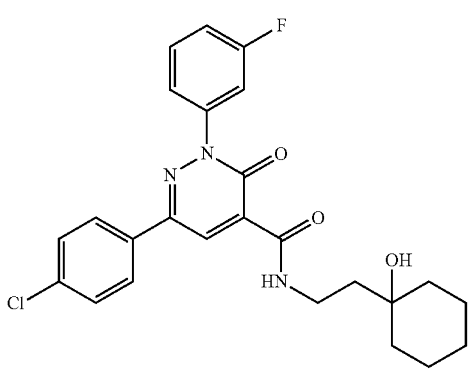 [SMILES: O=C(NCCC1(O)CCCCC1)c1cc(-c2ccc(Cl)cc2)nn(-c2cccc(F)c2)c1=O] | 6-(4-chlorophenyl)-2-(3-fluorophenyl)-N-[2-(1-hydroxycyclohexyl)ethyl]-3-oxo-2,3-dihydropyridazine-4-carboxamide | 6-(4-chlorophenyl)-2-(3-fluorophenyl)-3-oxo-2,3-dihydropyridazine-4-carboxylic acid, 1-(2-aminoethyl)cyclohexanol | $^1$H-NMR (400 MHz, DMSO-d$_6$): δ [ppm] = 1.17-1.66 (m, 13H), 3.41-3.47 (m, 2H), 4.20 (s, 1H), 7.34-7.41 (m, 1H), 7.53-7.64 (m, 5H), 7.97-8.01 (m, 2H), 8.62 (s, 1H), 9.43 (t, 1H). |

TABLE 5-continued

Examples 313-378

| Example | structure | IUPAC name | Starting materials | analytics |
|---|---|---|---|---|
| 321 | 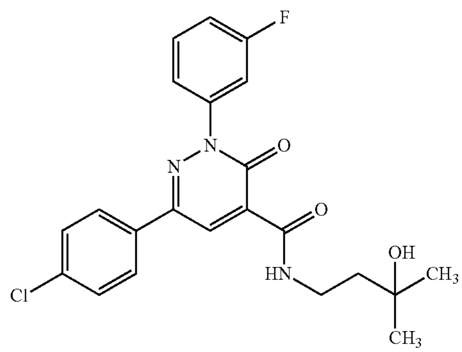 [SMILES: CC(C)(O)CCNC(=O)c1cc(-c2ccc(Cl)cc2)nn(-c2cccc(F)c2)c1=O] | 6-(4-chlorophenyl)-2-(3-fluorophenyl)-N-(3-hydroxy-3-methylbutyl)-3-oxo-2,3-dihydropyridazine-4-carboxamide | 6-(4-chlorophenyl)-2-(3-fluorophenyl)-3-oxo-2,3-dihydropyridazine-4-carboxylic acid, 4-amino-2-methylbutan-2-ol | $^1$H-NMR (400 MHz, DMSO-$d_6$): δ [ppm] = 1.13 (s, 6H), 1.61-1.66 (m, 2H), 3.41-3.47 (m, 2H), 4.42 (s, 1H), 7.35-7.40 (m, 1H), 7.53-7.64 (m, 5H), 7.97-8.01 (m, 2H), 8.62 (s, 1H), 9.45 (t, 1H). |
| 322 | 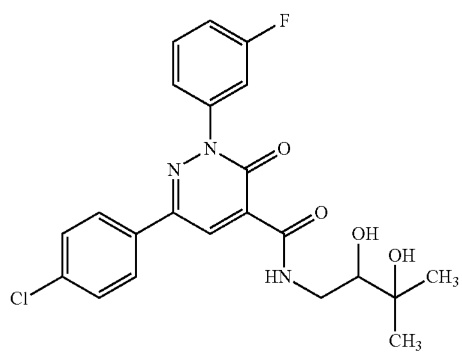 [SMILES: CC(C)(O)C(O)CNC(=O)c1cc(-c2ccc(Cl)cc2)nn(-c2cccc(F)c2)c1=O] | 6-(4-chlorophenyl)-N-[(2RS)-2,3-dihydroxy-3-methylbutyl]-2-(3-fluorophenyl)-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-1-amino-3-methylbutane-2,3-diol | $^1$H-NMR (400 MHz, DMSO-$d_6$): δ [ppm] = 1.05 (s, 3H), 1.10 (s, 3H), 3.09 (ddd, 1H), 3.30 (ddd, 1H), 3.78 (ddd, 1H), 4.41 (s, 1H), 5.02 (d, 1H), 7.36-7.41 (m, 1H), 7.54-7.65 (m, 5H), 7.97-8.02 (m, 2H), 8.66 (s, 1H), 9.58 (dd, 1H). |
| 323 | 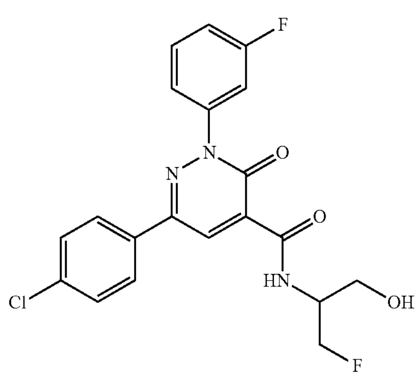 [SMILES: O=C(NC(CO)CF)c1cc(-c2ccc(Cl)cc2)nn(-c2cccc(F)c2)c1=O] | 6-(4-chlorophenyl)-N-[(2RS)-1-fluoro-3-hydroxypropan-2-yl]-2-(3-fluorophenyl)-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-2-amino-3-fluoropropan-1-ol hydrochloride (1:1) | $^1$H-NMR (400 MHz, DMSO-$d_6$): δ [ppm] = 3.48-3.55 (m, 1H), 3.57-3.63 (m, 1H), 4.18-4.31 (m, 1H), 4.47-4.54 (m, 1H), 4.59-4.66 (m, 1H), 5.16 (t, 1H), 7.36-7.42 (m, 1H), 7.54-7.65 (m, 5H), 7.98-8.03 (m, 2H), 9.60-9.65 (m, 1H), 9.62 (d, 1H). |
| 324 | 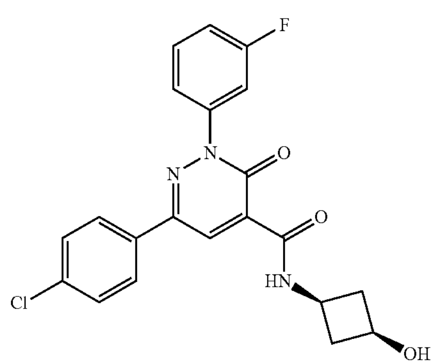 [SMILES: O=C(N[C@H]1C[C@@H](O)C1)c1cc(-c2ccc(Cl)cc2)nn(-c2cccc(F)c2)c1=O] | 6-(4-chlorophenyl)-2-(3-fluorophenyl)-N-(cis-3-hydroxycyclobutyl)-3-oxo-2,3-dihydropyridazine-4-carboxamide | 6-(4-chlorophenyl)-2-(3-fluorophenyl)-3-oxo-2,3-dihydropyridazine-4-carboxylic acid, cis-3-aminocyclobutanol hydrochloride (1:1) | $^1$H-NMR (400 MHz, DMSO-$d_6$): δ [ppm] = 1.76-1.85 (m, 2H), 2.60-2.69 (m, 2H), 3.82-3.99 (m, 2H), 5.14 (d, 1H), 7.36-7.42 (m, 1H), 7.36-7.42 (m, 1H), 7.54-7.66 (m, 5H), 7.97-8.02 (m, 2H), 8.60 (s, 1H), 9.45 (d, 1H). |

TABLE 5-continued

Examples 313-378

| Example | structure | IUPAC name | Starting materials | analytics |
|---|---|---|---|---|
| 325 | 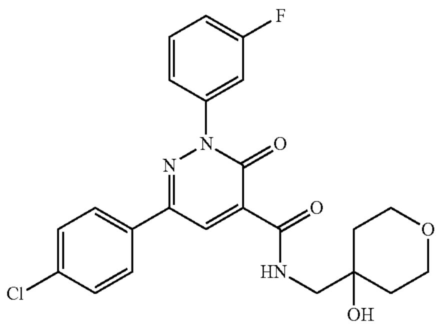 [SMILES: O=C(NCC1(O)CCOCC1)c1cc(-c2ccc(Cl)cc2)nn(-c2cccc(F)c2)c1=O] | 6-(4-chlorophenyl)-2-(3-fluorophenyl)-N-[(4-hydroxytetrahydro-2H-pyran-4-yl)methyl]-3-oxo-2,3-dihydropyridazine-4-carboxamide | 6-(4-chlorophenyl)-2-(3-fluorophenyl)-3-oxo-2,3-dihydropyridazine-4-carboxylic acid, 4-(aminomethyl)tetrahydro-2H-pyran-4-ol | $^1$H-NMR (400 MHz, DMSO-$d_6$): δ [ppm] = 1.40-1.47 (m, 2H), 1.50-1.59 (m, 2H), 3.39 (d, 2H), 3.55-3.65 (m, 4H), 4.76 (s, 1H), 7.36-7.42 (m, 1H), 7.54-7.65 (m, 5H), 7.98-8.03 (m, 2H), 8.66 (s, 1H), 9.55 (t, 1H). |
| 326 | 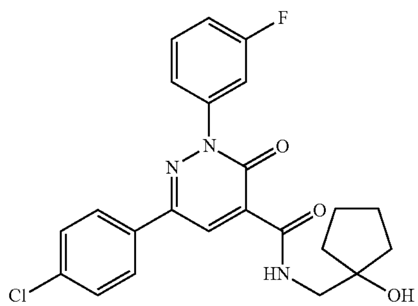 [SMILES: O=C(NCC1(O)CCCC1)c1cc(-c2ccc(Cl)cc2)nn(-c2cccc(F)c2)c1=O] | 6-(4-chlorophenyl)-2-(3-fluorophenyl)-N-[(1-hydroxycyclopentyl)methyl]-3-oxo-2,3-dihydropyridazine-4-carboxamide | 6-(4-chlorophenyl)-2-(3-fluorophenyl)-3-oxo-2,3-dihydropyridazine-4-carboxylic acid, 1-(aminomethyl)cyclopentanol hydrochloride (1:1) | $^1$H-NMR (400 MHz, DMSO-$d_6$): δ [ppm] = 1.47-1.60 (m, 6H), 1.64-1.76 (m, 2H), 3.42 (d, 2H), 4.65 (s, 1H), 7.36-7.42 (m, 1H), 7.54-7.66 (m, 5H), 7.98-8.03 (m, 2H), 8.66 (s, 1H), 9.59 (t, 1H). |
| 327 | 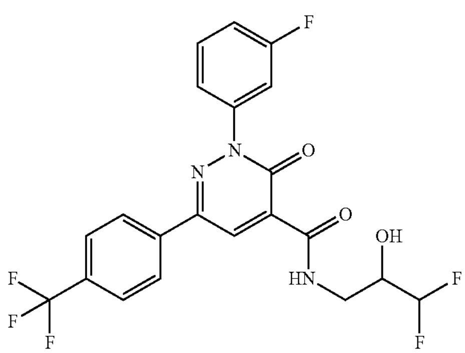 [SMILES: O=C(NCC(O)C(F)F)c1cc(-c2ccc(C(F)(F)F)cc2)nn(-c2cccc(F)c2)c1=O] | (−)-N-(3,3-difluoro-2-hydroxypropyl)-2-(3-fluorophenyl)-3-oxo-6-[4-(trifluoromethyl)phenyl]-2,3-dihydropyridazine-4-carboxamide, enantiomer 1, $[α]_D^{20}$ = −14.4° (c = 1.00, methanol) | N-[(2RS)-3,3-difluoro-2-hydroxypropyl]-2-(3-fluorophenyl)-3-oxo-6-[4-(trifluoromethyl)phenyl]-2,3-dihydropyridazine-4-carboxamide, Chiralpak IA 5μ 250 × 30 mm, eluent A: $CO_2$, eluent B: ethanol, isocratic: 18% B, 100 mL/min, 40° C., BPR: 150 bar, 254 nm | $^1$H-NMR (400 MHz, DMSO-$d_6$): δ [ppm] = 3.40 (ddd, 1H), 3.62-3.70 (m, 1H), 3.78-3.91 (m, 1H), 5.94 (dt, 1H), 6.00 (d, 1H), 7.37-7.43 (m, 1H), 7.55-7.59 (m, 1H), 7.60-7.67 (m, 2H), 7.89 (d, 2H), 8.20 (d, 2H), 8.73 (s, 1H), 9.56 (t, 1H). Rt = 2.38 min, Chiralpak IA 5 μm 100 × 4.6 mm, eluent A: $CO_2$, eluent B: ethanol, isocratic: 18% B, 4.0 mL/min, 37.5° C., BPR: 100 bar, 254 nm |
| 328 | 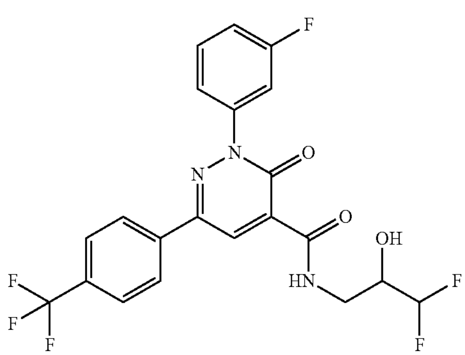 [SMILES: O=C(NCC(O)C(F)F)c1cc(-c2ccc(C(F)(F)F)cc2)nn(-c2cccc(F)c2)c1=O] | (+)-N-(3,3-difluoro-2-hydroxypropyl)-2-(3-fluorophenyl)-3-oxo-6-[4-(trifluoromethyl)phenyl]-2,3-dihydropyridazine-4-carboxamide, enantiomer 2, $[α]_D^{20}$ = +14.6° (c = 1.00, methanol) | N-[(2RS)-3,3-difluoro-2-hydroxypropyl]-2-(3-fluorophenyl)-3-oxo-6-[4-(trifluoromethyl)phenyl]-2,3-dihydropyridazine-4-carboxamide, Chiralpak IA 5μ 250 × 30 mm, eluent A: $CO_2$, eluent B: ethanol, isocratic: 18% B, 100 mL/min, 40° C., BPR: 150 bar, 254 nm | $^1$H-NMR (400 MHz, DMSO-$d_6$): δ [ppm] = 3.40 (ddd, 1H), 3.62-3.70 (m, 1H), 3.79-3.91 (m, 1H), 5.94 (dt, 1H), 6.00 (d, 1H), 7.37-7.43 (m, 1H), 7.55-7.58 (m, 1H), 7.60-7.67 (m, 2H), 8.21 (d, 2H), 8.73 (s, 1H), 9.56 (t, 1H). Rt = 3.39 min, Chiralpak IA 5 μm 100 × 4.6 mm, eluent A: $CO_2$, eluent B: ethanol, isocratic: 18% B, 4.0 mL/min, 37.5° C., BPR: 100 bar, 254 nm |

TABLE 5-continued

Examples 313-378

| Example | structure | IUPAC name | Starting materials | analytics |
|---|---|---|---|---|
| 329 | 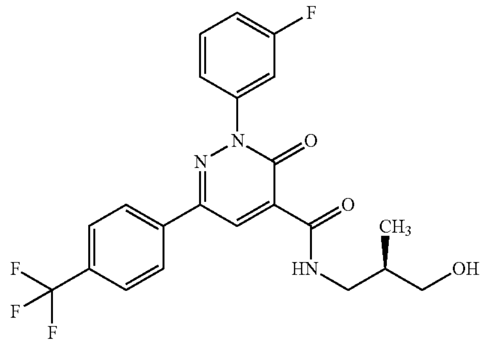 [SMILES: C[C@@H](CO)CNC(=O)c1cc(-c2ccc(C(F)(F)F)cc2)nn(-c2cccc(F)c2)c1=O] | (+)-2-(3-fluorophenyl)-N-[(2R)-3-hydroxy-2-methylpropyl]-3-oxo-6-[4-(trifluoromethyl)phenyl]-2,3-dihydropyridazine-4-carboxamide, enantiomer 1, $[\alpha]_D^{20} = +13.2°$ (c = 1.00, DMSO) | 2-(3-fluorophenyl)-N-[(2RS)-3-hydroxy-2-methylpropyl]-3-oxo-6-[4-(trifluoromethyl)phenyl]-2,3-dihydropyridazine-4-carboxamide, Chiralpak IF 5μ 250 × 30 mm, eluent A: $CO_2$, eluent B: methanol, isocratic: 27% B, 100 mL/min, 40° C., BPR: 150 bar, 254 nm | $^1$H-NMR (400 MHz, DMSO-$d_6$): δ [ppm] = 0.88 (d, 3H), 1.75-1.86 (m, 1H), 3.24-3.42 (m, 4H and water signal), 4.62 (t, 1H), 7.37-7.42 (m, 1H), 7.55-7.58 (m, 1H), 7.60-7.66 (m, 2H), 7.88 (d, 2H), 8.20 (d, 2H), 8.70 (s, 1H), 9.43 (t, 1H). Rt = 3.39 min, Chiralpak IF 5 μm 100 × 4.6 mm, eluent A: $CO_2$, eluent B: methanol, isocratic: 27% B, 4.0 mL/min, 37.5° C., BPR: 100 bar, 254 nm |
| 330 | 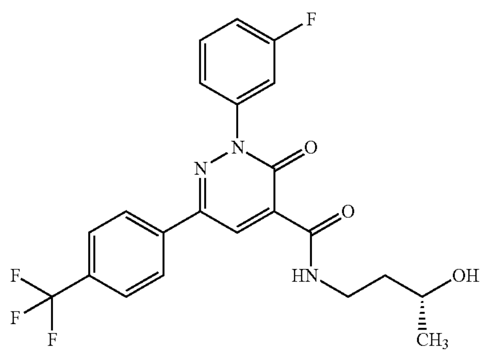 [SMILES: C[C@@H](O)CCNC(=O)c1cc(-c2ccc(C(F)(F)F)cc2)nn(-c2cccc(F)c2)c1=O] | (−)-2-(3-fluorophenyl)-N-[(3R)-3-hydroxybutyl]-3-oxo-6-[4-(trifluoromethyl)phenyl]-2,3-dihydropyridazine-4-carboxamide, enantiomer 1, $[\alpha]_D^{20} = -9.1°$ (c = 1.00, DMSO) | 2-(3-fluorophenyl)-N-[(3RS)-3-hydroxybutyl]-3-oxo-6-[4-(trifluoromethyl)phenyl]-2,3-dihydropyridazine-4-carboxamide, Chiralpak ID 5μ 250 × 30 mm, eluent A: hexane, eluent B: ethanol, isocratic: 40% B, 40 mL/min, 254 nm | $^1$H-NMR (400 MHz, DMSO-$d_6$): δ [ppm] = 1.08 (d, 3H), 1.49-1.66 (m, 2H), 3.36-3.50 (m, 2H), 3.65-3.74 (m, 1H), 4.62 (d, 1H), 7.36-7.42 (m, 1H), 7.55-7.58 (m, 1H), 7.59-7.66 (m, 2H), 7.88 (d, 2H), 8.20 (d, 2H), 8.70 (s, 1H), 9.42 (t, 1H). Rt = 5.81 min, Chiralpak ID 3 μm 100 × 4.6 mm, eluent A: hexane, eluent B: ethanol, gradient: 20-70% B in 7 min, 1.4 mL/min, 25° C., 254 nm |
| 331 | 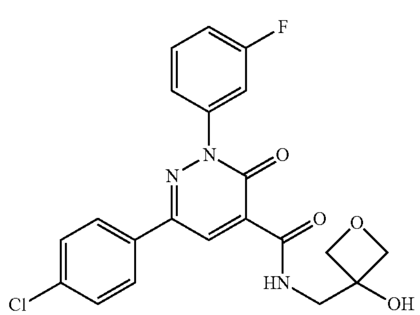 [SMILES: O=C(NCC1(O)COC1)c1cc(-c2ccc(Cl)cc2)nn(-c2cccc(F)c2)c1=O] | 6-(4-chlorophenyl)-2-(3-fluorophenyl)-N-[(3-hydroxyoxetan-3-yl)methyl]-3-oxo-2,3-dihydropyridazine-4-carboxamide | 6-(4-chlorophenyl)-2-(3-fluorophenyl)-3-oxo-2,3-dihydropyridazine-4-carboxylic acid, 3-(aminomethyl)oxetan-3-ol | $^1$H-NMR (400 MHz, DMSO-$d_6$): δ [ppm] = 3.72 (d, 2H), 4.37 (d, 2H), 4.43 (d, 2H), 6.13 (s, 1H), 7.36-7.41 (m, 1H), 7.53-7.65 (m, 5H), 7.98-8.03 (m, 2H), 8.69 (s, 1H), 9.59 (t, 1H). |

TABLE 5-continued

Examples 313-378

| Example | structure | IUPAC name | Starting materials | analytics |
|---|---|---|---|---|
| 332 | 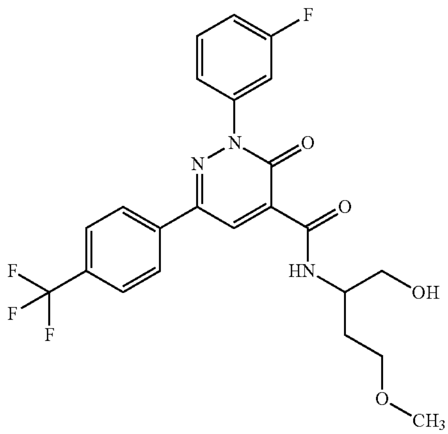 [SMILES: COCCC(CO)NC(=O)c1cc(-c2ccc(C(F)(F)F)cc2)nn(-c2cccc(F)c2)c1=O] | (+)-2-(3-fluorophenyl)-N-(1-hydroxy-4-methoxybutan-2-yl)-3-oxo-6-[4-(trifluoromethyl)phenyl]-2,3-dihydropyridazine-4-carboxamide, enantiomer 1, $[\alpha]_D^{20}$ = +30.5° (c = 1.00, methanol) | 2-(3-fluorophenyl)-N-[(2RS)-1-hydroxy-4-methoxybutan-2-yl]-3-oxo-6-[4-(trifluoromethyl)phenyl]-2,3-dihydropyridazine-4-carboxamide, Chiralpak IC 5μ 250 × 30 mm, eluent A: $CO_2$, eluent B: ethanol, isocratic: 13% B, 100 mL/min, 40° C., BPR: 150 bar, 254 nm | $^1$H-NMR (400 MHz, DMSO-$d_6$): δ [ppm] = 1.67-1.77 (m, 1H), 1.82-1.91 (m, 1H), 3.21 (s, 3H), 3.39 (t, 2H), 3.42-3.48 (m, 1H), 3.49-3.55 (m, 1H), 4.04-4.14 (m, 1H), 4.91 (t, 1H), 7.55-7.58 (m, 1H), 7.60-7.66 (m, 2H), 7.88 (d, 2H), 8.20 (d, 2H), 8.72 (s, 1H), 9.40 (d, 1H). Rt = 2.78 min, Chiralpak IC 5 μm 100 × 4.6 mm, eluent A: $CO_2$, eluent B: ethanol, isocratic: 13%, 4.0 mL/min, 37.5° C., BPR: 100 bar, 254 nm |
| 333 | 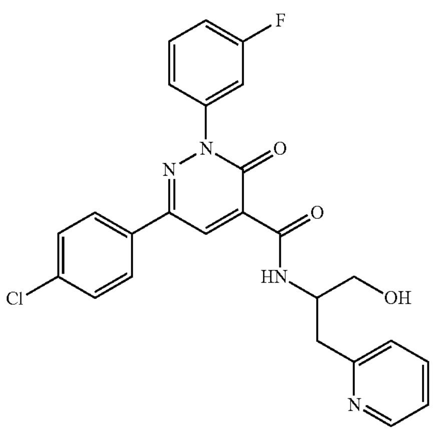 [SMILES: O=C(NC(CO)Cc1ccccn1)c1cc(-c2ccc(Cl)cc2)nn(-c2cccc(F)c2)c1=O] | 6-(4-chlorophenyl)-2-(3-fluorophenyl)-N-[(2RS)-1-hydroxy-3-(pyridin-2-yl)propan-2-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-2-amino-3-(pyridin-2-yl)propan-1-ol dihydrochloride | $^1$H-NMR (400 MHz, DMSO-$d_6$): δ [ppm] = 2.98 (dd, 1H), 3.09 (dd, 1H), 3.42-3.53 (m, 2H), 4.41-4.50 (m, 1H), 5.02 (t, 1H), 7.20 (ddd, 1H), 7.28 (dt, 1H), 7.36-7.42 (m, 1H), 7.53-7.65 (m, 5H), 7.69 (td, 1H), 7.96-8.00 (m, 2H), 8.48 (ddd, 1H), 8.60 (s, 1H), 9.59 (d, 1H). |
| 334 | 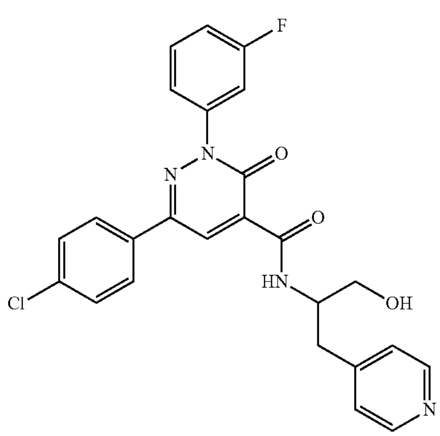 [SMILES: O=C(NC(CO)Cc1ccncc1)c1cc(-c2ccc(Cl)cc2)nn(-c2cccc(F)c2)c1=O] | 6-(4-chlorophenyl)-2-(3-fluorophenyl)-N-[(2RS)-1-hydroxy-3-(pyridin-4-yl)propan-2-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-2-amino-3-(pyridin-4-yl)propan-1-ol dihydrochloride | $^1$H-NMR (400 MHz, DMSO-$d_6$): δ [ppm] = 2.84 (dd, 1H), 2.97 (dd, 1H), 3.42-3.53 (m, 2H), 4.24-4.32 (m, 1H), 5.09 (t, 1H), 7.26-7.28 (m, 2H), 7.36-7.42 (m, 1H), 7.53-7.65 (m, 5H), 7.95-8.00 (m, 2H), 8.43-8.46 (m, 2H), 8.60 (s, 1H), 9.51 (d, 1H). |

TABLE 5-continued

Examples 313-378

| Example | structure | IUPAC name | Starting materials | analytics |
|---|---|---|---|---|
| 335 | 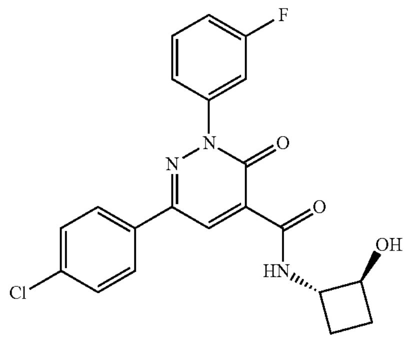 [SMILES: O=C(N[C@H]1CC[C@@H]1O)c1cc(-c2ccc(Cl)cc2)nn(-c2cccc(F)c2)c1=O] | (−)-6-(4-chlorophenyl)-2-(3-fluorophenyl)-N-(trans-2-hydroxycyclobutyl)-3-oxo-2,3-dihydropyridazine-4-carboxamide, enantiomer 1, $[\alpha]_D^{20}$ = −45.1° (c = 1.00, methanol) | 6-(4-chlorophenyl)-2-(3-fluorophenyl)-N-[(1RS,2RS)-2-hydroxycyclobutyl]-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm | $^1$H-NMR (400 MHz, DMSO-d$_6$): δ [ppm] = 1.28-1.39 (m, 1H), 1.42-1.53 (m, 1H), 1.92-2.03 (m, 2H), 3.95 (quin, 1H), 4.18 (quin, 1H), 5.42 (d, 1H), 7.35-7.41 (m, 1H), 7.54-7.66 (m, 5H), 7.98-8.02 (m, 2H), 8.62 (s, 1H), 9.53 (d, 1H). Rt = 4.75 min, Chiralpak IC 3 μm 100 × 4.6 mm, eluent A: hexane + 0.1 vol % diethylamine, eluent B: ethanol, gradient: 20-50% B in 7 min, 1.4 mL/min, 25° C., 254 nm |
| 336 | 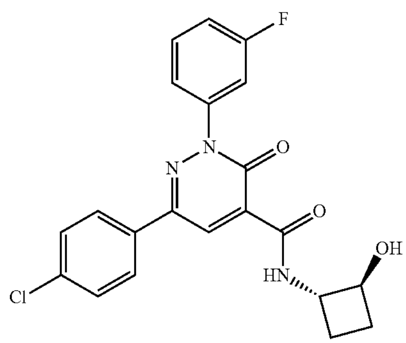 [SMILES: O=C(N[C@H]1CC[C@@H]1O)c1cc(-c2ccc(Cl)cc2)nn(-c2cccc(F)c2)c1=O] | (+)-6-(4-chlorophenyl)-2-(3-fluorophenyl)-N-(trans-2-hydroxycyclobutyl)-3-oxo-2,3-dihydropyridazine-4-carboxamide, enantiomer 2, $[\alpha]_D^{20}$ = +64.5° (c = 1.00, methanol) | 6-(4-chlorophenyl)-2-(3-fluorophenyl)-N-[(1RS,2RS)-2-hydroxycyclobutyl]-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm | $^1$H-NMR (400 MHz, DMSO-d$_6$): δ [ppm] = 1.28-1.39 (m, 1H), 1.41-1.53 (m, 1H), 1.93-2.03 (m, 2H), 3.95 (quin, 1H), 4.18 (quin, 1H), 5.42 (d, 1H), 7.35-7.42 (m, 1H), 7.35-7.42 (m, 1H), 7.54-7.66 (m, 5H), 8.00 (d, 2H), 8.62 (s, 1H), 9.53 (d, 1H). Rt = 5.97 min, Chiralpak IC 3 μm 100 × 4.6 mm, eluent A: hexane + 0.1 vol % diethylamine, eluent B: ethanol, gradient: 20-50% B in 7 min, 1.4 mL/min, 25° C., 254 nm |
| 337 | 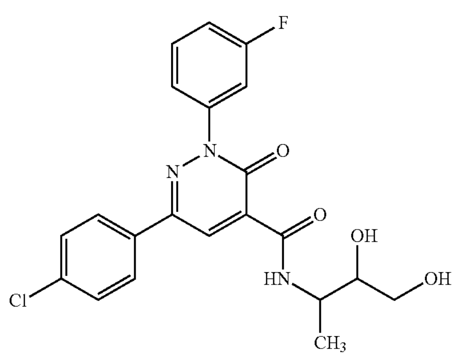 [SMILES: CC(NC(=O)c1cc(-c2ccc(Cl)cc2)nn(-c2cccc(F)c2)c1=O)C(O)CO] | 6-(4-chlorophenyl)-N-(3,4-dihydroxybutan-2-yl)-2-(3-fluorophenyl)-3-oxo-2,3-dihydropyridazine-4-carboxamide | 6-(4-chlorophenyl)-2-(3-fluorophenyl)-3-oxo-2,3-dihydropyridazine-4-carboxylic acid, 3-aminobutane-1,2-diol | $^1$H-NMR (400 MHz, DMSO-d$_6$): δ [ppm] = 1.08 (d, 3H, minor diast.), 1.18 (d, 3H, major diast.), 3.21-3.42 (m, 4H, both diast. and water signal), 3.46-3.58 (m, 2H, both diast.), 4.12-4.22 (m, 2H, both diast.), 4.61 (t, 1H, major diast.), 4.68 (t, 1H, minor diast.), 4.99 (d, 1H, minor diast.), 5.15 (d, 1H, major diast.), 7.35-7.42 (m, 2H, both diast.), 7.52-7.65 (m, 10H, both diast.), 7.96-8.02 (m, 4H, both diatst.), 8.65 (s, 1H, minor diast.), 8.66 (s, 1H, major diast.), 9.53 (d, 1H, major diast.), 9.61 (d, 1H, minor diast.). |

TABLE 5-continued

Examples 313-378

| Example | structure | IUPAC name | Starting materials | analytics |
|---|---|---|---|---|
| 338 | 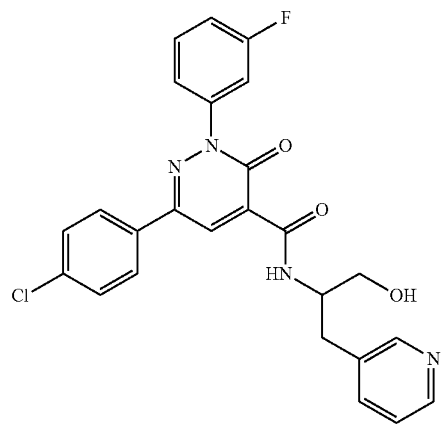 [SMILES: O=C(NC(CO)Cc1cccnc1)c1cc(-c2ccc(Cl)cc2)nn(-c2cccc(F)c2)c1=O] | 6-(4-chlorophenyl)-2-(3-fluorophenyl)-N-[(2RS)-1-hydroxy-3-(pyridin-3-yl)propan-2-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-2-amino-3-(pyridin-3-yl)propan-1-ol dihydrochloride | $^1$H-NMR (400 MHz, DMSO-d$_6$): δ [ppm] = 2.83 (dd, 1H), 2.97 (dd, 1H), 3.43-3.53 (m, 2H), 4.19-4.27 (m, 1H), 5.09 (t, 1H), 7.30 (ddd, 1H), 7.36-7.42 (m, 1H), 7.54-7.69 (m, 6H), 7.95-8.00 (m, 2H), 8.40 (dd, 1H), 8.45 (d, 1H), 8.59 (s, 1H), 9.51 (d, 1H). |
| 339 | 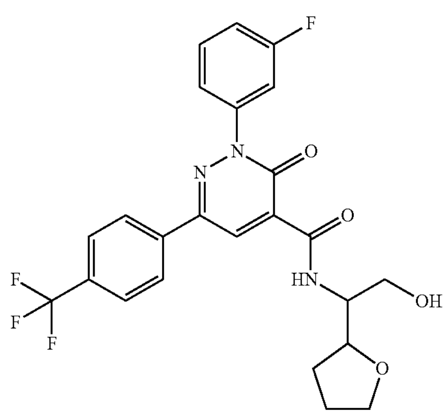 [SMILES: O=C(NC(CO)C1CCCO1)c1cc(-c2ccc(C(F)(F)F)cc2)nn(-c2cccc(F)c2)c1=O] | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, isomer 3, $[α]_D^{20}$ = +28.9° (c = 1.00, methanol) | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, Chiralpak IB 5μ 250 × 30 mm, eluent A: CO$_2$, eluent B: methanol, isocratic: 28% B, 100 mL/min, 40° C., BPR: 150 bar, 254 nm | $^1$H-NMR (400 MHz, DMSO-d$_6$): δ [ppm] = 1.69-1.93 (m, 4H), 3.47-3.53 (m, 1H), 3.61-3.69 (m, 2H), 3.75-3.81 (m, 1H), 3.92-3.98 (m, 1H), 3.99-4.06 (m, 1H), 4.89 (t, 1H), 7.37-7.43 (m, 1H), 7.37-7.43 (m, 1H), 7.55-7.58 (m, 1H), 7.60-7.66 (m, 2H), 7.88 (d, 2H), 8.20 (d, 2H), 8.74 (s, 1H), 9.56 (d, 1H). Rt = 3.56 min, Chiralpak IB 5 μm 100 × 4.6 mm, eluent A: CO$_2$, eluent B: methanol, isocratic: 28% B, 4.0 mL/min, 37.5° C., BPR: 100 bar, 254 nm |
| 340 | 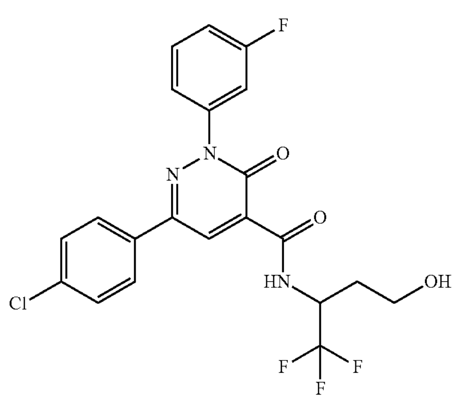 [SMILES: O=C(NC(CCO)C(F)(F)F)c1cc(-c2ccc(Cl)cc2)nn(-c2cccc(F)c2)c1=O] | 6-(4-chlorophenyl)-2-(3-fluorophenyl)-3-oxo-N-[(2RS)-1,1,1-trifluoro-4-hydroxybutan-2-yl]-2,3-dihydropyridazine-4-carboxamide | 6-(4-chlorophenyl)-2-(3-fluorophenyl)-3-oxo-2,3-dihydropyridazine-4-carboxylic acid, (3RS)-3-amino-4,4,4-trifluorobutan-1-ol | $^1$H-NMR (400 MHz, DMSO-d$_6$): δ [ppm] = 1.74-1.84 (m, 1H), 1.90-2.01 (m, 1H), 3.40-3.49 (m, 1H), 3.52-3.60 (m, 1H), 4.74 (t, 1H), 4.87-5.00 (m, 1H), 7.36-7.42 (m, 1H), 7.55-7.66 (m, 5H), 7.99-8.04 (m, 2H), 8.66 (s, 1H), 9.62 (d, 1H). |

TABLE 5-continued

Examples 313-378

| Example | structure | IUPAC name | Starting materials | analytics |
|---|---|---|---|---|
| 341 | 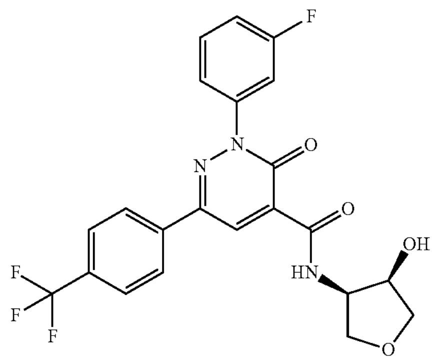 [SMILES: O=C(N[C@@H]1COC[C@@H]1O)c1cc(-c2ccc(C(F)(F)F)cc2)nn(-c2cccc(F)c2)c1=O] | 2-(3-fluorophenyl)-N-(cis-4-hydroxytetrahydrofuran-3-yl)-3-oxo-6-[4-(trifluoromethyl)phenyl]-2,3-dihydropyridazine-4-carboxamide | 2-(3-fluorophenyl)-3-oxo-6-[4-(trifluoromethyl)phenyl]-2,3-dihydropyridazine-4-carboxylic acid, (3RS,4RS)-4-aminotetrahydrofuran-3-ol hydrochloride (1:1) | $^1$H-NMR (400 MHz, DMSO-d$_6$): δ [ppm] = 3.45 (t, 1H), 3.61 (dd, 1H), 3.93 (dd, 1H), 4.01 (dd, 1H), 4.25-4.31 (m, 1H), 4.32-4.40 (m, 1H), 5.70 (d, 1H), 7.37-7.43 (m, 1H), 7.56 (ddd, 1H), 7.60-7.67 (m, 2H), 7.88 (d, 2H), 8.20 (d, 2H), 8.74 (s, 1H), 9.82 (d, 1H). |
| 342 | 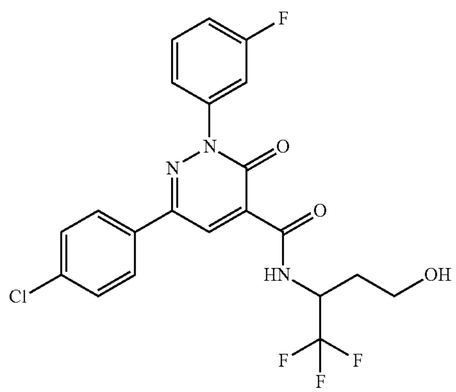 [SMILES: O=C(NC(CCO)C(F)(F)F)c1cc(-c2ccc(Cl)cc2)nn(-c2cccc(F)c2)c1=O] | (−)-6-(4-chlorophenyl)-2-(3-fluorophenyl)-3-oxo-N-(1,1,1-trifluoro-4-hydroxybutan-2-yl)-2,3-dihydropyridazine-4-carboxamide, enantiomer 2, $[α]_D^{20}$ = −38.5° (c = 1.00, methanol) | 6-(4-chlorophenyl)-2-(3-fluorophenyl)-3-oxo-N-(1,1,1-trifluoro-4-hydroxybutan-2-yl)-2,3-dihydropyridazine-4-carboxamide, Chiralpak IC 5µ 250 × 30 mm, eluent A: CO$_2$, eluent B: ethanol, isocratic: 12% B, 100 mL/min, 40° C., BPR: 150 bar, 254 nm | $^1$H-NMR (400 MHz, DMSO-d$_6$): δ [ppm] = 1.74-1.84 (m, 1H), 1.90-2.00 (m, 1H), 3.40-3.50 (m, 1H), 3.52-3.60 (m, 1H), 4.74 (t, 1H), 4.87-5.01 (m, 1H), 7.36-7.42 (m, 1H), 7.55-7.66 (m, 5H), 8.00-8.04 (m, 2H), 8.66 (s, 1H), 9.62 (d, 1H). Rt = 1.90 min Chiralpak IC 5µ 100 × 4.6 mm, eluent A: CO$_2$, eluent B: ethanol, isocratic: 12% B, 4.0 mL/min, 37.5° C., BPR: 100 bar, 254 nm |
| 343 | 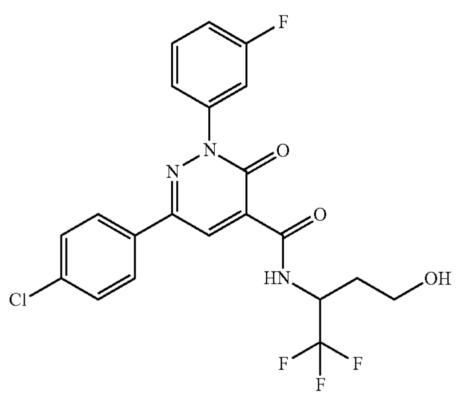 [SMILES: O=C(NC(CCO)C(F)(F)F)c1cc(-c2ccc(Cl)cc2)nn(-c2cccc(F)c2)c1=O] | (+)-6-(4-chlorophenyl)-2-(3-fluorophenyl)-3-oxo-N-(1,1,1-trifluoro-4-hydroxybutan-2-yl)-2,3-dihydropyridazine-4-carboxamide, enantiomer 1, $[α]_D^{20}$ = +69.4° (c = 1.00, methanol) | 6-(4-chlorophenyl)-2-(3-fluorophenyl)-3-oxo-N-(1,1,1-trifluoro-4-hydroxybutan-2-yl)-2,3-dihydropyridazine-4-carboxamide, Chiralpak IC 5µ 250 × 30 mm, eluent A: CO$_2$, eluent B: ethanol, isocratic: 12% B, 100 mL/min, 40° C., BPR: 150 bar, 254 nm | $^1$H-NMR (400 MHz, DMSO-d$_6$): δ [ppm] = 1.73-1.84 (m, 1H), 1.91-2.01 (m, 1H), 3.40-3.50 (m, 1H), 3.52-3.60 (m, 1H), 4.74 (t, 1H), 4.87-5.01 (m, 1H), 7.36-7.42 (m, 1H), 7.55-7.67 (m, 5H), 7.99-8.04 (m, 2H), 8.66 (s, 1H), 9.62 (d, 1H). Rt = 1.44 min Chiralpak IC 5µ 100 × 4.6 mm, eluent A: CO$_2$, eluent B: ethanol, isocratic: 12% B, 4.0 mL/min, 37.5° C., BPR: 100 bar, 254 nm |
| 344 | 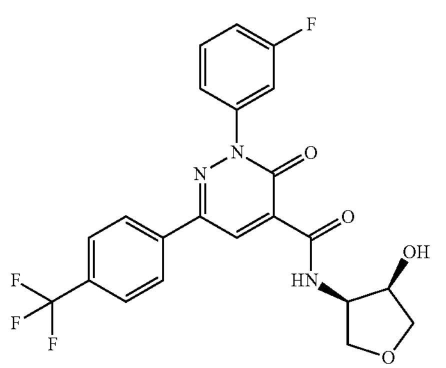 [SMILES: O=C(N[C@@H]1COC[C@@H]1O)c1cc(-c2ccc(C(F)(F)F)cc2)nn(-c2cccc(F)c2)c1=O] | (+)-2-(3-fluorophenyl)-N-(cis-4-hydroxytetrahydrofuran-3-yl)-3-oxo-6-[4-(trifluoromethyl)phenyl]-2,3-dihydropyridazine-4-carboxamide, enantiomer 1, $[α]_D^{20}$ = +23.7° (c = 1.00, methanol) | 2-(3-fluorophenyl)-N-[(3RS,4RS)-4-hydroxytetrahydrofuran-3-yl]-3-oxo-6-[4-(trifluoromethyl)phenyl]-2,3-dihydropyridazine-4-carboxamide, Chiralpak IC 5µ 250 × 30 mm, eluent A: CO$_2$, eluent B: ethanol, isocratic: 12% B, 100 mL/min, 40° C., BPR: 150 bar, 254 nm | $^1$H-NMR (400 MHz, DMSO-d$_6$): δ [ppm] = 3.45 (t, 1H), 3.61 (dd, 1H), 3.93 (dd, 1H), 4.01 (dd, 1H), 4.28 (ddt, 1H), 4.32-4.39 (m, 1H), 5.69 (d, 1H), 7.40 (tdd, 1H), 7.57 (ddd, 1H), 7.60-7.67 (m, 2H), 7.89 (d, 2H), 8.20 (d, 2H), 8.74 (s, 1H), 9.82 (d, 1H). Rt = 1.44 min Chiralpak IC 5µ 100 × 4.6 mm, eluent A: CO$_2$, eluent B: ethanol, isocratic: 12% B, 4.0 mL/min, 37.5° C., BPR: 100 bar, 254 nm |

TABLE 5-continued

Examples 313-378

| Example | structure | IUPAC name | Starting materials | analytics |
|---|---|---|---|---|
| 345 | 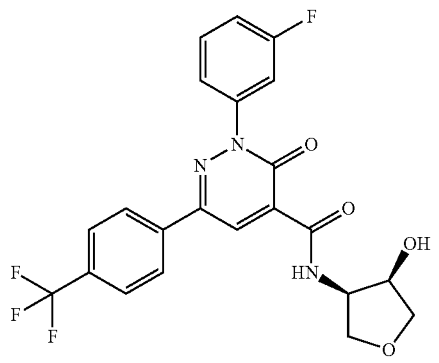 [SMILES: O=C(N[C@@H]1COC[C@@H]1O)c1cc(-c2ccc(C(F)(F)F)cc2)nn(-c2cccc(F)c2)c1=O] | (−)-2-(3-fluorophenyl)-N-(cis-4-hydroxytetrahydrofuran-3-yl)-3-oxo-6-[4-(trifluoromethyl)phenyl]-2,3-dihydropyridazine-4-carboxamide, enantiomer 2, $[\alpha]_D^{20} = -25.6°$ (c = 1.00, methanol) | 2-(3-fluorophenyl)-N-[(3RS,4RS)-4-hydroxytetrahydrofuran-3-yl]-3-oxo-6-[4-(trifluoromethyl)phenyl]-2,3-dihydropyridazine-4-carboxamide, Chiralpak IC 5μ 250 × 30 mm, eluent A: $CO_2$, eluent B: ethanol, isocratic: 12% B, 100 mL/min, 40° C., BPR: 150 bar, 254 nm | $^1$H-NMR (400 MHz, DMSO-$d_6$): δ [ppm] = 0.00-0.00 (m, 1H), 3.45 (t, 1H), 3.61 (dd, 1H), 3.93 (dd, 1H), 4.01 (dd, 1H), 4.25-4.30 (m, 1H), 4.32-4.40 (m, 1H), 5.70 (d, 1H), 7.37-7.43 (m, 1H), 7.56 (ddd, 1H), 7.60-7.66 (m, 2H), 7.89 (d, 2H), 8.20 (d, 2H), 8.74 (s, 1H), 9.82 (d, 1H). Rt = 1.90 min Chiralpak IC 5μ 100 × 4.6 mm, eluent A: $CO_2$, eluent B: ethanol, isocratic: 12% B, 4.0 mL/min, 37.5° C., BPR: 100 bar, 254 nm |
| 346 | 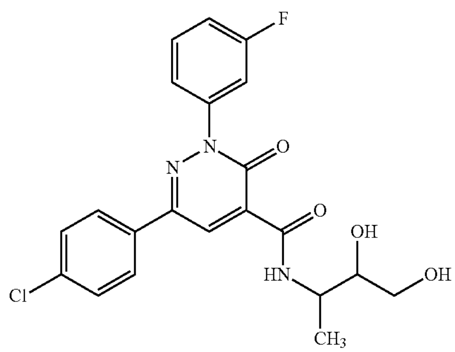 [SMILES: CC(NC(=O)c1cc(-c2ccc(Cl)cc2)nn(-c2cccc(F)c2)c1=O)C(O)CO] | 6-(4-chlorophenyl)-N-(3,4-dihydroxybutan-2-yl)-2-(3-fluorophenyl)-3-oxo-2,3-dihydropyridazine-4-carboxamide, isomer 4, $[\alpha]_D^{20} = -59.6°$ (c = 1.00, methanol) | 6-(4-chlorophenyl)-N-(3,4-dihydroxybutan-2-yl)-2-(3-fluorophenyl)-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm, and Chiralpak IA 5μ 250 × 30 mm, eluent A: $CO_2$, eluent B: methanol, isocratic: 25% B, 100 mL/min, 40° C., BPR: 150 bar, 254 nm | $^1$H-NMR (400 MHz, DMSO-$d_6$): δ [ppm] = 1.08 (d, 3H), 3.28-3.42 (m, 2H and water signal), 3.50-3.58 (m, 1H), 4.13-4.22 (m, 1H), 4.68 (t, 1H), 5.00 (d, 1H), 7.38 (tdd, 1H), 7.53-7.65 (m, 5H), 8.00 (d, 2H), 8.66 (s, 1H), 9.61 (d, 1H). Rt = 5.49 min, Chiralpak IA 5 μm 100 × 4.6 mm, eluent A: $CO_2$, eluent B: methanol, isocratic: 25% B, 4.0 mL/min, 37.5° C., BPR: 100 bar, 254 nm |
| 347 | 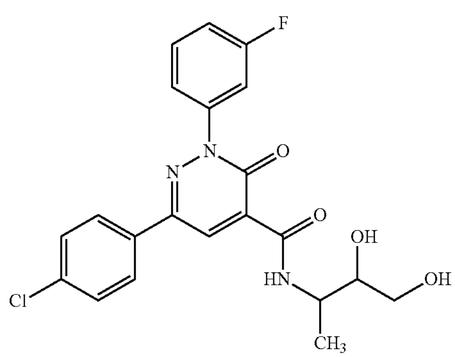 [SMILES: CC(NC(=O)c1cc(-c2ccc(Cl)cc2)nn(-c2cccc(F)c2)c1=O)C(O)CO] | 6-(4-chlorophenyl)-N-(3,4-dihydroxybutan-2-yl)-2-(3-fluorophenyl)-3-oxo-2,3-dihydropyridazine-4-carboxamide, isomer 3, $[\alpha]_D^{20} = -28.9°$ (c = 1.00, methanol) | 6-(4-chlorophenyl)-N-(3,4-dihydroxybutan-2-yl)-2-(3-fluorophenyl)-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm, and Chiralpak IA 5μ 250 × 30 mm, eluent A: $CO_2$, eluent B: methanol, isocratic: 25% B, 100 mL/min, 40° C., BPR: 150 bar, 254 nm | $^1$H-NMR (400 MHz, DMSO-$d_6$): δ [ppm] = 1.18 (d, 3H), 3.21-3.28 (m, 1H), 3.29-3.36 (m, 1H and water signal), 3.46-3.53 (m, 1H), 4.12-4.21 (m, 1H), 4.61 (t, 1H), 5.15 (d, 1H), 7.35-7.41 (m, 1H), 7.52-7.65 (m, 5H), 7.96-8.01 (m, 2H), 8.65 (s, 1H), 9.53 (d, 1H). Rt = 3.41 min, Chiralpak IA 5 μm 100 × 4.6 mm, eluent A: $CO_2$, eluent B: methanol, isocratic: 25% B, 4.0 mL/min, 37.5° C., BPR: 100 bar, 254 nm |

TABLE 5-continued

Examples 313-378

| Example | structure | IUPAC name | Starting materials | analytics |
|---|---|---|---|---|
| 348 | 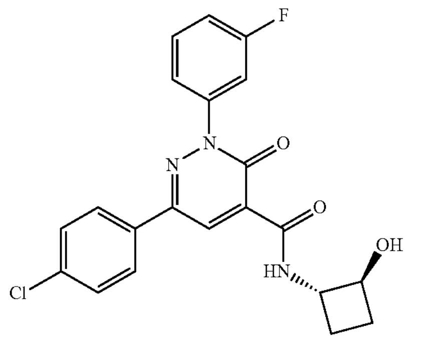 [SMILES: O=C(N[C@H]1CC[C@@H]1O)c1cc(-c2ccc(Cl)cc2)nn(-c2cccc(F)c2)c1=O] | 6-(4-chlorophenyl)-2-(3-fluorophenyl)-N-(trans-2-hydroxycyclobutyl)-3-oxo-2,3-dihydropyridazine-4-carboxamide | 6-(4-chlorophenyl)-2-(3-fluorophenyl)-3-oxo-2,3-dihydropyridazine-4-carboxylic acid, (1RS,2RS)-2-aminocyclobutanol hydrochloride (1:1) | $^1$H-NMR (400 MHz, DMSO-d$_6$): δ [ppm] = 1.27-1.39 (m, 1H), 1.42-1.52 (m, 1H), 1.92-2.03 (m, 2H), 3.95 (quin, 1H), 4.18 (quin, 1H), 5.43 (d, 1H), 7.35-7.41 (m, 1H), 7.54-7.65 (m, 5H), 7.97-8.03 (m, 2H), 8.62 (s, 1H), 9.53 (d, 1H). |
| 349 | 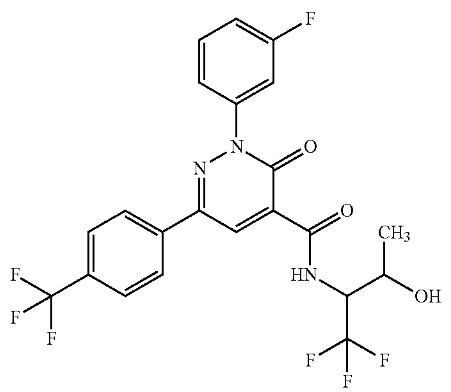 [SMILES: CC(O)C(NC(=O)c1cc(-c2ccc(C(F)(F)F)cc2)nn(-c2cccc(F)c2)c1=O)C(F)(F)F] | 2-(3-fluorophenyl)-3-oxo-N-(1,1,1-trifluoro-3-hydroxybutan-2-yl)-6-[4-(trifluoromethyl)phenyl]-2,3-dihydropyridazine-4-carboxamide, isomer 1, [α]$_D^{20}$ = +32.5° (c = 1.00, methanol) | 2-(3-fluorophenyl)-3-oxo-N-(1,1,1-trifluoro-3-hydroxybutan-2-yl)-6-[4-(trifluoromethyl)phenyl]-2,3-dihydropyridazine-4-carboxamide, Chiralpak IC 5μ 250 × 30 mm, eluent A: hexane, eluent B: 2-propanol, gradient: 20-50% B in 20 min, 40 mL/min, 254 nm | $^1$H-NMR (400 MHz, DMSO-d$_6$): δ [ppm] = 1.21 (d, 3H), 4.00-4.09 (m, 1H), 4.72-4.83 (m, 1H), 5.36 (d, 1H), 7.38-7.44 (m, 1H), 7.56-7.60 (m, 1H), 7.61-7.67 (m, 2H), 7.89 (d, 2H), 8.22 (d, 2H), 8.78 (s, 1H), 9.92 (d, 1H). Rt = 1.89 min Chiralpak IC 3μ 100 × 4.6 mm, eluent A: hexane + 0.1 vol % diethylamine, eluent B: 2-propanol, gradient: 20-50% B in 7 min, 1.4 mL/min, 25° C., 254 nm |
| 350 | 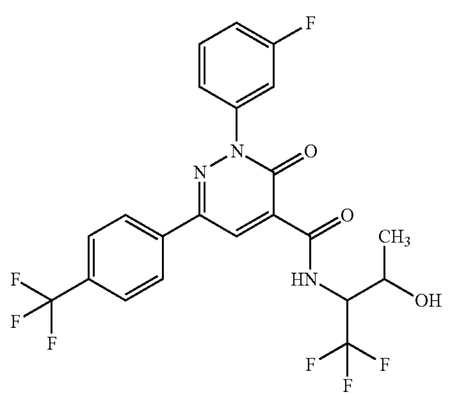 [SMILES: CC(O)C(NC(=O)c1cc(-c2ccc(C(F)(F)F)cc2)nn(-c2cccc(F)c2)c1=O)C(F)(F)F] | 2-(3-fluorophenyl)-3-oxo-N-(1,1,1-trifluoro-3-hydroxybutan-2-yl)-6-[4-(trifluoromethyl)phenyl]-2,3-dihydropyridazine-4-carboxamide, isomer 2, [α]$_D^{20}$ = −32.3° (c = 1.00, methanol) | 2-(3-fluorophenyl)-3-oxo-N-(1,1,1-trifluoro-3-hydroxybutan-2-yl)-6-[4-(trifluoromethyl)phenyl]-2,3-dihydropyridazine-4-carboxamide, Chiralpak IC 5μ 250 × 30 mm, eluent A: hexane, eluent B: 2-propanol, gradient: 20-50% B in 20 min, 40 mL/min, 254 nm | $^1$H-NMR (400 MHz, DMSO-d$_6$): δ [ppm] = 1.21 (d, 3H), 4.00-4.09 (m, 1H), 4.72-4.83 (m, 1H), 5.36 (d, 1H), 7.38-7.44 (m, 1H), 7.56-7.60 (m, 1H), 7.61-7.68 (m, 2H), 7.89 (d, 2H), 8.22 (d, 2H), 8.78 (s, 1H), 9.92 (d, 1H). Rt = 3.61 min Chiralpak IC 3μ 100 × 4.6 mm, eluent A: hexane + 0.1 vol % diethylamine, eluent B: 2-propanol, gradient: 20-50% B in 7 min, 1.4 mL/min, 25° C., 254 nm |
| 351 | 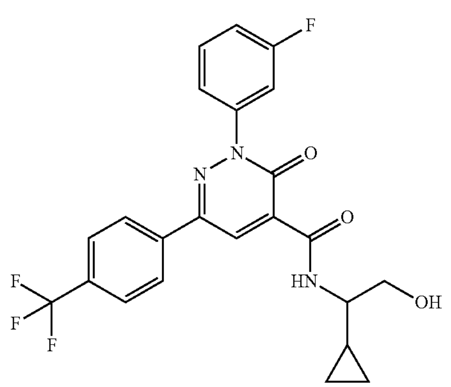 [SMILES: O=C(NC(CO)C1CC1)c1cc(-c2ccc(C(F)(F)F)cc2)nn(-c2cccc(F)c2)c1=O] | (−)-N-(1-cyclopropyl-2-hydroxyethyl)-2-(3-fluorophenyl)-3-oxo-6-[4-(trifluoromethyl)phenyl]-2,3-dihydropyridazine-4-carboxamide, enantiomer 1, [α]$_D^{20}$ = −24.7° (c = 1.00, methanol) | N-[(1RS)-1-cyclopropyl-2-hydroxyethyl]-2-(3-fluorophenyl)-3-oxo-6-[4-(trifluoromethyl)phenyl]-2,3-dihydropyridazine-4-carboxamide, Chiralpak IB 5μ 250 × 30 mm, eluent A: methanol + 0.1 vol % diethylamine, eluent B: ethanol, isocratic: 50% B, 40 mL/min, 254 nm | $^1$H-NMR (400 MHz, DMSO-d$_6$): δ [ppm] = 0.26-0.50 (m, 4H), 1.03-1.12 (m, 1H), 3.41-3.48 (m, 1H), 3.52-3.62 (m, 2H), 4.93 (t, 1H), 7.37-7.43 (m, 1H), 7.55-7.59 (m, 1H), 7.60-7.67 (m, 2H), 7.88 (d, 2H), 8.20 (d, 2H), 8.73 (s, 1H), 9.55 (d, 1H). Rt = 1.55 min Chiralpak IB 3μ 100 × 4.6 mm, eluent A: methanol + 0.1 vol % diethylamine, eluent B: ethanol, isocratic: 50% B, 1.4 mL/min, 25° C., 254 nm |

TABLE 5-continued

Examples 313-378

| Example | structure | IUPAC name | Starting materials | analytics |
|---|---|---|---|---|
| 352 | 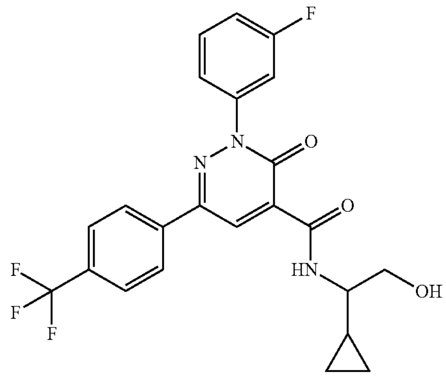 [SMILES: O=C(NC(CO)C1CC1)c1cc(-c2ccc(C(F)(F)F)cc2)nn(-c2cccc(F)c2)c1=O] | (+)-N-(1-cyclopropyl-2-hydroxyethyl)-2-(3-fluorophenyl)-3-oxo-6-[4-(trifluoromethyl)phenyl]-2,3-dihydropyridazine-4-carboxamide, enantiomer 2, $[\alpha]_D^{20}$ = +24.3° (c = 1.00, methanol) | N-[(1RS)-1-cyclopropyl-2-hydroxyethyl]-2-(3-fluorophenyl)-3-oxo-6-[4-(trifluoromethyl)phenyl]-2,3-dihydropyridazine-4-carboxamide, Chiralpak IB 5µ 250 × 30 mm, eluent A: methanol + 0.1 vol % diethylamine, eluent B: ethanol, isocratic: 50% B, 40 mL/min, 254 nm | $^1$H-NMR (400 MHz, DMSO-d$_6$): δ [ppm] = 0.25-0.51 (m, 4H), 1.03-1.13 (m, 1H), 3.41-3.48 (m, 1H), 3.52-3.63 (m, 2H), 4.93 (t, 1H), 7.37-7.43 (m, 1H), 7.55-7.59 (m, 1H), 7.60-7.67 (m, 2H), 7.88 (d, 2H), 8.20 (d, 2H), 8.73 (s, 1H), 9.55 (d, 1H). Rt = 2.96 min Chiralpak IB 3µ 100 × 4.6 mm, eluent A: methanol + 0.1 vol % diethylamine, eluent B: ethanol, isocratic: 50% B, 1.4 mL/min, 25° C., 254 nm |
| 353 | 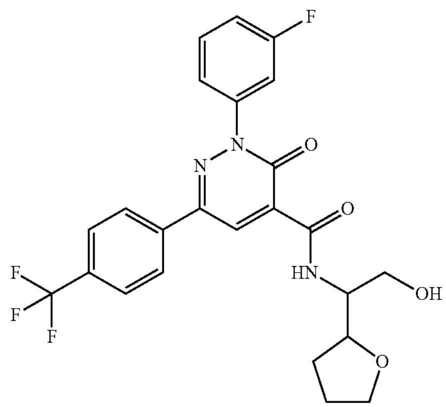 [SMILES: O=C(NC(CO)C1CCCO1)c1cc(-c2ccc(C(F)(F)F)cc2)nn(-c2cccc(F)c2)c1=O] | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, isomer 1, $[\alpha]_D^{20}$ = -23.9° (c = 1.00, methanol) | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, Chiralpak IB 5µ 250 × 30 mm, eluent A: CO$_2$, eluent B: methanol, isocratic: 28% B, 100 mL/min, 40° C., BPR: 150 bar, 254 nm, and Chiralpak IC 5µ 250 × 30 mm, eluent A: methanol, eluent B: ethanol, isocratic: 50% B, 60 mL/min, 254 nm, | $^1$H-NMR (400 MHz, DMSO-d$_6$): δ [ppm] = 1.56 (dq, 1H), 1.75-1.84 (m, 2H), 1.89-1.98 (m, 1H), 3.49 (t, 2H), 3.61-3.67 (m, 1H), 3.73-3.79 (m, 1H), 4.02-4.15 (m, 2H), 4.92 (t, 1H), 7.37-7.43 (m, 1H), 7.54-7.58 (m, 1H), 7.60-7.67 (m, 2H), 7.88 (d, 2H), 8.20 (d, 2H), 8.74 (s, 1H), 9.43 (d, 1H). Rt = 1.59 min, Chiralpak IB 5 µm 100 × 4.6 mm, eluent A: CO$_2$, eluent B: methanol, isocratic: 28% B, 4.0 mL/min, 37.5° C., BPR: 100 bar, 254 nm |
| 354 | 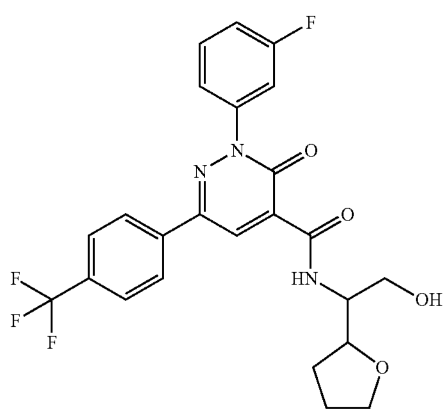 [SMILES: O=C(NC(CO)C1CCCO1)c1cc(-c2ccc(C(F)(F)F)cc2)nn(-c2cccc(F)c2)c1=O] | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, isomer 2, $[\alpha]_D^{20}$ = -22.7° (c = 1.00, methanol) | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, Chiralpak IB 5µ 250 × 30 mm, eluent A: CO$_2$, eluent B: methanol, isocratic: 28% B, 100 mL/min, 40° C., BPR: 150 bar, 254 nm, and Chiralpak IC 5µ 250 × 30 mm, eluent A: methanol, eluent B: ethanol, isocratic: 50% B, 60 mL/min, 254 nm, | $^1$H-NMR (400 MHz, DMSO-d$_6$): δ [ppm] = 1.69-1.92 (m, 4H), 3.47-3.54 (m, 1H), 3.61-3.68 (m, 2H), 3.75-3.81 (m, 1H), 3.92-3.98 (m, 1H), 3.99-4.06 (m, 1H), 4.89 (t, 1H), 7.37-7.43 (m, 1H), 7.55-7.58 (m, 1H), 7.60-7.66 (m, 2H), 7.88 (d, 2H), 8.20 (d, 2H), 8.74 (s, 1H), 9.56 (d, 1H). Rt = 1.78 min, Chiralpak IB 5 µm 100 × 4.6 mm, eluent A: CO$_2$, eluent B: methanol, isocratic: 28% B, 4.0 mL/min, 37.5° C., BPR: 100 bar, 254 nm |

TABLE 5-continued

Examples 313-378

| Example | structure | IUPAC name | Starting materials | analytics |
|---|---|---|---|---|
| 355 | 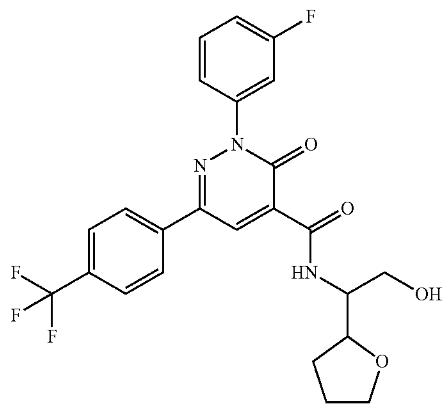 [SMILES: O=C(NC(CO)C1CCCO1)c1cc(-c2ccc(C(F)(F)F)cc2)nn(-c2cccc(F)c2)c1=O] | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, isomer 4, $[\alpha]_D^{20} = +22.5°$ (c = 1.00, methanol) | 1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol, Chiralpak IB 5μ 250 × 30 mm, eluent A: $CO_2$, eluent B: methanol, isocratic: 28% B, 100 mL/min, 40° C., BPR: 150 bar, 254 nm | $^1$H-NMR (400 MHz, DMSO-$d_6$): δ [ppm] = 1.56 (dq, 1H), 1.74-1.84 (m, 2H), 1.89-1.97 (m, 1H), 3.49 (t, 2H), 3.61-3.67 (m, 1H), 3.73-3.79 (m, 1H), 4.02-4.14 (m, 2H), 4.92 (t, 1H), 7.40 (ddt, 1H), 7.57 (ddd, 1H), 7.60-7.66 (m, 2H), 7.88 (d, 2H), 8.20 (d, 2H), 8.74 (s, 1H), 9.43 (d, 1H). Rt = 6.14 min, Chiralpak IB 5 μm 100 × 4.6 mm, eluent A: $CO_2$, eluent B: methanol, isocratic: 28% B, 4.0 mL/min, 37.5° C., BPR: 100 bar, 254 nm |
| 356 | 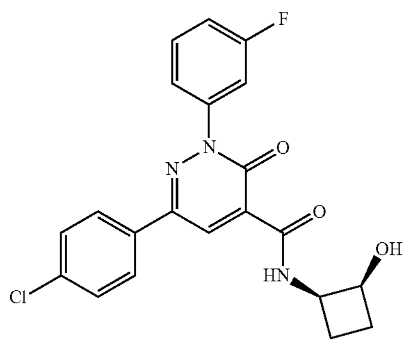 [SMILES: O=C(N[C@@H]1CC[C@@H]1O)c1cc(-c2ccc(Cl)cc2)nn(-c2cccc(F)c2)c1=O] | 6-(4-chlorophenyl)-2-(3-fluorophenyl)-N-(cis-2-hydroxycyclobutyl)-3-oxo-2,3-dihydropyridazine-4-carboxamide | 6-(4-chlorophenyl)-2-(3-fluorophenyl)-3-oxo-2,3-dihydropyridazine-4-carboxylic acid, (1RS,2SR)-2-aminocyclobutanol hydrochloride (1:1) | $^1$H-NMR (400 MHz, DMSO-$d_6$): δ [ppm] = 1.74-1.91 (m, 2H), 2.05-2.16 (m, 2H), 4.32-4.41 (m, 2H), 5.51 (d, 1H), 7.36-7.42 (m, 1H), 7.54-7.66 (m, 5H), 7.97-8.01 (m, 2H), 8.65 (s, 1H), 9.92 (br d, 1H). |
| 357 | 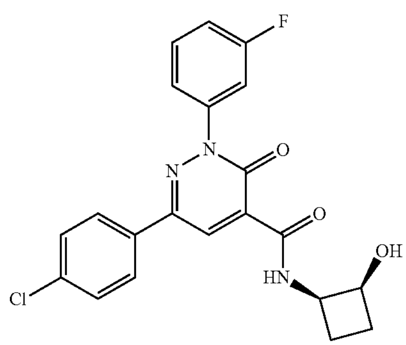 [SMILES: O=C(N[C@@H]1CC[C@@H]1O)c1cc(-c2ccc(Cl)cc2)nn(-c2cccc(F)c2)c1=O] | (+)-6-(4-chlorophenyl)-2-(3-fluorophenyl)-N-(cis-2-hydroxycyclobutyl)-3-oxo-2,3-dihydropyridazine-4-carboxamide $[\alpha]_D^{20} = +29.8°$ (c = 1.00, methanol) | 6-(4-chlorophenyl)-2-(3-fluorophenyl)-N-(cis-2-hydroxycyclobutyl)-3-oxo-2,3-dihydropyridazine-4-carboxamide, Chiralpak IB 5μ 250 × 30 mm, eluent A: hexane + 0.1 vol % diethylamine, eluent B: ethanol, isocratic: 50% B, 40 mL/min, 254 nm | $^1$H-NMR (400 MHz, DMSO-$d_6$): δ [ppm] = 1.74-1.91 (m, 2H), 2.05-2.16 (m, 2H), 4.32-4.41 (m, 2H), 5.51 (d, 1H), 7.36-7.42 (m, 1H), 7.54-7.66 (m, 5H), 7.97-8.01 (m, 2H), 8.65 (s, 1H), 9.92 (br d, 1H). Rt = 4.45 min Chiralpak IB 3μ 100 × 4.6 mm, eluent A: hexane + 0.1 vol % diethylamine, eluent B: ethanol, gradient: 20-50% B, 1.4 mL/min, 25° C., 254 nm |
| 358 | 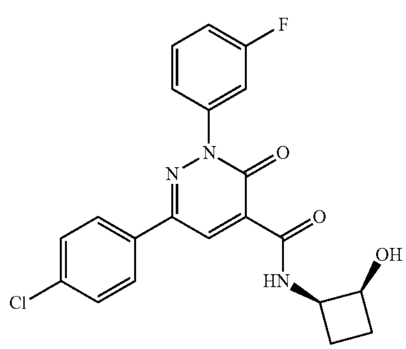 [SMILES: O=C(N[C@@H]1CC[C@@H]1O)c1cc(-c2ccc(Cl)cc2)nn(-c2cccc(F)c2)c1=O] | (−)-6-(4-chlorophenyl)-2-(3-fluorophenyl)-N-(cis-2-hydroxycyclobutyl)-3-oxo-2,3-dihydropyridazine-4-carboxamide $[\alpha]_D^{20} = -23.9°$ (c = 1.00, methanol) | 6-(4-chlorophenyl)-2-(3-fluorophenyl)-N-(cis-2-hydroxycyclobutyl)-3-oxo-2,3-dihydropyridazine-4-carboxamide, Chiralpak IB 5μ 250 × 30 mm, eluent A: hexane + 0.1 vol % diethylamine, eluent B: ethanol, isocratic: 50% B, 40 mL/min, 254 nm | $^1$H-NMR (400 MHz, DMSO-$d_6$): δ [ppm] = 1.74-1.91 (m, 2H), 2.05-2.16 (m, 2H), 4.32-4.41 (m, 2H), 5.51 (d, 1H), 7.36-7.42 (m, 1H), 7.54-7.66 (m, 5H), 7.97-8.01 (m, 2H), 8.65 (s, 1H), 9.92 (br d, 1H). Rt = 6.25 min Chiralpak IB 3μ 100 × 4.6 mm, eluent A: hexane + 0.1 vol % diethylamine, eluent B: ethanol, gradient: 20-50% B, 1.4 mL/min, 25° C., 254 nm |

TABLE 5-continued

Examples 313-378

| Example | structure | IUPAC name | Starting materials | analytics |
|---|---|---|---|---|
| 359 | 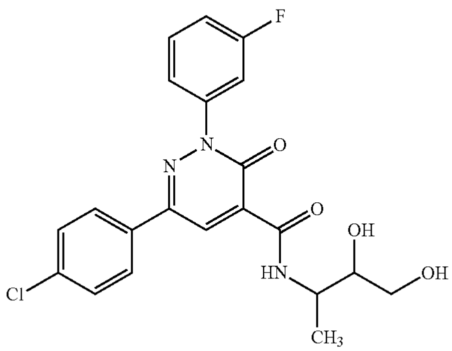 [SMILES: CC(NC(=O)c1cc(-c2ccc(Cl)cc2)nn(-c2cccc(F)c2)c1=O)C(O)CO] | 6-(4-chlorophenyl)-N-(3,4-dihydroxybutan-2-yl)-2-(3-fluorophenyl)-3-oxo-2,3-dihydropyridazine-4-carboxamide, isomer 1, $[\alpha]_D^{20}$ = +14.6° (c = 1.00, methanol) | 6-(4-chlorophenyl)-N-(3,4-dihydroxybutan-2-yl)-2-(3-fluorophenyl)-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm | $^1$H-NMR (400 MHz, DMSO-d$_6$): δ [ppm] = 1.18 (d, 3H), 3.21-3.28 (m, 1H), 3.29-3.37 (m, 1H and water signal), 3.46-3.53 (m, 1H), 4.12-4.21 (m, 1H), 4.61 (t, 1H), 5.15 (d, 1H), 7.35-7.40 (m, 1H), 7.53-7.64 (m, 5H), 7.97-8.01 (m, 2H), 8.65 (s, 1H), 9.53 (d, 1H). Rt = 3.53 min, Chiralpak IC 3 μm 100 × 4.6 mm, eluent A: hexane + 0.1 vol % diethylamine, eluent B: ethanol, gradient: 20-50% B in 7 min, 1.4 mL/min, 25° C., 254 nm |
| 360 | 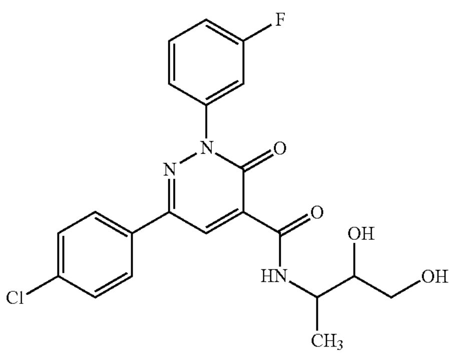 [SMILES: CC(NC(=O)c1cc(-c2ccc(Cl)cc2)nn(-c2cccc(F)c2)c1=O)C(O)CO] | 6-(4-chlorophenyl)-N-(3,4-dihydroxybutan-2-yl)-2-(3-fluorophenyl)-3-oxo-2,3-dihydropyridazine-4-carboxamide, isomer 2, $[\alpha]_D^{20}$ = +17.5° (c = 1.00, methanol) | 6-(4-chlorophenyl)-N-(3,4-dihydroxybutan-2-yl)-2-(3-fluorophenyl)-3-oxo-2,3-dihydropyridazine-4-carboxamide, Chiralpak IC 5μ 250 × 30 mm, eluent A: hexane, eluent B: ethanol, gradient: 20-50% B in 20 min, 40 mL/min, 254 nm | $^1$H-NMR (400 MHz, DMSO-d$_6$): δ [ppm] = 1.08 (d, 3H), 3.29-3.42 (m, 2H and water signal), 3.51-3.58 (m, 1H), 4.13-4.22 (m, 1H), 4.68 (t, 1H), 5.00 (d, 1H), 7.35-7.41 (m, 1H), 7.53-7.65 (m, 5H), 7.97-8.02 (m, 2H), 8.66 (s, 1H), 9.61 (d, 1H). Rt = 4.02 min, Chiralpak IC 3 μm 100 × 4.6 mm, eluent A: hexane + 0.1 vol % diethylamine, eluent B: ethanol, gradient: 20-50% B in 7 min, 1.4 mL/min, 25° C., 254 nm |
| 361 | 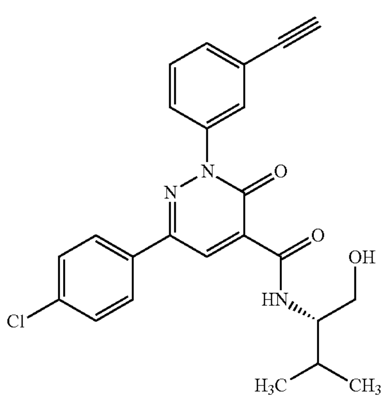 [SMILES: C#Cc1cccc(-n2nc(-c3ccc(Cl)cc3)cc(C(=O)N[C@H](CO)C(C)C)c2=O)c1] | 6-(4-chlorophenyl)-2-(3-cyanophenyl)-N-[(2S)-1-hydroxy-3-methylbutan-2-yl]-3-oxo-2,3-dihydropyridazine-4-carboxamide | 6-(4-chlorophenyl)-2-(3-cyanophenyl)-3-oxo-2,3-dihydropyridazine-4-carboxylic acid, (2S)-2-amino-3-methylbutan-1-ol | $^1$H-NMR (400 MHz, CDCl$_3$): δ [ppm] = 1.00-1.05 (m, 6H); 1.98-2.09 (m, 1H); 2.52-2.62 (m, 1H); 3.71-3.80 (m, 1H); 3.80-3.87 (m, 1H); 3.97-4.06 (m, 1H); 7.47-7.50 (m, 2H); 7.67 (t, 1H); 7.76 (td, 1H); 7.83-7.86 (m, 2H); 7.79 (ddd, 1H); 8.04 (t, 1H); 8.82 (s, 1H); 9.68 (bd, 1H). |

TABLE 5-continued

Examples 313-378

| Example | structure | IUPAC name | Starting materials | analytics |
|---|---|---|---|---|
| 362 | 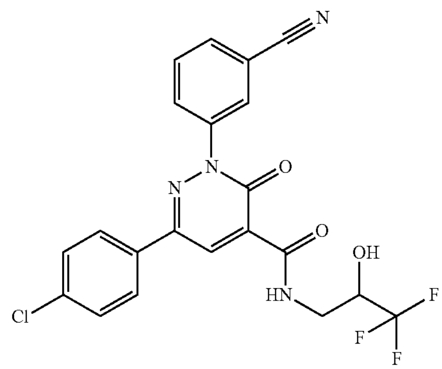 [SMILES: N#Cc1cccc(-n2nc(-c3ccc(Cl)cc3)cc(C(=O)NCC(O)C(F)(F)F)c2=O)c1] | 6-(4-chlorophenyl)-2-(3-cyanophenyl)-3-oxo-N-(3,3,3-trifluoro-2-hydroxypropyl)-2,3-dihydropyridazine-4-carboxamide | Intermediate 60, 3-amino-1,1,1-trifluoropropan-2-ol | $^1$H-NMR (400 MHz, CDCl$_3$): δ [ppm] = 3.69-3.78 (m, 1H); 3.91 (ddd, 1H); 4.16-4.32 (2m, 2H); 7.47-7.51 (m, 2H); 7.67 (t, 1H); 7.77 (td, 1H); 7.82-7.86 (m, 2H); 7.97 (ddd, 1H); 8.03 (t, 1H); 8.80 (s, 1H); 9.93 (bt, 1H). |
| 363 | 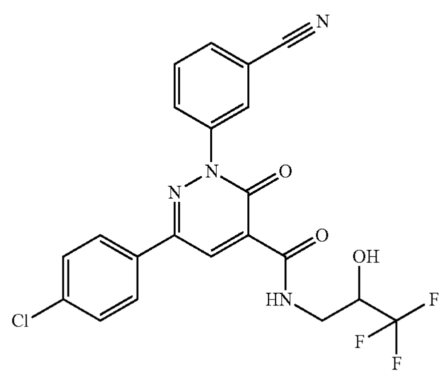 [SMILES: N#Cc1cccc(-n2nc(-c3ccc(Cl)cc3)cc(C(=O)NCC(O)C(F)(F)F)c2=O)c1] | 6-(4-chlorophenyl)-2-(3-cyanophenyl)-3-oxo-N-(3,3,3-trifluoro-2-hydroxypropyl)-2,3-dihydropyridazine-4-carboxamide, Enantiomer 1 | Example 362, Chiralpak ID 5μ 250 × 30 mm, eluent A: CO$_2$ B: 2-propanol, isocratic: 19% B, flow 100 mL/min, T = 40° C., 150 bar, 254 nm | $^1$H-NMR (400 MHz, CDCl$_3$): δ [ppm] = 3.69-3.78 (m, 1H); 3.91 (ddd, 1H); 4.16-4.32 (2m, 2H); 7.47-7.51 (m, 2H); 7.67 (t, 1H); 7.77 (td, 1H); 7.82-7.86 (m, 2H); 7.97 (ddd, 1H); 8.03 (t, 1H); 8.80 (s, 1H); 9.93 (bt, 1H). Rt = 2.34 min Chiralpak ID 5μ 100 × 4.6 mm, eluent A: CO$_2$ B: 2-propanol, isocratic: 19% B, flow 4 mL/min, T = 37.5° C., 100 bar, 254 nm |
| 364 | 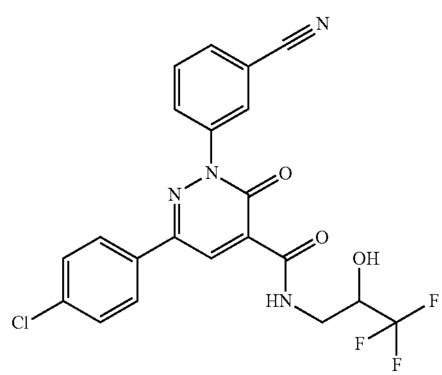 [SMILES: N#Cc1cccc(-n2nc(-c3ccc(Cl)cc3)cc(C(=O)NCC(O)C(F)(F)F)c2=O)c1] | 6-(4-chlorophenyl)-2-(3-cyanophenyl)-3-oxo-N-(3,3,3-trifluoro-2-hydroxypropyl)-2,3-dihydropyridazine-4-carboxamide, Enantiomer 2 | Example 362, Chiralpak ID 5μ 250 × 30 mm, eluent A: CO$_2$ B: 2-propanol, isocratic: 19% B, flow 100 mL/min, T = 40° C., 150 bar, 254 nm | $^1$H-NMR (400 MHz, CDCl$_3$): δ [ppm] = 3.69-3.78 (m, 1H); 3.91 (ddd, 1H); 4.16-4.32 (2m, 2H); 7.47-7.51 (m, 2H); 7.67 (t, 1H); 7.77 (td, 1H); 7.82-7.86 (m, 2H); 7.97 (ddd, 1H); 8.03 (t, 1H); 8.80 (s, 1H); 9.93 (bt, 1H). Rt = 3.81 min Chiralpak ID 5μ 100 × 4.6 mm, eluent A: CO$_2$ B: 2-propanol, isocratic: 19% B, flow 4 mL/min, T = 37.5° C., 100 bar, 254 nm |
| 365 | 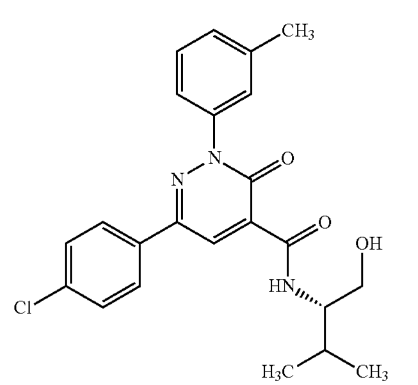 [SMILES: Cc1cccc(-n2nc(-c3ccc(Cl)cc3)cc(C(=O)N[C@H](CO)C(C)C)c2=O)c1] | 6-(4-chlorophenyl)-N-[(2S)-1-hydroxy-3-methylbutan-2-yl]-2-(3-methylphenyl)-3-oxo-2,3-dihydropyridazine-4-carboxamide | Intermediate 61, (2S)-2-amino-3-methylbutan-1-ol | $^1$H-NMR (400 MHz, CDCl$_3$): δ [ppm] = 0.98-1.04 (m, 6H); 1.95.2.07 (m, 1H); 2.48 (s, 3H); 2.78 (bs, 1H); 3.69-3.77 (m, 1H); 3.78-3.86 (m, 1H); 3.96-4.04 (m, 1H); 7.30 (bd, 1H); 7.37-7.46 (m, 5H); 7.82-7.86 (m, 2H); 8.78 (s, 1H); 9.85 (bd, 1H). |

TABLE 5-continued

Examples 313-378

| Example | structure | IUPAC name | Starting materials | analytics |
|---|---|---|---|---|
| 366 | 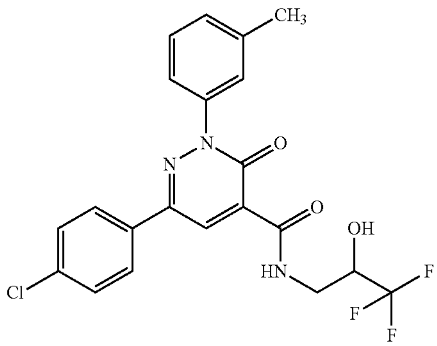 [SMILES: Cc1cccc(-n2nc(-c3ccc(Cl)cc3)cc(C(=O)NCC(O)C(F)(F)F)c2=O)c1] | 6-(4-chlorophenyl)-2-(3-methylphenyl)-3-oxo-N-(3,3,3-trifluoro-2-hydroxypropyl)-2,3-dihydropyridazine-4-carboxamide | Intermediate 61, 3-amino-1,1,1-trifluoropropan-2-ol | $^1$H-NMR (400 MHz, CDCl$_3$): δ [ppm] = 3.68-3.77 (nm, 1H); 3.85 (ddd, 1H); 4.14-4.24 (m, 1H); 4.48 (d, 1H); 7.31 (bd, 1H); 7.36-7.48 (m,m 5H); 7.83-7.86 (m, 2H); 8.77 (s, 1H); 10.15 (bt, 1H). |
| 367 | 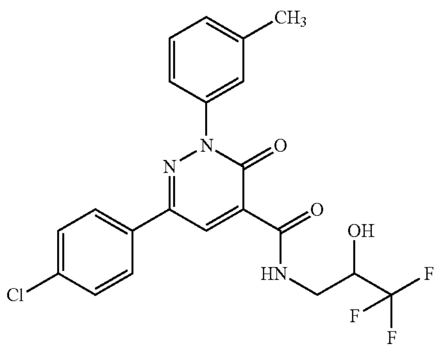 [SMILES: Cc1cccc(-n2nc(-c3ccc(Cl)cc3)cc(C(=O)NCC(O)C(F)(F)F)c2=O)c1] | 6-(4-chlorophenyl)-2-(3-methylphenyl)-3-oxo-N-(3,3,3-trifluoro-2-hydroxypropyl)-2,3-dihydropyridazine-4-carboxamide, Enantiomer 1 | Example 366, Chiralpak IB 5μ 250 × 30 mm, eluent A: CO$_2$ B: ethanol, isocratic: 11% B, flow 100 = mL/min,T 40° C., 150 bar, 254 nm | $^1$H-NMR (400 MHz, CDCl$_3$): δ [ppm] = 3.68-3.77 (nm, 1H); 3.85 (ddd, 1H); 4.14-4.24 (m, 1H); 4.48 (d, 1H); 7.31 (bd, 1H); 7.36-7.48 (m,m 5H); 7.83-7.86 (m, 2H); 8.77 (s, 1H); 10.15 (bt, 1H). Rt = 2.33 min, Chiralpak IB 5μ 100 × 4.6 mm, eluent A: CO$_2$ B: ethanol, isocratic: 11% B, flow 40 mL/min,T = 37.5° C., 100 bar, 254 nm |
| 368 | 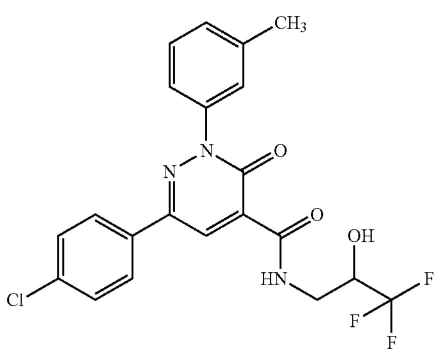 [SMILES: Cc1cccc(-n2nc(-c3ccc(Cl)cc3)cc(C(=O)NCC(O)C(F)(F)F)c2=O)c1] | 6-(4-chlorophenyl)-2-(3-methylphenyl)-3-oxo-N-(3,3,3-trifluoro-2-hydroxypropyl)-2,3-dihydropyridazine-4-carboxamide, Enantiomer 2 | Example 366, Chiralpak IB 5μ 250 × 30 mm, eluent A: CO$_2$ B: ethanol, isocratic: 11% B, flow 100 mL/min,T = 40° C., 150 bar, 254 nm | $^1$H-NMR (400 MHz, CDCl$_3$): δ [ppm] = 3.68-3.77 (nm, 1H); 3.85 (ddd, 1H); 4.14-4.24 (m, 1H); 4.48 (d, 1H); 7.31 (bd, 1H); 7.36-7.48 (m,m 5H); 7.83-7.86 (m, 2H); 8.77 (s, 1H); 10.15 (bt, 1H). Rt = 3.26 min, Chiralpak IB 5μ 100 × 4.6 mm, eluent A: CO$_2$ B: ethanol, isocratic: 11% B, flow 40 mL/min,T = 37.5° C., 100 bar, 254 nm |
| 369 | 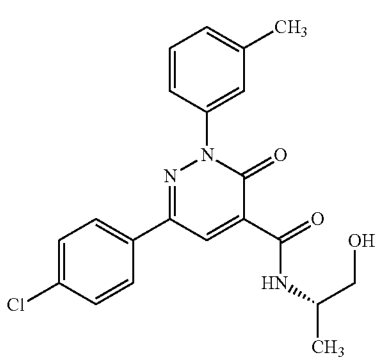 [SMILES: Cc1cccc(-n2nc(-c3ccc(Cl)cc3)cc(C(=O)N[C@@H](C)CO)c2=O)c1] | 6-(4-chlorophenyl)-N-[(2S)-1-hydroxypropan-2-yl]-2-(3-methylphenyl)-3-oxo-2,3-dihydropyridazine-4-carboxamide | Intermediate 61, ((2S)-2-aminopropan-1-ol | $^1$H-NMR (400 MHz, CDCl$_3$): δ [ppm] = 1.28 (d, 3H); 2.72 (t, 1H); 3.61-3.69 (m, 1H); 3.72-3.79 (m, 1H); 4.24-4.32 (m, 1H); 7.30 (bd, 1H); 7.35-7.47 (m, 5H); 7.83-7.86 (m, 2H); 8.78 (s, 1H); 9.78 (bd, 1H). |

TABLE 5-continued

Examples 313-378

| Example | structure | IUPAC name | Starting materials | analytics |
|---|---|---|---|---|
| 370 | 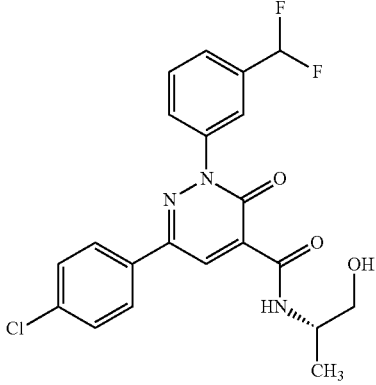 [SMILES: C[C@@H](CO)NC(=O)c1cc(-c2ccc(Cl)cc2)nn(-c2cccc(C(F)F)c2)c1=O] | 6-(4-chlorophenyl)-2-[3-(difluoromethyl)phenyl]-N-[(2S)-1-hydroxypropan-2-yl]-3-oxo-2,3-dihydropyridazine-4-carboxamide | Intermediate 62, ((2S)-2-aminopropan-1-ol | $^1$H-NMR (400 MHz, DMSO-d$_6$): δ [ppm] = 1.16 (d, 3H); 3.42-3.47 (m, signal below DMSO); 3.98-4.09 (m, 1H); 4.94 (t, 1H); 7.16 (t, 1H); 7.57-7.60 (m, 2H); 7.70-7.74 (m, 2H); 7.85-7.88 (m, 1H); 7.91 (bs, 1H); 7.97-8.00 (m, 2H); 8.66 (s, 1H); 9.45 (d, 1H). |
| 371 | 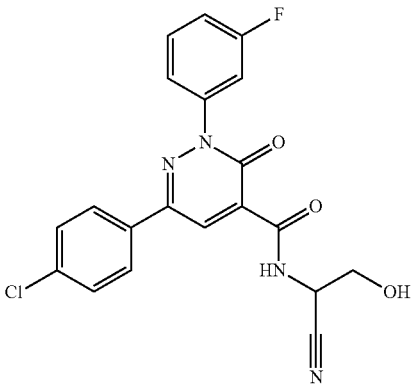 [SMILES: N#CC(CO)NC(=O)c1cc(-c2ccc(Cl)cc2)nn(-c2cccc(F)c2)c1=O] | 6-(4-chlorophenyl)-N-[(1RS)-1-cyano-2-hydroxyethyl]-2-(3-fluorophenyl)-3-oxo-2,3-dihydropyridazine-4-carboxamide | 6-(4-chlorophenyl)-2-(3-fluorophenyl)-3-oxo-2,3-dihydropyridazine-4-carboxylic acid, (2RS)-2-amino-3-hydroxypropanenitrile hydrochloride (1:1) | $^1$H-NMR (400 MHz, DMSO-d$_6$): δ [ppm] = 3.71-3.77 (m, 1H), 3.78-3.84 (m, 1H), 5.03-5.08 (m, 1H), 5.83 (br s, 1H), 7.39 (ddt, 1H), 7.54-7.66 (m, 5H), 8.00-8.04 (m, 2H), 8.70 (s, 1H), 9.99 (d, 1H). |
| 372 | 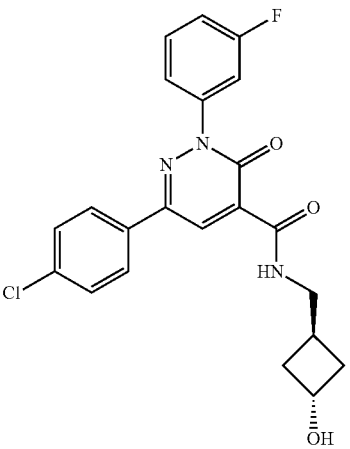 [SMILES: O=C(NC[C@H]1C[C@H](O)C1)c1cc(-c2ccc(Cl)cc2)nn(-c2cccc(F)c2)c1=O] | 6-(4-chlorophenyl)-2-(3-fluorophenyl)-N-[(trans-3-hydroxycyclobutyl)methyl]-3-oxo-2,3-dihydropyridazine-4-carboxamide | 6-(4-chlorophenyl)-2-(3-fluorophenyl)-3-oxo-2,3-dihydropyridazine-4-carboxylic acid, trans-3-(aminomethyl)cyclobutanol | $^1$H-NMR (400 MHz, DMSO-d6): δ [ppm] = 1.87-1.96 (m, 2H), 1.97-2.05 (m, 2H), 2.25-2.38 (m, 1H), 3.40 (dd, 2H), 4.19-4.29 (m, 1H), 4.99 (d, 1H), 7.35-7.41 (m, 1H), 7.53-7.65 (m, 5H), 7.97-8.02 (m, 2H), 8.63 (s, 1H), 9.38 (t, 1H). |

TABLE 5-continued

Examples 313-378

| Example | structure | IUPAC name | Starting materials | analytics |
|---|---|---|---|---|
| 373 | 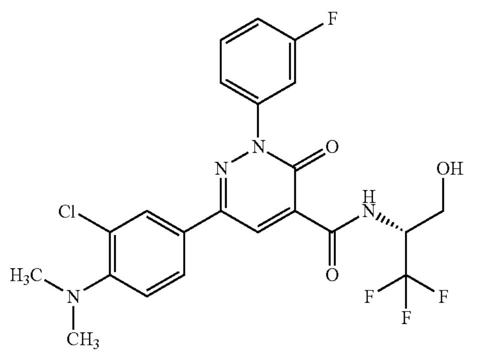 [SMILES: CN(C)c1ccc(-c2cc(C(=O)N[C@H](CO)C(F)(F)F)c(=O)n(-c3cccc(F)c3)n2)cc1Cl] | 6-[3-chloro-4-(dimethylamino)phenyl]-2-(3-fluorophenyl)-3-oxo-N-[(2R)-1,1,1-trifluoro-3-hydroxypropan-2-yl]-2,3-dihydropyridazine-4-carboxamide | 6-[3-chloro-4-(dimethylamino)phenyl]-2-(3-fluorophenyl)-3-oxo-2,3-dihydropyridazine-4-carboxylic acid; (2R)-2-amino-3,3,3-trifluoropropan-1-ol hydrochloride (1:1) | $^1$H NMR (400 MHz, DMSO-d6) δ ppm 2.81 (s, 6 H), 3.65-3.74 (m, 1 H), 3.82 (dt, 1 H), 4.79-4.90 (m, 1 H), 5.43 (t, 1 H), 7.23 (d, 1 H), 7.35-7.43 (m, 1 H), 7.52-7.57 (m, 1 H), 7.58-7.68 (m, 2 H), 7.88 (dd, 1 H), 7.95 (d, 1 H), 8.69 (s, 1 H), 10.02 (d, 1 H) |
| 374 | 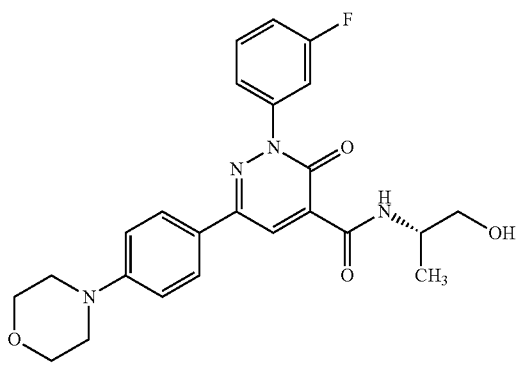 [SMILES: C[C@@H](CO)NC(=O)c1cc(-c2ccc(N3CCOCC3)cc2)nn(-c2cccc(F)c2)c1=O] | 2-(3-fluorophenyl)-N-[(2S)-1-hydroxypropan-2-yl]-6-[4-(morpholin-4-yl)phenyl]-3-oxo-2,3-dihydropyridazine-4-carboxamide | 2-(3-fluorophenyl)-6-[4-(morpholin-4-yl)phenyl]-3-oxo-2,3-dihydropyridazine-4-carboxylic acid; S)-(+)-2-amino-1-propanol (L-Alaninol) | $^1$H NMR (400 MHz, DMSO-d$_6$) δ ppm 1.16 (d, 3 H), 3.18-3.25 (m, 4 H), 3.39-3.50 (m, 2 H), 3.71-3.78 (m, 4 H), 3.98-4.09 (m, 1 H), 4.93 (t, 1 H), 7.05 (d, 2 H), 7.31-7.40 (m, 1 H), 7.50-7.55 (m, 1 H), 7.56-7.64 (m, 2 H), 7.82 (d, 2 H), 8.60 (s, 1 H), 9.50 (d, 1 H) |
| 375 | 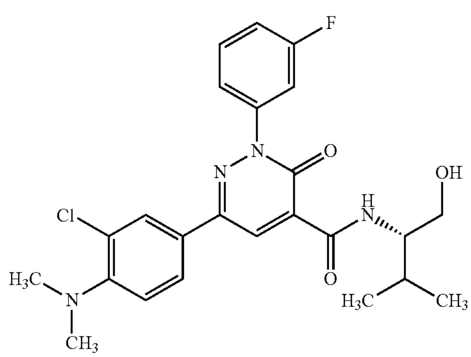 [SMILES: CC(C)[C@@H](CO)NC(=O)c1cc(-c2ccc(N(C)C)c(Cl)c2)nn(-c2cccc(F)c2)c1=O] | 6-[3-chloro-4-(dimethylamino)phenyl]-2-(3-fluorophenyl)-N-[(2S)-1-hydroxy-3-methylbutan-2-yl]-3-oxo-2,3-dihydropyridazine-4-carboxamide | 6-[3-chloro-4-(dimethylamino)phenyl]-2-(3-fluorophenyl)-3-oxo-2,3-dihydropyridazine-4-carboxylic acid; (S)-(+)-2-amino-3-methyl-1-butanol | $^1$H NMR (400 MHz, DMSO-d$_6$) δ ppm 0.89 (d, 3 H), 0.92 (d, 3 H), 1.97 (dq, 1 H), 2.81 (s, 6 H), 3.44 (dt, 1 H), 3.50-3.58 (m, 1 H), 3.80-3.89 (m, 1 H), 4.80 (t, 1 H), 7.23 (d, 1 H), 7.35-7.42 (m, 1 H), 7.50-7.56 (m, 1 H), 7.58-7.66 (m, 2 H), 7.85 (dd, 1 H), 7.92 (d, 1 H), 8.62 (s, 1 H), 9.42 (d, 1 H) |
| 376 | 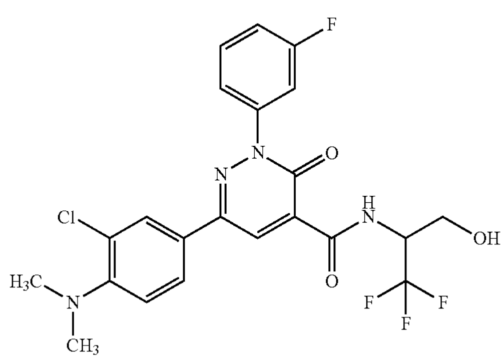 [SMILES: CN(C)c1ccc(-c2cc(C(=O)NC(CO)C(F)(F)F)c(=O)n(-c3cccc(F)c3)n2)cc1Cl] | 6-[3-chloro-4-(dimethylamino)phenyl]-2-(3-fluorophenyl)-3-oxo-N-(1,1,1-trifluoro-3-hydroxypropan-2-yl)-2,3-dihydropyridazine-4-carboxamide | 6-[3-chloro-4-(dimethylamino)phenyl]-2-(3-fluorophenyl)-3-oxo-2,3-dihydropyridazine-4-carboxylic acid; 2-amino-3,3,3-trifluoropropan-1-ol hydrochloride (1:1) | $^1$H NMR (400 MHz, DMSO-d6) δ ppm 2.81 (s, 6 H), 3.64-3.73 (m, 1 H), 3.81 (dt, 1 H), 4.78-4.89 (m, 1 H), 5.43 (t, 1 H), 7.24 (d, 1 H), 7.36-7.43 (m, 1 H), 7.52-7.57 (m, 1 H), 7.59-7.66 (m, 2 H), 7.88 (dd, 1 H), 7.95 (d, 1 H), 8.69 (s, 1 H), 10.02 (d, 1 H) |

TABLE 5-continued

Examples 313-378

| Example | structure | IUPAC name | Starting materials | analytics |
| --- | --- | --- | --- | --- |
| 377 | 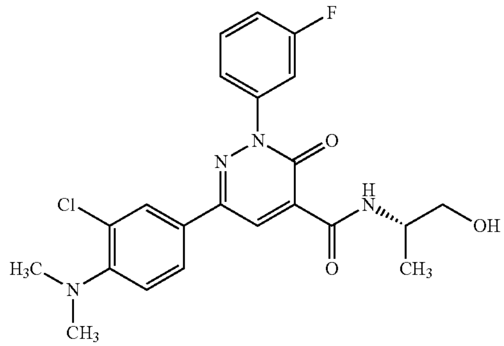 [SMILES: C[C@@H](CO)NC(=O)c1cc(-c2ccc(N(C)C)c(Cl)c2)nn(-c2cccc(F)c2)c1=O] | 6-[3-chloro-4-(dimethylamino)phenyl]-2-(3-fluorophenyl)-N-[(2S)-1-hydroxypropan-2-yl]-3-oxo-2,3-dihydropyridazine-4-carboxamide | 6-[3-chloro-4-(dimethylamino)phenyl]-2-(3-fluorophenyl)-3-oxo-2,3-dihydropyridazine-4-carboxylic acid; (S)-(+)-2-amino-1-propanol (L-Alaninol) | $^1$H NMR (400 MHz, DMSO-$d_6$) δ ppm 1.16 (d, 3 H), 2.79-2.83 (m, 6 H), 3.40-3.50 (m, 2 H), 3.98-4.08 (m, 1 H), 4.93 (t, 1 H), 7.24 (d, 1 H), 7.34-7.41 (m, 1 H), 7.51-7.55 (m, 1 H), 7.58-7.65 (m, 2 H), 7.86 (dd, 1 H), 7.93 (d, 1 H), 8.61 (s, 1 H), 9.44 (d, 1 H) |
| 378 | 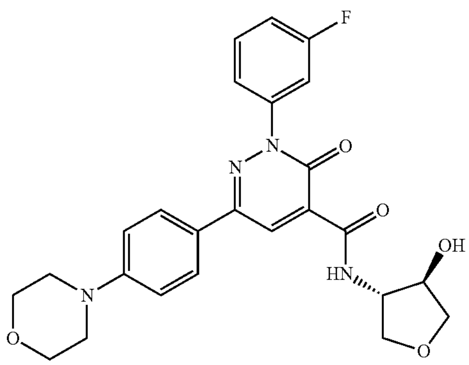 [SMILES: O=C(N[C@H]1COC[C@@H]1O)c1cc(-c2ccc(N3CCOCC3)cc2)nn(-c2cccc(F)c2)c1=O] | rel-2-(3-fluorophenyl)-N-[(3R,4S)-4-hydroxytetrahydrofuran-3-yl]-6-[4-(morpholin-4-yl)phenyl]-3-oxo-2,3-dihydropyridazine-4-carboxamide | 2-(3-fluorophenyl)-6-[4-(morpholin-4-yl)phenyl]-3-oxo-2,3-dihydropyridazine-4-carboxylic acid, rel-(3R,4S)-4-aminotetrahydrofuran-3-ol | $^1$H NMR (400 MHz, DMSO-$d_6$) δ ppm 3.19-3.24 (m, 4 H), 3.54 (dd, 1 H), 3.64 (dd, 1 H), 3.71-3.77 (m, 4 H), 3.89 (dd, 1 H), 3.97 (dd, 1 H), 4.17 (br s, 1 H), 4.24 (ddd, 1 H), 5.49 (d, 1 H), 7.05 (d, 2 H), 7.32-7.40 (m, 1 H), 7.50-7.55 (m, 1 H), 7.57-7.64 (m, 2 H), 7.82 (d, 2 H), 8.58 (s, 1 H), 9.53 (d, 1 H) |

TABLE 6

Examples 379-398

| Example | structure | IUPAC name | Starting materials | analytics |
| --- | --- | --- | --- | --- |
| 379 | 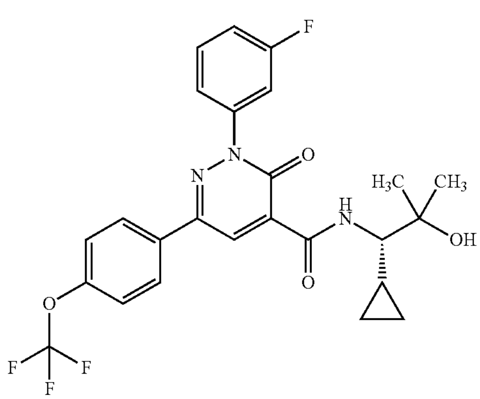 [SMILES: CC(C)(O)[C@@H](NC(=O)c1cc(-c2ccc(OC(F)(F)F)cc2)nn(-c2cccc(F)c2)c1=O)C1CC1] | N-[(1S)-1-cyclopropyl-2-hydroxy-2-methylpropyl]-2-(3-fluorophenyl)-3-oxo-6-[4-(trifluoromethoxy)phenyl]-2,3-dihydropyridazine-4-carboxamide | 6-[4-(trifluoromethoxy)phenyl]-2-(3-fluorophenyl)-3-oxo-2,3-dihydropyridazine-4-carboxylic acid; (1S)-1-amino-1-cyclopropyl-2-methylpropan-2-ol | $^1$H NMR (400 MHz, DMSO-$d_6$) δ ppm 0.26-0.39 (m, 3H), 0.51-0.60 (m, 1H), 1.07-1.11 (m, 3H), 1.11-1.17 (m, 1H), 1.28 (s, 3H), 3.35-3.39 (m, 1H), 4.67-4.70 (m, 1H), 7.35-7.42 (m, 1H), 7.47-7.52 (m, 2H), 7.54-7.67 (m, 3H), 8.07-8.12 (m, 2H), 8.68 (s, 1H), 9.63-9.68 (m, 1H) |

TABLE 6-continued

Examples 379-398

| Example | structure | IUPAC name | Starting materials | analytics |
|---|---|---|---|---|
| 380 | 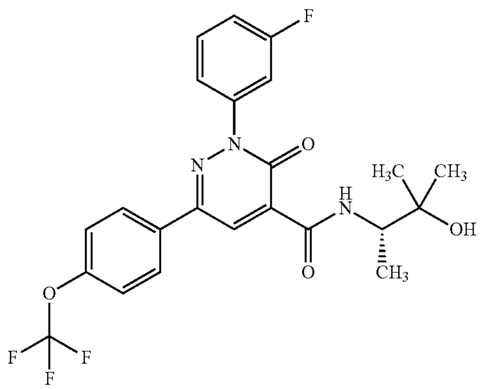 [SMILES: C[C@H](NC(=O)c1cc(-c2ccc(OC(F)(F)F)cc2)nn(-c2cccc(F)c2)c1=O)C(C)(C)O] | 2-(3-fluorophenyl)-N-[(2S)-3-hydroxy-3-methylbutan-2-yl]-3-oxo-6-[4-(trifluoromethoxy)phenyl]-2,3-dihydropyridazine-4-carboxamide | 6-[4-(trifluoromethoxy)phenyl]-2-(3-fluorophenyl)-3-oxo-2,3-dihydropyridazine-4-carboxylic acid; (3S)-3-amino-2-methylbutan-2-ol | $^1$H NMR (400 MHz, DMSO-d$_6$) δ ppm 1.08-1.19 (m, 9H), 3.87-3.96 (m, 1H), 4.64-4.67 (m, 1H), 7.34-7.42 (m, 1H), 7.47-7.53 (m, 2H), 7.54-7.57 (m, 1H), 7.58-7.66 (m, 2H), 8.07-8.13 (m, 2H), 8.67 (s, 1H), 9.51-9.58 (m, 1H) |
| 381 | 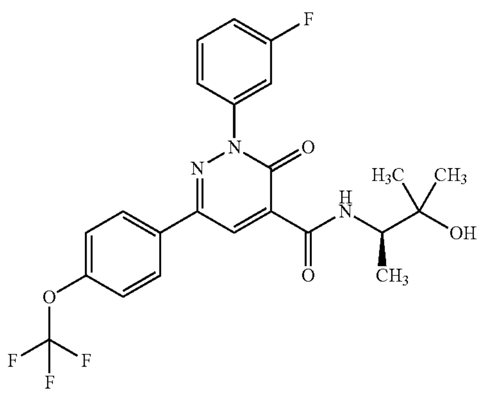 [SMILES: C[C@@H](NC(=O)c1cc(-c2ccc(OC(F)(F)F)cc2)nn(-c2cccc(F)c2)c1=O)C(C)(C)O] | 2-(3-fluorophenyl)-N-[(2R)-3-hydroxy-3-methylbutan-2-yl]-3-oxo-6-[4-(trifluoromethoxy)phenyl]-2,3-dihydropyridazine-4-carboxamide | 6-[4-(trifluoromethoxy)phenyl]-2-(3-fluorophenyl)-3-oxo-2,3-dihydropyridazine-4-carboxylic acid; (3R)-3-amino-2-methylbutan-2-ol | $^1$H NMR (400 MHz, DMSO-d$_6$) δ ppm 1.07-1.17 (m, 9H), 3.87-3.96 (m, 1H), 4.65 (s, 1H), 7.35-7.41 (m, 1H), 7.48-7.53 (m, 2H), 7.54-7.58 (m, 1H), 7.58-7.65 (m, 2H), 8.10 (d, 2H), 8.67 (s, 1H), 9.54 (d, 1H) |
| 382 | 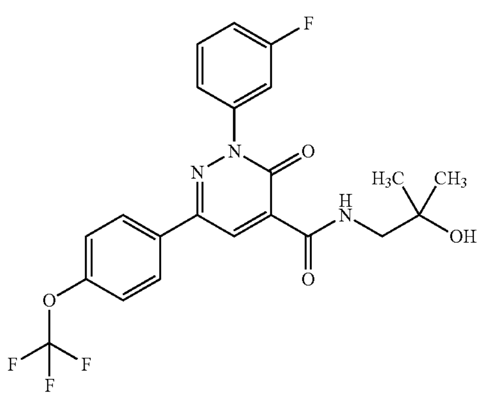 [SMILES: CC(C)(O)CNC(=O)c1cc(-c2ccc(OC(F)(F)F)cc2)nn(-c2cccc(F)c2)c1=O] | 2-(3-fluorophenyl)-N-(2-hydroxy-2-methylpropyl)-3-oxo-6-[4-(trifluoromethoxy)phenyl]-2,3-dihydropyridazine-4-carboxamide | 6-[4-(trifluoromethoxy)phenyl]-2-(3-fluorophenyl)-3-oxo-2,3-dihydropyridazine-4-carboxylic acid; 1-amino-2-methylpropan-2-ol | $^1$H NMR (400 MHz, DMSO-d$_6$) δ ppm 1.10-1.17 (m, 6H), 3.30-3.32 (m, 2H), 4.65-4.70 (m, 1H), 7.36-7.42 (m, 1H), 7.49-7.54 (m, 2H), 7.54-7.67 (m, 3H), 8.08-8.13 (m, 2H), 8.66-8.69 (m, 1H), 9.52-9.58 (m, 1H) |
| 383 | 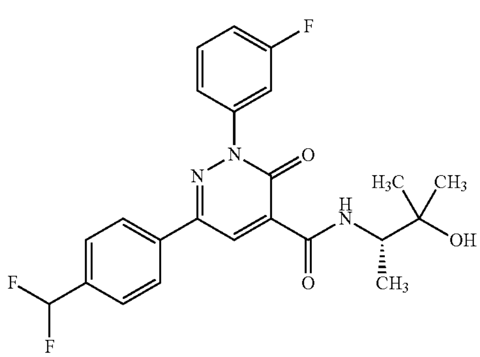 [SMILES: C[C@H](NC(=O)c1cc(-c2ccc(C(F)F)cc2)nn(-c2cccc(F)c2)c1=O)C(C)(C)O] | 6-[4-(difluoromethyl)phenyl]-2-(3-fluorophenyl)-N-[(2S)-3-hydroxy-3-methylbutan-2-yl]-3-oxo-2,3-dihydropyridazine-4-carboxamide | 6-[4-(Difluoromethyl)phenyl]-2-(3-fluorophenyl)-3-oxo-2,3-dihydropyridazine-4-carboxylic acid; (3S)-3-amino-2-methylbutan-2-ol | $^1$H NMR (400 MHz, DMSO-d$_6$) δ ppm 1.08-1.18 (m, 9H), 3.86-3.97 (m, 1H), 4.65 (s, 1H), 6.96-7.28 (m, 1H), 7.36-7.43 (m, 1H), 7.53-7.58 (m, 1H), 7.59-7.67 (m, 2H), 7.69-7.75 (m, 2H), 8.08-8.14 (m, 2H), 8.68-8.72 (m, 1H), 9.51-9.57 (m, 1H) |

TABLE 6-continued

Examples 379-398

| Example | structure | IUPAC name | Starting materials | analytics |
|---|---|---|---|---|
| 384 | 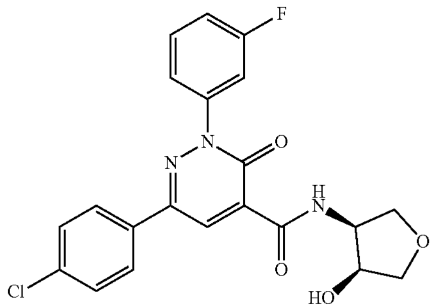 [SMILES: O=C(N[C@H]1COC[C@H]1O)c1cc(-c2ccc(Cl)cc2)nn(-c2cccc(F)c2)c1=O] | 6-(4-chlorophenyl)-2-(3-fluorophenyl)-N-[cis-4-hydroxytetrahydrofuran-3-yl]-3-oxo-2,3-dihydropyridazine-4-carboxamide, Enantiomer 1 | 6-(4-chlorophenyl)-2-(3-fluorophenyl)-3-oxo-2,3-dihydropyridazine-4-carboxylic acid, cis-4-aminotetrahydro-3-furanol hydrochloride (1:1); instrument: Sepiatec: Prep SFC100; column: Chiralpak IC 5 μm 250 × 30 mm; eluent A: $CO_2$, eluent B: 2-propanol; isocratic: 37% B; flow 100.0 mL/min temperature: 40 °C.; BPR: 150 bar; MWD @ 254 nm | $^1$H NMR (400 MHz, DMSO-$d_6$) δ ppm 3.41-3.48 (m, 1H), 3.59-3.64 (m, 1H), 3.90-3.96 (m, 1H), 3.97-4.03 (m, 1H), 4.22-4.30 (m, 1H), 4.30-4.39 (m, 1H), 5.66-5.71 (m, 1H), 7.35-7.43 (m, 1H), 7.52-7.66 (m, 5H), 7.97-8.02 (m, 2H), 8.66-8.69 (m, 1H), 9.82-9.86 (m, 1H); Rt = 2.55 min Chiralpak IC 5μ 100 × 4.6 mm, eluent A: $CO_2$, eluent B: 2-propanol, isocratic 37% B, flow 4.0 mL/min, 37.5 °C., 254 nm |
| 385 | 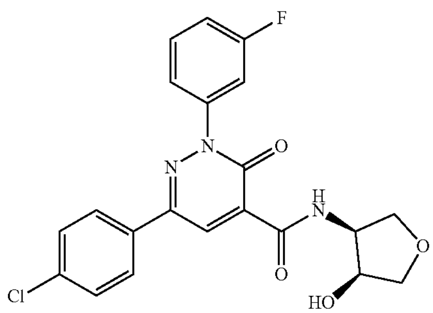 [SMILES: O=C(N[C@H]1COC[C@H]1O)c1cc(-c2ccc(Cl)cc2)nn(-c2cccc(F)c2)c1=O] | 6-(4-chlorophenyl)-2-(3-fluorophenyl)-N-[cis-4-hydroxytetrahydrofuran-3-yl]-3-oxo-2,3-dihydropyridazine-4-carboxamide, Enantiomer 2 | 6-(4-chlorophenyl)-2-(3-fluorophenyl)-3-oxo-2,3-dihydropyridazine-4-carboxylic acid, cis-4-aminotetrahydro-3-furanol hydrochloride (1:1); instrument; Sepiatec: Prep SFC100; column: Chiralpak IC 5 μm 250 × 30 mm; eluent A: $CO_2$, eluent B: 2-propanol; isocratic: 37% B; flow 100.0 mL/min temperature: 40° C.; BPR: 150 bar; MWD @ 254 nm | 1H NMR (400 MHz, DMSO-$d_6$) δ ppm 3.41-3.48 (m, 1H), 3.59-3.64 (m, 1H), 3.90-3.96 (m, 1H), 3.97-4.03 (m, 1H), 4.22-4.30 (m, 1H), 4.30-4.39 (m, 1H), 5.66-5.71 (m, 1H), 7.35-7.43 (m, 1H), 7.52-7.66 (m, 5H), 7.97-8.02 (m, 2H), 8.66-8.69 (m, 1H), 9.82-9.86 (m, 1H); Rt = 1.74 min Chiralpak 1C 5μ 100 × 4.6 mm, eluent A: $CO_2$, eluent B: 2-propanol, isocratic 37% B, flow 4.0 mL/min, 37.5° C., 254 nm |
| 386 | 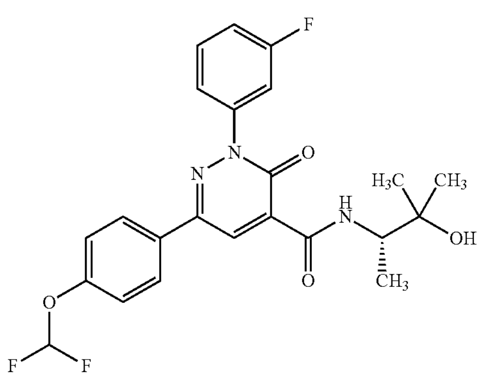 [SMILES: C[C@H](NC(=O)c1cc(-c2ccc(OC(F)F)cc2)nn(-c2cccc(F)c2)c1=O)C(C)(C)O] | 6-[4-(difluoromethoxy)phenyl]-2-(3-fluorophenyl)-N-[(2S)-3-hydroxy-3-methylbutan-2-yl]-3-oxo-2,3-dihydropyridazine-4-carboxamide | 6-[4-(difluoromethoxy)phenyl]-2-(3-fluorophenyl)-3-oxo-2,3-dihydropyridazine-4-carboxylic acid; (3S)-3-amino-2-methylbutan-2-ol | $^1$H NMR (400 MHz, DMSO-$d_6$) δ ppm 1.07-1.19 (m, 9H), 3.86-3.96 (m, 1H), 4.65 (s, 1H), 7.15-7.42 (m, 4H), 7.53-7.57 (m, 1H), 7.58-7.66 (m, 2H), 7.99-8.06 (m, 2H), 8.65 (s, 1H), 9.56 (d, 1H) |

TABLE 6-continued

Examples 379-398

| Example | structure | IUPAC name | Starting materials | analytics |
|---|---|---|---|---|
| 387 | 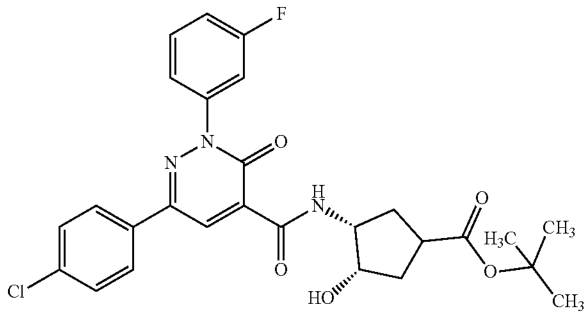 [SMILES: CC(C)(C)OC(=O)C1C[C@H](O)[C@H](NC(=O)c2cc(-c3ccc(Cl)cc3)nn(-c3cccc(F)c3)c2=O)C1] | tert-butyl (3R,4S)-3-({[6-(4-chlorophenyl)-2-(3-fluorophenyl)-3-oxo-2,3-dihydropyridazin-4-yl]carbonyl}amino)-4-hydroxypyrrolidine-1-carboxylate | 6-(4-chlorophenyl)-2-(3-fluorophenyl)-3-oxo-2,3-dihydropyridazine-4-carboxylic acid, (3R,4S)-N-Boc-3-amino-4-hydroxypyrrolidine | $^1$H NMR (400 MHz, DMSO-$d_6$) δ ppm 1.35-1.44 (m, 9H), 3.14-3.25 (m, 2H), 3.39-3.47 (m, 1H), 3.57-3.69 (m, 1H), 4.10-4.24 (m, 2H), 5.51-5.58 (m, 1H), 7.34-7.42 (m, 1H), 7.51-7.66 (m, 5H), 7.96-8.03 (m, 2H), 8.59-8.64 (m, 1H), 9.36-9.43 (m, 1H) |
| 388 | 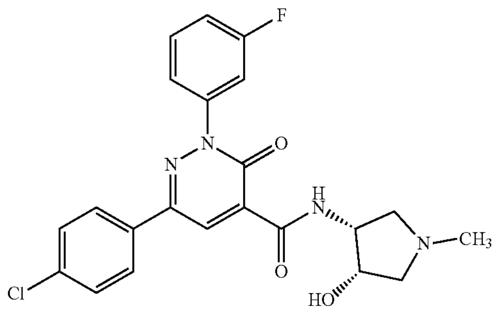 [SMILES: CN1C[C@H](O)[C@H](NC(=O)c2cc(-c3ccc(Cl)cc3)nn(-c3cccc(F)c3)c2=O)C1] | 6-(4-chlorophenyl)-2-(3-fluorophenyl)-N-[cis-4-hydroxy-1-methylpyrrolidin-3-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, cis-4-amino-1-methyl-3-pyrrolidinol dihydrochloride | $^1$H NMR (400 MHz, DMSO-$d_6$) δ ppm 2.51-2.53 (m, 1H), 2.82-2.91 (m, 3H), 3.12-3.27 (m, 1H), 3.53-3.69 (m, 1H), 4.36-4.44 (m, 1H), 4.62-4.80 (m, 1H), 6.32-6.39 (m, 1H), 7.36-7.43 (m, 1H), 7.51-7.67 (m, 6H), 7.99-8.04 (m, 2H), 8.66-8.70 (m, 1H), 9.89-9.94 (m, 1H) |
| 389 | 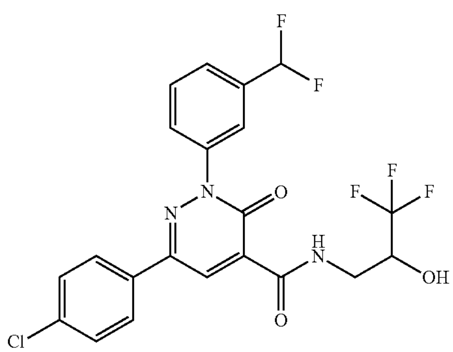 [SMILES: O=C(NCC(O)C(F)(F)F)c1cc(-c2ccc(Cl)cc2)nn(-c2cccc(C(F)F)c2)c1=O] | 6-(4-chlorophenyl)-2-[3-(difluoromethyl)phenyl]-3-oxo-N-(3,3,3-trifluoro-2-hydroxypropyl)-2,3-dihydropyridazine-4-carboxamide | 6-(4-chlorophenyl)-2-[3-(difluoromethyl)phenyl]-3-oxo-2,3-dihydropyridazine-4-carboxylic acid, 3-amino-1,1,1-trifluoro-2-propanol | $^1$H NMR (400 MHz, DMSO-$d_6$) δ ppm 3.43-3.52 (m, 1H), 3.69-3.79 (m, 1H), 4.22 (br s, 1H), 6.63-6.70 (m, 1H), 7.16 (t, 1H), 7.54-7.62 (m, 2H), 7.68-7.76 (m, 2H), 7.84-7.90 (m, 1H), 7.92 (d, 1H), 7.96-8.02 (m, 2H), 8.68 (s, 1H), 9.61-9.68 (m, 1H) |
| 390 | 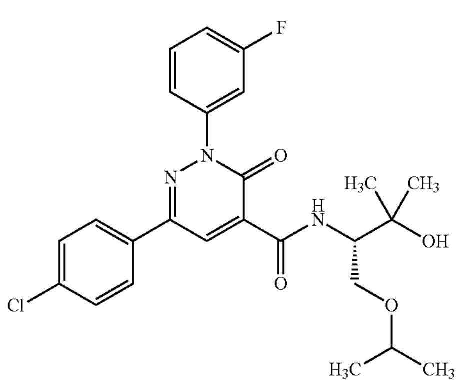 [SMILES: CC(C)OC[C@H](NC(=O)c1cc(-c2ccc(Cl)cc2)nn(-c2cccc(F)c2)c1=O)C(C)(C)O] | 6-(4-chlorophenyl)-2-(3-fluorophenyl)-N-[(2S)-3-hydroxy-1-isopropoxy-3-methylbutan-2-yl]-3-oxo-2,3-dihydropyridazine-4-carboxamide | 6-(4-chlorophenyl)-2-(3-fluorophenyl)-3-oxo-2,3-dihydropyridazine-4-carboxylic acid, (3S)-3-amino-4-isopropoxy-2-methylbutan-2-ol hydrochloride (1:1) | $^1$H NMR (400 MHz, DMSO-$d_6$) δ ppm 1.04-1.07 (m, 6H), 1.08-1.11 (m, 3H), 1.17-1.21 (m, 3H), 3.45-3.59 (m, 2H), 3.64-3.70 (m, 1H), 3.98-4.05 (m, 1H), 4.59-4.62 (m, 1H), 7.35-7.42 (m, 1H), 7.54-7.65 (m, 5H), 7.97-8.02 (m, 2H), 8.66-8.69 (m, 1H), 9.54-9.59 (m, 1H) |

TABLE 6-continued

Examples 379-398

| Example | structure | IUPAC name | Starting materials | analytics |
|---|---|---|---|---|
| 391 | 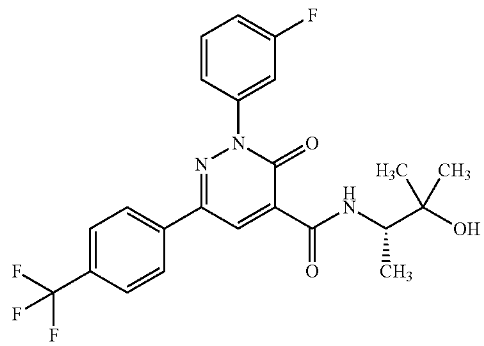 [SMILES: C[C@H](NC(=O)c1cc(-c2ccc(C(F)(F)F)cc2)nn(-c2cccc(F)c2)c1=O)C(C)(C)O] | 2-(3-fluorophenyl)-N-[(2S)-3-hydroxy-3-methylbutan-2-yl]-3-oxo-6-[4-(trifluoromethyl)phenyl]-2,3-dihydropyridazine-4-carboxamide, $[\alpha]_D^{20}$ = +31.4° (c = 1.00, methanol) | 2-(3-fluorophenyl)-3-oxo-6-[4-(trifluoromethyl)pheny;]-2,3-dihydropyridazine-4-carboxylic acid, (3S)-3-amino-2-methylbutan-2-ol | $^1$H-NMR (400 MHz, DMSO-d$_6$): δ [ppm] = 1.10 (s, 3H), 1.13 (d, 3H), 1.16 (s, 3H), 3.88-3.96 (m, 1H), 4.66 (s, 1H), 7.37-7.43 (m, 1H), 7.58 (ddd, 1H), 7.59-7.66 (m, 2H), 7.88 (d, 2H), 8.20 (d, 2H), 8.72 (s, 1H), 9.53 (d, 1H). |
| 392 | 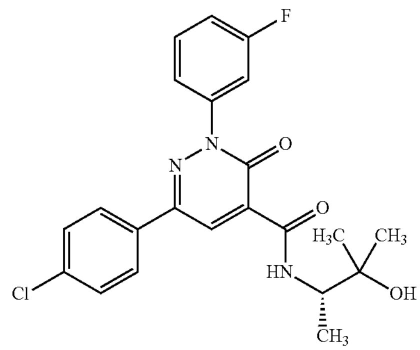 [SMILES: C[C@H](NC(=O)c1cc(-c2ccc(Cl)cc2)nn(-c2cccc(F)c2)c1=O)C(C)(C)O] | 6-(4-chlorophenyl)-2-(3-fluorophenyl)-N-[(2S)-3-hydroxy-3-methylbutan-2-yl]-3-oxo-2,3-dihydropyridazine-4-carboxamide, $[\alpha]_D^{20}$ = +31.1° (c = 1.00, methanol) | 6-(4-chlorophenyl)-2-(3-fluorophenyl)-3-oxo-2,3-dihydropyridazine-4-carboxylic acid, (3S)-3-amino-2-methylbutan-2-ol | $^1$H-NMR (400 MHz, DMSO-d$_6$): δ [ppm] = 1.10 (s, 3H), 1.13 (d, 3H), 1.15 (s, 3H), 3.87-3.95 (m, 1H), 4.65 (s, 1H), 7.36-7.41 (m, 1H), 7.53-7.65 (m, 5H), 7.97-8.01 (m, 2H), 8.66 (s, 1H), 9.54 (d, 1H). |
| 393 | 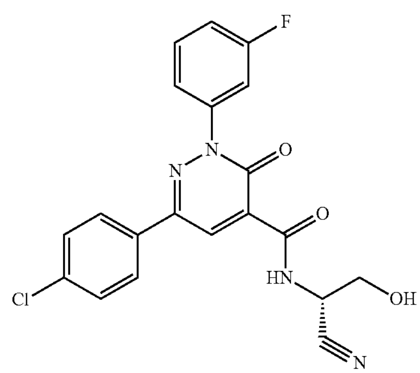 [SMILES: N#C[C@@H](CO)NC(=O)c1cc(-c2ccc(Cl)cc2)nn(-c2cccc(F)c2)c1=O] | 6-(4-chlorophenyl)-N-[(1S)-1-cyano-2-hydroxyethyl]-2-(3-fluorophenyl)-3-oxo-2,3-dihydropyridazine-4-carboxamide, $[\alpha]_D^{20}$ = −25.5° (c = 1.00, methanol) | 6-(4-chlorophenyl)-2-(3-fluorophenyl)-3-oxo-2,3-dihydropyridazine-4-carboxylic acid, (2S)-2-amino-3-hydroxy-propanenitrile hydrochloride (1:1) | $^1$H-NMR (400 MHz, DMSO-d$_6$): δ [ppm] = 3.71-3.78 (m, 1H), 3.78-3.84 (m, 1H), 5.03-5.08 (m, 1H), 5.83 (t, 1H), 7.37-7.42 (m, 1H), 7.54-7.67 (m, 5H), 8.02 (d, 2H), 8.70 (s, 1H), 9.99 (d, 1H). |
| 394 | 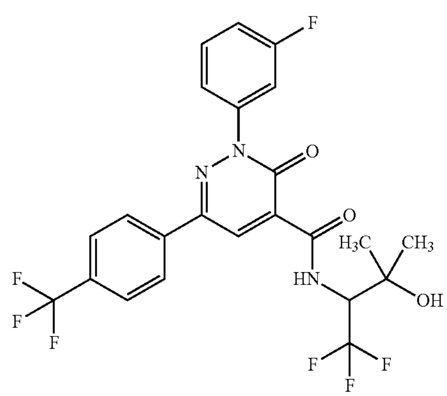 [SMILES: CC(C)(O)C(NC(=O)c1cc(-c2ccc(C(F)(F)F)cc2)nn(-c2cccc(F)c2)c1=O)C(F)(F)F] | (−)-2-(3-fluorophenyl)-3-oxo-N-(1,1,1-trifluoro-3-hydroxy-3-methylbutan-2-yl)-6-[4-(trifluoromethyl)phenyl]-2,3-dihydropyridazine-4-carboxamide, enantiomer 1, $[\alpha]_D^{20}$ = −23.4° (c = 1.00, methanol) | 2-(3-fluorophenyl)-3-oxo-N-(1,1,1-trifluoro-3-hydroxy-3-methylbutan-2-yl)-6-[4-(trifluoromethyl)phenyl]-2,3-dihydropyridazine-4-carboxamide, Chiralpak IA 5μ 250 × 30 mm, eluent A: n-hexane, eluent B: ethanol, gradient: 20-50% B in 20 min, 40 mL/min, 254 nm | $^1$H-NMR (400 MHz, DMSO-d$_6$): δ [ppm] = 1.20 (s, 3H), 1.35 (s, 3H), 4.67 (quin, 1H), 5.22 (s, 1H), 7.38-7.44 (m, 1H), 7.57-7.60 (m, 1H), 7.61-7.68 (m, 2H), 7.88 (d, 2H), 8.22 (d, 2H), 8.79 (s, 1H), 10.03 (d, 1H). Rt = 4.59 min, Chiralpak IA 3 μm 100 × 4.6 mm, eluent A: n-hexane, eluent B: ethanol, gradient: 20-50% B in 7 min, 1.4 mL/min, 25° C., 254 nm |

TABLE 6-continued

Examples 379-398

| Example | structure | IUPAC name | Starting materials | analytics |
|---|---|---|---|---|
| 395 | 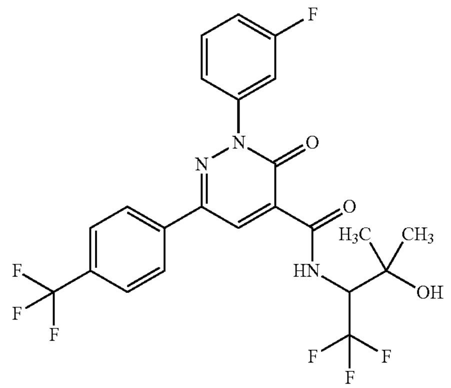 [SMILES: CC(C)(O)C(NC(=O)c1cc(-c2ccc(C(F)(F)F)cc2)nn(-c2cccc(F)c2)c1=O)C(F)(F)F] | (+)-2-(3-fluorophenyl)-3-oxo-N-(1,1,1-trifluoro-3-hydroxy-3-methylbutan-2-yl)-6-[4-(trifluoromethyl)phenyl]-2,3-dihydropyridazine-4-carboxamide, enantiomer 1, $[\alpha]_D^{20} = +24.2°$ (c = 1.00, methanol) | 2-(3-fluorophenyl)-3-oxo-N-(1,1,1-trifluoro-3-hydroxy-3-methylbutan-2-yl)-6-[4-(trifluoromethyl)phenyl]-2,3-dihydropyridazine-4-carboxamide, Chiralpak IA 5μ 250 × 30 mm, eluent A: n-hexane, eluent B: ethanol, gradient: 20-50% B in 20 min, 40 mL/min, 254 nm | $^1$H-NMR (400 MHz, DMSO-$d_6$): δ [ppm] = 1.20 (s, 3H), 1.35 (s, 3H), 4.67 (quin, 1H), 5.22 (s, 1H), 7.38-7.44 (m, 1H), 7.57-7.60 (m, 1H), 7.61-7.68 (m, 2H), 7.88 (d, 2H), 8.22 (d, 2H), 8.79 (s, 1H), 10.03 (d, 1H). Rt = 6.02 min, Chiralpak IA 3 μm 100 × 4.6 mm, eluent A: n-hexane, eluent B: ethanol, gradient: 20-50% B in 7 min, 1.4 mL/min, 25° C., 254 nm |
| 396 | 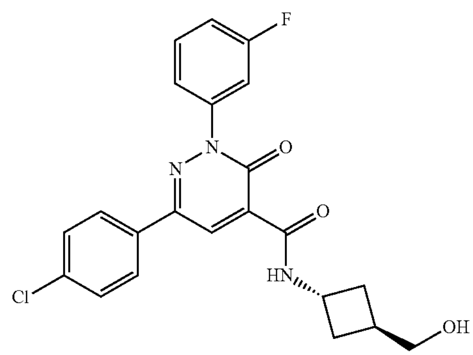 [SMILES: O=C(N[C@H]1C[C@H](CO)C1)c1cc(-c2ccc(Cl)cc2)nn(-c2cccc(F)c2)c1=O] | 6-(4-chlorophenyl)-2-(3-fluorophenyl)-N-[trans-3-(hydroxymethyl)cyclobutyl]-3-oxo-2,3-dihydropyridazine-4-carboxamide | 6-(4-chlorophenyl)-2-(3-fluorophenyl)-3-oxo-2,3-dihydropyridazine-4-carboxylic acid, (trans-3-aminocyclobutyl)methanol hydrochloride (1:1) | $^1$H-NMR (400 MHz, DMSO-$d_6$): δ [ppm] = 2.01-2.10 (m, 2H), 2.12-2.20 (m, 2H), 2.24-2.32 (m, 1H), 3.46 (dd, 2H), 4.40-4.51 (m, 1H), 4.64 (t, 1H), 7.36-7.41 (m, 1H), 7.54-7.66 (m, 5H), 7.97-8.02 (m, 2H), 8.60 (s, 1H), 9.54 (d, 1H). |
| 397 | 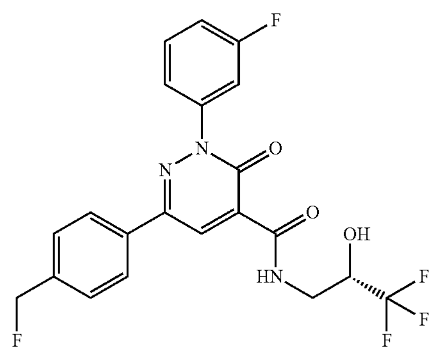 [SMILES: O=C(NC[C@H](O)C(F)(F)F)c1cc(-c2ccc(CF)cc2)nn(-c2cccc(F)c2)c1=O] | 6-[4-(fluoromethyl)phenyl]-2-(3-fluorophenyl)-3-oxo-N-[(2S)-3,3,3-trifluoro-2-hydroxypropyl]-2,3-dihydropyridazine-4-carboxamide, $[\alpha]_D^{20} = -16.2°$ (c = 1.00, methanol) | 6-[4-(fluoromethyl)phenyl]-2-(3-fluorophenyl)-3-oxo-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.47 (ddd, 1H), 3.76 (ddd, 1H), 4.17-4.29 (m, 1H), 5.50 (d, 2H), 6.67 (brd, 1H), 7.36-7.42 (m, 1H), 7.54-7.59 (m, 3H), 7.59-7.67 (m, 2H), 8.02 (d, 2H), 8.69 (s, 1H), 9.66 (t, 1H). |
| 398 | 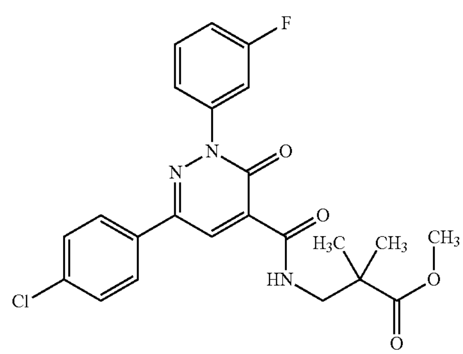 [SMILES: COC(=O)C(C)(C)CNC(=O)c1cc(-c2ccc(Cl)cc2)nn(-c2cccc(F)c2)c1=O] | methyl 3-({[6-(4-chlorophenyl)-2-(3-fluorophenyl)-3-oxo-2,3-dihydropyridazin-4-yl]carbonyl}amino)-2,2-dimethylpropanoate | 6-(4-chlorophenyl)-2-(3-fluorophenyl)-3-oxo-2,3-dihydropyridazine-4-carboxylic acid, methyl 3-amino-2,2-dimethylpropanoate | $^1$H-NMR (400 MHz, DMSO-$d_6$): δ [ppm] = 1.17 (s, 6H), 3.53 (d, 2H), 3.62 (s, 3H), 7.36-7.42 (m, 1H), 7.53-7.66 (m, 5H), 7.96-8.03 (m, 2H), 8.64 (s, 1H), 9.58 (t, 1H). |

Example 399

3-({[6-(4-Chlorophenyl)-2-(3-fluorophenyl)-3-oxo-2,3-dihydropyridazin-4-yl]carbonyl}amino)-2,2-dimethylpropanoic acid

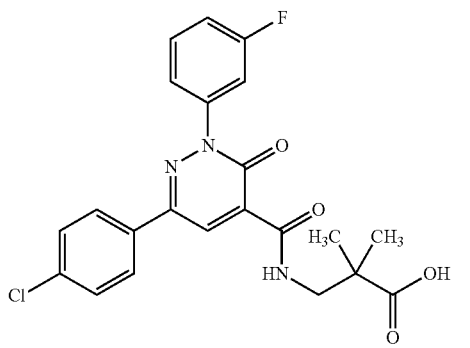 [SMILES: CC(C)(CNC(=O)c1cc(-c2ccc(Cl)cc2)nn(-c2cccc(F)c2)c1=O)C(=O)O]

Methyl 3-({[6-(4-chlorophenyl)-2-(3-fluorophenyl)-3-oxo-2,3-dihydropyridazin-4-yl]carbonyl}amino)-2,2-dimethylpropanoate (133 mg) was suspended in acetonitrile (2.5 mL). Lithiumhydroxide (19.6 mg) in water (0.3 mL) was added. The reaction mixture was stirred overnight at rt. Water (5 mL) was added and the pH was adjusted to 3 (2M HCl, 1.2 mL). The precipitate was filtered off, washed with water and dried at 50° C. under vacuum yielding 105 mg (84%) of the title product.

$^1$H-NMR (400 MHz, DMSO-d$_6$): δ [ppm]=1.14 (s, 6H), 3.50 (d, 2H), 7.35-7.42 (m, 1H), 7.53-7.65 (m, 5H), 7.96-8.02 (m, 2H), 8.66 (s, 1H), 9.62 (t, 1H), 12.53 (br s, 1H).

The following examples were prepared from the starting materials stated in the table using the procedure described in example 4. Enantiomers were separated from their racemates by chiral HPLC using the column and solvent conditions stated.

TABLE 7

Examples 400-405

| Example | structure | IUPAC name | Starting materials | analytics |
|---|---|---|---|---|
| 400 | | 6-(4-chlorophenyl)-2-(3-cyanophenyl)-N-[(2S)-1-hydroxypropan-2-yl]-3-oxo-2,3-dihydropyridazine-4-carboxamide | 6-(4-chlorophenyl)-2-(3-cyanophenyl)-3-oxo-2,3-dihydropyridazine-4-carboxylicacid, (2S)-2-aminopropan-1-ol | $^1$H-NMR (400 MHz, CDCl$_3$): δ [ppm] = 1.30 (d, 3H); 2.55 (t, 1H); 3.63-3.71 (m, 1H); 3.75-3.82 (m, 1H); 4.25-4.35 (m, 1H); 7.46-7.51 (m, 2H); 7.67 (t,1H); 7.76 (td, 1H); 7.82-7.87 (m, 2H); 7.96 (ddd, 1H); 8.02 (t, 1H), 8.81 (s, 1H); 9.59 (bd, 1H). |
| 401 | | 6-(4-chloro-3-fluorophenyl)-2-(3,5-difluorophenyl)-N-[(2S)-1-hydroxy-3-methylbutan-2-yl]-3-oxo-2,3-dihydropyridazine-4-carboxamide | 6-(4-chloro3-fluorophenyl)-2-(3,5-difluorophenyl)-3-oxo-2,3-dihydropyridazine-4-carboxylic acid, (2S)-2-amino-3-methylbutan-1-ol | $^1$H-NMR (400 MHz, CDCl$_3$): δ [ppm] = 0-98-1.07 (m, 6H); 1.98-2.09 (m, 1H); 2.52 (t, 1H); 3.72-3.79 (m, 1H); 3.83 (ddd, 1H); 3.98-4.06 (m, 1H); 6.96 (tt, 1H); 7.27-7.32 (m, 3H); 7.78 (ddd, 1H); 7.97 (dd, 1H); 8.77 (s, 1H); 9.67 (d, 1H). |
| 402 | | 6-(4-chloro-3-fluorophenyl)-2-(3,5-difluorophenyl)-N-[(2S)-1-hyd roxy propan-2-yl]-3-oxo-2,3-dihydropyridazine-4-carboxamide | 6-(4-chloro3-fluorophenyl)-2-(3,5-difluorophenyl)-3-oxo-2,3-dihydropyridazine-4-carboxylic acid, (2S)-2-aminopropan-1-ol | $^1$H-NMR (400 MHz, CDCl$_3$): δ [ppm] = 1.30 (d, 3H); 2.53 (t, 1H); 3.63-3.71 (m, 1H); 3.74-3.82 (m, 1H); 4.25-4.34 (m, 1H); 6.96 (tt, 1H); 7.26-7.31 (m, 3H); 7.78 (ddd, 1H); 7.97 (dd, 1H); 8.76 (s, 1H); 9.59 (bd, 1H). |

TABLE 7-continued

Examples 400-405

| Example | structure | IUPAC name | Starting materials | analytics |
|---|---|---|---|---|
| 403 | 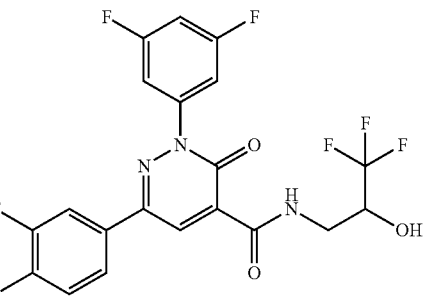 | 6-(4-chloro-3-fluorophenyl)-2-(3,5-difluorophenyl)-3-oxo-N-(3,3,3-trifluoro-2-hydroxypropyl)-2,3-dihydropyridazine-4-carboxamide | 6-(4-chloro-3-fluorophenyl)-2-(3,5-difluorophenyl)-3-oxo-2,3-dihydropyridazine-4-carboxylic acid, 3-amino-1,1,1-trifluoropropan-2-ol | $^1$H-NMR (400 MHz, CDCl$_3$): δ [ppm] = 3.70-3.79 (m, 1H); 3.90 (ddd, 1H); 4.17-4.25 (m, 1H); 6.97 (tt, 1H); 7.26-7.32 (m, 3H); 7.78 (ddd, 1H); 7.97 (dd, 1H); 8.76 (s, 1H); 9.93 (bt, 1H). |
| 404 | 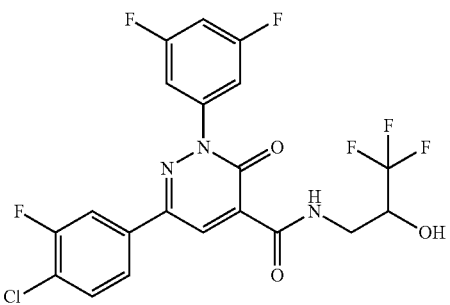 [SMILES: O=C(NCC(O)C(F)(F)F)c1cc(-c2ccc(Cl)c(F)c2)nn(-c2cc(F)cc(F)c2)c1=O] | 6-(4-chloro-3-fluorophenyl)-2-(3,5-difluorophenyl)-3-oxo-N-(3,3,3-trifluoro-2-hydroxypropyl)-2,3-dihydropyridazine-4-carboxamide, enantiomer 1, | 6-(4-chloro-3-fluorophenyl)-2-(3,5-difluorophenyl)-3-oxo-2,3-dihydropyridazine-4-carboxylic acid, 3-amino-1,1,1-trifluoropropan-2-ol, Chiralpak IA 5µ 250 × 30 mm, eluent A: methanol, eluent B: ethanol, 0.1% diethylamine isocratic: 50% B, 30 mL/min, 254 nm | $^1$H-NMR (400 MHz, CDCl$_3$): δ [ppm] = 3.70-3.79 (m, 1H); 3.90 (ddd, 1H); 4.17-4.25 (m, 1H); 6.97 (tt, 1H); 7.26-7.32 (m, 3H); 7.78 (ddd, 1H); 7.97 (dd, 1H); 8.76 (s, 1H); 9.93 (bt, 1H). Rt = 1.66 min, Chiralpak IA 3 µm 100 × 4.6 mm, eluent A: methanol, eluent B: ethanol, 0.1% diethylamine, isocratic: 50% B, 1.4 mL/min, 25° C., 254 nm |
| 405 | 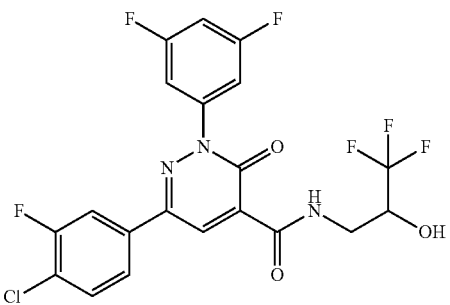 [SMILES: O=C(NCC(O)C(F)(F)F)c1cc(-c2ccc(Cl)c(F)c2)nn(-c2cc(F)cc(F)c2)c1=O] | 6-(4-chloro-3-fluorophenyl)-2-(3,5-difluorophenyl)-3-oxo-N-(3,3,3-trifluoro-2-hydroxypropyl)-2,3-dihydropyridazine-4-carboxamide, enantiomer 2 | 6-(4-chloro-3-fluorophenyl)-2-(3,5-difluorophenyl)-3-oxo-2,3-dihydropyridazine-4-carboxylic acid, 3-amino-1,1,1-trifluoropropan-2-ol, Chiralpak IA 5µ 250 × 30 mm, eluent A: methanol, eluent B: ethanol, 0.1% diethylamine isocratic: 50% B, 30 mL/min, 254 nm | $^1$H-NMR (400 MHz, CDCl$_3$): δ [ppm] = 3.70-3.79 (m, 1H); 3.90 (ddd, 1H); 4.17-4.25 (m, 1H); 6.97 (tt, 1H); 7.26-7.32 (m, 3H); 7.78 (ddd, 1H); 7.97 (dd, 1H); 8.76 (s, 1H); 9.93 (bt, 1H). Rt = 1.92 min, Chiralpak IA 3 µm 100 × 4.6 mm, eluent A: methanol, eluent B: ethanol, 0.1% diethylamine, isocratic: 50% B, 1.4 mL/min, 25° C., 254 nm |

EXPERIMENTAL SECTION—BIOLOGICAL ASSAYS

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Transactivation Assay in Human Cell Line (In Vitro Assays 1 and 2)

Transactivation assays were carried out in U87 glioblastoma cells (ATCC) endogenously expressing AHR. In addition the cells were stably transfected with an AHR inducible firefly luciferase reporter gene construct that carried AHR-binding sites (DRE) in its promoter and a renilla reporter gene construct with constitutively active promoter. Kynurenic acid is an endogenous AHR activating ligand and was used to prestimulate test cells prior to testing the antagonistic properties of compounds.

In Vitro Assay 1: Antagonism in Human Cell Line

Cells in medium (tryptophan free RPMI, 1% FCS, 2 mM Glutamine) supplemented with 150 µM kynurenic acid were grown for 20 hours in absence (negative control) or presence of increasing concentrations of test compounds (typical dilutions: 72 pmol/L, 0.25 nmol/L, 0.89 nmol/L; 3.1 nmol/L, 11 nmol/L, 38 nmol/L, 130 nmol/L, 470 nmol/L, 1.6 µmol/L, 5.7 µmol/L and 20 µmol/L in duplicates). As positive inhibition control cells supplemented with 150 µM kynurenic acid were incubated in presence of 5 µM Staurosporin. Normalization was done by positive and negative controls.

Firefly luciferase and Renilla activity was determined by the DualGlo Luciferase Assay System (Promega, #2920). Renilla activity was used to assess toxic effects of compounds.

In Vitro Assay 2: Agonism in Human Cell Line

Cells in medium (tryptophan free RPMI, 1% FCS, 2 mM Glutamine) were grown for 20 hours in absence (negative control) or presence of increasing concentrations of test compounds (typical dilutions: 72 pmol/L, 0.25 nmol/L, 0.89 nmol/L; 3.1 nmol/L, 11 nmol/L, 38 nmol/L, 130 nmol/L, 470 nmol/L, 1.6 µmol/L, 5.7 µmol/L and 20 µmol/L in duplicates). As positive activation control cells were incubated with 300 µM kynurenic acid. Normalization was done by positive and negative controls.

Firefly luciferase activity was determined by the Steady-Glo Luciferase Assay System (Promega, #2520).

In Vitro Assay 3: AHR-Regulated CYP1A1 Expression in Human Cell Line

To assess the AHR inhibitory activity of the substances described in this application, the ability thereof to antagonise ligand-induced AHR gene regulation in a dose-dependent manner was quantified. For this purpose, quantitative PCR analysis was used to determine expression of the AHR-regulated gene CYP1A1 in a human monocytic U937 cell line upon stimulation with 200 µM KA in the presence and absence of AHR inhibitor. U937 cells were sown at a concentration of $2\times10^5$ cells/well in 100 ul of growth medium (RPMI 1640, 20% FCS) in 96-well microtitre plates. CYP1A1 expression was induced with 200 µM KA (positive control) in the presence or absence of the substances for 6 hours. Human U937 cells were typically incubated with eight different concentrations of the substances (1 nM, 3 nM, 10 nM, 30 nM, 100 nM, 300 nM, 1 µM and 3 µM) and analyzed in duplicate on the same microtitre plate. After stimulation, cells were lysed with Nucleic Acid Lysis Solution (#4305895, Applied Biosystems) and RNA was isolated using the 6100 Nucleic Acid Preparation Station (Applied Biosystems) and reverse-transcribed to cDNA using SuperScript VILO cDNA synthesis kit (#11754-250, Invitrogen). Unstimulated cells were used as the negative control. Taqman probes for human CYP1A1 (Hs01054797_g1) and human HPRT (Hs02800695_m1) were used to analyze fold expression of CYP1A1 of HPRT. Quantitation was performed on a Taqman SDS7900HT.

TABLE 8

IC50 values of examples in in vitro assays 1-3

| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
|---|---|---|---|
| 1 | 2.98E−8 | | 3.10E−8 |
| 2 | 1.03E−8 | >2.00E−5 | 1.36E−8 |
| 3 | 3.03E−7 | | 1.31E−7 |
| 4 | 2.92E−8 | >2.00E−5 | |
| 5 | 1.65E−8 | >2.00E−5 | |
| 6 | 6.58E−8 | >2.00E−5 | |
| 7 | 6.40E−8 | | 1.23E−7 |
| 8 | 3.61E−8 | >2.00E−5 | |
| 9 | 1.81E−7 | | |
| 10 | 1.20E−7 | >2.00E−5 | |
| 11 | 7.94E−8 | >2.00E−5 | 1.71E−7 |
| 12 | 1.22E−7 | >2.00E−5 | |
| 13 | 1.43E−7 | >2.00E−5 | |
| 14 | 1.75E−7 | >2.00E−5 | |
| 15 | 2.62E−7 | >2.00E−5 | |
| 16 | 1.74E−7 | >2.00E−5 | |
| 17 | 2.11E−7 | >2.00E−5 | |
| 18 | 3.39E−7 | >2.00E−5 | |
| 19 | 3.91E−7 | | |
| 20 | 1.18E−8 | >2.00E−5 | 1.22E−8 |
| 21 | 1.89E−8 | | 3.54E−8 |
| 22 | 8.39E−8 | | |
| 23 | 3.99E−8 | >2.00E−5 | 7.07E−8 |
| 24 | 3.02E−7 | >2.00E−5 | |
| 25 | 3.75E−8 | >2.00E−5 | 5.86E−8 |
| 26 | 1.84E−8 | >2.00E−5 | 3.52E−8 |
| 27 | 1.06E−7 | >2.00E−5 | 2.44E−7 |
| 28 | 8.85E−8 | >2.00E−5 | |
| 29 | 9.15E−8 | >2.00E−5 | 1.55E−7 |
| 30 | 1.33E−7 | >2.00E−5 | 1.77E−7 |
| 31 | 1.61E−7 | >2.00E−5 | |
| 32 | 1.81E−7 | >2.00E−5 | |
| 33 | 2.11E−7 | >2.00E−5 | |
| 34 | 1.88E−7 | >2.00E−5 | |
| 35 | 1.92E−7 | >2.00E−5 | |
| 36 | 2.95E−7 | >2.00E−5 | |
| 37 | 1.31E−7 | >2.00E−5 | 1.56E−7 |
| 38 | 3.87E−8 | >2.00E−5 | |
| 39 | 2.76E−8 | >2.00E−5 | |
| 40 | 1.17E−7 | >2.00E−5 | |
| 41 | 2.15E−7 | >2.00E−5 | |
| 42 | 3.44E−7 | >2.00E−5 | |
| 43 | 4.89E−9 | >2.00E−5 | 1.08E−8 |
| 44 | 1.99E−8 | >2.00E−5 | |
| 45 | 1.02E−8 | >2.00E−5 | 1.18E−8 |
| 46 | 5.64E−8 | >2.00E−5 | |
| 47 | 3.08E−8 | >2.00E−5 | 2.52E−8 |
| 48 | 4.93E−8 | >2.00E−5 | |
| 49 | 3.42E−8 | >2.00E−5 | 4.92E−8 |
| 50 | 5.80E−8 | >2.00E−5 | 1.51E−7 |
| 51 | 4.16E−9 | >2.00E−5 | 1.15E−9 |
| 52 | 1.17E−7 | >2.00E−5 | |
| 53 | 8.85E−9 | >2.00E−5 | 7.42E−9 |
| 54 | 4.07E−8 | >2.00E−5 | 1.44E−7 |
| 55 | 1.80E−8 | >2.00E−5 | 1.54E−8 |
| 56 | 4.00E−8 | >2.00E−5 | |
| 57 | 3.49E−8 | >2.00E−5 | 3.83E−8 |
| 58 | 4.28E−8 | >2.00E−5 | 1.34E−7 |
| 59 | 4.96E−8 | | |
| 60 | 6.60E−8 | | |
| 61 | 5.14E−7 | | |
| 62 | 1.50E−7 | | |
| 63 | 8.99E−8 | >2.00E−5 | |
| 64 | 3.66E−7 | >2.00E−5 | |
| 65 | 3.00E−7 | | |
| 66 | 1.65E−7 | >2.00E−5 | |
| 67 | 3.89E−7 | | |
| 68 | 3.70E−7 | >2.00E−5 | |
| 69 | 4.41E−7 | >2.00E−5 | |
| 70 | 9.22E−8 | | 1.26E−7 |
| 71 | 4.05E−8 | | |
| 72 | 2.11E−6 | | |
| 73 | 3.07E−7 | | |
| 74 | 2.10E−6 | | |
| 75 | 3.45E−8 | >2.00E−5 | |
| 76 | 9.37E−8 | >2.00E−5 | |
| 77 | 7.28E−8 | >2.00E−5 | |
| 78 | 2.66E−7 | >2.00E−5 | |
| 79 | 2.82E−7 | | |
| 80 | 2.14E−7 | >2.00E−5 | |
| 81 | 1.12E−6 | | |
| 82 | 1.03E−7 | | |
| 83 | 3.60E−8 | | 2.39E−8 |
| 84 | 3.66E−6 | | |
| 85 | 8.61E−8 | | |
| 86 | 4.55E−8 | | 4.83E−8 |
| 87 | 7.26E−7 | | |
| 88 | 1.46E−7 | | |
| 89 | 1.15E−7 | | 1.88E−7 |
| 90 | 6.75E−7 | | |

TABLE 8-continued

IC50 values of examples in in vitro assays 1-3

| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
|---|---|---|---|
| 91 | 4.44E−9 | >2.00E−5 | |
| 92 | 1.20E−8 | >2.00E−5 | |
| 93 | 3.02E−8 | >2.00E−5 | |
| 94 | 1.54E−8 | >2.00E−5 | |
| 95 | 6.77E−9 | >2.00E−5 | 7.63E−9 |
| 96 | 2.92E−8 | >2.00E−5 | 4.03E−8 |
| 97 | 1.50E−8 | >2.00E−5 | 1.63E−8 |
| 98 | >2.00E−5 | >2.00E−5 | |
| 99 | 1.04E−8 | >2.00E−5 | 3.77E−9 |
| 100 | 1.09E−8 | >2.00E−5 | |
| 101 | 1.24E−8 | >2.00E−5 | 1.88E−8 |
| 102 | 4.22E−8 | >2.00E−5 | 4.37E−8 |
| 103 | 1.59E−8 | >2.00E−5 | 4.47E−9 |
| 104 | 1.57E−8 | >2.00E−5 | 1.64E−8 |
| 105 | 1.51E−7 | >2.00E−5 | |
| 106 | 1.98E−8 | >2.00E−5 | |
| 107 | 1.76E−8 | >2.00E−5 | 1.83E−8 |
| 108 | 2.40E−7 | >2.00E−5 | |
| 109 | 1.78E−8 | >2.00E−5 | 3.61E−8 |
| 110 | 1.79E−8 | >2.00E−5 | |
| 111 | 2.03E−8 | >2.00E−5 | 2.91E−8 |
| 112 | 2.22E−8 | >2.00E−5 | 2.71E−8 |
| 113 | 1.80E−8 | >2.00E−5 | |
| 114 | 2.30E−8 | >2.00E−5 | 5.27E−8 |
| 115 | 2.72E−8 | >2.00E−5 | 1.31E−8 |
| 116 | 2.90E−8 | >2.00E−5 | 9.69E−8 |
| 117 | 3.67E−8 | >2.00E−5 | |
| 118 | 3.25E−8 | >2.00E−5 | 3.13E−8 |
| 119 | 4.51E−7 | >2.00E−5 | |
| 120 | 4.47E−8 | >2.00E−5 | |
| 121 | 3.42E−8 | >2.00E−5 | |
| 122 | 1.38E−7 | >2.00E−5 | |
| 123 | 3.63E−8 | >2.00E−5 | 9.77E−8 |
| 124 | 3.65E−8 | >2.00E−5 | 3.59E−8 |
| 125 | 1.86E−7 | >2.00E−5 | |
| 126 | 5.13E−8 | >2.00E−5 | |
| 127 | 4.05E−8 | >2.00E−5 | 6.08E−8 |
| 128 | 1.70E−7 | >2.00E−5 | 6.00E−7 |
| 129 | 4.52E−7 | >2.00E−5 | 6.00E−7 |
| 130 | 4.37E−8 | >2.00E−5 | |
| 131 | 4.69E−8 | >2.00E−5 | 8.26E−8 |
| 132 | 1.36E−7 | >2.00E−5 | |
| 133 | 1.58E−7 | >2.00E−5 | |
| 134 | 1.72E−7 | >2.00E−5 | |
| 135 | 1.41E−7 | >2.00E−5 | 1.32E−7 |
| 136 | 1.43E−7 | >2.00E−5 | |
| 137 | 4.99E−8 | >2.00E−5 | |
| 138 | 5.02E−8 | >2.00E−5 | |
| 139 | 6.97E−8 | >2.00E−5 | |
| 140 | 2.05E−7 | >2.00E−5 | |
| 141 | 7.81E−8 | >2.00E−5 | |
| 142 | 9.15E−7 | >2.00E−5 | |
| 143 | 8.07E−8 | >2.00E−5 | |
| 144 | 8.37E−8 | >2.00E−5 | |
| 145 | 9.33E−8 | >2.00E−5 | 3.89E−8 |
| 146 | 2.94E−7 | >2.00E−5 | |
| 147 | 4.66E−7 | >2.00E−5 | |
| 148 | 5.33E−7 | >2.00E−5 | |
| 149 | 1.87E−7 | >2.00E−5 | |
| 150 | 2.35E−7 | >2.00E−5 | |
| 151 | 1.24E−7 | >2.00E−5 | |
| 152 | 1.32E−7 | >2.00E−5 | |
| 153 | 1.43E−7 | >2.00E−5 | |
| 154 | 1.69E−7 | >2.00E−5 | |
| 155 | 1.70E−7 | >2.00E−5 | |
| 156 | 1.99E−7 | >2.00E−5 | |
| 157 | 2.22E−7 | >2.00E−5 | |
| 158 | 2.75E−7 | >2.00E−5 | |
| 159 | 2.84E−7 | >2.00E−5 | |
| 160 | 3.11E−7 | >2.00E−5 | |
| 161 | 3.15E−7 | >2.00E−5 | |
| 162 | 4.83E−7 | >2.00E−5 | |
| 163 | 4.98E−7 | >2.00E−5 | |
| 164 | 5.96E−7 | >2.00E−5 | 2.00E−6 |
| 165 | >2.00E−5 | >2.00E−5 | |
| 166 | 4.05E−8 | >2.00E−5 | 4.47E−8 |
| 167 | 1.63E−7 | >2.00E−5 | 2.03E−7 |
| 168 | 6.92E−9 | >2.00E−5 | 2.16E−8 |
| 169 | 1.11E−8 | >2.00E−5 | 1.35E−8 |
| 170 | 1.19E−8 | >2.00E−5 | 1.42E−8 |
| 171 | 6.77E−7 | >2.00E−5 | |
| 172 | 2.63E−8 | >2.00E−5 | 2.68E−8 |
| 173 | 3.31E−8 | >2.00E−5 | 9.10E−8 |
| 174 | 3.33E−8 | >2.00E−5 | |
| 175 | 2.91E−8 | >2.00E−5 | 3.76E−8 |
| 176 | 1.71E−7 | >2.00E−5 | 1.02E−7 |
| 177 | 3.19E−7 | >2.00E−5 | 6.00E−7 |
| 178 | 1.27E−7 | >2.00E−5 | 1.13E−7 |
| 179 | 7.36E−8 | >2.00E−5 | |
| 180 | 1.24E−7 | >2.00E−5 | |
| 181 | 8.02E−8 | >2.00E−5 | 2.12E−7 |
| 182 | 3.41E−8 | >2.00E−5 | 5.90E−8 |
| 183 | 3.78E−8 | >2.00E−5 | 4.14E−8 |
| 184 | 1.34E−7 | >2.00E−5 | 1.29E−7 |
| 185 | 3.90E−8 | >2.00E−5 | 8.06E−8 |
| 186 | 1.88E−7 | >2.00E−5 | 1.34E−7 |
| 187 | 1.02E−7 | >2.00E−5 | 1.10E−7 |
| 188 | 7.88E−8 | >2.00E−5 | |
| 189 | 1.86E−7 | >2.00E−5 | 2.00E−6 |
| 190 | 2.77E−7 | >2.00E−5 | |
| 191 | 1.10E−7 | >2.00E−5 | |
| 192 | 1.97E−7 | >2.00E−5 | |
| 193 | 2.52E−8 | >2.00E−5 | |
| 194 | 1.21E−8 | >2.00E−5 | |
| 195 | 2.50E−7 | >2.00E−5 | |
| 196 | 1.04E−7 | >2.00E−5 | |
| 197 | 1.97E−8 | >2.00E−5 | 1.82E−8 |
| 198 | 1.34E−8 | >2.00E−5 | 1.49E−8 |
| 199 | 5.84E−7 | >2.00E−5 | |
| 200 | 7.50E−8 | >2.00E−5 | |
| 201 | 8.64E−8 | >2.00E−5 | |
| 202 | 1.02E−7 | >2.00E−5 | |
| 203 | 2.13E−7 | >2.00E−5 | |
| 204 | 3.85E−7 | >2.00E−5 | |
| 205 | 2.12E−7 | >2.00E−5 | |
| 206 | 6.25E−8 | >2.00E−5 | |
| 207 | 6.29E−8 | >2.00E−5 | |
| 208 | 2.00E−7 | >2.00E−5 | |
| 209 | 3.27E−8 | >2.00E−5 | 3.21E−8 |
| 210 | 4.12E−7 | >2.00E−5 | |
| 211 | 1.66E−8 | >2.00E−5 | 2.23E−8 |
| 212 | 3.59E−8 | >2.00E−5 | 4.92E−8 |
| 213 | 8.72E−8 | >2.00E−5 | 2.21E−7 |
| 214 | 8.32E−8 | >2.00E−5 | |
| 215 | 1.66E−7 | >2.00E−5 | |
| 216 | 1.16E−7 | >2.00E−5 | |
| 217 | | >2.00E−5 | |
| 218 | 6.88E−8 | >2.00E−5 | 1.51E−7 |
| 219 | 3.38E−6 | >2.00E−5 | |
| 220 | 1.03E−7 | >2.00E−5 | 6.00E−7 |
| 221 | 7.64E−8 | >2.00E−5 | |
| 222 | 4.87E−8 | >2.00E−5 | 9.14E−8 |
| 223 | 1.28E−7 | >2.00E−5 | |
| 224 | 2.79E−7 | >2.00E−5 | |
| 225 | 2.41E−7 | >2.00E−5 | |
| 226 | 1.42E−7 | >2.00E−5 | |
| 227 | 3.57E−7 | >2.00E−5 | |
| 228 | 3.35E−7 | >2.00E−5 | |
| 229 | 1.50E−7 | >2.00E−5 | 2.00E−6 |
| 230 | 1.37E−7 | >2.00E−5 | |
| 231 | 4.72E−8 | >2.00E−5 | 5.77E−8 |
| 232 | 1.19E−7 | >2.00E−5 | |
| 233 | 1.72E−7 | >2.00E−5 | |
| 234 | 1.56E−6 | >2.00E−5 | |
| 235 | 3.00E−6 | >2.00E−5 | |
| 236 | 8.23E−8 | >2.00E−5 | |

TABLE 8-continued

IC50 values of examples in in vitro assays 1-3

| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
|---|---|---|---|
| 237 | 1.23E−8 | >2.00E−5 | 2.46E−8 |
| 238 | 9.88E−8 | >2.00E−5 | |
| 239 | | >2.00E−5 | |
| 240 | | 6.56E−8 | |
| 241 | >2.00E−5 | 1.16E−7 | |
| 242 | >2.00E−5 | 1.18E−5 | |
| 243 | 3.13E−8 | >2.00E−5 | |
| 244 | 3.17E−8 | >2.00E−5 | |
| 245 | 3.72E−8 | >2.00E−5 | 5.44E−8 |
| 246 | 2.78E−8 | >2.00E−5 | 4.05E−8 |
| 247 | 8.35E−8 | >2.00E−5 | 1.71E−7 |
| 248 | 9.73E−8 | >2.00E−5 | 1.36E−7 |
| 249 | 8.84E−8 | >2.00E−5 | 1.07E−7 |
| 250 | 4.69E−8 | >2.00E−5 | 7.24E−8 |
| 251 | 5.09E−6 | >2.00E−5 | 3.67E−8 |
| 252 | 6.43E−6 | >2.00E−5 | |
| 253 | 2.89E−8 | >2.00E−5 | 3.62E−8 |
| 254 | 1.10E−8 | >2.00E−5 | 3.01E−8 |
| 255 | 1.09E−7 | >2.00E−5 | 3.89E−7 |
| 256 | 1.44E−8 | >2.00E−5 | 2.83E−8 |
| 257 | 6.37E−8 | >2.00E−5 | 1.34E−7 |
| 258 | 3.01E−8 | >2.00E−5 | 3.71E−8 |
| 259 | 3.82E−8 | >2.00E−5 | |
| 260 | | >2.00E−5 | |
| 261 | 2.26E−8 | >2.00E−5 | |
| 262 | 5.51E−8 | >2.00E−5 | 9.15E−8 |
| 263 | 3.54E−8 | >2.00E−5 | 6.06E−8 |
| 264 | 7.05E−8 | >2.00E−5 | 8.01E−8 |
| 265 | 6.04E−8 | >2.00E−5 | 2.15E−7 |
| 266 | | 7.84E−7 | |
| 267 | 2.90E−8 | >2.00E−5 | 1.05E−8 |
| 268 | >2.00E−5 | | |
| 269 | >2.00E−5 | 3.85E−9 | |
| 270 | 6.12E−9 | >2.00E−5 | 5.44E−9 |
| 271 | 2.06E−8 | >2.00E−5 | 3.01E−8 |
| 272 | 3.60E−8 | >2.00E−5 | 2.37E−8 |
| 273 | 4.31E−8 | >2.00E−5 | |
| 274 | 2.06E−8 | >2.00E−5 | |
| 275 | 1.81E−8 | >2.00E−5 | 3.39E−8 |
| 276 | 1.45E−7 | >2.00E−5 | |
| 277 | 4.94E−9 | >2.00E−5 | 2.08E−8 |
| 278 | 2.05E−7 | >2.00E−5 | |
| 279 | 6.07E−9 | >2.00E−5 | 2.89E−9 |
| 280 | 1.92E−8 | >2.00E−5 | |
| 281 | 2.20E−8 | >2.00E−5 | 7.59E−8 |
| 282 | 1.81E−7 | >2.00E−5 | |
| 283 | 1.91E−7 | >2.00E−5 | |
| 284 | 8.39E−7 | >2.00E−5 | |
| 285 | 9.39E−8 | >2.00E−5 | |
| 286 | 2.77E−7 | >2.00E−5 | |
| 287 | 1.29E−7 | >2.00E−5 | |
| 288 | 3.97E−8 | >2.00E−5 | 8.05E−8 |
| 289 | 1.44E−7 | >2.00E−5 | |
| 290 | 8.14E−8 | >2.00E−5 | |
| 291 | 8.51E−8 | >2.00E−5 | |
| 292 | 3.09E−7 | >2.00E−5 | |
| 293 | 4.92E−8 | >2.00E−5 | 6.98E−8 |
| 294 | 6.17E−7 | >2.00E−5 | |
| 295 | 8.30E−7 | >2.00E−5 | |
| 296 | 3.66E−9 | >2.00E−5 | 6.22E−9 |
| 297 | 8.72E−8 | >2.00E−5 | |
| 298 | 3.18E−8 | >2.00E−5 | |
| 299 | 7.42E−7 | >2.00E−5 | |
| 300 | 1.19E−7 | >2.00E−5 | 1.07E−7 |
| 301 | 2.73E−8 | >2.00E−5 | 8.10E−8 |
| 302 | 2.29E−7 | >2.00E−5 | |
| 303 | 8.73E−7 | >2.00E−5 | |
| 304 | 2.75E−7 | >2.00E−5 | |
| 305 | 1.21E−7 | >2.00E−5 | |
| 306 | 1.06E−7 | >2.00E−5 | 1.75E−7 |
| 307 | 2.22E−7 | >2.00E−5 | |
| 308 | 1.77E−7 | >2.00E−5 | |
| 309 | 9.87E−7 | >2.00E−5 | |
| 310 | 4.34E−7 | >2.00E−5 | |
| 311 | 6.60E−7 | >2.00E−5 | |
| 312 | 5.88E−7 | >2.00E−5 | |
| 313 | 1.67E−8 | >2.00E−5 | |
| 314 | 9.54E−8 | >2.00E−5 | 2.31E−7 |
| 315 | 8.53E−8 | >2.00E−5 | 2.00E−6 |
| 316 | 3.70E−7 | >2.00E−5 | |
| 317 | 1.77E−7 | >2.00E−5 | |
| 318 | 5.34E−8 | >2.00E−5 | |
| 319 | 5.02E−8 | >2.00E−5 | |
| 320 | 3.62E−7 | >2.00E−5 | |
| 321 | 2.64E−7 | >2.00E−5 | |
| 322 | 1.14E−7 | >2.00E−5 | |
| 323 | 2.43E−8 | >2.00E−5 | 3.2E−8 |
| 324 | 4.67E−8 | >2.00E−5 | 8.18E−8 |
| 325 | 9.65E−8 | >2.00E−5 | |
| 326 | 6.47E−8 | >2.00E−5 | |
| 327 | 1.66E−8 | >2.00E−5 | 1.38E−8 |
| 328 | 4.47E−8 | >2.00E−5 | 9.53E−8 |
| 329 | 2.80E−8 | >2.00E−5 | 3.22E−8 |
| 330 | 1.21E−7 | >2.00E−5 | |
| 331 | 7.87E−8 | >2.00E−5 | 1.42E−7 |
| 332 | 6.06E−8 | >2.00E−5 | |
| 333 | 1.34E−7 | >2.00E−5 | |
| 334 | 1.09E−7 | >2.00E−5 | |
| 335 | 4.05E−7 | >2.00E−5 | |
| 336 | 4.02E−8 | >2.00E−5 | 2.00E−6 |
| 337 | 4.58E−8 | >2.00E−5 | |
| 338 | 7.32E−8 | >2.00E−5 | |
| 339 | 4.59E−8 | >2.00E−5 | |
| 340 | 2.26E−8 | >2.00E−5 | |
| 341 | 8.45E−9 | >2.00E−5 | |
| 342 | 4.46E−7 | >2.00E−5 | |
| 343 | 1.49E−8 | >2.00E−5 | |
| 344 | 5.84E−9 | >2.00E−5 | 1.85E−8 |
| 345 | 1.58E−8 | >2.00E−5 | 5.4E−8 |
| 346 | 1.98E−7 | >2.00E−5 | |
| 347 | 1.69E−7 | >2.00E−5 | |
| 348 | 5.11E−8 | >2.00E−5 | 1.37E−7 |
| 349 | 3.54E−9 | >2.00E−5 | |
| 350 | 2.08E−7 | >2.00E−5 | |
| 351 | 4.84E−9 | >2.00E−5 | |
| 352 | 1.00E−7 | >2.00E−5 | |
| 353 | 2.00E−8 | >2.00E−5 | |
| 354 | 1.41E−8 | >2.00E−5 | |
| 355 | 1.20E−7 | >2.00E−5 | |
| 356 | 4.18E−8 | >2.00E−5 | |
| 357 | 2.13E−8 | >2.00E−5 | 2.70E−8 |
| 358 | 1.15E−7 | >2.00E−5 | |
| 359 | 2.67E−8 | >2.00E−5 | |
| 360 | 1.39E−8 | >2.00E−5 | |
| 361 | 1.66E−7 | >2.00E−5 | 2.96E−7 |
| 362 | 2.31E−7 | >2.00E−5 | |
| 363 | 2.22E−7 | >2.00E−5 | |
| 364 | 5.72E−7 | >2.00E−5 | |
| 365 | 4.18E−7 | >2.00E−5 | >1.00E−6 |
| 366 | 9.70E−7 | >2.00E−5 | |
| 367 | 5.00E−7 | >2.00E−5 | |
| 368 | 1.86E−6 | >2.00E−5 | |
| 369 | 9.73E−7 | >2.00E−5 | >1.00E−6 |
| 370 | 9.24E−7 | >2.00E−5 | |
| 371 | 1.63E−8 | >2.00E−5 | 5.69E−8 |
| 372 | 2.21E−7 | >2.00E−5 | |
| 373 | 1.69E−8 | >2.00E−5 | |
| 374 | 2.65E−8 | >2.00E−5 | >3.00E−7 |
| 375 | 3.05E−8 | >2.00E−5 | 5.73E−8 |
| 376 | 3.97E−8 | >2.00E−5 | 1.12E−7 |
| 377 | 1.36E−7 | >2.00E−5 | |
| 378 | 2.48E−7 | >2.00E−5 | |
| 379 | 9.6E−9 | >2.00E−5 | 6.9E−9 |
| 380 | 2.8E−8 | >1.00E−4 | 6.3E−8 |
| 381 | 4.7E−8 | >2.00E−5 | |
| 382 | 9.0E−8 | >2.00E−5 | |

TABLE 8-continued

IC50 values of examples in in vitro assays 1-3

| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
|---|---|---|---|
| 383 | 2.1E−8 | >2.00E−5 | 3.4E−8 |
| 384 | 2.4E−8 | >2.00E−5 | |
| 385 | 8.8E−8 | >2.00E−5 | |
| 386 | 6.5E−8 | >2.00E−5 | |
| 387 | 3.5E−7 | >2.00E−5 | |
| 388 | 6.9E−7 | >2.00E−5 | |
| 389 | 8.8E−7 | >2.00E−5 | |
| 390 | 9.4E−7 | >2.00E−5 | |
| 391 | 1.0E−8 | >2.00E−5 | |
| 392 | 2.6E−8 | >2.00E−5 | 5.7E−8 |
| 393 | 2.7E−8 | >2.00E−5 | 4.6E−8 |
| 394 | 2.8E−8 | >2.00E−5 | 9.5E−8 |
| 395 | | >2.00E−5 | |
| 396 | 1.3E−7 | >2.00E−5 | |
| 397 | 1.8E−7 | >2.00E−5 | |
| 398 | 4.2E−7 | >2.00E−5 | |
| 399 | 7.2E−7 | >2.00E−5 | |
| 400 | 8.0E−7 | >2.00E−5 | |
| 401 | 1.0E−7 | >2.00E−5 | |
| 402 | 3.7E−7 | >2.00E−5 | |
| 403 | 3.1E−7 | >2.00E−5 | |
| 404 | 2.7E−7 | >2.00E−5 | |
| 406 | 6.5E−7 | >2.00E−5 | |

In Vitro Assay 4: Rescue of TNFa Production from Human Primary Monocytes

The ability of the substances to enhance immune cell activity was determined. The substances were tested for their capacity to reverse KA-induced inhibition of TNFa production by LPS-stimulated human monocytes. Human monocytes were purified by negative selection from donor PBMCs using Miltenyi beads and seeded at 2×10$^5$ cells/well in complete growth medium (RPMI 1640, 10% FCS). Monocytes were incubated with 10 ng/mL LPS (0127:68, #L4516, Sigma) and 200 µM KA (#3375, Sigma) and substances were added at concentrations of 1 µM, 0.3 µM and 0.1 µM and cultured for 18 hours. LPS alone served as the positive control. TNFa production in the supernatant was measured by Meso Scale Discovery immunoassay and the ability of the substances to rescue TNFa production was calculated as a percentage of LPS stimulation and KA-induced inhibition and normalized to the donor-specific response with the reference AHR antagonist compound GNF-351 (Smith et al., J Pharmacol Exp Ther, 2011, 338 (1):318-27). Table 9 shows highest percent TNFa rescue relative to highest percent rescue with GNF-351 (observed at 0.3 and 0.1 µM) and the concentration at which highest rescue was observed with the test compound.

TABLE 9

Human monocytes: efficacy of selected examples in in vitro assay 4

| Example | Individual Donors % rescue TNFa normalised to ref cmpd | Individual Donors Conc of highest rescue |
|---|---|---|
| 11 | 55.2 | 1 µM |
| | 51.9 | 1 µM |
| | 98.9 | 1 µM |
| 23 | 88.3 | 1 µM |
| | 87.6 | 1 µM |
| | 90.4 | 1 µM |
| | 37.3 | 1 µM |
| | 57.9 | 1 µM |
| | 96.3 | 1 µM |
| | 36.9 | 1 µM |
| | 106.5 | 1 µM |
| | 75.9 | 1 µM |
| 26 | 92.8 | 1 µM |
| | 98.2 | 1 µM |
| | 47.2 | 1 µM |
| 27 | 40.9 | 1 µM |
| | 62.6 | 1 µM |
| | 40.3 | 1 µM |
| 29 | 54.6 | 0.3 µM |
| | 69.5 | 1 µM |
| | 26.5 | 1 µM |
| 30 | 76.6 | 1 µM |
| | 40.9 | 1 µM |
| | 37.8 | 1 µM |
| 43 | 92.9 | 0.1 µM |
| | 128.5 | 0.3 µM |
| | 47.9 | 0.3 µM |
| 45 | 98.9 | 1 µM |
| | 64.8 | 1 µM |
| | 139.7 | 1 µM |
| | 97.2 | 0.3 µM |
| | 84.4 | 1 µM |
| | 37.2 | 1 µM |
| 47 | 132.4 | 1 µM |
| | 131.4 | 1 µM |
| | 44.7 | 1 µM |
| 49 | 74 | 1 µM |
| | 100.5 | 0.1 µM |
| | 78.8 | 1 µM |
| 50 | 131.5 | 1 µM |
| | 137.8 | 1 µM |
| | 66.2 | 1 µM |
| 51 | 53.4 | 0.1 µM |
| | 103.4 | 0.3 µM |
| | 104.1 | 0.3 µM |
| | 137.7 | 0.3 µM |
| | 61.1 | 0.1 µM |
| 53 | 58.3 | 0.3 µM |
| | 68.1 | 1 µM |
| 54 | 13.7 | 1 µM |
| | 84.3 | 1 µM |
| | 60.5 | 1 µM |
| 55 | 75.5 | 0.3 µM |
| | 114.5 | 1 µM |
| | 16.4 | 1 µM |
| | 108.6 | 1 µM |
| | 91.4 | 1 µM |
| 57 | 79.5 | 1 µM |
| | 160.5 | 1 µM |
| | 66.2 | 1 µM |
| 58 | 79.5 | 0.3 µM |
| | 66.5 | 1 µM |
| | 56.7 | 1 µM |
| 99 | 101 | 0.3 µM |
| | 93 | 1 µM |
| | 90 | 0.1 µM |
| | 95 | 1 µM |
| 101 | 117 | 1 µM |
| | 53 | 1 µM |
| 102 | 124 | 1 µM |
| | 30 | 1 µM |
| 104 | 86 | 0.3 µM |
| | 61 | 1 µM |
| 111 | 10055 | 1 µM |
| | | 1 µM |
| 112 | 150 | 1 µM |
| | 87 | 1 µM |
| 115 | 140 | 1 µM |
| | 91 | 1 µM |
| 116 | 48 | 1 µM |

TABLE 9-continued

Human monocytes: efficacy of selected examples in in vitro assay 4

| Example | Individual Donors % rescue TNFa normalised to ref cmpd | Individual Donors Conc of highest rescue |
|---|---|---|
|  | 160 | 1 µM |
| 118 | 8425 | 1 µM |
|  |  | 1 µM |
| 124 | 172 | 1 µM |
|  | 100 | 1 µM |
| 127 | 88 | 1 µM |
|  | 140 | 1 µM |
| 128 | 39 | 1 µM |
|  | 45 | 1 µM |
| 129 | 30 | 1 µM |
|  | 29 | 1 µM |
| 164 | 61 | 1 µM |
|  | 20 | 1 µM |
| 168 | 72 | 1 µM |
|  | 196 | 1 µM |
| 172 | 149 | 1 µM |
|  | 70 | 1 µM |
| 173 | 79 | 1 µM |
|  | 123 | 1 µM |
| 175 | 140 | 1 µM |
|  | 74 | 1 µM |
| 176 | 76 | 1 µM |
|  | 132 | 1 µM |
| 177 | 42 | 1 µM |
|  | 62 | 1 µM |
| 178 | 117 | 1 µM |
|  | 120 | 1 µM |
| 183 | 98 | 1 µM |
|  | 70 | 1 µM |
| 184 | 64 | 1 µM |
|  | 59 | 1 µM |
| 186 | 157 | 1 µM |
|  | 91 | 1 µM |
| 209 | 43 | 1 µM |
|  | 107 | 1 µM |
| 213 | 66 | 1 µM |
|  | 123 | 1 µM |
| 220 | 23 | 1 µM |
|  | 112 | 0.3 µM |
| 237 | 87 | 1 µM |
|  | 118 | 1 µM |
| 250 | 134 | 0.3 µM |
|  | 213 | 1 µM |
| 256 | 80 | 1 µM |
|  | 103 | 1 µM |
| 272 | 156 | 1 µM |
|  | 109 | 1 µM |
| 279 | 53 | 0.1 µM |
|  | 72 | 0.3 µM |
| 288 | 82 | 1 µM |
|  | 88 | 1 µM |
| 290 | 91 | 1 µM |
|  | 58 | 1 µM |
| 300 | 122 | 1 µM |
|  | 119 | 1 µM |
| 301 | 112 | 1 µM |
|  | 115 | 1 µM |
| 306 | 58 | 1 µM |
|  | 84 | 1 µM |
| 374 | 41 | 1 µM |
|  | 201 | 1 µM |

In Vivo Assay: Efficacy of Compositions Comprising an Example Compound and a PD-1-L1 Axis Antagonist Animals were ordered from Charles River Sulzfeld, Germany and assigned to the study at the age of 8 weeks. Animal husbandry, feeding and health conditions are according to animal welfare guidelines. CT26 cells (aquired from ATCC) were cultivated with RPMI 1640 with 10% FCS and splitted at least 3 times before inoculation. Female Balb/c mice were inoculated with 500.000 CT26 tumor cells in 50% medium/50% matrigel subcutaneously in the flank. After 4 days the animals were randomized and therapeutic treatment started on day 5. 30 mg/kg example 23 were dissolved in Ethanol/Solutol/Water (10/40/50) and given BID, p.o. and 10 mg/kg of the antibody aPD-L1 q3d (TPP-3911), i.p.

The anti-PDL1 antibody is a chimera of the variable domain of atezolizumab with murine IgG1 CH1, 2 and 3 domains.

Tumor size was measured using calipers determining length (a) and width (b). Tumor volume was calculated according to:

$$v = \frac{a \times b^2}{2}$$

TABLE 10

Efficacy shown as ratio of tumor size under treatment versus tumor size in the control group (T/C)

|  | Control | aPD-L1 | Example 23 | Example 23 + aPD-L1 |
|---|---|---|---|---|
| T/C | 1.00 | 0.64 | 0.75 | 0.27 |

Significance of monotherapies and combination treatment was calculated versus control group as determined by 2-Way ANOVA analysis. All three groups have significantly smaller tumors compared to control.

Significance of AHRi+aPD-L1 combination group was calculated versus monotherapy AHRi and monotherapy aPD-L1 groups as determined by 2-Way ANOVA analysis. Combination therapy treated tumors are significantly smaller compared to monotherapies.

DESCRIPTION OF THE FIGURES

FIG. 1: Female Balb/c mice were inoculated with 500.000 CT26 tumor cells in 50% medium/50% matrigel subcutaneously in the flank. After 4 days the animals were randomized and therapeutic treatment started on day 5. 30 mg/kg example 23 was given BID, p.o. and 10 mg/kg aPD-L1 q3d, i.p. Tumor size was measured using calipers. Significance of monotherapies and combination treatment was calculated vs. control group as determined by 2-Way ANOVA analysis.

The invention claimed is:
1. A compound of formula (I):

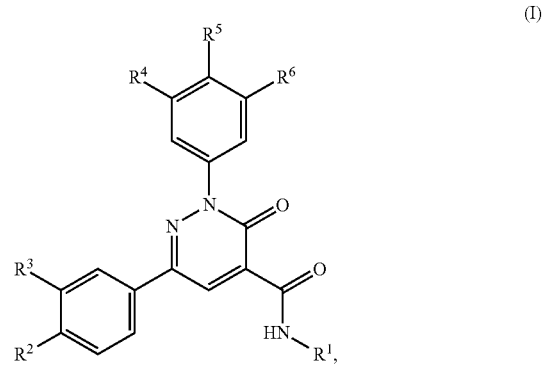

in which
$R^1$ represents $C_2$-$C_6$-hydroxyalkyl, wherein said $C_2$-$C_6$-hydroxyalkyl is optionally substituted once with $R^7$ and optionally one to three times with halogen, or R¹ represents $C_3$-$C_6$-cycloalkyl substituted once with hydroxy;

R² represents chloro, methyl, fluoromethyl, difluoromethyl, trifluoromethyl, methoxy or difluoromethoxy;

R³ represents hydrogen or methyl;

R⁴ represents hydrogen or halogen;

R⁵ represents hydrogen;

R⁶ represents hydrogen or halogen;

R⁷ represents $C_1$-$C_4$-alkoxy, $C_3$-$C_6$-cycloalkyl, 4- to 6-membered heterocycloalkyl or monocyclic heteroaryl;

or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing.

2. The compound according to claim 1, wherein:

R¹ represents $C_2$-$C_6$-hydroxyalkyl, wherein said $C_2$-$C_6$-hydroxyalkyl is optionally substituted once with R⁷ and optionally one to three times with fluoro or chloro, or R¹ represents $C_3$-$C_6$-cycloalkyl substituted once with hydroxy;

R² represents chloro, methyl, fluoromethyl, difluoromethyl, trifluoromethyl, methoxy or difluoromethoxy;

R³ represents hydrogen or methyl;

R⁴ represents hydrogen, fluoro or chloro;

R⁵ represents hydrogen;

R⁶ represents hydrogen or fluoro;

R⁷ represents methoxy, cyclopropyl, tetrahydrofuranyl, tetrahydropyranyl or imidazolyl;

or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing.

3. The compound according to claim 1, wherein:

R¹ represents $C_2$-$C_6$-hydroxyalkyl, wherein said $C_2$-$C_6$-hydroxyalkyl is optionally substituted once with R⁷ and optionally one to three times with fluoro;

R² represents chloro, methyl or difluoromethyl;

R³ represents hydrogen or methyl;

R⁴ represents hydrogen, fluoro or chloro;

R⁵ represents hydrogen;

R⁶ represents hydrogen or fluoro;

R⁷ represents methoxy or tetrahydrofuranyl;

or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing.

4. The compound which is selected from the group consisting of:

2-(3-fluorophenyl)-N-(1-hydroxy-3-methylbutan-2-yl)-6-(4-methylphenyl)-3-oxo-2,3-dihydropyridazine-4-carboxamide;

2-(3-fluorophenyl)-N-[(2S)-1-hydroxy-3-methylbutan-2-yl]-6-(4-methylphenyl)-3-oxo-2,3-dihydropyridazine-4-carboxamide;

2-(3-fluorophenyl)-N-[(2R)-1-hydroxy-3-methylbutan-2-yl]-6-(4-methylphenyl)-3-oxo-2,3-dihydropyridazine-4-carboxamide;

2-(3-fluorophenyl)-6-(4-methylphenyl)-3-oxo-N-(3,3,3-trifluoro-2-hydroxypropyl)-2,3-dihydropyridazine-4-carboxamide;

2-(3-fluorophenyl)-6-(4-methylphenyl)-3-oxo-N-[(2S)-3,3,3-trifluoro-2-hydroxypropyl]-2,3-dihydropyridazine-4-carboxamide;

2-(3-fluorophenyl)-6-(4-methylphenyl)-3-oxo-N-[(2R)-3,3,3-trifluoro-2-hydroxypropyl]-2,3-dihydropyridazine-4-carboxamide;

2-(3-fluorophenyl)-N-(1-hydroxypropan-2-yl)-6-(4-methylphenyl)-3-oxo-2,3-dihydropyridazine-4-carboxamide;

2-(3-fluorophenyl)-N-[(2S)-1-hydroxypropan-2-yl]-6-(4-methylphenyl)-3-oxo-2,3-dihydropyridazine-4-carboxamide;

2-(3-fluorophenyl)-N-[(2R)-1-hydroxypropan-2-yl]-6-(4-methylphenyl)-3-oxo-2,3-dihydropyridazine-4-carboxamide;

2-(3-fluorophenyl)-N-(2-hydroxy-3-methylbutyl)-6-(4-methylphenyl)-3-oxo-2,3-dihydropyridazine-4-carboxamide;

2-(3-fluorophenyl)-N-[(2S)-2-hydroxy-3-methylbutyl]-6-(4-methylphenyl)-3-oxo-2,3-dihydropyridazine-4-carboxamide;

2-(3-fluorophenyl)-N-[(2R)-2-hydroxy-3-methylbutyl]-6-(4-methylphenyl)-3-oxo-2,3-dihydropyridazine-4-carboxamide;

2-(3-fluorophenyl)-N-(2-hydroxypropyl)-6-(4-methylphenyl)-3-oxo-2,3-dihydropyridazine-4-carboxamide;

2-(3-fluorophenyl)-N-[(2S)-2-hydroxypropyl]-6-(4-methylphenyl)-3-oxo-2,3-dihydropyridazine-4-carboxamide;

2-(3-fluorophenyl)-N-[(2R)-2-hydroxypropyl]-6-(4-methylphenyl)-3-oxo-2,3-dihydropyridazine-4-carboxamide;

2-(3-fluorophenyl)-N-(2-hydroxy-3-methoxypropyl)-6-(4-methylphenyl)-3-oxo-2,3-dihydropyridazine-4-carboxamide;

2-(3-fluorophenyl)-N-[(2R)-2-hydroxy-3-methoxypropyl]-6-(4-methylphenyl)-3-oxo-2,3-dihydropyridazine-4-carboxamide;

2-(3-fluorophenyl)-N-[(2S)-2-hydroxy-3-methoxypropyl]-6-(4-methylphenyl)-3-oxo-2,3-dihydropyridazine-4-carboxamide;

2-(3-fluorophenyl)-N-(2-hydroxyethyl)-6-(4-methylphenyl)-3-oxo-2,3-dihydropyridazine-4-carboxamide;

6-(4-chlorophenyl)-2-(3-fluorophenyl)-N-[(2S)-1-hydroxy-3-methylbutan-2-yl]-3-oxo-2,3-dihydropyridazine-4-carboxamide;

6-(4-chlorophenyl)-2-(3-fluorophenyl)-N-[(2S)-1-hydroxybutan-2-yl]-3-oxo-2,3-dihydropyridazine-4-carboxamide;

6-(4-chlorophenyl)-2-(3-fluorophenyl)-N-(1-hydroxypropan-2-yl)-3-oxo-2,3-dihydropyridazine-4-carboxamide;

6-(4-chlorophenyl)-2-(3-fluorophenyl)-N-[(2S)-1-hydroxypropan-2-yl]-3-oxo-2,3-dihydropyridazine-4-carboxamide;

6-(4-chlorophenyl)-2-(3-fluorophenyl)-N-[(2R)-1-hydroxypropan-2-yl]-3-oxo-2,3-dihydropyridazine-4-carboxamide;

6-(4-chlorophenyl)-2-(3-fluorophenyl)-3-oxo-N-(3,3,3-trifluoro-2-hydroxypropyl)-2,3-dihydropyridazine-4-carboxamide;

6-(4-chlorophenyl)-2-(3-fluorophenyl)-3-oxo-N-[(2S)-3,3,3-trifluoro-2-hydroxypropyl]-2,3-dihydropyridazine-4-carboxamide;

6-(4-chlorophenyl)-2-(3-fluorophenyl)-3-oxo-N-[(2R)-3,3,3-trifluoro-2-hydroxypropyl]-2,3-dihydropyridazine-4-carboxamide;

6-(4-chlorophenyl)-2-(3-fluorophenyl)-N-(2-hydroxy-3-methylbutyl)-3-oxo-2,3-dihydropyridazine-4-carboxamide;
6-(4-chlorophenyl)-2-(3-fluorophenyl)-N-[(2S)-2-hydroxy-3-methylbutyl]-3-oxo-2,3-dihydropyridazine-4-carboxamide;
6-(4-chlorophenyl)-2-(3-fluorophenyl)-N-[(2R)-2-hydroxy-3-methylbutyl]-3-oxo-2,3-dihydropyridazine-4-carboxamide;
6-(4-chlorophenyl)-2-(3-fluorophenyl)-N-(2-hydroxy-3-methoxypropyl)-3-oxo-2,3-dihydropyridazine-4-carboxamide;
6-(4-chlorophenyl)-2-(3-fluorophenyl)-N-[(2S)-2-hydroxy-3-methoxypropyl]-3-oxo-2,3-dihydropyridazine-4-carboxamide;
6-(4-chlorophenyl)-2-(3-fluorophenyl)-N-[(2R)-2-hydroxy-3-methoxypropyl]-3-oxo-2,3-dihydropyridazine-4-carboxamide;
6-(4-chlorophenyl)-2-(3-fluorophenyl)-N-(2-hydroxypropyl)-3-oxo-2,3-dihydropyridazine-4-carboxamide;
6-(4-chlorophenyl)-2-(3-fluorophenyl)-N-[(2R)-2-hydroxypropyl]-3-oxo-2,3-dihydropyridazine-4-carboxamide;
6-(4-chlorophenyl)-2-(3-fluorophenyl)-N-[(2S)-2-hydroxypropyl]-3-oxo-2,3-dihydropyridazine-4-carboxamide;
6-(4-chlorophenyl)-2-(3-fluorophenyl)-N-[(2S)-1-hydroxy-4-methylpentan-2-yl]-3-oxo-2,3-dihydropyridazine-4-carboxamide;
6-(4-chlorophenyl)-2-(3-fluorophenyl)-N-[2-hydroxy-1-(-tetrahydrofuran-3-yl)ethyl]-3-oxo-2,3-dihydropyridazine-4-carboxamide;
6-(4-chlorophenyl)-2-(3-fluorophenyl)-N-{(1S)-2-hydroxy-1-[(3R)-tetrahydrofuran-3-yl]ethyl}-3-oxo-2,3-dihydropyridazine-4-carboxamide;
6-(4-chlorophenyl)-2-(3-fluorophenyl)-N-{(1S)-2-hydroxy-1-[(3S)-tetrahydrofuran-3-yl]ethyl}-3-oxo-2,3-dihydropyridazine-4-carboxamide;
6-(4-chlorophenyl)-2-(3-fluorophenyl)-N-{(1R)-2-hydroxy-1-[(3R)-tetrahydrofuran-3-yl]ethyl}-3-oxo-2,3-dihydropyridazine-4-carboxamide;
6-(4-chlorophenyl)-2-(3-fluorophenyl)-N-{(1R)-2-hydroxy-1-[(3S)-tetrahydrofuran-3-yl]ethyl}-3-oxo-2,3-dihydropyridazine-4-carboxamide;
6-(4-chlorophenyl)-2-(3,5-difluorophenyl)-N-[(2S)-1-hydroxy-3-methylbutan-2-yl]-3-oxo-2,3-dihydropyridazine-4-carboxamide;
6-(4-chlorophenyl)-2-(3,5-difluorophenyl)-3-oxo-N-(3,3,3-trifluoro-2-hydroxypropyl)-2,3-dihydropyridazine-4-carboxamide;
6-(4-chlorophenyl)-2-(3,5-difluorophenyl)-3-oxo-N-[(2S)-3,3,3-trifluoro-2-hydroxypropyl]-2,3-dihydropyridazine-4-carboxamide;
6-(4-chlorophenyl)-2-(3,5-difluorophenyl)-3-oxo-N-[(2R)-3,3,3-trifluoro-2-hydroxypropyl]-2,3-dihydropyridazine-4-carboxamide;
6-(4-chlorophenyl)-2-(3,5-difluorophenyl)-N-[(2S)-1-hydroxypropan-2-yl]-3-oxo-2,3-dihydropyridazine-4-carboxamide;
6-(4-chlorophenyl)-2-(3,5-difluorophenyl)-N-(2-hydroxy-3-methylbutyl)-3-oxo-2,3-dihydropyridazine-4-carboxamide;
6-(4-chlorophenyl)-2-(3,5-difluorophenyl)-N-[(2S)-2-hydroxy-3-methylbutyl]-3-oxo-2,3-dihydropyridazine-4-carboxamide;
6-(4-chlorophenyl)-2-(3,5-difluorophenyl)-N-[(2R)-2-hydroxy-3-methylbutyl]-3-oxo-2,3-dihydropyridazine-4-carboxamide;
2-(3,5-difluorophenyl)-N-[(2S)-1-hydroxy-3-methylbutan-2-yl]-6-(4-methylphenyl)-3-oxo-2,3-dihydropyridazine-4-carboxamide;
2-(3,5-difluorophenyl)-6-(4-methylphenyl)-3-oxo-N-(3,3,3-trifluoro-2-hydroxypropyl)-2,3-dihydropyridazine-4-carboxamide;
2-(3,5-difluorophenyl)-6-(4-methylphenyl)-3-oxo-N-[(2S)-3,3,3-trifluoro-2-hydroxypropyl]-2,3-dihydropyridazine-4-carboxamide;
2-(3,5-difluorophenyl)-6-(4-methylphenyl)-3-oxo-N-[(2R)-3,3,3-trifluoro-2-hydroxypropyl]-2,3-dihydropyridazine-4-carboxamide;
2-(3,5-difluorophenyl)-N-[(2S)-1-hydroxypropan-2-yl]-6-(4-methylphenyl)-3-oxo-2,3-dihydropyridazine-4-carboxamide;
2-(3,5-difluorophenyl)-N-(2-hydroxy-3-methylbutyl)-6-(4-methylphenyl)-3-oxo-2,3-dihydropyridazine-4-carboxamide;
2-(3,5-difluorophenyl)-N-[(2S)-2-hydroxy-3-methylbutyl]-6-(4-methylphenyl)-3-oxo-2,3-dihydropyridazine-4-carboxamide;
2-(3,5-difluorophenyl)-N-[(2R)-2-hydroxy-3-methylbutyl]-6-(4-methylphenyl)-3-oxo-2,3-dihydropyridazine-4-carboxamide;
2-(3-chlorophenyl)-6-(4-chlorophenyl)-N-[(2S)-1-hydroxy-3-methylbutan-2-yl]-3-oxo-2,3-dihydropyridazine-4-carboxamide;
2-(3-chlorophenyl)-6-(4-chlorophenyl)-N-[(2S)-1-hydroxybutan-2-yl]-3-oxo-2,3-dihydropyridazine-4-carboxamide;
2-(3-chlorophenyl)-6-(4-chlorophenyl)-N-[(2S)-1-hydroxy-4-methylpentan-2-yl]-3-oxo-2,3-dihydropyridazine-4-carboxamide;
2-(3-chlorophenyl)-6-(4-chlorophenyl)-3-oxo-N-(3,3,3-trifluoro-2-hydroxypropyl)-2,3-dihydropyridazine-4-carboxamide;
2-(3-chlorophenyl)-6-(4-chlorophenyl)-3-oxo-N-[(2S)-3,3,3-trifluoro-2-hydroxypropyl]-2,3-dihydropyridazine-4-carboxamide;
2-(3-chlorophenyl)-6-(4-chlorophenyl)-3-oxo-N-[(2R)-3,3,3-trifluoro-2-hydroxypropyl]-2,3-dihydropyridazine-4-carboxamide;
2-(3-chlorophenyl)-6-(4-chlorophenyl)-N-(1-hydroxypropan-2-yl)-3-oxo-2,3-dihydropyridazine-4-carboxamide;
2-(3-chlorophenyl)-6-(4-chlorophenyl)-N-[(2S)-1-hydroxypropan-2-yl]-3-oxo-2,3-dihydropyridazine-4-carboxamide;
2-(3-chlorophenyl)-6-(4-chlorophenyl)-N-(2-hydroxy-3-methylbutyl)-3-oxo-2,3-dihydropyridazine-4-carboxamide;
2-(3-chlorophenyl)-6-(4-chlorophenyl)-N-[(2S)-2-hydroxy-3-methylbutyl]-3-oxo-2,3-dihydropyridazine-4-carboxamide;
2-(3-chlorophenyl)-6-(4-chlorophenyl)-N-[(2R)-2-hydroxy-3-methylbutyl]-3-oxo-2,3-dihydropyridazine-4-carboxamide;
N-(1-hydroxy-3-methylbutan-2-yl)-6-(4-methylphenyl)-3-oxo-2-phenyl-2,3-dihydropyridazine-4-carboxamide;
N-[(2S)-1-hydroxy-3-methylbutan-2-yl]-6-(4-methylphenyl)-3-oxo-2-phenyl-2,3-dihydropyridazine-4-carboxamide;

N-[(2R)-1-hydroxy-3-methylbutan-2-yl]-6-(4-methylphenyl)-3-oxo-2-phenyl-2,3-dihydropyridazine-4-carboxamide;
N-(1-hydroxypropan-2-yl)-6-(4-methylphenyl)-3-oxo-2-phenyl-2,3-dihydropyridazine-4-carboxamide;
N-(2-hydroxyethyl)-6-(4-methylphenyl)-3-oxo-2-phenyl-2,3-dihydropyridazine-4-carboxamide;
6-(4-chlorophenyl)-N-[(2S)-1-hydroxy-3-methylbutan-2-yl]-3-oxo-2-phenyl-2,3-dihydropyridazine-4-carboxamide;
6-(4-chlorophenyl)-3-oxo-2-phenyl-N-(3,3,3-trifluoro-2-hydroxypropyl)-2,3-dihydropyridazine-4-carboxamide;
6-(4-chlorophenyl)-3-oxo-2-phenyl-N-[(2S)-3,3,3-trifluoro-2-hydroxypropyl]-2,3-dihydropyridazine-4-carboxamide;
6-(4-chlorophenyl)-3-oxo-2-phenyl-N-[(2R)-3,3,3-trifluoro-2-hydroxypropyl]-2,3-dihydropyridazine-4-carboxamide;
6-(4-chlorophenyl)-N-(1-hydroxypropan-2-yl)-3-oxo-2-phenyl-2,3-dihydropyridazine-4-carboxamide;
6-(4-chlorophenyl)-N-[(2S)-1-hydroxypropan-2-yl]-3-oxo-2-phenyl-2,3-dihydropyridazine-4-carboxamide;
6-(4-chlorophenyl)-N-[(2R)-1-hydroxypropan-2-yl]-3-oxo-2-phenyl-2,3-dihydropyridazine-4-carboxamide;
6-(3,4-dimethylphenyl)-2-(3-fluorophenyl)-N-(1-hydroxy-3-methylbutan-2-yl)-3-oxo-2,3-dihydropyridazine-4-carboxamide;
6-(3,4-dimethylphenyl)-2-(3-fluorophenyl)-N-[(2S)-1-hydroxy-3-methylbutan-2-yl]-3-oxo-2,3-dihydropyridazine-4-carboxamide;
6-(3,4-dimethylphenyl)-2-(3-fluorophenyl)-N-[(2R)-1-hydroxy-3-methylbutan-2-yl]-3-oxo-2,3-dihydropyridazine-4-carboxamide;
6-(3,4-dimethylphenyl)-2-(3-fluorophenyl)-N-(1-hydroxybutan-2-yl)-3-oxo-2,3-dihydropyridazine-4-carboxamide;
6-(3,4-dimethylphenyl)-2-(3-fluorophenyl)-N-[(2S)-1-hydroxybutan-2-yl]-3-oxo-2,3-dihydropyridazine-4-carboxamide;
6-(3,4-dimethylphenyl)-2-(3-fluorophenyl)-N-[(2R)-1-hydroxybutan-2-yl]-3-oxo-2,3-dihydropyridazine-4-carboxamide;
6-(3,4-dimethylphenyl)-2-(3-fluorophenyl)-N-(1-hydroxypropan-2-yl)-3-oxo-2,3-dihydropyridazine-4-carboxamide;
6-(3,4-dimethylphenyl)-2-(3-fluorophenyl)-N-[(2S)-1-hydroxypropan-2-yl]-3-oxo-2,3-dihydropyridazine-4-carboxamide;
6-(3,4-dimethylphenyl)-2-(3-fluorophenyl)-N-[(2R)-1-hydroxypropan-2-yl]-3-oxo-2,3-dihydropyridazine-4-carboxamide;
6-[4-(difluoromethyl)phenyl]-2-(3-fluorophenyl)-N-[(2S)-1-hydroxy-3-methylbutan-2-yl]-3-oxo-2,3-dihydropyridazine-4-carboxamide;
6-[4-(difluoromethyl)phenyl]-2-(3-fluorophenyl)-N-[(2S)-1-hydroxybutan-2-yl]-3-oxo-2,3-dihydropyridazine-4-carboxamide;
6-[4-(difluoromethyl)phenyl]-2-(3-fluorophenyl)-N-[(2S)-1-hydroxypropan-2-yl]-3-oxo-2,3-dihydropyridazine-4-carboxamide;
6-[4-(difluoromethyl)phenyl]-2-(3-fluorophenyl)-3-oxo-N-(3,3,3-trifluoro-2-hydroxypropyl)-2,3-dihydropyridazine-4-carboxamide;
6-[4-(difluoromethyl)phenyl]-2-(3-fluorophenyl)-3-oxo-N-[(2S)-3,3,3-trifluoro-2-hydroxypropyl]-2,3-dihydropyridazine-4-carboxamide;
6-[4-(difluoromethyl)phenyl]-2-(3-fluorophenyl)-3-oxo-N-[(2R)-3,3,3-trifluoro-2-hydroxypropyl]-2,3-dihydropyridazine-4-carboxamide;
6-(4-chlorophenyl)-2-(3-fluorophenyl)-3-oxo-N-(1,1,1-trifluoro-3-hydroxypropan-2-yl)-2,3-dihydropyridazine-4-carboxamide;
6-(4-chlorophenyl)-2-(3-fluorophenyl)-3-oxo-N-[(2S)-1,1,1-trifluoro-3-hydroxypropan-2-yl]-2,3-dihydropyridazine-4-carboxamide;
6-(4-chlorophenyl)-2-(3-fluorophenyl)-3-oxo-N-[(2R)-1,1,1-trifluoro-3-hydroxypropan-2-yl]-2,3-dihydropyridazine-4-carboxamide;
2-(3-fluorophenyl)-6-(4-methoxyphenyl)-3-oxo-N-(1,1,1-trifluoro-3-hydroxypropan-2-yl)-2,3-dihydropyridazine-4-carboxamide;
2-(3-fluorophenyl)-6-(4-methoxyphenyl)-3-oxo-N-[(2S)-1,1,1-trifluoro-3-hydroxypropan-2-yl]-2,3-dihydropyridazine-4-carboxamide;
2-(3-fluorophenyl)-6-(4-methoxyphenyl)-3-oxo-N-[(2R)-1,1,1-trifluoro-3-hydroxypropan-2-yl]-2,3-dihydropyridazine-4-carboxamide;
6-(4-chlorophenyl)-2-(3-fluorophenyl)-N-(cis-2-hydroxycyclohexyl)-3-oxo-2,3-dihydropyridazine-4-carboxamide;
6-(4-chlorophenyl)-2-(3-fluorophenyl)-N-[(1R,2S)-2-hydroxycyclohexyl]-3-oxo-2,3-dihydropyridazine-4-carboxamide;
6-(4-chlorophenyl)-2-(3-fluorophenyl)-N-[(1S,2R)-2-hydroxycyclohexyl]-3-oxo-2,3-dihydropyridazine-4-carboxamide;
2-(3-fluorophenyl)-N-(cis-2-hydroxycyclohexyl)-6-(4-methoxyphenyl)-3-oxo-2,3-dihydropyridazine-4-carboxamide;
2-(3-fluorophenyl)-N-[(1R,2S)-2-hydroxycyclohexyl]-6-(4-methoxyphenyl)-3-oxo-2,3-dihydropyridazine-4-carboxamide;
2-(3-fluorophenyl)-N-[(1S,2R)-2-hydroxycyclohexyl]-6-(4-methoxyphenyl)-3-oxo-2,3-dihydropyridazine-4-carboxamide;
6-(4-chlorophenyl)-2-(3-fluorophenyl)-N-(cis-2-hydroxycyclopentyl)-3-oxo-2,3-dihydropyridazine-4-carboxamide;
6-[4-(difluoromethoxy)phenyl]-2-(3-fluorophenyl)-N-[(2S)-1-hydroxy-3-methylbutan-2-yl]-3-oxo-2,3-dihydropyridazine-4-carboxamide;
6-(4-chlorophenyl)-2-(3-fluorophenyl)-N-[(1S,2R)-2-hydroxycyclopentyl]-3-oxo-2,3-dihydropyridazine-4-carboxamide;
6-(4-chlorophenyl)-2-(3-fluorophenyl)-N-[(1S,2S)-2-methylcyclohexyl]-3-oxo-2,3-dihydropyridazine-4-carboxamide;
2-(3-fluorophenyl)-N-[(2S)-1-hydroxy-3-methylbutan-2-yl]-6-(4-methoxyphenyl)-3-oxo-2,3-dihydropyridazine-4-carboxamide;
6-(4-chlorophenyl)-2-(3-fluorophenyl)-N-[(2S,3S)-3-hydroxybutan-2-yl]-3-oxo-2,3-dihydropyridazine-4-carboxamide;
6-(4-chlorophenyl)-2-(3-fluorophenyl)-N-[(1S,2S)-2-hydroxycyclopentyl]-3-oxo-2,3-dihydropyridazine-4-carboxamide;
2-(3-fluorophenyl)-N-[(2S,3S)-3-hydroxybutan-2-yl]-6-(4-methoxyphenyl)-3-oxo-2,3-dihydropyridazine-4-carboxamide;
6-(4-chlorophenyl)-2-(3-fluorophenyl)-N-(trans-2-hydroxycyclohexyl)-3-oxo-2,3-dihydropyridazine-4-carboxamide;

6-(4-chlorophenyl)-2-(3-fluorophenyl)-N-[(1S,2S)-2-hydroxycyclohexyl]-3-oxo-2,3-dihydropyridazine-4-carboxamide;
6-(4-chlorophenyl)-2-(3-fluorophenyl)-N-[(1R,2R)-2-hydroxycyclohexyl]-3-oxo-2,3-dihydropyridazine-4-carboxamide;
6-[4-(difluoromethoxy)phenyl]-2-(3-fluorophenyl)-3-oxo-N-(3,3,3-trifluoro-2-hydroxypropyl)-2,3-dihydropyridazine-4-carboxamide;
6-[4-(difluoromethoxy)phenyl]-2-(3-fluorophenyl)-3-oxo-N-[(2R)-3,3,3-trifluoro-2-hydroxypropyl]-2,3-dihydropyridazine-4-carboxamide;
6-[4-(difluoromethoxy)phenyl]-2-(3-fluorophenyl)-3-oxo-N-[(2S)-3,3,3-trifluoro-2-hydroxypropyl]-2,3-dihydropyridazine-4-carboxamide;
6-(4-chlorophenyl)-2-(3-fluorophenyl)-N-(trans-2-hydroxycyclopentyl)-3-oxo-2,3-dihydropyridazine-4-carboxamide;
6-(4-chlorophenyl)-2-(3-fluorophenyl)-N-[(1R,2R)-2-hydroxycyclopentyl]-3-oxo-2,3-dihydropyridazine-4-carboxamide;
6-(4-chlorophenyl)-2-(3-fluorophenyl)-N-[(1S,2S)-2-hydroxycyclopentyl]-3-oxo-2,3-dihydropyridazine-4-carboxamide;
2-(3-fluorophenyl)-6-(4-methoxyphenyl)-3-oxo-N-(3,3,3-trifluoro-2-hydroxypropyl)-2,3-dihydropyridazine-4-carboxamide;
2-(3-fluorophenyl)-6-(4-methoxyphenyl)-3-oxo-N-[(2R)-3,3,3-trifluoro-2-hydroxypropyl]-2,3-dihydropyridazine-4-carboxamide;
2-(3-fluorophenyl)-6-(4-methoxyphenyl)-3-oxo-N-[(2S)-3,3,3-trifluoro-2-hydroxypropyl]-2,3-dihydropyridazine-4-carboxamide;
6-(4-chlorophenyl)-2-(3-fluorophenyl)-N-[(1-hydroxycyclohexyl)methyl]-3-oxo-2,3-dihydropyridazine-4-carboxamide;
6-[4-(difluoromethoxy)phenyl]-2-(3-fluorophenyl)-N-(cis-2-hydroxycyclohexyl)-3-oxo-2,3-dihydropyridazine-4-carboxamide;
6-(4-chlorophenyl)-2-(3-fluorophenyl)-N-(3-hydroxybutan-2-yl)-3-oxo-2,3-dihydropyridazine-4-carboxamide;
6-(4-chlorophenyl)-N-[(2S,3S)-1,3-dihydroxybutan-2-yl]-2-(3-fluorophenyl)-3-oxo-2,3-dihydropyridazine-4-carboxamide;
6-(4-Chlorophenyl)-2-(3-fluorophenyl)-N-[(1R,2S)-2-hydroxycyclopentyl]-3-oxo-2,3-dihydropyridazine-4-carboxamide;
6-[4-(difluoromethoxy)phenyl]-2-(3-fluorophenyl)-N-[(2S)-1-hydroxybutan-2-yl]-3-oxo-2,3-dihydropyridazine-4-carboxamide;
2-(3-fluorophenyl)-N-(3-hydroxybutan-2-yl)-6-(4-methoxyphenyl)-3-oxo-2,3-dihydropyridazine-4-carboxamide;
2-(3-fluorophenyl)-N-[(1R,2S)-2-hydroxycyclopentyl]-6-(4-methoxyphenyl)-3-oxo-2,3-dihydropyridazine-4-carboxamide;
6-[4-(difluoromethoxy)phenyl]-2-(3-fluorophenyl)-N-(3-hydroxybutan-2-yl)-3-oxo-2,3-dihydropyridazine-4-carboxamide;
6-[4-(difluoromethoxy)phenyl]-2-(3-fluorophenyl)-N-[(2S,3S)-3-hydroxybutan-2-yl]-3-oxo-2,3-dihydropyridazine-4-carboxamide;
6-[4-(difluoromethoxy)phenyl]-2-(3-fluorophenyl)-N-[(2R,3R)-3-hydroxybutan-2-yl]-3-oxo-2,3-dihydropyridazine-4-carboxamide;
6-[4-(difluoromethoxy)phenyl]-2-(3-fluorophenyl)-N-[(2S,3R)-3-hydroxybutan-2-yl]-3-oxo-2,3-dihydropyridazine-4-carboxamide;
6-[4-(difluoromethoxy)phenyl]-2-(3-fluorophenyl)-N-[(2R,3S)-3-hydroxybutan-2-yl]-3-oxo-2,3-dihydropyridazine-4-carboxamide;
6-[4-(difluoromethoxy)phenyl]-2-(3-fluorophenyl)-N-{(2-hydroxy-1-tetrahydrofuran-3-yl)ethyl}-3-oxo-2,3-dihydropyridazine-4-carboxamide;
6-[4-(difluoromethoxy)phenyl]-2-(3-fluorophenyl)-N-{(1R)-2-hydroxy-1-[(3S)-tetrahydrofuran-3-yl]ethyl}-3-oxo-2,3-dihydropyridazine-4-carboxamide;
6-[4-(difluoromethoxy)phenyl]-2-(3-fluorophenyl)-N-{(1R)-2-hydroxy-1-[(3R)-tetrahydrofuran-3-yl]ethyl}-3-oxo-2,3-dihydropyridazine-4-carboxamide;
6-[4-(difluoromethoxy)phenyl]-2-(3-fluorophenyl)-N-{(1S)-2-hydroxy-1-[(3R)-tetrahydrofuran-3-yl]ethyl}-3-oxo-2,3-dihydropyridazine-4-carboxamide;
6-[4-(difluoromethoxy)phenyl]-2-(3-fluorophenyl)-N-{(1S)-2-hydroxy-1-[(3S)-tetrahydrofuran-3-yl]ethyl}-3-oxo-2,3-dihydropyridazine-4-carboxamide;
6-(4-chlorophenyl)-2-(3-fluorophenyl)-N-[2-hydroxy-1-(tetrahydro-2H-pyran-4-yl)ethyl]-3-oxo-2,3-dihydropyridazine-4-carboxamide;
6-(4-chlorophenyl)-2-(3-fluorophenyl)-N-[(1R)-2-hydroxy-1-(tetrahydro-2H-pyran-4-yl)ethyl]-3-oxo-2,3-dihydropyridazine-4-carboxamide;
6-(4-chlorophenyl)-2-(3-fluorophenyl)-N-[(1S)-2-hydroxy-1-(tetrahydro-2H-pyran-4-yl)ethyl]-3-oxo-2,3-dihydropyridazine-4-carboxamide;
2-(3-fluorophenyl)-N-trans-2-hydroxycyclohexyl-6-(4-methoxyphenyl)-3-oxo-2,3-dihydropyridazine-4-carboxamide;
2-(3-fluorophenyl)-N-(trans-2-hydroxycyclopentyl)-6-(4-methoxyphenyl)-3-oxo-2,3-dihydropyridazine-4-carboxamide;
6-[4-(difluoromethoxy)phenyl]-2-(3-fluorophenyl)-N-[(2S)-1-hydroxypropan-2-yl]-3-oxo-2,3-dihydropyridazine-4-carboxamide;
6-(4-chlorophenyl)-N-[(2S)-2,3-dihydroxypropyl]-2-(3-fluorophenyl)-3-oxo-2,3-dihydropyridazine-4-carboxamide;
6-(4-chlorophenyl)-N-[(1S)-1-cyclopentyl-2-hydroxyethyl]-2-(3-fluorophenyl)-3-oxo-2,3-dihydropyridazine-4-carboxamide;
2-(3-fluorophenyl)-N-{(2-hydroxy-1-[tetrahydrofuran-3-yl]ethyl}-6-(4-methoxyphenyl)-3-oxo-2,3-dihydropyridazine-4-carboxamide;
6-(4-chlorophenyl)-N-[(2R)-2,3-dihydroxypropyl]-2-(3-fluorophenyl)-3-oxo-2,3-dihydropyridazine-4-carboxamide;
6-[4-(difluoromethoxy)phenyl]-2-(3-fluorophenyl)-N-(2-hydroxy-3-methoxypropyl)-3-oxo-2,3-dihydropyridazine-4-carboxamide;
6-(4-chlorphenyl)-2-(3-fluorophenyl)-N-[(2R)-1-hydroxy-3-(1H-imidazol-5-yl)propan-2-yl]-3-oxo-2,3-dihydropyridazine-4-carboxamide;
6-(4-chlorophenyl)-2-(3-fluorophenyl)-N-(1-hydroxy-2-methylpropan-2-yl)-3-oxo-2,3-dihydropyridazine-4-carboxamide;
6-(4-chlorophenyl)-2-(3-fluorophenyl)-N-[1-hydroxymethyl)cyclopropyl]-3-oxo-2,3-dihydropyridazine-4-carboxamide;
6-(4-chlorophenyl)-2-(3-fluorophenyl)-N-(2-hydroxy-2-methylpropyl)-3-oxo-2,3-dihydropyridazine-4-carboxamide;

6-(4-chlorophenyl)-2-(3-fluorophenyl)-N-(3-hydroxypropyl)-3-oxo-2,3-dihydropyridazine-4-carboxamide;

6-(4-chlorophenyl)-N-(2-cyclopropyl-2-hydroxyethyl)-2-(3-fluorophenyl)-3-oxo-2,3-dihydropyridazine-4-carboxamide;

6-(4-chlorophenyl)-N-[(2R)-2-cyclopropyl-2-hydroxyethyl]-2-(3-fluorophenyl)-3-oxo-2,3-dihydropyridazine-4-carboxamide;

6-(4-chlorophenyl)-N-[(2S)-2-cyclopropyl-2-hydroxyethyl]-2-(3-fluorophenyl)-3-oxo-2,3-dihydropyridazine-4-carboxamide;

6-(4-chlorophenyl)-N-(1-cyclopropyl-2-hydroxyethyl)-2-(3-fluorophenyl)-3-oxo-2,3-dihydropyridazine-4-carboxamide;

6-(4-chlorophenyl)-N-[(1R)-1-cyclopropyl-2-hydroxyethyl]-2-(3-fluorophenyl)-3-oxo-2,3-dihydropyridazine-4-carboxamide;

6-(4-chlorophenyl)-N-[(1S)-1-cyclopropyl-2-hydroxyethyl]-2-(3-fluorophenyl)-3-oxo-2,3-dihydropyridazine-4-carboxamide;

6-(4-chlorophenyl)-2-(3-fluorophenyl)-N-[(1-hydroxycyclopropyl)methyl]-3-oxo-2,3-dihydropyridazine-4-carboxamide;

6-(4-chlorophenyl)-2-(3-fluorophenyl)-3-oxo-N-(1,1,1-trifluoro-3-hydroxybutan-2-yl)-2,3-dihydropyridazine-4-carboxamide;

6-(4-chlorophenyl)-2-(3-fluorophenyl)-3-oxo-N-[(2R,3R)-1,1,1-trifluoro-3-hydroxybutan-2-yl]-2,3-dihydropyridazine-4-carboxamide;

6-(4-chlorophenyl)-2-(3-fluorophenyl)-3-oxo-N-[(2R,3S)-1,1,1-trifluoro-3-hydroxybutan-2-yl]-2,3-dihydropyridazine-4-carboxamide;

6-(4-chlorophenyl)-2-(3-fluorophenyl)-3-oxo-N-[(2S,3R)-1,1,1-trifluoro-3-hydroxybutan-2-yl]-2,3-dihydropyridazine-4-carboxamide;

6-(4-chlorophenyl)-2-(3-fluorophenyl)-3-oxo-N-[(2S,3S)-1,1,1-trifluoro-3-hydroxybutan-2-yl]-2,3-dihydropyridazine-4-carboxamide;

6-(4-Chlorophenyl)-2-(3-fluorophenyl)-N-(3-hydroxy-2-methylpropyl)-3-oxo-2,3-dihydropyridazine-4-carboxamide;

6-(4-chlorophenyl)-2-(3-fluorophenyl)-N-[(2R)-3-hydroxy-2-methylpropyl]-3-oxo-2,3-dihydropyridazine-4-carboxamide;

6-(4-chlorophenyl)-2-(3-fluorophenyl)-N-[(2S)-3-hydroxy-2-methylpropyl]-3-oxo-2,3-dihydropyridazine-4-carboxamide;

6-(4-chlorophenyl)-2-(3-fluorophenyl)-N-[(3R)-3-hydroxybutyl]-3-oxo-2,3-dihydropyridazine-4-carboxamide;

6-(4-chlorophenyl)-2-(3-fluorophenyl)-N-[(3S)-3-hydroxybutyl]-3-oxo-2,3-dihydropyridazine-4-carboxamide;

6-(4-chlorophenyl)-2-(3-fluorophenyl)-N-(4-hydroxybutan-2-yl)-3-oxo-2,3-dihydropyridazine-4-carboxamide;

6-(4-chlorophenyl)-2-(3-fluorophenyl)-N-[(2R)-4-hydroxybutan-2-yl]-3-oxo-2,3-dihydropyridazine-4-carboxamide;

6-(4-chlorophenyl)-2-(3-fluorophenyl)-N-[(2S)-4-hydroxybutan-2-yl]-3-oxo-2,3-dihydropyridazine-4-carboxamide;

6-(4-chlorophenyl)-N-(1-cyclobutyl-2-hydroxyethyl)-2-(3-fluorophenyl)-3-oxo-2,3-dihydropyridazine-4-carboxamide;

6-(4-chlorophenyl)-N-[(1R)-1-cyclobutyl-2-hydroxyethyl]-2-(3-fluorophenyl)-3-oxo-2,3-dihydropyridazine-4-carboxamide;

6-(4-hlorophenyl)-N-[(1S)-1-cyclobutyl-2-hydroxyethyl]-2-(3-fluorophenyl)-3-oxo-2,3-dihydropyridazine-4-carboxamide;

6-(4-chlorophenyl)-2-(3-fluorophenyl)-N-[(1-hydroxycyclobutyl)methyl]-3-oxo-2,3-dihydropyridazine-4-carboxamide;

6-(4-chlorophenyl)-2-(3-fluorophenyl)-N-[1-(hydroxymethyl)cyclobutyl]-3-oxo-2,3-dihydropyridazine-4-carboxamide;

6-(4-chlorophenyl)-2-(3-fluorophenyl)-N-[1-(hydroxymethyl)cyclopentyl]-3-oxo-2,3-dihydropyridazine-4-carboxamide;

6-(4-chlorophenyl)-2-(3-fluorophenyl)-N-[1-(hydroxymethyl)cyclohexyl]-3-oxo-2,3-dihydropyridazine-4-carboxamide;

6-(4-chlorophenyl)-2-(3-fluorophenyl)-3-oxo-N-(4,4,4-trifluoro-3-hydroxybutan-2-yl)-2,3-dihydropyridazine-4-carboxamide;

6-(4-chlorophenyl)-2-(3-fluorophenyl)-3-oxo-N-[(2R,3R)-4,4,4-trifluoro-3-hydroxybutan-2-yl]-2,3-dihydropyridazine-4-carboxamide;

6-(4-chlorophenyl)-2-(3-fluorophenyl)-3-oxo-N-[(2S,3R)-4,4,4-trifluoro-3-hydroxybutan-2-yl]-2,3-dihydropyridazine-4-carboxamide;

6-(4-chlorophenyl)-2-(3-fluorophenyl)-3-oxo-N-[(2R,3S)-4,4,4-trifluoro-3-hydroxybutan-2-yl]-2,3-dihydropyridazine-4-carboxamide;

6-(4-chlorophenyl)-2-(3-fluorophenyl)-3-oxo-N-[(2S,3S)-4,4,4-trifluoro-3-hydroxybutan-2-yl]-2,3-dihydropyridazine-4-carboxamide;

6-(4-chlorophenyl)-N-(3,3-difluoro-2-hydroxypropyl)-2-(3-fluorophenyl)-3-oxo-2,3-dihydropyridazine-4-carboxamide;

6-(4-chlorophenyl)-N-[(2R)-3,3-difluoro-2-hydroxypropyl]-2-(3-fluorophenyl)-3-oxo-2,3-dihydropyridazine-4-carboxamide;

6-(4-chlorophenyl)-N-[(2S)-3,3-difluoro-2-hydroxypropyl]-2-(3-fluorophenyl)-3-oxo-2,3-dihydropyridazine-4-carboxamide;

6-(4-chlorophenyl)-N-(1,4-dihydroxybutan-2-yl)-2-(3-fluorophenyl)-3-oxo-2,3-dihydropyridazine-4-carboxamide;

6-(4-chlorophenyl)-N-[(2R)-1,4-dihydroxybutan-2-yl]-2-(3-fluorophenyl)-3-oxo-2,3-dihydropyridazine-4-carboxamide;

6-(4-chlorophenyl)-N-[(2S)-1,4-dihydroxybutan-2-yl]-2-(3-fluorophenyl)-3-oxo-2,3-dihydropyridazine-4-carboxamide;

6-(4-chlorophenyl)-2-(3-fluorophenyl)-N-(3-hydroxybutyl)-3-oxo-2,3-dihydropyridazine-4-carboxamide;

6-(4-chlorophenyl)-N-(1,3-dihydroxypropan-2-yl)-2-(3-fluorophenyl)-3-oxo-2,3-dihydropyridazine-4-carboxamide;

6-(4-chlorophenyl)-2-(3-fluorophenyl)-N-[(2S)-1-hydroxy-3-methoxypropan-2-yl]-3-oxo-2,3-dihydropyridazine-4-carboxamide;

1,4-anhydro-5-({[6-(4-chlorophenyl)-2-(3-fluorophenyl)-3-oxo-2,3-dihydropyridazin-4-yl]carbonyl}amino)-2,3,5-trideoxyhexitol;

1,4-anhydro-5-({[6-(4-chlorophenyl)-2-(3-fluorophenyl)-3-oxo-2,3-dihydropyridazin-4-yl]carbonyl}amino)-2,3,5-trideoxy-D-erythro-hexitol;

1,4-anhydro-5-({[6-(4-chlorophenyl)-2-(3-fluorophenyl)-3-oxo-2,3-dihydropyridazin-4-yl]carbonyl}amino)-2,3,5-trideoxy-D-threo-hexitol;

1,4-anhydro-5-({[6-(4-chlorophenyl)-2-(3-fluorophenyl)-3-oxo-2,3-dihydropyridazin-4-yl]carbonyl}amino)-2,3,5-trideoxy-L-threo-hexitol;

3,6-anhydro-2-({[6-(4-chlorophenyl)-2-(3-fluorophenyl)-3-oxo-2,3-dihydropyridazin-4-yl]carbonyl}amino)-2,4,5-trideoxy-D-erythro-hexitol;

6-(4-chlorophenyl)-2-(3-fluorophenyl)-N-[(2R,3R)-3-hydroxybutan-2-yl]-3-oxo-2,3-dihydropyridazine-4-carboxamide;

6-(4-chlorophenyl)-N-(2-cyclopentyl-2-hydroxyethyl)-2-(3-fluorophenyl)-3-oxo-2,3-dihydropyridazine-4-carboxamide;

6-(4-chlorophenyl)-N-(3-ethyl-2-hydroxypentyl)-2-(3-fluorophenyl)-3-oxo-2,3-dihydropyridazine-4-carboxamide;

N-(1-cyclopropyl-2-hydroxyethyl)-2-(3-fluorophenyl)-6-(4-methylphenyl)-3-oxo-2,3-dihydropyridazine-4-carboxamide;

2-(3-fluorophenyl)-N-[(2S)-1-hydroxypropan-2-yl]-3-oxo-6-[4-(trifluoromethyl)phenyl]-2,3-dihydropyridazine-4-carboxamide;

2-(3-fluorophenyl)-N-[(2R)-1-hydroxypropan-2-yl]-3-oxo-6-[4-(trifluoromethyl)phenyl]-2,3-dihydropyridazine-4-carboxamide;

2-(3-fluorophenyl)-N-[(2S)-1-hydroxy-3-methylbutan-2-yl]-3-oxo-6-[4-(trifluoromethyl)phenyl]-2,3-dihydropyridazine-4-carboxamide;

2-(3-fluorophenyl)-N-[(2R)-1-hydroxy-3-methylbutan-2-yl]-3-oxo-6-[4-(trifluoromethyl)phenyl]-2,3-dihydropyridazine-4-carboxamide;

2-(3-fluorophenyl)-N-(2-hydroxy-3-methylbutyl)-3-oxo-6-[4-(trifluoromethyl)phenyl]-2,3-dihydropyridazine-4-carboxamide;

2-(3-fluorophenyl)-3-oxo-N-3,3,3-trifluoro-2-hydroxypropyl)-6-[4-(trifluoromethyl)phenyl]-2,3-dihydropyridazine-4-carboxamide;

2-(3-fluorophenyl)-3-oxo-N-[(2R)-3,3,3-trifluoro-2-hydroxypropyl]-6-[4-(trifluoromethyl)phenyl]-2,3-dihydropyridazine-4-carboxamide;

2-(3-fluorophenyl)-3-oxo-N-[(2S)-3,3,3-trifluoro-2-hydroxypropyl]-6-[4-(trifluoromethyl)phenyl]-2,3-dihydropyridazine-4-carboxamide;

2-(3-fluorophenyl)-N-(3-hydroxy-2-methylpropyl)-3-oxo-6-[4-(trifluoromethyl)phenyl]-2,3-dihydropyridazine-4-carboxamide;

2-(3-fluorophenyl)-N-[(2S)-3-hydroxy-2-methylpropyl]-3-oxo-6-[4-(trifluoromethyl)phenyl]-2,3-dihydropyridazine-4-carboxamide;

2-(3-fluorophenyl)-N-[(2R)-3-hydroxy-2-methylpropyl]-3-oxo-6-[4-(trifluoromethyl)phenyl]-2,3-dihydropyridazine-4-carboxamide;

2-(3-fluorophenyl)-N-(3-hydroxybutyl)-3-oxo-6-[4-(trifluoromethyl)phenyl]-2,3-dihydropyridazine-4-carboxamide;

2-(3-fluorophenyl)-N-[(3S)-3-hydroxybutyl]-3-oxo-6-[4-(trifluoromethyl)phenyl]-2,3-dihydropyridazine-4-carboxamide;

2-(3-fluorophenyl)-N-[(3R)-3-hydroxybutyl]-3-oxo-6-[4-(trifluoromethyl)phenyl]-2,3-dihydropyridazine-4-carboxamide;

2-(3-fluorophenyl)-N-(3-hydroxypropyl)-3-oxo-6-[4-(trifluoromethyl)phenyl]-2,3-dihydropyridazine-4-carboxamide;

N-(1,3-dihydroxypropan-2-yl)-2-(3-fluorophenyl)-3-oxo-6-[4-(trifluoromethyl)phenyl]-2,3-dihydropyridazine-4-carboxamide;

2-(3-fluorophenyl)-N-(4-hydroxybutan-2-yl)-3-oxo-6-[4-(trifluoromethyl)phenyl]-2,3-dihydropyridazine-4-carboxamide;

2-(3-fluorophenyl)-N-[(2S)-4-hydroxybutan-2-yl]-3-oxo-6-[4-(trifluoromethyl)phenyl]-2,3-dihydropyridazine-4-carboxamide;

2-(3-fluorophenyl)-N-[(2R)-4-hydroxybutan-2-yl]-3-oxo-6-[4-(trifluoromethyl)phenyl]-2,3-dihydropyridazine-4-carboxamide;

2-(3-fluorophenyl)-N-(2-hydroxy-2-methylpropyl)-3-oxo-6-[4-(trifluoromethyl)phenyl]-2,3-dihydropyridazine-4-carboxamide;

2-(3-fluorophenyl)-N-[(2S)-1-hydroxy-3-methoxypropan-2-yl]-3-oxo-6-[4-(trifluoromethyl)phenyl]-2,3-dihydropyridazine-4-carboxamide;

2-(3-fluorophenyl)-N-[(2R)-1-hydroxy-3-methoxypropan-2-yl]-3-oxo-6-[4-(trifluoromethyl)phenyl]-2,3-dihydropyridazine-4-carboxamide;

2-(3-fluorophenyl)-N-(1-hydroxy-4-methoxybutan-2-yl)-3-oxo-6-[4-(trifluoromethyl)phenyl]-2,3-dihydropyridazine-4-carboxamide;

2-(3-fluorophenyl)-N-[(2R)-1-hydroxy-4-methoxybutan-2-yl]-3-oxo-6-[4-(trifluoromethyl)phenyl]-2,3-dihydropyridazine-4-carboxamide;

2-(3-fluorophenyl)-N-[(2S)-1-hydroxy-4-methoxybutan-2-yl]-3-oxo-6-[4-(trifluoromethyl)phenyl]-2,3-dihydropyridazine-4-carboxamide;

2-(3-fluorophenyl)-3-oxo-N-(1,1,1-trifluoro-3-hydroxybutan-2-yl)-6-[4-(trifluoromethyl)phenyl]-2,3-dihydropyridazine-4-carboxamide;

2-(3-fluorophenyl)-3-oxo-N-[(2R,3R)-1,1,1-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2R,3S)-1,1,1-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2S,3R)-1,1,1-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2S,3S)-1,1,1-trifluoro-3-hydroxybutan-2-yl]-6-[4-(trifluoromethyl)phenyl]-2,3-dihydropyridazine-4-carboxamide;

N-(3,3-difluoro-2-hydroxypropyl)-2-(3-fluorophenyl)-3-oxo-6-[4-(trifluoromethyl)phenyl]-2,3-dihydropyridazine-4-carboxamide;

N-[(2R)-3,3-difluoro-2-hydroxypropyl]-2-(3-fluorophenyl)-3-oxo-6-[4-(trifluoromethyl)phenyl]-2,3-dihydropyridazine-4-carboxamide;

N-[(2S)-3,3-difluoro-2-hydroxypropyl]-2-(3-fluorophenyl)-3-oxo-6-[4-(trifluoromethyl)phenyl]-2,3-dihydropyridazine-4-carboxamide;

N-(1,4-dihydroxybutan-2-yl)-2-(3-fluorophenyl)-3-oxo-6-[4-(trifluoromethyl)phenyl]-2,3-dihydropyridazine-4-carboxamide;

1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]hexitol;

1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]-L-threo-hexitol;

1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]-D-threo-hexitol;

3,6-anhydro-2,4,5-trideoxy-2-[({2-(3-fluorophenyl)-3-oxo-6-[4-(trifluoromethyl)phenyl]-2,3-dihydropyridazin-4-yl}carbonyl)amino]-D-erythro-hexitol;

1,4-anhydro-2,3,5-trideoxy-5-[({2-(3-fluorophenyl)-3-oxo-6-[4-(trifluoromethyl)phenyl]-2,3-dihydropyridazin-4-yl}carbonyl)amino]-D-erythro-hexitol;

N-[(2S)-2,3-dihydroxypropyl]-2-(3-fluorophenyl)-3-oxo-6-[4-(trifluoromethyl)phenyl]-2,3-dihydropyridazine-4-carboxamide;

N-[(2R)-2,3-dihydroxypropyl]-2-(3-fluorophenyl)-3-oxo-6-[4-(trifluoromethyl)phenyl]-2,3-dihydropyridazine-4-carboxamide;

2-(3-fluorophenyl)-3-oxo-N-(1,1,1-trifluoro-3-hydroxypropan-2-yl)-6-[4-(trifluoromethyl)phenyl]-2,3-dihydropyridazine-4-carboxamide;

N-(1-cyclopropyl-2-hydroxyethyl)-2-(3-fluorophenyl)-3-oxo-6-[4-(trifluoromethyl)phenyl]-2,3-dihydropyridazine-4-carboxamide;

N-[(1R)-1-cyclopropyl-2-hydroxyethyl]-2-(3-fluorophenyl)-3-oxo-6-[4-(trifluoromethyl)phenyl]-2,3-dihydropyridazine-4-carboxamide;

N-[(1S)-1-cyclopropyl-2-hydroxyethyl]-2-(3-fluorophenyl)-3-oxo-6-[4-(trifluoromethyl)phenyl]-2,3-dihydropyridazine-4-carboxamide;

2-(3-fluorophenyl)-3-oxo-N-(4,4,4-trifluoro-3-hydroxybutan-2-yl)-6-[4-(trifluoromethyl)phenyl]-2,3-dihydropyridazine-4-carboxamide;

2-(3-fluorophenyl)-3-oxo-N-[(2R,3R)-4,4,4-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2S,3R)-4,4,4-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2R,3S)-4,4,4-trifluoro-3-hydroxybutan-2-yl]-6-[4-(trifluoromethyl)phenyl]-2,3-dihydropyridazine-4-carboxamide;

2-(3-fluorophenyl)-3-oxo-N-[(2S,3S)-4,4,4-trifluoro-3-hydroxybutan-2-yl]-6-[4-(trifluoromethyl)phenyl]-2,3-dihydropyridazine-4-carboxamide;

6-(4-chlorophenyl)-2-(3-fluorophenyl)-N-[(2S)-1-hydroxy-3,3-dimethylbutan-2-yl]-3-oxo-2,3-dihydropyridazine-4-carboxamide;

6-(4-chlorophenyl)-2-(3-fluorophenyl)-3-oxo-N-(1,1,1-trifluoro-3-hydroxy-3-methylbutan-2-yl)-2,3-dihydropyridazine-4-carboxamide;

6-(4-chlorophenyl)-2-(3-fluorophenyl)-3-oxo-N-[(2R)-1,1,1-trifluoro-3-hydroxy-3-methylbutan-2-yl]-2,3-dihydropyridazine-4-carboxamide;

6-(4-chlorophenyl)-2-(3-fluorophenyl)-3-oxo-N-[(2S)-1,1,1-trifluoro-3-hydroxy-3-methylbutan-2-yl]-2,3-dihydropyridazine-4-carboxamide;

6-(4-chlorophenyl)-2-(3-fluorophenyl)-3-oxo-N-[1,1,1-trifluoro-3-hydroxy-2-(hydroxymethyl)propan-2-yl]-2,3-dihydropyridazine-4-carboxamide;

6-(4-chlorophenyl)-2-(3-fluorophenyl)-N-[(2R)-3-hydroxy-3-methylbutan-2-yl]-3-oxo-2,3-dihydropyridazine-4-carboxamide;

6-(4-chlorophenyl)-2-(3-fluorophenyl)-N-[(2S)-3-hydroxy-3-methylbutan-2-yl]-3-oxo-2,3-dihydropyridazine-4-carboxamide;

6-[4-(difluoromethyl)phenyl]-2-(3-fluorophenyl)-3-oxo-N-[(2R)-1,1,1-trifluoro-3-hydroxypropan-2-yl]-2,3-dihydropyridazine-4-carboxamide;

2-(3-fluorophenyl)-N-[(2S)-1-hydroxypropan-2-yl]-6-(4-methoxyphenyl)-3-oxo-2,3-dihydropyridazine-4-carboxamide;

2-(3-fluorophenyl)-N-[(2S)-1-hydroxybutan-2-yl]-6-(4-methoxyphenyl)-3-oxo-2,3-dihydropyridazine-4-carboxamide;

6-(4-chlorophenyl)-2-(3,5-dichlorophenyl)-N-[(2S)-1-hydroxypropan-2-yl]-3-oxo-2,3-dihydropyridazine-4-carboxamide;

6-(4-chlorophenyl)-2-(3,5-dichlorophenyl)-N-[2-hydroxy-1-(tetrahydrofuran-3-yl)ethyl]-3-oxo-2,3-dihydropyridazine-4-carboxamide;

6-(4-chlorophenyl)-2-(3,5-dichlorophenyl)-3-oxo-N-(3,3,3-trifluoro-2-hydroxypropyl)-2,3-dihydropyridazine-4-carboxamide;

6-(4-chlorophenyl)-2-(3,5-dichlorophenyl)-N-[(2S,3S)-3-hydroxybutan-2-yl]-3-oxo-2,3-dihydropyridazine-4-carboxamide;

6-(4-chlorophenyl)-2-(3-fluorophenyl)-N-[(2R)-1-hydroxy-3-methoxypropan-2-yl]-3-oxo-2,3-dihydropyridazine-4-carboxamide;

6-(4-chlorophenyl)-2-(3-fluorophenyl)-N-[2-(1-hydroxycyclohexyl)ethyl]-3-oxo-2,3-dihydropyridazine-4-carboxamide;

6-(4-chlorophenyl)-2-(3-fluorophenyl)-N-(3-hydroxy-3-methylbutyl)-3-oxo-2,3-dihydropyridazine-4-carboxamide;

6-(4-chlorophenyl)-N-(2,3-dihydroxy-3-methylbutyl)-2-(3-fluorophenyl)-3-oxo-2,3-dihydropyridazine-4-carboxamide;

6-(4-chlorophenyl)-N-[(2RS)-1-fluoro-3-hydroxypropan-2-yl]-2-(3-fluorophenyl)-3-oxo-2,3-dihydropyridazine-4-carboxamide;

6-(4-chlorophenyl)-2-(3-fluorophenyl)-N-(cis-3-hydroxycyclobutyl)-3-oxo-2,3-dihydropyridazine-4-carboxamide;

6-(4-chlorophenyl)-2-(3-fluorophenyl)-N-[(4-hydroxytetrahydro-2H-pyran-4-yl)methyl]-3-oxo-2,3-dihydropyridazine-4-carboxamide;

6-(4-chlorophenyl)-2-(3-fluorophenyl)-N-[(1-hydroxycyclopentyl)methyl]-3-oxo-2,3-dihydropyridazine-4-carboxamide;

6-(4-chlorophenyl)-2-(3-fluorophenyl)-N-[(3-hydroxyoxetan-3-yl)methyl]-3-oxo-2,3-dihydropyridazine-4-carboxamide;

6-(4-chlorophenyl)-2-(3-fluorophenyl)-N-[(2RS)-1-hydroxy-3-(pyridin-2-yl)propan-2-yl]-3-oxo-2,3-dihydropyridazine-4-carboxamide;

6-(4-chlorophenyl)-2-(3-fluorophenyl)-N-[(2RS)-1-hydroxy-3-(pyridin-4-yl)propan-2-yl]-3-oxo-2,3-dihydropyridazine-4-carboxamide;

6-(4-chlorophenyl)-2-(3-fluorophenyl)-N-(trans-2-hydroxycyclobutyl)-3-oxo-2,3-dihydropyridazine-4-carboxamide;

6-(4-chlorophenyl)-2-(3-fluorophenyl)-N-[(1S,2S)-2-hydroxycyclobutyl]-3-oxo-2,3-dihydropyridazine-4-carboxamide;

6-(4-chlorophenyl)-2-(3-fluorophenyl)-N-[(1R,2R)-2-hydroxycyclobutyl]-3-oxo-2,3-dihydropyridazine-4-carboxamide;

6-(4-chlorophenyl)-N-(3,4-dihydroxybutan-2-yl)-2-(3-fluorophenyl)-3-oxo-2,3-dihydropyridazine-4-carboxamide;

6-(4-chlorophenyl)-N-[(2S,3S)-3,4-dihydroxybutan-2-yl]-2-(3-fluorophenyl)-3-oxo-2,3-dihydropyridazine-4-carboxamide;

6-(4-chlorophenyl)-N-[(2S,3R)-3,4-dihydroxybutan-2-yl]-2-(3-fluorophenyl)-3-oxo-2,3-dihydropyridazine-4-carboxamide;

6-(4-chlorophenyl)-N-[(2R,3S)-3,4-dihydroxybutan-2-yl]-2-(3-fluorophenyl)-3-oxo-2,3-dihydropyridazine-4-carboxamide;
6-(4-chlorophenyl)-N-[(2R,3R)-3,4-dihydroxybutan-2-yl]-2-(3-fluorophenyl)-3-oxo-2,3-dihydropyridazine-4-carboxamide;
6-(4-chlorophenyl)-2-(3-fluorophenyl)-N-[1-hydroxy-3-(pyridin-3-yl)propan-2-yl]-3-oxo-2,3-dihydro-pyridazine-4-carboxamide;
6-(4-chlorophenyl)-2-(3-fluorophenyl)-3-oxo-N-(1,1,1-trifluoro-4-hydroxybutan-2-yl)-2,3-dihydropyridazine-4-carboxamide;
6-(4-chlorophenyl)-2-(3-fluorophenyl)-3-oxo-N-[(2S)-1,1,1-trifluoro-4-hydroxybutan-2-yl]-2,3-dihydro-pyridazine-4-carboxamide;
6-(4-chlorophenyl)-2-(3-fluorophenyl)-3-oxo-N-[(2R)-1,1,1-trifluoro-4-hydroxybutan-2-yl]-2,3-dihydro-pyridazine-4-carboxamide;
6-(4-chlorophenyl)-2-(3-fluorophenyl)-N-(cis-2-hydroxycyclobutyl)-3-oxo-2,3-dihydropyridazine-4-carboxamide;
6-(4-chlorophenyl)-2-(3-fluorophenyl)-N-[(1R,2S)-2-hydroxycyclobutyl]-3-oxo-2,3-dihydropyridazine-4-carboxamide;
6-(4-chlorophenyl)-2-(3-fluorophenyl)-N-[(1S,2R)-2-hydroxycyclobutyl]-3-oxo-2,3-dihydropyridazine-4-carboxamide;
6-[4-(difluoromethyl)phenyl]-2-(3-fluorophenyl)-N-[(2S)-3-hydroxy-3-methylbutan-2-yl]-3-oxo-2,3-dihydropyridazine-4-carboxamide;
6-[4-(difluoromethoxy)phenyl]-2-(3-fluorophenyl)-N-[(2S)-3-hydroxy-3-methylbutan-2-yl]-3-oxo-2,3-dihydropyridazine-4-carboxamide;
6-(4-chlorophenyl)-2-(3-fluorophenyl)-N-[(2S)-3-hydroxy-1-isopropoxy-3-methylbutan-2-yl]-3-oxo-2,3-dihydropyridazine-4-carboxamide;
2-(3-fluorophenyl)-N-[(2S)-3-hydroxy-3-methylbutan-2-yl]-3-oxo-6-[4-(trifluoromethyl)phenyl]-2,3-dihydropyridazine-4-carboxamide;
6-(4-chlorophenyl)-2-(3-fluorophenyl)-N-[(2S)-3-hydroxy-3-methylbutan-2-yl]-3-oxo-2,3-dihydropyridazine-4-carboxamide;
2-(3-fluorophenyl)-3-oxo-N-(1,1,1-trifluoro-3-hydroxy-3-methylbutan-2-yl)-6-[4-(trifluoromethyl)phenyl]-2,3-dihydropyridazine-4-carboxamide;
2-(3-fluorophenyl)-3-oxo-N-[(2R)-1,1,1-trifluoro-3-hydroxy-3-methylbutan-2-yl]-6-[4-(trifluoromethyl)phenyl]-2,3-dihydropyridazine-4-carboxamide;
2-(3-fluorophenyl)-3-oxo-N-[(2S)-1,1,1-trifluoro-3-hydroxy-3-methylbutan-2-yl]-6-[4-(trifluoromethyl)phenyl]-2,3-dihydropyridazine-4-carboxamide;
6-[4-(fluoromethyl)phenyl]-2-(3-fluorophenyl)-3-oxo-N-[(2S)-3,3,3-trifluoro-2-hydroxypropyl]-2,3-dihydropyridazine-4-carboxamide;
6-(4-chlorophenyl)-2-(3-fluorophenyl)-N-[(2R)-1-hydoxy-3-methoxypropan-2-yl]-3-oxo-2,3-dihydropyridazine-4-carboxamide;
6-(4-chlorophenyl)-2-(3-fluorophenyl)-3-oxo-N-[(2S)-1,1,1-trifluoro-4-hydroxybutan-2-yl]-2,3-dihydropyridazine-4-carboxamide; and
6-(4-chlorophenyl)-2-(3-fluorophenyl)-3-oxo-N-[(2R)-1,1,1-trifluoro-4-hydroxybutan-2-yl]-2,3-dihydropyridazine-4-carboxamide,
or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing.

5. A method of preparing a compound of formula (I) according to claim 1, said method comprising the step of allowing an intermediate compound of formula (VII):

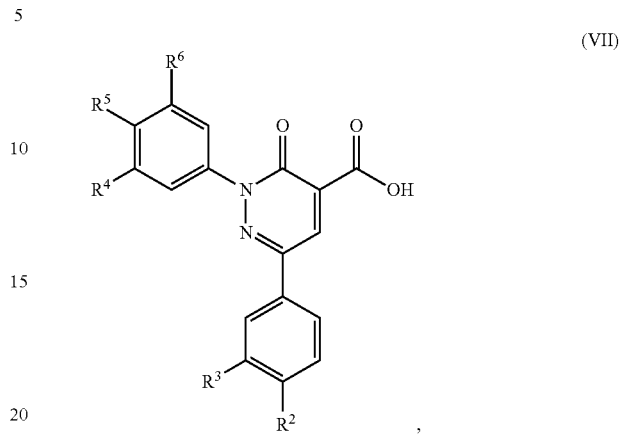

(VII)

in which $R^2$, $R^3$, $R^4$, $R^5$ and $R^6$ are as defined for the compound of formula (I) according to claim 1,
to react with a compound of formula (VIII):

in which $R^1$ is as defined for the compound of formula (I) according to claim 1, thereby giving a compound of formula (I):

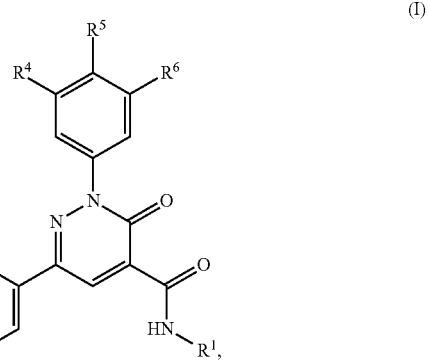

(I)

in which $R^1$, $R^2$, $R^3$, $R^4$, $R^5$ and $R^6$ are as defined for the compound of formula (I) according to claim 1.

6. A pharmaceutical composition comprising a compound of formula (I) according to claim 1, or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing, and one or more pharmaceutically acceptable excipients.

7. A pharmaceutical combination comprising:
one or more compounds of formula (I) according to claim 1, or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing, and
one or more pharmaceutical active anti cancer compounds or
one or more pharmaceutical active immune checkpoint inhibitors.

8. A compound of formula (VII):

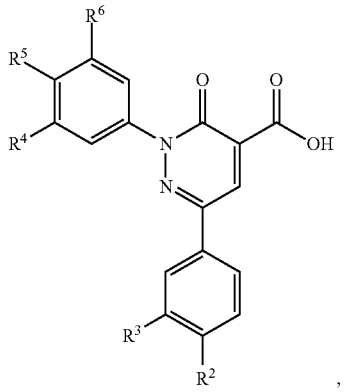

(VII)

in which
R² represents chloro, methyl, fluoromethyl, difluoromethyl, trifluoromethyl, methoxy or difluoromethoxy;
R³ represents hydrogen or methyl:
R⁴ represents hydrogen or halogen;
R⁵ represents hydrogen; and
R⁶ represents hydrogen or halogen.

9. A compound selected from the list consisting of:
6-(4-chlorophenyl)-2-(3-fluorophenyl)-N-(trans-4-hydroxytetrahydrofuran-3-yl)-3-oxo-2,3-dihydropyridazine-4-carboxamide;
methyl N-{[6-(4-chlorophenyl)-2-(3-fluorophenyl)-3-oxo-2,3-dihydropyridazin-4-yl]carbonyl}-L-serinate;
N-[(2S)-1-amino-3-hydroxy-1-oxopropan-2-yl]-6-(4-chlorophenyl)-2-(3-fluorophenyl)-3-oxo-2,3-dihydropyridazine-4-carboxamide;
N-(4-amino-1-hydroxy-4-oxobutan-2-yl)-6-(4-chlorophenyl)-2-(3-fluorophenyl)-3-oxo-2,3-dihydropyridazine-4-carboxamide;
N-{[6-(4-chlorophenyl)-2-(3-fluorophenyl)-3-oxo-2,3-dihydropyridazin-4-yl]carbonyl}-L-serine;
6-(4-chlorophenyl)-2-(3-fluorophenyl)-N-[(3S,4S)-4-hydroxytetrahydrofuran-3-yl]-3-oxo-2,3-dihydropyridazine-4-carboxamide;
6-(4-chlorophenyl)-2-(3-fluorophenyl)-N-[(3S,4R)-4-hydroxytetrahydrofuran-3-yl]-3-oxo-2,3-dihydropyridazine-4-carboxamide;
2-(3-fluorophenyl)-N-[(2S)-1-hydroxy-3-methylbutan-2-yl]-3-oxo-6-[4-(trifluoromethoxy)phenyl]-2,3-dihydropyridazine-4-carboxamide;
2-(3-fluorophenyl)-3-oxo-N-(1,1,1-trifluoro-3-hydroxypropan-2-yl)-6-[4-(trifluoromethoxy)phenyl]-2,3-dihydropyridazine-4-carboxamide;
2-(3-fluorophenyl)-3-oxo-N-[(2R)-1,1,1-trifluoro-3-hydroxypropan-2-yl]-6-[4-(trifluoromethoxy)phenyl]-2,3-dihydropyridazine-4-carboxamide;
2-(3-fluorophenyl)-3-oxo-N-[(2S)-1,1,1-trifluoro-3-hydroxypropan-2-yl]-6-[4-(trifluoromethoxy)phenyl]-2,3-dihydropyridazine-4-carboxamide;
2-(3-fluorophenyl)-N-[(2S)-1-hydroxybutan-2-yl]-3-oxo-6-[4-(trifluoromethoxy)phenyl]-2,3-dihydropyridazine-4-carboxamide;
2-(3-fluorophenyl)-N-[(2S)-1-hydroxypropan-2-yl]-3-oxo-6-[4-(trifluoromethoxy)phenyl]-2,3-dihydropyridazine-4-carboxamide;
2-(3-fluorophenyl)-N-[2-hydroxy-1-(tetrahydrofuran-3-yl)ethyl]-3-oxo-6-[4-(trifluoromethoxy)phenyl]-2,3-dihydropyridazine-4-carboxamide;
2-(3-fluorophenyl)-N-{(1R)-2-hydroxy-1-[(3S)-tetrahydrofuran-3-yl]ethyl}-3-oxo-6-[4-(trifluoromethoxy)phenyl]-2,3-dihydropyridazine-4-carboxamide;
2-(3-fluorophenyl)-N-{(1R)-2-hydroxy-1-[(3R)-tetrahydrofuran-3-yl]ethyl}-3-oxo-6-[4-(trifluoromethoxy)phenyl]-2,3-dihydropyridazine-4-carboxamide;
2-(3-fluorophenyl)-N-{(1S)-2-hydroxy-1-[(3R)-tetrahydrofuran-3-yl]ethyl}-3-oxo-6-[4-(trifluoromethoxy)phenyl]-2,3-dihydropyridazine-4-carboxamide;
2-(3-fluorophenyl)-N-{(1S)-2-hydroxy-1-[(3S)-tetrahydrofuran-3-yl]ethyl}-3-oxo-6-[4-(trifluoromethoxy)phenyl]-2,3-dihydropyridazine-4-carboxamide;
2-(3-fluorophenyl)-N-(3-hydroxybutan-2-yl)-3-oxo-6-[4-(trifluoromethoxy)phenyl]-2,3-dihydropyridazine-4-carboxamide;
2-(3-fluorophenyl)-N-[(2R,3R)-3-hydroxybutan-2-yl]-3-oxo-6-[4-(trifluoromethoxy)phenyl]-2,3-dihydropyridazine-4-carboxamide;
2-(3-fluorophenyl)-N-[(2S,3R)-3-hydroxybutan-2-yl]-3-oxo-6-[4-(trifluoromethoxy)phenyl]-2,3-dihydropyridazine-4-carboxamide;
2-(3-fluorophenyl)-N-[(2R,3S)-3-hydroxybutan-2-yl]-3-oxo-6-[4-(trifluoromethoxy)phenyl]-2,3-dihydropyridazine-4-carboxamide;
2-(3-fluorophenyl)-N-[(2S,3S)-3-hydroxybutan-2-yl]-3-oxo-6-[4-(trifluoromethoxy)phenyl]-2,3-dihydropyridazine-4-carboxamide;
2-(3-fluorophenyl)-3-oxo-N-(3,3,3-trifluoro-2-hydroxypropyl)-6-[4-(trifluoromethoxy)phenyl]-2,3-dihydropyridazine-4-carboxamide;
2-(3-fluorophenyl)-3-oxo-N-[(2R)-3,3,3-trifluoro-2-hydroxypropyl]-6-[4-(trifluoromethoxy)phenyl]-2,3-dihydropyridazine-4-carboxamide;
2-(3-fluorophenyl)-3-oxo-N-[(2S)-3,3,3-trifluoro-2-hydroxypropyl]-6-[4-(trifluoromethoxy)phenyl]-2,3-dihydropyridazine-4-carboxamide;
6-(4-chlorophenyl)-2-(3-fluorophenyl)-N-[(2R)-1-hydroxy-3-phenylpropan-2-yl]-3-oxo-2,3-dihydropyridazine-4-carboxamide;
6-(4-chlorophenyl)-2-(3-fluorophenyl)-N-[(2S)-1-hydroxy-3-phenylpropan-2-yl]-3-oxo-2,3-dihydropyridazine-4-carboxamide;
6-(4-chlorophenyl)-2-(3-fluorophenyl)-N-[(4-hydroxy-1-methylpiperidin-4-yl)methyl]-3-oxo-2,3-dihydropyridazine-4-carboxamide;
6-(4-chlorophenyl)-N-[3-(dimethylamino)-2-hydroxypropyl]-2-(3-fluorophenyl)-3-oxo-2,3-dihydropyridazine-4-carboxamide;
2-(3-fluorophenyl)-N-[(2S)-1-hydroxy-3-phenylpropan-2-yl]-3-oxo-6-[4-(trifluoromethyl)phenyl]-2,3-dihydropyridazine-4-carboxamide;
2-(3-fluorophenyl)-N-[(2R)-1-hydroxy-3-phenylpropan-2-yl]-3-oxo-6-[4-(trifluoromethyl)phenyl]-2,3-dihydropyridazine-4-carboxamide;
1,5-anhydro-2-({[6-(4-chlorophenyl)-2-(3-fluorophenyl)-3-oxo-2,3-dihydropyridazin-4-yl]carbonyl}amino)-2,4-dideoxy-D-erythro-pentitol;
6-(4-chlorophenyl)-N-[(trans)-3,3-difluoro-2-hydroxycyclohexyl]-2-(3-fluorophenyl)-3-oxo-2,3-dihydropyridazine-4-carboxamide;
6-(4-chlorophenyl)-N-[(1R,2S)-3,3-difluoro-2-hydroxycyclohexyl]-2-(3-fluorophenyl)-3-oxo-2,3-dihydropyridazine-4-carboxamide;

6-(4-chlorophenyl)-N-[(1S,2R)-3,3-difluoro-2-hydroxycyclohexyl]-2-(3-fluorophenyl)-3-oxo-2,3-dihydropyridazine-4-carboxamide;

methyl N-{[6-(4-chlorophenyl)-2-(3-fluorophenyl)-3-oxo-2,3-dihydropyridazin-4-yl]carbonyl}-D-serinate;

2-(3-fluorophenyl)-N-(cis-4-hydroxytetrahydrofuran-3-yl)-3-oxo-6-[4-(trifluoromethyl)phenyl]-2,3-dihydropyridazine-4-carboxamide;

2-(3-fluorophenyl)-N-[(3R,4R)-4-hydroxytetrahydrofuran-3-yl]-3-oxo-6-[4-(trifluoromethyl)phenyl]-2,3-dihydropyridazine-4-carboxamide;

2-(3-fluorophenyl)-N-[(3S,4S)-4-hydroxytetrahydrofuran-3-yl]-3-oxo-6-[4-(trifluoromethyl)phenyl]-2,3-dihydropyridazine-4-carboxamide;

6-(4-chlorophenyl)-2-(3-cyanophenyl)-N-[(2S)-1-hydroxy-3-methylbutan-2-yl]-3-oxo-2,3-dihydropyridazine-4-carboxamide;

6-(4-chlorophenyl)-2-(3-cyanophenyl)-3-oxo-N-(3,3,3-trifluoro-2-hydroxypropyl)-2,3-dihydropyridazine-4-carboxamide;

6-(4-chlorophenyl)-2-(3-cyanophenyl)-3-oxo-N-[(2R)-3,3,3-trifluoro-2-hydroxypropyl]-2,3-dihydropyridazine-4-carboxamide;

6-(4-chlorophenyl)-2-(3-cyanophenyl)-3-oxo-N-[(2S)-3,3,3-trifluoro-2-hydroxypropyl]-2,3-dihydropyridazine-4-carboxamide;

6-(4-chlorophenyl)-N-[(2S)-1-hydroxy-3-methylbutan-2-yl]-2-(3-methylphenyl)-3-oxo-2,3-dihydropyridazine-4-carboxamide;

6-(4-chlorophenyl)-2-(3-methylphenyl)-3-oxo-N-(3,3,3-trifluoro-2-hydroxypropyl)-2,3-dihydropyridazine-4-carboxamide;

6-(4-chlorophenyl)-2-(3-methylphenyl)-3-oxo-N-[(2R)-3,3,3-trifluoro-2-hydroxypropyl]-2,3-dihydropyridazine-4-carboxamide;

6-(4-chlorophenyl)-2-(3-methylphenyl)-3-oxo-N-[(2S)-3,3,3-trifluoro-2-hydroxypropyl]-2,3-dihydropyridazine-4-carboxamide;

6-(4-chlorophenyl)-N-[(2S)-1-hydroxypropan-2-yl]-2-(3-methylphenyl)-3-oxo-2,3-dihydropyridazine-4-carboxamide;

6-(4-chlorophenyl)-2-[3-(difluoromethyl)phenyl]-N-[(2S)-1-hydroxypropan-2-yl]-3-oxo-2,3-dihydropyridazine-4-carboxamide;

6-(4-chlorophenyl)-N-(1-cyano-2-hydroxyethyl)-2-(3-fluorophenyl)-3-oxo-2,3-dihydropyridazine-4-carboxamide;

6-(4-chlorophenyl)-2-(3-fluorophenyl)-N-[(trans-3-hydroxycyclobutyl)methyl]-3-oxo-2,3-dihydropyridazine-4-carboxamide;

6-[3-chloro-4-(dimethylamino)phenyl]-2-(3-fluorophenyl)-3-oxo-N-[(2R)-1,1,1-trifluoro-3-hydroxypropan-2-yl]-2,3-dihydropyridazine-4-carboxamide;

2-(3-fluorophenyl)-N-[(2S)-1-hydroxypropan-2-yl]-6-[4-(morpholin-4-yl)phenyl]-3-oxo-2,3-dihydropyridazine-4-carboxamide;

6-[3-chloro-4-(dimethylamino)phenyl]-2-(3-fluorophenyl)-N-[(2S)-1-hydroxy-3-methylbutan-2-yl]-3-oxo-2,3-dihydropyridazine-4-carboxamide;

6-[3-chloro-4-(dimethylamino)phenyl]-2-(3-fluorophenyl)-3-oxo-N-(1,1,1-trifluoro-3-hydroxypropan-2-yl)-2,3-dihydropyridazine-4-carboxamide;

6-[3-chloro-4-(dimethylamino)phenyl]-2-(3-fluorophenyl)-N-[(2S)-1-hydroxypropan-2-yl]-3-oxo-2,3-dihydropyridazine-4-carboxamide;

2-(3-fluorophenyl)-N-[(trans)-4-hydroxytetrahydrofuran-3-yl]-6-[4-(morpholin-4-yl)phenyl]-3-oxo-2,3-dihydropyridazine-4-carboxamide;

N-[(1S)-1-cyclopropyl-2-hydroxy-2-methylpropyl]-2-(3-fluorophenyl)-3-oxo-6-[4-(trifluoromethoxy)phenyl]-2,3-dihydropyridazine-4-carboxamide;

2-(3-fluorophenyl)-N-[(2S)-3-hydroxy-3-methylbutan-2-yl]-3-oxo-6-[4-(trifluoromethoxy)phenyl]-2,3-dihydropyridazine-4-carboxamide;

2-(3-fluorophenyl)-N-[(2R)-3-hydroxy-3-methylbutan-2-yl]-3-oxo-6-[4-(trifluoromethoxy)phenyl]-2,3-dihydropyridazine-4-carboxamide;

2-(3-fluorophenyl)-N-(2-hydroxy-2-methylpropyl)-3-oxo-6-[4-(trifluoromethoxy)phenyl]-2,3-dihydropyridazine-4-carboxamide;

6-(4-chlorophenyl)-2-(3-fluorophenyl)-N-[cis-4-hydroxytetrahydrofuran-3-yl]-3-oxo-2,3-dihydropyridazine-4-carboxamide;

6-(4-chlorophenyl)-2-(3-fluorophenyl)-N-[(3R,4R)-4-hydroxytetrahydrofuran-3-yl]-3-oxo-2,3-dihydropyridazine-4-carboxamide;

tert-butyl (3R,4S)-3-({[6-(4-chlorophenyl)-2-(3-fluorophenyl)-3-oxo-2,3-dihydropyridazin-4-yl]carbonyl}amino)-4-hydroxypyrrolidine-1-carboxylate;

6-(4-chlorophenyl)-2-(3-fluorophenyl)-N-[cis-4-hydroxy-1-methylpyrrolidin-3-yl]-3-oxo-2,3-dihydropyridazine-4-carboxamide;

6-(4-chlorophenyl)-2-[3-(difluoromethyl)phenyl]-3-oxo-N-(3,3,3-trifluoro-2-hydroxypropyl)-2,3-dihydropyridazine-4-carboxamide;

6-(4-chlorophenyl)-N-[(1S)-1-cyano-2-hydroxyethyl]-2-(3-fluorophenyl)-3-oxo-2,3-dihydropyridazine-4-carboxamide;

6-(4-chlorophenyl)-2-(3-fluorophenyl)-N-[trans-3-(hydroxymethyl)cyclobutyl]-3-oxo-2,3-dihydropyridazine-4-carboxamide;

methyl 3-({[6-(4-chlorophenyl)-2-(3-fluorophenyl)-3-oxo-2,3-dihydropyridazin-4-yl]carbonyl}amino)-2,2-dimethylpropanoate;

3-({[6-(4-Chlorophenyl)-2-(3-fluorophenyl)-3-oxo-2,3-dihydropyridazin-4-yl]carbonyl}amino)-2,2-dimethylpropanoic acid;

6-(4-chlorophenyl)-2-(3-fluorophenyl)-N-[(3R,4S)-4-hydroxytetrahydrofuran-3-yl]-3-oxo-2,3-dihydropyridazine-4-carboxamide;

6-(4-chloro-3-fluorophenyl)-2-(3-fluorophenyl)-3-oxo-N-(3,3,3-trifluoro-2-hydroxypropyl)-2,3-dihydropyridazine-4-carboxamide;

6-(4-chloro-3-fluorophenyl)-2-(3-fluorophenyl)-3-oxo-N-[(2S)-3,3,3-trifluoro-2-hydroxypropyl]-2,3-dihydropyridazine-4-carboxamide;

6-(4-chloro-3-fluorophenyl)-2-(3-fluorophenyl)-3-oxo-N-(3,3,3-trifluoro-2-hydroxypropyl)-2,3-dihydropyridazine-4-carboxamide;

6-(4-chloro-3-fluorophenyl)-2-(3-fluorophenyl)-3-oxo-N-[(2S)-3,3,3-trifluoro-2-hydroxypropyl]-2,3-dihydropyridazine-4-carboxamide;

6-(4-chloro-3-fluorophenyl)-2-(3-fluorophenyl)-3-oxo-N-[(2R)-3,3,3-trifluoro-2-hydroxypropyl]-2,3-dihydropyridazine-4-carboxamide;

6-(4-Chloro-3-fluorophenyl)-2-(3-fluorophenyl)-N-[(2S)-1-hydroxy-3-methylbutan-2-yl]-3-oxo-2,3-dihydropyridazine-4-carboxamide;

6-(4-Chloro-3-fluorophenyl)-2-(3-fluorophenyl)-N-[(2S)-1-hydroxypropan-2-yl]-3-oxo-2,3-dihydropyridazine-4-carboxamide;

6-(4-chloro-3-fluorophenyl)-2-(3-fluorophenyl)-N-[2-hydroxy-1-(tetrahydrofuran-3-yl)ethyl]-3-oxo-2,3-dihydropyridazine-4-carboxamide;

6-(4-chloro-3-fluorophenyl)-2-(3-fluorophenyl)-N-{(1R)-2-hydroxy-1-[(3R)-tetrahydrofuran-3-yl]ethyl}-3-oxo-2,3-dihydropyridazine-4-carboxamide;

6-(4-chloro-3-fluorophenyl)-2-(3-fluorophenyl)-N-{(1S)-2-hydroxy-1-[(3S)-tetrahydrofuran-3-yl]ethyl}-3-oxo-2,3-dihydropyridazine-4-carboxamide;

6-(4-chloro-3-fluorophenyl)-2-(3-fluorophenyl)-N-{(1S)-2-hydroxy-1-[(3R)-tetrahydrofuran-3-yl]ethyl}-3-oxo-2,3-dihydropyridazine-4-carboxamide;

6-(4-chloro-3-fluorophenyl)-2-(3-fluorophenyl)-N-{(1R)-2-hydroxy-1-[(3S)-tetrahydrofuran-3-yl]ethyl}-3-oxo-2,3-dihydropyridazine-4-carboxamide;

6-(4-chloro-3-fluorophenyl)-2-(3-fluorophenyl)-N-[(2S)-1-hydroxybutan-2-yl]-3-oxo-2,3-dihydropyridazine-4-carboxamide;

6-(4-chloro-3-fluorophenyl)-2-(3-fluorophenyl)-N-(3-hydroxybutan-2-yl)-3-oxo-2,3-dihydropyridazine-4-carboxamide;

6-(4-chloro-3-fluorophenyl)-2-(3-fluorophenyl)-N-[(2S,3S)-3-hydroxybutan-2-yl]-3-oxo-2,3-dihydropyridazine-4-carboxamide;

6-(4-chloro-3-fluorophenyl)-2-(3-fluorophenyl)-N-(cis-2-hydroxycyclohexyl)-3-oxo-2,3-dihydropyridazine-4-carboxamide;

6-(3,4-dichlorophenyl)-2-(3-fluorophenyl)-3-oxo-N-[(2R)-3,3,3-trifluoro-2-hydroxypropyl]-2,3-dihydropyridazine-4-carboxamide;

6-(3,4-dichlorophenyl)-2-(3-fluorophenyl)-3-oxo-N-[(2S)-3,3,3-trifluoro-2-hydroxypropyl]-2,3-dihydropyridazine-4-carboxamide;

6-(3,4-dichlorophenyl)-2-(3-fluorophenyl)-N-[(2S)-1-hydroxypropan-2-yl]-3-oxo-2,3-dihydropyridazine-4-carboxamide;

6-(3,4-dichlorophenyl)-2-(3-fluorophenyl)-N-[(2S)-1-hydroxy-3-methylbutan-2-yl]-3-oxo-2,3-dihydropyridazine-4-carboxamide;

6-(3,4-dichlorophenyl)-2-(3-fluorophenyl)-N-(2-hydroxy-3-methoxypropyl)-3-oxo-2,3-dihydropyridazine-4-carboxamide;

6-(3,4-dichlorophenyl)-2-(3-fluorophenyl)-N-(3-hydroxybutan-2-yl)-3-oxo-2,3-dihydropyridazine-4-carboxamide;

6-(3,4-dichlorophenyl)-2-(3-fluorophenyl)-N-[(2S,3S)-3-hydroxybutan-2-yl]-3-oxo-2,3-dihydropyridazine-4-carboxamide;

6-(3,4-dichlorophenyl)-2-(3-fluorophenyl)-N-[(2S)-1-hydroxybutan-2-yl]-3-oxo-2,3-dihydropyridazine-4-carboxamide;

6-(3,4-dichlorophenyl)-2-(3-fluorophenyl)-N-[2-hydroxy-1-(tetrahydrofuran-3-yl)ethyl]-3-oxo-2,3-dihydropyridazine-4-carboxamide; and 6-(4-chlorophenyl)-2-(3-cyanophenyl)-N-[(2S)-1-hydroxypropan-2-yl]-3-oxo-2,3-dihydropyridazine-4-carboxamide, or an enantiomer, a diastereomer, a racemate, a tautomer, an N-oxide, a hydrate, a solvate, a physiologically acceptable salt, or a solvate of a physiologically acceptable salt thereof, or a mixture of any of the foregoing.

* * * * *